US008435167B2

(12) United States Patent
Oohashi et al.

(10) Patent No.: US 8,435,167 B2
(45) Date of Patent: May 7, 2013

(54) METHOD AND APPARATUS FOR ENVIRONMENTAL SETTING AND INFORMATION FOR ENVIRONMENTAL SETTING

(75) Inventors: Tsutomu Oohashi, Tokyo (JP); Norie Kawai, Tokyo (JP); Emi Nishina, Tokyo (JP); Reiko Yagi, Tokyo (JP); Manabu Honda, Tokyo (JP); Satoshi Nakamura, Tokyo (JP); Susumu Nakamura, legal representative, Yokohama (JP); Michiko Nakamura, legal representative, Yokohama (JP); Masako Morimoto, Tokyo (JP); Tadao Maekawa, Tokyo (JP)

(73) Assignee: Action Research Co., Ltd., Tokyo (JP)

( * ) Notice: Subject to any disclaimer, the term of this patent is extended or adjusted under 35 U.S.C. 154(b) by 104 days.

(21) Appl. No.: 12/691,278

(22) Filed: Jan. 21, 2010

(65) Prior Publication Data
US 2010/0204540 A1    Aug. 12, 2010

Related U.S. Application Data

(62) Division of application No. 10/572,484, filed as application No. PCT/JP2004/013749 on Sep. 21, 2004, now abandoned.

(30) Foreign Application Priority Data

Sep. 18, 2003    (JP) ................................. 2003-326187

(51) Int. Cl.
*A61M 21/00*    (2006.01)
(52) U.S. Cl.
USPC .......................................................... 600/27

(58) Field of Classification Search .............. 600/26–28; 607/91
See application file for complete search history.

(56) References Cited

U.S. PATENT DOCUMENTS 6,896,693 B2 *    5/2005    Sullivan .......................... 607/91

FOREIGN PATENT DOCUMENTS

| CA | 2023843 | 3/1991 |
| EP | 0 798 009 | 10/1997 |

(Continued)

OTHER PUBLICATIONS

James Theiler, "Estimating Fractal Dimension", Journal of the Optical Society of America A, vol. 7, No. 6, pp. 1055-1073, 1990.

(Continued)

*Primary Examiner* — Christine Matthews
(74) *Attorney, Agent, or Firm* — Wenderoth, Lind & Ponack, L.L.P.

(57) ABSTRACT

A space is set substantially in a tropical rain forest type environment to activate a human's essential brain region and realize an environment suitable for the human's brain by arranging a device for setting the tropical rain forest type environment based on characteristics of activating human's essential brain region responsive to tropical rain forest type environment information, in a space such as an urban space, a housing space or other living space. The tropical rain forest type environmental information has higher density and higher complexity than those of urban space type environmental information, and includes at least one of auditory information, visual information, and super perceptual information of aerial vibration. The tropical rain forest type environmental information is comfortable for the human with no excessive stress, and is environmental information for effecting prevention and treatment of diseases due to stress by realizing the environment comfortable for the human's brain.

3 Claims, 87 Drawing Sheets

| | | SUPER PERSEPTUAL INFORMATION | PERCEPTUAL SPECIFIC INFORMATION |
|---|---|---|---|
| DEFINITION | | SENSORY INFORMATION CONSTITUTED BY PERSEPTIBLE INFORMATION AND INFORMATION (PREFERABLY REMARKABLY) EXCEEDING PERSEPTIBLE LIMIT | SENSORY INFORMATION CONSTITUTED ONLY BY INFORMATION WITHIN PERSEPTIBLE LIMIT |
| HEARING | DENSITY | HEARING INFORMATION DENSITY (NUMBER OF AERIAL VIBRATIONS PER SECOND) INCLUDES BOTH PERSEPTIBLE BAND EQUAL TO OR HIGHER THAN 20 Hz AND EQUAL TO OR LOWER THAN 20 kHz AND SUPER PERSEPTUAL BAND EXCEEDING 20 kHz AND PREFERABLY REACHING 200 kHz | HEARING INFORMATION DENSITY (NUMBER OF AERIAL VIBRATIONS PER SECOND) INCLUDES ONLY PERSEPTIBLE BAND EQUAL TO OR HIGHER THAN 20 Hz AND EQUAL TO OR LOWER THAN 20 kHz |
| | COMPLEXITY | IN HEARING INFORMATION HAVING ABOVE-MENTIONED DENSITY, SHAPE OF SPECTRUM SHOWING DENSITY AND POWER STRUCTURE IS TRANSFIGURED IN TIME REGION EQUAL TO OR LONGER THAN MAXIMUM TIME OF 100 msec AND EQUAL TO OR SHORTER THAN MINIMUM TIME OF 0.5 msec | IN HEARING INFORMATION HAVING ABOVE-MENTIONED DENSITY, SHAPE OF SPECTRUM SHOWING DENSITY AND POWER OF HEARING INFORMATION IS STATIONARY IN TIME REGION SHORTER THAN 100 msec |
| VISION | DENSITY | VISUAL STIMULUS DENSITY ((NUMBER OF PIXELS)/(ANGLE OF VISIBILITY)(MIN)) EXCEEDS MINIMUM DIFFERENCE THRESHOLD VISION AND IS PREFERABLY TEN TIMES AS HIGH AS MINIMUM DIFFERENCE THRESHOLD | VISUAL STIMULUS DENSITY ((NUMBER OF PIXELS)/(ANGLE OF VISIBILITY) (MIN)) DOES NOT EXCEED MINIMUM DIFFERENCE THRESHOLD VISION |
| | COMPLEXITY | IN VISUAL STIMULUS HAVING THIS DENSITY, FRACTAL DIMENSION(CAPACITY DIMENSION) OF VISUAL INFORMATION IS SUBSTANTIALLY EQUAL TO OR LARGER THAN 2.2 AND SMALLER THAN ABOUT 3.0 | IN VISUAL STIMULUS HAVING ABOVE-MENTIONED DENSITY OR VISUAL STIMULUS HAVING DENSITY EXCEEDING THIS DENSITY, CAPACITY DIMENSION OF VISUAL INFORMATION IS SUBSTANTIALLY EQUAL TO OR LARGER THAN 2.0 AND SMALLER THAN 2.2 |
| INFORMATION STRUCTURE | | INCLUDES SUPER HIGH DENSITY HIGHLY COMPLEXITY, NON-STEADINESS, AND TRANSFORMABILITY | INCLUDES LOW DENSITY MONOTONY, STEADINESS, AND GEOMETRIC REGULARITY |
| BRAIN REACTION | | HAVE TENDENCY TO ACTIVATE <SENSIBLE BRAIN> (COMPENSATION NERVOUS SYSTEM) CONSISTING OF DEEP PART OF BRAIN, RELEVANT MONOAMINERGIC PROJECTION SYSTEM, AND THE LIKE | HAVE TENDENCY TO DEACTIVATE <SENSIBLE BRAIN> (COMPENSATION NERVOUS SYSTEM) CONSISTING OF DEEP PART OF BRAIN, RELEVANT MONOAMINERGIC PROJECTION SYSTEM, AND THE LIKE |

FOREIGN PATENT DOCUMENTS

| | | |
|---|---|---|
| GB | 2 238 405 | 5/1991 |
| JP | 01-218463 | 8/1989 |
| JP | 03-210274 | 9/1991 |
| JP | 7-22749 | 4/1995 |
| JP | 09-313610 | 12/1997 |
| JP | 3231802 | 9/2001 |
| JP | 2002-182674 | 6/2002 |
| JP | 2003-177744 | 6/2003 |
| JP | 2003-195856 | 7/2003 |
| JP | 2003-223174 | 8/2003 |

OTHER PUBLICATIONS

Alfred Lit, "Visual Acuity", Annual Review of Psychology, pp. 27-54, 1968.

International Search Report issued Jan. 11, 2005 in International (PCT) Application No. PCT/JP2004/013749.

Reiko Yagi et al., "An influence of presentation conditions of hypersonic sounds on the sound reception reaction—research on hyper-real effect (I)", Proceeding of the 2003 Spring Meeting of Acoustical Society of Japan, Special Session of High definition audio technique, vol. 1, No. 3-8-10, pp. 721-722, Waseda University, Tokyo, Japan, Mar. 18, 2003 together with a partial English translation thereof.

Satoshi Nakamura et al., "Examination on indoor sound environment improvement effect using hypersonic effect—Research on hyper-real effect (II)", Proceeding of the 2003 Spring Meeting of Acoustical Society of Japan, Special Session of High definition audio technique, vol. 1, No. 3-8-11, pp. 723-724, Waseda University, Tokyo, Japan, Mar. 18, 2003 together with a partial English translation thereof.

Emi Nishina et al., "Examination on hypersonic effect using physiologically active substances as indicators—research of hyper-real effect (III)—", Proceeding of the 2003 Spring Meeting of Acoustical Society of Japan, Special Session of High definition audio technique, vol. 1, No. 3-8-12, pp. 725-726, Waseda University, Tokyo, Japan, Mar. 18, 2003 together with a partial English translation thereof.

Manabu Honda et al., "Neurophysiological examination on hypersonic effect by a positron emission tomography—research on hyper-real effect (IV)", Proceeding of the 2003 Spring Meeting of Acoustical Society of Japan, Special Session of High definition audio technique, vol. 1, No. 3-8-13, pp. 727-728, Waseda University, Tokyo, Japan, Mar. 18, 2003 together with a partial English translation thereof.

Yuzumi Yamashita, "Series "Five Senses Warn", Part 4: Sense of Hearing, Escape from "Sound Nutrient Deficiency" to Restore "Ancient's Ear"", Yomiuri Weekly, pp. 106-107, May 4-11, 2003, published by Yomiuri Shinbun together with a partial English translation thereof.

Reiko Yagi et al., "Multiparametric Evaluation of the Effects of Intensity of Inaudible High Frequency Sounds in Hypersonic Effects", Transaction of the Virtual Reality Society of Japan, vol. 8, No. 2, pp. 213-220, Jun. 2003 together with a partial English translation thereof.

Reiko Yagi et al., "A method for behavioral evaluation of the hypersonic effect", Acoustical Science and Technology, Acoustical Society of Japan vol. 24, No. 4, pp. 197-200, Jul. 2003.

International Preliminary Examination Report issued Mar. 30, 2006 in PCT/JP2004/013749, including Forms PCT/IB/338, PCT/IB/373, and PCT/ISA/237 (in English).

Canadian Office Action issued Sep. 21, 2007 in CA 2,539,272, which is a foreign counterpart to the present application.

\* cited by examiner

Fig.1

| TYPE OF REGION | | REFERENCE VALUE [dBLAeq] | |
|---|---|---|---|
| | | DAYTIME (6:00~22:00) | NIGHTTIME (22:00~6:00) |
| AA REGION THAT PARTICULARLY REQUIRES QUIETNESS | CONGREGATE REGIONS SUCH AS NURSING FACILITIES AND SOCIAL WELFARE FACILITIES | 50 OR LESS | 40 OR LESS |
| A AND B | RESIDENCE | 55 OR LESS | 45 OR LESS |
| C | REGIONS MAINLY INVOLVED WITH BUSINESS AND INDUSTRIES | 60 OR LESS | 50 OR LESS |
| IN CASE OF REGIONS FRONTING ROAD | | DAYTIME | NIGHTTIME |
| A | FRONTING TWO-LANE ROAD | 60 OR LESS | 55 OR LESS |
| B AND C | B:FRONTING TWO-LANE ROAD C:FRONTING ROAD HAVING LANE | 65 OR LESS | 60 OR LESS |
| SPECIAL CASE | | DAYTIME | NIGHTTIME |
| SPACE ADJACENT TO ROAD FOR PRINCIPAL TRAFFIC | | 70 OR LESS | 65 OR LESS |

Fig.2

| CLASSIFICATION | STATIONARY NOISE | NON-STATIONARY NOISE | | | |
|---|---|---|---|---|---|
| | | FLUCTUATING NOISE | INTERMITTENT NOISE | IMPULSIVE NOISE | |
| | | | | QUASI-STATIONARY NOISE | SEPARATED IMPULSIVE NOISE |
| RELEVANT EXAMPLE | WATERFALL SOUND, ORDINARY ENVIRONMENTAL SOUND | WAVE SOUND | PASSING SOUND OF CARS, TRAINS, AIRPLANES, AND THE LIKE | RIVET AIR HAMMER | DOG BARKING SOUND, DOOR SOUND |

Fig.29

| | ANALOG ←——————→ DIGITAL |
|---|---|
| STRUCTURE OF SUBJECT | CONTINUITY ←——————→ DISCONTINUITY<br>PHYSICAL QUANTITY ←——————→ INFORMATION AMOUNT<br>ENTITY ←——————→ SIGNAL |
| CHARACTER OF SUBJECT | CGS SYSTEM QUANTITY ←——————→ ABSOLUTE NUMBER<br>CONCRETE ←——————→ ABSTRACT<br>IMPLICIT ←——————→ EXPLICIT |
| CHARACTERISTICS OF INFORMATION | CONTINUITY ←——————→ DISCRETENESS<br>PROBABILISTIC CHARACTERISTICS ←——————→ DEFINITENESS<br>NONVERBAL CHARACTERISTICS ←——————→ VERBAL CHARACTERISTICS<br>EXPERIENTIAL CHARACTERISTICS ←——————→ COMMUNICATION CHARACTERISTICS |
| FORM OF INFORMATION PROCESSING | MEASUREMENT ←——————→ COUNTING<br>TOTAL ←——————→ SEQUENTIAL<br>INTUITIVE ←——————→ LOGIC |

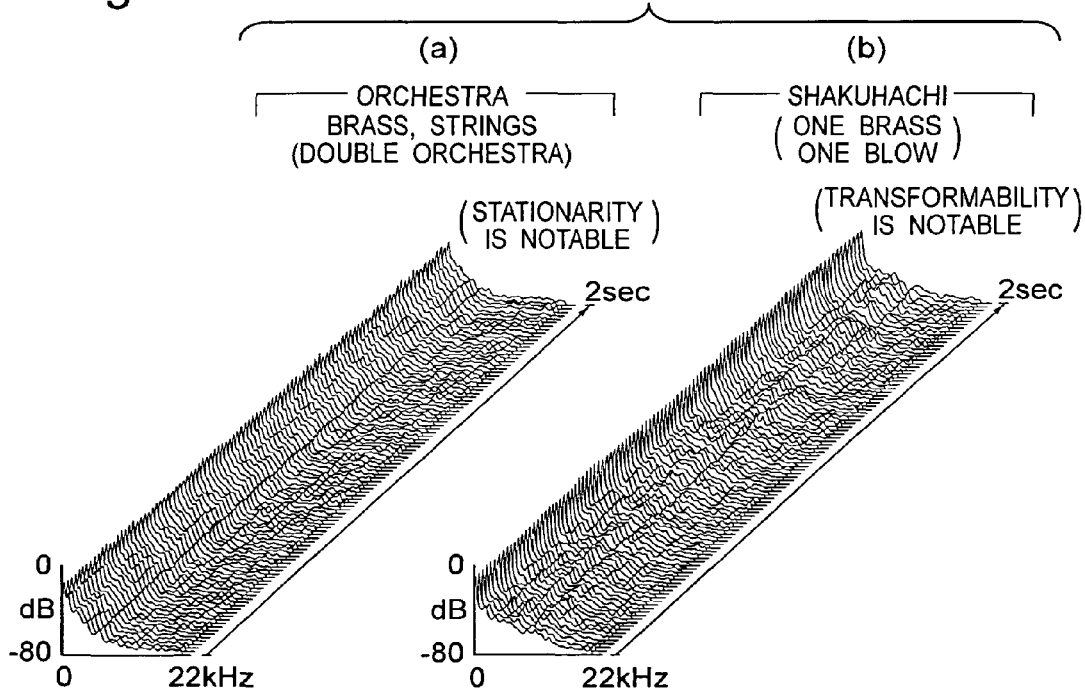

Fig.30

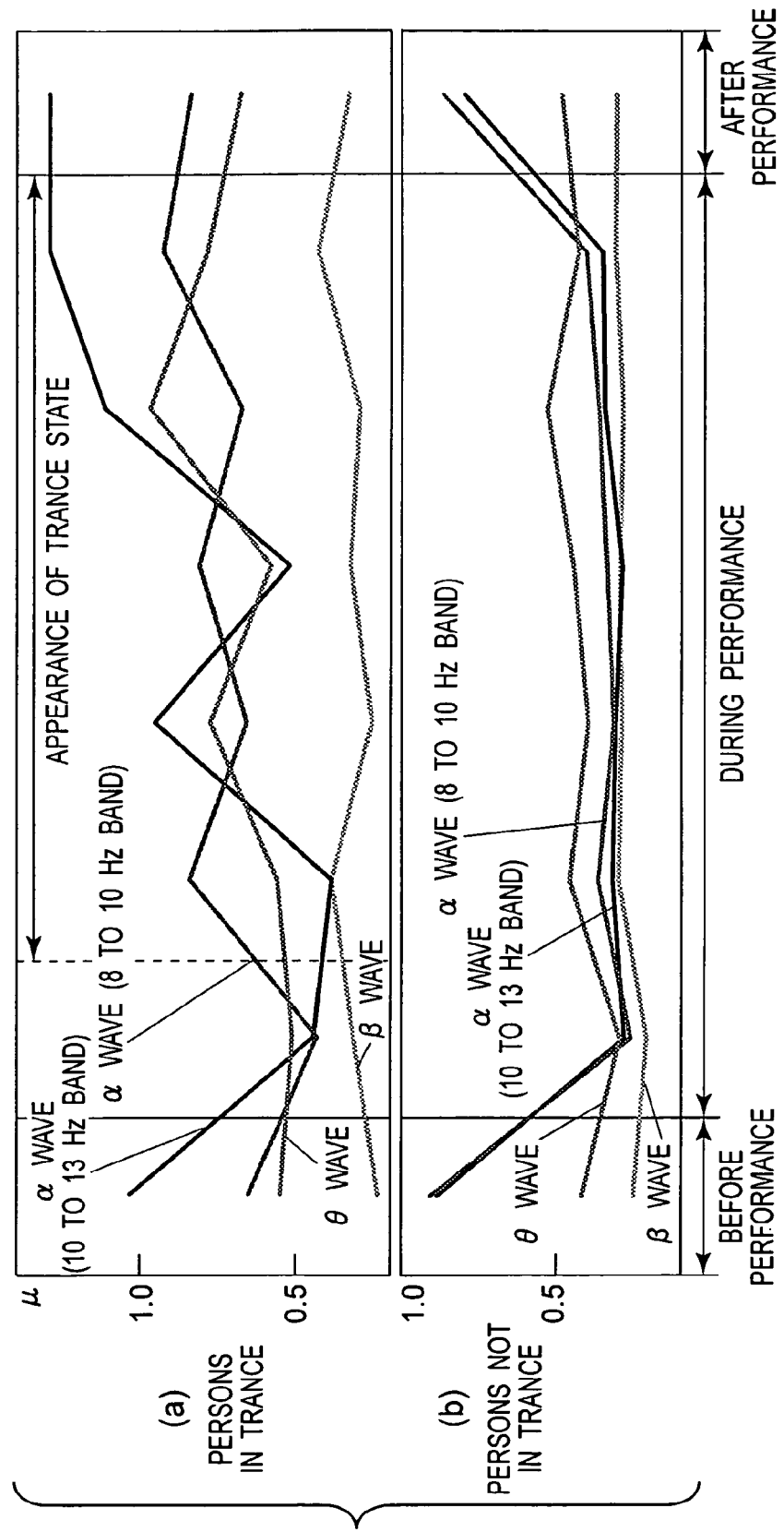

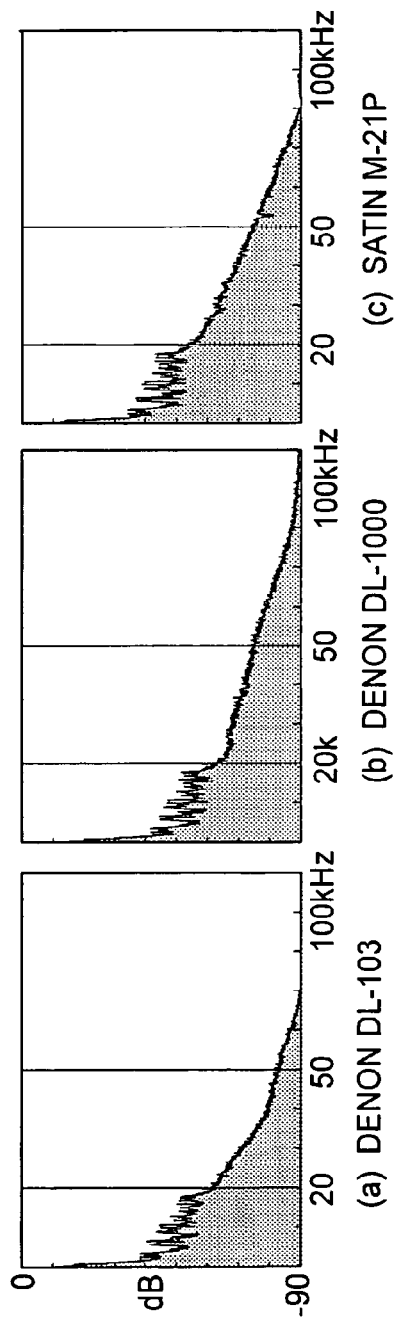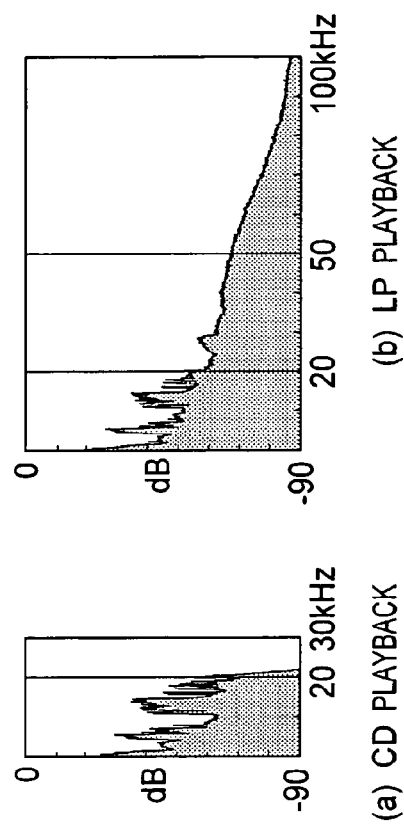

| NAME | CONCEPT | SOUND CONFIGURATION | EFFECT |
|---|---|---|---|
| RELAXATION ENVIRONMENTAL SIMULATOR "KAIMIN STUDIO a" *1 (PLEASANT SLEEP) | TO CREATE STRESS-FREE STATE BY A SYNERGIC EFFECT OF MUSIC HAVING A SOUND STRUCTURE OF TROPICAL FOREST TYPE, VIDEO IMAGE, INDOOR VISUAL ENVIRONMENT, PERFUME AND THE LIKE, AND TO INDUCE USER TO SLEEP PLEASANTLY | HYPERSONIC SOUND AT FREQUENCIES EXCEEDING 50kHz IS RECORDED AND EDITED BY HIGH SPEED SAMPLING AND ONE-BIT QUANTIZATION, AND PLAYED STEREOPHONICALLY IN TWO CHANNELS WITH A VOLUME EQUIVALENT TO THAT OF A TROPICAL RAINFOREST | MANY AND UNSPECIFIED PEOPLE ARE EFFECTIVELY INDUCED TO SLEEP PLEASANTLY. MANY USERS SAID, "HAD GOOD SLEEP" OR "FELT RELAXED". |
| INTERNATIONAL GARDEN AND GREENERY EXPOSITION, OUTDOOR PAVILION, WATER OBJECT "ALEPH" *2 | ENVIRONMENTAL ART FOR SYNCHRONIZING COMPLICATED CONFIGURATION AND GIGANTIC WATER PRODUCTION SYSTEM, ORIGINAL MUSIC AND LIGHTING, AND FOR CONTROLLING THE SYNCHRONIZED ITEMS BY COMPUTER | STRONG ULTRA-HIGH FREQUENCY VIBRATION FILLED WITH FLUCTUATION GENERATED BY A COLUMN OF WATER OR AN ARTIFICIAL WATERFALL ELECTRONIZED ENVIRONMENTAL SOUND OF TROPICAL RAINFOREST, ETHNIC MUSICAL INSTRUMENT SOUND AND THE LIKE ARE PLAYED STEREOPHONICALLY IN SIX CHANNELS | THIS PAVILION ATTRACTED 7.6 MILLION PEOPLE MOST GREATLY AMONG ALL PAVILIONS EXHIBITED IN THE INTERNATIONAL GARDEN AND GREENERY EXPOSITION OSAKA. |
| INTERNATIONAL GARDEN AND GREENERY EXPOSITION FESTIVAL-LIKE LARGE-SCALE OUTDOOR PLAY, LANDSCAPE OPERA GAIA AS MAIN EVENT *3 | SPECTACLE THAT MERGES LIVE PERFORMANCE BY ABOUT 1500 PEOPLE WITH LIGHTING INCLUDING LASER BEAMS AND SPECIAL EFFECTS, SUCH AS FIREWORKS, GUNPOWDER, AND THE LIKE WHILE WHOLLY USING "ALEPH" HARDWARE AND SOFTWARE | ULTRA-HIGH FREQUENCY VIBRATION GENERATED FROM WATER PRODUCTION DEVICE, ELECTRONIZED SOUND PLAYED FROM A 24-CHANNEL MULTI-TRACK SOUND SOURCE, LIVE MUSIC PERFORMANCE, AND SPECIAL EFFECT SOUND SUCH AS POWDER EXPLOSION. | THIS OPERA ATTRACTED PEOPLE MOST GREATLY AMONG ALL SPECIAL EVENTS OF EXPO90. THE FESTIVALIZATION EFFECT OF ENVIRONMENTAL INFORMATION BY HYPERSONIC SOUND IS VERIFIED. |
| HEALING ART "NATURAL MANDALA" IN PRIVATE EXHIBITION OF MADE WIANTA, ARTIST *4 | EXHIBITION THAT MERGES HIGH DENSITY AND COMPLICATED HEALING ENVIRONMENTAL DRAWINGS AND OBJECTS MADE OF AROMATIC NATURAL MATERIAL CREATED BY BALINESE CONTEMPORARY ARTISTS WITH HYPERSONIC SOUND AND COMPUTER-CONTROLLED LIGHTING PRODUCTION | TROPICAL RAINFOREST ENVIRONMENTAL SOUND AND ETHNIC MUSICAL INSTRUMENT SOUND OR THE LIKE HAVING TROPICAL RAINFOREST TYPE SOUND STRUCTURE ARE RECORDED AND EDITED IN SUPER-BROADBAND MULTI-CHANNELS BY HIGH SPEED SAMPLING AND ONE-BIT QUANTIZATION AND REPRODUCED STEREOPHONICALLY IN SUPER-BROADBAND TWO CHANNELS. | THIS ART DEEPLY ATTRACTED ART APPRECIATORS. STAY TIME OF THE PAVILION REACHED ABOUT THREE TIMES AS LONG AS THAT OF AN ORDINARY PAVILION. |
| HIGH DEFINITION MULTIMEDIA ART "WIANTA HEALING" *5 | TO ENHANCE BRAIN FUNCTION BY PROVIDING HIGH DEFINITION IMAGES OF WORKS OF ART OF NATURAL MANDALA IN HARMONY WITH HYPERSONIC SOUND FOR EXHIBITION | DITTO, PROVIDED AS HSACD AS SOFTWARE OF "HYPERSONIC AUDIO SYSTEM" *8 | GREAT EFFECT OF GETTING RID OF STRESS, ZERO STATE OF ACTIVITY OF a WAVE OF BRAIN WAVE REACHED TO HIGHEST LEVEL IN FIVE MINUTES. EFFECT ON ENDOGENOUS PSYCHOSOMATIC DISORDER AND DEVELOPMENT DISORDER IS EXPECTED. |
| HYPERSONIC SOUND SPACE "MEDIAGE ATRIUM SOUND ENVIRONMENTAL SYSTEM" *6 | TO SPREAD HYPERSONIC SOUND THROUGHOUT SPACES AT ALL AZIMUTHS BY CAUSING 116 SUPER-BROADBAND LOUDSPEAKER SYSTEMS TO INDIVIDUALLY MIXING SIGNALS | SIX-CHANNEL STEREOPHONIC SOUND FIELD GENERATED BY CONFIGURING AND EDITING A PLURALITY OF SOUND SOURCES OBTAINED BY SAMPLING AND ONE-BIT QUANTIZATION SUPER-BROADBAND RECORDING AT 3.072 MHz. | THIS SYSTEM ATTRACTED UNCONSCIOUS ATTENDANTS. THE NUMBER OF ATTENDANTS IS OVER TEN MILLION A YEAR EXCEEDS INTENDED NUMBER OF SIX MILLION BY FOUR MILLION. |
| HYPERSONIC MUSIC BOX *7 | TO CREATE AND SUPPLY DIRECT HYPERSONIC SOUND WITHOUT ACCOMPANIMENT OF CONVERSION TO ELECTRONIC SIGNALS USING SOUND OF ACTUAL MACCHINES AS SOUND SOURCE | A NEW SOUND PRODUCING MECHANISM GREATLY DIFFERENT FROM A CLASSICAL MECHANISM IS DEVELOPED AND SOUND AND VIBRATION MAINLY CONTAINING NATURAL ULTRA-HIGH FREQUENCY COMPONENTS ABUNDANT WITH FLUCTUATION ARE CONFIGURED | GENERATION OF HYPERSONIC SOUND ABUNDANT WITH FLUCTUATION AT FREQUENCY HIGHER THAN 120 kHz IN ATTRACTIVE HIGHLY COMPLICATED TONES IS REALIZED. |

*1 OWNER: LOFTY CO., LTD.; TOTAL DESIGNER: TSUTOMU OHASHI; ULTRA-BROADBAND DIGITAL RECORDER DESIGNER: YOSHIO YAMAZAKI; SOUND DESIGNER: MASAMI TOYOSHIMA; WALL DESIGNER USING 1/F FLUCTUATION: "OSHIMITSU MUSHA"; PERFUME DESIGNER: SHIZUO TORII; MUSIC PERFORMER: SHOJI YAMASHIRO AND TOSHIFUMI MORI; PLANNING AND PRODUCTION: ACTION-RESEARCH CO.; PERIOD: FIRST TERM: OCTOBER 31, 1989 TO MARCH 12, 1993; SECOND TERM: MARCH 12, 1993 TO PRESENT

*2 EXHIBITOR: KUBOTA CORPORATION AND SAISON GROUP JOINT INTERNATIONAL GARDEN AND GREENERY EXPOSITION OSAKA EXHIBITION COMMITTEE; TOTAL DESIGNER: WATER PRODUCTION SYSTEM DESIGNER AND PROGRAMMER: TSUTOMU OHASHI; COMPOSER: SHOJI YAMASHIRO; PERFORMER: YAMASHIRO-GUMI; SOUND PRODUCER: KIICH SUZUKI; LIGHTING PRODUCER: TAMON YAMAGATA; ARTS EDITOR: SETSU ASAKURA; PRODUCTION: DENTSU INC. AND ACTION-RESEARCH CO.; PERIOD: APRIL 1 TO SEPTEMBER 30, 1990

*3 SPONSOR: LANDSCAPE OPERA "GAIA" STEERING COMMITTEE; THE ASAHI SHIMBUN COMPANY ET AL.; PERIOD: MAY 19 TO 20, 1990 DIRECTOR: SHOJI YAMASHIRO; PRODUCTION: DENTSU INC., ACTION-RESEARCH CO. ET AL.; PERIOD: MAY 19 TO 20, 1990

*4 SPONSOR: EAST JAPAN RAILWAY CULTURE FOUNDATION (EJRCF) AND THE YOMIURI SHIMBUN; TOTAL DESIGNER AND PRODUCER: TSUTOMU OHASHI; LIGHTING PRODUCER: TAMON YAMAGATA; MUSIC PRODUCER: SHOJI YAMASHIRO; PERFORMER: YAMASHIRO-GUMI ET AL.; PERIOD: OCTOBER 10 TO NOVEMBER 29, 1999

*5 SPONSOR: ADVANCED TELECOMMUNICATIONS RESEARCH INSTITUTE INTERNATIONAL, HUMAN INFORMATION SCIENCE LABORATORIES (ATR-HIS); TOTAL DESIGN AND VISUAL PRODUCTION: TSUTOMU OHASHI; MUSIC: SHOJI YAMASHIRO; PERIOD: NOVEMBER 4 TO 6, 1999

*6 OWNER: SONY URBAN ENTERTAINMENT INC.; TOTAL DESIGN: TSUTOMU OHASHI; ADMINISTRATION AND DESIGN: MASAMI TOYOSHIMA; MUSIC: SHOJI YAMASHIRO; ACOUSTIC DESIGNER: TOMOYUKI OSAWA; SUPPORTED BY HIBINO CORPORATION; ACTION-RESEARCH CO.; PERIOD: APRIL 21, 2000 TO MARCH 31, 2002

*7 DEVELOPMENT: NEW GENERATION MUSIC BOX DEVELOPMENT PROJECT; GENERAL ARCHITECT: TSUTOMU OHASHI; MECHANICAL DESIGNER: AKIHIKO ISAKA; ACOUSTIC DESIGNER: NOBORU UENO AND KATSUNORI MIYAMOTO; VISUAL DESIGNER: TOMOKI HORIUCHI; PRODUCTION: ACTION-RESEARCH CO., LTD.; PROTOTYPE COMPLETED ON OCTOBER 2003

*8 HYPERSONIC SOUND DEDICATED REPRODUCTION SYSTEM W; MANUFACTURER: ACTION-RESEARCH CO., SINCE JUNE 2001

Fig. 59

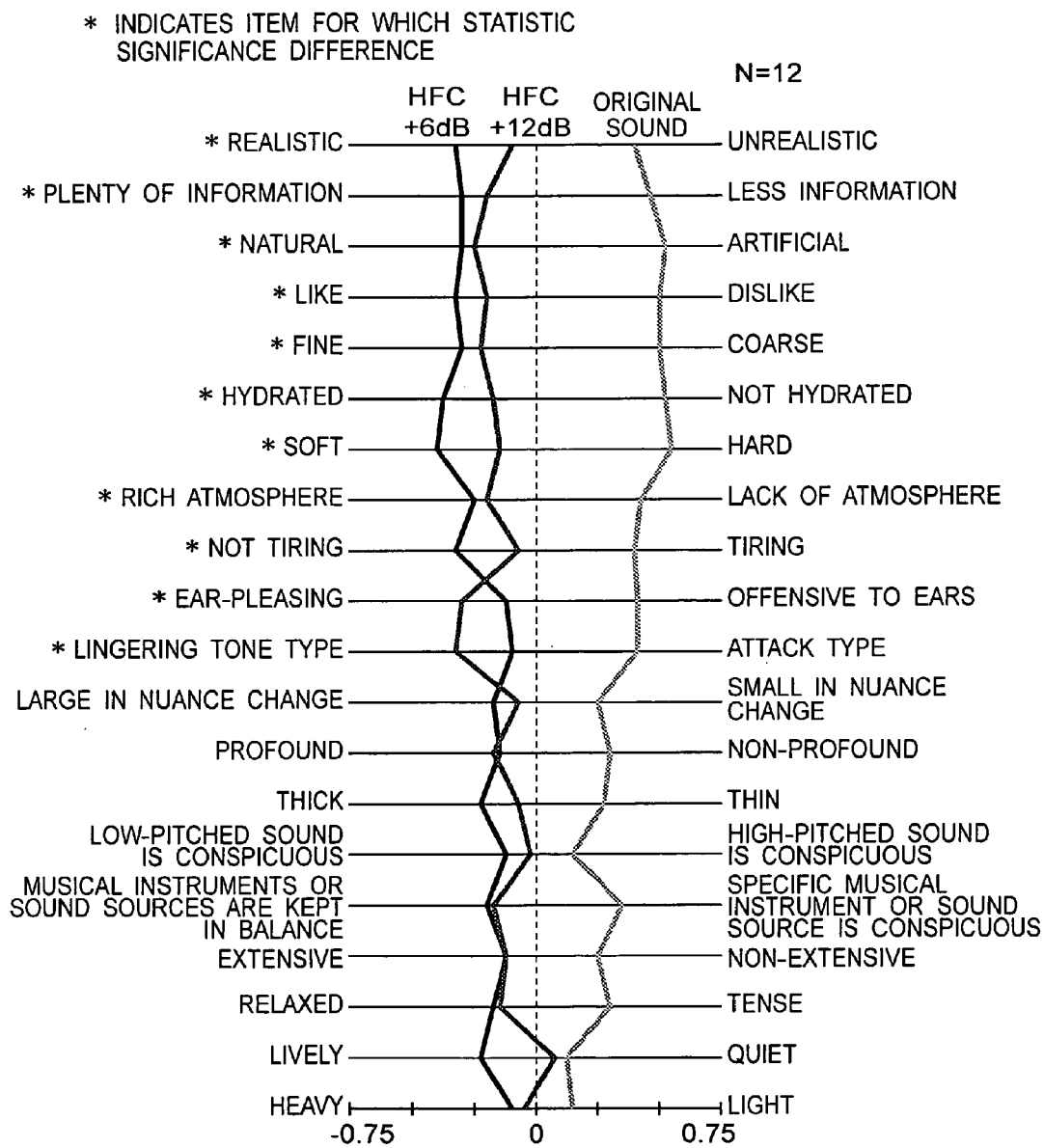

| | 6dB-ORIGINAL SOUND | 12dB-ORIGINAL SOUND | 6dB-12dB |
|---|---|---|---|
| REALISTIC VS UNREALISTIC | P<0.01 | n.s. | n.s. |
| PLENTY OF INFORMATION VS LESS INFORMATION | P<0.01 | P<0.01 | n.s. |
| NATURAL VS ARTIFICIAL | P<0.01 | P<0.01 | n.s. |
| LIKE VS DISLIKE | P<0.01 | P<0.05 | n.s. |
| FINE VS COARSE | P<0.01 | P<0.01 | n.s. |
| HYDRATED VS NOT HYDRATED | P<0.01 | P<0.05 | n.s. |
| SOFT VS HARD | P<0.01 | P<0.05 | n.s. |
| RICH ATMOSPHERE VS LACK OF ATMOSPHERE | P<0.05 | n.s. | n.s. |
| NOT TIRING VS TIRING | P<0.05 | P<0.05 | n.s. |
| EAR-PLEASING VS OFFENSIVE TO EARS | n.s. | P<0.05 | n.s. |
| LINGERING TONE TYPE VS ATTACK TYPE | n.s. | P<0.05 | n.s. |
| LARGE IN NUANCE CHANGE VS SMALL IN NUANCE CHANGE | n.s. | n.s. | n.s. |
| PROFOUND VS NON-PROFOUND | n.s. | n.s. | n.s. |
| THICK VS THIN | n.s. | n.s. | n.s. |
| LOW-PITCHED SOUND VS HIGH-PITCHED SOUND IS CONSPICUOUS VS IS CONSPICUOUS | n.s. | n.s. | n.s. |
| MUSICAL INSTRUMENTS OR SOUND VS SPECIFIC MUSICAL INSTRUMENT OR SOURCES ARE KEPT IN BALANCE VS SOUND SOURCE IS CONSPICUOUS | n.s. | n.s. | n.s. |
| EXTENSIVE VS NON-EXTENSIVE | n.s. | n.s. | n.s. |
| RELAXED VS TENSE | n.s. | n.s. | n.s. |
| LIVELY VS QUIET | n.s. | n.s. | n.s. |
| HEAVY VS LIGHT | n.s. | n.s. | n.s. |

Fig. 89

|  | INDICATOR | FRS | HCS | p-VALUE |
|---|---|---|---|---|
| CELLULAR IMMUNITY | CD4 | 0.993 | 1.007 | 0.3500 |
| | CD8 | 0.995 | 1.005 | 0.5218 |
| | CD4/CD8 | 0.999 | 1.001 | 0.9513 |
| | NK CELL ACTIVITY | 1.095 | 0.905 | 0.0439* |
| ENDOCRINE SYSTEM | CORTISOL | 1.019 | 0.981 | 0.7068 |
| | ADRENALINE | 1.038 | 0.962 | 0.2798 |
| | NORADRENALINE | 0.998 | 1.002 | 0.9505 |
| | DOPAMINE | 0.993 | 1.007 | 0.8353 |
| | β ENDORPHIN | 1.011 | 0.989 | 0.7642 |
| | PROLACTIN | 1.029 | 0.971 | 0.6462 |

\* MARK : SIGNIFICANT DIFFERENCE
PRESENT AT SIGNIFICANT LEVEL OF 5%

Fig. 90

| COMPARISON | CEREBRAL BLOOD FLOW INCREASED REGION | CEREBRAL BLOOD FLOW DECREASED REGION |
|---|---|---|
| FRS+HCS VS. BASELINE | PRIMARY AUDITORY CORTEX | (VISUAL ASSOSIATION CORTEX) |
| LCS VS. BASELINE | NONE | NONE |
| FRS VS. BASELINE | PRIMARY AUDITORY CORTEX (THALAMUS, UPPER BRAINSTEM) | (VISUAL ASSOSIATION CORTEX) |
| HCS VS. BASELINE | PRIMARY AUDITORY CORTEX | (VISUAL ASSOSIATION CORTEX) (UPPER BRAINSTEM, PRECUNEUS) |
| FRS VS. HCS | THALAMUS, UPPER BRAINSTEM | (SUPPLEMENTARY MOTOR AREA) |

(NOTE) PARENTHESIZED PART INDICATES TENDENCY

Fig.94

| COMPARISON | CEREBRAL BLOOD FLOW INCREASED REGION | CEREBRAL BLOOD FLOW DECREASED REGION |
|---|---|---|
| FRS+HCS VS. BASELINE | PRIMARY AUDITORY CORTEX | VISUAL ASSOSIATION CORTEX |
| LCS VS. BASELINE | NONE | NONE |
| FRS VS. BASELINE | PRIMARY AUDITORY CORTEX THALAMUS, UPPER BRAINSTEM | VISUAL ASSOSIATION CORTEX |
| HCS VS. BASELINE | PRIMARY AUDITORY CORTEX | VISUAL ASSOSIATION CORTEX UPPER BRAINSTEM PRECUNEUS |
| FRS VS. HCS | THALAMUS, UPPER BRAINSTEM | SUPPLEMENTARY MOTOR AREA |

Fig. 96
| | INDICATOR | FRS | HCS | p-VALUE |
|---|---|---|---|---|
| CELLULAR IMMUNITY | CD4 | 0.993 | 1.007 | 0.3500 |
| | CD8 | 0.995 | 1.005 | 0.5218 |
| | CD4/CD8 | 0.999 | 1.001 | 0.9513 |
| | NK CELL ACTIVITY | 1.095 | 0.905 | 0.0439* |
| ENDOCRINE SYSTEM INDICATOR | CORTISOL | 1.019 | 0.981 | 0.7068 |
| | ADRENALINE | 1.038 | 0.962 | 0.2798 |
| | NORADRENALINE | 0.998 | 1.002 | 0.9505 |
| | DOPAMINE | 0.993 | 1.007 | 0.8353 |
| | β ENDORPHIN | 1.011 | 0.989 | 0.7642 |
| | PROLACTIN | 1.029 | 0.971 | 0.6462 |
(NOTE) NORMALIZED VALUE FOR A PLURALITY OF MATTERS *P<0.05
Fig. 97
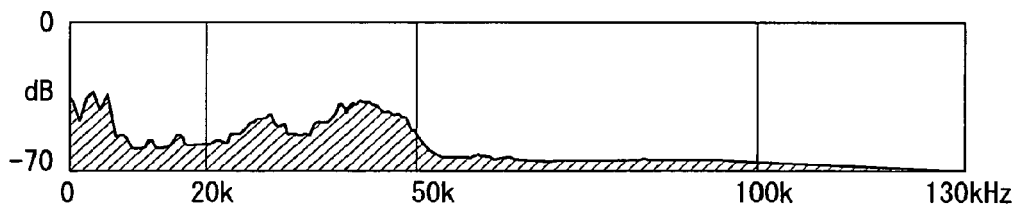
Fig. 98
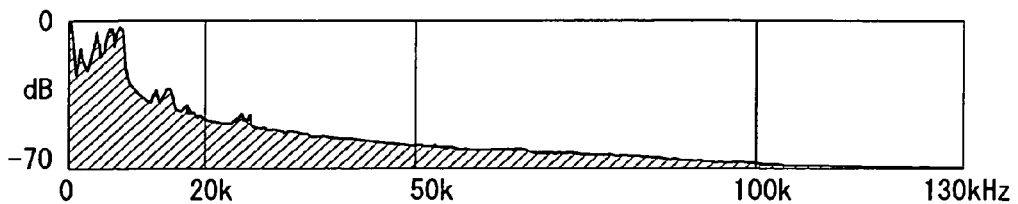

Fig.106

| DEFINITION | | SUPER PERSEPTUAL INFORMATION | PERSEPTUAL SPECIFIC INFORMATION |
|---|---|---|---|
| | | SENSORY INFORMATION CONSTITUTED BY PERSEPTIBLE INFORMATION AND INFORMATION (PREFERABLY REMARKABLY) EXCEEDING PERSEPTIBLE LIMIT | SENSORY INFORMATION CONSTITUTED ONLY BY INFORMATION WITHIN PERSEPTIBLE LIMIT |
| HEARING | DENSITY | HEARING INFORMATION DENSITY (NUMBER OF AERIAL VIBRATIONS PER SECOND) INCLUDES BOTH PERSEPTIBLE BAND EQUAL TO OR HIGHER THAN 20 Hz AND EQUAL TO OR LOWER THAN 20 kHz AND SUPER PERSEPTUAL BAND EXCEEDING 20 kHz AND PREFERABLY REACHING 200 kHz | HEARING INFORMATION DENSITY (NUMBER OF AERIAL VIBRATIONS PER SECOND) INCLUDES ONLY PERSEPTIBLE BAND EQUAL TO OR HIGHER THAN 20 Hz AND EQUAL TO OR LOWER THAN 20 kHz |
| | COMPLEXITY | IN HEARING INFORMATION HAVING ABOVE-MENTIONED DENSITY, SHAPE OF SPECTRUM SHOWING DENSITY AND POWER STRUCTURE IS TRANSFIGURED IN TIME REGION EQUAL TO OR LONGER THAN MAXIMUM TIME OF 100 msec AND EQUAL TO OR SHORTER THAN MINIMUM TIME OF 0.5 msec | IN HEARING INFORMATION HAVING ABOVE-MENTIONED DENSITY, SHAPE OF SPECTRUM SHOWING DENSITY AND POWER OF HEARING INFORMATION IS STATIONARY IN TIME REGION SHORTER THAN 100 msec |
| VISION | DENSITY | VISUAL STIMULUS DENSITY ((NUMBER OF PIXELS) /(ANGLE OF VISIBILITY)(MIN)) EXCEEDS MINIMUM DIFFERENCE THRESHOLD VISION AND IS PREFERABLY TEN TIMES AS HIGH AS MINIMUM DIFFERENCE THRESHOLD | VISUAL STIMULUS DENSITY ((NUMBER OF PIXELS) /(ANGLE OF VISIBILITY) (MIN)) DOES NOT EXCEED MINIMUM DIFFERENCE THRESHOLD VISION |
| | COMPLEXITY | IN VISUAL STIMULUS HAVING THIS DENSITY, FRACTAL DIMENSION(CAPACITY DIMENSION) OF VISUAL INFORMATION IS SUBSTANTIALLY EQUAL TO OR LARGER THAN 2.2 AND SMALLER THAN ABOUT 3.0 | IN VISUAL STIMULUS HAVING ABOVE-MENTIONED DENSITY OR VISUAL STIMULUS HAVING DENSITY EXCEEDING THIS DENSITY, CAPACITY DIMENSION OF VISUAL INFORMATION IS SUBSTANTIALLY EQUAL TO OR LARGER THAN 2.0 AND SMALLER THAN 2.2 |
| INFORMATION STRUCTURE | | INCLUDES SUPER HIGH DENSITY HIGHLY COMPLEXITY, NON-STEADINESS, AND TRANSFORMABILITY | INCLUDES LOW DENSITY MONOTONY, STEADINESS, AND GEOMETRIC REGULARITY |
| BRAIN REACTION | | HAVE TENDENCY TO ACTIVATE <SENSIBLE BRAIN> (COMPENSATION NERVOUS SYSTEM) CONSISTING OF DEEP PART OF BRAIN, RELEVANT MONOAMINERGIC PROJECTION SYSTEM, AND THE LIKE | HAVE TENDENCY TO DEACTIVATE <SENSIBLE BRAIN> (COMPENSATION NERVOUS SYSTEM) CONSISTING OF DEEP PART OF BRAIN, RELEVANT MONOAMINERGIC PROJECTION SYSTEM, AND THE LIKE |

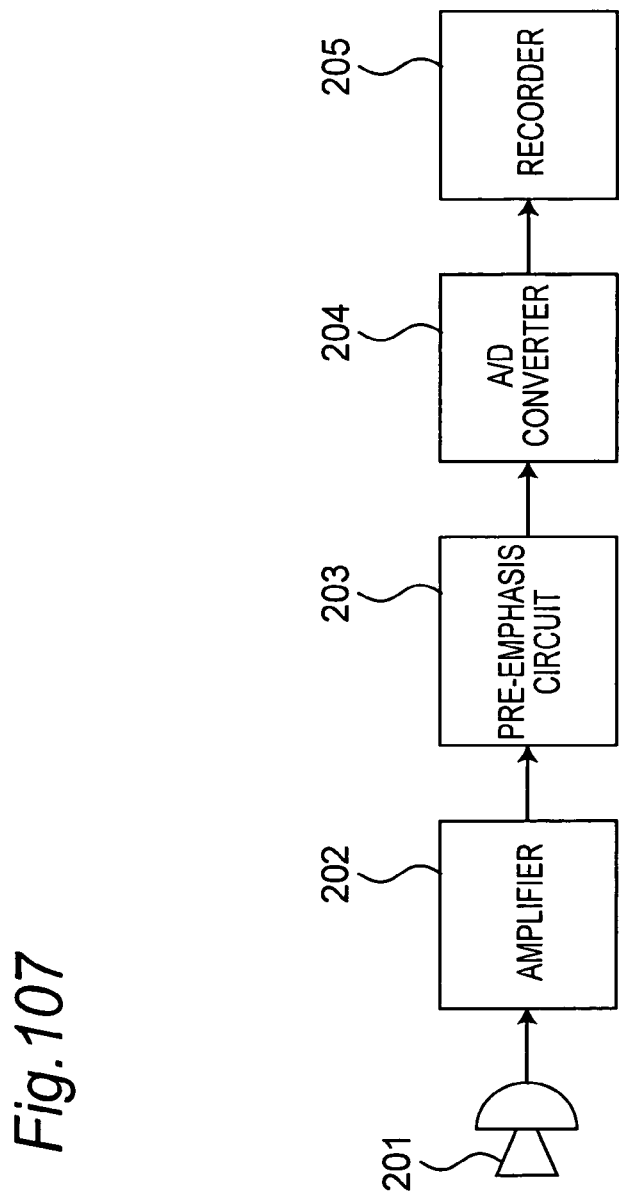

METHOD AND APPARATUS FOR ENVIRONMENTAL SETTING AND INFORMATION FOR ENVIRONMENTAL SETTING

This application is a divisional application of Ser. No. 10/572,484, filed Dec. 13, 2006 now abandoned which is a U.S. national stage application of International Application Serial No. PCT/JP2004/013749, filed Sep. 21, 2004.

BACKGROUND OF THE INVENTION

1. Technical Field

The present invention relates to a method for environmental setting, an apparatus for environmental setting, and information for environmental setting for urban regeneration in order to realize an environment comfortable for human beings.

2. Background Art

Conventionally, there have been proposed, in Patent Documents 3 and 4, "a sound generating method and a sound generating apparatus characterized by generating a non-stationary sound having a frequency in a first frequency range up to a predetermined highest frequency exceeding an audible frequency range and changing in a micro time area in a second frequency range exceeding 10 kHz, applying a sound in the audible frequency range among these sounds to a person's audible sense and applying a sound in a frequency range exceeding the audible frequency range to a person, and thus increasing a cerebral blood flow of the person". This can produce an ultrasonic effect, ease the person's tension, and relax the person. Therefore, this can advantageously exhibit getting rid of stress, improving the comfort of the mind of the person, and keeping the body of the person healthy.

Patent Document 1: Japanese Patent Laid-Open Publication No. 3-210274;
Patent Document 2: Japanese Utility Model Laid-Open Publication No. 7-022749;
Patent Document 3: Japanese Patent Laid-Open Publication No. 9-313610;
Patent Document 4: Japanese Patent Laid-Open Publication No. 2003-223174;
Patent Document 5: Japanese Patent Laid-Open Publication No. 2003-177744; and
Patent Document 6: Japanese Patent Laid-Open Publication No. 2003-195856.

BRIEF SUMMARY OF THE INVENTION

However, the prior art has the following problems. Only by generating the sounds proposed in the Patent Documents 3 and 4, an environment comfortable for human beings is not always realized, and they do not provide any fundamental solution means.

It is an object of the present invention to provide a method for environmental setting, an apparatus for environmental setting, and information for environmental setting, capable of solving the above-mentioned problems and realizing spaces that include an urban space, a residential space, and a living space as more comfortable environments for human beings.

According to a first aspect of the present invention, there is provided a method for environmental setting including a step of arranging means for setting a tropical rain forest type environment based on characteristics of an activating human being's essential brain region in response to tropical rain forest type environment information, in a predetermined space including at least one of an urban space, a housing space and a living space, to set the space substantially in the tropical rain forest type environment. This leads to activation of the human being's essential brain region to realize an environment suitable for the human being's brain.

In the above-mentioned method for environmental setting, the tropical rain forest type environmental information has higher density and higher complexity than that of an urban space type environmental information. In this case, the tropical rain forest type environment information includes at least one of auditory information, visual information and super perceptual information of aerial vibration. In addition, the tropical rain forest type environmental information is super perceptual information which is sensory information consisting of perceptible information and information exceeding a perceptual limit. In this case, the means for setting plays back the tropical rain forest type environmental information using at least one of an apparatus for representing visual information and a plurality of loudspeakers arranged by a matrix configuration method. In addition, an environment suitable for the human being's brain is an environment, which is comfortable for human beings, and which has no excessive stress. Further, the tropical rain forest type environmental information is environmental information for effecting prevention and treatment of diseases due to stress by realizing an environment suitable for the human being's brain.

According to a second aspect of the present invention, there is provided an apparatus for environmental setting including means for arranging means for setting a tropical rain forest type environment based on characteristics of activating human being's essential brain region in response to tropical rain forest type environment information, in a predetermined space including at least one of an urban space, a housing space and a living space, to set the space substantially in the tropical rain forest type environment. This leads to activation of the human being's essential brain region to realize an environment suitable for the human being's brain.

In the above-mentioned apparatus for environmental setting, the tropical rain forest type environmental information has a higher density and a higher complexity than those of urban space type environmental information. In this case, the tropical rain forest type environment information includes at least one of auditory information, visual information and super perceptual information of aerial vibration. In addition, the tropical rain forest type environmental information is super perceptual information which is sensory information consisting of perceptible information and information exceeding a perceptual limit. In this case, the means for setting plays back the tropical rain forest type environmental information using at least one of a plurality of loudspeakers arranged by a matrix configuration method, and an apparatus for representing visual information. In addition, the environment suitable for the human being's brain is an environment, which is comfortable for human beings, and which has no excessive stress. Further, the tropical rain forest type environmental information is environmental information for effecting prevention and treatment of diseases due to stress by realizing the environment suitable for the human being's brain.

According to a third aspect of the present invention, there is provided information for environmental setting including a step of arranging means for setting a tropical rain forest type environment based on characteristics of activating a human being's essential brain region in response to tropical rain forest type environment information, in a predetermined space including at least one of an urban space, a housing space and a living space, to set the space substantially in the tropical rain forest type environment. This leads to activation of the human being's essential brain region to realize an environment suitable for the human being's brain.

In the above-mentioned information for environmental setting, the tropical rain forest type environmental information has higher density and higher complexity than those of urban space type environmental information. In this case, the tropical rain forest type environment information includes at least one of auditory information, visual information and super perceptual information of aerial vibration. In addition, the tropical rain forest type environmental information is super perceptual information which is sensory information consisting of perceptible information and information exceeding a perceptual limit. In this case, the means for setting plays back the tropical rain forest type environmental information using at least one of a plurality of loudspeakers arranged by a matrix configuration method, and an apparatus for representing visual information. In addition, the environment suitable for the human being's brain is an environment, which is comfortable for human beings, and which has no excessive stress. Further, the tropical rain forest type environmental information is environmental information for effecting prevention and treatment of diseases due to stress by realizing the environment suitable for the human being's brain.

Therefore, according to the present invention, the means for setting a tropical rain forest type environment based on the activation characteristic of the human essential brain region for tropical rain forest type environment information is arranged in a predetermined space including at least one of an urban space, a living space, and a life space. This leads to setting of the space in the tropical rain forest type environment substantially and to activation of the human essential brain region to implement an environment suitable, comfortable or gentle for a human's brain. Accordingly, as compared with the prior art, the space can be realized into a more comfortable environment for people. Consequently, it is possible to remarkably eliminate a human stress and to further enhance a mental comfort in the space. This leads to maintaining of physical health to be excellent. Since the tropical rain forest type environment information implements an environment which is suitable, comfortable or gentle for the human's brain. Moreover, it serves to effect the prevention and treatment of diseases such as present-day diseases caused by the stress. Consequently, it is possible to carry out the prevention and treatment of diseases such as the present-day diseases.

BRIEF DESCRIPTION OF THE DRAWINGS

FIG. 1 is a table showing environmental sound restriction standard of Japan according to environmental standards regarding noise based on Article 16, paragraph 1 of Basic Environmental Law.

FIG. 2 is a table showing sound classification widely used thus far according to ISO2204-1979 (Acoustics) and ANSI-SI13.

FIG. 29 is a table showing an analog/digital spectrum.

FIG. 30(a) is a view showing a contrast of a sound spectrum appearing in a micro time structure of a first portion of a tune of "November Steps No. 1" by Tohru Takemitsu, illustrating an ME spectral array of an orchestra in Western Europe and FIG. 30(b) is a view showing an ME spectral array of Shakuhachi in the first portion of the tune of FIG. 30(a).

FIG. 45(a) is a graph showing a change in electroencephalogram power of any of the performers of FIG. 43 who is transformed and FIG. 45(b) is a graph showing a change in electroencephalogram power of any of the performers of FIG. 43 who is not transformed.

FIG. 46(a) is a spectral chart showing a high activity of media to be an LP, which is based on DENON_DL-103 illustrating that a cartridge changes a sound spectrum in relation to an averaged value spectrum for 84 seconds in all tunes from "Sanka" to "Shinkyou Darani" in the second movement of the "Rinne Symphony" by the Yamashiro-Gumi, FIG. 46(b) is a spectral chart based on DENON_DL-1000 in relation to the averaged value spectrum of FIG. 46(a), and FIG. 46(c) is a spectral chart based on SATIN_M-21P in relation to the averaged value spectrum of FIG. 46(a).

FIG. 47(a) is a chart showing a high activity of the media to be the LP, illustrating a CD playback indicative of recording and reproducing capabilities which exceed 100 kHz of the LP in relation to a partial spectrum from "Sanka" to "Kongoh Meiju" in the second movement of the "Rinne Symphony" by the Yamashiro-Gumi, and FIG. 47(b) is a spectral chart in an LP playback in relation to the spectrum of FIG. 47(a).

FIG. 59 is a table showing various spreads of the sound environment design which is suitable or comfortable for a brain.

FIG. 77 is a chart showing a result (1) of the psychological evaluation experiment according to the implemental example 2.

FIG. 78 is a table showing a result (2) of the psychological evaluation experiment according to the implemental example 2, that is, a list of results of a statistical test for each evaluation scale.

FIG. 89 is a table showing an averaged value of an in-blood physiological active indicator measured value (a normalized value in an examinee) according to an implemental example 5.

FIG. 90 is a table showing a cerebral blood flow changing portion on each condition according to an implemental example 6.

FIG. 94 is a table showing an area indicative of a significant change in CBF according to an implemental example 7.

FIG. 96 is a table showing an averaged value of a biological active matter according to the implemental example 7.

FIG. 97 is a chart showing an FFT spectrum of a tropical rain forest environmental sound in Borneo Island, the Republic of Malaysia which is measured by the inventors according to an implemental example 8.

FIG. 98 is a chart showing an FFT spectrum of a tropical rain forest environmental sound in Java Island, the Republic of Indonesia which is measured by the inventors according to the implemental example 8.

FIG. 106 is a table showing a difference between super perceptual information and perceptual specific information according to the present invention.

FIG. 107 is a block diagram showing an example of a system for recording super perceptual auditory information according to an implemental example 9.

FIG. 120 is a plan view showing an arrangement of a loudspeaker by taking note of the juxtaposition of a left loudspeaker and a right loudspeaker in the system of FIG. 119.

FIG. 121 is a perspective view showing an arrangement of a loudspeaker in a double helical matrix according to the implemental example 11.

FIG. 122 is a perspective view showing an arrangement of a loudspeaker in which two upper and central loudspeakers UC are provided in the arrangement of the loudspeaker in the double helical matrix of FIG. 121.

FIG. 123 is a block diagram showing an electrical circuit in which a plurality of loudspeakers is to be driven by using the double helical matrix coordination method according to the implemental example 11.

FIG. 124 is a perspective view showing a matrix unit to be a basic arrangement of a loudspeaker using the double helical coordination method according to the implemental example 11.

FIG. 125 is a block diagram showing structures of loudspeakers 241 to 265 having an amplifier of FIG. 123.

FIG. 126 is a plan view showing an arrangement of a loudspeaker in an office space 280 according to a first application example using the double helical matrix coordination method according to the implemental example 11.

FIG. 127 is a plan view showing an arrangement of a loudspeaker in a certain shopping street according to a second application example using the double helical matrix coordination method according to the implemental example 11.

FIG. 128 is a block diagram showing a structure of a system presenting a high density fractal stimulation reaching a super perceptual region according to an implemental example 12.

FIG. 129 is a front view showing a Landolt ring indicator used in a definition according to the implemental example 12.

FIG. 130 is a graph showing a change in a physiological active matter by the addition of a sound in a forest which is measured by the inventors according to an implemental example 13.

FIG. 131 is a graph showing an activation of the a wave the electroencephalogram by the addition of the sound in the forest which is measured by the inventors according to the implemental example 13.

Figure 132:
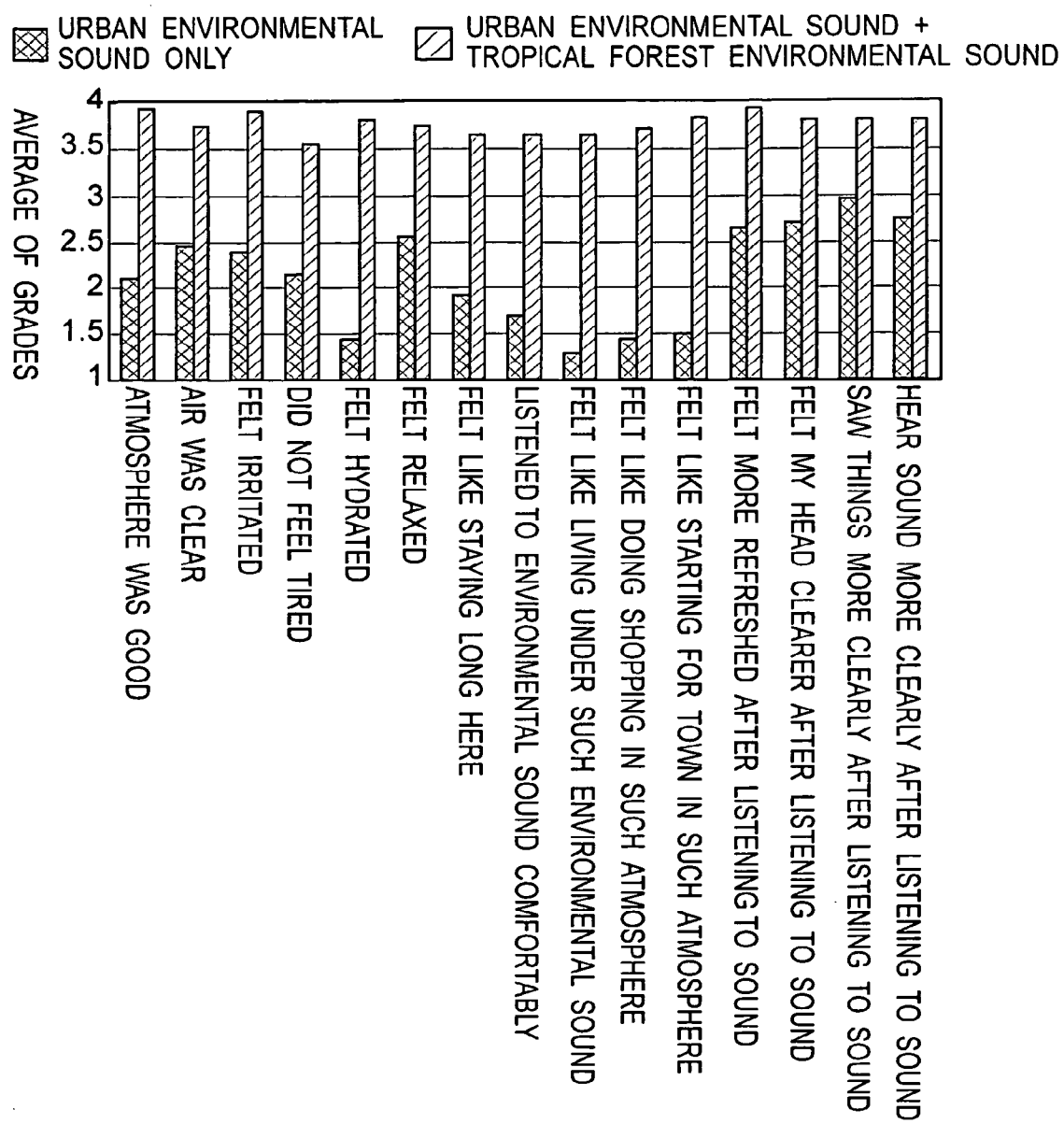

FIG. 132 is a graph showing an improvement in an impression on a sound environment by the addition of the sound in the forest which is measured by the inventors according to the implemental example 13.

Figure 133:
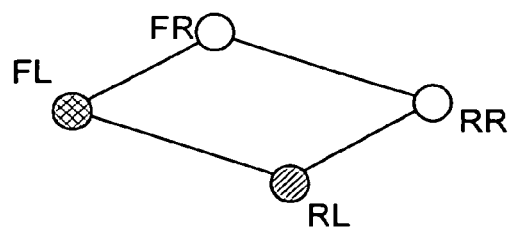

FIG. 133 is a perspective view showing an arrangement of a 4-channel surround sound loudspeaker according to the prior art.

Figure 134:
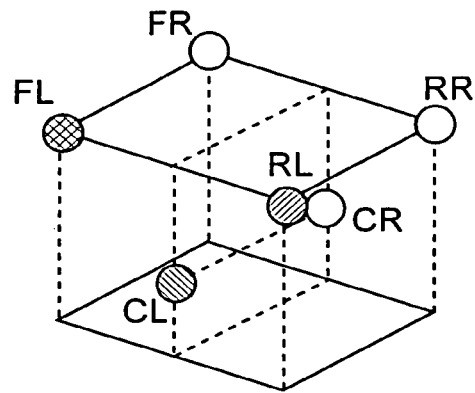

FIG. 134 is a perspective view showing an arrangement of a loudspeaker in a matrix disposed by using a six-dimensional continuous matrix coordination method according to an implemental example 14.

Figure 135:
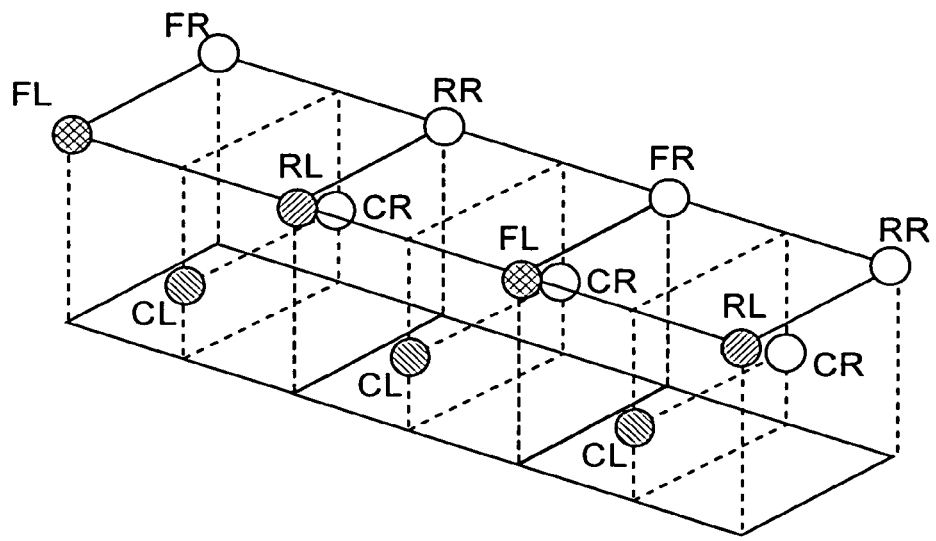

FIG. 135 is a perspective view showing an arrangement of a loudspeaker in which a matrix is disposed continuously and repetitively in one direction by using a six-dimensional continuous matrix coordination method according to the implemental example 14.

Figure 136:
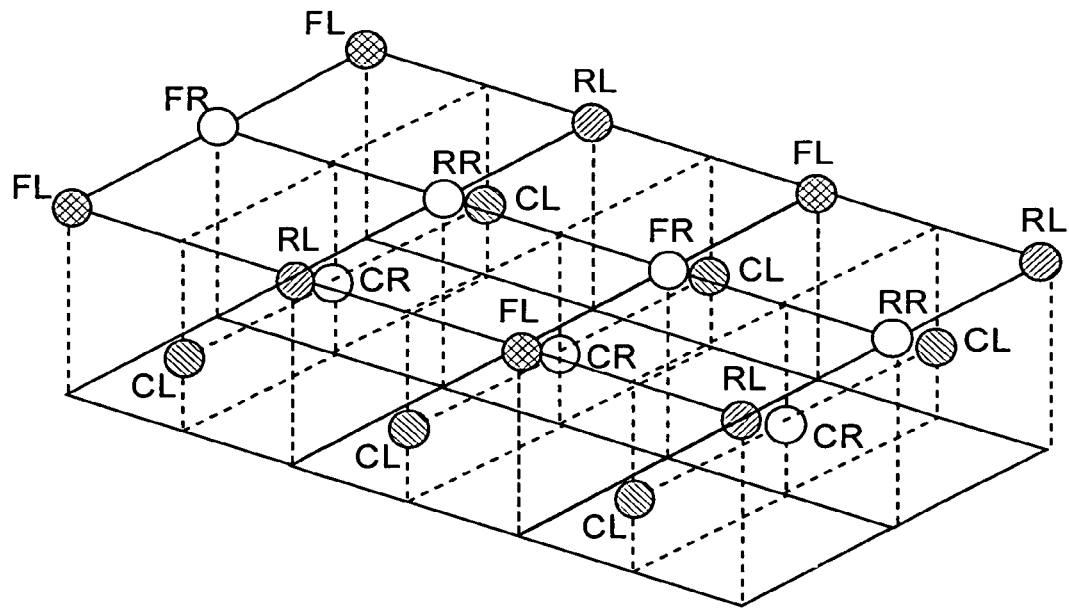

FIG. 136 is a perspective view showing an arrangement of a loudspeaker in which a matrix is disposed continuously and repetitively in two directions by using the six-dimensional continuous matrix coordination method according to the implemental example 14.

Figure 137:
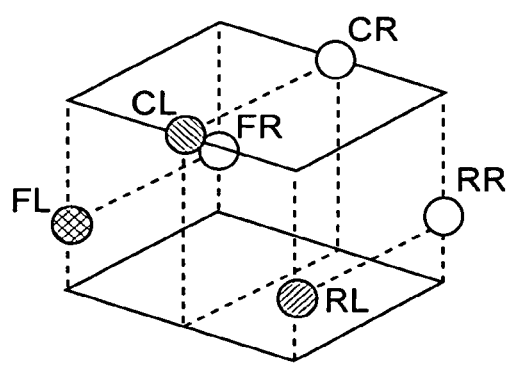

FIG. 137 is a plan view showing an arrangement of a loudspeaker to which two loudspeakers CL and CR are added in the system of FIG. 133.

Figure 138:
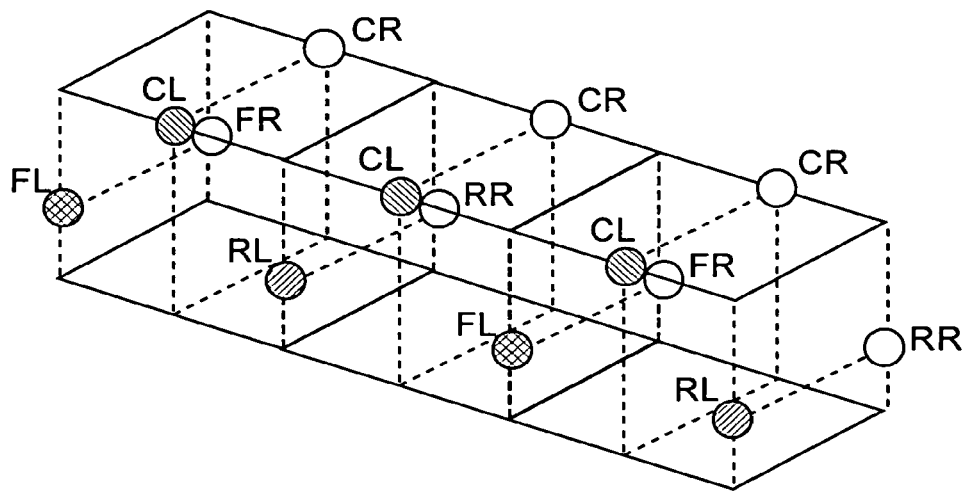

FIG. 138 is a perspective view showing an arrangement of a loudspeaker, in which the matrix of FIG. 137 is disposed continuously and repetitively in one direction.

Figure 139:
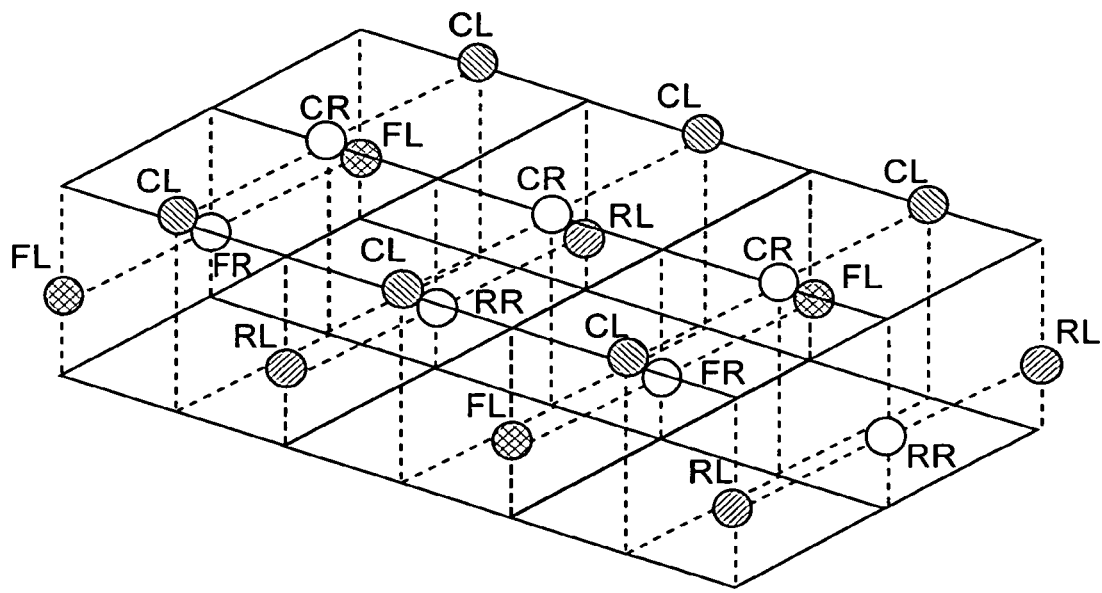

FIG. 139 is a perspective view showing an arrangement of a loudspeaker in which the matrix of FIG. 137 is disposed continuously and repetitively in two directions.

Figure 140:
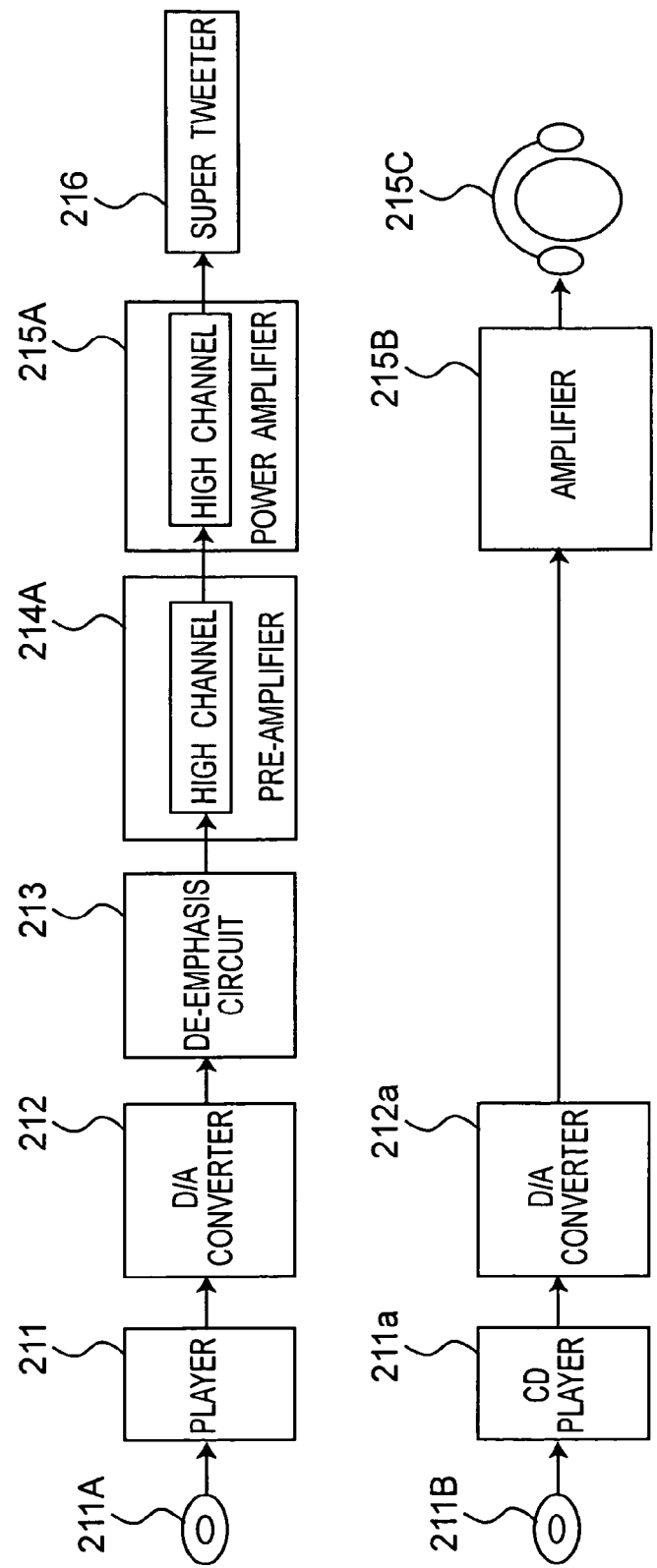

FIG. 140 is a block diagram showing a structure of a system for reproducing an acoustic signal including super perceptual auditory information according to an implemental example 15.

EXPLANATION OF THE NUMERICAL REFERENCES

101 . . . signal disc,
102 . . . hypersonic SACD player,
103 . . . fader,
104 . . . pre-amplifier,
105 . . . de-emphasis control circuit,
106 and 111 . . . high channel,
107 and 112 . . . low channel,
108 . . . high-pass filter,
109 . . . low-pass filter,
110 . . . power amplifier,
113 . . . super tweeter,
114 . . . Oohashi monitor,
115 . . . subject,
116 . . . remote controller,
120 . . . reproducing system,
151 . . . analysis program,
152 . . . filter,
153 . . . personal computer,
154 . . . receiver,
155 . . . antenna,
201 . . . microphone,
202 . . . amplifier,
203 . . . pre-emphasis circuit,
204 . . . A/D converter,
205 . . . recorder,
211 . . . player,
211a . . . CD player,
211A . . . optical disk,
211B . . . CD,
212 and 212a . . . D/A converter,
213 . . . de-emphasis circuit,
214 and 214A . . . pre-amplifier,
215 and 215A . . . power amplifier,
215B . . . amplifier,
215C . . . headphone,
216 . . . super tweeter,
217 . . . tweeter,
218 . . . woofer,
221 . . . surround sound source playback apparatus,
231 . . . first matrix unit,
232 . . . second matrix unit,
233 . . . third matrix unit,
241 to 245, 251 to 255, and 261 to 265 . . . loudspeakers with amplifier,
271 . . . pre-equalizer,
272 . . . power amplifier,
273 . . . loudspeaker unit,
274 . . . output buffer amplifier,
280 . . . office space,
281 to 285 . . . desk,
290 . . . footpath of shopping street,
291 and 292 . . . shop group,
301 . . . image storage media drive apparatus,
302 . . . controller,
303 . . . projector,
304 . . . screen,
CL . . . central left loudspeaker,
CR . . . central right loudspeaker,
FL . . . front left loudspeaker,
FR . . . front right loudspeaker,
RL . . . rear left loudspeaker,
RR . . . rear right loudspeaker,
UC . . . upper central loudspeaker,
OPA1, OPA2, OPA11 and OPA12 . . . operational amplifier,
T1 and T11 . . . input terminal,
T2 and T12 . . . output terminal,
T21 . . . input terminal,
T22 . . . through terminal.

DETAILED DESCRIPTION OF THE INVENTION

Preferred embodiments of a method for environmental setting, an apparatus for environmental setting, and information for setting environment according to the present invention, or more concretely, preferred embodiments of "sound and civilization" regarding a method for urban regeneration, an apparatus for urban regeneration, and information for urban regeneration will be described hereinafter with reference to the drawings. The components similar to each other are denoted by the same reference symbols, respectively.

<1> Introduction

As essential nutrients such as vitamins, are present in the world of materials, <essential factors> indispensable for living are present in the world of information. The present invention was born under the star which becomes the first publication for telling this truth with the help of the inventors.

The magnificent material civilization established on the earth of the technological civilization or, to be exact, the stage of the information civilization was suddenly born from the stage of the material and energy civilization and rapidly grown. As indicated by computer science, telecommunication technology or the like, these two stages appear to be smoothly continuous to each other and appear as if no boundary is present between them.

Now, we wonder if this vision is reliable enough to deserve our confidence. Actually, from a different position or angle of view, fathomless gaps are present everywhere between the stages of the two civilizations in which the fully-matured material civilization is separated from the just-born information civilization. The differences between them, which appear in the relationship between human existence and the environment, in particular, are rather shocking.

In other words, in our civilization, the material civilization, chemical materials or <essential nutrients>, which should be taken from the environment for human beings to live are explored in quite enormous depth. For each of them, an extraordinarily precise standard is set to the extent that, for vitamin B12, for example, a person should take two millionths grams per day as a recommended dietary allowance ((RDA) according to the US National Academy of Sciences). There is no avoiding noticing the ultimate state of the fully-developed and fully-refined civilization.

In contrast to that, how is the "information" environment?

Referring now to sound as the topic of this specification, we have never heard any administration or public organization of any country including the World Health Organization (WHO), which is the center that administers health and hygiene of the global population, provide a standard for the quality or quantity of "sounds necessary for existence". On the contrary, we are unable to find evidence of considering the setting of a standard. We could rather say that the very concept of "presence of sounds or information essential to the existence of human beings", that is, <essential information> is in a phase before creation.

The level of this cognition of the concept corresponds to a phase before the concept of essential nutrients such as vitamins was created in terms of the stage of the material civilization. This dates back approximately to the seventeenth or eighteenth century when people began to use citrus fruits to prevent scurvy, namely, the era when the steam engine appeared. In other words, the present stage of the information civilization may possibly be still an immature stage comparable to the dawn of the material civilization in terms of the cognition and the concept regarding sound.

Needless to say, if it is confirmed that no harm is done to the existence of human beings even by complete absence of sounds, the careless and prejudiced stance of the present status of this civilization on the sound environment is negligible.

However, if we rebuild the framework and probe again the relationship between sound and human beings more precisely with the development of a new approach so as not to deteriorate the exactness and trust of contemporary material civilization, an unimaginable and astonishing fact surfaces and destroys preconceived ideas.

In short, the information of "sounds" acts, in a manner almost similar to that of materials, quite strongly and intricately on the bodies and minds of human beings.

As an introduction to the present specification, a topic of conversation will be furnished concretely. Since the beginning of the twentieth century, our civilization has learned that even an unobservable material of a very small amount or a colorless, tasteless, and odorless material could have a serious effect on lives through vitamins or environmental chemical materials. Based on that knowledge, our civilization has strived to complete the material environment over unobservable and infinitesimal ranges.

However, the "sound" environment lives in a state in which it suffices to measure about half of, for example, the perceptual frequency ranges throughout the science, the health and hygiene, and the administration. In other words, the "sound" environment is still in the simple and optimistic state in which about half of what is perceived is ignorable. We wonder if people in future generations will denounce the present state of the information civilization as none other than barbaric and ignorant.

The inventors of the present invention tried doing an approach based on a different scheme from that known so far using various sciences such as information ecology and brain science that connect material civilization with civilization. Finally, the inventors of the present invention came across the astonishing fact.

It is not rare that some of the beautiful and comfortable natural sounds which the inventors collected from every region across the globe by novel means includes ultra-high frequency components several times as high as an upper limit frequency at which a person can hear a sound as such. As results of experiments conducted by the inventors, it was discovered that the sounds that include such non-perceptible components obviously enhance the activity of an essential brain region including a brainstem, a thalamus, and a hypothalamus.

The essential brain region and a neural network based in the essential brain region are the center that controls the mind and body of each person. Effectiveness of the non-perceptible ultra-high frequency components that activate the essential brain region and the neural network is as high as those of vitamins and trace elements. On the contrary, it was discovered that if these activators run short due to variation in the quality of the sound environment resulting from the urbanization, the activity of the essential brain region is unavoidably deteriorated. It is feared that this causes serious disorders of the mind and the body in a manner similar to that of lack of essential nutrients. Actually, there is a high probability of the connection of the deteriorated activity of the essential brain region with civilizational pathologies such as life-style related diseases, psychosomatic disorders, mental disorders, behavioral disorders, and development disorders, which threaten present society.

From different points of view, these knowledge signify that we have had a bright prospect of relieving us from the civilizational pathologies by reconstructing the sound environment blessed with <essential information>. It is very the theme of the present specification to express all aspects of the prospect.

Before doing so, the inventors of the present invention have to attempt to secede from Cartesian modern conceptions that limit the information world to "perceptible areas", and that extract and widely accept only explicit information of language signs from such areas. The inventors can also catch a glimpse of the prospect of all aspects. This is another important subject of the present invention.

The inventors' will to bring back the beautiful and comfortable sound environment has thus overcome the limit of the modern civilization itself and been identified with caring its way to the horizon of a new civilization.

<2> Find Out Sound Suitable or Comfortable for the Brain
<2-1> Recombination of Sound Science 1. Since the ancient Greek philosophy and Chinese musicology until the modern musicology and acoustics, music therapy, and soundscape, human beings have accumulated dazzlingly plenty of sound-related wisdoms, knowledge, and techniques. If tied up particularly with technical engineering, the present learning, techniques, and arts of sounds, as the climax of the accumulated ones, demonstrate their strong abilities as if they appear almost all-round. Nevertheless, they do not always function properly for illuminating and solving diverse serious sound, human being, and environment-related problems with which we are confronted. If investigating actual conditions, the inventors cannot help thinking that we are pressed to reconsider creating a framework for approaching the sounds, human beings, and environment per se.

As a quite familiar and very basic example, let us examine the functions of sound levels (physical indexes of a magnitude of a sound (dBA)), that is, an index formally used to judge whether or not the state of the sound in the environment conforms to human beings. A sound level in a present city is measured by an apparatus called "sound-level meter". If so, quietness starts decreasing nearly at a scale of the meter of about 45 dBA. If the sound level exceeds 50 dBA, most people feel uncomfortable. By the way, such an urban noise not only produces a psychological sense of disagreement but also obstructs life and adversely influences human bodies. Therefore, in our society, a law (such as an environmental standard) is enacted to restrict a magnitude of every environmental sound (FIG. 1). This restriction contributes to protecting people living in modern cities against the influence of negative sounds as an almost indispensable tool.

However, the inventors of the present invention themselves carried the sound-level meter into a village environment in monsoon Asia in which people practice wet rice agriculture, a forest in a tropical rainforest area in which food-gatherers still live their lives and actually measured the sound level. As a result, sound levels in these areas totally differed from those in the cities. In these areas, the sound-level meter continuously indicated about 50 dBA in the quiet village or basically indicated about 60 dBA in the refreshing forest. Besides, the level easily leaped up over 70 dBA only by the decent working of lives or the fluctuation of the ecosystem. Nonetheless, the quietness is kept unchanged and comfortableness does not fluctuate in terms of sensation and KANSEI (which means beauty and pleasure). An average value (equivalent sound level) of an environmental sound of a typical tropical rainforest often excels 60 $dBL_{Aeq}$ and even 70 $dBL_{Aeq}$.

What if the sound of such a village and that of such a forest are compared with the present noise restricted value? The sound of the quiet village and that of the refreshing forest are over an allowable limit of the sound level and judged to be too high, with the results that they are restricted one after another. In other words, the noise standard which our society currently uses and sound restrictions based on the standard are truly effective for environmental sounds of modern cities, which are exceptional and special in human history extending over several million years. However, they are totally ineffective for sounds of villages and forests which are far more ordinary environmental sounds in human history.

Despite such a limit that even endangers their raisons d'être, the current noise standard and restriction values are readily set by no means. On the contrary, extensive researches and investigations that constitute more than one science system and up-to-the-minute measurement and evaluation techniques are freely introduced into the standards and the restriction values. Furthermore, to set a standard that accompanies legal authorization, their legitimacy and validity have been considered with not a few discussions. In spite of them, why is such a contradictory situation derived?

The background of the situation may be that the attitude has been weak in grasping the relation between the sound and the human beings in light of human beings as a whole, including original lifestyle to ultramodern urban space within the same field of view, and approaching them from viewpoints of life science. On the contrary, this situation is derived from the fact that the urban environment located at a point where modern civilization, which is merely one system of human history, reaches and the response of people who live in the urban environment are dealt with as if they are a standard of human beings. We wonder if such an attitude is too shortsighted in terms of both human history and life science.

The limit that endangers the root of the concept causes one more serous problem, in an inconspicuous and potential state. The problem is that while the noise restrictions set so far provide for an upper limit of sound volume quite precisely, its lower limit is not at all mentioned but made loose both nominally and virtually. Besides, incompatibility between a "soundless" environment and human beings, and the like, are disregarded in current sound environment-related knowledge with few exceptions. However, in the examination of the realities that sensory deprivation of eliminating sounds and brainwashing procedures cause serious troubles to brain functions, the risk of the soundless environment is hardly lower than that of the noisy environment.

It should be pointed out that the same problem lies behind not only a view on the "quantity" of sound such as <sound level> but also the way of grasping the "quality". The ISO (International Organization for Standardization), which is one of the greatest standardization organization authorities in the global society, previously paid attention to pronunciation sources, namely, structures or "qualities" of sounds, and classified noises (FIG. 2). The classification includes quite interesting contents. First of all, there is no distinction between a sound such as an automobile sound or an air hammer sound, that feels negative in most cases, and a sound such as a wave sound or a waterfall sound, that often feels positive in the examination of compatibility with human beings. In addition, a mention of murmurs of trees and chirping of insects that are considered to occupy the largest region in the sound experience on human history is not made concretely. Further, the item of "ordinary environmental sound" which might involve them all is listed on this table, meaning that sounds evaluated to be negative spread over a range as wide as possible. Rather, a context in which almost all sounds are judged in a law court is constituted. By contrast, even if we try to imagine any sound that would not be listed on this table and not be excluded, we find it difficult to imagine the same.

If we are faithful to the context thus provided for, then the sounds the raisons d'être of which are positively recognized and which are permitted to be produced on earth unconditionally are limited to a part of artificial "language and music". On the other hand, all the other sounds have no positive raisons d'être but wholly negative effect. What we should be particularly cautious of is that such a context related to the sounds that the modern civilization owns can be interpreted that human are better off with "fewer" sounds other than the language and music, and that they "can do without" such sounds. In that interpretation, we not only cannot recognize even a trace of the concept that presence of some environmental sound may possibly be essential to healthy existence of human beings, but also cannot find out words that suggest the possibility of the concept. In other words, no care and cautions are taken at all for the idea that "a soundless environment may be harmful for bodies and minds", and there exists no critical viewpoint regarding the presence of essential environmental sounds and the securement of such sounds.

2. The view on the sound quality as seen from the attitude of the ISO signifies a limit to the sense of environment starting at the point where the civilization arrives and where every person stands, in a manner similar to that of the view which lies behind the restrictions to sound quantities or the sound level mentioned above. Both of these views may be said to be symbolic of the modern western sound culture that greatly provides for the modern civilization. In fact, if referring to the system of vast knowledge and technologies related to sounds that belong to a pedigree of this culture, we find that all but the gigantic systems related to language, phonetics, and music are of no significance in terms of those relevant to "sounds the positive raisons d'être of which are recognized". On the other side, we notice that science and technology systems for generally measuring, analyzing, and excluding sounds other than the language and music as "existences that have a negative value of noise" are developed to quite a high degree.

It would be really epochal in such a modern western sound culture that Murray Schafer advocated the soundscape in which the raisons d'être of sounds other than language and music are recognized and in which the assertion is systematically developed. In relation to that, the work "4'33"" released in 1952 by John Cage, a contemporary music composer, is worthy of note as one trial to challenge giving environmental noise a value as a musical sound and to serve as one impetus to the soundscape project. As well known, in this "work", with a piano placed on a stage as usual, a pianist appears on the stage at the fixed time, sits down to the piano, keeps sitting there without doing anything for four minutes and 33 seconds, and then leaves the stage. Cage's attempt is to let audience themselves listen to environmental noise generated by stirs produced by the audience who feel suspicious of the progress of the state of this "no musical performance", actions of objections and the like as music. This involves an assertion that the discrimination between the environmental sound and the music should be eliminated by claiming that "the environmental sound itself may serve as music". There is no denying the adequacy of that aspect.

Schafer established the soundscape concept based on this Cage's thought. In addition, he opened up a wide path to a breakthrough in the rule of the western sound culture that assumes that "nothing except music is sound". The system of the soundscape has been developed since the twentieth century until the twenty-first century, and is of significant value in that the soundscape is building a base that can be an only opponent against the classic thoughts of "preference to language" and "absolute belief in music" and social powers based on the thoughts. Expectations of this trend are unfathomable in every aspect.

Attention should now be paid to the fact that Cage and Schafer set the function, effect, and value of the environmental sound "to serve as music" or "equivalent to music". We could recognize an aspect of expanding a music range boundlessly under a slogan of "music is sound" in Cage's attempt. If such an attitude grows and the sound environment is regarded as one sphere of music, there would be risk of mistaking the means for the end. The reason is as follows. Sound perception of human beings itself is basically an environmental perception, and if a musical perception is present, the musical perception is a mere subsystem of the sound environmental perception. It will be necessary to keep it in mind that Schafer and the pedigree of the soundscape advocated by Schafer are inherited quite linearly from Cage's thought.

It is regrettable that the framework, namely, the paradigm of the fundamental idea of the soundscape starting from this does not satisfactorily coincide with the paradigm of the new sound science which the inventors of the present invention are opening up. It may not be impossible that some of the inconsistencies change to good consistencies in the future. However, as Thomas Kuhn, who is a philosopher of science and who advocated the contemporary concept of paradigm itself, pointed out in his main literary work "Structure of Scientific Revolutions" 7, a large gap of "non-commensurability" lies between different paradigms. For this reason, if the sound science proposed by the inventors is to stand depending on the paradigm of the soundscape to date, then it is required to adjust and overcome the paradigm gap as the first procedure. In order to do so, it should take lots of time and energy first.

Examples of main structures characteristic of the soundscape that concern the generation of this gap include the above-mentioned attitude of positioning the sound environment in the pedigree of music, the developing arrangement constituting cognition of the environment as seen in an outlook of the cosmos and the sense of value, a too naïve stance on natural science, and activity limits as the contemporary knowledge and the near future knowledge based on the absence of tools for the life science including, in particular, molecular biology, evolution biology, and brain science.

It is no doubt that the trend of the soundscape is the one and only hope to date for reviewing the relationship among the sound, the human beings, and the environment and for opening up a new path. However, it is quite difficult to establish a conceptual base of the inventors' sound science in the dimension of the paradigm. It must be more productive for the inventors themselves to build an independent paradigm suited for the sound science that they advocate and to open the door to the other paradigms so as to enable the paradigms to coexist while avoiding barren intellectual constraints and discords.

Therefore, the inventors decided to build up a framework for a new approach, on their own, which makes it possible to substantially fulfill minimum effectiveness for the inventors and which the inventors can accept even though it is incomparably poor and awkward to the existent dignified systems.

<2-1-2> Examine Framework for Ecology

1. Now, the term <sound ecology> will be used to refer to the sound science which the inventors of the present invention are establishing. In the framework for this knowledge, sound is regarded as an ultimate message carrier from environment and investigated thoroughly. In order to create the framework, what we cannot do without is not only the operations for extracting and rearranging effective knowledge from various systems related to sound, human beings, and the environment and established thus far, but also those for reconsidering and rearranging more underlying concepts and senses of view themselves and for devising new knowledge and methodology. If these are integrated, an operation for establishing a new system will more surely proceed.

Sound ecology must be an environmental science as well as a sound science. Due to this, special care should be taken to create the framework for sound ecology. As a matter of fact, a deep contradiction or friction associated with the heavy background of history and culture stands in the way between the science that is to belong to the ecology and the science that is to belong to modern western sciences. In order to harmonize them, it is unavoidably necessary to rearrange the conception or sense of value associated with the fundamental structure of the sciences and construct new intellectual framework. Therefore, the background of the actual condition will now be reconsidered in which modern western knowledge and concepts, on which the inventors currently rely, are expressly and almost essentially disharmonious with the subject of "environment".

René Descartes, who is called the founder of modern philosophy, criticized previous scholasticism that so clouded effectiveness as to become a synonym for an annoying and useless discussion. In addition, he tried to build up a new knowledge system that is truly reliable while "clear and distinct" knowledge, namely, that clear to everyone and incontestable, was set as a basis of the truth. Before doing so, Descartes tried to find out the infallible origin of knowledge first and then to formulate knowledge by objective and strict logic as mathematical procedures for the basis.

As well known, Descartes claimed that the presence of his mind that arouses doubts itself can be beyond any doubt after casting thorough doubts, named "methodological doubts", on all knowledge, and accepted that consciousness, that is, self-awakening mental functions as the first reliable substance. Further, Descartes accepted extensity, that is, spatial extension of the matter which can be grasped by his senses and which can be measured three-dimensionally as the second reliable substance that exists objectively. He also regarded the extensity as the nature of the matter and advocated dualism according to which the mind and the matter are separated from each other, and recognized and manipulated as independent substances. Needless to say, Descartes' dualism gave a character, which should be called <clear knowledge>, to a part of modern western knowledge, surprisingly developed solution and control of the material world, and laid an important foundation for enlightening contemporary technological civilization.

On the other hand, the Cartesian knowledge structure and its applied sciences have begun to clearly show various limitations, particularly since the latter half of the twentieth century. Global environmental issues must be one of the most serious manifestations of them. If modern technologies did not endlessly accelerate the discarding of nonverbal structures difficult to understand consciously and fracturing into specialized fields accompanied by self-blocking and simplified functions with enhancing operably to the nature to an ultimate goal, there would not have been derived the global environmental issues as seen at present.

As one more but modest cause for global environmental issues, one may be able to point out the problem of "confusion of an environmental view" based on the fact that Descartes' dualism was not always worked properly by those who succeeded Descartes. Before discussing various problems which the Cartesian knowledge structure itself confronts, there will be considered the problem which appears to influence the nature of the western civilization.

One important source of this confusion appears to lie in the fact that the way of thinking symbolized by "departure from consciousness" based on Descartes' famous "cogito ergo sum (I think, therefore, I am)" constructed to approach spiritual world also casts a shadow on environmental recognition. In the conceptual space in which Immanuel Kant, Edmund Husserl, and the like, succeeded Descartes and which is amplified to the so-called transcendentalist philosophy, the mental functions which a person oneself can perceive, that is, self-consciousness is positioned at an origin, and a space of knowledge and information is formed concentrically about the conceptual space. In this space, a realm spreading outside him or her is "environment". If the environment is grasped in the framework of "the subject and the environment", the subject has overwhelming or rather decisive preference over the environment. In this system, since there is "I who think", the environment exists around the subject. Unless "I" do not "think" or "I" do not "exist", the environment does not exist, either. That is similar to a chart in which a magnetic field is never generated until one magnet is present. Such an environmental concept can be referred to as a concept of "ego-inducing environment".

In the knowledge space constituted by such a cosmology, quite naturally, neighborhoods of a point where the subject stands tends to be a peak of information density and the information density is lower farther from the peak. As seen in the biased cognition of the noise previously exemplified, the existing modern western environmental view generally takes this position. Inevitably, in most science systems constructed on such an original constitution, a field of view of a person is largely within the person himself or herself, a region and a society to which the person belongs, and culture or civilized culture, in particular, and the information density concentrates on them. On the other hand, it is natural that it is difficult for regions, societies, cultures, and human beings and living things as living species distant from them to come within the field of view. Farther from the point where the person stands, the information density is lowered to be substantially equal to zero without keeping in mind continuity between them. As a result, the knowledge space created tends to be reduced to an unbalanced information structure in which a measurable gap is present between the knowledge space and the entity of environment.

Now going back to the starting point of Descartes, this way of thinking must be a thinking method used when approaching a genuinely mental thing assuming that the thing is present within an individual independently of a matter. In other words, it is difficult to believe that the way of thinking is provided as a procedure for making the material world spread outside the individual as a target. For reference, there has been explained above the instance in which the noise indexes set by the contemporary technologies with utmost efforts are effective only in the urban space, which is exceptional and special in human history, but ineffective in the other spaces. We wonder if the limitation of the environmental view that has been unsuccessful in assuming the mantle of Descartes' dualism is greatly reflected in the instance.

This is because, when thinking over the same, Descartes must have prepared another environmental concept different from the ego-inducing environmental view. That is to say, it is a concept that functions on the realm of "material is an extension" set to exist independently of "mind" centering around consciousness of an individual. The concept enables taking the stand that environment exists a priori independently of whether or not an ego is present or the content of the ego. The concept is possibly close to an environmental view that includes a view on forest ecosystem held by the African Mbuti said to lead original lifestyles of Homo sapiens and faith in the ecosystem widely seen in monsoon Asia, and is most unsophisticated and universal in human history. Whether those involved are aware or not, there can be basically applied to this framework an environmental view with which the environment is grasped as an ecosystem, and with which human beings or the "I" who belongs to the human beings is positioned more subordinately as either a module that constitutes this system or an element of the system. Such an environmental view can be distinguished from the ego-inducing environmental concept as a concept of "ecological environment", and it is effective to distinguish so. The environmental view is easily harmonized with a new environmental view that is reconstructed on the occasion of the global environmental issues.

On this recognition, the environment is none other than existence autonomously provided for by the structure and functions of the environment itself based on history of its own evolution. Accordingly, the environment cannot be provided for a posteriori by existence of any specific ego or by any society or culture as a collection of these egos. In other words, according to this concept, the environment overwhelmingly precedes the subject in the framework of "substance and environment". Whether "I" "think" or not whether "I" "am", the environment solemnly exists.

Thus, an eye suitable to view the environment should be able to obtain a representation more faithful to the entity of the environment which the environment itself is embodying and to which the environment is moving. In order to do so, the eye should be that independent of an observer's standpoint and unbiased to the whole environment. Species that cannot respond to that are reduced to natural selection. From this point of view, it appears that setting of the rational view in the coordinate space having, as an origin, the ego consciousness which Descartes constituted for the introspective spiritual world is accompanied by fundamental difficulties.

The global environmental issues that we confront are in the realm of "material is an extension". No grounding is found for substantiating that the global environmental issues can be appropriately controlled under the rule of the ego-inducing environmental view. Rather, modern cultural history is strongly indicating and suspecting that the modern ego is none other than the principal cause of the global environmental disruption. Unless people are free from the dominant rule and absolute rule of this sense of value, it is extremely difficult to appropriately construct a currently desired view on the environment.

As a background of actual difficulty in attaining the setting of the appropriate view on the environment, we should turn our eyes to the influence of cultural constitution present prior to sciences as well as modern western philosophy and thought. If the western civilization is regarded as an external look, there appears a peculiar way of thinking to grasp the relation between an individual and a whole (system constituted by individuals who are component elements of the system), which relation has prevailed since the Roman era comes to us. Concretely, the content is ego-inducing cosmology having consciousness as its starting point or a value system in which "a self takes preference over a system the self belongs".

Ludwig von Bertalanffy, systems scientist, said in this main work "General System Theory", "a system is a group of various elements interacting with one another" and made it clear that "the whole system exceeds a summation of parts". In order to claim the preference of one element which is a component element of the system thus characterized over the wholeness is nothing else than self-contradiction. The same is basically true for the social system.

Needles to say, this rule cannot apply to a remarkably artificial and non-habitat segregation type social environment that has diverged irrespective of an optimum group size set in human genes since the ancient empires until the modern nation-state system. It is often reasonable to decompose or reconstruct the system itself. However, the logic of paraphrasing the cognition specific to the highly adaptive social structure deviated from the original characters to general human beings is not considered to be reasonable. In a general lifestyle for human beings set in original naturalness including the habitat segregation type society and integrated with the ecosystem, the instance in which an individual can be claimed to take preference over the whole system is limited to quite a special exception between the wholeness of the lifestyle and an individual who is an element belonging to the lifestyle.

In this respect, attention is paid to the fact that the constitution of "grasping the environment as subordinate to human beings and individuals" which the ancient western world held as a culture increasingly tends to be put into ideology in modern times. In a society having a culture in which a value system of a higher priority to individuals becomes widespread, as represented by, for example, the United States established under the doctrine that the nation renders services to individuals, a situation tends to change to one in which anti-environmental characters are dominant. What needs to be taken care of is that this value system has become the flesh and blood of contemporary western culture almost completely. In the system, the peculiar concept that people, the society which each person belongs to, and, above all, each person himself or herself take precedence over the global environment tends to be grasped as if it is a universal rule and a standard for human beings.

However, in reality, the concept itself or the society in which the concept is publicly supported and advocated is neither universal nor standard for human beings. In many traditional societies giving satisfactory results such as food-gathering societies to which an overwhelmingly majority of people belong, a concept in contrast to this concept is present. Attention should be paid to the actual state in which the most common societies are the ones having the concept and value system of placing the environment with the highest priority and human beings, their societies, and individuals subordinate to the environment, and the background in which societies against such concept and value system are screened in terms of human history.

For reference, in terms of thought history, for example, the cosmology and value system of placing an individual over the environment have multiplied waywardly within short time equivalent to a moment on human history since around the days of the principle of laissez-faire introduced by "The Wealth of Nations" by Adam Smith until the present days when the global environmental issues were actualized, and are already at a standstill. They are not only by no means standard from the entire human culture from the past to the present, but also not any majority. The realities are rather similar to those that are an abnormal, local, and temporary phenomenon and a possible candidate of a screening target. At the same time, it should not go unheeded that these anti-ecological cosmology and value systems strongly suspected to be overturned from the general rules of lives on earth and inherent characters of human beings are becoming a considerably large and perhaps fatal Achilles' heel of western civilization and modern civilization established under western civilization.

2. In dealing with the several problems related to the modern knowledge structure originating in Descartes, what is first noticeable is a terrible limit of a function of approaching nonverbal information. Descartes' thought built a basis for making strong use of <explicit knowledge>, namely, ability of rational and logical thinking which human beings are endowed with in an effective state. Within its shooting range, it served even as a guardian angel of truth and justice. However, there is naturally a limit to the range. If Descartes' thought is applied to a system substantiated by a meaning structure which cannot be translated to a language, an information structure which cannot be processed by a finite logical operation, or the like, its divine power is instantly lost. As one aspect of the loss, at least, as of today, realizing Descartes' clearness in an area of consciousness causes a serious problem. It is based on the limitation of knowledge information processed in the human's brain essentially to the language system, that is, information having a connective structure configured as a one-dimensional row.

Descartes and orthodox members of modern civilization who are successors to Descartes developed sophisticated processing means for discontinuous and discrete information having a connective structure formed by using language or symbols as elements through a surprising approach, accumulated results, and established a grand explicit knowledge system. They limitlessly deserve praise. By contrast, an activity of recognizing and controlling nonverbal (non-symbol and non-connective) information, given overwhelmingly much weight among messages sent to us from the environment, that is, information having a symbolic structure or particularly a concrete structure has never been developed as compared with that for verbal information. The reality is that the nonverbal information came to be essentially discarded, forgotten, and totally weakened.

This unevenness had a strong impact on not only the attitude toward the natural information environment but also the whole social and cultural information environment. As a result, nonverbal information activity such as tacit knowledge as Michael Polanyi a scientific thinker put it, as well as <intuitive knowledge> <experimental knowledge>, <insight knowledge>, and <traditional knowledge> which may constitute tacit knowledge is denaturalized and reduced to decline. Needless to say, this tendency is also reflected in sound culture, and, as will be described later in detail, induces cognition of nonverbal sound information to a state nearly zero, and causes problems on the level of human history while opposing an excessively close deal with the verbal sound information. These actual conditions incessantly tell us that a control over the explicit world cannot be realized if separated from a control over the tacit world.

One more serious problem related to the modern knowledge structure originating in Descartes is the separation among sciences, technologies, and arts, starting with a division of the mental world from the material world based on the dualism and fractionalism of the sciences, technologies, and arts, that is, specialization. In the twentieth century, when "a way of life to engage in science" specific to a specialized field began to spread, Max Weber asserted "Retire into a specialized shell" and strongly recommended self-blocking and providing a mono-functional character. The following is an excerpt from his lecture manuscript "Science as a Vocation".

"Matters stand at a point where the individual can acquire the sure consciousness of achieving something truly perfect in the field of science only in case he is a strict specialist . . . . All work that overlaps neighboring fields is burdened with the resigned realization . . . . And whoever lacks the capacity to put on blinders, so to speak, . . . may as well stay away from science" (translated by Kunio Odaka).

The subsequent course of history transformed Weber's idea of this to a generally accepted idea, and this enabled human beings in the twentieth century the activities of whom were thus amplified to drive the technological civilization.

It is true that effectiveness of high specialization is splendid. However, it is necessary to take care that the effect has the following mechanism. The effect hits a peak in a phase in which traditional society in which the mono-functional character is not realized exists, specialization is introduced, and old and new activities form a multilayer structure. Thereafter, it multiplies gaps and blanks as tradition goes into decay. In the phase before the activities of tradition and the specialty form the multilayer structure, most of those receiving specialized education hold traditional multi-functional and ultra-specialized characters inwardly. In addition, traditional individuals and social systems having ultra-specialized and mobile activities remain as they are anywhere nearby. Due to this, a blank between fields which are attributes of high specialization, an incompatibility with an interactive system, and the like, are sufficiently covered by the activities of the tradition, are not revealed, and do not come to any failure. The point to see here is that an effect that is substantially a synergic effect between tradition and the specialty is mistook solely as the effect of specialization and overestimated. As the specialization progresses, the mono-functional character and self-blocking of the specialized field and a specialist are developed. However, a residual density of the traditional ultra-special activity is reduced. When most of the activities of the society are replaced by the mono-functional special activities, the limit and defect of the specialized function that is by no means perfect and faultless are dramatically revealed particularly in nonverbal and experiential realms such as "succession to tradition" or "human creation". At that time, since the traditional ultra-special issue dealing activities are already gone, one unavoidably faces difficulty finding measures to fill up the gap or blank.

Things and phenomena grasped as the concept of environment cannot be originally isolated or closed systems independent of the others but essentially have complicated relations with various things without few exceptions. Besides, it should be resigned that most of the connections lie hidden in an unknown world extending in a blank zone between the specialized fields. Even if each of these things is forced to apply to any one of currently fragmented specialized fields, it is difficult to evade the fate of losing or discarding an essential factor and an interaction. The inventors are seeing its typical end in the global environmental issues provoked by the twentieth century.

It is necessary to pay special care to create a science system targeting a phenomenon of the environment that basically accompanies characters incompatible with advanced specialization. History shows that a general way of creating a knowledge realm for deriving a new system from a self motion of a science using existing specialized fields only does not often bear fruit in face of the realities of the environment and lives. It is expected to be more effective both fundamentally and practically to start from the specific environmental issues that exist and that we are confronted with to creatively rearrange the existing knowledge and methodologies so as to be exactly compatible with such environmental issues, to create what will be able to fill up still remaining gaps anew, and to thus resolve the issues.

It goes without saying that this approach is difficult to realize as long as it depends on the highly fragmented specialized fields that dominate the present sporadically. Unavoidably, it is necessary to integrate them and manually create a new knowledge structure from almost zero. By accumulating such approaches and rearranging a structure with sufficient appropriateness from a high dimension using the accumulated approaches as a source, there may be able to be established framework appropriate for a science involved with the environment.

3. The sound ecology that is now newly constructed is none other than the science related to a message from the environment, a message carrier which carries the message, and a recipient of the message. If attention is paid to attributes, namely, information understood from the message, transmission of the message, reception of the message, and response to the message, sound ecology can be located as one realm of a more general information ecology. Systematization and application of information ecology have proceeded to some extent and results supporting effectiveness of the information ecology have begun to be accumulated. Despite its still beginning and experimental phase, the inherent effectiveness of new procedures for overcoming the limit of past specialized sciences is already appearing.

It is more natural than anything else to introduce a framework as a science that information ecology has accumulated and showed results so far, as well as various tools and methods for the concept and operational hypotheses into sound ecology and make use of them. In addition, it is reasonable to use them as a basis for constructing a framework for an upcoming new knowledge, and not a little efficiency, certainty, and safety are expected. At the same time, sound ecology uses information ecology as a direct foundation and is allowed to have a strong hierarchical structure connected to the base of general ecology through information ecology. Thus, sound ecology can serve as a paradigm that has both a highly reliable basic structure and wide and flexible applicability.

Taking these into account, the inventors of the present invention decided to constitute a framework for sound ecology based on the previously systematized information ecology.

<2-1-3> Paradigm of Sound Ecology

1. <Sound ecology> is a science that grasps sound, human beings, and the environment comprehensively from three dimensions of material, energy, and information based on information ecology, and that is growing as a system for investigating sound, human beings, and the environment.

This system has a distinction from Descartes' modern western knowledge structure in which while targets are limited to two dimensions of the material (extension) and the mind (consciousness), the material and the mind are separated from each other and grasped and investigated independently. Due to this, sound ecology does not adopt the specialization and fragmentation approach that accompanies the mono-functional character and the self-blocking which are attributes of modern sciences. Besides, sound ecology intends to free itself from the modern western unevenness that deeply separates explicit information on verbal signs from implicit information on nonverbal signs while being devoted to the explicit information. In this way, sound ecology intends to realize "a bridge between the matter and the mind".

In order to ensure realization of these, sound ecology inherits a thought framework "knowledge space in which information science and molecular biology are regarded as both coordinate axes, respectively", in which information and matters are integrated with each other, from the information ecology that is the mother of the sound ecology. In addition, sound ecology inherits concepts of <life> and <information> to be incorporated into this framework from information ecology as follows.

In the first place, <life> is defined as "an automaton capable of duplicating itself and evolving". At this time, attention is paid to the fact that a life on earth, which is one specific manifestation of life, is a chemical life constituted by molecules and that elementary steps of all life phenomena on the earth progress as chemical reactions at a molecular level without any exception. As a result, it is possible to build a grounding for bridging matter with information.

Next, an application range of <information> serving as a tool of the concept used by the sound ecology is restricted to "life phenomena and their relevant regions". In addition, <information> is defined as "a scientific concept related to a time space structure (pattern) that may possibly produce some reaction of life". As for the life phenomena on earth to which this information concept is applied, it is assumed that some molecular biological thing lies as its background at least ideally. It will be able to effectively prevent an arbitrary independence of the information concept and contribute to an improvement in the reliability of the information concept in accordance with an improvement in effectiveness of sound ecology.

2. Sound ecology is grounded on life sciences related to sound, human beings, and the environment. Among the massive number of organic species that constitute lives on earth, human beings are actually nothing but species having peculiar activities. However, it is impossible to ignore the actual fact that human beings are first of all organic things rather than being human beings. If the environment called the ecosystem is taken into consideration, in particular, it is essential to grasp the human beings as continuous to the other living things and it is the most effective to do so.

The first fundamental area which sound ecology makes a great account of among the life sciences spread quite widely is molecular biology, which plays an important role. Sound ecology investigates a stand of gene determinism in the background of molecular biology. In addition to molecular biology, sound ecology makes much of evolutionary biology, brain science, ecology, ethology, and the like as indispensable tools.

Furthermore, sound ecology makes much of a historical view on sound and the environment and takes the stand of earth history, human history, and civilization history. Among contemporary human beings, there exists the Mbuti living in tropical rainforests in central Africa who are believed to still maintain their original lifestyle. On the other hand, among groups apart from the original lifestyle and following a road to industrialization, there exists a pedigree of modern westerns who rebuilt the environment on a large scale of earth history and human history, which considerably changed the nature of the sound environment. Sound ecology established a viewpoint of grasping an overview of such a macroscopic transition in the sound environment on a large scale of the history of civilization, human history and the earth's history, and strives to always keep the viewpoint. If necessary, "a view on extraterrestrial intelligence" is set as a more macroscopic and more neutral view that exceeds these views.

Moreover, sound ecology makes much of an ethnological view related to the sound. It is a treasure-house of traditional knowledge to succeed to cultures which various races elaborated perpetually. While senses to sound, consciousness, and response modes are stubbornly universal among human beings, they are diversified according to regions, races, and cultures. While being intended to enable all of them to come into view with unevenness as small as possible, sound ecology grasps specific characters of the respective sound cultures as a spectrum as clear as possible.

Needless to say, sound ecology takes an ecological stand and does not take any stand of the ego-inducing environmental view as a stance in the cosmology for grasping the environment.

3. In a manner similar to that of information ecology, sound ecology takes the responsibility of discovering and solving problems and has a preference for tackling existing and important problems related to sound, human beings, and the environment. In order to do so effectively and surely, an intellectual system for solution is established in an input oriented state whenever each of the target problems occurs. In this respect, sound ecology differs in principle from the specialization and fragmentation approach of distributing the problems on fixed and specific finite kinds of problem processing means and for acquiring routine outputs of the means. Although an intellectual excitement and a pleasant sensation after solving a problem generated to accompany such an approach, and an intellectual development derived from a self motion of the science itself, or the like, are not denied by any means, it is considered that a state of having a preference for them mistakes the means for the end.

In a manner similar to that of information ecology, sound ecology that gives the highest priority to discovering and solving impending problems introduces both traditional knowledge and contemporary knowledge according to purposes, reconstitutes and makes the most use of both knowledges. As a source of traditional knowledge, sound ecology attaches much importance to not only the cultures which various races on earth inherit but also a current of wisdom tracing well back to the origin of human beings and starting at the most original lives on earth, and learns them as the source of ideas and identification. At this moment, giving serious consideration that the essence of the information structure constituting traditional knowledge is within the realm of tacit knowledge such as an intuitive knowledge, an experiential knowledge, and an insight knowledge, sound ecology strives to improve nonverbal (non sign juncture) information processing capabilities corresponding to them to a high level and to secure them. As for contemporary knowledge, sound ecology masters the technology which is the so-called strongest means for dealing with the problems acquired by lives on earth, centering on an effectively used strategy. At the time of processing, the "clear and distinct" approach that assumes the mantle of Descartes and that is an excellent and good manner of the modern knowledge should be taken into consideration.

This leads to the expectation to provide discernment, insightfulness, reliability, precision, reproducibility, predictability, legitimacy, successfulness, and the like, at the highest level possible for contemporary human beings.

In relation to this, sound ecology emphasizes the stance of making full use of modern technologies. A direct starting point of a decisive incompatibility between the sound environment and human beings may be said to be an industrial revolution. Needless to say, subsequent modern technologies come to be impeached to cause destruction of the global environment and the devastation of the mental world while providing material abundance to the part of all human beings. A stance of denying or excluding the technologies themselves is present as to how to deal with negative inheritances from the technologies. Nevertheless, the inventors of the present invention consistently insisted that substantially only one countermeasure is expected to have reliability and effectiveness to solve the negative effects of the technologies to date, and that is none other than technology, and considered how to use the same. It is confirmed again that sound ecology is no exception at all.

Furthermore, sound ecology assumes a consistent attitude of dealing with sound, human beings, and the environment while integrating the three activities of science, technology, and art at a high level. Ways of approaching things that connect sound, human beings, and the environment are open to the respective three realms of the science, the technology, and the art. However, if an actual problem is to be dealt with, it is rare to use a single approach from one of the three ways. Rather, it is desired, in most problems, to use a complicated structure in which two or three of them are mutually and closely connected. Due to this, it is not enough to overcome the fragmentation simply within the three realms but it is essential to reunite and integrate them. In noninvasive brain function analysis, for example, acoustics, physiology, and metrology are associated with the sound ecology. In addition, in sensation information processing, sound ecology uses artistry, work creativity, and a grasping power of response to a KANSEI generated by a recipient. In such an aspect, there is no avoiding the introduction of a serious structure by division of the interrelation among science, technology, and art both positively and negatively. If so, a general and comprehensive system is established in which necessities to deal with a problem over a plurality of realms required by the problem itself including potential necessities are investigated and in which they are not separated into respective realms by any means, so as to deal with the problem. In short, a person involved in sound ecology is required to be simultaneously a scientist, an engineer, and an artist.

4. As an important strategy of sound ecology, the mind and matter that have been separated are reunited through a brain. In order to reunite the mind and matter in a state in which development of modern knowledge after Descartes is not inverted and reverted has been a desperately unsuccessful theme though desired by some. In this respect, the inventors of the present invention were lucky. This is because brain science has developed dramatically. Taking an opportunity of this situation, the stance of reuniting the mind and materials that have been separated since Descartes has been established in the forefront of the Descartes' knowledge system with brain functions related to sensitivities serving as contacts.

On the side of the mind, it may be said to be an almost self-evident common ideal for modern people that the platform of a function of the mind related to beauty and arts such as creation and appreciation is present in the brain. Simple but firm, universal cognition is grounded on this. As another grounding, the inventors of the present invention opened up a wide road of grasping the mechanism and the functions of the brain as an information processing apparatus that a living thing owns, and could utilize the apparatus at the practical level on the side of the material science. In these backgrounds, the inventors of the present invention set the mechanism and functions of the brain related to beauty and pleasure, namely, <sensible brain>, and systematized an approach of investigating the mechanisms of beauty and pleasure both theoretically and practically, paying attention to structure and functions of the sensible brain, into a framework of <sensible science>. This setting is often decisively effective for sound ecology.

As conditions for executing this stance, it is required to satisfy the above-mentioned requirement that "a person involved must be simultaneously a scientist, an engineer, and an artist". This causes a researcher's behavioral rule, a motive, and a way of life themselves to be reconsidered in a wider framework that is not confined to the contents of the sciences themselves, and a framework for scientific methods in a narrow sense. Actually, it is a theme which Descartes was aware of himself, how rationally "connection between the mind and the materials" held firmly within experiences of the inventors of the present invention is explained. The model of "pineal body" often referred to as an example of an unscientific character of Descartes can be actually a pioneering hypothesis filled with outstanding penetration in terms of the strategy of connecting the mind to materials through the brain. The stance of connecting the mind to materials through the sensible brain may be able to be said to a stance of realizing Descartes' strategy at the present point in time.

<2-2> Promised Sound Environment

<2-2-1> Town Sound, Village Sound, and Forest Sound

1. Why cannot we help being conscious of serious problems with the ways of sounds in the environment? Needless to say, this is because a sound environment created by a modern lifestyle derived from history or, particularly, the sound environment of a city is harshly opposed to the existence of human beings. At present, this opposition is mainly attributed to mechanical noises in cities. Although this is undoubtedly true, it is also easy to imagine that the problem is not that simple if no problem occurs unless the mechanical noises are present. Therefore, attention is first paid to the sound environment of a contemporary city or town, namely, <town sound>, which is the heart of the matter. In addition, a structure and characteristics of the town sound will be reviewed making effective use of various approaches as much as possible.

A typical modern life environment in the background of technologies can be seen in a highly dense residential space of the city. States of sounds in the space include unprecedented states not only for human beings but also for the level of all life on earth in many respects. Now, one may outline a daily transition in environmental sound starting at a time when a person living in the city wakes up in the morning and experienced by the person. The worlds of sounds covering up the waking of those who live in towns are extremely diversified. However, a typical example of the worlds is an indoor space enclosed by concrete and glass. Thanks to the high sound-insulation of the latest building materials, many people can see an unexpectedly quiet morning. However, by listening carefully, they incessantly hear a characteristic sound in which a low rumbling of the earth and groans are mixed up in many cases. What <physical structure> causes such a sound as an aerial vibration?

In this case, one can use a scale of measuring a magnitude, which is the simplest physical structure of the sound, first. What happens if a magnitude of an indoor sound in the morning is at a sound level which is the international standard of the scale? The magnitude variously differs according to the location or structure of a building. If the magnitude is measured in a medium to high-rise building typical of an urban residence in the early twenty-first century and using new building materials, the sound-level meter indicates at most somewhere around 20 $dBL_{Aeq}$ in the room in the early morning unless a sound generating source such as an air-conditioner or a television set is present. This measured value is actually rather abnormal. That may be unexpected or may be surprising to acoustic professionals. This is because the value is sufficiently equal to a quietness level required in a broadcasting studio, a music hall, an audio laboratory, or the like, as written in an architectural design textbook, or the like.

Such a shortage-of-sound living environment can hardly exist in the evolutionary history of the great apes including human beings from time immemorial. Even for Homo sapiens, it is difficult to meet a sound environment close to that living environment unless they are under special conditions, such as a high-shielding residence in a cold district such as a snowbound house, except for a contemporary up-to-date residence. Due to this, it is doubtful how a program that resists such a shortage of sound is prepared in the wide adaptable variations of human genes. In reality, there is little difference in the deficiency of auditory stimulus between the condition of this living environment and that of a sensory deprivation experiment that attracted people in relation to brainwashing or a sensory reduction experiment conducted as a simulation of an information environment in a spaceship. In all of these experiments, there is pointed out a negative effect of the deficiency of auditory stimulus on the mind and the body.

Figure 3:
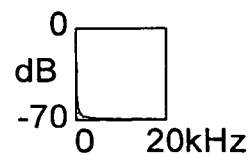
FIG. 3 is a chart showing an FFT spectrum of a quiet indoor sound among spectrums of the sounds in a town.

The structure of this faint environmental sound will be examined while considering not only the magnitude of the sound (a sound pressure or an amplitude) but also components of the sound. To this end, an excellent method referred to as "fast Fourier transform (FFT)" is put into practical use. Now, the morning sound in the same room will be analyzed by using this FFT to draw a time-average frequency power spectrum. A sound force is larger on a left side of FIG. 3, namely, on a low frequency side and lower at its right side, namely, at a high frequency side. The frequency distribution has an upper limit of about five kHz and hardly includes higher frequency components than five kHz (FIG. 3). In the drawings of the present invention, an FFT spectrum and an ME spectral array are shown. The FFT spectrum illustrates a relative level of the sound to frequency whereas the ME spectral array illustrates the sound with passage of time as well as its relative level.

Figure 4:
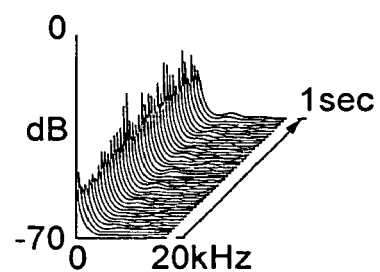
FIG. 4 is a chart showing an ME spectral array of the quiet indoor sound among the spectrums of the sounds in the town.

On the other hand, the FFT may be said to be an analysis method characterized by cutting off an average value of the frequency distribution of the sound per a certain time region, like a still picture, and seeing cut sections. However, this method is not very effective to see a manner in which a complicated sound structure of environmental sound, music, or the like, continuously changes from one minute to the next. Considering this, the inventors of the present invention developed a new method <ME spectral array method> for visualizing a state in which a frequency spectrum changes in a microscopic time region from one minute to the next as a spectral array. According to the ME spectral array of the morning indoor sound, the spectrum having gentle rise and fall monotonously continues without very remarkable changes (FIG. 4).

Figure 5:
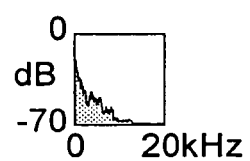
FIG. 5 is a chart showing an FFT spectrum of an indoor sound when television is turned on among the spectrums of the sounds in the town.
Figure 6:
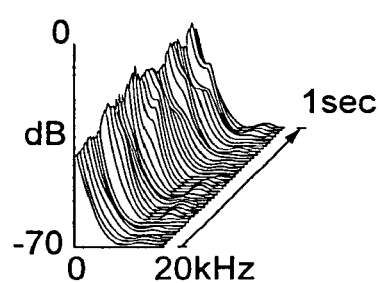
FIG. 6 is a chart showing an ME spectral array of the indoor sound when television is turned on among the spectrums of the sounds in the town.

In a morning indoor space thus deficient in sound, an aspect of the sound is usually changed discontinuously and instantly on occasion of turning on an electronic media such as a television set or a radio. While a volume of the sound produced from loudspeakers is various and not uniform, a sound pressure level rises to about 50 to 70 dBA. At the same time, a spectral structure of the indoor sound has a dramatic change. The entire spectrum spreads into a right-side high frequency region to exceed ten kHz and shows complicated irregularities to some extent. However, a state in which the upper limit of the spectrum is close to 20 kHz is not shown so often. The ME spectral array also has a more complicated change (FIGS. 5 and 6).

If the characteristics of the sound produced from the electronic media is regarded as <information structure>, then words are above all a main current of the information structure to be followed by music, and the other sounds only function as background. However, the words and music that play the lead have a similarity in that they are artificial matters each having a <connected information structure> in which it is hardly seen that animals other than human beings really use them.

In the morning indoor space in which sound from the electronic media spreads, far fewer isolated sounds than the words or the music are present. However, this balance changes when actual sounds resulting from life activities such as breakfast are added to the morning indoor sound. A sound of contacting tableware with each other, or the like, has a pattern in which a person can hear the sound "beautiful" or "noisy". The sound has a <symbolic information structure> which is not any unit having a connected structure, but an independent sound module. In addition, there appears sound, such as a sound of quiet boiled water, from which information cannot be cut out as a sound particle having a symbolic characteristic because of unclear temporal intervals, but which has a <concrete information structure> in which a structure of a signal itself can certainly transmit information. Further, if those who live have conversations, connected sound, namely, a language is added to the actual sound.

In this way, the morning indoor sound environment which is a starting point of the day of a person living in a city has a marked deficiency of sound first as a bare characteristic. Accordingly, the environment is easily dominated by sounds produced by electronic media following startup of the media. This change of the sound environment occurs discontinuously when a power of the media is turned on. Subsequently, while connected (language and music), symbolic, and concrete sounds coexist, information on the connected sound originating in the media overwhelms information on the other sounds. As a result, the information on the sound having concrete structure concluding at the signal level is relatively quite deficient.

Figure 7:
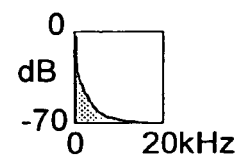
FIG. 7 is a chart showing an FFT spectrum of a diachronic outdoor noise among the spectrums of a sound in a town.
Figure 8:
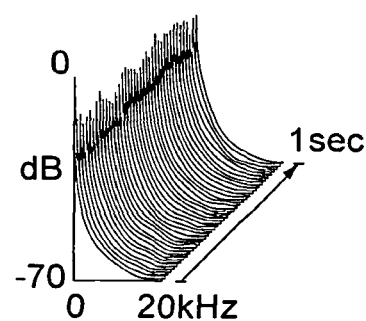
FIG. 8 is a chart showing an ME spectral array of the diachronic outdoor noise among the spectrums of the sound in the town.
Figure 9:
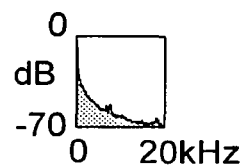
FIG. 9 is a chart showing an FFT spectrum of a sound of a road through which a truck passes among the spectrums of the sound in the town.
Figure 10:
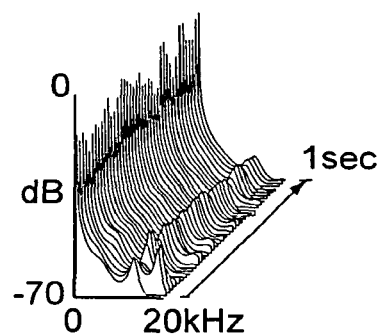
FIG. 10 is a chart showing an ME spectral array of the sound of the road through which the truck passes among the spectrums of the sound in the town.

As a step of an action subsequent to wakeup and breakfast (often omitted) of persons living in the contemporary city, many of them leave their rooms to go to office or school and are exposed to an outdoor sound environment. As a person moves from inside the room to outside the room, the sound environment also has a dramatic and discontinuous change. In many cases, the moment each person leaves a room or a building, he or she is surrounded by strong urban noises mainly including mechanical noises generated from traffic and transportation devices such as automobiles, motor bicycles, and trains. They have a structure discontinuous to that of the indoor sound almost completely. A background sound of the noises rolled forth diachronically forms a sound signal symbolism of which it is difficult to recognize and which is confused. A sound pressure level of the background sound is often so high as to exceed 70 dBA, for example, near an arterial road. On this baseline, miscellaneous and strong artificial noises suddenly cross one another. These sounds tend to be disliked as offensive sounds to almost all human sensations and sensibilities. Each of the FFT power spectrums of these sounds, except for an impact sound produced at a close range, has a continuously decreasing form having a sharp inclination quite in a manner similar to that of the previously explained indoor environmental sound, but has a far larger level than that of the indoor environmental sound (FIGS. 7 and 8). However, an upper limit of frequency of components of each sound is not high by any means at most points except for the point directly hit by a vehicle sound along the road (FIGS. 9 and 10). It is about 15 kHz at the highest and frequency regions equal to or higher than 15 kHz are in a so-called silent world. From the forms of these spectrums, it can be estimated that the spectrum of the indoor sound in the morning in a state with no sound-producing objects results from the fact that the outdoor background sound invades the room, house or building with attenuation by shielding means and constitute most of the environmental sounds.

Next, referring to ME spectral arrays of the outdoor environmental sounds, each ME spectral array has a form roughly close to that of the previously explained indoor environmental sound. The ME spectrum itself does not show a structure unless a vehicle is driven at excessive speed in front of a person (FIGS. 9 and 10). A temporal change of the spectrum is monotonous and quite vague (FIGS. 7 and 8).

At the time of commutation, the inventors of the present invention are surrounded by a sound of a train, an inside sound of a bus or an inside sound of a station superimposed on such background noise. At these locations, various announcements are broadcast often with a music phrase serving as a call sign, which enhances distribution of the connected information. Despite numerous efforts, these sounds normally tend to be regarded as negative environmental sounds deficient in comfortableness.

A working space or a study space which is a goal of commuting of the person living in the city and which is a base of subsequent activities often becomes an environment which excludes sounds at a higher degree as the space is closer to a residential space, except for a civil engineering and construction, industrial production, practical or physical training space, and the like. In this space, language sounds that constitute conversations and lectures mainly constitute the environmental sounds. Recently, a ratio of artificial sounds produced from communication electronic media such as telephones and educational electronic media is rapidly increasing. Most of these sounds are language sounds and a supreme order for them is to clearly transmit meanings and contents. On the other hand, as results of a requirement of a reduction in cost and reductions in apparatus size and weight, each media shows a marked tendency to reduce a communication capacity to the minimum with which a sound can function as connected information. Due to this, for a telephone, for example, a reproduction frequency band is limited to be equal to or smaller than four kHz, and a call sound of the telephone, or the like that, is accompanied by a high-degree and complicated spectral change considered as sensory information does not gain an advantage. As can be seen, the working or study space shows a marked tendency of an emphasis of the connected information and a degeneracy of the symbolic and concrete information. In parallel to the tendency, one cannot deny a tendency to sacrifice comfortableness and beauty of sounds.

On the other hand, needless to say, in sites of industrial production, civil engineering and construction, traffic and transportation, and their practical sites, and the like, sounds generated by machines are dominant. Most of them are rotary machine sounds, which is high in temporal continuity, small in change, and quite low in information density (FIGS. 9 and 10). An impact sound (for example, a sound produced when a rivet is hit) that tends to have a smaller distribution often has an intermittent change and acts as symbolic information. These sounds generally tend to be extremely high in sound pressure, and have remarkable negative influences (unpleasant influences) on the sensation and the KANSEI of a person involved.

A sound environment on a person's way home from work or learning may be considered to be almost equal to that during the commutation in the morning. In the indoor space after the person's return home, or indoor or outdoor commercial facilities which the person stops by for purposes of dining together, entertainment, or the like, there overwhelmingly exist artificial sounds produced in consideration of the entertainment effect and transmitted from electronic media. Contents of these sounds are that a ratio of the language is higher mainly due to the TV in the person's house and a ratio of music is higher in ordinary commercial facilities. However, except for an amusement environment that is occupied by strong electronic effect sounds exhibiting high symbolism, all environments are similarly dominated by sounds such as music and words, each having the connected information structure. The physical structure of each sound is close to an ordinary sound structure when electronic media sounds are dominant, and its sound volume tends to be high. A nightclub or an amusement arcade is flooded by sounds at extremely high volumes to exceed 100 dBA. In such an entertainment artificial sound environment, efforts and measures are done to improve comfortableness and above all pleasantness. Although these efforts are considerably effective, they unavoidably and potentially produce various problems as to whether they enable approaching a sound environment to which human beings truly aspire.

As can be seen, in the indoor environment among these sound environments normally seen in contemporary cities, the presence of sounds is extremely scarce. On the other hand, the sounds generated from the electronic media and filling up blanks are not sufficiently rich since an acoustic structure of software is restricted by standards and techniques. In addition, since fidelities of hardware including a frequency response and a transient response have not a few limits, a restriction is given to the information structure appearing on a time axis or particularly an information density. Further, each outdoor environmental sound is high in sound pressure and has a frequency distribution offset to a low frequency side. In addition, each sound is quite simple in spectral structure and deficient in a temporal change of the spectral structure. Due to this, in the outdoor environment, in a manner similar to that of the indoor environment, the information density is extremely low.

In summary, from macroscopic viewpoints, the town sound has a structure that appears as if a mixture of fragments considerably low in temporal and spatial continuity. Only by a slight difference in location or time, the acoustic structure of the town sound greatly changes and has a remarkable temporal and spatial discontinuity. People who live there are forced to experience striking changes in many sound environments which are so different that it is impossible to recognize continuity and similarity in physical structure and information structure in accordance with slight changes in time and location. However, in the partial residential culture of Europe, or the like, where rock or brick walls and stiff doors are frequency used, the sound environment originally tends to be accompanied by a temporal and spatial discontinuity, which is a forerunner of the sound environments of modern residences having quite exceptional and remarkable discontinuities on human history. If it is assumed that each of the fragments of the town sound is a <physical structure>, each fragment is narrow in frequency band, deficient in temporal change, and has a simple spectral structure. Due to this, an <information structure> of the fragment is extremely low in information density. In these circumstances, while the language and the music, that is, the connected information is the largest force particularly through the electronic media, the symbolic information and the concrete information, in particular, are quite scarce. Furthermore, from viewpoints of a <response structure>, numerous people living there normally tend to be incompatible with the sound environment both consciously and unconsciously, and to feel somewhat unpleasant or disgusting. It goes without saying that the tendency stirs up a strong consciousness of problems in the sounds in the environment.

2. In considering information environment, a residential system created by a rural community, namely, a village, which was a base of primary industries such as agriculture and cattle-breeding, is worth notice as a settlement system that appeared on human history prior to the town. Regretfully, an information environment of the rural community suitable as a comparison with that of the city existing in developed countries is strongly influenced by urbanization in various respects, and a sound environment of the village is not any exception. However, some of villages in the Asian monsoon zone that maintain quite excellent contents of the information environment still exist although remarkable development is underway. If wet rice agriculture societies residing in evergreen broad-leaved forests are carefully searched, it is possible to discover villages that secure typical <village sound>. Examples of these villages include traditional villages sporadically present in the Japanese Islands and each constituted by Yashiki forests (premises forests) and Balinese farm residences.

It appears that these villages were created after people simply settled in primitive natural environments. However, actually, many of them are highly advanced and artificial residential environments originally constructed by quite fine traditional techniques. The techniques and results of the artificial matters are in no way inferior to those of modern city residences. Nevertheless, since the concept of the villages focuses on integration with and coexistence with nature, they assume a paradoxical character that the more the artificiality in that direction advances and succeeds, the rarer the artificial traces are and the more greatly the natural character is increased. Accordingly, in the case of approaching such a traditional residence, we are apt to lose our way to an evaluation which cannot sense and decrypt the existence of the artificial nature if we do not have a sufficient backing including profound experience and deep insight.

If the village sound is compared with the town sound, what is noticeable is a difference in temporal and spatial continuity. The town sound is lacking in continuity both temporally and spatially. The village sound, by contrast, is high in continuity both temporally and spatially, accompanies non-stationary fluctuation, and shows a strong tendency that sound changes incessantly and smoothly despite changes in time and location. Besides, the continuity of the village sound is seen in both a macroscopic region and a microscopic region.

The summer comfortableness of residences surrounded by Yashiki forests which are still built in various parts of Japan is a supreme one that only one who knows can really appreciate. The sound environment of the residence is quite similar to that of a typical Balinese village. The indoor sound of a room well ventilated and well opened is hardly different from an outdoor sound. In addition, natural environmental sound serving as the background sound slowly changes well in a continuous state from morning to day, night, and to morning again. In this respect, the village sound greatly differs from the town sound where the sound structure of which rapidly changes as time passes or whenever a person passes through a door. Further, while the town sound is dominated by artificial sounds generated by human beings directly or indirectly, the village sound is dominated by vibrations generated from living bodies other than human beings. The rustle of woods produced by wind, the chirping of insects, and the singing of birds create a colorful sound space, which is studded with voices and words of human beings and sounds produced from living activities.

Normally, such a village sound causes a sensation and KANSEI of a person to have a quiet and comfortable response to the sound. However, a sound pressure of the village sound as a physical index is not at all lower than that of the urban sound. For instance, a measured value of the sound pressure in Desa Ubud in Bali is 55 to 65 $dBL_{Aeq}$ in the morning, 45 to 60 $dBL_{Aeq}$ in the daytime, and over 60 $dBL_{Aeq}$ and instantaneously over 70 dBA in the night. In any of these cases, when fast and slow winds shake trees, the sound pressure further rises. If the sound structure of the village sound is examined in terms of a frequency spectrum, it is found that the frequency spectrum spreads into high frequency ranges as compared with the frequency spectrum of the town sound. In a garden of a Balinese village, the Yashiki forest in the summer of Japan, or the like, there is often recognized a complicated spectrum that is well over 20 kHz, which is an upper limit of frequency audible to human beings as sound, and is even over 50 kHz. If the ME spectral array of the village sound is analyzed, various irregularities in power and temporal changes of the irregularities appear everywhere on the spectrum spreading into the high frequency ranges (FIGS. 11 to 14).

Another ordinary character of the village sound is that the temporal continuity of the village sound is interrupted at a specific date and enters another phase. This corresponds to the sound environment when the village is turned into a festival space. Notable examples can be seen particularly in Balinese villages. Sounds of a bronze percussion orchestra called "Gamelan Gong Keybar" made up with a large number of percussionists echoing throughout the village symbolize the sound environment of the festival space. Among gamelan pieces, Beleganjur marching gamelan for which performers march through the village while playing portable music instruments covers the village sound environment with a flood of powerful sounds.

The way of the village sound in a normal state will be examined from an aspect of the information structure. The whisper and rustle of the leaves of trees, the lasting chirping of insects, and the like, form sound having high concreteness and high temporal continuity. In addition, the singing of birds, the intermittent chirping of insects, and the like, form symbolic images, and words, music, and the like, of human beings form connected sound. While these forces are changing with the passage of time, a world peculiar to the village sound is created. In that world, the force of connected sound information created by human beings is by no means dominant over sound information having the concrete structure and that having the symbolic structure except for the festival space.

Figure 11:
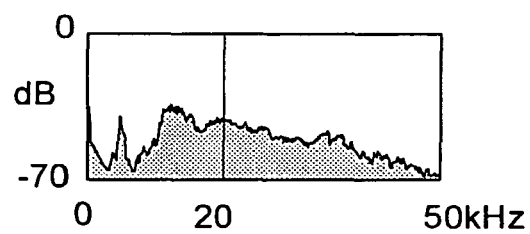
FIG. 11 is a chart showing an FFT spectrum of an environmental sound of a resident forest in Japan (Tsukuba) among spectrums of a sound of a village.
Figure 12:
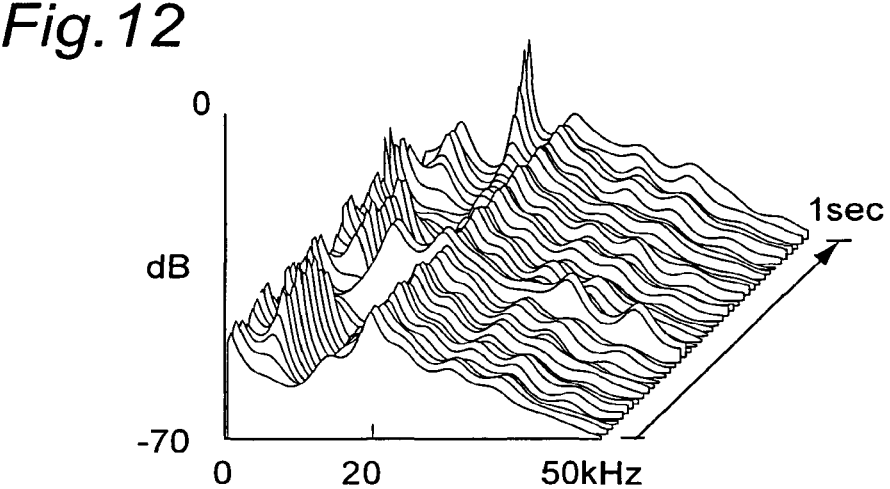
FIG. 12 is a chart showing an ME spectrum array of the environmental sound of the resident forest in Japan (Tsukuba) among the spectrums of the sound of the village.
Figure 13:
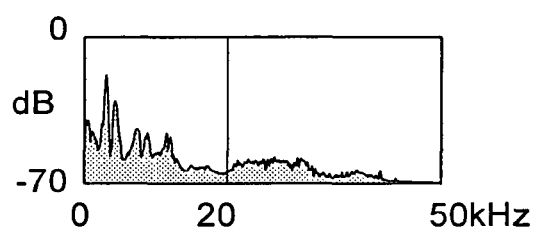
FIG. 13 is a chart showing an FFT spectrum of an environmental sound in a village of Bali island among the spectrums of the sound of the village.
Figure 14:
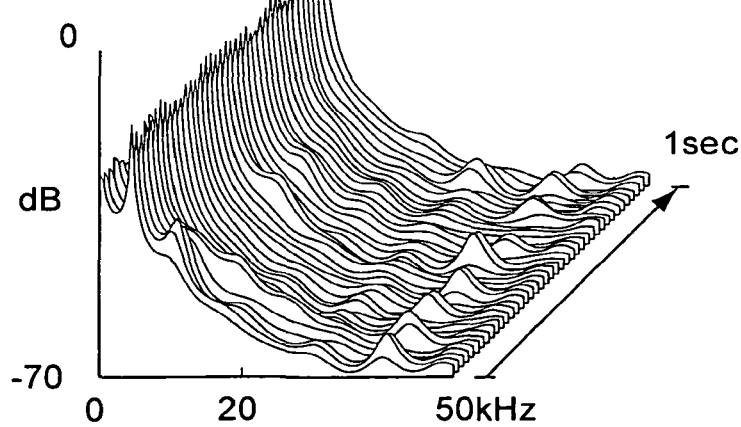
FIG. 14 is a chart showing an ME spectral array of the environmental sound in the village of Bali island among the spectrums of the sound of the village.
Figure 15:
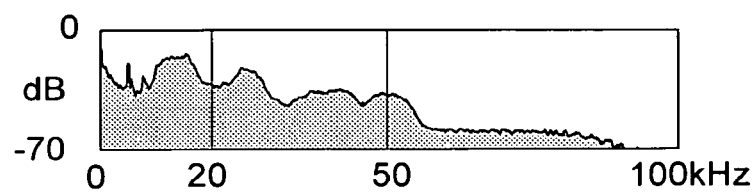
FIG. 15 is a chart showing an FFT spectrum of an environmental sound of a tropical rain forest in Panama among spectrums of a sound of a forest.
Figure 16:
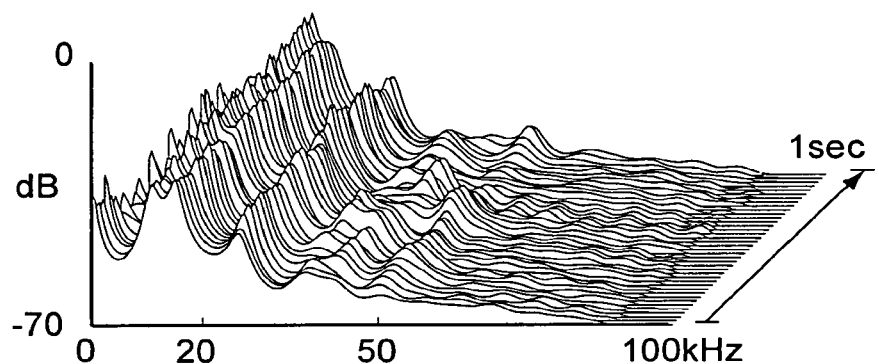
FIG. 16 is a chart showing an ME spectral array of the environmental sound of the tropical rain forest in Panama among the spectrums of the sound of the forest.
Figure 17:
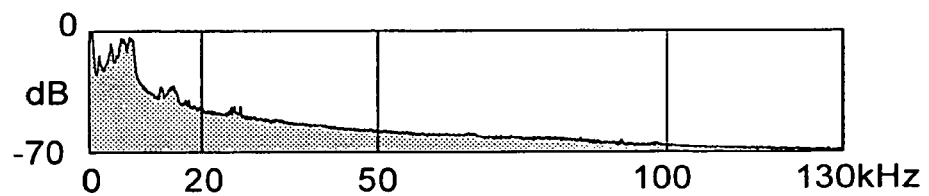
FIG. 17 is a chart showing an FFT spectrum of an environmental sound of a tropical rain forest in Java Island among the spectrums of the sound of the forest.
Figure 18:
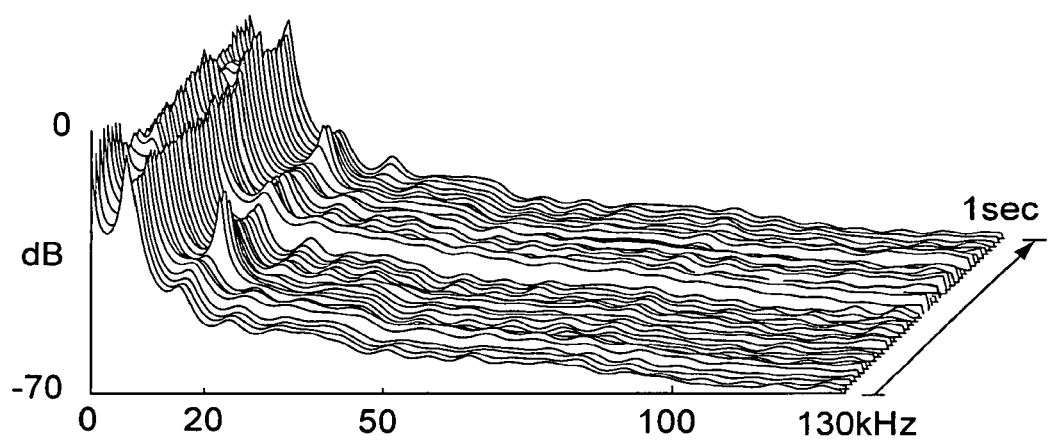
FIG. 18 is a chart showing an ME spectral array of the environmental sound of the tropical rain forest in Java island among the spectrums of the sound of the forest.

As can be seen, the village sound in the Asian monsoon zone that represents the rich sound environment in human society that engages in the primary industries usually has temporal and spatial continuity, is considerably low in the relative ratio of the connected information, and high in the relative ratio of the symbolic and concrete information, as compared with the town sound. The spectrum of the village sound spreads more widely toward the high frequency side than the town sound and has a high-density structure in which the change in the village sound is more abundantly and clearly recognized in a microscopic time range. Such a sound structure evidently produces comfortableness. If this village sound is moved into the unusual festival space, the sound pressure of the village sound is changed to a higher sound pressure level, the frequency spreads toward an ultra-high frequency side, and the village sound is changed to a unique sound space that has strong concrete, symbolic, and connected information structures, and that is characterized by a diversified temporal change with a spectrum having an extremely high density (FIGS. 11 and 12). A sound environment appearing in this sound space invites human beings to a pleasant world different from the usual world.

3. The <town sound> that covers up contemporary cities symbolizes a transmutation of the sound environment in human society after the people came to engage in the secondary industries. The <village sound> remaining in villages in the Asian monsoon zone symbolizes the comfortable sound environment created by the human society engaging in the primary industries. In contrast to them, it can be said that what symbolizes a sound environment in human society which has selected a road that does not follow industrialization is <forest sound> that reverberates through tropical rainforests where numerous food-gatherers have lived.

At present, the permanent and invariable tropical rainforests are increasingly becoming scarce. Nevertheless, as existing famous rainforests, there are known several large tropical rainforests including the Ituri Forest on the African Continent, and forests in Malaysia, Brunei, Java in Asia as well as jungles in Costa Rica and Panama, the Atlantic Forest ranging along the Atlantic Ocean in Brazil and the Amazon located inland in Brazil. Among them, it is experientially known that the rainforests which people having the lifestyle of food-gathering actively selected previously and select at present as residences are extremely beautiful and comfortable. The <Ituri Forest> adjacent to the Great Rift Valley in Africa regarded as the base of human evolution is, in particular, remarkably beautiful and comfortable. As well as the excellence of mind of the Mbuti who still continue their high-purity food-gathering lives, the beauty and comfortableness of the Ituri Forest have been praised by influential fieldworkers such as Mitsuo Ichikawa and Cohn Turnbull.

It is true that the Ituri Forest is comfortable and beautiful incomparably even in the experience of Tsutomu Oohashi, the inventor of the present invention, himself, and that the nobility of souls and behaviors of the Mbuti living there, their high-level creativity and transmitting and receptive capacities and abundance in relation to the beauty, and the like, are far beyond Oohashi's imagination. Supreme sensory and sensible reactions provoked by the perfect information environment which they brought about are beyond expression and description. The world of sound is not excepted. For Oohashi, the world of sound is rather an outstandingly attractive headspring that colors the forest.

Needless to say, the tropical rainforests existing on the earth have their characteristic sound environments, respectively. In addition, each of the sound environments has a striking diversity temporally and spatially. Despite such diversity, there is clearly recognized a character common to the information structures of the respective sound environments.

Generally speaking, the tropical rainforests as selected by food-gatherers are thoroughly filled with fertile sounds irrespective of time and space. There are not a few components of each tropical rainforest common to the good village sound. However, the number of kinds and quantities of sound sources of the forest sound are extraordinarily large. In addition, the space distribution density and the spread of the forest sound is nothing to be compared with the village sound. In the Ituri Forest, for example, large trees exceeding 50 meters or sometimes exceeding 70 meters grow thick on an undulating mountainous terrain 900 meters above sea level on average. With a background of the din and rustle of large trees that fill up a gigantic space, just like a gothic cathedral, created by trunks and crowns of the trees, a very complicated sound palace is constructed while the chirping of insects, the singing of birds, and the cries of animals are reverberated. The sound continues to move slowly but colorfully in an eternal current of time forever.

If the environmental sound of the tropical rainforest is examined in terms of a physical structure, it is surprising to see that such a forest environmental sound that a person senses as a sufficiently quiet sound has an unbelievably high sound level according to the sound-level meter. The sound level exceeds 70 $dBL_{Aeq}$ considered to the allowable limit as an urban noise, and sometimes exceeds 80 dBA, though momentarily. Nevertheless, every human having a standard sensation and a standard KANSEI cannot help feeling that the comfortableness of the sound space of the forest is the supreme bliss. The concept of the noise created by civilized society and the scales of the sound-level meter are so distant from the sensory and sensible reactions and the physiologic reaction of the person who listens to the forest sound that they are utterly no good.

The inventors of the present invention may be the first in the world that investigated a spectrum of such a tropical rainforest environmental sound up to an ultra-high frequency band imperceptible as a sound on a full scale. The investigation told the inventors an actual condition which could not be imagined without any measurement. The frequency distribution of the environmental sound spreads toward the high frequency side as much as possible and sometimes well over 100 kHz. A spectral change of the environmental sound in the microscopic time region ranges through entire frequency bands, and a current of continuous change is abundantly inlayed with particles of discontinuous change without any flaw (FIGS. 15 to 18). The strongest force in the environmental sound of the tropical rainforest is concrete information having high continuity such as the din and rustle of trees and the chirping of insects with fewer interruptions, which forms a baseline of sound as rushing as a large river. The baseline is inlayed with and filled with symbolic information such as the singing of birds, the cries of animals, and the chirping of insects with interruptions and melodies endlessly. In contrast, connected information resulting from human beings such as words and music are merely present as a miraculous exception within a region of human existence just like a drop in the bucket in a huge dense forest. However, dialogs and music of the Mbuti, which are a concrete form of existence, are integrated with natural environmental sounds in the forest and give us sounds full of fineness similar to natural matters and full of heavenly beauty.

Figure 19:
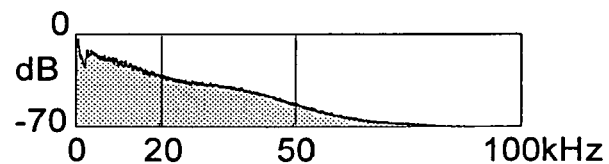
FIG. 19 is a chart showing an FFT spectrum of a sound of a national holiday space in Bali Island among spectrums of a healing sound and a relaxing sound.
Figure 20:
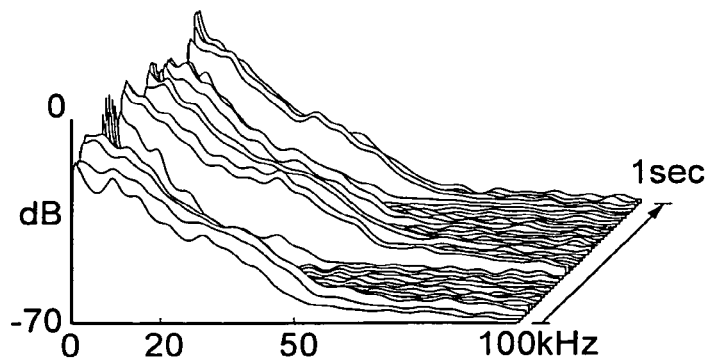
FIG. 20 is a chart showing an ME spectral array of the sound of the national holiday space in Bali island among the spectrums of the healing sound and the relaxing sound.
Figure 21:
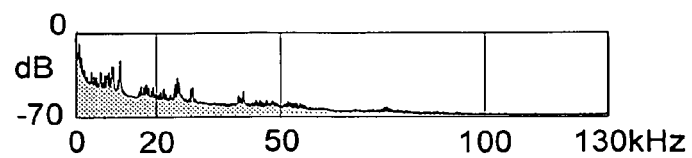
FIG. 21 is a chart showing an FFT spectrum of a sound of a hypersonic music box among the spectrums of the healing sound and the relaxing sound.
Figure 22:
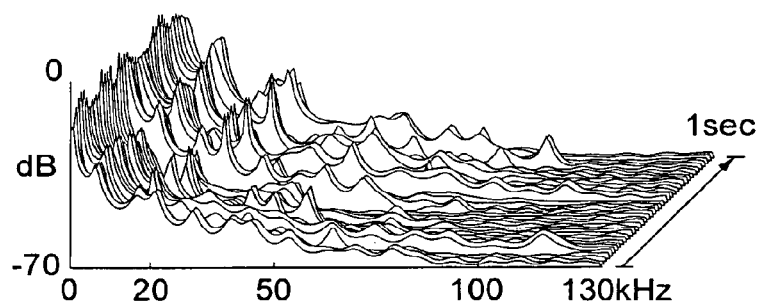
FIG. 22 is a chart showing an ME spectral array of the sound of the hypersonic music box among the spectrums of the healing sound and the relaxing sound.

4. According to spectral analysis data, the physical structure of the environmental sound of the fertile tropical rainforest is surprisingly quite similar to that of the village sound of the village throughout which gamelan sound rings on the day of a festival. When a gamelan procession passes by in front of people on the road, the sound pressure of the gamelan sound with which people are flooded is well over 90 dBA and sometimes even over 100 dBA, and often reaches a sound pressure level far higher than that along the arterial road in a town. However, people do not feel uncomfortable with the sound at all but rather positively construct such a sound space for their own pleasure and enjoy the same. An average power spectrum of the sound spreads widely toward the high frequency side and almost reaches 100 kHz. Further, a spectral array of the sound shows presence of a tremendous ultra-high frequency component instantly exceeding 100 kHz while a complicate waveform of the component is greatly changing temporally (FIGS. 19 and 20). The sound acts quite effectively as healing sound or relaxation sound. As a good metal sound source similar to such gamelan sound, attention is paid to a sound producing mechanism of a disk-type music box. A hypersonic music box that exhibits a healing effect was developed based on this sound producing mechanism. A spectrum of a sound produced by the music box includes a component having a frequency over 100 kHz and filled with fluctuation, in a manner similar to that of the gamelan sound, and shows the similarity to the forest environmental sound (FIGS. 21 and 22).

Figure 23:
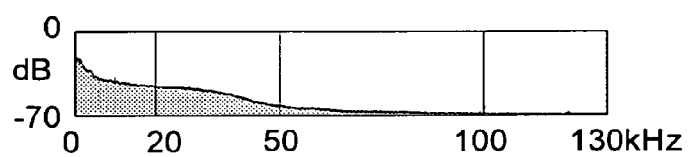
FIG. 23 is a chart showing an FFT spectrum of a sound of a song of a babbling brook in the Mongol plain among the spectrums of the healing sound and the relaxing sound.
Figure 24:
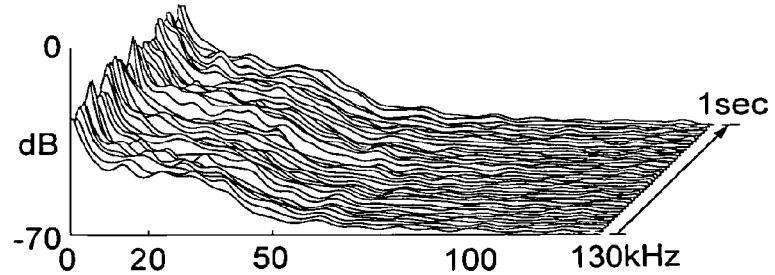
FIG. 24 is a chart showing an ME spectral array of the sound of the song of the babbling brook in the Mongol plain among the spectrums of the healing sound and the relaxing sound.

As the essence of another healing and relaxing sound in a contrast to the metal sound source, an environmental sound <a murmur of a little stream> which the Japanese are most fond of should not be overlooked. Actually, in investigating an information structure of this environmental sound minutely, presence of background noise prevents investigation in a usual sound environment influenced by human activities. Due to this, the murmur of the little stream running through grasslands on the Mongol plateau was recorded and analyzed. As a result, presence of a surprisingly ultra-high frequency component having rich fluctuation and well over 100 kHz was discovered (FIGS. 23 and 24).

Referring to FIGS. 19 to 24, the time average FFT spectrums in ten to 60 seconds' time and ME spectral arrays at intervals of 25 milliseconds are shown.

5. In summary, the sound environment of the tropical rainforest where food-gatherers live obviously differs from that of the highly dense city residence that emerged near the end of the challenge of modernization. The tropical rainforest sound is characterized, in terms of physical structure, by a complicated power spectrum in a super wide band over 100 kHz, high-level continuity in the macroscopic spatial-temporal region, a perfect fluctuation structure in the microscopic time region, and super high density at time series. In terms of the information structure of the forest sound, a concrete information structure is overwhelmingly substantial, followed by a rich symbolic information structure, with a connected information structure only in a rare distribution.

As all the people who actually experienced a sound environment of the tropical rainforest emphasize, human beings' responses to such sound environment is an extremely high sense of comfort and an extremely low sense of discomfort. The responses are in good harmony with the actual state in which an overwhelming majority of people who adopted the food-gathering lifestyle that is intrinsic to Homo sapiens live in tropical rainforests, where a sign of incompatibility with the information environment is hardly recognized. The tropical rainforest sound is nothing but a source of ultimate comfortableness as can be seen from the sensory and sensible reactions of the inventors themselves.

<2-2-2> Habitat and Way of Life Coded in Genes

1. Is an ideal sound environment for human beings possible? If it is possible, what is the ideal sound environment like? <original-adaptation model> of information ecology suggests a probability of presence of the sound environment coded in human genes and opens up a way for searching the same.

Figure 25:
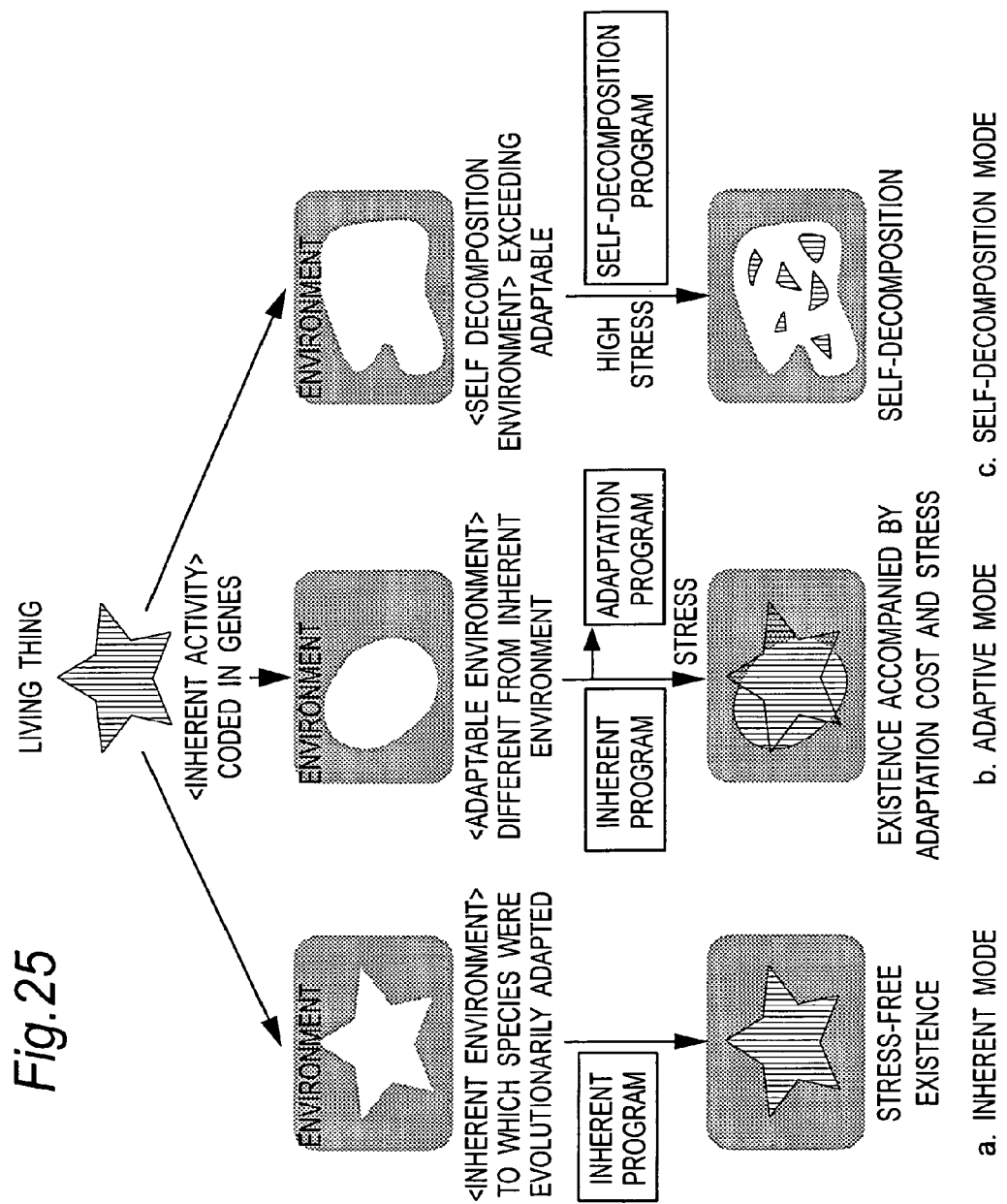
FIG. 25 is a view showing inherent, adaptive and self-decomposition models, where "a" is a view showing an inherent mode, "b" is a view showing an adaptive mode, and "c" is a view showing a self-decomposition mode.

The <original-adaptation model> itself will be explained. This is developed from an idea of <adaptation in biology> by Seiichiro Uchida and Hiroshi Sugawara, constituted by the inventors of the present invention, and advocated as a hard-core model of information ecology. In other words, a life on earth owns an activity in perfect accord with, just like a key and a keyhole, a habitat where the species was born, that is, the environment in the ecosystem which was evolutionally adapted and which becomes a cradle in which genes characteristic of the species are configured, as an <original program> in the genes and a cranial nerve system designed by the genes. The original program is started in an always operable state and operates or stands by. The environment in this case is referred to as <original environment> and an activity appearing in the original environment is referred to as <original activity> (FIG. 25a). A structure of the characteristic sound that is reverberated through the <original environment> characteristic of such a species is none other than a specific figure of the ideal sound environment coded in its genes.

When confronting an environment or a situation in which it could not live only by its original activity, a living thing awakens a series of programs which are usually dormant in the genes or the brain, by a stimulus of a stress generated at that time so as to try to continuously exist. The programs will be referred to as <adaptation programs>, activities that appear at that time will be referred to as <adaptation activities>, and time, materials, energy, and information used there will be referred to as <adaptation investments>. In addition, an environment in which the living thing can exist by this mechanism will be referred to as <adaptable environment> (FIG. 25b).

Next, there will be explained a <programmed self-decomposition model>. If a living thing is put in an environment considerably different from the original environment and cannot cover itself by a menu of the adaptation programs prepared in genetic information, then the living thing starts the same <self-decomposition programs> as those started at the time when the living thing lived out its natural life in response to a stimulus of a high stress generated there. The <self-decomposition programs> cause the living thing to stop its living activity by itself, to decompose its body, and to return the materials that constitute the living thing and the living space occupied by its body to the ecosystem (FIG. 25c). This mechanism is extraordinarily strange at a glance. However, the mechanism is actually an extremely refined and high-level existence strategy. It contributes to restoring the environment to the status quo to makes it possible to repeatedly utilize the ecosystem, accelerates evolution of living things in the system, and contributes to complicating and stabilizing the system. These series of life scientific processes will be referred to as <programmed self-decomposition>.

In this case, it is effective to introduce a mechanism in which an animal autonomously controls original, adaptation, and self-decomposition living activities in its behavior, that is, <emotion and KANSEI-basis behavioral control model>.

In other words, an emotion-KANSEI circuit functions so that if the habitat and the behavior are more original and more optimum, comfort is high and discomfort is low, and so that if adaptation degree is higher, the comfort is lower and the discomfort is higher. Thus, the emotion-KANSEI circuit forms a mechanism in which the behavior toward the original side is preferentially selected. Due to this, as long as an abnormal bias is not applied, each species lives while converging into the original environment and the optimum behavior determined by genes. However, if the species exceeds an adaptation limit and enters an inadaptable self-decomposition area, then the emotion-KANSEI circuit inverts a positive and negative phase upside down, and starts to function so that the comfort is high and the discomfort is low on the side on which self-decomposition is excessive and so that the comfort is low and the discomfort is high on the side on which the species can exist. The emotion-KANSEI circuit accelerates behaviors (such as anorexia nervosa, wrist-cutting, and particularly suicide) that drive the species to self-destruction just like a state in which a snowman tumbles down a slope.

Figure 26:
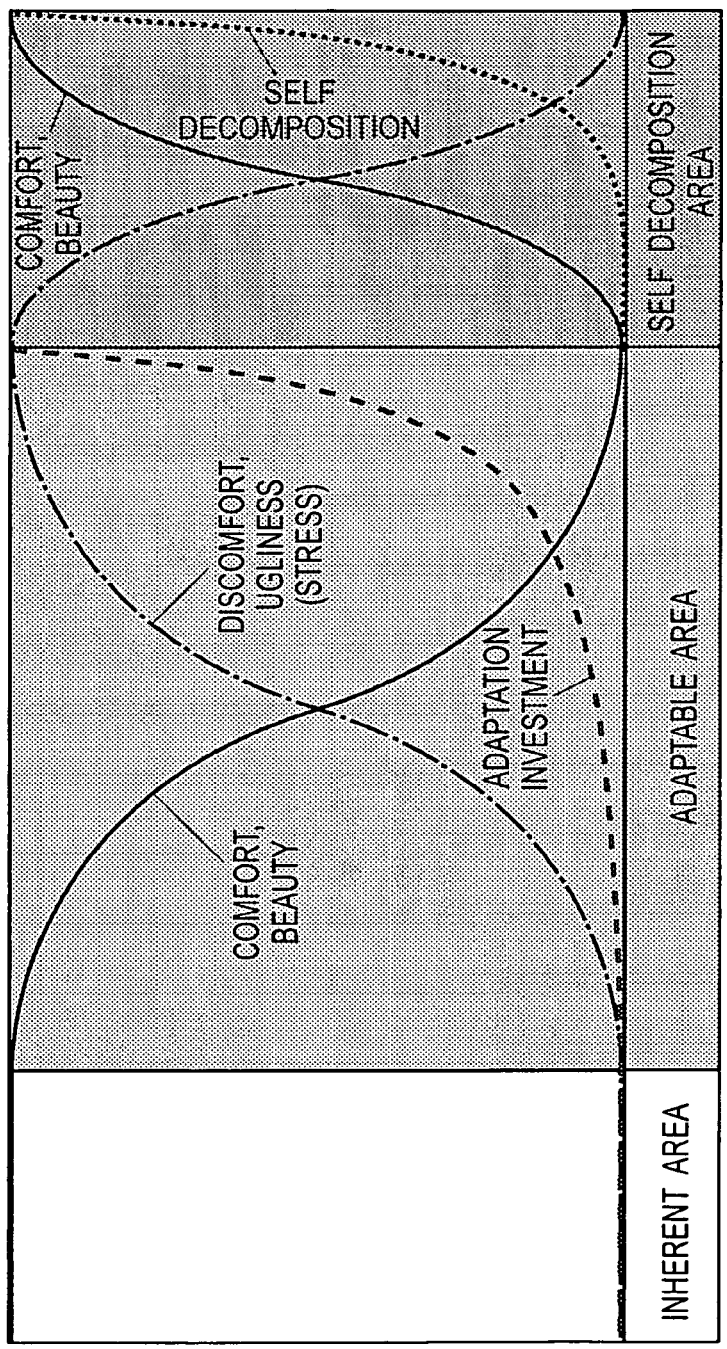
FIG. 26 is a graph showing an action control model based on an emotion and a KANSEI (sensitivity).

If the <original-adaptation model>, the <programmed self-decomposition model>, and the <emotion and KANSEI-basis behavioral control model> are connected with one another, it is possible to explain a mechanism in which in the global ecosystem, habitat and activity time are shared among species or groups to excellently realize <habitat segregation>. Thus, the connected models are in perfect conformity with the actual way of life that only each of higher animals can show with very rare exceptions (FIG. 26).

However, it is difficult for us human beings to hastily conclude where the original environment of each human is since the habitat continues to spread so widely. This solely relates to the fact that <modern human beings> genetically equal to us acquired adaptation activities reinforced unprecedentedly in history. The <civilization> originating in agriculture and cattle-breeding (primary industries) generated in this background has continued to strongly shake the entire lifestyle, including habitats, by its strong bias. If so, if people for whom civilization degree is very small to the extent that it is ignorable, and who still keep the original lifestyle to human beings can find out habitats selected autonomously according to the <emotion and KANSEI-basis behavioral control> in a non-biased and natural state, they will become hopeful candidates of the <original environment> coded in our genes.

2. Needless to say, such a solution of a riddle should be made carefully not by depending on a single approach but by combining a plurality of approaches different in dimension. The inventors of the present invention set and considered approaches such as brain evolution, human paleontology, and movement and brain reaction of existing human beings. It appears that this challenge could lead to a lucky solution.

Figure 27:
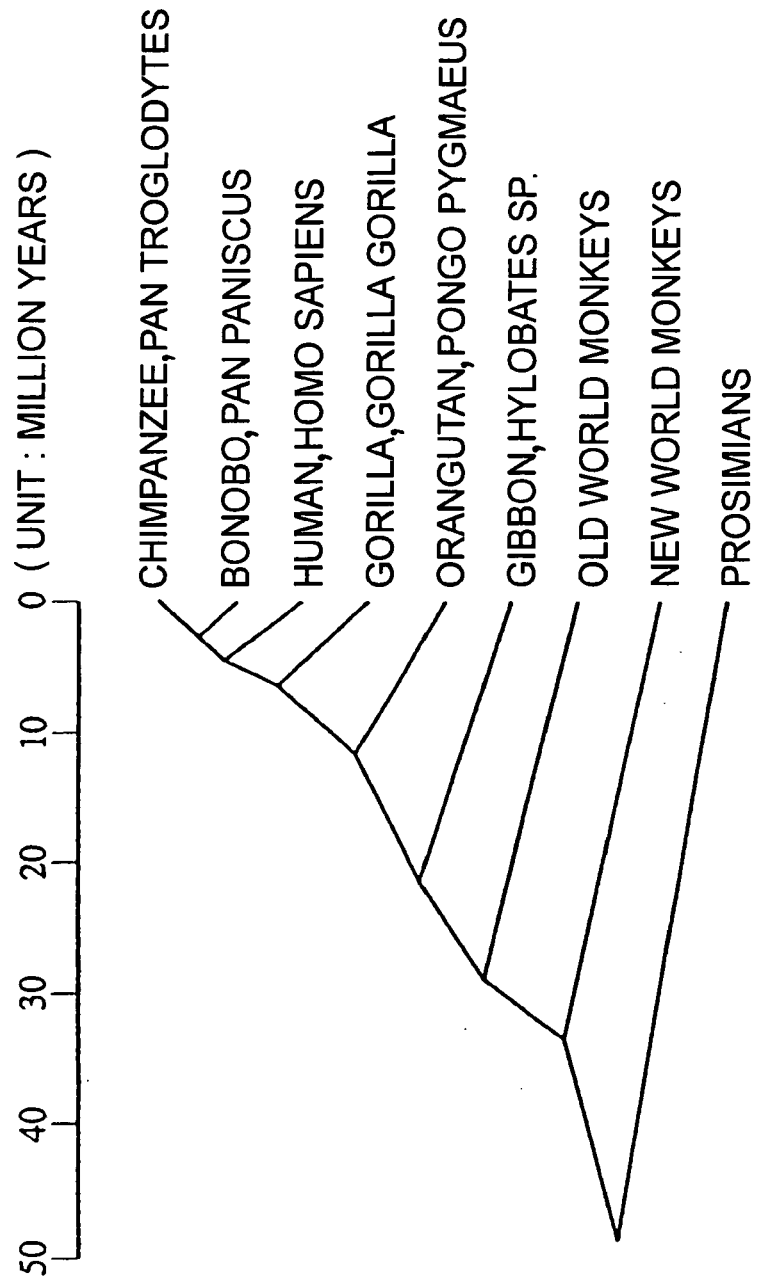
FIG. 27 is a view showing a phylogenetic tree of Primates.

First of all, the relationship between an evolutionary construction of the brain including a sensory nervous system and acting as a life information processing apparatus and the environmental information structure of the natural ecosystem which functions as a cradle or a shipyard of the brain will be considered, although this approach may not be the talk of evolutionary biology (note that as for the relationship between a society information environment and brain evolution, <Machiavellian intelligence hypothesis> written by Richard Burn et al. has been known). As indicated by latest DNA analysis, we belong to the group of great apes on an evolutionary family tree and, in a wider framework, belong to primates. When compared with emergence of the first animal about six hundred million years ago and with emergence of the first mammal about two hundred million years ago, primates emerged very recently or about seventy to fifty million years ago (FIG. 27). The arena of the emergence and evolution is an arboreal environment in a forest ecosystem in which Gymnospermae was replaced by Angiospermae on the boundary between the Mesozoic and the Cainozoic. The animals having a new concept produced by this new ecosystem which must have reached unprecedented richness and complexity on the global environment both in terms of quality and quantity are none other than primates. It is necessary to take due care about the fact that a basic design recognized in developed hands and feet, the visual system that enables stereopsis, the refined auditory system, the explosively enlarged cerebrum that serves as a control center therefor, and the like, is extremely effective as an evolutionary adaptation strategy for the forest ecosystem that embodies the information environment having the highest information density and the highest complexity on earth. To this end, the inventors of the present invention intend to highlight the definiteness of the information environment as a factor for the evolution and the screening comparable to material and energy environments in the ecosystem which is an evolution adaptation target or <a model> in the evolutionary adaptation substantially engaging in developmental DNA recombination.

From this point of view, it is an undoubtedly a natural consequence that the ancestors of giant apes (orangutan, gorilla, human, bonobo, chimpanzee) who developed brains, as a center of an information processing apparatus, at the largest degree in the forest ecosystem about twenty million years ago, with tropical rainforests that reach the top of the forest ecosystem in abundance of information serving as a cradle, emerged as a forerunner of evolution of primates. From this, the ecosystem having the most complicated information environment on earth, namely, the tropical rainforest surfaces as the prominent candidate of the model of the human's brain evolution.

3. In an area of the paleontology, the view that humankind originates in a savanna according to a classical model or so-called "East Side Story" advocated by Yves Coppens is well known as to from what natural environment humankind emerged. According to the view, a west wall of the Great Rift Valley protruded in Eastern Africa about eight million years ago. Following a change of an east side of the west wall from a tropical rainforest to a savanna due to a precipitation reduction, great apes evolved in a west-side tropical rainforest and were urged to be bipedal in the east-side savanna, and human beings emerged. This view once gained support as the most prominent hypothesis. However, thereafter, it made it clear by paleoenvironmental science that the east side of the Great Rift Valley was changed to the savanna two million years ago at the earliest. In addition, the emergence of human beings is about seven million years ago according to fossils (*Sahelanthropus tchadensis*, unearthed in 2001) and about five million years ago according to mitochondrial DNA analysis (calculation on assumption that divergence between orangutan and gorilla is thirteen million years ago). Inconsistency thus occurred. Further, evidence is not still provided that African apes spread differently between the east side and the west side of the Great Rift Valley. On the other hand, as to the origin of bipedalism, it was pointed that *Orrorin tugenensis* discovered in Kenya in 2000 and estimated to be about six million years to five million eight hundred thousand years old was adapted to arboreal life according to the shape of upper limbs and to bipedalism according to the shape of lower limbs. The discovery made it difficult to connect evolution to savanna. *Ardipthecus Ramidus* estimated to be about four million four hundred thousand years old, and famous *Australopithecus afarensis* fossils of which suggested bipedalism and which existed about three million five hundred thousand years ago are estimated to be bipedal at least in a forest environment although it is unclear if the forest is a tropical rainforest. From these, it was difficult to conclude that human beings and the bipedalism of human beings originate in the change to the savanna. Furthermore, the discovery location of *Sahelanthropus tchadensis* unearthed in the Republic of Chad in the north central region of the African Continent, and as old as any hominid fossil to date, ended the East Side Story certainly as "story". This is because Toros-Menalla where *Sahelanthropus tchadensis* was unearthed is far on the west of the Great Rift Valley, that is, the west side thereof.

4. As a matter of fact, attention is to be called to the fact that the ground surface of the pure tropical rainforest is without any bushes and very suitable for bipedalism, unlike imagination. When Oohashi visited the Mbuti who enter the deepest part of the Ituri Forest in bee season, the ground of the forest and a carpet of dead leaves which was spread all over the ground, wet, and flat allowed Oohashi, who turned fifty at that time, to make a spurt. Such an experience is not very adapted to the classic scenario of the development of bipedalism and the emergence of human beings as results of changing the tropical rainforest to the savanna.

The prolonged evolutionary history of primates produced some species away from the forest environment, which is an origin of evolution, evolutionarily adapted to a new environment successfully. It is no doubt that human beings having enhanced adaptation to a level ground thanks to its bipedalism, in particular, tried to launch into grasslands such as savannas and steppes, different from forests too numerously. Human beings may have selected to return from grasslands again to forests. In this connection, from about three million years ago until about one million five hundred thousand years ago, it appears that a plurality of kinds of hominid species such as the *Paranthropus* genus, the *Australopithecus* genus, and the Homo genus existed in parallel throughout the African Continent. Further, Homo erectus emerging in Africa migrated through Eurasia and Asia from one million eight hundred thousand years ago to three hundred thousand years ago.

However, except for modern human beings still smaller in results, hominid species that went farther from the origin of the evolution were eventually extinct without leaving descendants while living checkered fortunes at various places. It appears that new hominid species always emerged from "a reactor core" of evolution somewhere in Africa. Truly, it should be an ultimately extravagant ecosystem corresponding to all dimensions of materials, energy, and information that become a cradle which receives an evolutionary vector of human beings, the most extravagant species on the history of life on earth and which enables recombination of DNAs of the human beings in a complication direction. It is suspected that it is uneasy to find a more prominent candidate than the tropical rainforest from viewpoints of the earth history.

Nevertheless, one difficult problem arises in the verification of this hypothesis. The problem lies in an extreme inadaptability between fossil studies and the tropical rainforest environment. There is no other inappropriate matter but forest leaf mold that looks like a lump of an enzyme that decomposes living bodies and that are warm and wet for formation of fossils that require miraculous conditions for keeping structures of living bodies stable and eternal time for petrifaction. It is true that such sites as the Gobi Desert and Olduvai Gorge believed to be meccas for unearthing fossils must be environments having characteristics in contrast to the tropical rainforests. However, a human being's life may be too short to find fossils of hominid species in tropical rainforests while even marvelous experts are allowed to unearth fossils only numerable times in their lifetimes on a wall of sedimentary rocks ranging over a hundred meters in Olduvai Gorge said to be a treasure-house of fossils. From an outsider's standpoint, the inventors of the present invention hope that scientific imbalance apt to leave such areas as tropical rainforests blank in fossil studies will be someday overcome.

In the meantime, the inventors of the present invention have been recently bestowed with an exquisite knowledge that fills up this blank that might be fatal to an investigation of the core of human evolution. In other words, that is discovery of the hominid fossil *Sahelanthropus tchadensis* estimated to be about seven million years old. As stated above, Toros-Menalla where *Sahelanthropus tchadensis* was unearthed is located in a north central region of the African Continent. A line extending southward from this site crosses a line extending westward from the Lake Victoria in a vast tropical rainforest belt reaching the Great Rift Valley across the African Continent. We wonder if there are few environments having suitable conditions for the cradle of the human evolution like this zone where genuine food-gatherers such as the Mbuti and the Akha still live. Because the tropical rainforest ecosystem is most abundant with materials, energy, and information on earth, the environment must accord with the basic design of the great apes or particularly that of extravagant human beings, just like a key and a keyhole. The large-scale climate change throughout the ice age introduced various ups and downs such as mixture of forests and grasslands and change of forests to grasslands to the earth. There must have been times when our ancestors continued to exist in the unadapted environments by activating adaptation activities. Despite the inadaptability, environmental conditions for permitting the existence of human beings may have maintained consecutively. In addition, for a considerably long portion of the times, our ancestors may have been blessed with the fertile tropical rainforest information environment in accord with a vector of brain evolution. Now, on second glance, hominid fossils were found at various sites surrounding the great tropical rainforest region in central Africa and satisfying conditions suitable for unearthing them. It seems as if the composition suggests that the core of the human evolution as well as the Missing Link lurks in the deepest part of the forest which declines fossil studies.

5. Attention will next be paid to the movement of <modern Homo sapiens ((Homo sapiens)=(modern human beings)) genetically equal to us. Unfortunately, a point where our direct ancestor emerged is not specified yet by studies done so far. As an alternative approach, it is effective to investigate the <original environment> coded in our genes in the ancient common habitats autonomously selected by those who continue to keep the original lifestyle to human beings at a high level and for whom a degree of civilization is small according to the <emotion and KANSEI-basis behavioral control>.

First of all, it will be considered what the environments of the habitats selected naturally and autonomously by those who live with the original food-gathering lifestyle, that is, selected under strong control of inborn behavioral programs are alike. In the environments, almost all food-gatherers in Africa, Asia, and the New World except for a few examples of the San (Bushman) who were driven away by Bantu agricultural people and who went southward in the Kalahari desert and Australian natives (Aborigines) persecuted by the Anglo-Saxons who invaded Australia follow surprisingly common lifestyles with quite similar ecosystems such as tropical rainforests and, in particular, border regions between the tropical rainforests and woodlands continuous to the rainforests. For reference, Keiichi Omoto, a molecular evolutionary biologist, noticed that the forms of the bodies and the way of life are much in common to food-gatherers in Africa, Asia, and the New World although they are further from one another in genetic distance in the genus of the modern human beings. Considering this, he conducted a study of crossing various food-gatherers (Negritos) living in the Sunda Islands. Omoto said as follows.

"Ancestors of Negritos must have lived in Sundaland. It is considered that the Sunda Islands were separated from the Asian Continent by a rise of sea level during interglacial phases twenty thousand years ago and hereafter and isolated. At last, I would like to think of why short stature happened to the Negritos. I would like to consider that their similarity to African pygmies possibly results from adaptational evolution to a common environment. The similarity may be also called "adaptational parallel phenomenon". The common environment must be the tropical rainforest. We can imagine that Sundaland used to be covered with thick forests right on the equator in a manner similar to that of the present central parts of Africa."

It is twelve thousand years ago at best that our ancestors discarded the original food-gathering lifestyle, adopted the agriculture and cattle-breeding lifestyle, and made the first step toward civilization. In other words, in the history of modern human beings that exceeds one hundred forty thousand years before them, the standard lifestyle is none other than the lifestyle of forest food-gatherers' excepting instances in which people are in a transient state or an adapted state including an instance in which people are in the process of spreading throughout the globe and an instance in which people are driven away from habitats by something else. As for the actual state, Takakazu Yumoto, an ecologist, stated as follows.

"There were people who kept living from the ancient times in tropical rainforests anywhere in the world. We can hardly find uncivilized tropical rainforests wherever we go and, if any, they are just exceptional. A species of human beings is a member of numerous animals, plants, and microorganisms that constitute each tropical rainforest. It is impossible and unnatural at all to ignore the presence of human beings in considering the tropical rainforest . . . . "

From the viewpoints of ecological anthropology, the directivity of food-gatherers who currently live on earth to the tropical rainforest type environment indicated by the <emotion and KANSEI-basis behavioral control> is far stronger than any other directivity. This fact is also substantiated by the ways of hunting and gathering performed around us standing at the apex of culture as <hobby and preference> that form a system of desire and pleasure. Furthermore, a high-performance air conditioning realized by making free use of the technological civilization as well as a convenience store readily providing life resources including various kinds of foods, and the like, may possibly be the evidence that our genes are hardly freed from a state constructed by using the tropical rainforest as a model. Granting that our genes are freed from this state, we wonder if there is no denying that the polar regions, deserts, and grasslands are not any optimum place for our genetic design.

What characteristics are kept secret in the emotion-KANSEI circuit of the brain of each of us as human beings living in the artificial environment created by contemporary civilization in the directivity toward the information environment? As for this, the inventors of the present invention gain an important revelation in a series of experiments conducted to brains of currently existing Japanese people inhabiting in the same islands at least for over ten thousand years, and tracing the history of a typical technological civilization starting from food-gathering and then through agriculture. The environmental sounds that are one powerful realm of information and that possibly strongly act on the emotion-KANSEI circuit are higher in time density (frequency upper limit) in the order of a sound of a city near a desert or a grassland, a sound of a village near a woodland, and a tropical rainforest sound. As results of examining a difference in reaction introduced to the brain by a density difference among presented sounds and a difference in <preferable levels> of listening sound volumes reflected in degrees of preference for sounds (volumes unconsciously selected by preference), it is found that the activity of the emotion-KANSEI circuit of the brain, namely, <behavioral control circuit> mainly based on a <compensation system> and the degree of preference for sound both rise as the density of the presented sound is higher and, above all, higher so as to exceed a perceptual limit (see FIGS. 39, 41, 51, and 52 for detailed description). The same tendency is recognized in an experiment about visual information, suggesting that our sensation and KANSEI direct toward the super high density environmental information on the tropical rainforest. Further, as results of examining a functional linkage among brain parts involved in <two-dimensional perceptual model of hypersonic effect>, it is found that the activity of the <behavioral control circuit> and that of a <bio-control circuit> mainly consisting of a brainstem and a hypothalamus are linked to each other. This linkage crosses a bridge between the emotion and KANSEI-basis behavioral control and the bio-control that determines whether the model is the "original", "adaptation" or "self decomposition" model. This strongly supports that our mind and our genes in turn are constructed assuming that the super high density highly complexity information environment on the sound of the tropical rain forest is the original environment.

These results suggest that even for modern Homo sapiens who emerged about one hundred sixty thousand years ago and who experienced the adaptation history to reductions in temperature and humidity caused by large-scale climate changes such as that in the Wurm glacial stage and to simplification of the natural ecosystem derived from the reductions, characteristics of their genes and brains still hardly changed from a state in which the super high density highly complexity environmental information on the tropical rainforest is cast into the genes and brains as the original environment.

6. However, a huge barrier stood in our way until quite recently in considering such a view that the genes and brains of ours, namely, modern Homo sapiens were constructed on the assumption that the tropical rainforest is the original environment. That is presence of <multiregional hypothesis> as the hypothesis of origin of modern human beings.

Until only recently, this <multiregional hypothesis> has been dominant as to where and when modern human beings were born. According to this hypothesis, <Homo erectus (group including so-called Peking Man and Java Man)> appeared in Africa about one million eight hundred thousand years ago migrated out of Africa into various regions on earth since one million and several hundreds of thousand years ago. Members of the genus evolved independently in their respective regions into various modern human beings. Assuming that a main current of the shipyard of great apes or genes of all human beings is the tropical rainforest environment, DNAs of modern human beings were created in quite diversified environments. Based on the original-adaptation model, there cannot be denied the probability that the original environment coded in genes is not limited to the tropical rainforest environment but diversified.

On the other hand, Allan Wilson et at advocated the <Out of Africa hypothesis (so-called "Mitochondrial Eve")> based on mitochondrial DNA analysis, and aroused a bitter controversy with physical anthropologists such as Milford Wolpoff and Alan Thorne who are proponents of the <multiregional hypothesis>. Thereafter, in the 1990s, Satoshi Horai et al. performed mitochondrial DNA analysis, and drew an evolutionary family tree including precise divergent epochs about females. In the 2000s, the Out of Africa hypothesis gained support from male <Y-chromosome DNA> and autosomal <micro-satellite> analyses, and repeatedly intensified. Further, in 2003, Hisao Baba et al. unearthed new Homo erectus fossils in Java, thus pointing out that an important structural index of the fossils of so-called Java Man traced an evolutionary direction inconsistent with that of Australian natives. This signifies that Thorne's "evolutionary model from Java Man to Australian natives" which was the last grounding for the multiregional hypothesis cannot be held. These made it quite difficult to maintain the multiregional hypothesis. Besides, in 2003, Tim White et al. unearthed fossils believed to oldest Homo sapiens dated back to one hundred sixty thousand years ago in Ethiopia. Any modern human fossils discovered all around the world are newer than these fossils.

As can be seen, the Out of Africa hypothesis about modern human beings has been establishing its indisputable position. According to this hypothesis, <Homo erectus> who emerged about one million eight hundred thousand years ago in the human evolution progressed in Africa widely migrated on earth until about three hundred thousand years ago and then went extinct without any further evolution. On the other hand, it is estimated that the ancestors of our <modern human beings> were born somewhere on the African Continent as a species having new genes about one hundred sixty thousand years ago, diverged maybe into several branches since about fifty thousand years ago to spread throughout the globe until present. Judging from this knowledge, the brain evolution, the movement of modern human beings, and the knowledge obtained from such approaches as adaptability between brain and sound studied by the inventors of the present invention collectively as a whole, one can support quite a high probability that the cradle of the evolution of the modern human beings is the African tropical rainforest, which is the base of the main current of the evolution of great apes and which is the core of the human evolution, or a location which is not so away from the neighborhoods of the African tropical rainforest.

We, thus created, are highly likely to have been assimilated into the most fertile ecosystem on earth for perpetual time that is nearly twenty million years if we are members of apes, that is, the tropical rainforest environment, and have coexisted with the other living things living there. In addition, we are highly likely to belong to the main current of the family tree of living things, the genes of which have been continuously recombined with a view to making themselves more complex so as to be adapted to the environment. The brain reaction of each person living in a city which has already been transformed into the vessel of civilization in the environmental information, which is adapted to the super high density and high complexity, suggests that we, as modern human beings, are still in a state of a species adapted to the tropical rainforest environment.

It is extremely difficult for us modern human beings to pick up environments other than the tropical rainforest environment as a candidate of the "original" habitat coded in the genes.

<2-2-3> Paradise in the Name of Tropical Rainforest

1. How can the tropical rainforest be defined as an ecosystem? In the Cretaceous (one hundred forty four million years to sixty five million years ago) which is an end of the Mesozoic when dinosaurs lived in splendor, earth flora went through an unprecedented and dramatic change. The change is "an incident" on Earth's ecological history that Gymnospermae (having naked seeds) such as ferns and cycads at the zenith of their prosperity were suddenly replaced by Angiospermae (having seeds enclosed in an ovary) that arrived on the scene. The force of Angiospermae was so terribly strong, and it is estimated that at the beginning of the Cenozoic when Mammalia and birds that replaced extinct dinosaurs played an active role, the new type Angiospermae already occupied about 80 percent of all plant species (96 percent at present).

The old type Gymnospermae mainly depends on wind as a method for diffusing pollens and seeds that carry DNAs. Since this method (anemophily or wind dispersion) limits a dispersal range of descendants, there tends to be created an ecosystem like a coniferous forest in the Frigid Zone where plants of same kinds monotonously grow in crowds. Angiospermae, by contrast, depend on such animals as insects, birds, and mammals for DNA diffusion and extraordinarily amplify the dispersal range. Since this method (zoophily or animal dispersion) mutually distribute other descendants into a wide range, there tends to be created a complicated ecosystem in which many species are mixed up. With plants cherishing new activities playing a main role, a highly advanced and organic ecosystem consisting of huge-scale living things from microorganisms to primates in both quantity and quality was created. After all, the ecosystem which is most fertile on the earth and which reached the climax of evolution while repeating unique polishing is none other than the tropical rainforest.

The living things setting such tropical rainforests as their original habitats are destined to live as those blessed with the most luxurious environment on earth in terms of both materials and information. At the same time, this suggests that the tropical rainforest can be the cradle of evolution which can grow the most complicated and most advanced lives structurally and functionally. In fact, all the apes currently positioned on the top of animal evolution have lived in the tropical rainforests and their vicinities, whether they are Asian apes or African apes. Modern human beings prior to the industrialization are not any exception. There is a high probability that we were originally derived as parts of the tropical rainforests.

Referring again to the <original-adaptation model>, if the tropical rainforest is the original habitat for us, we must be able to live depending on activities based on the programs original to human beings, constructed autonomously in the living bodies, and always operating or being in a standby state in that environment except for special circumstances. What is believed to be the thus realized lifestyle original to human beings can be recognized in high-purity food-gatherers still living in the tropical rainforests. The lifestyle is realized in a form of <food-gathering> in which people only hunt and gather abundant living resources in the name of the grace of the forest fostered by the ecosystem.

On the other hand, as the destiny of life on earth, if put in an environment different from this original environment, human beings cannot live only with the original lifestyle, either. In order to correct the gap between the living activity original to human beings and the environment, it is necessary to activate the <adaptation program> normally dormant in his or her brain or genes by a stimulus of a stress resulting from environmental incompatibility, actualize a special activity, and try to adapt himself or herself to the food-gathering life in the original forest environment. In order to do so, it is required to invest materials and energy for the adaptation and to use excessive time. In addition, if the gap between the living activity and the original environment or life is so high as to exceed a limit and no adaptation program for overcoming the difficulty is present, then the <self-decomposition program> is activated in turn and the human beings are to follow a decomposition and liquidation process physiologically and behaviorally on their own.

In this model, the civilization history of modern human beings coincides with their lifestyle quite interestingly. Forest people living in the tropical rainforest that is the original environment to human beings may well directly hunt and gather necessary foods from the forest where they live according to the lifestyle original to human beings, as already described above. In principle, it is unnecessary for human beings to artificially increase or grow the foods but the forest itself produces and grows them. Therefore, as long as the ecosystem is healthy, people can always acquire them sufficiently.

However, those who have discarded forest and moved their habitat into an environment in which such benefits are unavailable have to artificially produce and grow foods which would have been given automatically by the forest. In order to do so, they take the trouble to conduct <adaptation behaviors> such as agriculture and cattle-breeding, which are originally unnecessary, and live while producing foods having the closer effect as that of those which people ate at the time of living in the forest. In compensation for this, it is necessary to excessively use materials, energy, and time. We call this adapted lifestyle "the primary industries".

In phases of the mining and manufacturing industries which are the secondary industries built on this structure and further advanced industrialization after the tertiary industries, the gap between the forest environment and the lifestyle further widens and adaptation energy rises steadily. For reference, it is estimated that an entire energy quantity which one genuine Mbuti in the Ituri Forest requires per day is about 3500 kilocalories. In the highly industrialized society where we live, by contrast, an energy consumption amount of one person per day exceeds several hundreds of thousand of kilocalories and possibly exceeds even a million kilocalories.

Surprisingly enough, it can be interpreted that the goal which the contemporary society that has reached this advanced adaptation level pursues with the help of technologies accompanied by vast energy investment, and which begins to be partially achieved at quite a high level is to approach the environment and life in the tropical rainforest as closely as possibly as far as the dimension of materials and energy is concerned. As a typical example of this, one can consider a remarkably luxurious air-conditioning system that is complicatedly controlled to adjust temperature, humidity, wind fluctuation, ion composition, and even concentrations of physiologically active chemicals such as phytoncide. That is eventually nothing but a high-level approach to the atmospheric environment characteristic of the tropical rainforest such as the Ituri Forest. Further, providing that there is no register for paying money, the manner of procuring a variety of living materials from a nearby convenience store is fabulously similar to the food-gather's behavior of gathering benefits of abundant forest in the neighborhood of his or her habitat in order of preference. On one occasion, Tsutomu Oohashi, who returned from the life of the Ituri Forest where he lived with the Mbuti to Japan and who noticed these surprising realities, could not help rearranging his own concept and his sense of value fundamentally thereafter.

Actually, such examples of similarity and approach as the air-conditioning system and the convenience store are available as many as one wishes. Considering these, the inventors of the present invention cannot help but believe that technologies of which the modern civilization can boast must be the system of adaptation behaviors in which people far away from tropical rainforests intend to make their lifestyle similar to the original environment and life of the forests with guide by the genetic program.

These realities strongly suggest that DNAs of modern Homo sapiens have no change at all in a state in which the forest life is set as the original life. It is true that traces of various adaptive radiations can be recognized in habitation environments, lifestyles, statues, skin colors, and the like, of modern human beings after they started agriculture and cattle-breeding. Nevertheless, genes of modern human beings who continuously improved their functions that do not depart from the main current of the evolution of apes and that make use of the forest environment for such an eternal time of close to twenty million years from the origin of the great apes or five million years or more from the divergence from chimpanzees must have hardly any time of rewriting genetic information on the backbone of existence such as the original habitat and lifestyle in the time frame of industrialization of only about ten thousand years since a part of modern human beings discarded the original life in the forest. This fact also supports our model created on the assumption that the standard of the environment and the lifestyle preset to human genes is the life of food-gathering in the tropical rainforest.

According to the <emotion and KANSEI-basis behavioral control model>, when each human lives the life of food-gathering, which is the original lifestyle, in the tropical rainforest, which is the original environment, he or she must be in a state in which the degree of comfort is the highest and the degree of discomfort or stress is the lowest. As repeatedly described for the comfortableness of the tropical rainforest, in terms of the lifestyle, the original living behaviors, namely, hunting and food-gathering, coded in human genes are accompanied by a desire and a pleasure that may be preset to DNAs. Obviously, human beings are induced by an emotional and sensible compensation, that is, a response to pleasure and beauty to be willing to do the behaviors of hunting and food-gathering. Even if these behaviors are accompanied by occurrence of substantial burden, pain or danger, they basically remain in the sub position and are very rarely given a higher priority than the hunting and food-gathering.

There are many excellent materials that suggest the probability that the correlation between the behaviors of hunting and food-gathering and the emotion and KANSEI is based on an original program universally preset to human beings. Examples of these include presence of the hunting as a hobby similar to a sexual behavior of a male animal in that the powers or the riches of all ages and cultures who acquired self-will of high-level behavior spend their money, use their ingenuity, sweat freely, and search for hunting targets regardless of running a risk, and presence of enthusiasm toward the hunting of female customers who are rushed to bargain sales of department stores, which excels a view of necessity. Any of these examples quite reveals the possibility.

Next, as the degree of dependence on the adaptation program is larger to be away from such an original environment and an original lifestyle, each human finds himself or herself that the comfort is lower and the discomfort is higher. It is true that if the human beings start engaging in the primary industries, they are forced to excessively perform many adaptation behaviors such as agricultural works and breeding of domestic animals which were not necessary in the original lifestyle in forests. In this adaptation behavior called "labor", a cycle of smooth and happy occurrence and success of the desire and the comfort as coded in genes as acquired in the food-gathering and hunting is not expected except for partial or accidental one. Furthermore, the burden and pain are dominant with quite a high degree, and the tendency of controlling behaviors based on emotion and KANSEI of "I do not want to select it" becomes conspicuous. This tendency is nothing but an environment inadaptability response both in nature and society. For reference, generally in the human society that turned into the adaptation mode of industrialization, bias apparatuses designed using various "carrots and sticks" such as "the power", "the class", "the honor", and "the economic value" for forcing people to do such disliked labors have been developed in order to resist the natural behavioral control mechanism based on the emotion and KANSEI to avoid the labor, that is considered to be more uncomfortable than the hunting and food-gathering. Configurations and maintenance of these apparatuses, control over discords that occur to follow, and the like further increase the adaptation stress and adaptation investment.

In the industrialized society after the secondary industries built based on such primary industries, the separation of the originality in the realm of the information environment tends to be more dramatically accelerated in place of approach to the originality in materials and energy, which tendency continues at present. This may suggest that the inadaptability between the human emotion and KANSEI and the information environment nears its limit or often exceeds the limit, and enters a realm in which the <programmed self-decomposition> is activated. A decomposition mechanism introduced by the self-decomposition program basically consists of decomposition of cells by hydrolase in case of a unicellular organism. However, the evolution of lives also causes evolution of this mechanism, so that the mechanism in human beings has been quite complicated, diversified, and become finer. In short, these are <gene-determining common diseases>. More concretely, they include a wide range of diseases such as <life-style related diseases>, e.g., cancers and diabetes, <psychosomatic disorders>, e.g., a gastric ulcer and asthma, <mental and behavioral disorders>, e.g., depression, schizophrenia, abnormal violence, and eating disorders, and <development disorders>, e.g., autism and childhood chronic fatigue syndrome. These models similarly apply to the actual facts with which we are confronted. As for the sound environment, we cannot help calling attention to the seriousness of the problems.

2. It is essential for a higher animal that has unprecedentedly increased self-will of behaviors to function to not only secure the originality to decrease the adaptation degree but also monitor the information environment so as to avoid entering the self-decomposition region. Sensory and sensible systems responsible for these functions diverge widely. Among the divergent systems, the <auditory system> that remotely receives <sound> serving as an ultimate message carrier from the environment and that continuously and totally senses the ecosystem undoubtedly plays one central role. This monitor system gives relaxation and serenity in the sense of comfort in the rich sound space original to human beings and spreading in the tropical rainforest. If a person moves into a sound space having a structure apart from that of the human original sound environment, then the sense of comfort decreases and stress increases. This generates a motivation to intend to return to the original. Finally, using the sound environment as one clue, the human behavior must have been induced to the original region. If this is not realized, the person will be instructed to conduct the adaptation behavior of avoiding the environmental sounds far away from the original ones as much as possible and of acquiring something that can replace "irreplaceable sound" missing from the original sound environment. The inventors of the present invention wonder if almost all approaches for enlargement of various acoustic and music industries and improvement of the sound environment characteristically recognized in the modern society belong to this category of adaptation behaviors.

Furthermore, as the problem to which attention should be particularly paid in association with the programmed self-decomposition model, it is necessary to consider an instance in which the emotion and KANSEI determines that the separation of the sound environment from the original sound environment is so great to exceed the adaptation limit and the incompatibility cannot be overcome. This is because there is no grounding at all that only <sound environmental incompatibility> can be excluded from factors that activate the self-decomposition program that is active in this situation. Rather, it is at least safe to think that the very sound plays a principal role of notifying human beings of the environmental incompatibility as the ultimate message carrier from the environment and highly likely pulls the trigger of the self-decomposition.

<2-2-4> Reference to Sound Environment Original to Human Beings

Sound ecology establishes the paradigm in which the sound reverberated through the tropical rainforests is assumed as the standard of the sound environment original to human beings, and utilizes the paradigm. With this, it is possible to open up a new way to approach sound, human beings, and the environment, the grounding of which is the clearest ever, and which is expected to produce an effect. This is because the paradigm can provide us with a concrete and comprehensive entity existing as a reference to an optimum sound environment coded in human genes. The presence of this reference, which corresponds to natural foods that gave actual results in case of materials, makes it possible to scientifically compare the actual sound environment artificially produced with the standard of the promised sound environment. This, in turn, enables us to accurately grasp the compatibility or the separation between a specific sound environment of interest and the human beings. It is possible to define "which sound to leave, which sound to spread, and which sound to increase" as advocated by Murray Schafer in terms of life science and information science. It appears that the reference or <standard> having such functions is an unprecedented one in various approaches made thus far for the harmony among sound, human beings, and the environment.

Needless to say, the existing sound space of the tropical rainforest is exposed to considerable diversities. However, it is no doubt that an inherent and universal structure clearly different from that of the sound space of the city is provided in the space according to investigations actually made by the inventors of the present invention. Accordingly, by setting appropriate parameters, it is possible to grasp a phase of the sound structure that is at least significant, and even essential, for human beings. It is also possible to analytically compare it with actually present various sound environments. Based on this comparison, a wide view can be opened in which one can scientifically analyze the relation between the physical structure and information structure of the sound space and life scientific effects of the sound space, create means for solving problems, put the means to practical use, and evaluate the effectiveness of the means.

However, this approach is accompanied by considerably heavier burden and constraint in study means and validation procedures than the previous approach of dealing with the harmony between the sound and the human beings. Development of a super-high sensitivity and super-high accuracy recording and analyzing systems, global-scaled field work using these systems, physiological experiments mainly focusing on analysis of brain functions, and the like, in particular, requires both hardware and software-related measures that go beyond frameworks of equipment and methods employed thus far in various aspects. In addition, following grasping the sensory and sensible reactions within the scientific framework, a strong, esthetic, and artistic approach is required in a state highly integrated with natural scientific logic and validation and up-to-the-minute technologies. Besides, operations are required while considering verifiability, falsifiability, reproducibility, statistic significance, and the like, both theoretically and practically. Furthermore, there are newly generated unprecedented burdens such as increase of constraints, suppression of self-will, and submission of substantial evidence ensuring reproducibility derived from these conditions.

However, results that sufficiently compensate for these burdens, particularly effectiveness, reliability, rationality, objectivity, accuracy, and the like, are considerably enhanced. They certainly not only widely deepen and expand knowledge on basic sciences but also guide us to effective and safe means and methods having a clear distinction from the conventional means and methods for solving and clearing the problems and produce effects of the means and methods.

As the most fundamental step for starting such an approach, attention is paid to the <physical structure> and the <information structure> of the sound environment among the stereoscopic approaches that capture sound environment, and there will be roughly considered again the difference between the sound environment original to human beings and expanding in a tropical rainforest and that of a contemporary city largely distant from the tropical rainforest.

One can consider the most fundamental sound pressure level in the physical structure first. The sound level of the tropical rainforest has a structure with its baseline smoothly changing with gentle ups and downs at so consistently high level that it is rarely below 60 dBA. The sound level of the town is characterized by having irregularities from a level almost close to a soundless level to an extreme level of volume, and by being distributed discontinuously with cutting off the time spatially. That is, the human original sound reverberated through the forest extremely differs from the town sound in the structure of the sound pressure.

Next, there will be compared the time densities of the respective environmental sounds in the frequency distribution. The forest sound abundantly includes ultra-high frequency components that exceed the upper limit of the audible frequency of 20 kHz and often exceeds 100 kHz. The town sound shows a structure, at almost all points except for proximity to sound producing sources, in which power is offset only toward the low frequency side from about ten kHz. Further, there will be compared the manners in which frequency spectrums of the respective environmental sounds change in the microscopic time region. The forest sound reaches high complexity in that the structures of details of the spectrums are full of fluctuations and continuously change with the passage of time. The town sound only shows a monotonous structure in which sudden abnormal spectrums sometimes appear in repetition of a flat waveform lacking in fluctuation. As can be seen, the structural difference which may be nearly ultimate is seen between the forest sound original to human beings and the sound of the town where they live already at the most fundamental level of physical structure (FIGS. 3 to 10, and 15 to 18).

While attention is paid to the difference in information structure between the forest sound and the town sound, the difference will be considered from the hierarchical approaches of <concreteness>, <symbolic representation>, and <connection>. The forest sound has a structure in which a baseline as firm as a rock on which high continuity concrete information is never cut off while having detailed structures complicated and abundant in change is built, and which is inlayed with symbolic information transmitted from animals. In addition, sign connected sound information almost limited to human words and music is distributed in a far smaller range than those of concrete and symbolic sound information even in a human living region from which the sign connected sound is transmitted.

In the town sound, by contrast, distribution structures of information on these three hierarchies differ discontinuously according to temporal or spatial positions and are diversified. In most cases, mechanical noise the structure of which is unclear overflows; otherwise, discontinuously connected information generated artificially is dominant. In the town sound, one can recognize a structure almost inverted from that of the forest sound. That is, even from the aspect of the information structure, the difference between the forest sound and the town sound is so great that it is impossible to easily find common characteristics to both the sounds.

The forest sound and the town sound will be compared more comprehensively. First of all, as for a macroscopic structure that can be sensed and that can be explicitly grasped, that of the forest sound environment is in one continuous spreading form as a whole while showing abundant variations according to parts. The macroscopic structure of the town sound is in a form of a collection of fragments numerously divided in time and spatially, and different from each other in quality. Accordingly, from the viewpoint of the macroscopic time space, the forest sound shows a simple structure which is uniform and in which it is difficult to recognize changes whereas the town sound shows an extremely changing structure in which the overall structure of the sound totally changes according to time and locations. However, this relationship is inverted when attention is paid to a microscopic region constituting detailed parts of the environmental sound at interval of one meter or less spatially and one second or less temporally. In addition, while the forest sound is characterized by super-high density, complexity, and changes of the density and complexity, the town sound is characterized by low density, simplicity, and monotonousness with smaller changes.

As stated above, the consideration framework which is established by sound ecology, and in which the tropical rainforest sound is regarded as the reference to the sound environment original to human beings, provides new approaches of analysis to huge and extremely confusing problems related to the destruction of the harmony between the sound environment and human beings, namely, the problems with which the contemporary society is confronted. The framework opens up particularly the way of objectively grasping the separation between the original sound environment adapted to human beings and the town sound environment. In addition, the framework converges the separation between them into a diagram of [super-high density, high complexity, and changeability of the forest sound] versus [low density, simplicity, and monotonousness of the town sound] at the microscopic level as well as [continuity in the forest sound] versus [discontinuity in the town sound] in the macroscopic level.

The original-adaptation model will be applied to this diagram. If so, the original sound environment adapted to human beings is characterized by the complicated structure which is macroscopically continuous and which microscopically has a high density and a transfiguration. The sound environment of the contemporary city is, by contrast, characterized by the structure which is macroscopically discontinuous and which microscopically has a low density, simplicity, and monotonousness. In the diagram, the fact that the sound environment of the contemporary city is in a directly opposite position to the sound environment coded in human genes is drawn without any room for question. Thus, a composition surfaces in which we are notified that the great separation of the urban sound environment from the original sound environment in the physical and information structures causes the incompatibility between the sound environment of the contemporary city and the human beings. From this new recognition, there is provided an approach of searching and reconstructing the adaptational relationship between the sound environment and the existence of human beings while attention is particularly paid to the continuity of the sound space macroscopically and to the density, complexity, and changeability microscopically. This approach makes an epochal advance in the acquisition of new knowledge and also provides unprecedented and strong means particularly for solving actual problems.

<2-2-5> Angles of Approach to Sound

1. There will be outlined again angles of approach as to how to decode the <sound> itself which is a concrete target which sound ecology challenges.

A remotely acceptable virtual message carried by the ultimate message carrier from the environment, namely, <sound> is formed into an encrypted signal, and the meaning and content of the message are not revealed until the signal is decrypted based on a codebook buried in us. A part of the sense of sound formed through the auditory system is compared with a group of high-degree messages (a meaning recording memory) stored in the brain. In addition, there is proceeded an information processing for listening and recognition such as "murmurs of trees", "murmurs of a brook", "singing of birds", "cries of intimidation", "words of love", or "songs praising Gods". This processing includes a process of entering an area of the higher brain function that controls reason and KANSEI. In the course of this processing, there is widely seen a phenomenon that evaluates the sound itself based on its biological value structure such as whether it is "comforting or discomforting" in terms of KANSEI and whether "beautiful or ugly" in terms of sensation.

The codebook that decrypts the message and that functions during this processing can be considered to consist of three types of codes. The first type is "a <read-only> code inherent to each species and present inherently and universally", such as the code for the voice of intimidation. The second is "a <write-once> code inherent to the society and culture where a person was born and grew up, universal inside, inserted in childhood, and then fixed thereafter", such as listening to his or her mother tongue. The third is "a <random-access> code always rewritten for each individual" such as the way in which the person hears the sound of an unfamiliar person who the person passes on the street. In addition, the codebook has a double structure of <physiological codes> that roughly include an area in which the process or results of the decryption is hard to be conscious of and <sensory and sensible codes> or <psychologically recognizable codes> that constitute an area in which the process or results of the decryption tends to be conscious of as a part of the code.

The process of receiving and decrypting the sound complicatedly hierarchized and divided provides a net of close interaction spread over appropriate portions but also deepens the correlation among various other sensible processes including a visual process.

As means for grasping the message carried by the message carrier or sound having such a complicated and variegated organic structure as accurately as possible, the inventors of the present invention prepared for three structures relevant to one another but largely different in characteristics, and configured the approach that associates them with one another. The three approaches that decrypt the sound environment are <the physical structure>, <the information structure>, and <the response structure>.

2. The most fundamental or first angle of approach is the angle of the <physical structure> that is a vibration phenomenon which the sound itself always owns as its nature. If being inquired into, the sound is equal to a physical phenomenon called an "elastic wave" which mainly uses the air as a medium. The messages carried by the sound are all filled with the physical phenomenon of vibration. On the side of a life, reception of the sound starts at "reception of a vibration". The physical phenomenon named "vibration" is a very origin of the approach to the sound and an ultimate return point.

If the air is used as the medium, the sound is the phenomenon, namely, low-density wave the pressure of which is spatially spread while continuously fluctuating with the passage of time. Therefore, by tracking a trace of a pressure change serving as only one indicator on a one-dimensional time axis, a manner of the sound at a measurement point can be drawn. In order to set various indicators for the basic characteristic or temporal change of this sound pressure (amplitude) to extract constituent factors, to quantify each of the factors or to deduce equations to process each factor mathematically, and to "visualize" each factor have been developed as central means for acoustics and are recognized at present as such.

The most general indicators among them are the <sound-level meter> measuring the magnitude of an environmental noise and the <sound level> based on which the noise is measured. As a basis for these indicators, a unit called a sound pressure level (SPL) that represents an energy carried by the low-density wave of the air by logarithmic scales of decibels (dB) has been known. A unit obtained by adding a weight to the sound pressure level in consideration of nonlinearity of the auditory sense of each person due to a difference in the frequency of sound is the <sound level (dBA)>, and a temporal average of the sound level (dBA) is <equivalent sound level <$dBL_{Aeq}$>, both of which levels are widely used as international standards.

The most direct and concrete, namely, least symbolic approach for visually grasping the physical structure of the sound may be a time waveform obtained by converting the temporal change of the air pressure at a certain observation point, that is, the invisible phenomenon of the sound pressure or amplitude change into an electric signal, and by displaying the electric signal on a cathode-ray tube of an oscilloscope. However, not so many regularly-ordered sounds proving the effectiveness of this method are present as sound environments existing in the natural world. Almost all of the respective sounds that are actually present have complicated structures in which vibrational components having different frequencies and different strengths coexist except for the artificial sound concretely made electronically or mechanically. Even the sounds magnitudes of which are indicated equal according to the sound pressure level meter boundlessly differ in content such as "the sound concentrating on a single frequency", "the sound divided at several frequency points", and "the sound spreading over entire frequency", and properties of which differ accordingly.

In order to catch an overall image of each of these sounds, the scale or the sound pressure level that pays attention only to the magnitude of the sound is too simple, and a graph that shows the relationship between frequency and sound pressure power, namely, a frequency power spectrum is effective. However, as compared with simple measurement of the sound pressure, the measurement of the spectrum is quite difficult. For this reason, methods for dividing the frequency into predetermined bandwidths and for calculating a power average within a certain time for every divided frequency bandwidth such as an octave band analysis method and a method using a spectral analyzer have been widely used.

Moreover, it is more appropriate to recognize the power distribution over the entire frequency without any intermissions instead of dividing the frequency into the frequency bands. In order to do so, normally used are the means for visualizing and decoding the characteristic of the sound space such as the environmental sound which is irregularly changing with various vibrational components mixed up, as a sound pressure distribution without any intermissions on the frequency axis, namely, the continuous spectrum. As for these means, a frequency analysis method and its variations provided in the background of development of the algorithm for the fast Fourier Transform (FFT) and that of computer technologies play a central role as sound visualizing means. Further, as for the verbal sound having the discontinuous chain structure, <sonargram> that shows discrete spectrums of the verbal sound while connecting them on the time axis is widely put to practical use.

However, each of these methods is intended to show the frequency spectrum by averaging certain time on assumption that the sound is a stationary sound. Naturally, if observation time is shorter as compared with a waveform cycle, error greatly increases.

Considering this difficulty, in order to analyze a sound considerably short of the stationary state, for example, a temporary sound such as an explosive sound, there has been developed an analysis method based on a function system which does not use a sinusoidal wave and a cosine wave as bases such as a wavelet function. However, the wavelet function has a sudden increase from zero and a convergence into zero, so that the function does not appear adaptable to the continuously flowing sound such as the environmental sound.

Currently, the main methods for visualizing sound are divided into two, namely, the analysis method adaptable to quite stationary sounds and the analysis method adaptable to quite non-stationary and temporary sounds. It is difficult to draw the sound having the characteristic as that of the natural environmental sound that continuously changes with passage of time so as to faithfully reflect its actual state in the drawing. In order to overcome such a limit, the inventors of the present invention developed an ME spectral array method (MESAM=maximum entropy spectral array method) for visualizing the temporal transfiguration of the sound structure based on the maximum entropy method developed by John Parker Burg in the field of earth science and on an autocorrelation analysis method developed by Hirotsugu Akaike in the field of industrial chemistry. Using this MESAM, it was possible to draw a fluctuating state of the entire spectrums in the microscopic time region.

Murray Schafer said, "many experts involved in study of sound today such as acousticians, psychologists, and audiologists are not at all skillful in all dimensions other than vision for the sound. They only read sound from what can be seen", "acoustics is now merely a science of reading what is seen", and "all visual projections about sound are arbitrary and false". There is certainly some truth in what he said.

However, these do not substantiate that there are lack of raisons d'étre in measurement and visualization of the physical structure of the sound. As for the phenomenon that is imperceptible but measurable, presence of measurable materials were made light of because it was imperceptible and harshly retaliated by the global environment in a stage of the material civilization. Examples of the retaliation are too many to enumerate. They include Minamata disease resulting from neglecting emission of methylated mercury which is colorless, tasteless, and odorless, and which does not show any toxicity even if it is temporarily taken by a substantial amount. There is no knowing how many sound structures in which it is difficult to replace a sensory response by consciousness such as a fluctuating structure of Shakuhachi sound and in which it is difficult to grasp by the auditory sense such as <hypersonic effect> are present among those having some influence on human beings and measurable as physical quantities. Based on this fact, it is emphasized in sound ecology to keep an approach attitude in which the sensation and KANSEI and the physical measurement are closely associated with each other.

3. The second angle of approach to sound is the angle of the information structure. As for this, classification according to <<hierarchical structures>> and that according to <<transmission functions>> are prepared and utilized depending on problems.

First of all, as the hierarchical structures, sounds that reach our ears include some which are audible temporally continuously but each of which has an inaudible independent unit structure internally. On the other hand, a chain (a module) of sounds each of which has a temporally intermittent, discontinuous, and finite length. These sounds are hierarchized into three information structures categorized as <concreteness>, <symbolic representation>, and <connection>.

The <hierarchy of the concrete information structure> includes, for example, a so-called "whisper of the wind among the pines> that is audible when water is boiling in a high-quality teakettle, and an oscillating sound of a sinusoidal wave at a specific frequency, which is electronically generated in an acoustic laboratory. In other words, sounds in this hierarchy correspond to those carrying information in a state in which sounds similar in quality continue for arbitrary time during which the sounds are continuously audible without any discontinuous breaks. Needless to say, it is possible to continuously change pitches, intensities, tones, and the like, of these sounds according to a change in a generation state or a conduction state without any interruptions. The overall information structure of such sounds consists of the physical phenomenon of the aerial vibration, namely, a signal that is not accompanied by any symbolic representation per se, and the overall concrete and comprehensive structure of the sounds carries all pieces of information. In other words, the entity of the existing specific vibrational phenomenon cannot be separated from the information which the entity includes. In addition, these sounds have various physical and information structures according to angles of the approach. These sounds will be referred to as "sounds having a concrete information structure completed at entity level (concrete sounds)".

Strictly speaking, it is difficult to code information having such a concrete information structure into a discrete sign. Due to this, it is often effective to discriminate the information having the concrete information structure from codable information such as symbolic information and verbal information, and to classify the concrete information structures into <uncodable information structures>, <experienced information structures>, <non-communicable information structures>, and the like. In the transmission of the information carried by sound depending only on this formation, separation between a message and a signal is unclear, and the signal directly functions as the message. If attention is paid to this respect, the transmission corresponds to direct cognitive transmission that is not accompanied by intermediaries of a translation phase and a cipher. Due to this, the action of sound information including this category on human beings tends to assume a hybrid characteristic between the direct cognition and the indirect cognition. This characteristic poses a very complicated problem to a sign processing on such a sound or an electronic sign processing on and communication of the sound.

The <hierarchy of the symbolic information structure> corresponds to sounds which are configured as a module of independent sounds having inherent and finite temporal lengths, respectively, as often seen in the chirping of insects and the singing of birds, that is, as discrete sound particles. In addition, the hierarchy has an inherent signal structure serving as a subsystem internally. The hierarchy forms a pattern consisting of a pitch, an intensity, and a tone of the particular sound as well as their temporal changes. This pattern can serve as a cipher that carries a message, and possibly produces some meaning or content by decoding the internal signal structure of the module on a reception side even if the module is one module of isolated sounds. If such an effect is derived, these sounds function as a <symbol> that transmits information. This process can apply to Shannon's model. As can be seen, the discrete module of isolated sounds each having the finite temporal length, which is accompanied by an inherent signal structure as a subsystem, can be referred to as "sounds having a symbolic information structure (symbolic sounds)".

In order to accomplish the symbol function, it is necessary that the sound module has specific sound structures serving as parameters (indicators), respectively. At the same time, it suffices that the sound module has those structures. In other words, if attention is paid to a specific symbolic sound, the whole entity as the physical vibration, namely, the whole concrete signal structure is not necessarily essential in order for the symbolic sound to function as a symbol. A method for omitting the signal structures other than the indicator structures with attention paid to this respect is an abstraction method as a traditional human technique. Transmission volume saving techniques in signal processing such as band limitation and compression in the recent field of electronic information processing belong to the abstraction method. Although such a processing method does not cause many problems for symbolic sound, it causes non-negligible serious problems for a system in which the concrete sound functions as the direct cognition per se both theoretically and practically.

The <hierarchy of the connected information structure> refers to words, music, and the like, and is a higher hierarchy than those of the concrete sounds and the symbolic sounds. The hierarchy is a category in consideration of information on a sound in the formation of a sign or code system. In the hierarchy, a discrete sound module (speech sound) having the same specific signal structure internally as that of the symbolic sound module and a <word> or <sign> formed by a combination of the modules is used as a unit. The <words> or <signs> are aligned on a time axis while having some organic association with one another, to constitute an interacting time series system, that is, a Markov process. Various messages can be transmitted according to used modules and an arrangement order of the modules. This structure can be grasped as a framework of a system in which units of sounds, that is, <words> having a <double articulation> structure advocated by André Martinet for human languages are connected in chains. The inventors of the present invention turned their attention to the fact that <"Rensetsu" (connection)> is present in Japanese to correspond to an instance in which the articulation representing a segment indicates such a connection structure, and decided to refer to the system constituted by arrangement of such sound modules as "sounds having connected information structure (connected sounds)".

The presence of a simple form of information communication using sounds as signs is recognized in birds (society finch), mammals (dolphin), and the like, and has been studied. Further, an ability of gestural communication is recognized in great apes such as chimpanzee. Almost all of the information communications have <addition type language system> in which the arrangement of signs is does not have any order effect, in which respect the <addition type language system> greatly differs from <sentence building type language system> recognized in modern human beings.

As can be seen, if the message carriers or sounds from the environment are viewed in an information system, then the message carries can be grasped as the three hierarchies of the "hierarchy having the concrete structure (concrete sound)" which is the most fundamental and which cannot be separated from the vibration or physical entity, the "hierarchy of the symbolic structure (symbolic sound)" which is the sound module in which a signal is formed in an inherent pattern, and the "hierarchy having the connected structure (connected sound)" in which discrete sound units having the signal structure close to that of the symbol are connected.

4. As for the hierarchy of the symbolic information structure, unit modules having different various functions currently tend to be grasped collectively in the name of "signs" not only in relation to sound but also generally. However, at least in sound ecology, it is considered that this way of grasping is so rough that it is not suitable to actually use the same.

The reason is as follows. A signal of a cry produced by a monkey constitutes a complete system capable of transmitting a particular message by an isolated sound. Since a code for decoding the signal and the content of the message are fixed as firm ones among the party concerned (monkeys), the signal functions actually as <a symbol>. On the other hand, one voice in words a person speaks has a structure of the module of independent sounds if the voice is regarded as a signal. However, that is only a unit or a part of the language or system that constitutes the <connected structure> in which various sound modules are aligned on the time axis, and which is higher than the symbol information structure by one hierarchy. The particular message does not appear until the sounds are decoded as a structure (so-called part of sentences) systemized and reaching a connection level. Besides, as characteristics of a system that exhibits a Markov process, namely, language, a meaning or content of one unit (one voice) varies according to a correlation among another (prior and posterior) units, that is, a context. In other words, only "the words of one voice" constituted by one sound module cannot fulfill the function comparable to the "symbol" that transmits the particular and complete message. In this sense, it is less contradictory to apply the sound module that functions as a subsystem or a unit of the connected structure to the concept of <sign> than to the concept of <symbol>.

On the other hand, following the appearance of communication means such as a facsimile machine and a modem, the inventors of the present invention had to contrive another category for the discrete module of sounds as well as the symbol and the sign. In a digital communication using sound as seen in the facsimile machine, there is adopted binary coding of translating a message along the time axis into the alternative formation of whether a pulse is "present (1)" or "absent (0)". This sound system corresponds to the connected structure and is similar to words in that a module of independent sounds is set as a unit, and a message is carried according to arrangement of the modules. However, if individual sound modules are observed, they are all equal in pulse structure and cannot be distinguished from one another. Considering this respect, this sound system non-negligibly differs from the "sign" in which various modules have their respective inherent signal structures. Further, using such a pulse sequence, it is possible to draw or communicate some other signal, symbolic, or concrete sound structure. If the sound module having such a function is considered equivalent to the "symbol" and the "sign", confusion will follow. Therefore, attention is paid to the fact that a sound module to be used is completely neutral in meaning per se, and this sound module is allowed to correspond to the concept of <code> so as to distinguish it from the modules corresponding to the concepts of <symbol> and <sign>.

In this way, the modules of discrete sounds independent in terms of time and signal structure will be dealt with while classifying them into the concepts of <symbol>, <sign>, and <code> according to each structure and function. Based on this, the hierarchical structures as information systems of sounds in the environment will be considered again. First of all, it appears that there is no problem to place the <concrete structure> in the most fundamental hierarchy. In addition, the modules of independent and discrete sounds are classified into the three categories of the symbol, the sign, and the code. The modules in the category of <code> are rarely consideration targets in relation to the sound environment, and those in the category of <sign> necessarily move to the modules in the connected structure hierarchy because they belong to the connected structure. Therefore, it will be appropriate to consider the <symbolic structure> as the independent hierarchy. Further, for human beings and perhaps some animals, the <connected structure> configured as a sign sequence is placed as a more complicated and higher hierarchy. As yet another angle of approach, the sounds can be classified while attention is paid to the transmission function. Active communications which human beings hold using sound can be classified into three categories of "signal", "word (speech)", and "music". The communications in these categories have their particular transmission functions, respectively, which functions are deeply associated with a temporal structure of a signal. In addition, they lead to quite interesting and serious problems.

Taking the above into consideration, the "information structure of the sound environment" will now be reconsidered. If so, it is seen that the "information structure of the sound environment" constitutes the highest-order sound system including all the categories set above in terms of both the hierarchical structure and the transmission function.

5. The third angle of approach to the sound is a <response structure> which the arrival of the message carrier or sound from the environment introduces into our bodies.

A phenomenon provoked first at the time of contact between a sound or an elastic wave and us, as well as all responses provoked by vibrating each of our bodies including the eardrums, the skin, and internal organs, temporarily enter a category of <physiologic reactions>. Among them, a mechanism and a function of the <auditory system> through the eardrums have been quite well known. Following complicated development of the physiologic reactions, the <sensory and sensible (psychological and cognitive) reactions> characterized in that each person can experience part of the reaction process consciously is derived based on the physiologic reactions. Since the person is conscious of these sensory and sensible reactions by introspection to a considerable degree, it tends to be grasped more emphatically than the other reactions. On the other hand, some physiologic reactions have a serious influence on our living activities despite the lack of a strong influence on the consciousness. As for these reactions, we should take due care of the fact that colorless, tasteless, and odorless chemicals and toxicants are present.

What are expected to exhibit the highest effectiveness at present as means for grasping the physiologic reactions derived from the sound are considered to be various methods for analyzing noninvasive brain functions. Quite active development of a method has recently been underway in which an activation state of the brain is observed from outside without damaging the brain. These methods will be briefly explained. They include the following various methods: a method (electroencephalography=EEG) for estimating a comprehensive status of a synapse discharge from a surface potential of the brain, a method (magneto-encephalogram=MEG) for estimating the comprehensive status of the synapse discharge from a change in magnetic wave, methods (positron emission tomography=PET, and single photon emission computed tomography=SPECT) each for producing a tomogram of a brain bloodstream or a cerebral metabolic activity using radioisotopes as tracers, a method (functional magnetic resonance imaging=fMRI) for producing an image by receiving a signal changed by oxygenation of hemoglobin within cerebral blood vessels using nuclear magnetic resonance, a method (near-infrared spectroscopy=NIRS) for receiving information on oxygenation of hemoglobin within cerebral blood vessels as a change in absorption factor of a near-infrared ray, and a method for referring to biological indicators related to the autonomic nervous system such as an electrical activity of the heart, a muscle electrical activity, and an electric conductivity of the skin. Recently, it has been known that presence states of nerve activators consisting of nerve mediators and their related materials in the bodily fluid, hormones, immune activities, and the like serve as good indicators.

6. The <sensory reaction> in the sensory and sensible reactions is a subjective brain reaction that occurs first when a person receives various pieces of environmental information including sound. The sensory reaction has a strong property as a physiologic reaction universal to human beings and reflecting in pattern cognition at an initial stage. In the sensory reaction, there is a spread of a spectrum from a strong nonverbal response associated with presence/absence of a stimulus and physiological comfort/discomfort to a psychologically cognitive reaction easy to grasp verbally. The sensible reaction forms a complicated response structure in which verbal, nonverbal, conscious, and unconscious responses derived as a final result of all intra-cerebral information processings including that of a higher brain reaction developed with stimulation by input information are integrated with one another. The sensible reaction is a highly independent and complicated response obtained by integrating the inherent reaction universal to human beings, particular reactions set according to time spatial regions of history, society, and culture, respectively, a reaction reflecting an originality and a history of an individual, and the like.

The word of "sensibility" or "KANSEI (beauty and pleasure)" is originally an ordinary and general Japanese, and the meaning and content of the KANSEI are characterized by vagueness and ambiguity as often recognized in the Japanese. However, in recent years, terms and concepts of "sensible science", "sensible engineering", "sensible information processing", and the like have been proposed as academic tools in technological regions in the background of notable scientific situations particular to Japan. They have already been put to practical use. However, it has not been very long since introduction of the concept of the KANSEI into the realm of science to date and no common recognition is established yet. Therefore, in sound ecology, a conceptual tool for the "KANSEI" and the "sensible brain" responsible for sensible functions is prepared mainly based on the structure and functions of the brain, and tentatively used. The concept of the KANSEI will be reviewed again and defined. Before doing that, there will be described the mechanism and functions of the brain for controlling behaviors of higher animals.

Almost all emotional responses such as excitation of an eating behavior in response to an empty stomach and stopping of the eating behavior in response to a full stomach, and emergence of a sensation of fear and escape in response to emergence of a predator, in a narrow sense are controlled mainly by the behavioral programs preset to the brainstem and most primitive responses of comfort and discomfort connected to the behavioral programs, namely, <emotion> in quite a reflective form. An output from the brainstem that motivates the primitive desires, comfort, and discomfort is amplified serially by a limbic system, causes feelings of joy and anger, that is, <chord> or <feeling> to spur the behavior or to output them as visual and auditory information such as expression and voice to the environment so as to act the information on the other living things including those of the same species and same kinds and to introduce a situation advantageous in attainment of an objective. The mental functions constituted by the brainstem and the limbic system are also referred to generically as <emotion>. The <emotion-basis behavioral control> is a fundamental mechanism that introduces an animal behavior to an "original" side coded in genes and accompanied by less adaptation burden just like a carrot and a stick.

However, as results of recklessness in hunting and courtship behavior tell us, the probability of success in the behavior linearly controlled only by the emotion programs is low. In that case, it can be said that the functions of <reason> mainly based on a cerebral neocortex or particularly a prefrontal cortex exercises a negative control as if it apparently resists against the functions of the emotion and improves the possibility of success through strategy and tactics such as waylaying accompanied by endurance and detouring.

That is, while it appears that reason is opposed to emotion, the action of reason is not at all against emotion, differently from what has been believed so far. The reason functions to suppress the emotion in terms of phenomenon and functions as a supporting apparatus in terms of effects in a manner similar to that of a negative feedback circuit that improves a performance of an electronic apparatus. That is analogous to, for example, "a liege subject faithfully supporting his liege lord, prudent but nagging". In this respect, reason corresponds to an auxiliary circuit of emotion.

Figure 28:
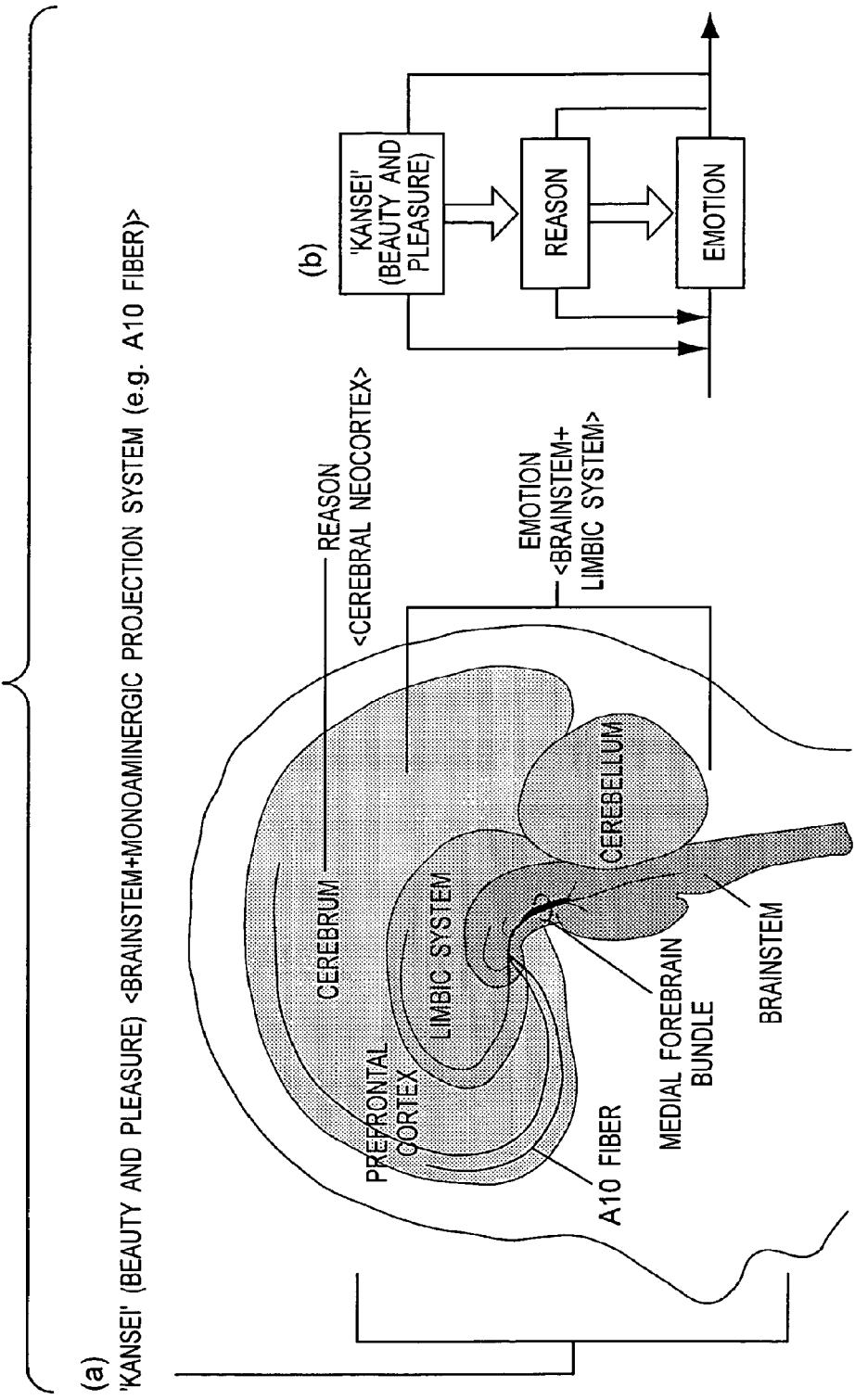
FIG. 28(a) is a sectional view showing a relationship with a region of a brain in a multiple feedback control model of a behavior and FIG. 28(b) is a block diagram showing the multiple feedback control model of the behavior of FIG. 28(a).

We regard functions of the <KANSEI> as a feedback control mechanism that exhibits effects of inducing the functions of the reason to a higher level, and subliming them from mere subjective rationality to reach the integrated stage of truth, goodness, and beauty. It is a system consisting of the brainstem and members of a monoaminergic projection system including <medial forebrain bundles=MFB> extending in various parts of the brain including the prefrontal cortex, which is believed to be the highest brain that serves the function. This system is worthy of the name <sensible brain>. That may be said as the system is complicatedly configured by various actions toward truth, goodness, and beauty in a positive feedback manner and various actions for avoiding falsehood, the bad, and ugliness. This system enables a feedback control for inducing a behavior to be exerted on various parts of the brain as projection targets. This system has a circuit configuration in which a control signal is transmitted directly from the brainstem, which is the origin of the desire and behavior themselves, to various areas of the brain including the area of the reason which is generally perceived as the "highest" in the human's brain functions. This leads to the system being completed by being positioned at the highest order of a brain multiple feedback circuit related to the behavioral control. According to this circuit configuration, it is noticed that the system is configured so that the logic taught by <reason> which is conventionally said to stand at the top of human thinking and judgment but which is actually a prudent liege subject must follow the esthetics of the <KANSEI> which the brainstem, the true liege lord, informs us as "a word ex cathedra" through the monoaminergic projection system (FIG. 28).

In the brain circuit which functions as the <emotion> and the <KANSEI>, like a carrot and a stick, such as comfort and discomfort or beauty and ugliness, a system that functions like the carrot and a system that functions like the stick are referred to as a <compensation system> and a <warning system>, respectively. These systems control our behaviors in a mechanism of a kind of a functional control. We rearranged them as the <emotion and KANSEI-basis behavioral control model>. This circuit functions so that the comfort is the highest and the discomfort (stress) is the lowest when the habitat or behavior is within the <original area> and so that the comfort is lower and the discomfort is higher as the adaptation degree is higher. By so functioning, the behavior toward the original area tends to be preferentially selected. However, if a life departs from the <adaptable area> and enters the <self decomposition area>, then positive and negative phases of the emotion and the KANSEI are inverted by 180 degrees, the comfort is higher and, at the same time, the discomfort is lower on the side on which the degree of the self decomposition is higher, and the comfort and the discomfort are in inverted states on the side on which the life can exist. As a result, the behavior that drives the animal to the self-destruction side is accelerated in a state in which it is difficult to return to the original (FIG. 26).

As a typical example of the function of the sensible brain, the presence of the <A110 nervous system> is interesting. Neurons (nervous cells) constituting this circuit have <somata>, as their respective bases, put in a <ventral mesencephalic tegmentum area> in the upper part of the brainstem, and have <axons> directly and intensively spread to the prefrontal cortex, which is considered to be the highest area in the brain, from the <ventral mesencephalic tegmentum area>. A neurotransmitter, namely, dopamine is accumulated and awaited in vast synapse terminals. On occasion, the dopamine is emitted to synapse gaps, and activates a mechanism that generates physiological compensation of "comfort" in the higher brain. The function must exhibit a positive feedback effect as a strong <compensation system>.

In the monoaminergic projection system including a medial forebrain bundle, or the like, various functions using noradrenaline and serotonin besides dopamine as neurotransmitters are discovered and their reactions are diversified. Some of them generate feeling of hatred and feeling of ugliness, which may be referred to as negative sensible reactions, and are suspected to function as the <warning system> in the negative feedback manner. It is easy to imagine that the control action executed when these various functions act generally and properly reaches quite a refined and excellent level.

Based on these backgrounds, it is defined that <KANSEI> is "the highest behavioral (including thought) control mechanism in the brain with the positive emotion set as an essential attribute, which exhibits the control effect on the activity of the higher brain". In this case, attention is turned particularly to the "reason" as the higher brain function to be controlled. Further, it is defined that <sensible brain> is the concept related to brain hardware responsible for those functions, or concretely, "a system configured by integrating the brainstem with the monoaminergic projection system developed into the various brain areas including the higher brain with the brainstem as a starting point".

Among the sensory and sensible reactions, those which can be grasped as psychological and cognitive reactions obviously cannot do without any new attempts upon approaching a new sound. However, as a whole, accumulation of vast methodologies obtained thus far based on experimental psychology, cognitive science, psychoacoustics, and the like, can be utilized. The sensory and sensible reactions which are standard for human beings and which everybody has are often circuits that near the truth of the sound more accurately than any other scientific method stated above. It was made clear that the "amateur's sensation and KANSEI", which was the only means for LP supporters but which was laughed off by academism in the past "LP-CD" dispute hit the nail on the head thanks to later discovery of hypersonic effects, and the like. The details are full of revelation and teachings.

Finally, the inventors of the present invention take notice that, as one important result of the process of the physiologic, sensory, and sensible responses in the body, variable <behavioral reactions> to the received sound are sometimes output to the environment. They form an endlessly diversified and huge realm from quite simple reflective responses as seen in insects and fishes to extremely complicated behaviors which the human higher brain function are involved with.

Development of the methodology of the detection and measurement of the behavioral reactions to sound is historically new, buds, and is underway in a state similar to the measurement of the sensory and sensible reactions. In the methodology, methods enabling quite effective detection of reactions difficult to grasp consciously or verbally are developed, and we expect much from the methods for further development.

<2-3> Continuation and Discontinuation

<2-3-1> Why is "thunderclap" a bolt from the blue?

1. A thunder rumbles in the blue sky without any signs, and blocks of ices hit on the ground harshly: "thunderclap".

Some planets in eternal space may always suffer from these discontinuous phenomena. Even Mercury having temperature changing from 350° C. in the daytime down to −170° C. in the nighttime and Venus having concentrated sulphuric acid rain in the atmosphere at 500° C. are present in the closer solar system family.

Providing that lives living on an infinitesimal globe in the name of an elementary particle existed, species prosperous there must have been given a higher evolutionary priority by associating with, obtaining as their daily bread, and making full use of the thunderclap. Life living in the world dominated by the quantum theory are destined to set, as their original habitat, the space-time divided into pieces and isolated from the others and to live their lives assuming that a discontinuous environment which continues to change from one state to a totally different state without any signs and traces is an optimum environment. For them, the thunderclap may be considered an expression that describes a daily, quiet, and comfortable situation.

However, for us or lives on earth, the thunderclap has an opposite meaning to that described above and is nothing but symptoms that tell us sudden occurrence of an unfavorable state, scattering of dailiness, and, in most cases, arrival of a crisis. From where does this difference come? The difference is based on a structure in which the global environment in which we live is constituted by one space-time system that spreads endlessly without any intermissions, and in which an encounter with a very rare and sudden discontinuity should be suspected of that of a state of emergency.

Macroscopic occurrences clearly recognizable by lives on earth, with few exceptions, interact with the strong continuity spreading spatio-temporally. It is essentially difficult for whichever phenomenon to suddenly appear or disappear in a spatio-temporally isolated state without any signs or traces.

For instance, even the "falling of a thunderbolt", which should be mentioned as a typical example of outbursts of occurrences, has a prior process in which maldistribution of electrons between a thundercloud and the ground is developed abnormally and grew greater, and in which a fall of the potential reaches its limit. This process is a spatio-temporally continuous change. If the change is measured by an appropriate method, a sign of the change can be obtained. Needless to say, there is no avoiding the probability that some living thing senses the sign. Further, the rumbling of the thunder accompanying the falling of the thunder emerges first as a difference in atmospheric pressure due to an impulse corresponding to an instant discharge. However, the rumbling of the thunder is not the last phenomenon but it instantly produces an elastic wave as a vibration repeating in the atmosphere or the ground. A wave motion of the elastic wave not only propagates through a wide range for certain time but also experiences reflections and interferences in the process of propagation. As a result, for a considerably long time that cannot be compared with the time of the discharge, which is a direct phenomenon, the atmosphere or ground is affected by the complicated sequel of the thunder. Thus, even for a physical phenomenon such as thunder, which is typical of a temporary phenomenon occurred on earth with relatively fewer constraints of the continuity and the interaction, the signs and traces of the phenomenon cannot be ignored.

On the other hand, a molecular chemical phenomenon that substantially constitutes lives on earth or a chemical change that plays a principal role in the occurrence, in particular, is extraordinarily high in intensities of the continuity and the interaction and cannot be compared with the physical phenomenon such as the thunder. For reference, free electrons that play a main role in a dynamic aspect of an electromagnetic phenomenon can transmit electric energy at a velocity close to the velocity of light, which is an upper limit of viable velocities in this cosmos. On the other hand, water, which is the strongest physical force in lives on earth, forms a liquid system, like a lump of causes and effects, in which $H_2O$ molecules that would have been discontinuous particles independent spatially are bound with the nearest other $H_2O$ molecules by hydrogen bonding having a bonding energy of about seven kilocalories per molecule of one gram, and in which they constrain each other complicatedly. A molecular system called "water" thus obtained not only provides hydrogen bonding between the $H_2O$ molecules as components of the water but also easily produces similar bonds with molecules of other various types and integrates the $H_2O$ molecules with the other molecules. This phenomenon corresponds to dissolution of matters into water, and almost all elementary processes of living activities on earth proceed in a form of the interaction of molecules or change in structure within the thus produced aqueous solution, that is, in a form of a chemical reaction in the aqueous solution.

Furthermore, the process of the chemical reaction itself emphatically shows continuity in that the number of molecules that constitute one phenomenon or the number of reactions is quite large. For instance, in the process of producing one-gram water by bonding oxygen and hydrogen, oxygen molecules of about $1.67 \times 10^{22}$, namely, ten billion times as large as 1.67 trillion and hydrogen molecules of $3.35 \times 10^{22}$, namely, ten billion times as large as 3.35 trillion, that is, molecules of $5.02 \times 10^{22}$ or ten billion times as large as 5.02 trillion in all are associated. This number amounts to 8.23 trillion times as large as about 6.1 billion, which is the world's population at the beginning of the twenty-first century. Because of such a super high density elementary level, the chemical reaction life on earth is actually realized as a typical continuous process without any intermissions spatio-temporally even if a fundamental unit of the chemical reaction consists of discontinuous phenomena of collisions, combinations, and divisions of molecules that are independent spatially and that form lumps.

In a biological phenomenon built in the background of such a chemical phenomenon, the continuity and the interaction are further amplified and the complexity is increased without limit. Due to this, the biological phenomenon is unavoidably constantly in a state of being far gentler in start, progress, and end, and a far closer interaction with the other phenomena than not only the physical phenomenon but also the chemical phenomenon. This is why the biological phenomenon is necessarily accompanied by great and diversified signs and traces in any event. The environment where life on earth gathers constitutes an ecosystem that is a highly advanced organism including various living things and nonliving things, and all things in nature are involved with one another quite complicatedly in such an environment. In the environment, the continuity and the interaction are further intensified, so that it is not exaggeration to say that no events without any signs and traces can be present.

It is no doubt that life on earth or animals, in particular, evolved in a direction of making best use of the structure of the ecosystem having such continuity in nature and the rules derived from the ecosystem. For over several hundreds of millions of years and even now, the mechanism of predicting a future of the ecosystem surrounding itself based on various signs read from the message from the environment, programming a behavioral plan, behaving itself, and loading traces of the behavior from signs of an upcoming phenomenon has possibly continued to evolve. If the ecosystem is the ecosystem dominated by the quantum theory, living things may cast dice rather than read signs.

However, a highly stable information loop circulating in life and environments seen in the global ecosystem is not as universal or eternal as to be close to perfection. It is sometimes intermittent and cut off discontinuously, which greatly shocks the animals.

One of the examples of intermittence is so-called extraordinary phenomena in heaven and earth, that is, outbreak of a highly uncontrollable accident beyond a category of living activities arising in realms of earth science and astronomy. This corresponds to the thunderclap. One example of that may be the bombardment of huge meteorites on the Yucatan Peninsula, which caused an atmospheric upheaval about sixty-five million years ago and which is believed to make the dinosaurs, which had been already declining, become extinct.

Another example belongs to the category of living activities, namely, a set of sudden behaviors that form a part of the living strategies of animals and that are artificially produced. A typical example of this intermittence may be a predator attack on preys. In this case, if the predator more strongly suppresses transmission of information that indicates presence of the predator based on some evolutionary or artificial strategy and further succeeds in producing a fabricated environment of peace and comfort, the progress of the situations has increased the discontinuity. The effect of the attack is further enhanced, and shocks of the preys are serious both materially and physically. In the circumference of us, even if such a situation including social behavior of human beings is grasped on the side of victims, this is often called "thunderclap" based on a comparison with the uncontrollable extraordinary phenomena in heaven and earth. Among numerous uses of this word since it was exploited by people living on the Chinese Continent until present, it appears that this metaphorical and symbolic example has been used far more frequently.

On planet Earth, a miraculous exception might be an instance in which the thunderclap that causes interruptions in the stream of time is not followed by negative value, whether it is a natural disaster or an artificiality. In other words, almost all thunderclaps are normally unwelcome events and most of them are tied with serious disasters. The "intermittence and discontinuity of the environmental information" as symbolized by the thunderclap are basically inadaptable to life on earth and may lead to highly advanced warning responses and stresses. In other words, the "continuity of the environmental information" is the very fundamental message that ensures comfort and peace.

2. Undoubtedly, the remotely acceptable system of animals that monitor the environment with sound or light used as the message carrier assumes great expectation and high responsibility as for perception of discontinuous phenomena and signs and traces of the phenomena serving as indicators of "unwelcome events" arising in the environment. Then, how do we make both the visual system and the auditory system deal with those discontinuous phenomena? A greatly noticeable fact is an extreme gap lying between the visual sensation and the auditory sensation in receiving an intermittent and discontinuous signal.

As a matter of fact, the thunderclap may not be so shocking an occurrence in the realm of visual sensation for the following reasons. A <profile> that constitutes the most important region in a visual image is none other than an intermittent image formed by an object existing in this world on a boundary with the other object. The profile is possibly the largest domain in the originally rare and discontinuous structures in the environment. An action of detecting the spatial intermittence is the fundamental and important role of the visual sensation. Therefore, if remembering a shock whenever encountering an intermittence, the visual sensation must be unable to fulfill its required function.

Further, every visual image instantly becomes intermittent when a person closes his or her eyes and replayed instantly when the person opens his or her eyes. In other words, the visual image is discontinuously switched over between zero and all. For reference, it is appropriate to express "instance", that is, "time for blinking ones eyes" as a notation for a minimal time for a change of the intermittence. In addition, the visual system accepts excessive input over a processing limit and temporarily turns inoperable by an easy behavior of directly viewing the sun. Accordingly, when blinking our eyes toward the sun, our visual systems quickly switch over input from zero to full-scale. For the visual system having these properties, the discontinuous change over a wide dynamic range of signal input is not always abnormal or rare. Therefore, it is highly likely that the discontinuous change is not tied with a shock as expected from the word of "thunderclap". In order to break the wall of insensibility, it will be necessary to forcibly conduct such a behavior of dilating the pupils and setting off a strobe light in the dark room or of covering one's entire field of view and then making the predator suddenly appear before one's eyes by removing the cover.

Considering the above, it is difficult to regard the visual sensation as principal in the sensor for the discontinuous change in the environmental information as symbolized by "thunderclap". It appears that a situation in which the visual sensation pulls a trigger of shock or fear consists of a higher pattern recognition level far slower in transient response than the auditory sensation, at which level a visual image that symbolizes a fatal situation recognized through analysis and storage of the meaning cooperate with each other.

3. A response of the auditory system to the discontinuous change in the signal arriving from the environment is more faithful to the change, sharper, and surprisingly sometimes more accurate than that of the visual system. The large background of the higher faithfulness of the auditory system lies in the constant continuity of the auditory system itself which cannot be closed intentionally but which is always open to all directions, differently from the visual system capable of shutting off all inputs by his or her eyelids. The auditory system having these properties must capture the change in the information input based on the environmental change more easily than the visual system. The reason is as follows. In the visual system that incessantly tracks a target based on autonomy of the animal subject, a baseline of a space of the visual image constituting the changing field of view always continues to drastically change. It will be necessary to carry out considerably complicated processing procedures so as to extract only a changing part departed from environmental constancy among such changes and to detect the extracted changing part as information.

On the other hand, in the auditory system that continues to accept all inputs of environmental information in a manner of fixed point observation and faithfully because of incapability to operate autonomously, it suffices to discover a phenomenon that does not apply to a realm of the constancy while monitoring a state of the wave motion appearing on the one-dimensional time axis. Therefore, there is a high probability that the auditory system detects the discontinuous change different from a general state more instantly, easily, and sharply than the visual system. Accordingly, it appears that the auditory system recognizes a sudden appearance of a sound which is not constantly present in the environment or a sudden disappearance of a sound which is constantly present in the environment more sensitively and more stressfully than the visual system perhaps irrespective of a magnitude of the sound. This is indicated by the following fact. Birds and mammals having developed vocal organs transmit sound signals to other individuals to call their attention or bring forward proposition of their behaviors. In addition, most of their cries or songs for calling out to the other individuals about the signals tend to have a pattern that emphasizes the discontinuity of the sound structure easy to distinguish from the background sound. (However, it is noted that an alarm call of each bird is sometimes under fade-in and fade-out type control so that their natural enemy does not perceive a position of the bird that transmits the signals.)

From our experience, such an impulsive response of the auditory system has a wide dynamic range and is followed by a sufficient analytical action. Amplitudes of a sound of a twig snapping in the serenity of the forest, an explosive sound of crackers at one's feet, the roar of an explosion of large firearms, and the like, may possibly differ in energy by about over billion times. We distinguish and accept them both qualitatively and quantitatively, and exhibit suitable impulsive responses, respectively.

The auditory system having these properties functions most directly as a sensor for intermittent and discontinuous changes in information inputs reflecting in abnormalities of the environmental ecosystem such as the thunderclap. Quite highly likely, the auditory system plays a principal role in this function.

This brings up an important and serious problem about the sound environment of contemporary cities, the problem that has been hardly pointed out so far. The town sound is cut out almost in all directions by the spatio-temporal discontinuity, in direct opposition to the highly advanced spatio-temporal continuous structure of the forest sound environment original to human beings. Numerous faults of the sounds lying in the cuts wait for "human beings who cannot feel at ease unless they are in the continuous sound environment" and who are passing through the faults while preparing for the experience of the sound of something like the thunderclap. If a person encounters one of the sound faults, a crisis detector circuit in the brain is stimulated through the auditory system which plays the principal role in the sensor for the environmental discontinuity. In addition, the impulsive responses and warning responses that tell the person the sudden occurrence of an unfavorable state, scattering of dailiness, and the arrival of a crisis will echo throughout the body. At the same time, those responses provoke stress-related negative sensory and sensible responses including discomfort and dislike. This inevitably requires adaptation behaviors including avoidance or evasion for urging the person to return to his or her original environment or rejection of the present environment.

Furthermore, as the most formidable situation, one must consider an instance in which <separation from the original sound environment> such as destruction of the sound continuity which continuously attacks city inhabitants and wave of assaults by the sound faults extends or continues to exceed the adaptability coded in genes. This is because the probability of triggering the <self-decomposition programs> prepared in genes in a manner similar to that of the <original-adaptation programs> is considerably increased. This instance derives lifestyle diseases as physiological self-decomposition, behavioral disorders as the behavioral self-decomposition, and the like in a state in which inversion of phases of comfort-discomfort responses accompany the diseases or disorders to drive a person himself or herself toward destruction.

In approaching the stressful urban sound environment in which people are forced to continuously experience "small thunderclaps" or sound faults whenever they open or closes doors, it will be essential to carefully introduce the new angle of approach called "continuity and discontinuity" and give due reconsiderations to the new angle of approach.

<2-3-2> Analog and Digital

1. If attention is paid to the change in sound environment derived particularly from urbanization in relation to sound and civilization, the important angle of approach called "continuity" and "discontinuity" surfaces. As for this, it is desirable to go back to the starting point to grasp it again, and to sufficiently prepare materials for thinking. In this section, <continuity> and <discontinuity> will be considered using framework of <analog> and <digital> which already has an non-negligible history as a tool to deal with such a problem and which is popular and ripe enough as a material. In short, "analog is a technological concept that represents a continuous structure" and "digital is a technological concept that represents a discontinuous (discrete) structure". Every thing or phenomenon cannot be irrelevant to one of or, more strictly, both of the two characteristics.

If <the earth> itself is taken as an example of the phenomenon located within our reach and having a particularly complicated and advanced structure, both of the analog and digital characteristics reach their ultimate levels in the earth. It is dispensable to turn our eyes on such a phenomenon both analogly and digitally. On the other hand, as an example of the phenomenon having the simplest and most compact structure, there has been known a <binary coding> information system constituted only by two symbols: [1] and [0]. This structure is nothing but an ultimate discrete structure. In principle, it is essential to turn our eyes to this structure only digitally. As a general tendency, a concrete phenomenon or a substantial phenomenon closely relates to an analog structure. As an abstraction degree of the phenomenon is larger, its analogness is lower and digitalness is relatively emphasized. For instance, a phenomenon accompanied by standards (CGS system) of physical quantities (namely, length (cm), mass (g), and time (sec)) is higher in analogness. As a distance to each CGS system is farther, the phenomenon tends to be stronger in digitalness (FIG. 29).

In actual phenomena, the analog and the digital variously form intricate relations and are changed according to angles of approach. For example, someone's weight is a continuous amount without any intermissions. Since the value of the weight is present at any time, the weight is wholly continuous. This system consists only of an analog structure and elements of the system all belong to a CGS system. On the other hand, since the number of persons present in a certain room is countable at any time, it is continuous temporally. However, since the number is an absolute number such as 1, 2, . . . , that is discontinuous and without any CGS systems, an analog structure and a digital structure coexist in the number. Further, meteorological data such as atmospheric pressure, measured at the hour is measured discontinuously at one-hour intervals. Measured values of the data are continuous and in [mass/area], that is, belong to the CGS system system, in which the analog and digital structures coexist, in a manner similar to that of the above. As graduations on a digital clock, symbols (figures) discontinuously switched over in seconds appear on a discontinuous time axis at one-second intervals, thus forming a system only consisting of the digital structure. The symbols themselves are abstract and are not tied with the CGS systems.

As an important point of view, there will be arranged the analog and the digital in the structures or functions of lives on earth. Basically, the elementary process of each life on earth is constituted by chemical reactions which proceed in an aqueous solution. The neural transmission of emitting electric impulses, and human motions and thoughts are substantially proceeded as chemical reactions without any exceptions. There is no information communication or system control in a living body, specific form of which is not a chemical reaction.

Chemical materials that constitute a life phenomenon form independent matters called molecules and have inherent structures, respectively. They may be referred to as digital in that they are independent matters and as analog in that they have their inherent structures. Each chemical reaction arises according to a fixed rule dominated by an analog molecular structure, is proceeded, and forms new molecules on the occasion that two or more molecules directly encounter each other except that the molecules are decomposed themselves. A macromolecular information DNA inherent to each living body digitally describes an amino acid sequence of a protein by combination of three out of four types of monomers (unit molecular structure) that constitute the DNA. In the case of a <regulator enzyme> that functions to control metabolism, a catalysis is digitally on-off controlled for every molecule by an analog reaction in which a specific molecule is fitted into a keyhole structure called <allosteric site> responsible for the switchover of activation of the enzyme in an electronic lock fashion.

As can be seen, in the chemical phenomenon related to life, the analog characteristic associated with a three-dimensional structure of a molecule is emphasized within the molecule, and a digital phenomenon occurs between the molecules in which an integer number of molecules are gathered or scattered according to the certain rule. On the other hand, there is a quite large number of molecules present in a living body and constituting the living body (about 108 to 109 per cell except for water), and rates of biochemical reactions are, in most cases, considerably high (a rate of a reaction catalyzed by an enzyme is normally 103 to 104 times per second for every molecule and often as high as 108 times per second). Therefore, according to a flow of a chemical reaction that is possibly of significance for a life, digital involvement of the respective molecules in the reaction is substantially of no significance but the reaction is adapted to an analog reaction rate theory. Besides, by elaborately organizing such an analog reaction, there are created digital processes such as impulse transmission of a motor nerve or a cerebral cortex neuron. Thus, the mechanism of a life constituted by hierarchical characteristics and reciprocities of the analog structure and the digital structure is present as an a priori characteristic that cannot be changed even by any technologies.

2. In order to make a natural scientific approach to a certain phenomenon, it is often effective to prepare for highly adaptable and inherent technological procedures in consideration of the analog and digital structures of the target as well as an objective of the approach. For instance, in the technical region, the target has been divided into a continuous time system and a discrete time system, and inherent processing systems have been constructed for the respective systems. In a telecommunication and computer related region, even if the target has an originally continuous structure in light of the effectiveness of digital information processing, there has been widely adopted the <coding> of temporarily <encoding> the target into a digital signal, carrying out digital information processing procedures, and <decoding> the digital signal into an analog signal.

How can we translate a phenomenon having an analog structure and strongly exhibiting characteristics as a physical quantity into digital information capable of being used in high-speed digital communication and subjected to a computer processing? In order to do so, it is necessary to separate the phenomenon from physical entities and the CGS system as far as possible, and convert the phenomenon into pure coded information having high abstraction degree. Ideally, the phenomenon is translated into two signs of [1] and [0]. In addition, since the basic concept of communication and computers established thus far is on the major premise of one-dimensional information flow, even a multidimensional or generic phenomenon should be translated into sequential and logical information format on the one-dimensional time axis.

As a currently most popular method as almost decisive means for converting an analog signal into a digital signal (abbreviated as "AD conversion"), there has been known a <pulse code modulation or PCM> method. This enables realizing almost perfect abstraction stage, differently from all <pulse time modulation or PTM> without any quantization and <pulse number modulation or PNM> without coding. According to the PCM, the analog structure of an input signal is basically drawn minutely by digital sentences and described and each target part is determinately copied. In addition, it is possible to suppress any other information (noise) as much as possible. Therefore, the PCM is strong against attenuation following information transmission and shows high evaluation and results mainly in the information communication field.

A system of this PCM is configured as follows. The <sampling> is first performed on the one-dimensional analog signal to be input (if an input signal is an image or a moving image having a multidimensional structure, the signal is translated into one-dimensional information in advance by a method such as scanning). By the sampling, an analog quantity pulse sequence referred to as <PAM (pulse amplitude modulation) wave> or <time sequence> is obtained in the course of extracting input signal values (amplitudes) at <sampling points> configured discretely on the time axis, respectively. Next, <quantization> is performed. In this case, the individual PAM wave amplitudes obtained by the sampling are digitized by applying the amplitudes to scales discretely configured in binary notation in a manner in which the amplitudes are rounded to the nearest whole number. These digital values thus obtained are normally coded into a binary bit sequence using an electric or optical impulse. Although <quantization errors> occur since detailed parts are rolled forward or backward in the quantization stage, it is possible to improve faithfulness and reduce the errors by increasing the number of quantization bits.

In a communication system or computer, after many inputs are processed into digital information coded in binary notation, it is required to restore (decode) the digital signals to analog signals and to output the analog signals. This digital-to-analog conversion (abbreviated as "DA conversion"), which is opposite in process to the coding, derives a PAM wave from a binary code sequence and outputs a one-dimensional analog wave based on the binary code sequence. The PCM method, which has been intensified to follow highly advanced relevant techniques including correction of errors generated in the course of these procedures and information compression, is infiltrated into every aspect as an indispensable tool to use of the information communication and computers that support the contemporary society. The actual and potential influences of the PCM are incalculable.

Furthermore, there has been known an analog=digital mutual conversion method based on <high-speed sampling and one-bit quantization> developed by Yoshio Yamazaki, an information scientist, using this PCM as a prototype. The method is a surprising technique that overwhelmingly improves functions while realizing both the improvement of performance and the simplification of signal processing procedures by modifying the $\Sigma\Delta$ (sigma-delta) method, which is one of AD conversion methods for the PCM. The gist of the analog=digital mutual conversion method is so elegant that solely an increase or decrease of an amplitude of a signal is observed on each of measurement points set at quite high density and quite finely on the time axis, coded to a one-bit signal of [1] or [0], and that the digital signal can be decoded even by a simple low-pass filter. With this method, omission of information in the quantization stage, which is fatal to multi-bits, occurs less frequently. Despite disadvantages such as a so-called one-bit noise processing that fundamentally accompanies this method, it is possible to code signals from DC (direct-current) signals to signals in ultra-high bands exceeding 100 kHz quite efficiently. In addition, this method facilitates mutual conversion with the other formats and ensures quite excellent sound quality. Applications of this method have spread at high speed mainly for, in particular, music recording and replaying in the name of DSD (direct stream digital) method, or the like.

3. As explained above, the contemporary digital information processing continues to develop illimitably and is growing as an indispensable partner for human beings. The binary coding system constituted only by the two elements: [1] and [0], in particular, has derived excellent functions from a digital computer or high-speed large-capacity digital communication, and enabled intellectual activities of human beings to fly up to a height comparable to positions of gods, as compared with those prior to emergence of the system. The abstraction characteristic of the system cuts a path for freely dealing with information without any constraints while separating the information from all physical quantities, that is, a path for versatility. At the same time, the system enables executing all information processing in a definite state without any ambiguity, that is, perfection. Therefore, if a problem originally having a discrete structure and adaptable to this method is to be dealt with, it is expected to deduce a quite advanced or sometimes perfect answer thanks to the versatility and perfection of the method.

If adaptability to the target reaches such a high level, effects produced by the coding in this formation are noticeable. As a first and direct effect, recording, storing and transmission of the phenomenon are realized at an extremely high level in accordance with accurate and definite acquirement of the phenomenon as information. Far more noticeable are the effects produced by activating a computer that cannot be put to practical use until information is described in binary notation. In other words, it is possible to open up a path for causing a given code system to operate autonomously and powerfully, and replace human's brains by the computer to sometimes far excel human abilities at high level in such aspects as logical operation, analysis, inference, and prediction.

One of the simple but clearest examples of the effects can be seen in trajectory calculation for predicting the relationship between shell launching conditions and an impact area, which calculation greatly motivates development of a present von Neumann-type computer. This is none other than the effect of a function of processing large quantities of calculations too complicated for human beings at high rate and accurately to far excel human abilities. As examples of deriving a highly reliable analysis result from vast amounts of data, there are known numerous up-to-date measurement and analysis techniques including the noninvasive brain function analysis and techniques using a radio telescope. As a new topical example, there has been known a virtual reality technique for calculating artificial sensory information by a quite complicated and high-rate calculation and allowing an non-existent space to feel as if it is an actual world. Further, the activity popularly referred to as simulation is worthy of note as a new ability acquired by human beings. Specific examples of the simulation include <genome analysis> for cutting a long gene's DNA sequence into pieces, individually analyzing the sequence pieces, and estimating a connected image or a whole image from an extraordinarily large amount of calculation, and <artificial life> that enables an effective experiment to be conducted on a computer for evolution of life on earth which has been conventionally difficult to experimentally verify because of need of perpetual time. The activity or simulation derives quite shocking functions of the actual world.

As can be seen, the coding acts as an entrance to such a powerful computer utilization. However, if the structure of a coding target problem itself exhibits, even partially, the continuity as its nature, it is required to conquer the continuous structure based on some operational hypothesis at the time of coding, which leaves room for various negative effects. As problems that cause incompatibility between this continuous system and the digital information processing, the presence of a <coding> stage and a <decoding stage> are particularly serious. In the coding stage, an analog structure in a form of an original physical entity itself is separated from the entity, and the analog structure is rewritten to digital data, which is a highly abstract form. In the <decoding> stage, the analog structure is decoded from the code.

As can be understood from the above-stated PCM method, the elementary process of conversion from analog to digital corresponds to a process of cutting the target into pieces in very small time space regions based on some operational hypothesis, measuring physical quantities of the respective cut pieces, rewriting the measured physical quantities to abstract numeric values, respectively, and describing the abstract numeric values as a huge sign sequence. As for the sound, the process corresponds to a process of measuring amplitudes (sound pressures) at measurement points (sampling points) finely set on the time axis and completely writing the measured amplitudes (sound pressures) in quite a detail. Every physical quantity can be measured by setting specific angles of approach based on some operational hypothesis while the other are disregarded. Due to this, if those omitted in this process are actually non-negligible, problems occur. Among such problems, one must specially take care of "omission of dimension" and "omission of density".

As for the dimension, the present digital information processing is a discrete and sequential processing on the one-dimensional axis both basically and practically. A so-called parallel processing includes a process corresponding to a one-dimensional sequential processing. There lies an essential problem in a process of coding multidimensional continuous target using a medium having such constraints and subjecting the coded target to digital information processing. As one means for considering this problem, Shannon's model is useful, having a communication system expanded to a multidimensional information space. In other words, if a signal space of information has a certain multidimensional continuous structure, it is necessary to perform a topological mapping capable of mapping the information with no lack of any points while maintaining the continuous structure as it is, and of decoding the information by inverse mapping in order to faithfully transmit the space structure to the destination. This principle itself is difficult to adapt to digital processing having a discontinuity in its nature. In order to succeed in this mapping, there is required a condition that a dimension of a signal space of an information source coincides with that of a circuit space. If the dimension of the circuit space is smaller than that of the information source, there occurs an antinomy that "the dimensions do not coincide with each other to maintain continuity and the continuity cannot be maintained to make the dimensions coincide with each other". Electronic communication circuits available at present are essentially limited to the one-dimensional circuit space with few exceptions.

Since the omission of density is rational or irrational depending on circumstances, the problem has quite a complicated substance. First of all, the process of digital conversion like the PCM is necessarily accompanied by sampling process. Since the sampling is intended to measure the physical quantity of the target at sporadic points either temporally or spatially, all continuous structures originally included in the target are temporarily decomposed. However, for a signal having a completely limited band, if the band is equal to or lower than the Nyquist frequency, it is considered that the original continuous structures are decodable (in which case, quantization is disregarded).

Therefore, in short, the setting of infinite sampling conditions must be possible to ensure the continuity. However, this method is difficult to carry out in reality. The principle of this problem can be explained by the idea of "in order to acquire information, energy according to the amount or accuracy of the information should be injected" originating from famous "Maxwell's Demon" and advocated by Leo Szilard and Léon Brillouin, information scientists. That is, if accuracy is improved, the energy for measuring and determining the physical quantity based on which information is provided is increased unlimitedly, thus unavoidably disembodying the information.

In what case can the coding hold sufficient validity in actual sound transmission? Examples of this can be seen in levels of the <symbol> and the <sign> in hierarchies of the information structure of a sound. If a certain type of sound module indicates <a signal> or <a word>, the module functions as a <symbol> or a <sign>, respectively, in a human communication using the sound as a message carrier. In order to do so, each sound module should have a sound structure internally to serve as a parameter for displaying its meaning and content. In this case, it suffices that the sound module includes necessary and sufficient parameters and does not include the other structures. Besides, if the sound module includes such other structures, they sometimes make recognition complicated or give rise to difficulties.

The actual sound will be considered while paying attention to this respect. As for a processing performed on the <connected> (verbal) information configured so that sound modules each functioning as <symbol> or particularly as <sign> are connected in chains, if digital conversion that can ensure sufficient density to accurately draw the structure of an indicator necessarily and sufficiently is realized, then a message can be transmitted accurately enough, and high level validity can be expected in the process of this message transmission.

On the other hand, as for a processing performed on a sound having a <concrete information structure> having so high a continuity that it is difficult to recognize the sound itself or a finite number of independent units in the sound, it is difficult to define a specific internal structure as a parameter differently from the symbolic or sign information. Considerations should be given particularly to the fact that the continuously changing signal structure itself often exhibits complexity and transfigurability and that the signal structure as a whole constitutes a meaning and a content as a comprehensive message. In order to code information having such an analog structure, it is indispensable to appropriately recognize and discern both the dimension and the density in terms of the range and the limitation of coding.

Further, as an original and serious problem, it is doubtful whether the operational hypothesis itself for allowing the digital=analog mutual conversion is valid. Yutaka Yamamoto, information scientist, pointed out that the <Nyquist frequency> that plays a definite role as a mediator of decoding digital data into the analog structure cannot be applied unconditionally but is accompanied by many constraints in actual decoding, and that it is dangerous to adhere strictly to the <Nyquist frequency>. In addition, Yamamoto proposed more refined procedures necessary for avoiding this risk based on a <sampled value control> method.

As can be seen, the limitations cannot by ignored by any means even for the PCM that appears to reign over the analog-to-digital conversion as a perfect and faultless coding method. Sharp insight and KANSEI are required for the already visual limitations and even unnoticed limitations. The requirement of the insight and the KANSEI ranges not only a knowledge phase but also sensory and sensible phases.

As examples which the inventors of the present invention directly experienced, the problem of setting of sampling frequency upon recording music in music recording media such as compact discs (CDs) is full of lessons. The CD is a surprising technique that was put to practical use at an ordinary civic life level using the principle of the PCM and a compact optical disk medium mainly by Sony Corporation in Japan and Royal Philips Electronics in the Netherlands. It is no exaggeration to say that the CD is a brilliant technology in human history. In setting a recording density in the process of defining standard of this method, a sampling frequency of 44.1 kHz (number of quantization bits of 16) that can theoretically cover up to 22 kHz with an allowance added to the audible frequency band was selected as the sampling frequency of the CD for the following reasons. A frequency range of vibrations audible to human beings as sounds is within a range of 20 Hz to 20 kHz, and presence or absence of high frequency components included in presented sound and equal to or higher than 15 kHz could not be detected as a sound quality difference by official psychological experiments.

However, after the CD was put to practical use, the limitations of the CD were revealed through the "LP-CD" dispute starting at an assertion that this CD sounds lower in quality than the LP (with a response to a ultra-high frequency range exceeding the upper limit of the audible range that is far superior to the CD) that was a main media before the CD, discovery of the hypersonic effect showing that a sound including high frequency components exceeding the audible frequency is more harmonized with human beings than a sound excluding them physiologically, psychologically, and behaviorally, and the like. In these backgrounds, there have emerged new sound media such as a SACD and DVD audio capable of recording ultra-high frequency components inaudible to human beings as a sound.

For reference, Heitaro Nakajima, an information engineer, who played a central role of development of the CD is a forerunner also in that he kept his eye on the limitations inherent to the CD. Thanks to his uncommon resolution and endeavor supported by his good sense, there was born in 1999 the SACD, which is the first ordinary digital media recording sound up to the high frequency far higher than the audible range.

If reviewing the tendency of the method, in the name of coding that symbolizes human intelligence and fills again with glory the course of human beings who struggle to get at the truth of the relationship between the sound and the human beings, we actually see that contrivances obtained by exerting all powers of human intellects are often lost in a maze and unexpectedly caught in a trap at world history level. We cannot help having serious and critical minds.

<2-3-3> Abyss of Identification of Quantity with Number

1. From the end of the twentieth century to the beginning of the twenty-first century, amazing was the force of diffusion of personal computers while improving their functions in geometric progression. That may be said to be the largest development since writing instruments were invented and the use of such instruments got on the right track in the history of tools for supporting human intellectual activities. Needless to say, the computer means herein the von Neumann-type computer, which is an apparatus for arranging combinations of only two discrete numbers of [1] and [0] and for rearranging the numbers. Although the apparatus arose purely as a calculation tool, it was named <versatile computer> due to its subsequent explosive diffusion of applications and has functioned to be intended at almost all things from totally abstract numeric values to concrete physical quantities.

It appears that the mechanism and function of such a present computer has brought the tendency of identifying <quantity> with <number>, which has been continuously strengthened through modern western times to an ultimate level at a stroke. It appears that <identification of quantity with number> has completely ruled over minds of people living in contemporary society from professionals to ordinary people and up to the unconscious world. In the already beginning situations of a turnabout from the material civilization to the information civilization, there is an extremely high probability that a pitfall or a source of crisis that casts an unfathomably dark shadow everywhere in a realm where human beings and high technology cross each other, and that is related to continuity and discontinuity or analog and digital lurks in the thinking, or rather already in the sensation, regarding this identification of quantity with number. We will dig up this problem still lying outside the consciousness perhaps because it has been hardly pointed out before in the civilization where we live, so as to pay attention to it again.

2. It may be said that the technological civilization enlightened by the western world far surpasses the ancient Greek civilization while respecting it as a standard. The surpassing state of the technological civilization is particularly seen in material science. Needless to say, it is too hard and inappropriate to use, as comparison materials, Thales who believed that the origin of all things was <water> in pre-classical Greece and Anaximenes who believed that the origin of all things was <air>. However, even if Democritus' atomic theory, Archimedes' physics and engineering, Hippocrates' physiology and medical science, and the like praised as the essence of the ancient Greek material science later in the period of Thales and Anaximenes are included as comparison materials, nothing can compare with the contemporary material science realizing nuclear fission and fusion, travel to the moon, and gene manipulation. One cannot afford not to recognize predominance of the contemporary science that discontinuously surpasses the ancient Greece produced by repeated epoch-making rapid progresses.

Nevertheless, if our eyes are once turned to the mathematical world or particularly the world of geometry, the level of the ancient Greece is astonishingly high even at contemporary times. It is difficult to state that a fall of the ancient Greece from the modern world is discontinuous and obvious differently from that seen in the material science. The Elements, written by Euclid, which was a compilation of abundant ripening of the classic times praised as the golden days of Greek mathematics continued to reign alone as the original of geometry and still reigns firmly. Hellenistic Greek geometry symbolized by prominent genius Archimedes is praised as the final stage of intellectual activities human beings can reach. This Greek geometry appears to more than awe many modern mathematicians particularly for its strictness, rule, and soundness. The mathematicians are particularly awed by how to grasp the relationship between <quantity> and <number>.

Archytas of Tarentum (about 428 BC to about 347 BC) who was a Greek mathematician and educator in antiquity and who was known as a good supporter of Plato compiled mathematics into four branches, named "four upper-level courses of study", according to Pythagorean tradition. The famous seven liberal arts (believed to be cultural studies suitable for unfettered people in Ancient Greece) composed of the four upper-level courses of study and three lower-level courses of study, namely, grammar, rhetoric, and logic formed the backbone of the European knowledge structure for the subsequent two thousand years.

The four courses of study set by Archytas of Tarentum are "art and science related to static numbers", namely, <arithmetic>, "art and science related to static quantities", namely, <geometry>, "art and science related to moving numbers", namely, <music>, and "art and science related to moving quantities", namely, <astronomy>. If this system is applied to our present situations, a large majority of fields that belong to currently mathematical regions such as arithmetic, algebra, and analysis and <music> belong to the "arts and sciences related to numbers", that is, <mathematics> according to Archytas of Tarentum. Further, original (general or non-analytic) geometry, physics, astronomy, and the like, are the "arts and sciences related to quantities" and, therefore, worthy of being called <quantitative sciences>.

It is said that this attitude of strictly distinguishing quantity from number was established by Eudoxus of Cnidus (about 408 BC to about 355 BC), who walked one step after Archytas and who was praised as the greatest mathematician in classical Greece. The works of Eudoxus were deeply involved in thoughts of Pythagoreans' absolute belief in number, peculiar social behaviors in the background of the thoughts, and their catastrophe.

The Pythagoreans apparently dominating intellectuals in pre-classical Greece while announcing the dawn of the history of civilization, respected <natural numbers> (positive integers) as the origin of all things and as of being supreme value. Naturally, quantities belong to numbers. As positions in studies, arithmetic dealing with numbers is placed at a top position and geometry dealing with quantities abides by being placed under arithmetic. The source of the Pythagorean conception is believed to be largely influenced by the Ancient Mesopotamian civilization or particular the Babylonian civilization extremely devoted to numbers. However, the Pythagoreans' absolute belief in numbers and ideological radicalism for extending it even through social behaviors and individual lives had peculiarity singular in other civilizations with exception of the contemporary technological civilization or particularly absolutization of economic value as only one similar example.

There is no avoiding feeling something unusual about various similarities between these two civilizations on both ends of the history. For instance, Pythagoreans' way of representing a number by arranging stones. As for the famous triangular number or quadrangular number (square number), pebbles are placed at predetermined positions in a dot pattern set on the sand in advance, and are expressed and recognized as basic units of numbers. In an L frame called "gnomon", in particular, the dot pattern has a serial line. That constitutes a completely discrete system in which a state in which no pebbles are placed means [0] (it is noted, however, that the concept of zero which the inventors of the present invention refer to was not present in Greece of the day) and in which a state in which pebbles are placed means [1]. If attention is paid to this respect, this system is exceptionally quite similar to a bit array including only [1] and [0] as elements in an ultimately discrete binary coding system, which is essential expression means when we use computers.

Furthermore, with a view of rationalizing their own principle that provides that numbers having a discrete structure in nature are the origin of all things and that such numbers rule over the universe, the Pythagoreans considered that space and time consist of <indivisible units> of a discrete "assembly of points" and a discrete "assembly of moments" while considering that the space and the time undeniably and intuitively form a continuous structure. In addition, they reached a surprising concept that all of space and time discretely correspond to numbers and are ruled by the numbers. This may be the very beginning of the identification of quantity with number.

However, the absolutism of numbers established by the Pythagoreans carried the seeds of disruption. One of them is that the numbers which the Pythagoreans deified are limited to natural numbers, namely, positive integers and their simple combinations.

According to the Pythagoreans, all things in nature in this universe consist of beautiful and simple combinations of natural numbers. For example, in relation to sounds that constitute music, they pointed out that if a length of two strings serving as the sound source is a simple integer ratio, the two sounds from respective strings produce a consonance. In this case, the numbers used are limited to 1, 2, 3, and 4 that constitute a perfect number of 10 which they deified. If the ratio is 1:2, a consonance of an octave is obtained. If the ratio is 2:3, a consonance of a fifth is obtained. If the ratio is 3:4, a consonance of a fourth is obtained. They ignored more complicated ratios. By contrast, Johannes Kepler pointed out that "the Pythagoreans were caught in such a numerical philosophy", criticizing that "for that reason, they failed in holding judgment by their ears . . . they defined, only by numbers, what is a harmonic scale and what is not . . . and ran the whole gamut of outrages against essential judgment by ears".

It is said that the ancient Greek mode follows tetrachord including quarter tones different in nature from the Western music scale from the middle ages on. Therefore, a frequency ratio that may appear in the tetrachord inevitably includes a quite complicated one. In this respect, it is estimated that separation between the Pythagoreans' rhythmics and actual ancient Greek music is more intense.

The situation of the encounter with <incommensurables> (irrational numbers) which the Pythagoreans confronted and which cannot be divided by any combinations of integers must have been certainly a fatal shock for the Pythagoreans who thus believed that the universe consists of natural numbers (arithmos=measurable numbers) and their simple ratios. Besides, the irony was that a segment ratio of two unequal sides is incommensurable in an isosceles right-angled triangle, which has the best-ordered constitution among right-angle triangles treated as materials for the Pythagorean theorem that is the monument of the Pythagoreans. In other words, this is emergence of the well-known irrational number of $\sqrt{2}$ (to be exact, the irrational quantity since targets are segments). It is believed that this discovery occurred within the Pythagoreans themselves and greatly shook the Pythagoreans (we wonder if they should be called a group of devotees to natural numbers). The depth of the shock which this incident delivered to the Pythagoreans is inferred from the fact that they named such irrational numbers "alogon", that is, "what should not be said" and tried to completely conceal them from the outside. In addition, there were many historical events related to sanctions against these numbers by death from generation to generation. Those included, for example, the episode that a person who leaked the presence of irrational numbers to those other than the Pythagoreans were sunk to the bottom of the sea, and the episode that the person who was sunk to the bottom of the sea is Hippasos, who was a member of the Pythagoreans that discovered the presence of irrational numbers. They darkly colored the opening scene of the Greek mathematics history.

A subsequent finishing stroke against the Pythagoreans that were in a dilemma because of the widespread presence of irrational numbers was made by Zeno of Elea (about 490 BC to about 1430 BC) belonging to the Eleatics led by Parmenides (about 515 BC to about 445 BC). That is historically known "Zeno's paradoxes". He took notice of the limit to the Pythagoreans' concept of identification of quantity with number. In the Pythagoreans' concept, "continuous quantities" of the time and the space are identified with "discrete numbers" and each of the quantities consists of <points> without sizes (note that moments are considered points in case of the time) which are geometrical units, as elements while the respective points are considered to exhibit properties as numbers. Needless to say, the numbers are given a higher priority than the quantities. The quantities are put in the position where they are controlled by the numbers.

In order to set up against this framework, Zeno of Elea constructed strong paradoxes using, as a material, a phenomenon of motion. According to Aristotle's "Physics", we are currently able to know four examples of the paradoxes. Among them, according to the paradox of "Achilles and the tortoise", "the tortoise has a head start of a certain distance, and the faster Achilles will never overtake the tortoise because he must first reach the point where the tortoise started, and then the point the tortoise had reached when he reached its starting point". According to the paradox of "the Arrow", Zeno argued that "the pointed head of the flying arrow occupies a certain point in locomotion at any moment, that is, a time unit that is further indivisible. Therefore, while the pointed head is occupying this point, the arrow must be at rest. If this object moves even a little, this follows that the smallest time unit is further divided. Therefore, as long as the time and the space are indivisible quantities, the arrow is at rest".

Although Zeno's paradoxes are not only flawless as a language system of logic but also formally convincing, they are completely opposed to actual experience. For that reason, they caused confusion in people's mind regarding the relationship between truth and falsehood or it cannot be denied the possibility of being referred to as examples of malignant sophistries that overturn them. Furthermore, Aristotle who introduced these paradoxes in "Physics" refuted them at the same time and formally turned them down. However, Zeno's arguments defy conjecture and the problems which Zeno posed do not lose their raisons d'étre to date. The gist is to ask "if the distance is considered to consist of an assembly of points without lengths, and the time is considered to consist of an assembly of moments without any continuations, then why should not the motion be considered to consist of an assembly of states without any movements?" In addition, it is indicated how it is irrational and difficult to arbitrarily deny only one of the three respects of the concept. This indication is an unusual argument and takes on an impenetrable assertive force. In this way, there were brought into relief in a dilemma the limit and risk of the paradigm of identification of quantity with number based on the advantage of discrete numbers as remarkably advocated by the Pythagoreans.

Zeno's paradoxes acted as a blow to the Pythagoreans that were badly hurt by the discovery of irrational numbers and caused the overthrow of the school. It can be readily imagined that complications until the collapse of the Pythagoreans were accepted as a deplorable event that shook the Greek mathematics world to its foundations, and that serious reflection and revision were given. Consequently, as can be understood from *The Elements* written by Euclid, a strict and moderate new track was realized as was just like Greece. On the track, people abandoned both the Pythagoreans' belief in the absolute advantage of number and the notion of identification of quantity with number based on the belief, and severely sealed the abstract concept difficult to control and verify as symbolized by <infiniteness> and <indivisible unit>.

As what embodies this revision, geometry dealing with continuous and concrete quantities held the first place in place of arithmetic dealing with discrete and abstract numbers and having holding the first place until that point. How this selection was appropriate is eloquently substantiated by the fact that Greek geometry constructed on the new track still shines as the ultimate essence of human intellects.

<3> Creating Sound Coded in Genes
<3-1> Message from Non-Verbal Brain
<3-1-1> How the Sound of Shakuhachi is Created 1. The present inventors think that "<November Steps No. 1> for Shakuhachi, Biwa, and Orchestra" (1967) composed by Tow Takemitsu, a Japanese composer has a historic importance as a masterpiece which combines Eastern sound expression symbolized by Shakuhachi and Biwa with Western sound expression symbolized by symphony orchestra music, and which condenses a sharp contrast of two kinds of sounds in one tune. The ultimately exquisite orchestral sound created with the unique, extremely sophisticated orchestral music technique of Takemitsu along with the direction of Seiji Ozawa, who has been realizing the technique of Takemitsu in sound to an ultimately high level since his first performance, is surely one of the best sound expressions of the 20th century. In addition, it is an undeniable fact that a single Shakuhachi and a Biwa always overwhelm the sound of Western music inexorably and ruthlessly.

When Sadao Betsumiya, a composer, listened to the premiere of this tune, he expressed his opinion in his article: "The orchestra (Japan Philharmonic Orchestra directed by Seiji Ozawa) was induced to produce sound that goes well with Shakuhachi and Biwa with Western instruments, and I thought of the sensitivity and inventiveness of Takemitsu. However, the sharp sound of a harp and the percussion could not beat Biwa, nor could the continuing sound of string and wind instruments beat Shakuhachi by far in expression strength. I doubt the competence of an orchestra, which consists of several dozens of people, as a sound-producing medium for this kind of music. However, it is a very good work if you want to show the essence of Japanese unique music." (The Asahi Newspaper: "Hyo (review)" Jun. 8, 1968). Indeed, this opinion is at the heart of the matter.

It can be learned from Takemitsu's publicly-expressed opinions and passage of his move related to this tune thereafter that the experience of this tune was unusually serious to Takemitsu himself. As an example, some parts of his writing "One Sound" that are related to the awareness of the present inventors will be cited herein.

"The sound of Japanese instruments gains utmost freedom when it is being played . . . it threatened Tsutomu Oohashi violently to an extent that it destroyed his logical thinking during the creation. One stroke or one blow of sound has such complexity that it can no longer serve a role of conveying logic, and it is already self-completed . . . the sound has lost its intended meaning, and while becoming sophisticated, it nears emptiness like a natural sound of decayed bamboo . . . what can I newly add to the sound?"

In this opinion, he understood the essence surprisingly well as if he had been to the current world by a time machine and had seen the ME spectral array, which has just been appeared before the present inventors. A wide range of the degree of freedom of the spectrum that Japanese instruments like Shakuhachi and Biwa can utilize in playing was clearly recognized. In addition, the complete structure and function that allow only one sound to create music before the logical combination of sounds were clearly recognized. The sound of the above mentioned instruments allows players to construct all the microscopic information structure of invisible ingredients as an improvisation at a given place freely and decisively. On the contrary, musical notes which are assumed to express the sound visually cannot retain the unique signal structure and signification inherently and fixedly, or unambiguously. Accordingly, the composition method unique to Western culture, which creates music in a style that uses a musical score where musical notes and other symbols of sound are arranged, is not able to complete the process of forming concrete information structure of music as long as the abovementioned sound is concerned. Even if a music score of a work is considered a music mold, its effect is quite limited. This is because, in a Western style composing scheme which is done as an operation in which marks and combinations of symbols are written on a paper, there is not exist any of the idea and the technical basis for describing the microscopic continuous structure that constitutes the inside of a sound at the same level of clarity as the macroscopic discrete structure (a sequence of musical notes).

However, in Shakuhachi and Biwa music, the continuous transformability of the analog structure that has a decisive effect as music is constructed and built up in synchronization with an actual performance by a player. In the case of Shakuhachi, in particular, the discrete and connected digital structure that can be described on a staff notation is extremely simple and has ultra-low-density in most cases. The musical effect of staff notation is usually indirect and diluted, except for continuity. Accordingly, it is quite questionable to entirely and unconditionally entrust a Western-style "composer" to be a true creator of this type of music that focuses on musical instruments and expressiveness, because the Western-style composer is only in charge of describing discrete connected structure and has to leave the construction of continuous transformable structure to a player.

It is quite likely that Takemitsu was wise enough to have noticed a jeopardy that threatens the act of "composing" in a Western way. By the way, despite the great success of this tune and strong demand for more tunes that are on the same line (it is likely that most of the people who like Takemitsu like this tune the best among his work), the path to deepen his search for the contrast of East and West has never surfaced as his option. Takemitsu's decision not to seek the potential success and glory ahead of "November Steps" is noteworthy. It is related to a reality that the fruit is decisively dependent on the sound or stroke of a skillful player from non-Western world, regardless of whether or not a composition is good, which is often the case with music created through the combination of sound cultures that is different from Western artistic music. It may have given an unfair impression about the Western-style composition and composer. Takemitsu's decision contributes to preventing such an impression to be formed or spread. In addition, it slows the speed at which the internal inconsistency hidden in the music paradigm of Western civilization and music-related social system based on the music paradigm becomes apparent, and it also may have had silent effect as a sacrifice to prevent the system from collapsing. Further, it means that the ultimate, attractive work that only potentially existed and only Takemitsu could have created, has become unreachable for people who enjoy music, before it becomes realized in the world.

There is a conflict like this between Maintenance and territorializing or prolongation of the "music society" dominated by professionals, which Western artistic music has built, and joy of sound to which people are looking forward. In the backdrop, there is a tendency toward further specialization as found in Western civilization, which has attributes like over-simplification of functions, sense of deadlock, and over-competition. This tendency prevents Takemitsu from going straight to the music the human genes look for, as he seriously takes such an attribute that he pledged in "One Sound", "I want to go on as a composer trained in Western ways."

Only a single Shakuhachi and a Biwa create complexity of air vibration and strength transformability, which often overshadows the sounds composed with the exquisite modern orchestral music technique and played by a symphonic orchestra. At the same time, the rare composer is threatened to an extent that "the logic of thinking is torn apart". The new findings in "November Steps" posed a new, very interesting and also very serious problem for us.

Figure 31:
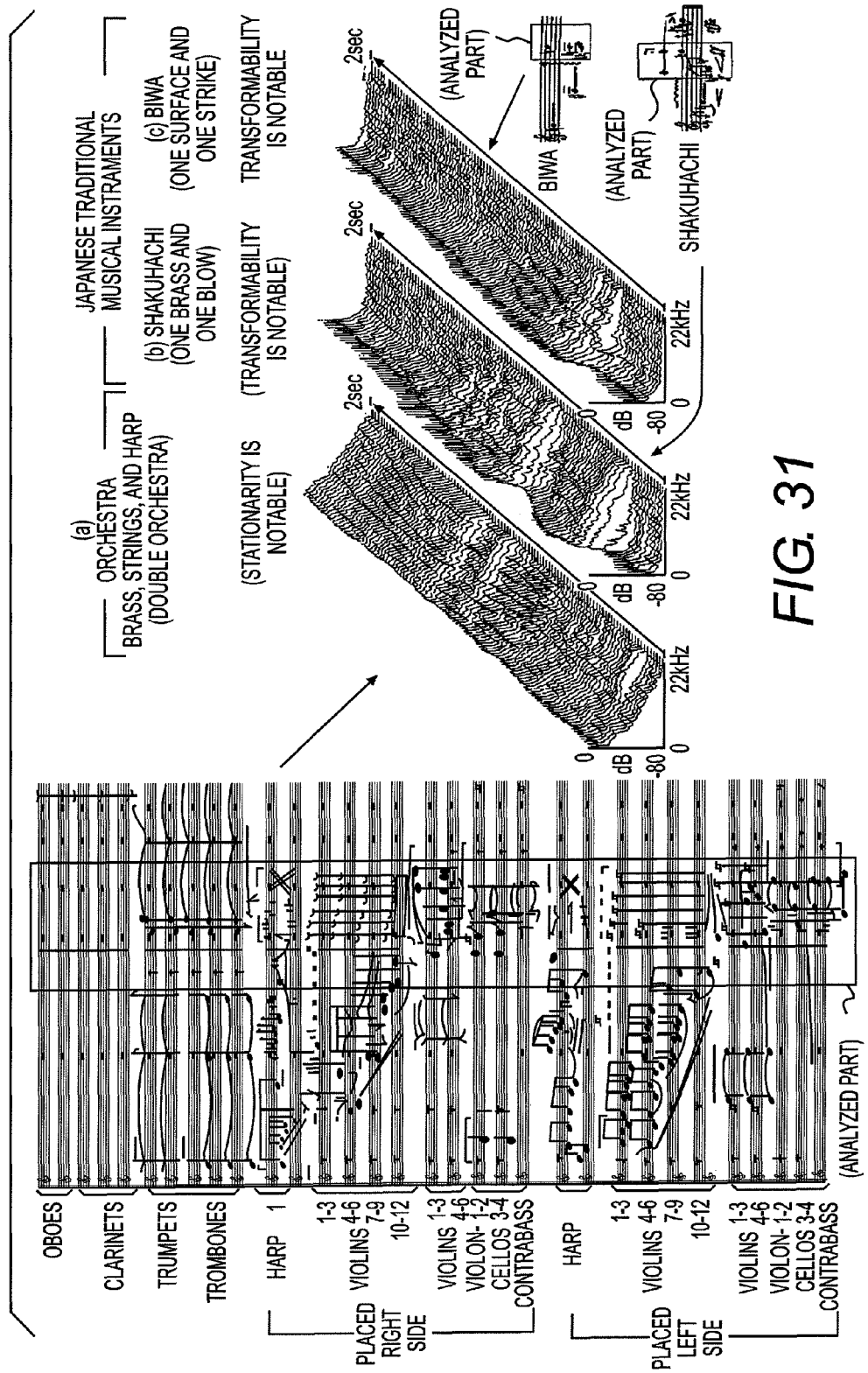
FIG. 31(a) is a view showing a contrast of a sound spectrum appearing in a micro time structure of a second portion of a tune of "November Steps No. 1" by Tohru Takemitsu, illustrating an ME spectral array of an orchestra in Western Europe.
FIG. 31(b) is a view showing an ME spectral array of Shakuhachi in the second portion of the tune of FIG. 31(a)
FIG. 31(c) is a view showing an ME spectral array of a Biwa in a third portion of the tune of FIG. 31(a).

Waveforms of the sound which is created by masters of Shakuhachi and Biwa from simplest musical notes, and which is shown by a ME spectral array for the first time transforms so kaleidoscopically that waveforms created with the complex, exquisite score by the sounds of double orchestras, consisting of several dozens of people, look rather stationary and static (FIG. 30 and FIG. 31: Toronto Symphony Orchestra directed by Seiji Ozawa). Regular and geometric patterns cannot be found in the waveforms of Shakuhachi and Biwa. However, it is not possible to look upon the waveforms of Shakuhachi and Biwa as a completely random and irregular phenomenon. The unique patterns of the waveforms, which look like such a pattern that is made from wire-framing of 3D computer graphics of Yoichiro Kawaguchi, induce us to look upon them as an "objet d'art". When we try to find out shapes similar to these waveforms from the visual memory area of our brain, these waveforms look like wave under high wind, rugged mountains and valleys, cells of plants and animals shown by an optical microscope. They cannot help but make us assume the existence of complex systems against the backdrop of fractals and chaos.

Namely, the spectral array quite resembles to an inevitability based on various rules ranging from universal to unique working together with coincidence, and ecological natural phenomena or simply nature, which results from the inevitability and a contingency surpassing the inevitability. The nature exists beyond contrivance of each form of life, and everything in it means "completeness and perfection". Takemitsu's words "The ultimate sound of a master Shakuhachi player is the sound made by wind while it is going through withered bamboo bushes (from "One Sound" by Takemitsu)" are appropriate for the nature. That a sound is equivalent to nature means it must contain a completely finished structure within the same. The sound made by the master Shakuhachi player must contain some structure, perhaps in the complete form, resembling nature even in more microscopic dimensions than the ME spectral array of the present inventors has shown.

Now, how can the masters create a vibration in the air in a moment, and continue to create them?

If the same thing is executed in such a way that depends on the verbal function which arranges explicit notes on the time axis, like playing the piano and other keyboards, the dimension and speed of information processing are far behind and unrealistic. Players of Shakuhachi try to escape from the control of conscious operation by the verbal brain and make efforts to make themselves free of all distracting thoughts. In playing classical tunes, in particular, players' immersion and self-devotion are intense just in order to play one sound, and the trend that one sound is complete in itself strengthens.

The playing stance of classical tunes, in particular, requires "one sound to reach enlightenment" as the norm, and players try to express the universe in just a sound. On the skill side, players are required to master skills to generate analog fluctuating structure in a continuous sound in beautiful and rich manners. The body of a player at this moment behaves instinctively and reflexively, reflecting the state of the non-verbal brain where complex dimensions and a huge amount of information are whirling, and this is effective in carving and transmitting sounds. Listeners assimilate the sound as a lump of objet d'art into their bodies before decoding the vibrations with objective, extrinsic codes, becoming one with the implicit message that urges them to be close to a cosmic scale.

In this process, the environmental recognition functioning of the non-verbal brain, which has been trained evolutionally by the ultra-dense, complex environmental information of tropical rain forests, must be working as a decisive reception system. At the same time, decoding and assimilation of a huge amount of messages written by biological codes and cultural codes, transitions of brain's internal state induced by this, and re-structuring of body's receptive system to be ready for next sound occur. A time-space called "ma" is necessary as indispensable in order for these processes to proceed and complete.

It can be said that "the states of mind of the players free from any ideas and thoughts", which is the start point of these processes, is a state where the control of the verbal brain is suppressed to an extreme degree and the non-verbal brain is activated to maximum. It is not so difficult for master Shakuhachi players of classical tunes, which derived from the Fukeshu sect of Zen Buddhism, to form an implicit, huge informational space that is cosmic and thus is hard to encode in words. When such a state of mind is perfected, the body cannot help but respond to the same.

The next step is to connect the response of the mind and the body with the act of carving air vibration and continuation. That requires preparation of a mechanism that is sufficiently rational and effective and that can continue encoding the state of mind and body into sound spectral codes in a speed of a god without any interruption. It is without doubt that what the Fuke Shakuhachi established and bloomed based on the sound culture of Japan is this rational and very effective methodology. However, what is interesting is that this rational mechanism has often been referred to as if it were a symbol of irrationality since the encounter of traditional Japanese culture and modern Western culture. Indeed, the mechanism peculiar to Shakuhachi seems, at least from the point of view of Western music, to be extremely far away from the rationality as a sound-producing device or as a skill.

2. Shakuhachi, a wind instrument made of bamboo without any reed, originated in ancient China, and developed uniquely in Japan. The structure thereof is apparently very simple. The upper end of a bamboo pipe is cut diagonally to be a mouthpiece. A player blows his breath into a sharp edge made between the slope of the cut and the internal wall of the bamboo pipe to generate air vibration. The sound generated through this very unstable mechanism has many harmonic overtones and lacks regularity. Further, the number of finger holes, which determine the pitch, is only five. By contrast, the Boehm flute of West has a metal mouthpiece designed to be suitable for stable quality and quantity of sound, and 13 or 14 finger holes along with small holes for trills. It really has a perfect structure for manipulating tones. However, Shakuhachi has only five finger holes. Accordingly, the number of natural tones produced digitally by opening and closing these finger holes are only the five of the traditional Japanese <12-tone musical scale>. However, Shakuhachi provides a highly effective expressional system, which is quite different from opening and closing the finger holes. From a point of view of the pitch control, analog pitch shift skills are very effective in producing every level of sound continuously and freely to fill the vacancy between one natural tone and another. These pitch control skills include <kazashi>, <meri (meru in verb form)> and <kari (karu in verb form)>.

Kazashi is a method to lower the pitch by holding a finger diagonally over a finger hole to close the hole halfway and elongate the effective length of the pipe, and this realizes a declined tone by a little more than a semitone. Meri and kari form a system of skills that are more complex and full of transformability. One basic method is to make a varying degree of half-opening of a finger hole, like kazashi. Another basic method is moving the chin up and down to change the angle at which breath is breathed into a mouthpiece. Karu means moving up the chin that is touching the mouthpiece at the upper end of the pipe. With karu, the pitch goes up. Meru means moving the chin down, resulting in a lower pitch. Of course, these changes are continuous, and the pitch goes anywhere within a certain changeable range. The pitch difference that can be created through meri and kari, that is moving the chin up and down, and closing holes halfway, is as large as one whole tone and a half. The pitch differences are called big meri, middle meri, and small meri depending on the size of the pitch difference. Meri and kari produce pitch changes completely continuously within an allowable pitch control range, making every kind of analog transformation of pitches possible. The mechanism of transformation of the sound system is particularly unstable. The angle of the chin and the strength of breath can immediately change not only pitches but also the tone of the sound. In short, this means a strong non-linearity and also a mechanism that contributes to the formation of complex spectra and rapid transformation of them.

A basic technique to utilize the mechanism is a series of movements of the chin, which constitutes the biggest part of learning to master Shakuhachi, and there is even a phrase "It takes three years to learn to swing the neck". The technique includes not only meri and kari, which is moving up and down, but also <yuri>, which means the repetition of the movements, and <lateral yuri>, which is the repetition of lateral swinging. These skills are often used. There are much more skills than the above mentioned skills. One is <ago-meri>, which produces a sound lower than a natural tone performed with fingers by a whole tone by only moving the chin down, without halfway closing the finger hole. Another is <nayashi>, which gradually heightens the above mentioned tone made by <ago-meri> to a natural tone. The transformation of sound made by swinging the neck, together with the angle, quantity, and sharpness of breath, not only changes fundamental tones explicitly but also gives a more drastic change to implicit harmonic overtones.

While the chin movement contributes to the analog sound transformation, which emphasizes continuity to a great degree, there are a variety of skills that induce sound transformation that emphasizes the discreteness and that is accompanied by digital-like nuance. While <oshi/okuri> is quickly opening a closed finger hole and closing again immediately, <uchi> is, on the contrary, closing an open finger hole quickly as if tapping and opening again. <Koro> is a kind of a trill performed with fingering. <Oshiyuri> is accelerating <oshi> to change it to <yuri>.

In addition to this, the Fuke Shakuhachi has unique skills, and expressions resembling a sound effect play a great part. Among the skills, <muraiki> has a great effect in the climax of a tune, resulting in the heart-moving experience of the audience. It is a skill where the lips are somewhat relaxed and opened wider to blow maximum breath into a mouthpiece to produce a sound that resembles a kind of random noise. <Komibuki> is a skill to shake sound by manipulating abdominal muscle so as to change the pressure of breath. <Tabane> means vibrating the tongue and rolling sound. Even such skill as <Tamane> is used. It is a skill to vibrate the uvula. As has been described, there are many skills. All of these skills add drastic turning points to the flow of sound, and have highlighting effects. Sound with an extraordinary spectrum is created by this system of various skills to manipulate air vibration highly effectively.

The unique structure of Shakuhachi is often considered irrational and associated with lower functions from a conventional view about a flute as a musical instrument. However, it should be noted that the unique structure of Shakuhachi has a decisive role in establishing methods of transforming sound spectra in real-time and kaleidoscopically. A typical point can be seen in the structure of a mouthpiece, where a small change such as the angle and strength of breath can change spectra greatly, resulting in changed pitches, tones, and volume. Under the influence of the idea of Western music, this characteristic is often considered negatively as "unstable". However, from a viewpoint that analog spectral transformation should be used as expressional strategies, it is quite a long way off the mark to regard the function of a Shakuhachi mouthpiece as unstable. At least, it should be evaluated highly as a sophisticated function that responds "sensitively" or "shrewdly".

The piano is one of the instruments that are positioned at the extreme opposite in this respect. The sound spectra of the piano are highly stable. As is shown by the fact that it is difficult to distinguish the sound made by a cat from that by a human, the form of the spectra has reached the level where there is little effect of the player on the same. In other words, the piano is at the top in terms of manipulation of fixed musical tones, and if seen from a different angle, it is extremely insensitive in terms of real-time transformability of sound spectra.

The fact that Shakuhachi has only five finger holes is easily associated with the concept of "primitive" and is used as a criterion to emphasize the functional limit in manipulating pitches. However, it is the structure that makes it possible to change pitches highly flexibly with a large difference between high and low pitches. At the same time, using bamboo, a natural material, can give inherent difference to the attributes of each fundamental tone. Accordingly, the sound of Shakuhachi generates inherent tones following the pitches. It is manifestation of naturalness, and thus it can lender effectiveness to the expression that is intended to be as close as possible to ecological naturalness or simply nature. Shakuhachi, a traditional Japanese instrument, and its traditional playing method, have a sophisticated manipulation of the analog sound spectra, and they have established an extraordinary stronghold in the history of human music culture.

By the way, in the cultural history of sound, music synthesizers appeared to become a big stream in the latter half of the 20th century, which might threaten the stronghold of Shakuhachi in terms of transformation of sound spectra. The function that changes sound by a program or in real-time has reached a level far beyond the point that any other non-electronic method has ever achieved. A newer stream may be the scratching technique contrived by a disk jockey, who controls the heart of sound at a disco, to manipulate the rotating speed and rotating directions of LP players. It is successful in exercising complex transformation of sound spectra in real-time, although it is limited. In addition, although on an experimental basis, the <morphing> technique, which skillfully exchange sounds with different sound sources and substantially different sound spectra in continuity, has been developed and introduced into the composing of electronic music.

In order to execute <modulation>, or transforming waveforms with a synthesizer, at least you have to keep producing a series of sounds with the manipulation of the keyboard. One hand maybe used to produce a series of sound with fingers, and the other hand may be used to manipulate the <modulation wheel (a disk which is positioned near the keyboard usually, and by rotating which one can adjust the depth of transformation)>. Other option is to use both hands for producing sound, and use a knee, a foot, or pressure of breath to manipulate a modulation lever or volume control. This means that the manipulation of producing sound and the manipulation of changing the tone are in a tradeoff relation. However, in the case of Shakuhachi, producing sound and changing the tone are inseparable, integrated and mutually complementary, as can be shown typically by the example of meri and kari skills. Or rather, it can be safely said that they are synergistic. The effect in carving continuously and complexly transforming the "state of mind" in sound spectra in real-time is far greater than and overwhelming the present synthesizer.

When we look at the <dimension> of modulation, what synthesizers are allowed to do is only to choose any of the prepared programs, in most cases one, and thereafter increase or decrease the parameter on one dimension. This is an inevitable limit because the manipulation of sliders and wheels is limited to level control, or in other words, "simply increase or decrease". Of course, it is not impossible to make it multi-dimensional by changing it to a joy stick, or the like, as far as a circuit configuration is concerned. However, if you do so, there will be by far more need for consciousness and thought to intervene than when one-dimensional parameters are manipulated, and it will be more difficult to follow the state of mind of a player which keeps changing in real-time. Or rather, it will hinder the formation and maintenance of higher-dimensional <state of mind>.

Now, seen from this viewpoint, what is the characteristic of Shakuhachi? The formation of macroscopic continuing sound begins with fingers closing and opening finger holes to decide the effective length of a pipe, just as fingers on the synthesizer produces sound. In other words, the two are alike in that fingers play the pivotal role. On the other hand, the change of tone, or in other words, the modulation of vibration, is addressed by an area consisting of organs on and around the face including the oral cavity and lips in first place and the muscle in the head including the neck that moves the chin together with the nerve system that supports them all. This area in our body, on the other hand, has muscle and nerve elements networked in highest density, like fingers, and is ultimately a luxurious motor system. This system occupies one of the largest areas, along with fingers, of the motor area and the sensorial area of cerebral cortex, which controls the system, or in other words, the largest number of nervous cells. These systems enable programming, execution and feedback control of extremely complex and sophisticated operations probably at the highest level of all parts of a human body. It is notable that the face, in particular, has a cluster of muscles that directly reflect the state of the brain and can output "expression" in response to information about the state of mind and change in it as soon as such information is received.

These systems are most suitable for translating the change of the face position and muscle structure of a player, whose mouth is touching the mouthpiece, into the modulation of sound in coordination with fingers, which is another manipulation system. The training of how to directly reflect the bodily change on the spectral structure of sound as complex dimensions and high-density information has been handed down for generations as the essence of traditional Shakuhachi skills.

Namely, these mechanisms are even superior to the real-time sound spectra manipulation function of a keyboard synthesizer, which is a historic success that the sound technology of the modern civilization has built. In other words, Shakuhachi is superior in inconsistency between the macroscopic sound structure formation and its microscopic transformation, multi-dimensionality and complexity of modulation parameters and freedom of its manipulation, quickness, comprehensive mutual-influence between the brain activity and sound, and time-wise unity (no delay).

3. Now, it is time to compare the development processes of the Japanese Fuke Shakuhachi, which is unique as hardware, with those of <the Boehm flute> as representing Western flutes, and explore the meaning of the evolution of instruments in two different sound cultures.

Western flutes had had six finger holes until the <renaissance flute> era of the 17th century, and they are almost the same as a prototype of Shakuhachi. Gradually, starting at the latter half of the 17th century, the mechanism thereof began to be improved. The trend was toward more finger holes, after 4-key, 6-key, and 8-key flutes were made, Theobald Boehm, a German flute player, established the prototype of <the Boehm Flute> in 1847. This type of flute has 13 (or more) finger holes and 2 tremolo keys. In addition, the inside diameter of the finger hole was designed to be physically ideal. However, the size had become bigger than a finger can cover, and then a mechanism to close the hole using a pad was adopted. In this way, flutes (including all ranges from piccolos to bass flutes) that can respond chromatically to all 12 equal temperaments and have homogeneous tones appeared.

The origin of Japanese Fuke Shakuhachi dates back to the 7th century, when Shakuhachi was introduced from China as a flute that is a part of traditional Japanese ceremonial court music. At present there exist 9 pipes which are estimated to have come to Japan around the 8th century. They have five holes on the front side thereof and one on the rear side thereof, so six holes altogether. In short, Shakuhachi and flutes had the same starting point in terms of the number of finger holes. However, in the medieval period, Japanese Shakuhachi began to evolve in the opposite direction to Western flute when <hitoyogiri: a slightly smaller Shakuhachi, which uses a bamboo pipe in the opposite direction to Fuke Shakuhachi)> or the previous form thereof appeared. The number of finger holes was reduced to five from the original six, with four on the front and one on the rear. <Hitoyogiri> is believed to be the precursor of <Fuke Shakuhachi>, which in turn is simply called <Shakuhachi> in general. The choice may appear to be retrogressive and incomprehensible from the view point of Western flute culture represented by flutes and of the modern rationalism at the base thereof. However, the reduction of the number of finger holes, which apparently seems to be retrogressive, is a good move for the flight of expressive functions of Shakuhachi symbolized by meri and kari, and an epoch-making <evolution> that is as excellent as the development of the key system in the Boehm flute.

This mechanism is extremely latent and hard to grasp from the surface as a cause-effect structure. The effectiveness of this reform is highlighted as a photographic negative while none of the repeated trials of increasing the number of finger holes of Shakuhachi were successful in the history. Relatively well-known trials for increasing the number of finger holes include <7-hole Shakuhachi> and <9-hole Shakuhachi> which were produced in the 1920s to utilize fingers unused in 5-hole Shakuhachi, as well as <Okurauro>, into which the Boehm flute key system was transplanted. Each of these improved manipulation of digital sound structure considerably compared to a conventional 5-hole Shakuhachi. However, both Shakuhachi players and listeners didn't welcome the increased-hole Shakuhachi. The reason is always, in a few words, that "the sound lacks tastefulness", and "the sound is not interesting."

The sharp difference between Shakuhachi and a recorder, which has the same sound-producing principle, is notable. Actually blowing the two will reveal a contrasting difference, especially so to beginners. That's because it is rare for a first-time Shakuhachi beginner to produce a sound, while any beginner can produce a sound with a recorder no matter unskillfully he or she handles the same. The difference is caused by the fact that a recorder has a mouth hole and a duct before a mouthpiece so that breath can be blown in at a suitable angle against the edge of the mouthpiece, while Shakuhachi does not have this system.

Vertical flutes that have a sound-generating mechanism like Shakuhachi and recorder usually have a fixed windway before a mouthpiece and a mouth hole before it, so as to eliminate unstable sound production. An "ocarina" is a good example. By simplifying the windway, the transformation of lips can be reflected on the sound spectral transformation to a considerable degree. <Surin> or contrivance to induce analog transformation of sound is prevalent in Indonesia and other Southeast Asian countries. Further, a Chinese flute called "dosho" has an exposed mouthpiece like Shakuhachi, but the inside of the mouthpiece is gouged so as to make it easy to generate sound. However, only Shakuhachi has refused such "rational contrivance" and stuck to the traditional mouthpiece structure where it is difficult to produce sound. The attitude of Shakuhachi like this may appear to be an incomprehensible obsession to the eyes of other flute cultures. However, as has been seen already, if you want to continue transforming the sound spectral structure as you like and in a complex and quick manner, the mouthpiece that is designed to respond extremely sensitively to the state of breath demonstrates incomparable high performance. In the history of Shakuhachi, the effect and benefit of this highly implicit expression strategy has been virtually objectively verified and the value has been directed as the consensus. It has to be admitted that behind this undeniable reality is the society itself and its constituents that have the sensitivity and judgment to the non-expressive implicit sound world, which is worthy to be called the acme of nonverbal brain function, as cultural codes (that is the characteristics of society).

By the way, in the <modern music> field in the West, since the development of "Prepared piano" by John Cage and the proposal of "Musique concrete" by Pierre Schaeffer in the 1940s, a flow had been formed where traditional instrumental sound was made into objet d'art. Flutes were no exception (for example, "Sequenza I" by Luciano Berio; 1958). However, for the purpose of this (to make objet d'art), that is the carving of air vibration, the Boehm flute is not suitable, and the achievements of the Boehm flute are quite limited compared to those of Shakuhachi.

Not all of the reform trials of the Fuke Shakuhachi have been unsuccessful as the increase in the number of holes, but some of them had good effects and are established completely. One such example is the reform of mouthpieces mostly in Kinko-school and Tozan-school. Originally, the edge was made by cutting the bamboo. This edge was replaced with "hasami-guchi" made by processing buffalo horn or ivory. This reform makes it easier to generate sound and strengthens the mouthpiece. Another example is <nakatsugi>. A typical Fuke Shakuhachi uses the seven joints of long-jointed madake bamboo near the root. The mouthpiece is set at the top joint, and three finger holes are made between the second and third joints, and two finger holes are made between the third and fourth joints. Nakatsugi is a kind of fitting mechanism like a socket made between the second and third joints so that the bamboo can be disassembled and assembled easily. This mechanism not only enhance portability but also plays an important role in adjusting tones by adjusting the variations between joints that are common among natural bamboo. In addition, <jinuri> is done to finish the inside of the pipe. First of all, the inside of the pipe is polished into a flat cylinder, and then a mixture of urushi lacquer and tonoko polishing powder (sometimes gypsum is used) is spread, and finally the surface is finished with red or black urushi lacquer. This type of Shakuhachi, which is processed, is called <jinuri-Shakuhachi>, and is most popular.

These improvements are countermeasures taken after the modern era in order to standardize and stabilize the functions as far as sound expressions are not hindered. There is the need for ensembles with other instruments and music, in particular, with koto and shamisen in an ensemble called <sannkyoku-gasso> behind this move. There arose a need to standardize the pitches and maintain them.

Traditional Shakuhachi whose structures and functions have not been processed as described above, are called <kokan>, <nobekan (meaning without any nakatshugi)> or <jinashi Shakuhachi>. Without nakatshugi, there is no choice but look for a bamboo with appropriate lengths between joints that can satisfy basic structural conditions as it is in natural state. Some are without hasamiguchi for the mouthpiece, increasing instability. Further, some are called <fushi-nokoshi-shiki>, and have the joints removed but not completely polished. These joints are carved off little by little while tones are adjusted. Some part of the joints are left inside, and the inside surface is not flattened nor coated. The bamboo is left to nature's complex creativity. This kind of pipe is far away from regularity, physically or geometrically. On the other hand, it has a structure that emphasizes complexity and non-linearity because natural characteristics of a plant have been assimilated. Needless to say, this is closely associated with improved function as a sound-generating device that is aimed at highlighting the complexity. In this case, what is found is a vector that is directed toward the increased analog complexity, which is in the opposite direction to the Boehm flute, which is made with precision metal processing utilizing modern technology. In <Myouan schools> they stick to <koten (classical) honkyoku> and never play <gaikyoku> such as Sankyoku ensembles. Jinashi Shakuhachi, as described above, is treasured without doubt in these schools. In Kotokoryu, when <honkyoku>, which does not need the restrictions of pitches, is played, not a few players try to use jinashi Shakuhachi. This choice may seem irrational, at least from the viewpoint of people who idealize the Boehm flute of the West. However, from the viewpoint of the unique expression strategy of Shakuhachi, this choice just hits the nail on the head and is an excellent rational judgment.

The two types of mutually opposing ideas of rationality associated with Fuke Shakuhachi and the Boehm flute should be noted. Shakuhachi strongly materializes the rationality that is associated with the control of ultra-dense complex structure that the nonverbal brain proclaims and that continuously transforms. On the other hand, the Boehm flutes (from piccolo flutes to bass flutes) materialize the rationality associated with the control of logical connected structure made up of neutral symbols that the verbal brain proclaims. The sharp contrast between the two kinds of flutes that represent the East and West are against the background of the fundamental phase difference that lies between the culture that prioritizes implicit non-verbal-brain functions and the civilization that prioritizes explicit verbal-brain functions.

4. By the way, the function of Shakuhachi that can transfer the state of mind directly to the sound structure or rather amplify it to form the sound structure, makes it possible to make the tone similar to the biological code that human voice expression has and strengthen the feature to transmit. As a result, if the brain of a player is in a state that is controlled by the activities of the brain area that affects feelings and emotions, such as the cerebral limbic system, forceful emotional expression directly associated with emotions such as delight, anger, sorrow and pleasure is made possible. This, in one aspect, leads to effective expression and successful performance. However, there is some risk of hollowing out the message that respond to higher mechanisms such as <sensible brain> and <prefrontal cortex>, which is the seat of reason and works as a negative feedback system to the emotional system to support the achievement of goals. The <sensible brain> is composed of the brainstem and the monoaminergic projection system that applies positive and negative feedback control to <prefrontal cortex> so as to transcend from the simple rationality to supreme beauty.

In fact, it is a very important pitfall from the viewpoint of Fuke-sect Zen Buddhism, which is the source of Shakuhachi. Accordingly, an important task in the mainstream of Fuke Shakuhachi is to transcend from shallow egocentrism, and to create ecological expression of souls integrated into one with nature and universe. It is related to the mental training with the utmost goal of making "sound made by wind while it is going through withered bamboo bushes" and with the wish to be "one sound to reach enlightenment". The reason why Shakuhachi has a decisive meaning as a Fuke-sect ritual vessel (training tool) is that one sound of Shakuhachi represents the state of the trained soul of a monk, who walked around in lonely mountains and went around the towns and villages asking for alms. In other words, the most important justification for existence of one sound of Shakuhachi played by a Fuke-sect monk is that it is the index of the mental training, in particular, the decisive index for how far away from egocentrism.

<Nohkan> is a flute used in <hayashi> of <nohgaku>, and the nohgaku has a conspicuous characteristic in Japanese sound culture that it worries emotion-oriented characteristics could lead to the erosion of high-dimensional brain activities. <Nohkan> uses a different type of hardware (for example, setting of "nodo" or throat) and software (for example, playing method called "hishigi") from Shakuhachi to make emotion-oriented expressions difficult physically.

The music world of Shakuhachi is the result of improvement and utmost sophistication since the medieval era through the modern times, created from an expressional strategy of <music without any rhythm> that came floating along the oasis and grassland routes of the Silk Road. However, this expressional strategy is not unique to Shakuhachi. It has had a wide-reaching yet deep, invisible influence upon all ranges of Japanese sound culture. Various developments can be found in an enormous system of choral chanting by Buddhist priests, traditional narrative chanting such as jyoruri, gidayu and naniwabishi, minyo or folk songs and enka, shamisen and Biwa music. These are systems that see the essence of music in continuous, non-stationary structure, in contrast with Western music, which tried to see the essence of music in systems of discrete symbols represented by staff notation system and 12 equal temperaments.

Shakuhachi is notable because it deliberately aims to carve the air to form continuously transforming complex structure in real-time in a sophisticated manner. Shakuhachi has been perceived under the name of "primitive" with strong negative impression of simplicity ever since the encounter of Western modern sound culture and Japanese traditional sound culture. However, on the contrary in fact, attention should be paid to the fact that Shakuhachi has rationally built up a sound information manipulation method equipped with tremendous complexity and swiftness.

The shock that "November Steps I" by Tow Takemitsu gave seems to mean that a crack that was tearing up the basis of Western sound culture was brought to light by the sound of Shakuhachi, as described above, and Biwa.

<3-1-2> Knowledge Structure that Surpasses Verbal Characteristics and Communication Characteristics 1. Ludwig Wittgenstein, a scientific thinker famous for his logical positivism, said in his "Tructatus Logico-Philosophicus" (1921) that "whereof one cannot speak, thereof one must be silent". That means nothing but a negative reason for existence for non-verbal information. On the other hand, Michael Polanyi, a scientist turned philosopher with the background of physical chemistry (a brother of Karl Polanyi, who advocated economic anthropology), advocated <tacit knowledge> and said that "we can understand what cannot be said".

The term "tacit knowledge" is often under suspicion for irrationality, anti-scientific characteristics, or mysticism because of its unique nuances. However, in reality, it can be safely said that it is an intellectual device prepared sufficiently rationally and elaborately.

M. Polanyi paid attention, in his book "The Tacit Dimension" (1966), to nonverbal information, which seemed to have been forgotten completely as screening out and abstraction had been rampant after Descartes in the Western world. Polanyi built up his thought about its existence and effects quite regularly and effectively, and advocated it under the name of "Tacit Knowledge". It is related to all aspects of scientific thought, but in particular, it heightens our expectation to have a new and effective view on how to perceive the structure of sound. This model can be summarized in the two-tier systematized concept, as described below.

In short, tacit knowledge clarifies the important relations between the following two items together with the understanding of a comprehensive being that they cooperate to build up. The first item is details that constitute the comprehensive being, and humans can perceive it but cannot say it explicitly in words. These items are called <proximity items>. The second item is the whole image of a comprehensive being looked at through the first items, and humans can distinguish the same from the others. This is called <remote item>.

This model resembles the model which has been nurtured in sound ecology, and by which the present inventors perceive the sound that constitutes music in dual structure between the macroscopic and the microscopic structures. The present inventors and the others visualized the structure of sound that constitutes music with the use of ME spectral array method, and the structure, in particular of Shakuhachi and Gamelan, will be a good material. First of all, the implicit structure that is too complex and too minute to perceive with consciousness, and that can not be depicted with words, which is depicted in the microscopic time field, matches the first item, that is the proximity item, very well. A comprehensive whole being that includes all these inside it, in other words, an explicit structure depicted on the macroscopic time field that can be perceived by the consciousness, explained in words, and translated into musical notes, matches the second item, that is the remote item very well. Whether this understanding is appropriate or not, and how far it is effective, will be verified in the processes where analog to digital conversion is applied to music via staff notation of Western music and the analog-digital conversion is tracked with the use of ME spectral array.

Figure 32:
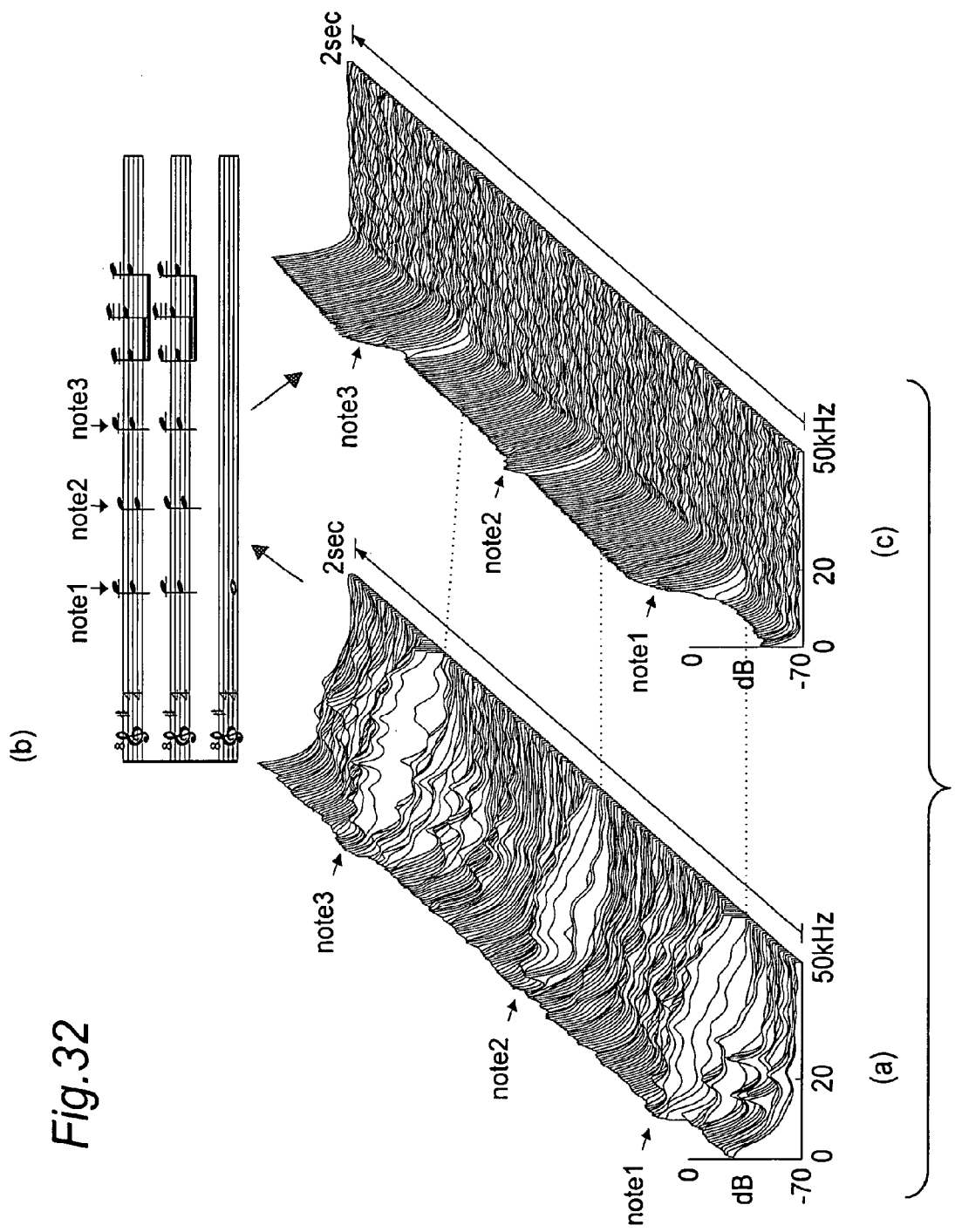
FIG. 32(a) is a view showing an analog/digital conversion of a music through a music score, illustrating an ME spectral array of a sound of a gamelan.
FIG. 32(b) is a view showing the music score based on FIG. 32(a)
FIG. 32(c) is a view showing an ME spectral array of a sound of a piano played based on the music score of FIG. 32(b).

Bali Gamelan, which is a typical music of a culture outside the staff notation system, was chosen as a material to facilitate consideration. Performance of one of its traditional tunes, which is titled "Gambang Kuta", was recorded in Bali. Next, the structure of the recorded sound was shown by the precise ME spectral array, and the discrete connected structure of this tune was mapped on a staff notation. Further, the mapped score was played with the piano, which is the most common standard interface when the staff notation is converted to sound in Western music, and the piano sound was shown on the ME spectral array in the same condition as Gamelan (FIG. 32).

The spectral array of Gamelan shows that the overtone area has more components than the fundamental tone, and the transformability of the spectra is notable. It spreads over a wide frequency range of 100 kHz, and changes tremendously intricately in a microscopic time field. In addition, continuous, non-interrupted transformation of the spectral structure occurs at every point over a time field corresponding to one stroke of sound, if seen on the score.

Our brain has a function to perceive the extremely quick and complex transformation of sound structure, as seen here. Through the function, we doubtlessly sense the atmosphere of a genuine delight and good performance of Gamelan sound. An information structure as shown by the microscopic time field of Gamelan sound matches the concept of the proximity items of tacit knowledge without much inconsistency, as described in this way: "detailed items that constitute a comprehensive being, and people can perceive them but cannot tell them in words". The high speed and complex information processing in the brain corresponding to them is by far beyond the limit of the processing capacity of the verbal brain module, and it should be addressed by the non-verbal brain equipped with a suitable function.

By contrast, in the macroscopic time field, there can be seen a state that a sound corresponding to a stroke rises and falls, which can be easily perceived by the consciousness and can be coded in musical notes on a staff notation. The whole of one sound constitutes a unity made up of continuously intricately transforming microscopic sound structures that are proximity items. It is "a whole image looked at through the first items, and humans can perceive it as distinguishable from the others" and it can safely be said that it matches the second item of tacit knowledge, which is remote items.

The Gamelan music was coded and mapped on a staff notation, and reproduced with the piano (FIG. 32). The spectral array of the sound resembled those of the original Gamelan sound in the macroscopic field, and coding and reproducing were achieved to a high degree. By contrast, in the microscopic field, sound components are quite scarce compared to the Gamelan, and the frequency range is almost limited to an area within 10 kHz. There are few changes in spectra except for a change occurring upon pressing a key, and steadiness prevails.

In other words, in the case of the piano sound, with respect to the remote items, sounds that are close to the ideal musical sound are generated accurately and arranged on the time axis on the staff notation. However, components that constitute proximity items and that are not depicted on the staff notation almost disappeared, and sounds are in general changed to have a discrete, connected structure. The decline was too substantial to inquire about tacit knowledge. The conversion system using a staff notation and the piano could not secure the proximity item, that is the first item of tacit knowledge, and a very large ratio of the proximity items was lost during the process.

Thus, the coding to a staff notation and the reproduction using the piano preserved the Gamelan sound with a strong emphasis on discrete, connected verbal information structure, while they highly skillfully screened out and discarded the temporally continuously transforming nonverbal information structure that plays an indispensable role in creating what music should have to be music. The knowledge structure of the verbal dictatorship of the modern times Polanyi criticized by advocating the concept of tacit knowledge revealed a decisive limit in the music world.

As described above, the transfer characteristics of the staff notation system are poor in terms of complex sound structure and its transformation in the microscopic field. However, in reality, most instruments, unlike the piano, produce sounds that are far from the ideal musical sound and secure analog structural transformation to a considerable degree, and therefore, they can prevent the fault from becoming visible. On the other hand, with respect to the piano, with the support from acrobatic tuning, composition, and playing techniques, the fault is compensated and thus it has become successful. In another aspect, African Americans in U.S.A. found a highly effective function of "rhythm instrument that can also play a melody" and "percussion instrument that can play chords", and a new road was opened to commercial music through jazz and pop, resulting in developing a new demand. Further, musical synthesizers overcame the early-stage disadvantage that a steady oscillation sound (musical sound itself) could not function as music material, and were finally put to practical use due to the envelope generation that gives non-steady structure thanks to transformation of amplitudes in one sound such as what is called attack, decay, and sustain as well as low frequency modulation. These achievements resulted from the fact that continuously transforming analog sound structure, which Western music theories have ignored and, it seems, tried to cast out, was brought to reality. It looks as though the principle of Western music was overturned and beaten by biological inevitability.

2. Just as the staff notation was used in the past to perceive the macroscopic structure of music as a visual pattern, the ME spectral array created by the present inventors has depicted the microscopic structure of music. Then, can this spectral array play a role as "visual image equivalent to music" or something near to it like "highly normative music mold", just as the staff notation has done, and should it do so? Polanyi talked about a question of this nature, "I know that outright clarity destroys the understanding about complex phenomena of the present inventors. As you probe into details of a comprehensive being, the meaning will be wiped out, and the concept of the present inventors about that being will be destroyed". This opinion points out a negative side of converting the ME spectral array into a staff notation. Or rather, before that, his opinion is notable in that it also points out the need to reconsider the current practice that the quantitative musical scores made out of staff notation are regarded as equivalent to music, and the Western music paradigm that tries to define details of music with discrete symbols despite the fact that music is in itself continuous.

The viewpoint of sound ecology, is shown in the following remarks. In the first place, the image of the sounds of Shakuhachi and Gamelan depicted by the ME spectral array, and in particular, the structure that changes in the microscopic area are the elements of music, but they also belong to the category of natural biological phenomenon, which can never be reproduced. That can be likened to a tracking of a chase made by a lion hunting a deer. The analytical record of that one-time chase may offer precious learning for the purpose of the accumulation of experience and lessons for the future. In particular, it will lead to a tremendous value as a resource for insight. However, can it really lead to a positive effect as a "mold die for a hunt"? Further, how difficult to make a mold and to cast the behaviors of animals into the mold? It may be true that the details of hunting behavior are basically controlled by biological codes, while concretely they are formed in the time-space framework influenced by accident and inevitability, in other words a one-time historical entry that will never repeat itself again.

In a manner similar to that, the microscopic structure of music inherent to human beings is being created while integrating a great influence from accident including the information environment of the performance site, although its basic protocol is also controlled by biological codes and cultural codes. The ME spectral array that cut out the state at that moment is depicting a section view of sounds you yourself are creating and appreciating that could not be visible as it is. The effectiveness of the ME spectral array lies in that it reveals the activity of the nonverbal brain that is carving out and reading out this complex thing, and that it removes curtains covering the eyes that were applied by a modern civilization too focused on the verbal world. In addition, it is expected to play a role in reconsidering the relation between men and sounds, opening a new path to gain wisdom and insight, and reevaluating the progress and achievements.

3. Polanyi said, "When the present inventors try to use something as the proximity item of tacit knowledge, they take it into their own body or enlarge their bodies so as to enclose it inside, to be a person that houses it". In fact, good listeners assimilate sounds as objet d'art of a lump of sounds before analyzing the complex air vibration created by a master player that drastically transform with codes of verbal characteristics, decompressing the super-compressed encryption with biological codes and cultural codes that constitute another system and assimilate them with message. However, if a person does not know Shakuhachi, how far is it possible to convey to the person, using words, the content and structure of information processing and the emotions created in the body?

First of all, the brain of humans appropriately depicts the height and length of played sounds or the number of sounds with verbal characteristics or symbolic connected means such as words, numbers, symbols and marks to a certain degree that enables production by other people. The staff notation Western civilization has invented shows an excellent example. However, it is nearly impossible to convey details of sounds such as, for example, spectra of tones and their transformation in the same degree of accuracy. (FIG. 30 and FIG. 31)

Now, look at another example of behaviors in "a drinking party". It is possible to convey by means of verbal characteristics how many glasses of alcoholic drinks were drunk by whom, and how much he or she drank in a party to other persons who were not at the party with a considerable precision. However, when you want to tell people who do not know what alcoholic beverage is like about something like the taste of the drink the persons at the party enjoyed or how they felt after they were drunk with a means of verbal characteristics, it will be inevitably very difficult.

If there is a need to tell about the graceful and emotional tones of Shakuhachi to a person who has never experienced Shakuhachi, or to tell the taste of a famous alcoholic beverage dubbed nectar, it will surely turn out to be a vain effort however hard you may try. However, the communication which is so difficult to do with verbal procedures can be achieved without any flaw with the easy procedure of letting the person listen to a sound of master player's Shakuhachi or proposing a drink of the excellent beverage.

A new problem posed here about the transfer subject and transfer method may not have been attracted much attention in recent years, but it must be treated as a fundamental and highly important one. About this problem, we found the idea of Blaise Pascal, which emphasized concreteness and demonstrativeness and did away with abstraction, and <empiricism> advocated by John Locke, George Berkeley, and David Hume, which pointed out the limit of rationalism advocated by Descartes. However, it is not realistic to approach the problem posed herein as an extension of their thinking. Accordingly, the present inventors reconsidered this in a framework of sound ecology, and decided to give the name of "communicative information" to information that can be understood by communicative means including verbal, discrete, connected processes, and the name of "experiential information" to information that is understandable only through the process of experiencing it actually, which can be said to be high in nonverbal characteristics, so that we can distinguish the two types of information.

Experiential information communication means that it requires the process through which acceptance of information is realized physically by exposing the body in the existing information space. This is similar to what Polanyi said: "Whether intellectual or practical, our body is the ultimate tool for all the external knowledge of the present inventors". By the way, an information processing process serving as the core in what Polanyi called "body" is exactly what we call the activity of the nonverbal brain. In a manner similar to above, his words implicitly support that not only <indirect recognition> information which is <remotely receivable> but also <direct recognition> information that is accompanied by <close reception> is very important. However, communicative verbal information and experiential nonverbal information are not completely polarized but spread on a kind of spectrum with different degrees. In this sense, they are similar to the analog-digital spectrum.

There are many aspects that can be used as the indicator of the difference between communicative and experiential in the information phenomenon. In particular, quantitative attributes of a subject such as information quantity, dimensions, transformation speed are important. In relation to this, the processes and the time needed to construct or re-construct the subject information system sometimes become important. Further, the mobility of the information transmitted by the subject or the mobility of the information source may sometimes have a decisive importance. Still further, the storage characteristics and reproducible quality cannot be ignored. It will be possible to organize information based on these aspects in a gradual layered system stretching from communicative to experiential quality with respect to the information structure and information communication.

Now, let us see concrete examples. The top layer that is most communicative and most suitable for artificial electronic information communication contains information that has one-dimensional, simple discrete symbols or discrete connected structure, such as numbers, formula, words, text, small-scale computer programs. These are small in capacity, and easy to prepare, and have high mobility that enables them to go smoothly through artificial communication channels. In the next layer which is larger in capacity, with the above information developed, documents and books (only those with letters and symbols excluding images) are found. Up to this level, almost all the information can be processed by the verbal brain function.

Following these layers, should come a layer of data that contain sounds and images that were originally analog and then converted to signals as they were still analog or digitalized data of them. The activity of the nonverbal brain is involved in these, and the capacity becomes incomparably large as compared to information consisting only discrete, verbal symbolic connected information. In addition, image data are two-dimensional. However, these data storable in various media can be practically communicated by substantially simple communication means. Next is the layer of audio-visual information which integrates remotely-receivable information such as words, voices, and visual and audio information. Still further, comes a layer of multimedia and virtual reality that has increased dimensions with controlling signals and the like integrated by the intervention of computers. Up to this layer, all the layers have an information structure that can be responsive to both verbal brain function and nonverbal brain function, and all can be readily communicated by means of transmission. All these have an <indirect recognition> information system that is <remotely receivable>.

However, considering layers higher than this, there is a situation where movement of information in itself, or in other words, communication by means of transmission, is hard to achieve. For example, see art objects. The effect is dependent not on the object itself but on the "art information" transmitted there from. In other words, the information system that is mainly composed of light information, but sometimes also of information that stimulates audio, tactile, olfactory, and somato-sensory system. However, the art information that an art object has as its effective element cannot be separated from the material object in itself, unlike other media such as photographs, prints, and videos. In a strict sense, art appreciation cannot be realized unless the recipient is in the <direct recognition> communication mode, often accompanied by <close reception>, and under the condition that the retina of the recipient can directly receive the light signals transmitted from the art object. In other words, whether or not the recipient has seen "the real one" has a decisive meaning. This communication style, needless to say, belongs to the experiential area, and the dimensions, quantity, and transformation degree increase incomparably, and more emphasis is put on the area of nonverbal brain function.

The information communication realized here cannot be put on the flow of "communication" by its nature. However, it is possible to transfer the information. It can be realized by moving the art object, which is the source of the information, to a place where it will be appreciated. This phenomenon implies that information communication is not exactly the same as a transfer of information. A similar style can be found in the other communication of information which clearly is experiential in nature, such as appreciation of live <music> and <performance art>. Players are moved to realize communication. Of course, people who appreciate such information can move to where performers are. In either case, the communication of information is realized through the act of moving human bodies in an act of travel, and in this way, the complexity, multi-dimensionality, and transformability of communicable information can be increased.

Some <rituals>, which is live performance nonetheless, can be transferred, and some cannot be transferred. In this case, the executers and participants of the rituals should move to a predetermined ceremony space, and the mobility of information is lost. On the other hand, there are only exceptionally few cases where transferring <festivals>, which is often closely related with rituals, is possible. In this case, the source of information is away from a place where a festival takes place. Along with this, the relative importance of experiential characteristics becomes substantially remarkable. Further, in the case of natural, or partly artificial, <landscape>, mobility of information is not possible at all. At the level as high as this layer, a process of moving a recipient in a form of <travel> is indispensable. This is nothing but an act of experiencing the information space, which is different from the recipient ordinary space, as an environment, resulting in a much sharper emphasis on the characteristic that it is dependent on experiential information communication and nonverbal brain function.

The present inventors have information activity areas related to the transfer of information systems of a larger scale such as learning <skills>, <mental training> and <cross-cultural exchange>. These require a longer experience in a form of <stay> than <travel>, which is temporal. What is the ultimate that follows this type of information of experiential characteristics? Probably, it can be found in the lifestyle handed over while people are settled in an environment made up by a <natural ecosystem> and a <traditional community>.

There is no room for doubt about the mutually complementary nature of verbal communicative information and nonverbal experiential information in first place. It should be noted that the spectra of the two on the surface are so different that they are often perceived as opposing. In order to reduce confusion or misunderstanding as much as possible, it is effective to summarize the phase difference of the two as an information processing process with a view to the functions of the brain.

Communicative information has a structure that is relatively simple and explicit, and has strong discrete characteristics and high suitability for digital information processing. Humans can take this kind of information into the brain via communicative media such as words and symbols. This corresponds to information of <indirect recognition> characteristics communicable by <remote reception> proposed by the present inventors. This is the background of the concept of "communicable information". Although the information processing process goes on in a complex manner after reception, the main component can be put on the flow of the information processing of the verbal brain module, and usually this is the mainstream. This process consists of smaller processes: storing the one-dimensional sequence of words and symbols in the data storage system of the brain; logical processing, which means retrieving stored data to a work space memory, which is the "cooking table" of brain information processing, and reorganizing them; storing them again in the storage system to memorize; and outputting them into an outer environment after converting them into communicative information such as voice, letters, and sign language via bodily functions working as an output interface. This process is generally suitable for monitoring by consciousness and also for reporting the contents with words. If this characteristic is utilized, the method of the information processing and communication of the contents can be readily and effectively commissioned to rational learning process, which means <education> in the style in which knowledge is encoded and communicated.

On the opposite, experiential information, as it is, is not very suitable for digital information processing, since the information structure is more complex, implicit, and continuous in characteristics. It is impossible for humans to convert this kind of information into media having language/symbol characteristics to put into the brain without losing the essence of the information. In other words, experiential information cannot be communicated. Instead, after direct contact with the subject information source and the information space, what was experienced, can be transplanted (mapped) into the nonverbal brain as a comprehensive whole, as an information system that spreads continuously on a complex and fluctuating dimensional structure. This property goes well with the information concept of <direct recognition> characteristics proposed by the present inventors. In this case, the input response led by the contact with the information source ranges in an area related to sensing, sensory perception, and perception, where nonverbal characteristics are strong.

This experiential information forms an information system far greater in capacity than communicative information. Accordingly, the experiential information should be memorized in a large-capacity data storage system within the brain in a different way from communicative information. This category of memory does not match well with major classification methods including the dichotomy of long-term memory of Larry Squire. If anything should be found to match, probably, it ranges widely from a large part of <procedural memory> and semantic memory and episodic memory of <declarative memory>.

These data can be transferred or copied into a large-scale multi-dimensional continuous workspace memory system, which will work as a "cook table" for information processing inside the brain, so as to be processed, and the results of the processing will be recorded as postscript or stored in a data storage system. However, the experiential information stored in the data storage or the workspace memory cannot be outputted to an external environment as it is, unlike communicative information (for example, if our body had a function as a video projector by nature, some part of output would be possible). In addition, because of the high-density complexity and high speed transformability, the processing process of experiential information cannot be monitored by the consciousness circuit in the brain nor reported by means of verbal characteristics, as is possible with communicative information. However, after storing this kind of experiential information in the nonverbal brain, it is highly possible to realize converting stored experiential information into digital information so as to transfer the digital information to the verbal brain.

In this way, experiential information processing has such an important quality that it proceeds mainly by the activity of the nonverbal brain which is far beyond the conscious area. This kind of brain activity is inherently implicit and tacit, however intellectual it may be, and therefore we cannot help but consider it as a black box. In addition, the handover of this activity to next generations cannot be sufficiently effective by means of explicit, rational "education", which is done mainly through communicating once-encoded knowledge. Accordingly, it will require depending more on "tradition", which can control implicit information world more effectively.

4. It is desirable to refer to this intellectual activity related to experiential information as <experiential knowledge>. To summarize again, it is intellectual activity that enables creation, reception, storage, reconstruction and output in forms including actions of such information as has dimensions, density, and complexity surpassing the communicative level. Now it is necessary to pay attention to the nonverbal brain function, a whole of combined functions of brain and body, as a base for this activity, where information that cannot be translated into words can be taken into the "body"—rather nonverbal brain in fact—and assimilated, and the result will be outputted as actions.

The nonverbal brain and the verbal brain modules that constitute our brain work as one, needless to say. Then, isn't it possible to reconsider tacit knowledge in a way that the whole of intellectual activity in which nonverbal brain is involved as a indispensable and decisive factor is what we call tacit knowledge. Aside from experiential knowledge, which has been considered so far, <intuitive knowledge>, <insight knowledge>, and <traditional knowledge> are assumable. It may still be elementary but some description of these concepts will follow.

Probably, <intuitive knowledge> is an intellectual activity that can be considered as related to <intuition>, which is the most implicit and whose transient response is the quickest of all the brain functions of a human. The intuition has a characteristic of a black box, as it performs information processing reflectively and quickly, either in response to input from outside or from the internal environment or sole voluntarily, without the intervention of analytic logical thinking as part of verbal process, and the intuition immediately constructs a sort of information structure that includes programming and execution for action, and outputs the same. The core of this function can be described as an essentially fixed program system that is based on programs preset in the human's brain inherently in accordance with the genetic information, and combined with write-once operating system imprinted socially and culturally.

Whether this activity is considered essentially inherently fixed or essentially trainable depends greatly on culture and society, and that defines the level of activity of nonverbal brain of a whole society almost decisively. On one hand, there is a society where the function is considered inherently fixed and cannot be the target of learning, and therefore there is no awareness, opportunity nor means available to train and develop it, like in the modern West, for example. The activity of intuitive knowledge remains in a germinal stage even if a person is already an adult or even an elderly man because it has been left unnoticed in the social environment as described above. In some cases, a person may end up with his intuitive knowledge below the level of an infant, seen by the human standard. If such a contracted intuitive knowledge is entrusted for major decision, faults and catastrophes may occur repeatedly, thus declining the reliability and evaluation of intuitive knowledge furthermore. In such a social environment entrapped in a vicious cycle, intuitive knowledge and the nonverbal brain function that practically supports it will have to assume a negative position that it is an inherently unreliable, poor, dangerous activity of the brain and you should never depend on the same. In the modern civilization, this trend seems to be prevailing.

However, in other societies and cultural regions, regardless of whether they are conscious or not, people seem to believe that inherent intuition is an activity material like other abilities, and the germ will develop into full-fledged activity only through certain learning and training. In a social group where this trend is conspicuous, the will, opportunity, and means to train and develop intuition will never be missing. In such a society, a social standard for evaluating the talent, attainment, and performance related to intuition has been established substantially explicitly, and the constituents of the society are evaluated by that ability. The intuition of a person trained in this preferable social environment is sophisticated, reliable, and high in repeatability, and it deserves the name of <intuitive knowledge>. Attention should be paid to the fact that there is a society where this kind of brain function is given a high position as a core area that is highly effective and highly reliable, and it is secured there supported by experience and achievement.

By looking at the difference between the two views about intuitive knowledge through the window of culture of flute sound, as has been described so far, the Western art music that has produced the Boehm flute is the typical example of the attitude where adding intuitive knowledge to the main stream of thought was avoided, and its working was considered unusual. In contrast, Japanese sound culture that has developed Shakuhachi may be considered as an example where intuitive knowledge is considered as one part of the main stream of thinking and its activity is utilized as decisive. There, for example, under a slogan "three years for neck swings and eight years for good sound" neck swinging, which may seem what anyone can do, is completely trained in a traditional system with good records, and a system of abilities has been established so that the control of extremely complex and quick sound can be achieved precisely even without thinking.

When the Western modern world which has been built while dependence on intuitive knowledge has been avoided theoretically and practically, is facing a critical limit, it seems that reviewing the treatment of intuitive knowledge should not be put aside. In order to do this, it will be effective to explore concrete materials like flutes that represent both the West and the East and their cultures, and to try to integrate the intellectual activity such as logic and intuition that has been separated.

<Insight knowledge> can be seen as an important area of intellectual activity to which nonverbal brain function contributes, and it has been developed based on insight which has been gained by the brain of higher animals. <Insight> which is a biological concept means the process found in higher animals in which sudden and direct problem solving behaviors are found after some explorative or trial-and-error approaches based on a comprehensive recognition of the environment and the subject. It is extremely non-analytic and illogical. Insight knowledge here can be described as instant, dramatic, super-logical intellectual activity that develops based on insight with analytical, logical thinking of human verbal brain module integrated. It includes from implicit information world that is not easy to perceive or know consciously and at best can be sensed, or detected, to explicit information world that can be clearly perceived and known consciously, and it is built up with all rational wisdom, logical wisdom, intuitive knowledge, and experiential knowledge employed. It will bear fruit as intellectual activity that leads predicatively to highly perfect prophecy-like recognition with both dramatic and mature characteristics, which is not realized if only logical and verbal thinking was entrusted. Lucid judgment and prediction on things that are beyond rational inference and cannot be covered by knowledge or experience are the prime example. For example, in the history of development of Shakuhachi, non-linear, unexpected, and appropriate flash of wit, such as the decision to "reduce the number of holes that is already small" can be an example of manifestation.

<Traditional knowledge> can be described as intellectual activity through which tacit knowledge that requires experiential knowledge, intuitive knowledge, and insight knowledge, in which nonverbal brain functions are indispensable factors, is introduced into a wide field called society and history, and their effectiveness are verified in actual practices and they are handed down. This process inevitably accompanies evolution and selection. Accordingly, things that have good achievement worthy of the name of tradition ensure "tacit rationality". Especially, it is notable that it often appears in the form where "the mechanism cannot be explained, but the fruit is assured by good track records and thus reliable". By the way, Japanese traditional mathematical operation techniques (abacus and mental arithmetic) and the traditional sound culture of Bali give us a glimpse of astonishing activity.

With respect to how cultural codes that transmit and decode implicit non-verbal information can remain communicated from one generation to another in a society, Polanyi said, "great philosophical movement stemmed from the Enlightenment means rejection of the reasons for which human's completely intellectual decision was praised". "Continuing generations, in particular the constituents of them, reject the possibility of testing all teachings that nurtured them", and he takes a position not to abide by "the rejection by science of all authorities or tradition". Further, while "statements induced clearly by explicit presumptions can be critically tested by reviewing the presumptions and the inference process that induced them", he argues that "if we know many things that cannot be told . . . the concept of knowledge based on completely explicit grounds will be destroyed, and we have to conclude that the communication of knowledge from one generation to another is mainly implicit".

Based on this idea, Polanyi tries to restore <tradition>, which the Enlightenment tried to destroy together with <authority>, as a decisive means to communicate tacit dimension to other generations. In other words, "traditionalism requires believing before knowing, or in order to know. It is based on deeper insight on the essence of knowledge and communication of knowledge, than scientific rationalism, which only permits us to believe clear statements that are based on clear data and stylized inference there from, and that allow repeated testing". His observation is excellent.

By the way, throughout the 20th century during which Western civilization continued to have a great influence on Japan, Shakuhachi was doubtlessly one of the areas that were most affected and whose value system was undermined because of the phase difference between West and East sound cultures. The effort to develop and spread multiple-hole Shakuhachi, which began to be prevalent from the 1920s, was induced by the pressure of such a cultural environment. In particular after the World War II, Western arts established a predominantly superior position, and during the process, Shakuhachi was often likened to be a symbolic instrument of pre-modern characteristics that are a negative value of Japan. Its primitiveness, simplicity, irrationality, ideality, authority, and mysteriousness were pointed out, and as Shakuhachi had been exposed to harsh criticism, there was even a time when it would have seemed natural if Shakuhachi had been described as "collapsed."

Taking this opportunity, various efforts were begun to review the history and the state of Shakuhachi, and in particular, internationalization and modernization were pursued seriously. Against such backdrop, the success of "November Steps I" of Tow Takemitsu and Katsuya Yokoyama, the young Shakuhachi soloist who played for it, was invaluable. "November Steps I" overcame the adverse situation surrounding Shakuhachi, and unveiled the fundamental power of Shakuhachi in an astonishing way for the frontier of the world music. It is difficult to accurately evaluate how much this encouraged budding Shakuhachi players who were facing difficulties. Among such budding players, Hozan Yamamoto was remarkable and went into Jazz successfully. The others followed to be players who get much international attention.

The progress from collapse to restoration of Shakuhachi was in an easy-to-see style of expansion of applications on the surface. However, what should be noted here is that while applications became more varied, there was also increased interest in classical Honkyoku, which can be said to be the essence of Fuke Shakuhachi. As a result, valuation of the structures of traditional instruments and their playing methods began to be established. As for "kokan", which was once almost abandoned, convincing recognition has been established, for example, about the difference between <jinashi Shakuhachi> and <jinuri Shakuhachi>, for example. The recognition is that even though both look the same, there exist differences between them in instrumental characteristics. The former is suited for classical "honkyoku" while the latter is suitable for sankyoku ensemble and modern tunes.

When you inquire about what is the background of the restored recognition of kokan and honkyoku, many theoretical supports or promotion by slogans were not found in the records. Instead, it seemed to be natural outcome as if water exudes from ground. It vividly shows that the history of Shakuhachi has been tacitly supported by the coding system of Japanese sound culture and its source "traditional knowledge", which have been passed down widely, deeply, and assuredly and kept alive continuously in Japanese society. In consideration of what is the substance of the life functions supporting this activity, it is impossible to think of anything but the nonverbal brain. It is remarkable that the activity has survived the inappropriate historical cultural environment such as Japan after World War II and has been secured as the essence of a social group.

<3-1-3> Can the Coded Sound Revive the Brain?

1. The sounds coded in the human genes have traced a path toward extinction in the modern civilization that originated in the West. The footsteps were exposed before us. There are many heavy negative legacies: the basic concept of regarding music as discrete, symbolic, connected information; a musical sound as an atom of sound defined as the elements; staff notation where sounds are coded and arranged in a quantitative coordinate space; the identification that the staff notation that is visible information with the substance being electromagnetic waves is equal to and mutually convertible with music that is audio information with the substance being air vibration; 12 equal temperaments calculated to achieve this irregardless of the inherent scale; and absolute pitch that is the 12 temperaments which cast doubt on the physiological adaptation to humans imprinted irreversibly in the verbal brain of infants. The process of considering these in detail based on the framework of sound ecology revealed that the root of these wide ranging ill phenomena converge to the thought that screens out nonverbal, tacit information, which is difficult to grasp for the consciousness that emphasizes verbal, explicit information easily perceivable by the consciousness.

It was also revealed that the nonverbal information structure, the essence of music, has been richly developed in the cembalo, which was replaced with the piano in the process where this thought dominated Western music world; Gamelan of Bali, which is now in the limelight; and the sound of Japanese Shakuhachi, which is based on a view in contrast with Western music. These types of sounds that are beyond the description of words have a lot in common with the environment sound of the rain forest, which is the most promising candidate for the inherent sound environment that was coded in human genes. This kind of environment sound has been screened out without much attention in Western civilization.

Exploring the background behind the separation from the sound coded to human kinds from the viewpoints of "brain function" seems to indicate that the idea which values verbal brain function with the <consciousness> placed at the top has been armed with theoretical backing, and made into belief or rather religious faith, and that this idea is a leading force. The influence can be seen vividly, for example, in the classical brain model in which the asymmetric hemisphere is divided into two and the left brain is named the superior brain with verbal functions and the right brain the inferior brain without any verbal functions.

In contrast, the present inventors reviewed the position of verbal brain from the point of view of sound ecology framework, and made a new model showing "the main body of brain which has nonverbal characteristic and common with all animals and the verbal brain module stemmed from it at the stage of great apes". A consideration based on this model is highlighting that the nature of Western civilization, which prioritizes verbal characteristics by reversing the relation between the nonverbal main brain and the verbal brain module, is inseparably linked with the decline of "sounds coded in genes."

Getting rid of this present state that may deserve the name of "verbal brain worship", needs to be hastened partly in order to keep the health of the body and mind of humans living in this civilization. However, it is not easy. That's because once a system is set to place the priority on the verbal brain function, in particular <consciousness>, which is quite upside down, there are also many layers of mechanisms ready to prevent escape and return to the original state. It is reminiscent of triggering a kind of <self-decomposition program>.

First of all, one example of an acute symptom mainly affecting individuals is a pathology whose cause is that consciousness occupies the operating system of the main body of the brain, which is originally multi-dimensional and comprehensive. That narrows the scope of vision of the human mind, makes thought one-dimensional, discrete, and low-speed, and closes its circuit to make emotionally independent system. There, as far as logical formality is appropriate, "absolute confidence" is created regardless of whether it is true or not, and it continues to grow indefinitely.

Next, a chronic symptom affecting the society is that the vicious cycle triggered by downplaying nonverbal brain function is becoming worse. The validity of implicit, nonverbal brain function that constitutes tacit knowledge such as intuitive knowledge, experiential knowledge, insight knowledge and traditional knowledge, is essentially probabilistic. If this is to be excluded from society for lacking reliability as compared to the definitive validity, which is the essence of verbal brain function, tacit knowledge which is coupled with nonverbal brain function and the learning process of tacit knowledge will be excluded from society. In other words, opportunities to train nonverbal brain function are lost, and the activity of non-verbal function, which needs much more time to nurture than verbal functions, will deteriorate at an accelerating pace. This will in turn decrease the opportunity and achievement of intuitive knowledge and traditional knowledge in the society, and decrease the authority of such knowledge indefinitely. If this type of vicious cycle has continued for several generations, as in the modern civilization, it is impossible to estimate how far the nonverbal brain function humans are inherently equipped with will keep deteriorating.

Further, from a completely different angle, "professionalization and specialization of learning and arts (later gymnastics included)" are not ignorable as a phenomenon to worsen the deterioration of nonverbal brain function and make it difficult to review or return at the level of civilization history. <High specialization> appeared around the middle of the 19th century in the Western world, continued to be legitimized due to the predominant effectiveness and grew considerably over the 20th century. Although it seems to have dominated the world, it has started to weaken increasingly.

As a perspective, it is possible to say that the Western specialization of learning and arts was a strategy developed to professionalize the approach to <the true, the good and the beautiful>, which is the ultimate activity that the evolution of the brain has built up. As was described with <sensible brain model> by the inventors, the sensible brain function performs positive and negative feedback on the linear and simple rationality of reason, breaks the limit to transcend to rationality that is optimized for more multi-dimensional and large-scale time-space system. The sensible brain function is the reward system related to the true, the good and the beautiful. Accordingly, it essentially does not go alongside with <interests> of direct nature that reason tries to output, but transcend them and it has a property of a control circuit. Seen from this viewpoint, a lifestyle in which people earn by professionalizing "the true, the good and the beautiful" houses a mechanism leading to self-defeating contradiction.

In modern civilization, in order for those who want to be professionals as their occupation to legitimize their existence, they are required to show publicly that they are superior in their specialized abilities, first to non-professionals, and then to other would-be professionals of the same profession. Accordingly, what is recommended to maintain and improve their positions is to develop extremely primitive arithmetic strategies on how to produce achievements for evaluation as efficiently as possible within a limited capacity. In other words, they narrow their views, narrow down their target to as small as possible by specialization, and focus their energy into the same.

Max Weber is one of the theoretical leaders who encouraged professionalization and specialization of learning at the beginning of the 20th century. Max Weber described, in his book "Science as a Vocation", without any hesitation, about the essence of the strategies, which do not seem very noble, and encourage them. He insists: "those who cannot wear eye masks are not suited to pursue academic learning." (Japanese translation by Kunio Odaka) It imposes self-occlusion and single-functioning on the development of brain of a person who aspires for academic excellence (and art) functions as "justice". In a highly specialized society where people earn their living within a specialized, cut-out area, there are education systems and institutions ready to educate candidates for professionals on one hand, and on the other hand, there are fewer positions for earning than the number of candidates produced from such institutions. In short, selection in a form of cutthroat competition is an indispensable preset process. This structure is rarely found in a society which is at the level of primary industry. The candidate cannot escape selection based on their specialized abilities because of the competition for survival required by this framework.

More attention needs to be paid, although there has not been any example pointing this out so far, to the fact that "competition" thus created leads to a negative effect that is detrimental on the implicit, nonverbal brain function. The mechanism is as follows: in order to progress this competition, selection and screening-out flow in a fair manner, it is indispensable to <express> the rules and make objective, rational judgment based on the rules. In contrast, if there are no predetermined <explicit rules>, or if judgment is made insightfully or depending on the circumstances after seeing the result, it leads to self-destruction. Accordingly, the value standard used in this system should be suitable for descriptions as explicit and objective as possible, and preferably, candidates should be arranged on a line in accordance with one-dimensional, quantitative, discrete scale to make the screening-out simple and clear.

In short, in this value system, the complex, implicit, and ambiguous activity created by the multi-dimensional, continuous, large-capacity information processing of the nonverbal main brain are hard to be related to positive values, more predestined for negative value counting and more likely to be the target of exclusion. In contrast, the activity related to the verbal brain module that covers only the one-dimensional, discrete information processing can play a part as predominantly prioritized evaluation target. Now, after the old civil service examination in China was discontinued, the modern Western civilization we live in has a much stronger tendency toward competition tilted toward the verbal function than any other cultures, and it seems to be strengthening.

As described above, seen from the viewpoint of brain functions, consciousness dominates the brain as an acute symptom, nonverbal brain functions deteriorate as a chronicle symptom, and increased competition in line with the high specialization directly and indirectly accelerate both symptoms. All of these lead to deterioration of nonverbal information world and accelerated depletion of tacit knowledge in the present state of Western civilization. It seems that the system as spread all over the lives of citizens. A daily manifestation of such a system can be seen vividly in a discussion of two of the world top primatologists. One is Birute Galdikas, one of the "Leakey Trio" (primate-studying trio as found and trained by Luis Leakey, a queen of fossil-anthropology). The other is Tetsuro Matsuzawa, famous for his "Ai Project" that studied the intelligence of chimpanzees. The record is featured in "Eco-Sophia No. 5" (2000). An excerpt from a relevant part is cited below.

Matsusawa: Welcome to Japan. I think this is your first visit to Japan. What is your impression?
Galdikas: A beautiful country and it is safe.
Matsusawa: I can understand why you say that it is safe, but what made you say beautiful?
Galdikas: The way towns look is beautiful. Roads are beautiful. No trash. Dust bins are also beautiful. The gas storage tanks are decorated with flowers.
"Beauty" or a sense of beauty can be perceived in every detail.
Matsusawa: Safe, beautiful . . . what do you think of people?
Galdikas: I think they are good. Polite, kind, and don't talk unnecessary things. They are calm when responding to me. In America, where Tsutomu Oohashi lived, people always talk loudly with each other. Otherwise, they cannot understand each other. They cannot feel safe or they cannot keep bond with each other unless they keep talking. However in Japan, there is no need to talk loudly. They sit silently, and they can understand each other's feeling. I never get nervous.
Matsusawa: Your talk reminded me of my experience in America. For example, there is a bench in a station for waiting for a train. When you want to sit next to a stranger, you have to talk to him or her from a distance, "Good afternoon", "Good weather today", or "How about . . . ?" while crouching your back, smiling, and moving your eyebrows up and down. If you quickly approach the person without these actions and sit next to him or her, he or she will jump up out of a surprise. However, these actions are unnecessary in Japan. There is nothing strange in silently sitting next to a stranger. The stranger would never get surprised. Even if you don't send a lot of signals conveying "I'm not a dangerous person for you", or without any verbal explanation, people can coexist without becoming nervous.
Galdikas: You are right. You don't have to use unnecessary energy for relating with people. It is really nice to be able to relate to the others without speaking. It is a delight, too. In American culture, people are forced to be nervous every time they relate with other people. When people depart, the same thing happens as when people meet. Say something, pat the shoulder, hug, smile, move your eyebrows up and down, have a small talk, and confirm the bond before departing. In Japan, they will only see each other, bow, and say "Good morning". When they depart, only saying "Good-by" will suffice. I hope the calm and great traditional culture of Japan like this can be maintained without being engulfed by the wave of global change.

This conversation is an example showing that non-verbal communication called heart-to-heart communication is working effectively in a society as a cultural code, and that even if this is changed to verbal communication, it does not always means improvement, but it rather leads to a loss of time and energy and increased tension, which is a negative effect.

Rita Carter, a medical journalist, considers the problem in a framework of left (verbal) and right (non-verbal) brain and argues in her book "Mapping the Mind" as follows:

"The prosperity of homo sapiens as a species can be attributed to the left brain. You can calculate, communicate your intention, and make a complex plan and execute it because you have the left brain. However, there are good and bad things. The bad reputations of Western society, including materialism, aspiration for dominance, and apathy, are derived from the left brain. In contrast, the right brain has characteristics such as gentle, emotional, and aspiration to become one with nature, and it reminds us of the East."

Further, the ultimate form of verbal information is the <number> of <economic value>. It should not be ignored that the number is now self-propagating and dominates the world. Currently, the world total of Gross Domestic Production is 30 trillion dollars, while the total of currency trading reaches 300 trillion dollars within a year. Michael Ende, a literary person, spent his last days accusing the unethical currency trading, and left the following words: "As far as I can see, the problem of money today is that money itself is traded as a commodity. By nature, money should be a compensation for equivalent value, but now it is a commodity in itself, and that's the most decisive problem." (cited from "Ende's Last Message")

The most positive movement to get rid of this situation is that there is a full-fledged momentum, which is unprecedented, to reconsider modern rationalism and technological civilization within Western civilization in itself. The force is manifested in the movements of Galdikus and the others of Leakey's Trio of Women. At least, it is doubtless that they are paving the way to reevaluation and re-approach to intuition, experience, insight and tradition and they are gaining momentum. The biggest problem of this approach is that of all things, the nonverbal brain function, the "seed", is beginning to be depleted. Other problems include the unpredictable length of time needed for reconstruction, which will be long, increased risk of verbal priority strengthened during the time, which must be opposed and prevented, and taking countermeasures against such risk.

2. On the other hand, what is possible as an approach from the side of cultures that have preserved nonverbal brain function? When the wave of Western modern civilization spreads with the Enlightenment, Descartes' dualism, and physics of Newton upheld, some of the traditions of the East presented a particularly sharp rupture with them. The philosophy of Laozi and Zhuangzi, Zen, and sound culture of Shakuhachi are typical examples. Deciphering the background using functions of the brain revealed that there are ideas that treasure nonverbal brain function and strongly suppress verbal brain function, in contrast with Western civilization.

Interestingly enough, the origin of these ideas that dated back into ancient times has something in common in some senses with the inventors who take precautions against the flood of verbal information. That's because the philosophy of Laozi and Zhuangzi, which values experience over words, originated in China when it was already building the best culture of letters at that time, and Zen, which is said to begin with "extralingual transmission of the Zen dharma (heart-to-heart, non-verbal communication without using words in the scriptures)", dates back to ancient India when it was building up scriptures that must have contained the largest number of letter sequences in the world at that time. The era of "Chu", when Laozi and Zhuangzi were believed to live in (fifth century B.C.), is roughly the same as the era Buddha lived in. In addition, both expressed strong caution against letters and words. Then, it implies that the activation of language use in the country and society they were living in was causing some side effects, or some signs of them were appearing, and that such phenomena were causing worries and sufferings of the ordinary people. Such worries and sufferings were in turn the starting point of the wise men in the past for their thought and actions. It may be that at that time already, there had arisen some situation that needed appropriate control of information of verbal characteristics, and that was not ignorable anymore.

It is supposed that the original language coded in human genes had been simple like Malayan and Lingala. Then, the languages of the civilization that were advancing rapidly, such as ancient India when Buddha lived, and the "Spring and Autumn and Warring States periods" when Laozi and Zhuangzi lived, were already far away from the original characteristics, and were already deep into more sophisticated adjustment state than the standard state that had been preset in the genes. The keen eye of the wise men may have seen something worrisome in the state of that time and the future.

Zen and the Philosophy of Laozi and Zhuangzi encountered each other in China, and from the interaction between them came out Zen Buddhism. It was further transferred to Japan repeatedly from the Kamakura era to the Edo era, and it gradually got settled, leaving much influence in the development of Japanese culture. Fuke-shu Zen Buddhism, which is the basis of Shakuhachi culture, is one of the important streams. Fuke Shakuhachi is a good material to be used to reveal the contradiction and limits ingrained in the paradigm of Western art music. Japanese Zen, which produced Fuke Shakuhachi, has been developed continuously from the Kamakura era through the present times, although there have been some ups and down. Since the Meiji era, in particular after World War II, it has been spreading with momentum internationally, and it has improved the substance.

In this connection, Zazen, which is the core of the training of Zen Buddhism, can be perceived as learning and checking to suppress the behavior of the verbal brain function at will. For example, Zazen of Japanese Soto-shu sect is performed sitting facing a wall in a style called <Kekka-fuza>. In this style, environmental information is considerably removed, and therefore, the circuit of verbal brain module is closed to form feedback loop, and consciousness begins an oscillation and will be in a better position to control the whole brain. It is extremely difficult for ordinary people to push it back and secure the dominance of the nonverbal brain. It is the essence of training to become able to counteract it and realize the mental state of <freedom from all ideas and thoughts>. In this training, the trainer monk uses a Zen stick and a hit on the shoulder if he senses some mental distraction. This is one form of bio-feedback mechanism incorporated in the training, and is a contrivance to train the body to learn to control the power of consciousness with thought control. A brain that is trained in this way can have the power to counteract a situation overwhelmingly where the verbal brain would naturally dominate.

The rituals of Mikkyo or esoteric Buddhism should be noted as an example in contrast with the strategies of Zen. In Japanese esoteric Buddhism, multi-dimensional, continuous, high-density, complex, highly transformable sensorial information is provided for the environment to send it all into every sensory window of a man overwhelmingly. Such information includes the setting of <odan>, the display of <mandala> visually, chanting <shomyo> auditorily, and burning of goma and ko or scent. Further, in Kegon-shu Buddhism, in the same orientation, a magnificent ceremony called Shunie is held incorporating natural ecosystem in Todai-ji Temple. These things automatically open the information reception space of a brain multi-dimensionally, and the strong power removes without any difficulty the one-dimensional control by verbal functions, in particular by <consciousness>. Notably, the environment full of sensory information created this way has much in common with the information environment of rainforest and the performance of the Mbuti Pygmies held against the environment, with respect to the structure. In this respect, it can be said that the strategies of esoteric Buddhism and Kegon-shu Buddhism have taken a very clever intellectual strategy that is developed by decoding the basic design of human's brains and utilized the decoded information.

Focusing on the strong power of Zen in suppressing the verbal brain implies that it is in the best position to promote conversion of recognition and thought of the modern West where presumably the nonverbal brain function is indefinitely deteriorating in line with the out-of-control abuse of the verbal brain function. In addition, such effort is being promoted consciously. It is not sure whether the present time is already at the stage where such an effort should be evaluated, but for sure this approach is very hard to get on track beyond expectation.

Zen has ultimate slogans developed through the long history, for example, "ishin denshin or heart-to-heart communication (the truth which is impossible to communicate in words is communicated from a teacher to a disciple)" and "furyu-monnji or intuitive discernment of Buddhahood (a Zen term that means nonverbal communication is conducted because enlightenment cannot be communicated in words or letters)". These slogans not only mean the predominance of the nonverbal brain function, but also strongly mean the denial and exclusion of the verbal brain function. This tendency has been strengthened in ideologically violent move during, for example, religious disputes, and the exclusive, solitary, absolute value of the nonverbal function was advocated, and there has been an increasingly strong tendency to force the disciples and the outsider altogether to abandon verbal functions. This is exactly the opposite to Descartes' idea of making consciousness absolute. However, in terms of exclusiveness, both have something in common, and this poses a problem. Authentic Zen approaches must limit the use of words, in particular, objective, logical, and rational use of them. However, the knowledge structure of the West at present has left the communication channels other than verbal functions to decay, and the inherent biological codes are, in high probability, lost. There is no receptive function left there for the communication mode of Zen, which denies verbal characteristics. This may be one part of the background behind slow progress although Zen has long been expected to be a candidate to play a role in bridging a deep gap between Eastern and Western thoughts.

In order to add to this structure, there are problems that will be described below, which may have been there for a long time. For example, one problem is related to the characteristics of experiential information. While it is desperately difficult to communicate experiential information such as the sound of Shakuhachi or taste of alcohol beverage using verbal information, just one sound of kokan played by a master player, or a sip of nectar will at an instance accomplish the transfer of enormously complex information perfectly. Among people who have trained and nurtured the nonverbal brain function to a stage where a person begins to play Shakuhachi when he feels excited enough and he knows it takes time to produce nectar, communication called "ishin denshin or heart-to-heart communication" is easily performed, which cannot be perceived explicitly or objectively. It enables communication almost always certainly and exactly in all the dimensions of tacit knowledge including intuitive knowledge, experiential knowledge, insight knowledge and traditional knowledge, depending on the degree of training.

By the way, it is impossible for people who have attained the level of activity of the nonverbal brain as high as this to communicate the essence of tacit knowledge by means of verbal characters, and the impossibility is recognized at present so clearly that it is almost idiotic to try to do this under the current language system. Accordingly, discussing this matter with people who are able to receive only verbal information, or those who believe they are, is not promising at all.

Under the circumstance, from the viewpoint of people who are good at tacit knowledge, they try to do "ishin denshin or heart-to-heart communication" and "furyu-monnji" at the first phase of interpersonal relation, and then to people with whom such communication cannot be established, they have to change the communication mode down to the one limited to verbal information area, and usually this remains the norm. The lack of a counterpart in mutual relationship cannot help but have a negative effect.

The same kind of limit can be found in the philosophy of Laozi and Zhuangzi, which is merged in Japanese society through integration with the Zen platform. For example, not a few first-rate engineers working at recording studios knew in the 1970s to 1980s that even high-frequency components which cannot be heard as sound by humans because they are above the audible upper limit have some effect in improving the sound quality, and there were effective skills actually used to utilize such components. Against that backdrop, in relation to the establishment of a standard for digital recording, many research papers appeared claiming that there was no difference in sound even if high-frequency components above 16 kHz didn't exist in the area of authentic acoustic psychology, and that became established in the academic circle. What happened after that? Many of competent engineers officially remained silent while they didn't change their belief at all. On the surface, there was no argument or resistance during the period. This strange situation continued more than ten years.

Despite the knowledge and confidence, no one argues nor takes actions. This attitude is the same as "mui-shizen (abandoning artifice and being oneself)", which is the essential slogan of the philosophy of Laozi and Zhuangzi in ancient China, as the philosophy was closely aimed at the weak, and established in a small country called "Chu" founded out by the posteriors of a conquered race. Studio engineers are superior in skills of processing and carefully selecting sound but they are in a sense "the weak" because they are subordinate to clients, who may be good or bad in their abilities.

As seen in this example, it should be noted that those who know the nonverbal brain function very well and have mastered it have, at the same time, a tendency to shut up to people who don't understand "ishin denshin" or "furyu-monnji" and are often arrogant. This is often the case with the relation between civilizations and cultures. This reality keeps telling us about the great difficulty in restoring and returning to the nonverbal brain function. Nevertheless, at present when technological civilization is very active as if it were all mighty and it is also going astray, it seems that stopping the out-of-control behaviors dominated by the verbal brain, which seem to be in the deep root of the problem, must be addressed before anything else. If there is any idea that might be effective or any plan that has not been verified, isn't it good to be positive enough to try them? This is one of the tasks or rather obligations of sound ecology.

The inventors considered that the vector which is moving away from "sound coded in human genes" is one important sign symbolizing the inherent limit of modern civilization, based on the framework of sound ecology. Besides, the inventors plan to create an opportunity to overcome the limit of this civilization by re-discovering the existence and the effect of the sound coded in the genes and the brain in the civilization as well as formulating remedy to restore the same.

What is to be solved here first is that Western civilization has lost "coded sound" and the civilization has been built up to be pure with only the verbal information world focusing on consciousness, based on dualism of Descartes. In contrast, in Eastern cultures influence by the philosophy of Laozi and Zhuangzi and Zen, where coded sound has been preserved to a great extent, the verbal information has been strictly suppressed, and the environment has been built up so that rational logical explanation is hardly allowed in a strict sense. Without bridging the gap between the two, prescribing a solution is difficult. However, in reality, in the modern philosophy like that of Descartes, the verbal information world controlled by consciousness was exclusively selected, while the idea of Laozi and Zhuangzi and Zen exclusively selects the nonverbal information world transcending conscious world. Accordingly, the cultural codes of the two have nothing in common in key areas. In other words, not much can be expected from conventional ways that tried to bridge the gap between the two by using existing cultural codes skillfully.

Thus, it will have a significant importance to consider whether there is any new code system that transcends the two cultural codes, and whether, if there is any, they can be used. In this regard, at least one promising candidate exists. That's exactly the natural sciences, which originated in Western civilization of course but now are beginning to function as an effective critical force to Western culture. Moreover, regardless of whether in East or West, or North or South, restructuring of material, energy, informational infrastructure of modern society has been almost completed under the paradigm of modern technology, and it is impossible to escape from under it, in reality. There, inevitably, a transition to a new system accepting, sharing, and utilizing a new cultural code called "technological codes" was force, and already a long time has passed since the turn in that direction. In other words, whether in a society with Descartes cultural codes or in the codes of Laozi and Zhuangzi and Zen, incorporating technological codes into the social system and operating in them have been put on track to a considerable degree, and it is working. In addition, these codes are high in cultural neutrality. Accordingly, the inventors recognized technological codes as a coding system transcending cultural codes, and think it worth considering using the technological codes as a bridge between separated cultural codes. What is notable is that the brain has become the very important subject of the natural sciences, and the science of brain has gained effectiveness. Of course, the physical machine of the brain assumes the substance in the mental activity which was excluded from scientific approach in Descartes' dualism. Sound ecology took this situation as a strong basis to establish the paradigm.

Further, the inventors considered the structure of important strategies. That is whether to begin with the position where coded sound was lost and to start from scratch and do all-inclusive, exploring approach, or to begin with the position where coded sound has been preserved and to take hypothesis-validation approach. In this aspect, the inventors thought it better to utilize the experience of individual researchers, and selected the second, hypothesis-validation approach. The biggest reason is that it means it will not take long to get the result, if a hypothesis is right.

The inventors have created a framework of sound ecology, and are trying to do the following: a person who knows the relation between the mechanism and functions inherent to the nonverbal brain and experiential information should be in charge of the research; and one of the strategies is to translate the information status that has not been encoded verbally, first about sound, and if possible about other things, into technological codes. The inventors plan to develop contrivances to perceive and describe the complex, multi-dimensional nonverbal information using verbal means including modeling with the help of technologies, and plan to devise ways to communicate such information so that even the typical brain in the modern West, which has already been highly specialized in verbal function, can receive and understand the same. To name a few examples of the contrivances, the ME spectral array visualized the stormy sound of Shakuhachi, the FFT Spectra depicted the existence of ultra-high-frequency wave above the audible range. In addition, brain images of positron emission tomography showed the effect of the above (hypersonic effect) on the brain. These things were developed to externalize experiential information and convert it to verbal information, and to communicate the content and meaning using rational, logical procedures to make it acceptable. The inventors intend to translate the structure, existence, and effect of sounds that transcend verbal, explicit world into the most neutral and reliable coding system, that is the concept of science, for the people of cultural regions where the activity related to nonverbal brain function about sound has already deteriorated, in an attempt to communicate through the verbal function, which is a closed circuit already, that the above mentioned sound is an undeniable fact. The inventors intend to establish a new recognition as a start.

There are things to be noted here. One thing is to take cautions to preclude unnecessary desperation caused by the perception of the present state that the nonverbal activity has been irreversibly lost in oneself or their culture. A countermeasure to prevent it should be prescribed. For this, a model of brain function will be effective if it raises expectation that the verbal brain function can be effectively controlled and the nonverbal brain function can be activated. The inventors have prepared a hypothesis developed from two hand-made models and a model of the operating system function of prefrontal cortex. The former includes a model of the nonverbal main brain and the verbal brain module and a model of a sensible brain structured with layers. The latter was made by Shintaro Funabashi and Toshiyuki Sawaguchi.

First of all, the brain of animals has evolved originally as a nonverbal brain, and a verbal brain module was added at the stage of apes on the way of evolution. However, the integration function of all has stayed in the OS function module of prefrontal cortex, and it keeps operation with multi-dimensional, continuous, and high-capacity characteristics. The verbal brain module is attached under the control of the above, but the verbal brain module also has an independent local OS, that is <consciousness>. In this case, if the activity of the verbal brain module exceeds a certain level, the OS function module of the main brain is occupied by consciousness and changed to the one-dimensional, discrete, consecutive information processing mode, and during that time, the exclusive characteristic of consciousness forces the strong suppression or deterrence of the multi-dimensional, continuous, comprehensive information processing of the main brain. In addition, once this state is established, the tendency strengthens irreversibly, and a vicious cycle is likely to occur. In this case, if you follow the commonly accepted theory that the prefrontal cortex, on which the OS of the main brain is mounted, is the supreme structure without anything upon it, the consequence is that there is nothing to control the conscious-dominant state, nor anything to help escape the same.

The sensible brain model of the present inventors is effective in that it can offer a possibility to give relief to this situation. In this model, <emotion>, which starts an action, is placed at the bottom of the brain circuit that controls actions. Then, <reason> responds as a negative feedback circuit to preclude the risk of "reckless rush" caused by emotion directly controlling the action and increase the safety and success rate. However, reason has linear and near-sighted characteristics, or in other words, it may be likened to the brain of reptiles, which is cool, goal-oriented, and rational. Then, <sensitivity> works to control the limits of reason with positive and negative feedback in a complex manner, to sublimate an action into the true, good and beautiful status and to induce it to be optimized in a expanded multi-dimensional time-space system. Accordingly, there are three layers in the structure, as described above.

It is assumed that the brain structures related to sensitivity are a combination of the <brain stem> and the monoaminergic projection system including the medial forebrain bundle that spreads in the higher brain from the brain stem. It is remarkable that this circuit of sensitivity can control the associative higher brain represented by the prefrontal cortex. In particular, A10 dopaminergic neurons, which mainly target the area from the upper brainstem (midbrain) to the prefrontal cortex, have the function of generating positive rewards, and with this function, A10 dopaminergic neurons must have strong effect on the control of various functions presiding in the prefrontal cortex, in particular, the central operating system function.

Thus, if this sensitivity circuit is set so that the nonverbal brain function is activated, the autocracy of consciousness can be effectively defeated. Further, it is most likely to occur with the input of information from the environment, in particular, ceremonial information. A good example is the fact that a countless number of Western intellectuals got enlightened with just a one-time encounter in ceremonies of esoteric Buddhism and the Bali Hindu religion.

Still further, the lifestyle of pure hunter-gatherers living in the rainforest, which is directed by the human inherent genes, is a good manifestation. For example, the performance of Mbuti in African jungle teaches in nonverbal way how the human's brain can exercise its functions when the brain is working on an inherent balance. In the rainforest that has nurtured the genes of apes including humans for tens of millions of years, pure Mbuti live in the hunting-gathering lifestyle which is inherent to humans, and they are always beaming with joy as scientists and as artists. The spontaneous and perfect life of them tells with delight that the genetic design of the present humans was one of the ultimate beings among the life on earth.

With the knowledge that this kind of manifestation does exist, the inventors believe that a window for a new start will be open most readily for those whose verbal brain is well trained, when communicated to in natural science codes which are verbally exquisite with respect to verbal ways, and through carefully selected sensible experience.

<3-2> A Private Experience that has Awaked the "Promised Sound"

<3-2-1> Encounter with "Sound Cooks"

The conflicting schema such as verbal and non-verbal characteristics, explicitness and implicitness, logic and intuition, reason and sensitivity, etc., the Western culture has give birth to and brought up and intensified critically in the latter half of 20th century was also brought in the world of music with a sharp relief. Tsutomu Oohashi himself happened to have an encounter with destiny to place him in the center of this issue in the two worlds of the music and sound environment in the 1970s and 1980s. That experience has led to a background to plant a seed of <Sound Environment Scholarship>, and to grow it and bring it up. The point is simply an awakening of the "Sound promised by gene" led by his contact experience with implicit sound universe that cannot be transcribed in any language group. With respect to such experience that has changed Tsutomu Oohashi himself largely, it is difficult to talk about it in general expression because it is personal matter in its nature. However, one cannot avoid the same.

Although it is a personal matter, Tsutomu Oohashi determined to testify by himself this experienced information. In this case, an encounter with "Sound Cooks" experienced by entering the world of record music production will be explained.

In 1975 when LP was at the peak of boom, the Inventor Tsutomu Oohashi was given an opportunity to work as a musician in a core environment of commercial record production. For Tsutomu Oohashi, who had never got musical education from the start and never received any systematic training, this was an astounding event. At that time, Tsutomu Oohashi was engaged in a research at a laboratory of certain national university of a mechanism that synthesizes a group of chemical substances (ergot alkaloids) that causes an interesting reaction to the brain and nerve system of animals of the higher orders, and at the same time, he was in a position to run an amateur performance group (Yamashiro-gumi) established in 1974 under the name of <Shoji Yamashiro> and to lead its representation territory.

While Yamashiro-gumi was provided by Fumio Koizumi, who was a folk music scholar, with strong support, it paid its attention to various and different music cultures of various folks on the earth in such a Japanese music world where the Western music was the only and totally committed music and promoted activities to practice such music culture. This group started practicing since its establishment <Meta Musicality> (an activity that the same individual person or a group plays music belonging to a culture area of mutually different and multiple systems). There is a high possibility that this activity has become an example of realization of that point for the first time in the world.

These activities promoted by Yamashiro-gumi drew the attention of a critic Toyo Nakamura, who had strong influence on the record industry. Under proposal from Toyo Nakamura, Hiroyuki Iwata (later Chairman and Director of Universal Music Co., Ltd.) who was a keen and moderately tough rising director took the charge. Through production by Nakamura himself, it was determined to produce and market a record by (then) Victor Music Industry Co., Ltd., an affiliate of Victor Company of Japan, Ltd. (JVC). Incidentally, the label to which the work of Yamashiro-gumi, which did not fall in any existing category, was set in the category of popular music called <Invitation> instead of art music. Thus from the winter of 1975, the activities of the Inventor, etc. started as artists in a blessed environment of record producing at an internationally highest standard.

Tsutomu Oohashi discovered there the shrewd sound engineers called <Mixers>, namely the "Sound Cooks". Under the lead of legendary mixer and engineer Heizo Yoda, the group of recording engineers of JVC at that time was fully staffed by a large number of talented men and women. The project started with such a strong line-up that Engineer Yoda himself took charge of the recording of Yamashiro-gumi and young Kazuyoshi Matsushita took charge as a sub-mixer. It can be said that Yoda, with whom Tsutomu Oohashi met for the first time, had a type of more musical existence than any of the musicians he had met before. Yoda had accumulated superb performances in the on-the-spot broadcasting of "Todaiji Temple Shuuji-kai" (Omizutori), which was said to be the greatest treasure in the recorded works and also recording of major works of Tow Takemitsu and was admired as a "God of Music" from the people around him. As Tsutomu Oohashi noticed it, the ability of Yoda searching for and creating beautiful and good feeling sound introduced a transcendental and absolute impression.

Interestingly, Yoda advised that Yamashiro-gumi was a special interesting existence when observed from the standpoint of a recording engineer. It goes without saying that it is desirable for an artist of commercial record to have features as commercial goods surpassing the others, namely, distinct sales points. They can be sometimes a melody adhering to and not departing from the ears, startling song lyrics or rhythm with punch in the same. Under a circumstances as such, it was said that our music was such a very unique and novel one that among the others the "Ringing of the sound itself" could become the sales point.

In determining whether or not the proposal made by Nakamura that the record of Yamashiro-gumi should be accepted and when JVC studied internally how such a unique music (rather a senseless or unreasonable music) should be handled in order to attain a certain result, the remark made by Yoda that "The sound itself has a value as commercial goods" became a decisive backup, which according to JVC. In this relation, Yoda made his points as a mixer that although the surfacing posture and shape are different in the representation strategy, the level of commonality with the works of Tow Takemitsu which Yoda had previously promoted and succeeded was high. In addition, Yoda advised Tsutomu Oohashi that his desire and comfort was linked to the creation of "Sound Objet" and somewhat natural gift and aptitude could be expected for the same. (In the meantime, Tsutomu Oohashi received lectures from time to time about recording engineering from Yoda, became almost an apprentice of Yoda and was helped bringing up his skills to a practical level as a recording engineer. In that sense, Yoda was a master for Tsutomu Oohashi.)

Under the circumstance as such, it was determined to put the music of the Inventor, etc. in the producing process under a grand strategy to make it solid in a package in a more emphasized state if possible without prejudicing the elegance of the unique sound. To that end and in a thoroughgoing manner from the start, every luxury imaginable was concentrated in selecting the hall and/or studio considered most suitable for the composition of the music and depending on the piece of music, visiting the editing room of other recording companies competing with each other in the market to use more adequate editing table (mixing console).

In the process as such, the sound created by the Inventor, etc. has largely exceeded the capacity of the device and equipment established in the culture of traditional sound and the defense range such as the technology, know-how, etc. used to operate such device and equipment. Hence, they encountered several times with such situations that they needed to establish new technology. For example, even in case of a microphone that should be the inlet port of the sound, the series of models made by Neuman Company, which were said to be the best in the world at that time, displayed a lack of resolution capacity that was not acceptable by the sound the Inventor, etc. created. This issue was solved by introducing a series of microphones made by Shops Company, of which marketing was just started with the resolution capacity improved remarkably. At the editing phase, it was attempted to establish surrealistic sound experience. However, because no effectors, etc., effective to that end were available in the world at that time, "Unreasonable and tough trials and errors" were repeated also.

After the process of such series of electronic post production, the cutting and pressing process continued in order to reproduce "Things called LP". At the time this phase has been reached, an issue was found that the works of the Inventor, etc. were not possible to be produced. The signal structure recorded in the master tape as the first album of Yamashiro-gumi was largely beyond the permissible design range of the cutting head that should become the core of the <cutting lath>

(a machine to carve the grooves of sound on the lacquer master disk). Because not only the machine that should send these signals cannot follow but also there is a fear that the head may be damaged, a limiter circuit has been incorporated in the cutting machine to control the signals within the set value and maintain the safety. However, this safety circuit was incompatible with the signals created by the Inventor, etc. Accordingly, they faced an issue that, from the grooves carved on the lacquer master disk, only sound of a different nature in which the essence of the original sound was missing was reproduced.

Around that time at JVC Shin-koyasu Plant which engaged in the processes of cutting and pressing, such very young engineers as Mitsuo Yamaguchi (25 years old) and Kohei Nakamura (20 year old) had already established their own skills and played an active part in the engineering forefront world. They first detected that the limiter circuit was the root cause of deterioration of sound quality. The method to clear the cause they introduced next was such a bold attempt to remove the safety circuit from the machine, regardless of the possibility of the very expensive cutter head made by US Westlake Company might be damaged, and to carve the grooves on the lacquer disk under a straight condition under which more excellent sound quality could be expected. It was rumored that their boss who permitted such an attempt had a <Letter of Apology> in his pocket to submit to his company in the worst case. Thanks to their skills and good fortune, they were successful in this attempt.

However, when the mother disk was produced from the lacquer master disk produced as such and the final product was produced after the pressing process, the grooves carved on the original disk were too uneven and their shapes were too complicated so that the pressing process was not carried out under such a condition able to keep the shape completely accurate. It was made clear that a sound far from the lacquer master was produced only when the disk was replayed. This issue was solved by an excellent technology which had been developed before but not put into actual use. The reason why such a technology had been set aside and remained unnoticed was that the structure having the sound signals within a master tape that had been handled until then did not need any technology higher than the traditional pressing technology and that no difference in sound technology was introduced between the traditional technology and new technology.

As such, the first LP "Osoresan" of Yamashiro-gumi that finally appeared in the marketplace through innovations of the every point in the traditional technology was highly evaluated by audio related magazines first due to its taste and real appeal, so that it spread through the broad record journalism, resulting in a growth of distribution of the products and in a success more than expected.

At the same time however, a troublesome issue has occurred anew in the replaying technology. The grooves carved on the final product LP were so uneven that the unevenness exceeded the value expected at the time of designing in many product cartridges that should trace the grooves by a record player and convert into electric signals. The needle of the cartridge was not able to follow the too much unevenness of the grooves, causing the sound to warp or the needle to skip the groove(s). The reaction the record market at that time showed was an encouraging one. The cartridge manufacturers provided its solution through the improvement of performance by setting a new target whether or not this troublesome disk could be traced, instead of discriminating or rejecting such disk that had been outside the standard.

It can be considered that the multiplier effect of the contents production of such record and technical innovation accompanied with all of the albums of Yamashiro-gumi to some extent. The hearty and sincere reaction received from the production site and market environment at that time was a highly valuable favor to the creator.

Those recording engineers and cutting engineers with whom Tsutomu Oohashi has got acquainted through the opportunity of LP production owned surprising ability and personality that he had never known before and were experts living in a really implicit dimensional world. An encounter with these people and joint work with them for not a short period thereafter gave immeasurable impacts to the personality of Tsutomu Oohashi himself, including his thoughts and behaviors. Tsutomu Oohashi believes that he was able to acquire the passport to enter the implicit dimensional world. These people to whom he owes much must be explained in details.

Because they are engineers relating to the sound, it is no wonder that they own ability and personality far different from those of men of letters, plastic artists or researchers in the field of humanities and social science. However, it was surprising to find that they were the race almost different from the engineers engaged in audio equipment development and researchers in the field of sound science who should be present very closely or the engineers (but excluding those studio musicians to be referred to below) with whom they were contacting almost every day. If one should attempt to find any group of people having at least the same commonality as these unique people in the atmosphere of professionals who risk their lives on a single taste of sound, a cook working at a first class Japanese-style restaurant or a chef at a leading restaurant who risks his life on a single kitchen knife may be close to them. In that sense, it would be appropriate to call them "Sound Cooks".

Not only the age but also the career does not matter for the qualification of an ultra first class sound engineer who is always requested to give taste to the sound. In fact, very few people who learned music or sound science at a university were successful. On the other hand, it must be noted that many people graduating from high school or having a lower level of academic background tend to be successful. It is unquestionable that there is no past record that any systematic education has brought up any excellent sound engineer. The successful people are brushing up their skills through an apprentice system and autonomous study without any exception. It is deeply related to the fact that the core of the study contents is overwhelmingly a type of nonverbal and implicit type.

As excellent cooks do not believe or rely on any such explicit media as a recipe, excellent sound engineers do not yield themselves to any theory or knowledge. They only depend on the feeling and sensitivity backed up by the actual result they have brushed up and the skills handcrafted by them. Accordingly, excluding peculiar exceptions, the taste of sound does not care about any authority. In other words, there can be no authority against taste of sound. It is a background an innovative methodology may jump out that rises above any theories. On the other hand however, it simply cares about the feeling, sensitivity and liking of unspecific people in general organizing the society, namely obvious and potential users. What is imagined there is not a professional in the field of music or sound society, but ordinary record fans, audio enthusiasts and those "music amateurs" who would become the candidates of such fans and enthusiasts. The sound engineers come in contact with those people as much devoutly and modestly possible as if they serve the god. Doing their best, they dig out the likings of those "ordinary" people, hear out their real motives and try best to come closer to such likings and real motives. Such likings and real motives are often very indifferent to the intentions of the specialists in the field of music sound, including the producers or directors whose abilities are questioned and display a clear contrast.

In addition, these people strictly evaluate and select their joint workers. Those directors or artists who were invited to the studio as clients under certain social system or formally can never escape from the refined "qualification test" to be performed in a very "non-attacking" manner. In order to proceed with the joint work in an implicit dimension, it is essential that nonverbal communications but accurate communications are to be established for such world which is not adequate to understand through any language. Prior to such establishment of communications, it must be questioned whether or not the joint worker participating anew owns such vitalities able to travel in the implicit dimension even if potentially.

This verification includes such very severe substances that, when the sound to be processed has been damaged to some extent especially at the starting phase of joint work mainly by the engineer's mistake or intentionally from time to time, how sharply or stolidly the directors or artists react, or whether or not they do not notice a critical damage, or whether or not they react in a positive manner when any splendid skill has been realized, and what kind of personality does such react reflect. They will respect sincerely those clients who displayed remarkable vitalities in such trials and see, become confident and prostrate themselves when they should encounter with any ability or personality surpassing their own ability or personality. In order to master the taste of sound, such sound engineers and the studio musicians who are their indispensable partners have spirits prepared to drink with devils and dance with dragons. Toughness together with high grade principle is overflowing there.

From what background has such unique world where this principle and toughness are formed in a harmonious whole appeared? In this world, "marketable sound" among the others is a supreme directive. As a destiny of copied information products, almost all of the various type of and many disks as launched in the marketplace endlessly can only attain results not able to recover the money invested and disappears leaving only one single work together with the artists concerned. Only a small number of projects among the others becomes successful and collects a profit including the recovery of the fund wasted by most of the projects. It is a sort of gambling mechanism aimed at the society. It is also a world of "Might is right". Therefore in such a world, one must continue creating attractive sound which the general public feels "tasty" and pays money for it without any hesitation.

What the product value of the music contents in such a destiny depends on is not musical compositions or musical performances, unless an artist having a reasonably big name, but the process of production starting from recording and ending at the studio or factory. The main player is a group of sensitive engineers such as <mixing engineers (mixers)>, <mastering engineers>, <cutting engineers>, etc. who process, edit and convert the sound. In fact, depending on the skills and fighting spirits of these people, the appealing level of produced work is poles apart. They are the very basis for the corporate power. Accordingly, star engineers at a leading studio are astute people. Their social and organizational status and power in the music industry is so strong that no outsider can really understand. In that point also, it can be said the status of sound engineers in the record industry is very similar to that of cooks at leading Japanese-style restaurants or chefs at leading restaurants.

In this case, one should touch on another large factor that gives deep and subtle ambiguities to their humanity. The first class engineers are not only engineers only pursuing the sound physically, but also experts in personal relationships. The background thereof is such that the standard business form of a recording studio is to set up a room acoustically controlled, equipment and engineers and lease them to the directors retaining artists as a means to support them to create music. In other words, this business form cannot be unrelated to such nature of a sort of a service trade. Hence, the staffs of the studio are placed in an environment to have to work strictly in accordance with each of the desires of various types of clients which may change every day. Inevitably the staffs at the studio must stand neutral in the business in their likings and sense of values of the "sound" which is their own business. Accordingly, from the point of principle that they have to work respecting the desires of clients as a supreme directive, they are very afraid of making their private subjectivity public in their business. This structure leads to a reaction to change themselves immediately to "people closing their mouths" against oppressive clients having defects in their social activities or clients lacking charm as a human being.

When seeing such works or people of the sound cooks carrying real nature of the contents creation of the present and most exhaustive music, it cannot be denied that every portion that composes its essence is relating to the implicit dimension of nonverbal characteristics. It is the task with highest priority imposed on the cooks of sound to operate and control such implicit dimension on an equal footing with the explicit dimension.

For such a "function to control the implicit dimension", the modern and present Western culture does not have matured orthodox concept, strategy and system with respect to the excavation of its nature, its sorting out and fostering and its evaluation. The fact that the balance between explicitness and implicitness is at an almost pathologically biased level would have to be admitted without any doubt if one compares it with the repletion level of present system in the "orthodox" science, art and technology relating to the explicit dimension. It carves in sharp relief the limit of Western culture that is equipped with highly maintained science technology.

Tsutomu Oohashi feels he was very lucky being able to get guidance by establishing a close relationship as working colleagues with those outstanding people among those living in such an implicit dimension covered by a large shade because the modern culture was not able to discuss it in a proper manner. It was those "Sound Cooks" who had found some seeds in me who stood before them as an entire amateur with no background in both natural gifts and knowledge, brought up the signs of my success and led me to become closer to a sort of an artist in any way possible.

Under such circumstances, Tsutomu Oohashi himself also was unconsciously taking the path toward the "Sound cooks leading to the implicit dimension". It brought a fortune to Tsutomu Oohashi, as a researcher, which he had never expected before.

<3-2-2> Discovery of "Information Environment"

Tsutomu Oohashi, taking the opportunity that the university he had been belonging to was reorganized and moved to Tsukuba Science City in the early part of 1980s, moved to Tsukuba and started research in molecular biology with respect to the return to the original state of the global ecological system, and at the same time took charge in the graduate school of environment science which was established anew. He then was awakened to an entirely new environmental view.

The outset traces back to the scene of Tsukuba Science City that surfaced in those days. This artificial city that Japan, then attempting to return to the frontline of the international society as an economic giant, constructed at the risk of her dignity was on its way to be well organized and established that it should display an ideal in the modern city concept. The construction of an ideal city with the world highest standard in those days was commenced and promoted in an almost empty wilderness.

Tsukuba, it is a science city in a neat layout, clean, and let the people remember the perfection of artificial beauty. In the research laboratories built in the city and equipped with the world's most advanced and highest grade equipment and devices, a rich research environment was prepared that had never been experienced by the Japanese researchers before. In the meantime, disasters probably nobody was able to imagine suddenly occurred. There were frequent suicides committed by the researchers. The frequency of such suicides was remarkably high, exceeding the Japanese average suicide rate by several times. In addition, the cause was not clear. Most of the cases were shocking suicides for which the causes were in fact not clear. Such a phenomenon has not been observed with the original residents living in the outskirts of Tsukuba. The suicides occurred only to the researchers who should be feeling the first and probably last happiness in Japan with the surrounding ideal research environments.

The point as to how to deal with and approach this pathology that has become called as the <Tsukuba Disease> in an unnoticed manner has brought up a very important question as to the raison d'etre for Tsukuba Science City where Japanese leading specialists had got together, including the environment sanitation. However, no adequate response to the issue was obtained easily. On the other hand, it has brought the substantial defects in the modern knowledge structure originated in the Western Europe into sharp relief. For example, when one pays its careful attention to the fact that this pathology occurs inherently relating to the regional environment such as Tsukuba Science City, it can be understood as an environmental issue like Minamata disease and should be solved through environmental improvements. However, on the side of the then environmental science and technology which should took charge in the solution of environmental issues, a mechanism to capture the environments in a physical manner and partly as an issue of energy had been made available, but any other mechanism was in fact almost next to nothing. Accordingly, nobody was able to find any specialized field that should provide the measures for dealing with the Tsukuba disease and discover a flow to solution with a higher suitability.

In the field of psychology and psychiatry on the other hand, the cause must be captured by converting it into the inherent situations and conditions of an individual person. It was not possible to open the path to search for the key to pursue the cause and solve the issue on the side of macro structure such as urban environments. In addition, such a trend was clearly observed that an action to deal with the issue in a proper manner against such Tsukuba disease not falling in any defense range of each existing science is hardly taken by changing such a defense range from the side of a specialized field. For example, in the world of researchers composing the base group of the people having knowledge and ability to solve the issue, there is such a structure that any researcher is released in fact from the responsibility by only stating "I am not a specialist in the field of this issue". Especially when encountering with any disaster not experienced before, the structure is such that, because no specialized field exists because such a disaster did not occur in the past, any and all researchers are exempted from the direct responsibility to solve the issue. The actual situation surrounding the Tsukuba disease was not an exception.

A speech was made to justify the behaviors of researchers as such that, "It is not the responsibility of the specialists that they are not able to solve any issues occurring in an area not belonging to any specialized field like Tsukuba disease. If there should be any responsibility, it should be on the side of the issue itself that has occurred in the blank area outside of any specialized fields". This speech is really against the humanity and morality, but it also simply and frankly expressed the level of heartlessness beyond the permissible limit contained in the basic structure that the modern specialization has changed their position to a single function and self-blockade state.

The Tsukuba disease is questioning how a science that is substantially different from such traditional and specialized science should be. Then, what would it be? The point as to whether or not a specialization should be adopted is an issue of science as well as an issue of the ideas and practices prevailing in the society or in the culture area. Tsutomu Oohashi determined to popularize the issue at a level of such dimension and consider the same.

If the environmental issues have been investigated clearly in a material scientific manner by the end of 20th century and any justifiable measures to solve the issues based on the knowledge obtained from such an investigation has been presented, it will display a very strong social compelling power and sometimes could have become an international political power that may bind military super powers. However, with respect to the area of spiritual activities as seen in the case of Tsukuba disease, the issue is handled simply as an issue of the "mind" and is largely different from the material science in a sense there is a remarkable limit in its social influencing power.

The issues brought forward by the Tsukuba disease have brought the substantial limit in the modern and present knowledge structure and science system into sharp relief. If this should be summed up, one of the summaries is the "absolutism of reliance on specialization" and other is the "separation of <thing> and <mind>". These are negative inheritances left by the modern and present science system which has been established based on the orthodox Western ideology since the dualism of Rene Descartes. If one should challenge this issue from the front, a fundamental review of the modern Western knowledge structure should inevitably accompany as predestined.

An opportunity to develop such sense of issues happened to occur. As one of the events in the national project "The international Exposition, Tsukuba, Japan, 1985", "International Symposium EXPO'85" has been held each year from 1982 until 1985. Tsutomu Oohashi participated as one of the special committee members and later as one of the planning members. Yoichiro Murakami, who took a charge of a coordinator in the "Environment" subcommittee of the first symposium held in March 1982, declared at the beginning that there was a limit in the hitherto environmental view that had captured the environment in 2 dimensions such as material and energy only, that a dimension of information should be added anew to it, and that the subcommittee should be promoted by setting the newly brought forward "Information Environment" as its main subject. Tsutomu Oohashi, taking the opportunity of participating in the planning and implementation of the subcommittee, determined to give backbones and body to the concept of information environment just given birth under the guidance of the above Murakami and the psychiatrist Susumu Oda, and bring it up to a prototype as one of the sciences and promote it by incorporating the verifications through its practice.

The science system of the modern Western culture differentiated in each specialized field has been built up through the separation of material world from spiritual world starting from Descartes and through the self-blockade and conversion of specialists into single function accelerated by Weber, etc. The Tsukuba disease has appeared piercing through the blanks among the fields which were fatally the weak point of such a system. Actions to develop another and new specialized field for this Tsukuba disease would be effective itself. However, in addition to such a symptomatic treatment should a search for a new concept of science that has overcome the limit of the specialization system of Descartes=Weber types be given the first priority through this case? Under the circumstances as such, Tsutomu Oohashi has determined to make a model of a science framework in such a direction that it would be able to defeat the Tsukuba disease.

It was not possible to control the Tsukuba disease through the 2 dimensions of material and energy which were the measures for the natural science to capture the environments. It has become possible for the first time in a substantial and direct fashion by introducing such a dimension as information. When forming such approach to the new born "Information Environment" into a science system, what would happen if traditional processes should be followed? It would result in the conversion of information environment only in a subject as separated from the others and build up a science system to approach the environment solely from information side. However, if one should follow such a process, it is impossible to depart from the category of specialized system of Descartes=Weber type. Under the circumstances as such, Tsutomu Oohashi has determined to build up the science system separately where the approach from information to environment has been inseparably linked to the approach from material and energy and to establish it as <Information Environment Science> as follows. Namely, he has determined to build up information environment science as a science system composed under the frame work of ideas to capture the environment as a science systematically integrated by adding the concept of information to the concept of material and energy.

In 1983 under such a circumstance, Tsutomu Oohashi made a trip to a tropical rain forest which he regarded as a cradle of the evolution of present mankind. He visited the M'Bochi people living in the huge tropical rain forest (Ituri Forest) spreading in the northeast of the Democratic Republic of Congo (former Zaire) and located in the deepest part of Africa. The purpose was to investigate the actual conditions of the forest which had served as an environment for the African anthropoids including mankind to have their genes matured and to observe through his eyes the lifestyle original to mankind following the genes with a higher originality of the M'Bochi people living there.

The travel was not an easy one for him, but the level of comfort of the environment where M'Bochi people with whom he was able to encounter with at last in such a deepness of the huge forest expanding in 70,000 square kilo-meters and their lives and beauty of their spirits and characters were so surprising, far from what he had expected. The experience has become the origin of information environment science and the center of the sound environment science.

The experience among others of the unbelievable fertility of the environment sound in the Ituri Forest and of its comfort and freshness was more than what destroyed the then concept of Tsutomu Oohashi as per the common sense that "The environment sound is preferable if it becomes less and less."

What Tsutomu Oohashi encountered was close to the opposite direction of the generally accepted idea toward environment sound. In addition, it must be rich and have a certain structure fundamentally different from that of artificial urban noise. Because it is a natural thing not having any verbal characteristics and/or symbolic characteristics, it must be exceeding any perception or conscious. As our foods must contain invisible <essential nutrition>, there should be any <essential information" in the environment sound that exceeds our perception.

For Tsutomu Oohashi, who returned from Africa with various types of experiences and materials to be considered filled up within his body, the first information environment he got in touch with for the first time when returned to Tsukuba was in the poorness of the sound which he felt almost eerie once after he had got to know the sound of Ituri Forest. That vicious impression together with the impression of that beautiful and dense forest scene has immediately led him to a work hypothesis that "Malnutrition of environment information invites the Tsukuba disease". Then, he started experiments to search for the materials that would support such hypothesis from responding reactions of human against sound environment. From his experiences in the sound of Ituri Forest, he paid careful attention among others to nonverbal sound structure which is difficult to be noticed. In the concrete, he attempted first to detect how human would react against the high frequency ingredient which would possibly be removed first because of the poorness of sound source in the urban high-density living space and/or because of the existence of sound shielding obstacles, especially the reaction against the high frequency ingredient exceeding the upper limit of audible range. This attempt has set off with uncertain steps from sadly inexperienced psychological and experimental procedures available at that time.

As such, the approach by the Inventor, etc. to the sound outside the perceivable range has started.

<3-2-3> Surprised when "Metempsychosis Symphony" Was Created

In 1985 when the CD appeared in 1982 was get going, an experimental, market oriented and new project was proposed by Yamashiro-gumi at (then) Victor Music Industry Co., Ltd. under the conditions of a joint work to link hitherto music and technology. The aim was to have Tsutomu Oohashi, alias a musician Shoji Yamashiro who had acquired a certain level of record producing/manufacturing technology and on the other hand a scientist himself, compose a music customized to the new electronic media <CD> and carry out its recording through the perform by Yamashiro-gumi. It was a proposal most welcome to Tsutomu Oohashi as a creator had been often forced strongly to control himself in the representation of the sound potentially realizable, due to not only the fact it contained enough reason to take charge in the project in a sense as he was told but also there was a functional limit to the reproduction of record of a media called LP.

Director Hiroyuki Iwata took charge in the project as before and Tsutomu Oohashi took the charge of a producer. "Victor Studio Project Team" was organized as an engineer group and Heizo Yoda took the charge of a project chief and recording supervisor. As a chief engineer, Hideo Takada, who was a sharp person already distinguishing himself in the field of popular music and stood later at the zenith of Japanese recording engineers, took direct charge. The organization was such imposing one that Makoto Yamada was staffed as a sub-engineer and Keiichiro Yoshioka as an assistant engineer, including 3 other members. "Metempsychosis Symphony" was newly composed consisting of 4 movements with a chorus as its overall baseline adopting Gamelans and Jegogs of Indonesia, Bali, Japanese 30-string koto and drums and statements as sound materials.

In this work, Yamashiro-gumi retained so-called <studio musicians> earnestly for the first time from the creation phase. Those performing musicians called studio musicians can be called musicians having the largest capacity and power in their technique and sensitivity. Instead of showing up in a live performance, most of them confine themselves mostly in a studio and display their ultra superb skills. They are very well acquainted with sound technology and work in close collaboration with the recording engineers. The top class studio musicians often include those having fanatical skills. The musicians participated in this work were really ranked at its top. Taking this opportunity, Tsutomu Oohashi has become working continuously jointly with those members, among others with Keiji Urata of synthesizer, Tsuyoshi Kon of guitar and Shoji Namba of keyboard.

It appeared that recording was still under a process of changing from analogue to digital. In addition, no digital recorder with multi-channel was in a real use. With a background of technical environment as such, the first, second and fourth movements were recorded by very perfect multi-track analogue recording and on the other hand, the third movement only was recorded by partially unsophisticated 2-channel PCM recorder.

The analogue master tape of Yamashiro-gumi's "Metempsychosis Symphony" which had been produced in a more elaborate manner than before was cut in LP as it was (because when this album was launched in the market place in 1986, the number of CD players spread in public just exceeded the level of 10% only and the number of CD sold just caught up with LP and therefore the LP market could not be disregarded), and on the other hand it was digitally converted to produce CD. As such, both LP and CD were given birth from entirely the same master.

Tsutomu Oohashi will not be able to forget for his life the shocking memory he got on the day he listened to both test disks of the completed LP and the CD and compared them. Holding the both disks in his hands securely, he hastened to the house located in Komae of Makoto Takahashi (then professor at Shirayuri Women's College) who was actively working as an audio critic and had been his friend since junior high school days. Takahashi had built an audio room like a fortress armored with <Goto Unit>, which was the world's most sensitive phone speaker driver, at a suitable location along the Tama River and established probably the world prominent reproducing environment based on its quite a function able to reproduce heavy and low pitched sound. It is without saying that a CD player for commercial use of Philips had already been incorporated. Only several sets of that player were available in Japan at that time.

In this case, the LP of "Metempsychosis Symphony" was reproduced first. Tsutomu Oohashi felt with confident that it was apparently an epoch-making work in the LP series of Yamashiro-gumi which already numbered 9. CD was also reproduced in endlessly expanding expectations of how impressive the sound could be generated from the CD that claimed itself as a "dream audio", if LP could give such an impression.

While listening to the starting <tone cluster> for several seconds, Tsutomu Oohashi felt as if his blood had been draining out of his body. It was a sort of a mental state, like "I have done it at last. There is nothing to be done about the same. Everything has come to its end." As he had a foreboding, the taste of such unwelcoming sound did not change from the first impression until the end. He considers that a feeling of wrongness as such was the first one for him in his sound experiments he had until then. However, the interpretation made by Tsutomu Oohashi for such feeling was such undistinguished one as follows. Namely, although CD is a medium having different principles from LP as seen in the manufacturing technology of LP which has been matured through repeated brushing up, most of CD's technology is still at a stage needing further brush up and technical development specialized in the CD, which fact is probably preventing the sound quality from being improved temporarily. Accordingly, when a technology highly customized to CD like LP should appear in the mean time, its real merits will be demonstrated then.

Awhile later however, Tsutomu Oohashi noted that there might be a very significant relation between his research of the influence on human by the high frequency ingredient exceeding the audible range, which research was accompanied with a simple experiments at the laboratories in Tsukuba, and the phenomenon of sound quality difference between LP and CD that he had experienced in the project of "Metempsychosis Symphony". It was because that Shoji Yamashiro, who was the Inventor acting as a minor player of the "Sound Cooks" working at studios, already understood that not only a level of the super frequency ingredient, that exceeded the most upper limit of the audible range for human, had been really included in such a medium as LP, but also it had related to a wonderful contribution.

How was he able to know it? Its distant background traces back to the 4-channel surround record reproduction method which utilized as its medium the LP of a type <CD-4> developed by JVC. This method was to adopt as its carrier 30 kHz that exceeded the audible range, and to record the matrix signals by frequency modulation method in the bandwidth of plus/minus 15 kHz above and below of that range and to restore the surround signals for 4 channels through a calculation of the stereo signals of 2-channel recorded in the audible range and these matrix signals. In order to realize it, there must be an excellent recording and reproducing function up to the super high frequency bandwidth of 45 kHz or more far exceeding the audible upper limit. Being led by an extremely high level technical requirements as such, the LP cutting system of JVC had reached an ultra high performance level which could be considered abnormal from the standpoint of general LP cutting.

To tell the truth, the tough engineers and artists were improving their skills not relating to any theory by keeping their eyes on such a mechanism which was almost abandoned in the fossil world as good for nothing. Under such a situation, Tsutomu Oohashi was, through consultations with young and challenging cutting engineers, using such a compromised technology to emphasize the ultra high range far exceeding the audible upper limit of 20 kHz when cutting his work on the lacquer master disk from master tape. If this processing should be successful, the reproduced sound from LP would brighten up in a really incredible and charming fashion. The upper limit of the recording frequency of LP which had fully matured then was surprisingly exceeding 100 kHz. The response capacity of an excellent cartridge reproducing it was also exceeding 100 kHz. However, this is a fact that the Inventor, etc. came to know for the first time through experiments and is almost not known to the public.

While repeatedly listening to the CD of "Metempsychosis Symphony", Tsutomu Oohashi has become aware that the reproduced sound was providing a flat and uninteresting sound taste that had overturned the compromised technology above. He then doubted that the sound had been created by cutting off entirely the inaudible high frequency above 22 kHz. This was nothing else but a revelation from the heavens. At this very moment, the meaning that the implicit structure of a sound and the skills of the cooks managing that structure have been integrated with explicit theory and validation surfaced up.

Among the record users in those days in Japan where the marketing of CD was started in advance of the world movement and Japan has became an advanced market, a doubt against the sound quality of CD was raised and growing. In the meantime, it has developed in a schema of "Dispute between LP and CD". It started from a part of consumers who did not have any orthodox career as specialists in music and audio technology. They claimed that "Compared with the LP records with which those consumers have been accustomed to listen to, the sound quality reproduced from CD is worse." A strong counter argument was raised against such claim, resulting in a start of the LP-CD Dispute.

The opinions supporting LP were laughed off as nostalgia for a traditional technology with which they were accustomed for a long period of time. As a topic always accompanying at the dawn of technical innovation, it was expected that such opinions would disappear before long. As experienced with other examples, the claims and behaviors to highly evaluate and love LP did not take a path which was said to exterminate itself in due course. Instead, it took a path to survive firmly, reestablished its base again in 1990s and started to display its energy to increase as high-end audios. Toward the end of 20th century where those DJs (disk jockeys) living in en environment of <Disco> indifferent from such high class audio started to compete their skills from scratch using LP record, the revival of LP started get going with a background of its increased demand.

In the meantime, although so-called LP-CD Dispute hit several turning points, the dispute never faded out because both parties never admitted themselves defeated and thus it continued almost until the end of 20th century. After the launching of SACD in 1999, a report of discovery of hyper sonic effect in 2000 and the start sales of DVD audio in 2001, the situation changed in the early part of 21st century in such a direction that the CD supporters made their exit from the dispute silently.

The structure of this dispute is considerably unique. When viewed from the flow of time, at its starting point, there was a schema of the "Specialized theory of present science technology well organized against the sensitivities of popular and traditional audio maniacs". At the stage of curtain fall, it ended in a schema where the limit of the specialized theory so far seated on the orthodox position was revealed and new scientific and technical idea has surfaced up.

The structure of both parties in the Dispute has been clearly divided in 2 until around the last phase. The LP supporters were the so-called audio maniacs, namely the amateur lovers of hi-fi audio excluding the specialists in the sound science and technology. What they pursued was simply "tasty sound". There, brain compensation system, namely a stronger activation of nerve circuit of pleasant feeling is given a priority over any other various situations such as convenience in use, price, feeling of ownership, business interest, etc. The CD supporters on the other hand has built up a broad structure formed mainly by the orthodox specialists in the field of sound science and audio technology and businessmen who had to support CD in their business activities, including general people armed with common sense in science and technology.

In other words, it can be said that main members of LP supporters included those people whose vitality in their non-verbal brain was superior, and on the other hand, main members of CD supporters included those people who had modern spirits controlled by the vitality of verbal brain. With a background as such, LP supporters insist "Regardless of any theory, good sound is good sound and bad sound is bad sound". On the other hand, CD supporters insist "Theoretically and scientifically, the sound quality of CD is superior to that of LP and there should be no such case that it is inferior to LP". Such a schema has been drawn up. CD has really raised the upper limit frequency of 20 kHz that human could hear as a sound by providing a further allowance to 44.1 kHz as a specimen, expanded the upper limit of reproducible frequency up to 22 kHz and was recorded using the then highest level of technical PCM method. As a precondition to determine this format, the question as to how the human auditory sense would be affected by setting a limit to the high-frequency range of music and/or bandwidth noise has been studied through close psychological experiments and the fact that the sound quality difference was not affected regardless of the presence of any high-frequency ingredient of 16 kHz or more has been confirmed. It really appears that "In any possible consideration, the sound quality of CD is always superior to that of LP, but there is no such a case it is inferior to that of LP".

In this case, what divides the human into 2 types is such differences that "whether or not a thing that could never exist in any possible consideration" has a meaning equal to "a thing really can never exist" and whether "a thing that cannot exist in any consideration", namely logic can have mutually independent meaning with "a thing really cannot exist", namely, reality.

Despite of the fact that LP group has been argued down repeatedly by CD group armed with theory at a full high level, the LP group often retorted, "There should be a limit to the sensitivity of the CD group that cannot differentiate the sound". It is hardly possible that such a retort cannot invite a strong anger from those people whose specialties or whose occupations are sound engineering or sound psychology. The dispute has changed to a confrontation between the two groups and such confrontation has turned to a barren confrontation. However under a commonly accepted social sense, it appeared that the LP support theory should be positioned having to submit to any obscurity because it lacked any scientific ground and that the superiority of CD over LP has been established.

However, the views of sound cooks within a recording studio where such a social common sense did not reach displayed an entirely different picture. Without any direct relation with the frame work of dispute of whether LP or CD, their views surfaced up first as the "unfavorable sound" from the digital signal processing devices which appeared all in together from around the middle part of 1980s. These devices were manufactured in a direction to save the specimen frequency or number of quantization bits as much as possible reflecting the technical standards then sprouting. Such effectors or synthesizers not satisfying 44.1 kHz specimen 16 bits quantization similar to the CD were prevailing. To those engineers and musicians who were not able to endure such sound, the sound from a synthesizer such as <Fairlight> or <Synclavia> sounded endlessly attractive. Many artists were dying to get the same. On the other hand, it was often observed that the specialists of sound engineering and/or electronic engineering taught and warned of course with goodwill the musicians and engineers on site that it was senseless to use any high level devices or equipment, because those ingredients above 22 kHz would be abandoned before recording on CD even if the bandwidth was expanded to a higher frequency when recording or editing.

However to the sound cooks, any theory can never take precedence over their own feelings and sensitivities, although it cannot be said that the theory is meaningless, as they are not pleased if they are to be forced to use any knives or foods materials they do not like. Namely, they were able to disregard calmly any of almost complete scientific recognitions. Among others however, the firm view backed up by practices of Rupert Nieve, who was a deified giant as a designer of a mixing console, which was the core of the hardware for producing recorded art, certified later that his sense had been the very "God". Under the studio environment as such, it appears that, as far as Tsutomu Oohashi was aware, more than half of the sound cooks had firmly captured, whether consciously or non-consciously, the effects of the super high frequency ingredients exceeding the audible range.

Within Tsutomu Oohashi himself, a sort of fragment as a sound cook to live in the implicit dimension was growing in those days. Since such a personality and the personality as a natural scientist aiming for a verification of the effectiveness of the information environment science have been bonded together, a new seed attempting to chase and capture the sound outside the perception range sprouted and grew up.

<3-3> Sound in Outer Sphere of Consciousness

<3-3-1> Tool for Collecting Inaudible Sounds

1. Among the messages coming to us from the environment, there is such a message that has a definitive factor that activates on the life just as a certain kind of a nutrient or a toxin, although the message cannot be grasped using a sense.

The microstructure of sounds of Shakuhachi and Gamelan or their transformability that has been shown for the first time by the ME spectrum array are not capable of being grasped by consciousness or defined by words. However, for example, when the structure is changed by changing a music instrument or by substituting a player, the change can be felt as a different taste of sounds. In addition, when the complex fluctuation of the spectrum is electronically flattened, the quality of the sounds is differently felt for us. Namely, it cannot be denied that the present inventors feel a structure or transformability which emerges on a micro-region over the consciousness and react to the same.

From the viewpoint of the model in which "music takes a form of non-stationary information structure continuously transforming relative to time" and which has been introduced by the environmental study of the sounds, the core portion of "information structure continuously transforming" conceals itself as a tacit message in a micro-spherical unseen area. The present inventors have decided that we will find out the existence and the effect of the message existing in the outer sphere of consciousness which has been neglected or forgotten by the civilization in which we live.

In this case, we will simply sort out how human being responses to the difference of messages varying from tacitness to clarity. The present inventors may <sense> a message having deepest tacitness such as an indication, without knowing what is the medium of the information. We may <detect> a message, when the tacitness of the message is reduced and the image of the medium is conceived as a light or a sound. The present inventors may react with respect to a message or the present inventors are <perceptible> in the message as a clear response to these, when which sense is used as an inlet for a messenger of the message is clarified. When the message is clear one as it can be described by words, we are <conscious> of the message. Needles to say, the degrees of tacitness between sensing, detecting, being perceptible, and being conscious are differed and continuous, and there is not a break which is capable of being defined. Among these, being perceptible and being conscious are superimposed with the framework of <cognition>.

Michael Polanyi said "Percept is to play the poorest form of tacit knowledge". If this is applied to the case where music is encoded and recorded, the statement of Polanyi may support in an implied manner that if the sound is closely encoded as far as it is capable of being perceptible, the tacit information is not collected. Certainly, the encoding by a staff notation which is used only for describing the structure which is capable of being conscious and symbolized by words completely has had failure. In contrary to this, it is a CD (compact disc) mounting a bit sequence which has been encoded by a PCM method in which the structures of sounds as far as human being is capable of being perceptible have been almost completely encoded, and is capable of performing the recording and playback by taking all possible measures to ensure. In the CD, sounds are digitized with a sampling frequency of 44.1 kHz and a number of bits for quantization of 16 bits, so as to cover all of the frequency ranges of the air vibration which can be heard by human being as a sound, and which is from 20 Hz to 20 kHz, with some allowance. Namely, the CD can be considered as "a sort of musical note" in which all of the sounds capable of being perceptive are described. Needless to depend on the statement of Polanyi, the CD must be completely grasped through out both dimensions of clarity and tacitness. Regardless to the concept of tacit knowledge, the modern society has believed that.

However, if the LP-CD debate which has been occurred by making CD use in practice and the negative response that musicians and engineers working in a studio have indicated with respect to digital audio devices are not silly, differently from the concept of Polanyi, such a possibility that there exists a tacit dimension in a CD which has encoded all of the sounds capable of being perceptible cannot be denied. Some events and experiments that we have encountered involving with the medium of sounds of CD may require the reconsideration about the possibility that a tacit structure influencing on the human being exists even in the air vibration existing out of the perceptible area. If it is grasped in a self-determining way from the viewpoint of "a high frequency component which exceeds over the audible range and influencing on human being", it is clear for Tsutomu Oohashi who is a cook for sounds that these are surely within the experiences which is obvious by itself for Oohashi, and Oohashi actually has experienced. For example, that is an indication of a game concealing oneself behind the tacit forest, and it is natural for a hunter that it turns to the next procedure to hunt the same. In the latter of 1980s, Tsutomu Oohashi became a "hunter for sounds" who devoted himself to suit for and grasp this invisible game with his accompanying coworkers.

2. The reality that some essential tools for hunting this unknown game do not exist in this world blocked his way at the time when he started to travel around hunting sounds existing in the outer perceptible area.

First of all, there was a problem involving a microphone for converting the air vibration into an electric vibration. It was estimated from the knowledge of the past that a microphone which could secure an uppermost limit of the response frequency up to 100 kHz or higher was needed, if the air vibration generated from a variety of the events regardless of whether or not it was audible was tried to grasp. However, a microphone may originally convert "audible sounds" into an electric signal, therefore, it was natural that the close response is not considered with respect to a component exceeding over 20 kHz which is the uppermost limit of the audible range of human being even in the case where the microphone has the highest quality developed for recording in a studio. These could not be the subject of consideration by the present inventors. However, if it is used for studies and researches, since there were necessities that the destruction or vibration by an explosion of the object matter was measured, a microphone for collecting the air vibration which was not heard by human being as a sound existed, and the manufactures in Denmark and Japan had manufactured the same. But there was another limitation. Because these aimed at collecting musical notes, sounds involving with the sensibility could not be collected from viewpoint of noise and the quality of sounds. Moreover, in order to draw the performances which are critical, it was a subject that could not be used in safety unless it is under the restricted conditions. For example, in the environment in which it is easily a high temperature and moist such as a tropical rain forest, gardens in Bali Island, dew condensation on the vibration plate generates a spark, and subjected to the damage which is not capable of being recovered. However, since there was no other thing to be substituted, finally it became to make use of it by utilizing the operation techniques at the site, that is to say, the artisan work by enhancing the signal versus noise ratio (S/N ratio) by means of modifying the electronic circuit and by contriving a method of preventing dew condensation.

The specifications of a recording machine was a next problem. A recording machine having a response up to around 20 kHz which was supposed to be the uppermost limit of the audible range went as a first class machine for business. That was a time when all of the recorders were analog recorders. Since performances of the analog recorders were not applicable, a response up to about 40 kHz was made flattened by modifying a recorder manufactured by NAGRA, Co., Ltd. However, the frequencies of many music instruments and the environmental sounds exceeded over the uppermost limit, and limitation of modified recorder was elucidated. Although among the recorders for data recording, a recorder having a response characteristic up to 60 kHz was developed, when the sounds were actually collected, there was still a limitation for the frequency uppermost limit. Needless to say, the international standards of DAT (digital audio tape) prepared during that time, had the frequency uppermost limit of 24 kHz, and it was not suitable for the object of the studies and researches of the present inventors. On the other hand, the present inventors have constructed a digital signal processing system having a sampling frequency of 500 kHz and a number of quantization of 16 bits by making D-RAM as a recording medium, because there was a necessity on the way of promoting and carrying out the studies and researches of the analysis of signal structure and the like. However, it was a large scale complex device system, besides that, the recording volume was finished only by 2 minutes and 12 seconds.

The invention of a high-speed-sampling one-bit-quantization analogue to the digital conversion method made by Yoshio Yamazaki (Professor of Waseda University) solved the problem of data recording which had been extremely difficult to solve. The existence of this signal processing method was suggested by Takeo Yamamoto, Vice president (at that time) of Pioneer, Co., Ltd. and by his recommendation, first of all, an excellent small sized system which was extremely excellent in transportability was made by Professor Yamazaki. This indicated the frequency response of −3 dB from DC to 100 kHz and was completed as a recorder which upset the concept of all of the audio signal recorders until then. The studies and researches of the present inventors were accelerated at that time and set the studies and researches on their way owing to many recorders having an actually beautiful sound notes by Professor Yamazaki who developed many by making the first machine as the starting point.

The next problem following the recording problem was an acoustic analysis. In addition, in this case, there was a problem which is the same with the case of the microphone and recorder from the viewpoint that all of spectrum analyzing devices for audio were limited up to 20 kHz. And then, the correspondence with this problem was extremely difficult rather than the case of the microphone and recorder at least at the initiation period, and showed a terrible situation. The present inventors could not measure to which frequency components of the sounds to be analyzed by the present inventors reached, at all. On the way of determining the specifications of the whole of the research and study system, the present inventors would like to analyze it up to about 100 kHz at least. However, in the field of the acoustic analysis in the beginning of 1980s, it was only the crazy thing to think of the same. Needless to say, there was no device that makes it possible.

Then, over the other fields except for acoustical engineering as far as it was possible, the retrieve was carried out whether or not FFT analysis up to about 100 kHz was performed. As a result of this, in the van of an era in weather observation, which was not regarded with sounds, it was understood that there was a technology that used a laser radar. In the laser technology, the FFT analysis up to 100 kHz was performed. Further, it was elucidated that the analyzing software is mounted on the mainframe of weather agent weather institute (at that time) located in Tsukuba Kenkyu Gakuen City. Then, the present inventors have asked many persons in the various fields, and with the favorable helps of persons with whom are not acquainted, the data of the sounds of the present inventors were inputted to this main frame in an unorthodox way and could be subjected to FFT. As a result, such a judgment was introduced that, among the sounds the present inventors actually in contact with, there existed the comparatively large number of the components falling within an ultra high frequency range exceeding over the uppermost limitation of the audible range, and that the frequency analysis up to 100 kHz should be executed if these components were subjects on the experimental science from a point of view of safety. However, what on earth does such a kind of FTT analyzing machine exist and where is it?

This troublesome problem was solved by an automatic FFT analyzer, which was capable of analyzing data up to 100 kHz, available in the market, and manufactured by one of the Japanese major manufactures of the measuring device (manufactured by Ono Measuring Machine, Co., Ltd.). This device was introduced into the laboratory of Professor Hiroo Yamazaki (at that time) of Tokyo University who was acquainted with. We progressed with the study and research by lending it sometime. But, this solution means had the weight of 80 kg which is comparatively heavy as a weight of human being, and therefore, we encountered the comparatively miserable situation that a female researcher who was short even among Japanese carried using her own hands from Tokyo to Tsukuba by an electric train. However, a device which was a smaller but had a high performance emerged and the circumferences have taken turn for the better.

As the next stage, a regenerator system for showing a variety of sounds to the subjects has to be constructed. Particularly, if the high frequency component up to 100 kHz is included in view in this study, a speaker system having an extremely high performance for converting the electric signal into the air vibration spanning over the relevant range and excellent amplifiers and the like for driving it are required. Originally, this problem was extremely difficult, however, almost all of the respective parts could be available in the market from the members for use in the high quality audio, and this problem was solved. The background of the technology is in a signal reaching up to 100 kHz at which the groove of LP being at the peak of the boom was engraved containing the content of sounds that cannot be dipped up if it is tried to enhance the regenerating system. Accordingly, if it is considered from the viewpoint of orthodox technical specifications developed in the field of the high quality audio, it may be a part or a system having an excessive quality provides a sound quality which is not considered from the viewpoint of theory at the time when it is actually used. As a result of this, strictly saying, it is not technically sufficient, but actually, the device and members of it having the level resistant to the experiment of the present inventors have been accumulated in the audio market. However, concerning a speaker unit for regenerating ultra high frequency, the problem was too large, and it was solved by the technique that diamond is vaporized, and thereafter re-crystallized into a dome shape.

Rather, the most impact point concerning with the existing regenerating system was a configuration of a "orthodox" circuit used for the purpose of examining the state where a high frequency component introduces the sound quality difference in the field of the acoustical study. The circuit is configured so that the original electric signal which is a sound source is branched into two, and one is passed through as it is, and the other is passed through a low pass filter having a certain characteristic (an electronic circuit for cutting off a high frequency component higher than a predetermined value). Owing to this, a signal including all of the band components and a signal only without the high frequency component can be made. The two signals were listened to by the subjects, where the two signals were switched in such a state that the subjects cannot understand the switching. Then, the subjects answered whether or not he/she felt it as a difference in sound quality by writing his/her answer on a questionnaire, and the results were subjected to the statistical treatment.

First of all, the present inventors carried out the experiment concerning with some sound sources including a rich high frequency in accordance with the method. The results that support whether or not the subjects can hear and distinguish that there was a high frequency of 20 kHz or higher were obtained, although it was a simple level. At this time, Tsutomu Oohashi himself tried to intuitively taste the sound quality difference in such a way of what is called a cook for sounds, needless to say, in the case of 20 kHz and 30 kHz, but also a high frequency exceeding over 50 kHz is cut off, the sound quality difference could be felt.

As I have determined that I would publish these results in 1984 in a Society of acoustical study which was the highest authority in Japan, since I thought that it was sufficiently valuable for that although it was in a stage where there was only a sign, but it was also grounded by the experiences that Tsutomu Oohashi himself had. The lecture publication performed by a graduate school student was noted from the scientific journalism, on the other hand, he was furiously offended by those who were concerned with CD which was available in the market by a format in which the component of 22 kHz or higher was cut off and who were concerned with PCM digital audio at that time.

Needless to say, among the researchers in the field of orthodox acoustic sense, there are some who were diligently interested in the same. Through debates with these people, there was emerged a doubt concerning with the official method in which an orthodox circuit universally used and also used herein, that is, a high cut signal passing through the low pass filter and a full range signal not passing through the low pass filter but passing through the sole copper wire are switched and thereafter, through the same regenerating system, the outputted regenerated sounds are heard and compared with.

Even if a filter circuit is simply made, it has to configure an electronic circuit including a plurality of elements. It cannot be avoided that it has a convex and concave of the characteristic in the frequency area where it was not the object of insulation and it should be flat, which cannot be neglected comparing to the sole copper wire. Moreover, it cannot be also neglected that speeds at which frequency components pass through the circuit are changed <group delay characteristic> according to the frequency components. Further, in an amplifier and speaker after the filter circuit, the <non-linear distortion (IM distortion)> is capable of being generated by the intermediate action between frequency components different with one another, and it cannot be avoided that it is not equal by the difference of the components of signals passing through the circuit. Then, any of these three may be a factor causing the difference of the sound qualities. That is, between a signal passing through such a filter circuit and a signal not passing through it and directly going solely through the copper wire, it cannot be avoided that there is a difference between signals emerging by a group of causing factors regardless of the difference of the frequency component set as the experimental object except for the difference of the frequency component set as the experimental object, and there is no proof that it does not introduce the difference of the sound qualities.

In the current orthodox system having such a nature, although it is not a problem in the case where the difference of the sound quality was not detected, if the difference of the sound qualities were detected, no one knows that whether or not it is due to the difference of frequency components that the difference of the sounds causes, whether or not it is due to the limitation of the flatness of the filter, whether or not it is due to the difference of group delays, or whether or not it is due to the difference of non-linear distortions. Probably and actually, these may be compromised causing factors. Tsutomu Oohashi himself has felt the sound quality difference even if the insulating frequency was moved to any location in the frequency variable filter since he might not solely hear the difference of the frequency component.

By the way, the present inventors as a cook for sounds know that the changing of the sound quality which is not capable of being neglected occurs by exchanging the kinds of cable for carrying signals in a studio or in audio room, and take care of selecting of the same. However, it is hardly thought that the sound quality difference generated between the complex filter circuit and the simple copper wire is smaller comparing to the sound quality difference between cables. If it is considered in such a way, this circuit model which may be now still orthodox is very peculiar one whose effectiveness can be claimed only in the case where the sound quality difference is not detected, therefore, it is difficult to upset such a blame that it logically has a defective.

From the viewpoint of Tsutomu Oohashi who has received training as a life scientist, the logic of this circuit configuration may be at a level of not being probably and academically hardly admitted as an experimental model of the modern biology. Then, we have considered whether or not a circuit model capable of avoiding the logic defective can be configured. Concerning with this, we have obtained excellent hints from both critics of audio, Saburo Egawa and Isao Shibazaki, and we could completed the configuration of a system which is called as a <bi-channel regeneration system> and is capable of avoiding all of the prior logic defectives. The main point of this is in that first, the original regenerative electric signal is divided into an audible range component and a super-audible range high frequency component, the respective ones are made capable of switching on/off, and then a circuit is made so that both are completely independent and regenerates it into the air vibration. Then, if both switches are turned on, the full range sounds can be regenerated, if only the switch for the audible range component is turned on, a high cut sound can be regenerated, and if the switch for the super-audible range component is turned on, a low cut sound (inaudible high frequency) can be regenerated. In this circuit, all of the logic defectives listed above within the pathway from the sound source to the speaker that the current orthodox circuit has been solved (however, the probability that has an influence on the sound quality by generation of interaction between the air vibrations discharged from the speakers apart from one another which are spatially separated remains, therefore, the settings of the experimental conditions are required to be carefully taken). The regeneration system whose backbone has been established in this way was continued to carry out the enhancement and develop it again sometimes. As a particularly important development, there are developments such as the development of a speaker system (<OOHASHI MONITOR> system in which the fidelity is higher, more sensitive, stronger and more excellent in sound quality not only statically but also dynamically than the conventional systems, the development of a player in which the packaging of signals exceeding over 100 kHz by setting the special specification using SACD format using DVD as a medium has been realized, the construction and publication of an authentic hypersonic audio system capable of carrying out almost all of the supplementary examinations of the researches and studies performed by the present inventors by integrating these developments and the like are listed.

3. As subsequent problems, the experimental model for detecting the influence on human being by sounds in the outer sphere of consciousness area has to be constructed. In approximately the 1980s, prior to making it into practical use of a digital audio by PCM method, many experiments for evaluating how high the high frequency component up to a certain degree influencing on the sound quality have been carried out in Japan as a center of the same. Among these, there was an experiment of a large scale with the high severity using a group of the subject including studio engineers who admit the effect of the ultra-high frequency component over 20 kHz or higher usually utilize the same. The results of the experiment which was universally admitted as an authoritative one are in that whether or not there is a high frequency component in a music can be detected as a sound quality difference for human being is limited up to 14 kHz and in the case where it is 16 kHz or higher, whether or not there is a high frequency component in a music cannot be felt by human being as a sound quality difference. From the experiment showing it by insulating the high frequency area of white noise step by step for the purpose of pursuing the same in Germany, it has shown that whether or not there is a high frequency component having 10 kHz or higher has no influence on the sound quality difference. These have become the proof of the regulation of sampling frequency in digital audio (32 kHz, 44.1 kHz, and 48 kHz).

These experiments, their results and the attitudes of the expert researchers backed up by these exerted the action that denies the sensitive sense of some of the diligent studio engineers having particularly excellent sense and became the subjects of the experiments against the fact. As a result of this, it has introduced the case where even the unreasonable and pitiful event in which the subjects were fallen into unbearable distress and became in bad shape occurred. While Tsutomu Oohashi who was in contact with people in the situation knows that the experimental data is grounded with an authoritative theory and is an acknowledgment introduced by the sufficiently set experiment, he did not feel hesitant that he proposes the doubt against the authority and tests it experimentally. For Shoji Yamashiro who is an inventor as a cook for sounds, "sounds in the outer sphere of consciousness" which is measured as 20 kHz, 50 kHz and 100 kHz are the essence of peculiar taste made by him, it is obviously true from the non-verbal internal point of view. At the same time, it was an experienced knowledge commonly shared by "telepathy" between studio engineers and musicians having a sort of sensitive sense. Next, as seen from scientist Tsutomu Oohashi living in the same living body with this Shoji Yamashiro, if the experienced fact which is so obvious cannot detected by the current research method, it means that the existence of limitation of the research method itself is put in our view and contemplated to overcome the problems.

In order to approach these problems, a strategy that makes an encircling net by integrally coupling multiple methods in accordance with the principle of being largely distanced and separated from the already known methods as far as possible, and securely chases the games into the net becomes effective. Although it is difficult as a conventional concept of the academic world which is highly specialized and deepened into a mono-functionalization, if it is started from the peculiar state of Tsutomu Oohashi in which a cook for sounds and a natural scientist are fused in one person, it was considered it cannot be said that the possibility for satisfying it is zero.

From the viewpoint of this, as an initiation of the research for grasping the influence on human being by the sounds in the outer sphere of consciousness, it was decided that a new approach which is completely different from the current psychological approach is introduced, and we were noted of the physiological methods which was not untouched at that time. As the subject of it, as the device, there is no other thing except for "brain" that receives the sounds and introduces the taste. Fortunately, the present inventors were gaining the opportunities capable of utilizing a variety of non-invasive brain function analyzing methods for the first time for human being. Some methods are opened to the pathway for describing the brain activity. If these are appropriately combined, it is not a dream that the valuable acknowledgement is obtained such that it could not be imagined before the time has not passed long.

However, almost all of these methods were originally developed for the purpose of utilizing these in medical care, almost all of these are required to invest a large sum of facility investment, and there are many measuring devices and methods having the natures which become a problem by themselves at the time when the sound is proposed and its sound is listened to. Moreover, there is a fear, which cannot be neglected at the time when it is measured, that these give a negative psychological emotional bias to the subject. Namely, it is difficult to use as it is for the purpose of pursuing the response of the sounds in the outer sphere of consciousness which could not detected by the present inventors because of its fineness even if these are effective for use in the medical care purposes such as findings of diseases, the physiological abnormality and the like. Accompanying with these, the experimental place, occasions, frequency and the like are significantly limited. Particularly, it is necessary to consider that at the stage of <retrieval research> where a new research is initiated, experiments are widely carried out as many as possible and the statistical treatments are frequently performed. Then, we have retrieved what exists as a physiological index suitable for this retrieval research. As a result of this, provided that the already existing technologies are basically reconsidered and two or three problems are overcome, the fluctuation of electrical potential on the scalp which is well known as an index of brain activity, that is to say, it was concluded that it is most hopeful that the reconstruction of a method of grasping the electroencephalogram (EEG) is performed.

In the history of electroencephalogram researches, first of all, <spontaneous electroencephalogram> has been noted, and analysis has been performed from the old age in the respective separate frequency band such as alpha wave (=alpha rhythm: 8 to 13 Hz), beta wave (13 to 30 Hz), theta wave (4 to 8 Hz), delta wave (1 to 4 Hz) and the like. Subsequently, the notification to <evoked electroencephalogram (EP)> was enhanced and in recent years, the application of <event related potential> (ERP) which has been developed from the above-described method has been frequently performed. If the effectiveness that these methods have as a sound quality evaluation index is considered, the suitability of a method of induction potential system for detecting the transient reaction against the single stimulation is not high for the purpose of this research for evaluating the harmony between the sound phenomenon such as an environmental sound, a music or the like which is listened continuously for a long time period and the brain of human being. For the purpose of performing this research that the reaction of mind and body to the environmental information inputted continuously for a certain time period is totally grasped, it must be more unstable and the measurement and analysis become difficult, however, it can be said that spontaneous electroencephalogram that reflects "base state" of the brain is more suitable as an index. Particularly, the alpha wave is well known not only as an index of peacefulness and/or conformity or concentration under the condition of wakefulness, but also has been known that it is suppressed by uncomfortable sound is noted as a candidate of an index. Then, the working hypothesis in which the electric activity of alpha band is made index for suitability between the brain and information environment is constituted as the followings, and the development of living organism influence evaluation method by electroencephalogram has been progressed.

In the researches of induction electroencephalogram, a brain potential activity is grasped as a reflective output with respect to certain information input based on a "stimulation=reflection" model. On the other hand, concerning with spontaneous electroencephalogram, the modeling for grasping it through input=output relation has not been clearly performed. However, actually, the concept that grasps it through the input=output relationship which is close to the concept of induction electroencephalogram is tacitly in a dominant state. If daring to say, it is a concept such that "alpha wave is not generated as an initiation condition and it emerges as a response to some information input". This concept is described in a method in which when the influence of sounds is evaluated using an electroencephalogram as an index, "no sound state" is made standard, and at the time when a certain sound is proposed, what kind of power is outputted in the electroencephalogram is measured.

However, the no sound state which is standardized in this model is an extremely peculiar sound environment from the viewpoint of the biological field if it is supposed that human being or its ancestors such as large anthropoid evolved in the environment consisting of the forest, scarcely encountered even if it is exceptional through the process. It can be said that it is a typical type of a sound environment most separated from "original sound environment" for bringing up the genes of human being. Accordingly, there is a probable possibility that the no sound state extremely strongly acts on human being as an abnormal negative stimulation for human being. Then, it was considered that it is risky that we agree with the present conventional concept considering it is the standard or a control.

In the tropical rainforest where it is estimated that the genes of human being has been brought up in this original environment, the environmental sounds are extremely rich. Namely, concerning with the standard of the sound environment at the time when the suitability between human being and the sound is evaluated, it is more appropriate that the rich sound environment having information structure of the tropical rainforest is considered as the standard rather than the no sound state. Then, one working hypothesis was introduced that it is supposed that using "original—adaptation model", the activity of the alpha wave is positioned as an index for "brain's original state" or "stress free state", originally, it is always generated at a comparative level. Namely, the stress is lowered to the lowest level under the peaceful situation where the adaptation reaction exists most slightly, and the original life activity has been most highly realized in the original environment of human being, and the activity of alpha wave is most highly enhanced. It is considered that the stress is generated or increased accompanying with the separation from the original state, the level up of the adaptation is promoted and the activity of the alpha wave is lowered in accordance with it as well. In this way, if the alpha wave is an index for <originality>, in the case where informative factor causing stress emerges by shifting out from the original environment, the power of the alpha wave of electroencephalogram should be suppressed. If it is put in one's view, whether or not conventional electroencephalogram measuring method takes a treatment for excluding the information environmental factor as suppressing the emergence of the alpha wave emerges as a new problem.

The measurement of electroencephalogram has been carried out in the environment of medical care institutions where the negative psychological bias is easily accompanied with except for slight number of cases. Particularly, since the electroencephalogram tends to easily receive the influence of exogenous electromagnetic induction noise by a weak electric phenomenon, there is a remaining of the old days when the devices whose sensitivity is high and S/N ration is low were used, the subject is put into the exclusive examination room having a sufficiently threatening atmosphere by electromagnetic shielding and sealing, and it has been recommended that the subject closes his/her eyes and the visual sense is insulated, the body movement is prohibited and then the measurement is performed. In the case where it is not performed in that way, the settings for the purpose of performing the medical care within the examination room and the environment made by room furniture cannot help generating the anxiety and fear in the normal people. Needless to say, in order to detect the abnormal electroencephalogram to be an index of the diseases and observe the reflective induction electroencephalogram reaction in an extremely short time, these measuring environments may scarcely influence on the results. However, in the case where spontaneous alpha wave of electroencephalogram continuously emerging by reflecting the conformity and psychological peacefulness is observed, the measuring environment causing the anxiety and stress for the subject influences on the results by itself, and it works suppressive against the emergence. Then, on the occasion when the working office of Tsutomu Oohashi was transferred to National University Common Utilization Institution located in Metropolitan area from Tsukuba, it is determined that the experimental environment is newly constructed so that the problem is made smaller. The design and execution of work was progressed by Professor Masami Toyoshima who is the top class studio designer in the world and constructed Abby Road studio in England, Nippon Victor, Aoyama studio, and the like, and successfully completed.

In this case, among many things, particularly the structure and functions that the subject is not subjected to psychological stress were considered as an important factor. For example, with contrast to the conventional acoustic experimental room, whose priority is to exclude the sound and make a complete insulated state also in visual environment, in the present experimental room, a double glass window treated by performing sound insulation was opened widely towards the outside and the visual image of natural light and outside was secured. The interior was finished with the design of natural oriented based on ligneous system and arranged the environmental pictures, foliage plants, and the like, here and there. Further, the experimental devices except for speaker were placed out of the view of the subject, at the same time, cables were inputted within the pit, and endeavored to reduce the degree of visual association making the subject conscious of the experiment. In addition to these, in order that a variety of acoustic spaces can be simulated as many as possible, and moreover, the beautifulness of sounds and natural nature is not lost, a new method of controlling the acoustic characteristic by changing the materials on the wall of the room was developed. The wall was configured by triangle columns of rotational type, and three surfaces of each of the triangle columns were covered with three kinds of materials having different acoustic characteristics, that is to say, marble, cherry material, sound absorbing material plus jersey cloth having a high density. By rotating the triangle columns one by one, it became possible that a variety of species and kinds of acoustic spaces whose sounds are beautiful are created while the design of the natural room was secured.

The method of delivering the electroencephalogram from the subject was also reconsidered. The procedure itself which is troublesome, uncomfortable and is generally seen in the examination room of the hospital and the like provides too much negative emotional action so that the positive effect of the music cannot cancel. Then, the system in which the cap that electrodes have been already mounted is put on, and the electroencephalogram data of multi-channel can be sent by wireless by means of FM multiple transmissions from a small sized transmitter put in the pocket of the subject was made. Owing to this, it made possible that the electrodes are swiftly set and the subject attends to the measurement while the subject freely behaves without being restricted by its cable.

The nature that the enhancement of the stability and reliability of data is extremely difficult finally blocks in the experiment whose index is electroencephalogram. The electroencephalograph collects the fluctuations of the electric potential on the scalp at the micro-volt level. However, there, the possibility that extremely strong potential occurring at the time when the muscle moves is mixed always exists. Moreover, randomized noise might have been mixed in the fluctuation component in the range from 8 Hz to 13 Hz where the measuring device meters all as alpha wave. Further, the fluctuation of the electric potential whose causing factor is not known occurs at the locations on the scalp and it may be in an abnormal state. Unless it is the electroencephalogram is qualified by the test checking all of these possibilities not considered in a usual situation, it cannot be the index of the particularly delicate experiment such as the experiment for examining the reaction to the sounds in the outer sphere of consciousness.

Concerning with this point, in order to contemplate the rigidity and enhance the reliability, the checking was performed by providing multiple rigid barrier usually not provided at the time when data is analyzed. First of all, data is collected through multi-channel and "time wave type" is monitored and whether it is polluted with noise or not is checked. Next, the potential data per each electrode is subjected to FFT, and whether or not an independent peak from the noise component per noted frequency point is formed is checked. Further, brain electrical activity map=BEAM of the whole of scalp is depicted based on FFT per unit time period of data of all the channels, and whether or not the electric potential distribution on the scalp is abnormal is checked. In the case where there was no problem concerning with all of these, the time integrated value of alpha wave power from the specific region on the scalp is calculated based on the foregoing BEAM, and quantization data of the alpha wave power is obtained. This is normalized so that the individual difference is canceled, and then, the data from corresponding number of the subjects is subjected to the statistical analysis. The stability and reliability of the electroencephalogram data was enhanced by leaps and bounds by these treatments. It played the critical roll to lead the researches of the present inventors to its success accompanying with the height of time resolution that the electroencephalogram indicates the most noted power.

The retrieval research by electroencephalogram lead to extremely valuable findings concerning with the peculiar time characteristic of the physiological reaction to which the frequency in the outer sphere of consciousness leads. However, the electroencephalogram is excellent in time resolution, to the contrary, the space resolution is extremely low. But in the brain function research, unless the localization of the spacious function is specified at the organ level within the brain, the definitive factor is deleted, and we are obliged to be satisfied with an insufficient acknowledgement. The methods most suitably used now are fMRI and PET, which are at the top of these. However, the above-described functional magnetic resonance imaging method (fMRI) impulsively generates a strong magnetic force, the scanner itself where the subject enters vibrates as a giant speaker and it may generate such a noise that may make the subject deaf, and it is not suitable for research of the sounds. In the case of positron emission tomography (PET), since it is not accompanied with such a noise, it is highly suitable for experiment of sounds. However, since it uses radioactive isotope, it cannot ask the same subject repeatedly participate the experiment in a short time period. Accordingly, it is necessary to carry the plan for several years in accordance with the experiment plan sufficiently and carefully constructed.

The experiment of the present inventors had no precursors and there were many peculiar problems. Among these strategic plans, the psychological and behavior experiment and the analysis of the physiologically active substances in blood stream could exert the effectiveness comparatively and smoothly started from the general method. However, since it should be originally realized by the preposition that a unique acknowledgement of temporal asymmetry of the response obtained from the physiological experiment in which many devices were considered being made nucleus, when the experimental conditions is observed, it is largely different from the respective original methods.

In this way, hunting of sounds in the outer sphere of consciousness of the present inventors is a hunting in which we did not chase the game from single expertise field in one direction, but we did progress the plan in accordance with the strategy that makes an encircling net by integrally coupling multiple means and methods from a variety of fields and securely chases the games into the net.

4. Finally, as a definitive task, we have to refer to the preparation of stimulating sound source that makes the air vibration containing strong ultra high-frequency wave power which will be an impact striking the tacit sensitivity that human being has. In this case, there is a structure similar to the structure in which the experiment depends on how the accelerator accelerates an elementary particle and ion beam, and on how high the energy projected at the time when particle strikes is enhanced in the nuclear physics. Moreover, it is necessary to appropriately consider such an important code system of natural and cultural system that is governing the life of human being.

In order to satisfy these conditions, materials have been searched and collected over twenty years on the global scale mainly by field work, from among cultural spheres that have highly secured the nature and traditions, with paying attention to the sound source constituting the music that has historical achievement on affinity with human being. (About 50 titles, which are part of the collection of the present inventors, are included in "JVC world sounds" which is one of the international collection CD of ethnical music, and available in the market).

Figure 33:
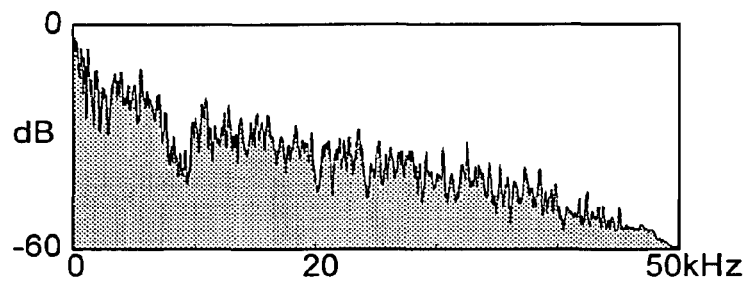
FIG. 33 is a chart showing a power spectrum of a Gambang Koota of the gamelan music, illustrating an average FFT spectrum of all tunes (for 200 seconds).
Figure 34:
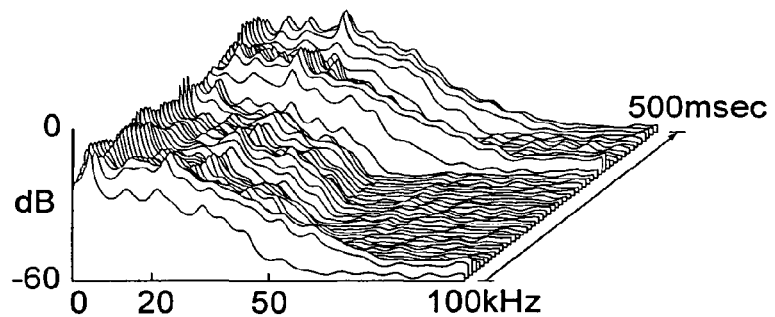
FIG. 34 is a spectral chart showing a change with a passage of time in which all of the tunes of FIG. 33 are observed as an ME spectral array.

From among relatively large number of searched materials on several tens of music cultural spheres, a piece of music which is extremely suitable for the purpose of the experiment by the present inventors could be selected. The piece of music is "Gambang Kuta" which was played in one form of gamelan music <gamelan semar pegulingan> of Bali Island. The piece of music has a full length of about 200 seconds that is ideal length for the experiment of the present inventors, and has such an eminent structure that one will not be tired even if one listens to it repeatedly in the natural stream. Then, although the piece of music is mild as gamelan music of Bali Island, over the whole of the piece of music, it is full of ultra high-frequency components that cannot be observed in other examples. When the piece of music is analyzed with using FFT, an average power spectrum of the whole of the piece of music reaches to 50 kHz (FIG. 33). What means this average value is understood by the fact that in the case where the same piece of music is played by a piano, it reaches only to about 10 kHz. Further, when the structure of micro time region of the piece of music is analyzed with using ME spectrum array, the uppermost of the frequency often exceeds over 100 kHz, and as a whole, a complex analog structure is continued to significantly change (FIG. 34).

It was understood that this non-stationary fluctuation structure is essential as a sound source for use in the research of the present inventors by the later consideration. This is because the effect the sound source is lost or a negative effect is introduced, when this ultra high-frequency component is substituted by stationary band noise which has no fluctuation with the average power spectrum being made equal, or when this ultra high-frequency component is changed to sine wave having a periodical cycle.

When this piece of music was recorded in Bali Island and carried to Japan and developed in the experimental environment that has been prepared as carefully as possible on the other hand, the breakthrough, that was considered to be impossible initially, began.

<3-3-2> Discovery of First Essential Information "Hypersonic Effect"

Figure 35:
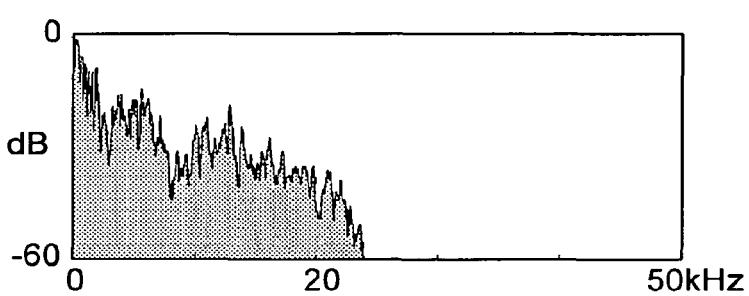
FIG. 35 is a spectral chart showing a reproduced sound in an audible range in a position of an examinee in relation to the tune of FIG. 33.
Figure 36:
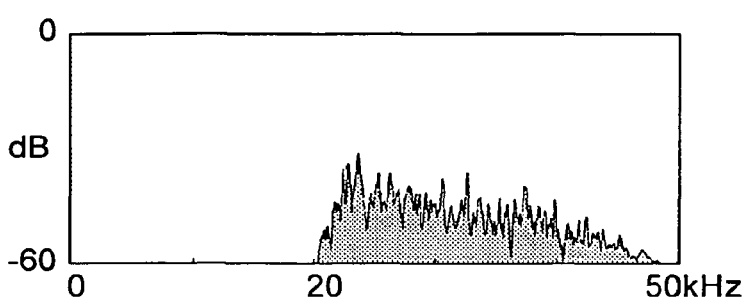
FIG. 36 is a spectral chart showing a reproduced sound in a super-high range in the position of the examinee in relation to the tune of FIG. 33.

The first and decisive game of the hunting, in which the effect of ultra high-frequency sound in the outer sphere of consciousness is pursued, was obtained from the physiological experiment whose index is an alpha wave of electroencephalogram (alpha rhythm). The data was introduced from an approach, in which the change in the brain activity is measured by an electroencephalogram measurement with high time resolution, and which is a turf of the electroencephalogram measurement, in an experiment in which subjects listen to the gamelan music of Bali Island. When the subjects listen to the piece of music by switching between full range sound, which is full of non-stationary fluctuation of gamelan music and which richly contains ultra high-frequency in the outer sphere of consciousness, and high cut sound which is obtained by excluding only ultra high-frequency component of 26 kHz or higher from the full range sound (FIG. 35 and FIG. 36), power of the alpha wave of electroencephalogram for all of the subjects are integrated, and an integrated power for the full range sound is larger than that for the high cut sound. When the transition of alpha wave power of each of the subjects is observed in detail at the interval of 20 seconds, such a tendency exists that a timing of the increasing and reducing of alpha activity is shifted from a timing of switching between the two proposed sound. Then, the alpha wave power of the eleven subjects are normalized, respectively (processing for canceling the individual differences), normalized alpha wave power are averaged at every unit time period, and thereafter resultant alpha wave power are arranged relative to an time axis. A course of time which could not be imagined by anybody was found. The course of time was actually unexpected, and at the same time, it provided a definitive fortunate to the research of the present inventors.

First of all, such a fact was emerged that the activity of the alpha wave is significantly enhanced by the full range sound containing ultra high-frequency, and it requires from several seconds to a dozen seconds for the value of the activity of alpha wave to reach to a <high level> (FIG. 37 to FIG. 42: physiological, psychological, behavior reactions that hypersonic sound by hyper sonic effect containing ultra high-frequency). Later, the electroencephalogram was analyzed in detail with using ME spectrum array method, and it was found that the activity of the alpha wave decreased immediately after the proposed sound was reached, and thereafter increased to a higher value after a delay time of about 7 seconds in average. Next, after the alpha wave reached to the higher value, when the proposed sound was switched to the high cut sound by excluding only high frequency component, an averaged value of the alpha wave power was maintained at the high level and remained at the high level for about 100 seconds, and thereafter the averaged value of alpha wave power rapidly decreased and maintained to a <low level>. Then, the value during 100 seconds from the initiation of the proposition of the sound was excluded from the subject of the calculation, so that the influence of the delay or remaining of the electroencephalogram activity variation is made smaller, and a statistical treatment was performed by limiting the subject only to stabilized value. As a result, it was found that the alpha wave power is higher when the subject listened to the full range sound than when the subject listened to the high cut sound, with a significance level at which the result was statistically significant ($p<0.05$).

The present experiment showed a fact that the sound containing the ultra high-frequency component which exceeds over the uppermost limit of the audible range and which is not heard as a sound for human being enhances the activity of alpha wave of electroencephalogram, than a sound without the ultra high-frequency component. Namely, the present experiment clearly showed a fact that the sound containing the ultra high-frequency component had an influence on the brain of human being, with a statistical significant difference, for the first time. Needless to say, the meaning of the fact is inestimable. A large game which is comparative to this fact is an unexpected fact that the changing in brain activity of the enhancement of the alpha wave power introduced in this way emerges after a delay of several or a dozen seconds from the timing of initiation of the stimulating sound, and remains for 60 to 100 seconds after the stimulation was finished. When this fact was found, it was understood that undeveloped dimension binding between sound and human being emerged in front of the present inventors, and the present inventors could not help feeling joy and excitement.

This phenomenon will shake the base of the physiology and psychology of acoustic sense. Since the acoustic sense system of a human being has a much more sharper time resolution than visual sense has, information will reach for about 9 milliseconds from cochlear nerve, which is the inlet, to the primary optic area. In this case, by the general knowledge or theory about the acoustic nerve system, there is no clue to explain a phenomenon, which was found by the present inventors for the first time, that the activity of the alpha wave of electroencephalogram changes with delaying and remaining in the scale from several seconds to 100 seconds according to difference in sounds. The discovery of this delaying and remaining phenomenon leads to the exposure of pitfalls existing behind the already existed psychological experimental methods which are the pride of the authority.

By setting the discovery of delaying and remaining in the activity change of alpha wave, which has highly succeeded as a retrieve experiment, as a premise, as the next stage, the brain function analysis experiment with enhanced space resolution was expected. The present experiment was carried out concurrent with the electroencephalogram analysis using PET (Positron Electron Emission Tomography), and this has lead to the remarkable results overwhelming almost completely the field of the acoustic physiology.

PET performs the tomographic imaging of the volume of bloodstream (localized brain bloodstream) of the respective parts of the brain using radioisotope. The degree of nerve activity of the whole of the brain can be examined with a high space resolution, by utilizing the nature that the activity of nerve cell corresponds to the brain bloodstream of that site. However, since the radioisotope having extremely short half-life should be prepared at the site and should be immediately administered to the subject, a large scale facility including cyclotron where these nucleus species are made and a large number of staffs having a highly sophisticated knowledge and technologies. Then, we carried out the research in cooperation with the group of Professor Hiroshi Shibazaki of Kyoto University, Brain pathologic physiology (at that time) and Professor Yoshiharu Yonekura of Fukui Medical University, High energy medical research center. At this time, the electroencephalogram was also measured in parallel. It should be noted that the environment of the PET measurement room was made comfortable as much as possible, with the same concept as the experiment performed by setting the electroencephalogram as an index.

In the experiment site, there was a group which should be referred to as a "PET scanning unit", including an expert for nuclear physics experiment who carries out cyclotron, an expert for synthetic chemistry who prepares chemical substance for administration (in this case, $H_2^{15}O$) from obtained nuclear species (in this case, $^{15}O$), a physician who pluralizes an experimentalist and takes charge of correspondence to the subjects including administration of the isotope to the subjects, a physician who pluralizes an experimentalist, monitors and controls the proceedings of the experiment, and performs the setting of the conditions, and a physician who pluralize an experimentalist and collects and analyze data in real time. In this case, plural members participated in each of sections, depending on the sections. Further, a "proposing the sounds and electroencephalogram measuring unit" who takes charge of sending out the proposed sounds, monitoring the regeneration state, settings of electroencephalogram measuring system, monitoring and collection of the electroencephalogram data, interlocking regulation with PET scanning, and the like were added to the "PET scanning unit", so as to construct a comparatively highly complex system as a whole.

Besides the system, the securing of the subjects is a large burden. The total amount of radioactive administered per one subject in a year has to be suppressed within a level which is not so different from the total amount of trace of radioactive ray received from the nature, for the purpose of completely securing safety. Since the number of experiments is strictly limited by this regulation, it is extremely difficult to carry out comparative number of experiments using the same subjects group, so as to subject the results to the statistical treatment. The present inventors fixed up a group of the subjects, where a population of the group includes twelve healthy adults, and secured the group for three years, so as to collect data to which the statistical treatment can be executed.

The sound source used in the present experiment was gamelan music "Gambang Kuta" of Bali Island, which is the standard of the present inventors. The sound source was divided into an inaudible ultra high-frequency component of 22 kHz or higher and an audible range component, the frequency of which is lower than that of the ultra high-frequency component. Then, how the brain responded to four kinds of conditions of sounds, (a) a sound containing both of the ultra high-frequency component, (b) a sound only containing the audible range component, (c) a sound only containing the inaudible ultra high-frequency component, and (d) a background noise sound without any sound.

The present experiment showed that, according to the difference in the proposed sounds, the amount of the brain bloodstream at a variety of sites of the brain was changed and the activity of the brain was changed. As a response which is not changed from the expected response at that time, the temporal lobe in which the acoustic nerve systems are gathered was activated, under such a condition that the music being heard (at the time when sound including the ultra high-frequency component and audible sound and the audible sound were proposed), as compared with the temporal lobe in such a condition that the ultra high-frequency component without the audible music was proposed or a background noise condition.

Next, the site of the brain where the difference of activity emerges between at the time when a sound containing ultra high-frequency is listed and at the time when a sound without the ultra high-frequency is listened was searched. The statistically significant difference between the activities in two areas located at the deepest site of the brain was found. The two sites belong to the <brain stem> and <the left thalamus>, respectively. However, these sites do not correspond to <the inferior colliculus> and <medial geniculate body> which are relay points of acoustic nerve system. Namely, in the area belonging to the acoustic system, the change in nerve activity was not found depending on whether or not the sound contains ultra high-frequency component, and the neural circuit indicating the specific response with respect to the sound containing ultra high-frequency in the brain stem and thalamus is different from acoustic system. The rise of the activity emerging at this brain stem and thalamus is the effect made by ultra high-frequency component contained in gamelan sound.

By the way, in the experiment in which only the ultra high frequency component, that was a causing factor of the rise of the activity, was proposed, the activation of the brain stem and thalamus, which was seen at the time when it was proposed accompanying with audible sounds, was not found. Accordingly, the peculiar effect emerges only when the music component in the audible range and ultra high frequency component in the outer sphere of consciousness exceeding over the audible range coexist. It was elucidated that, when it was further examined in detail, both at the brain stem and the thalamus, the activity rose at the time when the sounds containing the ultra high frequency were proposed as compared with the activity at the time when the dark noise without any music existed. On the other hand, it should be noted that in the case where the ultra high frequency was removed, the activities at these sites were lowered as compared with the activities at the time when the dark noise without any music existed.

Figure 38:
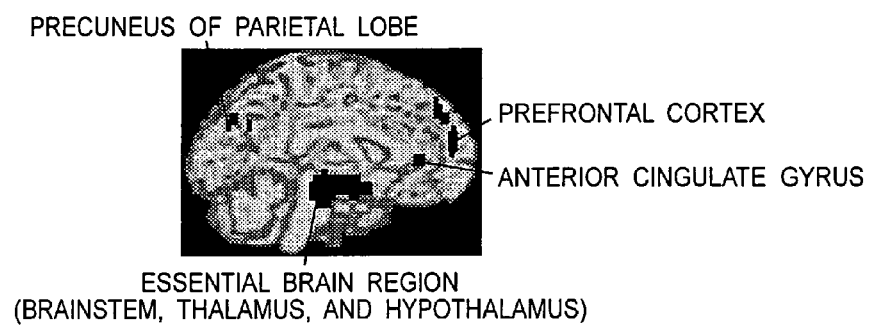
FIG. 38 is a view showing that the hypersonic sound activates an essential brain region network.

Further, a principal component analysis was applied using enormous amount of blood flow data recorded from the overall brain, so as to try to extract the overall view of the neural circuits, which respond to different kind of sound, relate with each other, and work together as a unit. As a result, the auditory area of the temporal lobe was extracted as the first principal component, which shows the highest activity, as was expected. As for the second principal component, the notable finding was that the neural circuit centering around the brainstem, thalamus, and hypothalamus, going through the orbital frontal lobe to the frontal cingulated gyrus, that is the <essential brain region network> as well as the precuneus of the parietal lobe, were extracted (FIG. 38). The former neural circuit appropriately corresponds to the conventional auditory neural circuit, and the latter neural circuit appropriately corresponds to the emotional neural circuit that has its base at a deeper area of the brain and projects to the cerebral limbic system and cerebral cortex. In particular, the latter neural circuit corresponds well to the <life brain> that is responsible for biocontrol in accordance with <sensible brain>, which the inventors propose.

The above-mentioned effect of the sound that richly contains the ultra-high frequency component higher than the audible limit cannot be observed when only the ultra-high frequency components are presented. In addition, when only audible components are presented, the neural activity of these areas is rather suppressed. As described above, the measurement of local brain blood flow using PET provided more findings full of stimulation and implications than expected.

The auditory cortex, which was activated when music was presented, has been known classically for a long time as a part of the auditory system that processes sound. In the experiment of the present inventors, this part was activated when the audible range components were present, or in other words, when music was played there, regardless of whether or not the ultra-high frequency components were contained in the music. On the other hand, in the area included in the essential brain region that got activated only when the ultra-high frequency components were contained in the music, the neural activity was rather lower when music without the ultra-high frequency components was played. In short, these areas worked differently from the classical auditory system.

In the upper brainstem (mesencephalon) where activation was found by ultra-high frequency sounds, there is a concentration of neural cells, which work as a neural network center related to "pleasure and beauty response" and which are altogether called <compensation system>, and such network includes monoaminergic projections system, opioidergic neural system and others. They are closely related to the generation of pleasure, and play an important role in general emotional responses and adjustment. It is also known that, drugs, stimulants, and other psychotropic chemicals work on the monoaminergic system and the opioidergic system so as to realize their effect, and it is also known that they mainly function in the brainstem. Seeing the brain core network extracted in the experiment as a compensation system, it is very notable that the activation was found in an excellent proportion because the areas such activation was found in included the mesencephalon, which is the seat of the most basic biological emotion such as eating and sex, the frontal cingulated gyrus, which is the seat of positive feelings such as love and pleasure, and the prefrontal area, which is the seat of the most sophisticated emotions such as beauty and inspiration.

The thalamus is an important relay center for various information communications connecting the inner brain and the outside thereof, and almost all sensory information is processed through the same. In addition, it is also a part of cerebral limbic system, and is considered to be linked with emotion because cocaine and other psychotropic chemicals affect this area.

The hypothalamus is the supreme center of autonomic nervous system and at the same time directly controls the hypophysis cerebri, which controls the hormone system, and works in close coordination with immune system as the seat of activity to cope with environmental change to maintain the homeostasis of the internal environment of the body. At the same time, here are centers of various behaviors that are indispensable for life such as eating, drinking, body temperature, sleep, and sex gathered, and it is valued so much as to be called <life brain>.

Thus, the fact that sounds containing inaudible ultra-high frequency wave activated the essential brain region including the brainstem, thalamus, and hypothalamus strongly indicates the possibility that sound information including sound outside perceptible range as its important ingredient is related to feelings and emotions, and is also related to the activity of the brain nervous system, which is responsible for the core of the very life activity.

By the way, this activation of the essential brain region network discovered and reported by the inventors in 2000 and 2003, it has a high degree of common ground with the report by Zatore et al. that music is "the acceptance by the brain mechanism with responses resembling 'shivering'."

2. The PET experiment of the inventors aims at the following: electroencephalograms are concurrently measured in parallel and two indexes of the brain blood flow with high spatial resolution and the brain potential with high time resolution are intersected, so that reliability is enhanced and, also, potential response mechanism involving sounds outside perceptible range is floated. In this case, electroencephalogram data itself is referred to. Even under the conditions of PET measurement, alpha wave power was considerably increased only when "music containing ultra-high frequency components" was played. And in other conditions, that is "music without any ultra-high frequency component", "only inaudible ultra-high frequency components", or "only background noise no presentation of sounds", there was no increase in alpha wave power, supporting the previous findings of the inventors.

Figure 39:
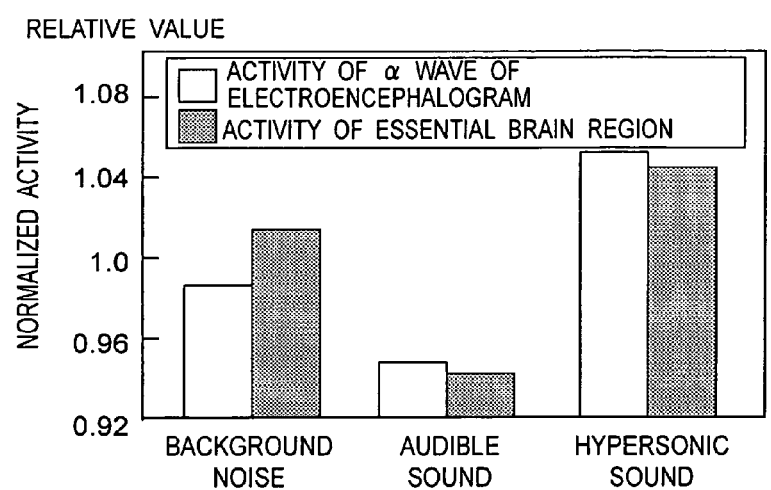
FIG. 39 is a chart showing that an activity of the essential brain region and that of activity of a wave of electroencephalogram are related to each other.

Further, the inventors looked for a part where <local brain blood flow> and <band-specific power of electroencephalogram> correlated. In this analysis, very valuable facts were found. First of all, a search for a part where the brain blood flow correlates with the alpha wave power of the electroencephalogram found that there was a significant positive correlation in the left thalamus. As the blood flow increases in this area, the power of the alpha wave increases. However, this relation existed regardless of the existence of music. Thus, it implies that the thalamus is also involved in the generation and adjustment of the alpha wave, and also that the activity of the alpha wave can be a good index of the activity of the thalamus, reflecting it in high correlation. In addition, this area is almost the same area as the area where the brain blood flow increased with the sound including ultra-high frequency wave. Further, the fluctuation of the second principal component, which was extracted by the principal component analysis of the brain blood flow data, goes in line with the alpha wave power (FIG. 39).

From these findings, a mechanism can be assumed where listening to sounds containing ultra-high frequency wave increases alpha wave. First of all, there is a general relation that alpha wave increase closely reflecting the increase of the blood flow in response to the state of activity of the essential brain region network centering the thalamus. On the other hand, there is a specific relation that listening to sounds containing high-frequency components increase the blood flow of the essential brain region including the thalamus. It can be inferred that combining the general relation and specific relation will activate the essential brain region network with the sounds containing ultra-high frequency wave, and it will be reflected on the power increase of alpha wave. That means the activity of alpha wave of the electroencephalogram can be used as an index of the activity of the essential brain region network in other experiments using various sensory input including visual information besides sound or aerial vibration.

The present inventors discovered biological response that highly unsteady sounds containing high-frequency wave above the audible range increase the alpha wave power of the electroencephalogram and activate the essential brain region including the brainstem and the thalamus. The inventors named this discovery <hypersonic effect> by combining psychological responses discovered alongside with the above. In addition, the sounds having this effect were named <hypersonic sound>. Further, the inventors released a detailed report of the study in the "Journal of Neurophysiology" an American physiology journal, in June, 2000. This report paper was ranked as one of the top 50 most-frequently-cited papers every month in succession for more than 2 years as of May, 2003, when this writing was drafted. So, it has kept drawing a lot of attention. Since around 2002, research groups other than the present inventors began full-fledged research to detect various phenomena of hypersonic effect using natural environmental sound and instrumental sound.

Next, the present inventors gained interesting and useful knowledge by considering the relation between listening to music and the activity of beta wave of the electroencephalogram and the blood flow in the same experiment, and released a report. First of all, when music was played, the beta wave power was statistically significantly increased compared to when there was no music. The beta wave is supposed to increase with the recognition activity of various kinds, and in this case, music my have made some kind of recognition activity more active within the brain.

A search for areas where the blood flow and beta wave potential are correlated found that several areas were found in the <premotor area> and the <cingulated gyrus> on both sides where the brain blood flow and the beta wave potential correlate regardless of whether there is music or not. In addition, there were areas in the <precuneus of parietal lobe> where correlation could be found specifically when there was music. This implies that there is a neural circuit that changes activity mode in accordance with input of continuously changing, non-steady sound such as music and, probably, natural environmental sound including forests and villages, and that the information processing mode of the brain was converted to the inherent, specific condition under the circumstance that the inventors recognized the existence of such music. The implications are important.

As one region of important means of estimating the active state of the brain, there is a method to measure the existence of physiological activity within bodily fluid. The target substances include a group of neurotransmitters and their related metabolism substances and a group of hormones that reflect the output of the brain activity. Immune activity may be a good index. These indexes that directly reflect the mutual relation between mind and body are closely linked to the understanding of the relation between the pathology of cities and the collapse of the urban information environment as well as other practical problems related to the restoration of cities. Accordingly, they are important.

Figure 42:
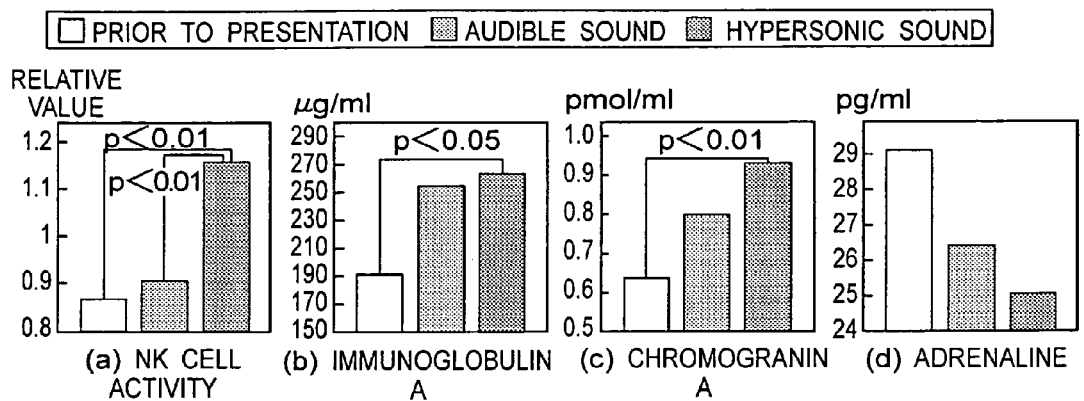
FIG. 42(a) is a graph illustrating that an immune activity and a stress resistant activity are enhanced if the hypersonic sound is heard, showing a relative value of an NK cell activity.
FIG. 42(b) is a graph showing an absolute value of an immunoglobulin A which is obtained by the hypersonic sound or the like as shown in FIG. 42(a)
FIG. 42(c) is a graph showing an absolute value of a chromogranin A which is obtained by the hypersonic sound or the like, and FIG. 42(d) is a graph showing an absolute value of an adrenaline which is obtained by the hypersonic sound or the like as shown in FIG. 42(a).

This kind of approach will be the important tasks for the inventors in the future. However, even at present, the inventors had progress in exploratory research and have begun to gain important findings. For an example, in an experiment where Gamelan music "Gambang Kuta", which contains ultra-high frequency wave, was played repeatedly for 40 minutes and also "Gambang Kuta" was played in the same way but with high-frequency wave cut out, the hormone activity and immune activity were compared. As a result, an important finding, it can't miss, were obtained, which compared to the audible range sounds with high-frequency cut out, the activity of NK cells, which are the main resistance force against cancer cells, increased statistically significantly after listening to the hypersonic sound containing high-frequency wave. This is an important finding. In addition, immunoglobulin A, which is contained in saliva and shows the strength of the biological defense activity and comfortableness, and chromogranins A, which shows the strength of psychological stress-coping activity, both increased statistically significantly, and the blood adrenaline level, which is a stress index, decreased. All these results in support that the ultra-high frequency wave had positive effect on the entire body (FIG. 42).

3. The hypersonic effect leads the bodies of the inventors to health through the activation of the essential brain region, physiologically speaking. In addition, with respect to sensibility and sensitivity, it fills people with responses to pleasure and beauty. This hypersonic effect, which can be called elixir for healthy and comfortable life, is surely being generated uninterruptedly in the sound environment of rainforests and the traditional festival space.

In the effort of the inventors to discover the hypersonic effect, the sound of Bali's Gamelan music played a decisive role with its enormous brain-stimulating effect. Gamelan is an ensemble of bronze percussions with scales, and is played throughout the Sunda archipelago. Gamelan has its origin in the ancient Dongson civilization. It is estimated that Gamelan started orchestration earlier than the Western wind and string music. Gamelan has been developed and sophisticated until now. As described above, the inventors chose instrumental tune "Gambang Kuta," which has been handed down in Bali and is played in an ensemble called <Semarpegulingan>, as the presentation music source, among enormous amount of Gamelan music.

As of the beginning of the 21st century, there are about 15 styles of Gamelan in Bali. Among the main styles, three are really conspicuous: <Gamelan Gong Gede>, which was transferred from courts of Jog Jakarta, Solo, and others of Middle Java areas together with Hindu religion; <Gamelan, Semarpegulingan>, which was the environment music embracing the residence of Bali's royal family and at the same time used as the music to accompany dancing, characterized by its gorgeous and still graceful and shiny tone; and <Gamelan Gong Kebyar>, which was developed as late as the beginning of the 20th century, and spread all over the island as the music source for festivals of farming village communities.

Semarpegulingan, in particular, is the style of court music, which played an important role in embracing the sleep of royal families with the feeling of safety and ease and healing effect using the elegant tone. Semarpegulingan is also the name of the set of instruments. This type of instrument is required to have sweet and graceful tone although volume may be conservative. To produce such a tone, a lot of precious metal is used for the base metal as the material of instruments, and utmost care is taken to cast them. When a set of instruments are successful in producing extraordinarily sweet and graceful tone and become known to people, the fame will spread all over Bali Island.

Figure 37:
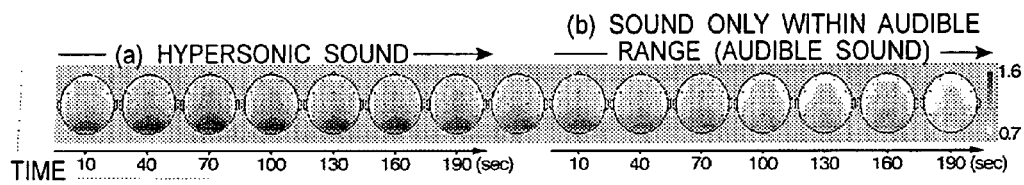
FIG. 37 is a view showing physiological, psychological and behavioral reactions of a hypersonic sound including a hypersonic effect ultra high frequency, illustrating that the hypersonic sound including a super-high frequency increases a wave of electroencephalogram with a time difference.

The present inventors went measured the spectra of various Gamelan sound in the field and was surprised that the more famous and prestigious the instrument set was, the more ultra-high frequency components above the upper limit of audible range were contained, and that there were almost no exceptions in that tendency. It was simply amazing. The several sets at the top of all produced sweet and gorgeous to the ear. However, the spectra spread to the ultra-high-frequency area almost exceeding 100 kHz while preserving the strong power (FIGS. 33 and 34). Further, the noninvasive brain function measurement experiment by the inventors revealed that the tone activate the brain core and heal both body and mind (FIGS. 37 and 42).

In short, the cutting-edge technology revealed, transcending space and time, that the people of Bali Island who nurtured Gamelan Semarpegulingan can read the ultra-high frequency aerial vibration from Gamelan sound, as if they were equipped with an ultra-broad band automatic FFT analyzer or brain function measurement equipment, utilize the effect cleverly, and take advantage of their experience to cast new better instruments. The inventors were really shocked to meet the traditional knowing that nurtures Gamelan of Bali Island, which is in no way inferior to Japanese Shakuhachi, and could not help paying respect to the sound culture there.

The Bali people's traditional sensitivity to the ultra-high frequency sound outside the perceptible range makes a good match with Japanese sound culture, which has nurtured Shakuhachi as the cultural codes to grasp the implicit, tacit tone characterized by the complex-dimensions, enormous density, and quick change. People of Bali Island have known since the ancient times that the existence of the ultra-high frequency components not only makes tones more pleasant and beautiful, but also leads, through the exposure to the unusually strengthened power and through activity change of mind and body (in actual, it is the brain) to an unusual mode, eventually to a <trance> accompanied by a change in consciousness. Due to the knowledge, people of Bali Island have developed procedures to deliberately induce a collective trance among the general public, that is the constituents of the community, and operate it to suit the objective, and such procedures have been handed down as cultural codes so as to sublime the time-space of festivals and rituals to a gorgeous euphoria.

Bali Island is a volcanic island and its slopes are covered with beautiful terraced fields. The society of Bali, a rice farming community, has an elaborate irrigation mechanism to fill the fields with water, and the biggest threat to it is nothing but a water dispute caused by selfishly drawing water to a certain field. Accordingly, the most prioritized task is to establish the supremacy of the water supply system that also requires suppression of selfishness. It is now being unveiled that the "Gods and Festivals" of Bali is a mechanism to neutralize the permanent conflict-prone pressure caused by the social structure, reduce stress, and materialize the "Paradise on Earth". Only with the help of ecstasy, trance, and catharsis induced by the pleasure of powerful festivals that transcend the daily life can the farming community of Bali establish the steady unity. The development of festivals is nothing but the major strategy for survival for Bali Islanders. Clifford Geertz, an anthropologist, was astonished at the "multi-dimensional groupism" covering all the villages of Bali Island, and that made the anthropologist have an idea of "theater nation". However, it should never be overlooked that behind the multi-dimensional groupism is another structure deeply related to the water supply control and festivals, which Geertz could not see exactly. That's the value system of "the predominance of ecosystem over individuals" underlying the cosmology of Bali Island, which has a sharp contrast with the modern Western individualism, and the pleasure mechanism including ecstasy and trance that induce miraculous groupism by controlling the brain functions.

Any one would be surprised at the fact that the sounds containing powerful ultra-high frequency wave have been utilized as a key to release pleasure and trance, just as if cutting-edge brain science had been applied, have built an ecological social system transcending individuals, and have contributed to the stabilization and increased comfort of the same. The typical example is a theatrical ritual called <charonarang> conducted on "odalan" (the anniversary of the temple foundation every 210 days on the religious calendar "uku" unique to Bali Island) of Pra Daran (temple of the dead). Any independent village has built a Pra Daran. The religious ritual starts with a classical drama, but on the way, unspecified players and audience get into a consciousness transformation mode, and a group of people altogether get into a strong trance, which is so strong that some lose consciousness, and it finally ends in chaos. It is nothing but a play for souls that sublime in one unity with gods, ecosystem and the community in a trance.

Figure 43:
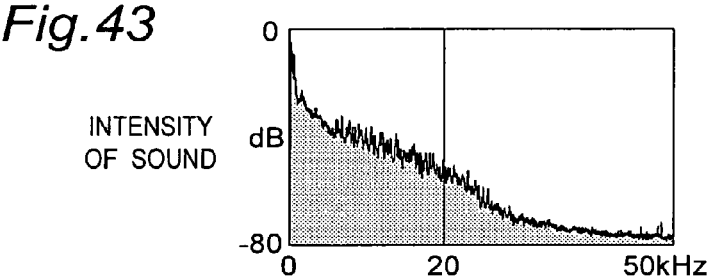
FIG. 43 is a spectral chart showing a transformation of a consciousness of a performer of a mysterious dedicatory play "Charonalan" in Bali Island and a physiological change, illustrating a super-high frequency component which is rich in an appended music tectecan sound.

In order to induce this physiological/psychological state, the high-frequency wave made from Gamelan and <tektekan (a musical instrument and its playing method, made of a one joint big bamboo with a slit on it, and this is beaten ferociously with sticks to make sound)> are employed as an indispensable element. As for tektekan, several dozens of men, each having this instrument, sit on the ground tightly packed, with naked upper bodies. They beat the instrument ferociously in a 16-beat rhythm with a combination of sounds, to accompany dramas. These players are exposed to the high-frequency wave from each other's instrument (FIG. 43), and many of them get into an enormous trance.

Figure 44:
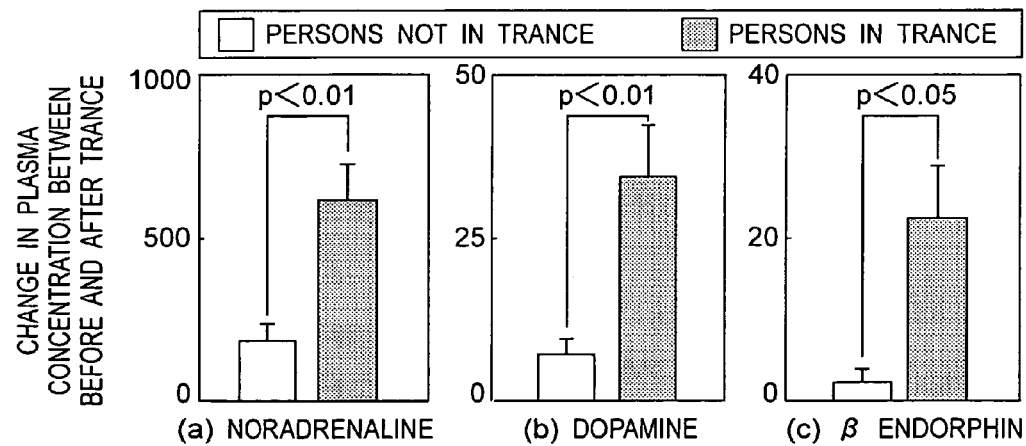
FIG. 44(a) is a graph showing a change in plasma concentration of a noradrenaline in plasma concentration of a neural active matter in a blood of the performer of FIG. 43.
FIG. 44(b) is a graph showing a change in plasma concentration of a dopamine in the density of the neural active matter in the blood of the performer of FIG. 43.
FIG. 44(c) is a graph showing a change in plasma concentration of a β endorphin in the density of the neural active matter in the blood of the performer of FIG. 43.
Figure 48:
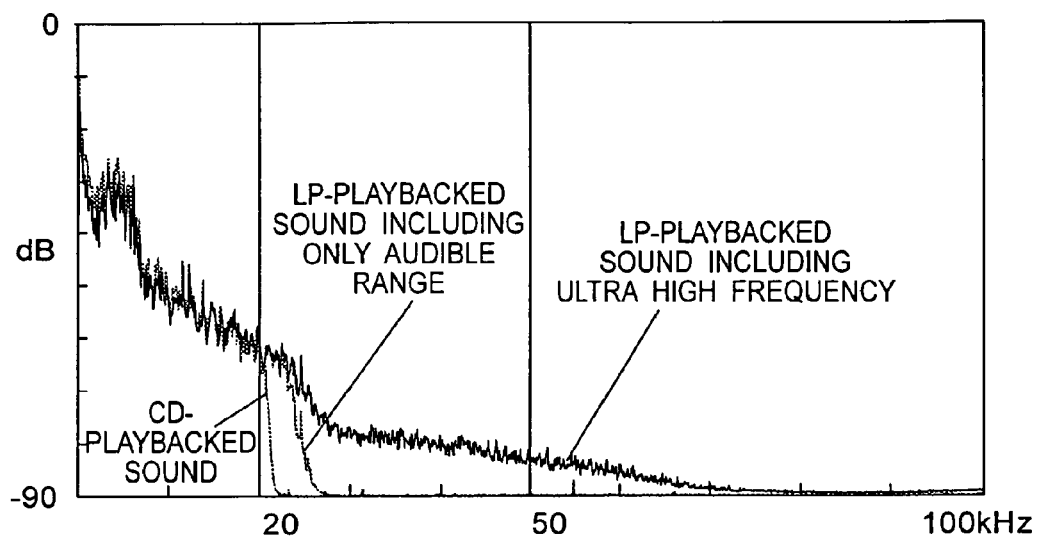
FIG. 48 is a spectral chart showing that an LP playback sound including an ultra high frequency is gentler or more comfortable for a human body and a mind than a CD playback sound, illustrating a frequency power spectrum of a sound used in an experiment.
Figure 49:
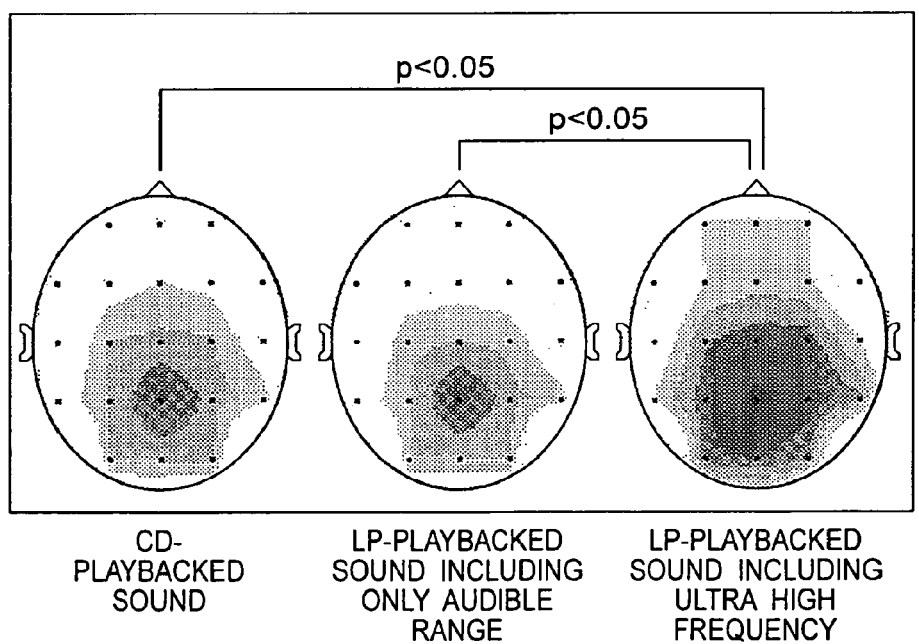
FIG. 49 is a sectional view showing a position of the generation of the a wave of the electroencephalogram indicating that the LP playback sound including an ultra high frequency increases the a wave of the electroencephalogram when the sound of FIG. 48 is used.
Figure 50:
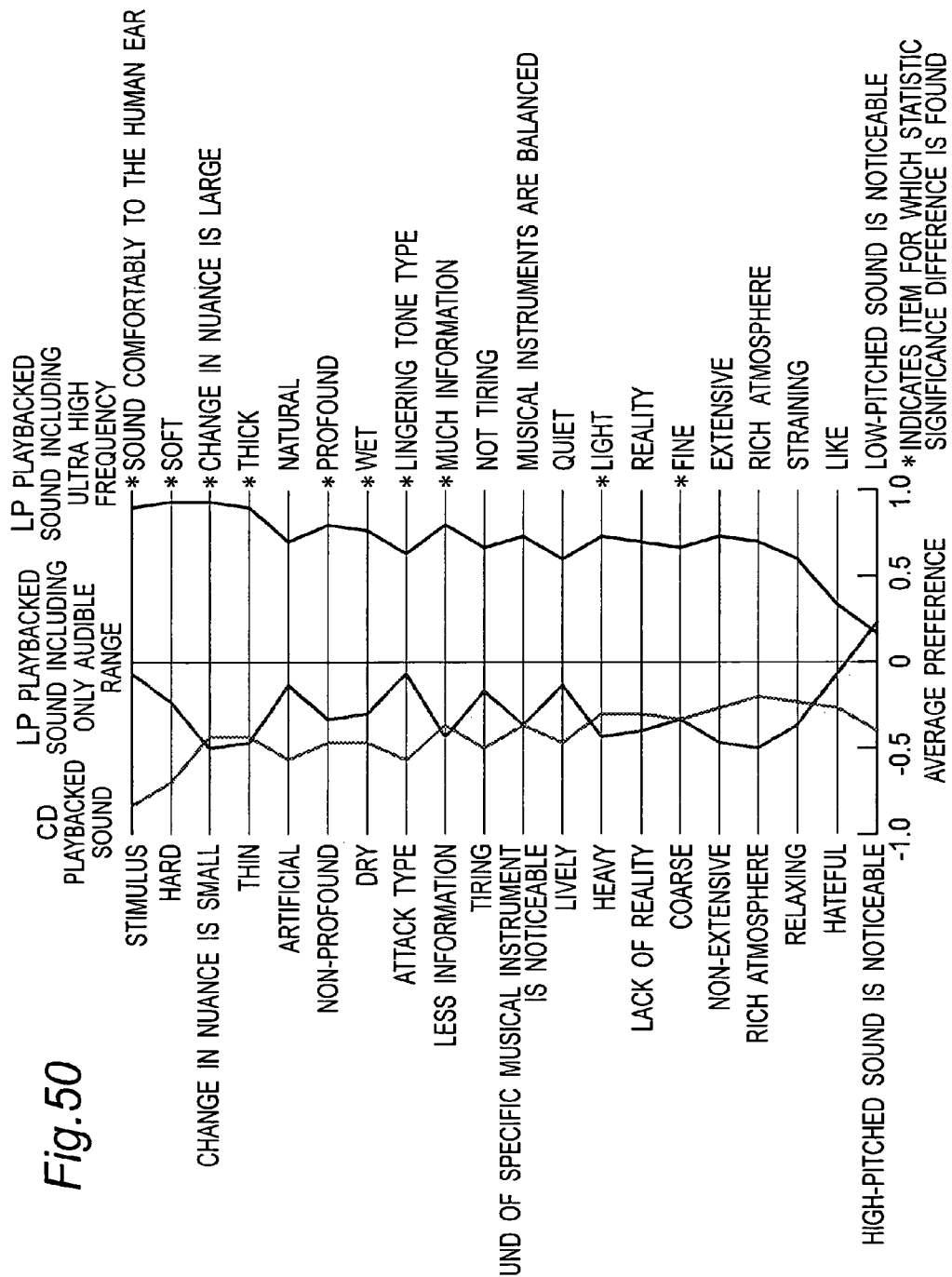
FIG. 50 is a chart showing results of a measurement indicating that the LP playback sound including the ultra high frequency is wonderful and comfortable when the sound of FIG. 48 is used.

The present inventors measured the physiological state of the players from before the ceremony to after it using electroencephalogram (wireless measurement using telemetry) and blood level of neuroactive substances as the indexes, and tracked them. After more than ten years, the measurement was done successfully, probably for the first time in history. From a series of experiments, it was found that the players of charonarang change their brain activity to a pleasure mode, which is very different from the usual state. Players who are in a trace have a much more considerable difference, with statistically significant differences in the indexes of brain alpha waves, theta waves, and neuroactive substances, beta endorphin, dopamine, noradrenalin (FIGS. 44 and 45).

The trance of Bali Island has a transmission structure like a chain reaction. When the inside of the brain has accumulated rich ceremonial, artistic information and has critical conditions ready for a trance, reactions progress rapidly with just a trigger from some stimulation. The first trigger is some one who gets into a trance, and this is a change in situation, and then with this trigger, people began to jump repeatedly, and get into collective trance. In Bali Island, this kind of chain reaction can be seen as a common pattern of collective trance among several performances including the ceremony charonarang. Above all, the player of <lion mask> of the lion mask disguise called "barong", which is manipulated by two men, is specifically the most likely trigger of the trance.

In first place, throughout Asia and Africa, it is a common phenomenon that players with masks on are more likely to get into a trance, with many examples available. Limited vision and breathing, violent actions, exposure to high-frequency wave can be cited as the contributing factors, and it is notable that these are things that directly have physiological effect. Studying whether various disguise arts have trance-inducing factors revealed that barong in Bali Island is one of the performances that have the most factors.

It can be inferred that the people in Bali had learned by experience the mechanism of a trance to a great degree and based on the knowledge, they positioned the player of the barong as the trance trigger. A close observation revealed that there existed traditional knowledge that devised to concentrate every trance-inducing input on this player to strengthen the trance-inducing power so that collective trance can be excited most effectively.

Above all, the inference that they know the effect of ultra-high frequency sound on the brain, and therefore they have used it cleverly can be supported to an almost undeniable level by an interesting example. That is the bells on the barong mask. They are heavy and strong bells carved out from bronze and brass ingot, and about a dozen are clustered, generating gorgeous sharp sound with many ultra-high frequency components. These bells are mounted inside the lion mask, and audience cannot see them. Even the sound cannot be heard in a garden full of Gamelan and tektekan sounds, except for the lion mask player. In short, there is almost no possibility of these bells to have any effect on other players or the audience, and therefore they are not functioning as a rendition. However, the lion mask player keeps exposed to the powerful ultra-high frequency sounds generated by the bells inside a kind of container covering the naked upper body. In short, the bells are nothing but a device that provides ultra-high frequency sounds solely for the lion mask player, and the sound source is set at a place where it can exercise the trance-inducing effect most powerfully. An experiment of wearing that mask reveals that the impact of the powerful bells is really extraordinary.

Focusing on this point, the present inventors tried to measure the frequency distribution of the sound the player is exposed to inside the cavity of the baron. The barong mask that is actually used in Bali (bells are mounted inside) was swung in the same way as is usually done there, and a microphone was positioned at around the same position as the face of the player to record the sound. The recorded signals were analyzed with a broad band FFT analyzer. As a result, far above the upper limit of the audible range of 20 kHz, high-frequency up to 80 kHz were contained quite considerably. Further, when the upper and lower teeth were hit against each other, as is often done in the Barong performance, summing up the sounds of the bells and the wood clapping resulted in the spectra upper limit reaching near 100 kHz.

This demonstrates that the player is exposed to direct attack of impact sounds containing ultra-high frequency at point-blank range. The hypersonic effect induced by this sound must be a big factor in inducing the physiological/psychological state into a trance. The people of Bali Island have found the bio-scientific mechanism from daily experience and have used it rationally, and the intuitive knowing and insight knowing of the people have attained an enormous level.

4. The human society recognized many achievements including Eiffel Tower to space rockets as explicit results of technology, tried to incorporate it into the socially-accepted idea, and made it known to everybody through systematic education. By the way, although there may be a wide difference, the villagers of Bali has built up a system of festivals and pleasure from them that contribute to water supply control, and therefore, the achievement of villagers of Bali must be a significant milestone that compares favorably with the explicit achievements of modern technological civilization. Or rather, it is worthy of attention now as a good index of a non-verbal brain's thought mechanism, which works complexly and sophisticatedly transcending the thought mechanism of the verbal brain module, which in turn led to the explicit results of modern technological civilization. The modern civilization should revive the lost ability to read these things, and restore it to the level that allows appropriate valuation of and response to the non-verbal brain.

The FFT power spectra of the Gamelan sound of Bali and the ME spectral array of the sound of Japanese Shakuhachi demonstrated the information structure characterized by the complex-dimensionality, enormous density, and quick change on the artificial sound space. That is reminiscent of the high-density and complexity of the environment sound of rainforest that nurtured the human genes. In traditional cultures that nurture Gamelan and Shakuhachi, the nonverbal brain functions that create, communicate, accept, and respond to the information structure as described above are developed naturally. Moreover, they are prevalent all over the society just as a property of the society without any specialized procedures such as specialization and manifest themselves.

What the inventors glimpsed using only the two examples of Shakuhachi and Gamelan must be very limited compared to the overall nonverbal brain functions. However, admitting that, the inventors who have just been awakened think that only the limited findings look like a mountain high and soaring. There is a need to look for a good and powerful way to understand how to restore the recognition of this activity, and how to reinstate the same.

<3-3-3> "Two-Dimensional Perception Model" that Transforms a Hypothesis into a Theory 1. The series of experiments of the inventors revealed that sounds including the inaudible ultra high frequency range that has been placed out of scope of the study of contemporary acoustics because of its characteristics as imperceptible to the senses have unignorable effects to activation of the human body. However, this issue starts from the domain of, as it were, psychological reactions of perceptibility and sensitivity, such as perceptional difference in the quality of sound between a long-playing record and a compact disc and inferior quality of sound of digital apparatus for studio after removing ultra high-frequency range. Oohashi, indeed, started from such perceptional difference of sounds. Such origin cannot be neglected. The opportunity and tools to solve such problem have been derived from measurement data of activity of the α wave of electroencephalogram as the largest basis of and contributor for the inventors' physiological study (FIG. 37).

The method of paired comparison that analyzes short-term memory of a sound, has been served as an authoritative method for assessing sound quality. The inventors learned that the authoritative method might have a decisive error from the phenomenon of time course asymmetry shown in the change of activity of the α wave of the electroencephalogram, or the delay and retention in reactions against ultrasonic sound. The power of the α wave of the electroencephalogram observed in the experiments made a gradual increase after starting emitting sounds including ultra high-frequency to reach to a <high plateau>, and after the sound was switched to only audible range, the plateau maintained for approximately 100 seconds and then abruptly decreased to a <low plateau>. This suggests that an activation level of certain nerve activities, reflected by the activity of the α wave of the electroencephalogram is dramatically enhanced by not a simple mechanism of the sound containing ultra high frequency, which remains strongly for a long time after the presentation of the sound stops.

The power of the α wave depicts the comprehensive conditions of ever-changing brain activation in very high time resolution. There are no elements supporting that a significant change of nerve activities reflected by the difference of the α wave activity level has nothing to do with the brain activation that senses the sound quality difference. In other words, it is certain that there is a change in the conditions of internal brain between ultrasonic sound mode containing ultra high frequency is heard and high-cut sound mode containing only an audible range is heard. No one can say that a hearer does not sense two different sounds as the same sounds or two same sounds as different ones, based on such differences. It cannot be negated that such change and retention in brain activation can cause an impact or disruption on the recognition and assessment of the next sounds.

Conventional experiments of acoustic-psychology employ a paired comparison method that is highly dependent on short-term retention of sounds. A subject of the paired comparison method is given two sounds and asked if the two sounds are the same or different. It is said that subtle difference of sound quality can more easily be sensed when two sounds is given for a short time of period in a short interval. For this reason, International Radio Consultative Committee (CCIR) once organized the international standard for electronic communication (current International Telecommunications Union-Radio communications, ITU-R) recommends that the sound samples used for the paired comparison method should continue less than 15 to 20 seconds, and the interval be 0.5 to 1 second, based on the limit of short-time memory of humans. Major experiments done in the past presented musical sound for 10 seconds or so, and synthesized sounds for less than 1 second with a shortest possible integral.

Indeed, it may be an effective method to make a judgment easier that two different events are made small in length and in distance and presented side by side when the events are compared. However, our measurement results of the electroencephalogram revealed that a presentation of sounds containing ultra high-frequency changes the conditions or mode of internal brain and the sounds retains in the brain for 100 seconds after cessation of the input. Suppose that the shift of such a brain mode would affect how sounds are sensed. Under such condition, the sounds of several to ten seconds are presented by switching one sound to another and vice versa, a reaction of the present sound is accumulated on that of the previous sound with a certain time lag, causing the psychological response against the current sound is mixed with the response against various sounds previously presented. So as to cancel such hysteresis, the duration of each sound stimulant should be made more than 100 seconds or the maximum retention period for brain activation mode led by an ultra high-frequency sound. The problem here is a significant decrease in accuracy and sensitivity of detection because such method cannot rely on the short-term retention performance of brain. This means that the two sounds to be presented should have a significant difference in sound quality beyond the level of such short-term retention performance of brain. Standing upon such preconditions, the inventors dared to break the conventional practice to use a whole music of Gambung Kuta that continues for approximately 200 seconds for our paired sound quality assessment test. In the test, the modified version of paired comparison method of Scheffe was employed that provides comparison of sound quality by a small number of presentation intervals of sounds.

Figure 40:
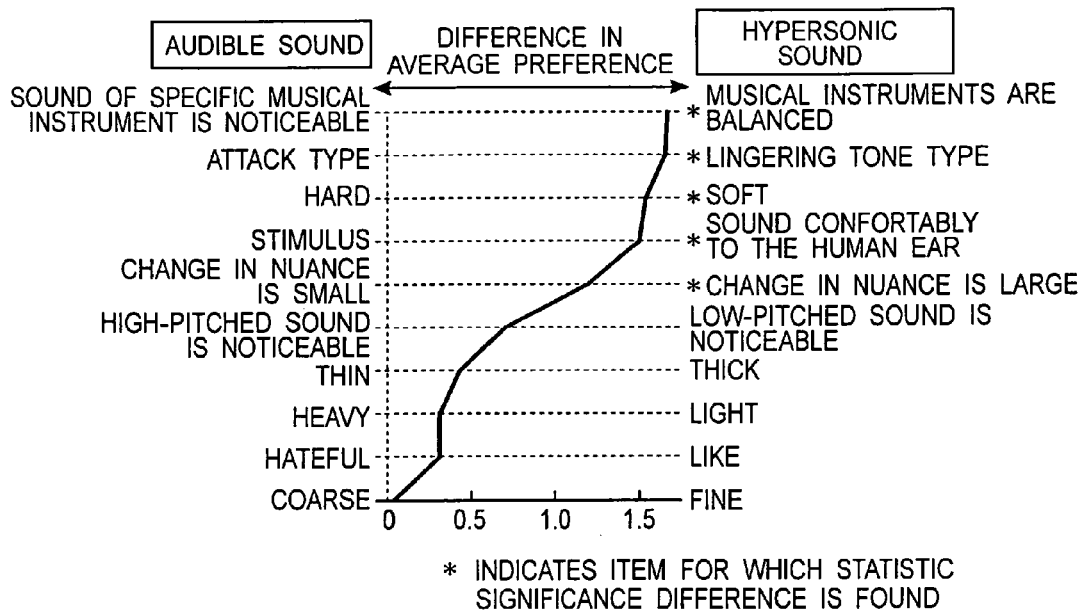
FIG. 40 is a chart showing that the hypersonic sound can be heard wonderfully and comfortably.

Comparing with the conventional paired comparison method, this method normally requires recognition of significant quality differences to obtain clear results. However, after practicing it, a significant difference of assessment point between sounds including ultra high-frequency and those containing only audible range in five out of 10 assessment scales (FIG. 40). At the same time, sounds containing inaudible ultra high frequency are heard and accepted more comfortable and more ear-pleasing than sounds not containing inaudible ultra high frequency. This can be said that the element of ultra high frequency serves the detectable difference of sound quality is certified by the academically orthodox procedure, and we have now a chance to conquer the limit that has existed in acoustic-psychology.

The results of the present experiment were effective enough to expose that the pair comparison method by presenting sounds for a short time that have been formalized and utilized as an international standard (for example, ITU-R) has latent unignorable inconsistency, because, while its focus is mainly on the short-time memory of the stimulant sounds not lost, the method does not mostly support itself when the retention of the stimulant sounds is beyond the duration of presenting them.

Thus, a method was sought to explore the limit of the pair comparison method for presenting sounds for short time of period, which is universally used as an international standard. Gamelan music was used as a sound sample to make <a sample pair> which consisted of a repetition of 12-second typical phrase presented in a 3 seconds' interval. A session of a sample consisted of 20 pairs of sound presentation sequence divided into two 10-pair sessions, with a pose of the length recommended by the official method. One 10-pair session included ultra high-frequency sounds and audible range in a proportion of 3 to 1, while the other session had their proportions of 1 to 3. Then, for each session, the presentation sequence was shuffled and an experiment was done as per the official method.

The results were quite instructive. In terms of the experiment as a whole, there were no significant difference observed between the distribution of correct answers given actually and those given by chance. This is the same result as the past authoritative study indicated that the difference of sound quality between those having ultra high-frequency elements and those not having ultra high frequency was not detected. However, in terms of sub-sessions, sound quality differences of those having more audible range distinguished were statistically significant ($p > 0.05$). On the other hand, the sub-sessions having more ultra high-frequency sounds, the proportion of incorrect answers given were statistically significant (p>0.005), which is quite unusual. The two data of opposite tendency are offset with each other, and the experiment as a whole showed that the sound quality difference could not be detected.

When examining the distribution of incorrect answers given in the session having more ultra high-frequency sounds, the case of "the sound including ultra high-frequency sounds incorrectly sensed as that having only audible range" was not significant, but in the case of "the sound including audible sound incorrectly sensed as that having ultra high-frequency sounds", the distribution of incorrect answers given were more significant than the case of correct answers given by chance (p>0.05). This supports statistically that when audible range are presented while sounds including ultra high-frequency sounds are frequently shown, audible range are likely to be incorrectly sensed as they have ultra high-frequency sounds. The results supports that the inventors' working hypothesis, ultrasonic effects remain after the presentation of sounds, is correct. The reason why the effects of high frequency beyond the audible range have not been detected by the conventional orthodox method is that the psychological model used by the orthodox method could be so simple against the complexity of brain function, especially time asymmetry.

2. Detection of ultrasonic effects is not an easy task, because it can easily disappear however small the samples are cut and however hard one tries to listen to sense it correctly. This is a typical example of what Michael Polanyi an advocator of the theory of tacit knowledge said "it explains how hardly the defenseless clearness can destroy the understanding of the inventors. Thorough investigation of various detailed items as to the comprehensive existence will wipe off the meaning and the idea of the inventors on its existence will be destroyed". However, when hearing the sounds nonchalantly as the nature goes without any preoccupation, a clear and distinguishable difference between the audible range and sounds containing the ultra high-frequency suddenly appears as if it were a relief picture. The trend is, to be quite mysterious, tend to be clearly observed with a course of loosening the experiment conditions and giving sounds for a longer time.

Let us go back to the original position that made the inventors aware of the existence of insensible sounds, the sound quality difference between "a long-playing record and a compact disc". The inventors possess a long-playing record and a compact disc of "Ecophony Rinne" by Geinoh Yamashirogumi that were cut from the original analog sound master. The masterpiece made the inventors to have awareness to insensible sounds. The inventors tried to utilize the music fully.

First of all, a comparison was made to the signals contained in a long-playing record and a compact disc. The frequency range of the sound signals encoded in pulse code modulation is contained in 22.05 kHz or below or the standard of PCM. The replaying signal of a long-playing record is not so simple. While the response of a phonograph needle is not good to regenerate the frequency as it traces the grooves of a long-playing record, the frequency regenerated cannot reach 20 kHz, some good quality needles can response to 100 kHz or larger frequency. A vibrating body consisting of a cantilever with a diamond chip needle, a fine coil, a magnet and a damper mounted onto the cantilever is itself a "musical instrument" that is manufactured using a special technique to generate sounds as beautiful as possible. In fact, the improvement in sound quality experienced by changing a low quality needle with a high quality one can be larger than the sound quality difference between a Stradivarius and a Guarnerius. FIG. 46 shows a FFT spectrum of sounds of the same phrases of "Ecophony Rinne" of a long-playing record, using three different types of phonographic needle, representing 1980s when the music was first released, to compare the replay signal difference between the three types of needles. For all the three needles, the performance of reproducing sound is significantly better than a compact disc version of "Ecophony Rinne" of the same phrases, reaching beyond the ultra high-frequency range, conspicuously indicating the difference of sound generation performance of the three needles. Next, the needle that showed the best response to the highest frequency range was used to replay the second movement of Ecophony Rinne, in which a bell called Gentrak used in Bali Gamelan is played, and the FFT spectrum was taken. The needle reproduced the frequency of 100 kHz or above (FIG. 47).

Next, using the same long-playing record, a part containing sounds of folk instruments and environmental sounds of a tropical rainforest was replayed using the best-response needle used above. The analog signal was then digitalized by high-speed sampling one-bit quantization method to use it as an experimental sound source. The 160-seconds source was then processed to make three sound samples; sounds having ultra high-frequency, those having only audible range (its power spectrum being almost the same as that of a compact disc), and master sound recorded in a compact disc. Using these three samples, a physiological test of the $\alpha$ wave of the electroencephalogram and a psychological test of the paired comparison method of Scheffe were conducted.

The physiological test result showed that the $\alpha$ wave power of electroencephalogram surged significantly after listening to the sounds containing ultra high-frequency of a long-playing record, while it decreased when listening only to the audible range of a long-playing record and a compact disc sound. The psychological test showed a significant difference of impression in 14 pairs of evaluation words for audible long-play sounds and compact disc sounds. The sounds with ultra high frequency were heard more comfortably. Between the long-play sounds having ultra high frequency and the compact disc sounds, there were significant difference in 7 evaluation items, and 6 out of the 7 evaluation items were shared by the compact disc sounds and the long-play sounds with only audible range. There were no significant difference in sound quality between the long-play sounds with only audible range and the compact disc sounds.

Both the physiological and psychological tests, the comparison was made between the sounds containing ultra high-frequency against long-play sounds with only audible range, and compact disc sounds. In other words, the clear difference is shown between the sounds with ultra high frequency and those without any ultra high frequency. On the other hand, the sound quality difference is not likely to be so conspicuous between the long-play sound with only audible range and compact disc sounds.

These experiments showed that there is an essential difference physiologically and psychologically between long-play sounds and compact disc sounds and suggests in a quite straightforward manner that the major cause of such difference is governed by information outside of sensible ranges or the existence or non-existence of ultra high-frequency elements.

3. As discussed so far, the ultra high-frequency inaudible elements tell a lot to us more eloquently though they are outside of the audible range. If so, humans who receive such messages should naturally give an action response against such physiological and psychological reaction drawn by such elements. The next experiment tries to explore this.

In addition to Gamelan music, a hypersonic musical box was designed that generates rich sounds containing ultra high frequency. For this purpose, a prototype musical box was created jointly with Sankyo Seiki Manufacturing Co., Ltd. which has unparalleled musical box development technology to make the sounds as additional sound source. From these sources, samples having ultra high frequency and having audible sounds only were made. The samples were presented to subjects without identifying one from another. The subjects controlled the volume of the amplifier using a remote controller, to the sound level most comfortable to them, without knowing the sound level. (The preliminary inspection confirmed in advance that the full-range and high-cut sounds had a sound quality difference within the ignorable ranges of ±0.1 dB under the same output power of the audible range.)

Figure 41:
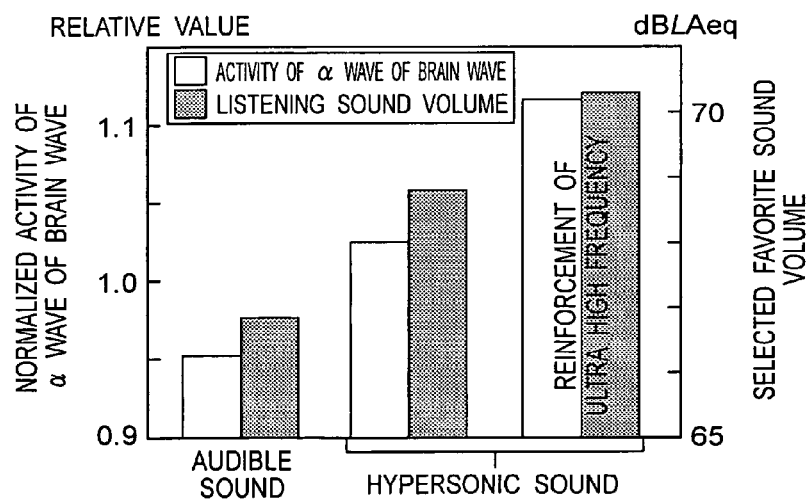
FIG. 41 is a chart showing that the hypersonic sound is heard in a large volume and enhances the activity of a wave of electroencephalogram.

The sound volumes generated were measured as an equivalent noise level ($dBL_{Aeq}$) using an integrating sound level meter and the data of multiple subjects were statistically analyzed. As a result, whether it was Gamelan or musical box, the subjects unconsciously and voluntarily controlled the sound volume larger by 0.5 to 2 dB for sounds containing ultra high frequency than those containing only audible range, which was statistically significant. In addition, appropriate reinforcement of ultra high frequency, for example, by +6 dB caused the listening level up additional 1 dB or above, and their α wave of electroencephalogram grew in proportion to the strength of such ultra high frequency (FIG. 41).

The significance of the present experiment aiming at detecting and comparing the <optimum listening level> lies in that it can examine how humans will respond to and behave against an acoustic environment containing insensible elements but sought unconsciously by them, and that eliminating such elements in a form of model in a laboratory. Especially, the sound structure with ultra high frequency components predominance showing better likability is close to the environmental sounds of tropical rainforest that humans originally have had, and that of less sensitive sounds with only audible range is closer to the environmental sounds of urban area as a nest of the pathology of the modern and contemporary civilization. This is worth noting.

4. The hypersonic effects have many characteristics peculiar to them, which cannot be dealt under the existing framework of acoustics and acoustic physiology. For humans, sounds containing ultra high-frequency air vibration elements that are inaudible to humans hear more comfortably for humans than those not having such elements. The inventors extracted high-frequency components of 14 kHz or above, 18 kHz or above and 22 kHz or above from the Gamelan sound used for the experiment, and checked whether or not 25 subjects were able to sense them. As a result, 22 out of 25 subjects sensed the sound of 14 kHz or above, and 15 sensed the sound of 18 kHz or above. However, none was able to sense the sound of 22 kHz or above, which is experimentally presented by the inventors.

Even with this fact, whether or not a sound has high frequency component makes sound quality heard differently. The α wave power of electroencephalogram is reinforced, but all the reactions against it are accompanied by time lags and retention. Such effects do not appear when only a high frequency component exists, but appear when the component coexists with audible sounds. In parallel with this is a surge of activation of the area of deep inside of brain belonging to brainstem and thalami having no relationship with acoustic sense, while no significant change is observed to nerve domains that is directly related to the same. Such phenomenon has never been reported so far, and there are no established knowledge and theories such as acoustics and auditory physiology, that can rationally explain the same. So as to explain consistently the overall picture of such hypersonic effects, a new model that has not been existed so far should be established.

When the issue is restricted to psychological reaction, there is a theory called "a non-linear distortion theory" as a similar phenomenon. This theory argues that, in the case of high-frequency component constructed in a circuit with a filter and a direct circuit, a sound may be heard differently due to the difference of non-linear distortion that is unrelated to the composition of such a component. The theory has a certain raison d'etre in the framework of acoustics as one of the persuasive explanation for such phenomenon. Unfortunately, the bi-channel replay system used by the inventors is so designed that such phenomenon cannot be shown; it cannot be a scope of such theory. In addition, there are no means to explain such significant time lags and retention, which is unusual under the nerve transmission system of physiological response against hypersonic sounds.

It is extremely difficult to explain the phenomenon discovered by the inventors consistently and without any contradiction using the framework of existing knowledge and theories. It is necessary to construct a robust model by removing such framework and securing broader materials and direction of developing thinking.

So as to explain the mechanism of hypersonic effects, the inventors tried to construct a model with recalibrating the knowledge structure as flexible as possible. In the course of the efforts, a concept of "two dimensional sensory model", which can explain such a unique phenomenon without any major contradiction, based on a completely new idea of "the response of humans against air vibration has a two-dimensional structure" was invented.

The first dimension constructing the model is explicit; it is a known auditory reaction against the air vibration components of 20 Hz to 20 kHz audible frequency range. The audible frequency range is treated by a conventional auditory nerve system, and may act as a <message carrier>. The second dimension is tacit; it is a reaction against ultra high-frequency component probably consisting of 20 kHz as the lower limit and 100 kHz or more as the upper limit. The initial reaction caused directly to a human body by this component is transmitted to the central nerve system through a certain path, and activates brainstem, thalami, hypothalamic area and other brain core parts including reward system. In other words, the inventors think that the ultra high-frequency component changes the internal state of brain, and that it acts as a <modulator> that makes the response induce pleasure or lead to the direction of alleviating negative stimulation.

Figure 51:
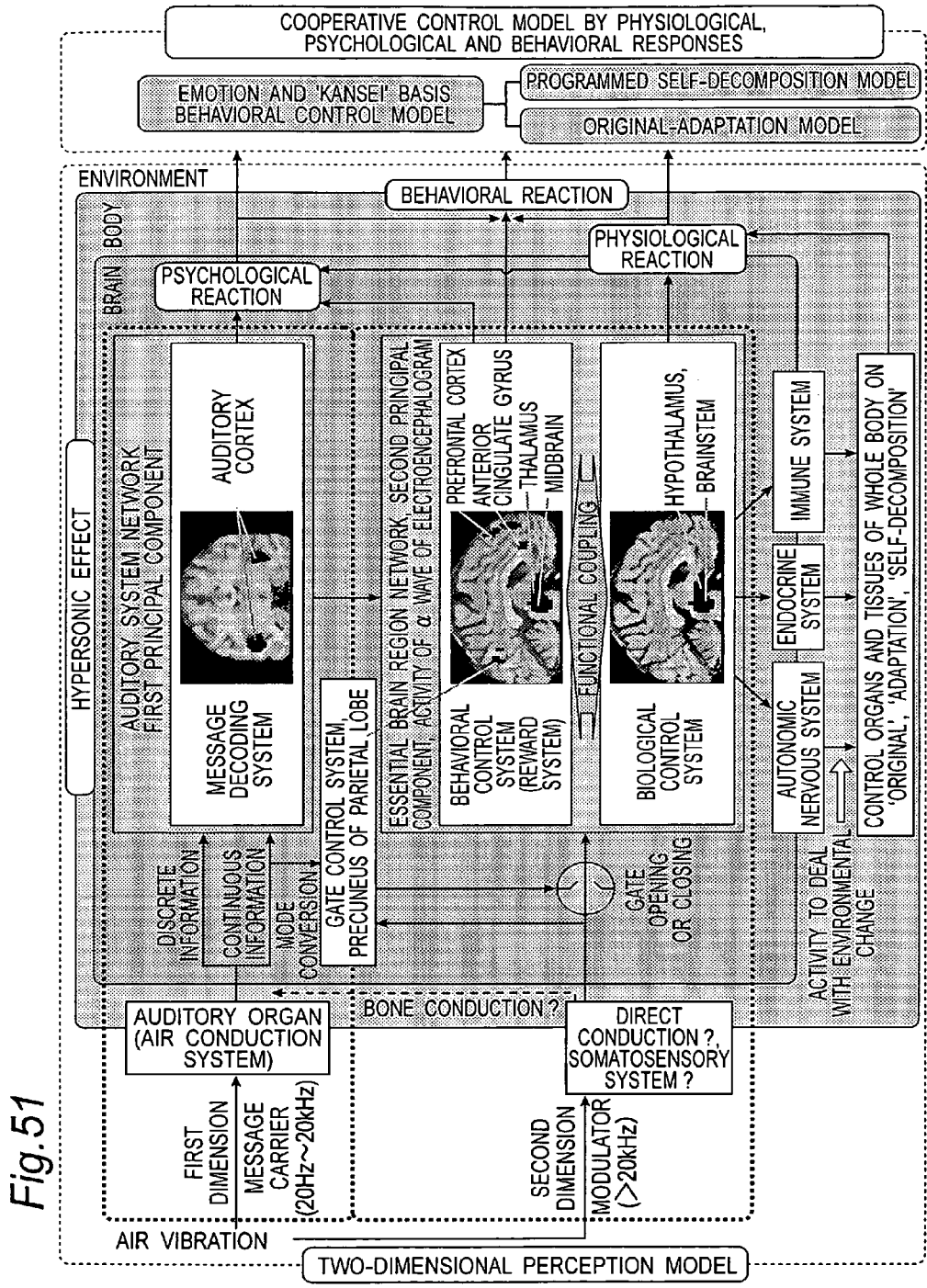
FIG. 51 is a diagram showing that a two-dimensional perception model and a functional relevance between ability regions change a hypothesis into a theory, illustrating that the two-dimension perceptual model supports a physiology, psychology and behavior associated control model.

Important to note here is that input of a single ultra high-frequency component does not generate any hypersonic effects. Thus, it is necessary to think a mechanism that a circuit of reward system is not activated simply by an input of such component, but by a certain interaction with audible sounds. As a background of this, the inventors focused on internal brain of the area where cerebral blood supply has a positive correlation with the activity of β wave of electroencephalogram, which was identified in the PET experiment. For the ultra high-frequency component that cannot be heard as music, or under the background noise conditions, the area is restricted to the premotor region of the frontal cortex, while, for under the conditions that a serial signal of audible music is presented, the precuneus of the parietal lobe is added to the same. The finding is in good harmony with an idea that there is a special meaning to have a common information structure of music and environmental sounds of the tropical rainforest changing serially in terms of time that are proposed by sound ecology. Based on this idea, when a sound that serially changing in terms of time, such as music and a forest sound, is inputted into the brain, the information processing mode in the brain makes a change under the engagement of the precuneus of the parietal lobe and opens a gate leading to a circuit that carries the modulation signal of ultra high-frequency into deep brain. Then the action of the ultra-high-frequency component after passing the gate reaches to the core brain part network including the reward system, and activates the area, as assumed by the inventors. This can explain the mechanism of generating hypersonic effects without any major contradiction (FIG. 51).

The core part of the brain has a dense distribution of cells belonging to the monoamine neuron projection system and the opioidergic nerve system that has an important role in reward reaction, or generation of reaction against pleasure and beauty. The results of the sound quality experiment make it possible to interpret that activation of these portion of brain causes a positive emotional action against tacit sound perception to which the reaction against explicit sound is multiplied.

In the reward system nerve circuit to which neuromessengers, such as monoamine and oipioidpeptide substances, is engaged, transmitter substances coming from synaptic gap do not so instantly disappear by enzyme reaction just like motor portion or auditory nervous systems. Rather, the transmitter substances tend to remain in the synaptic gap longer because such disappearance is controlled mainly by re-absorption and natural flow-out. In addition, the volume of transmitter substances accumulated in the synaptic cells tends to augment due to cascade amplification caused by the second messenger and related enzyme groups, and the duration of action tends to be longer. The accumulative effects of molecular biology mechanism that amplifies and retains the signal inputted, causes significant retention of nerve activities, and realizes transition response with a long delay. Such interpretation from molecular biology harmonizes well with the fact that reinforcement of the $\alpha$ wave by sounds containing ultra high frequency shows significant delay and retention.

The model makes the imaginary Turing machine proposed by Alan Turing, a prototype of von Neumann type digital computer which the inventors are fond to use, have some internal structure, and is in a form that the Turing machine is expressed in an analog system. The Turing machine features that it transitions from the current internal state to other finite number of internal state defined by information inputted to the current internal state. It is so designed that each internal state shows unique output characteristics.

When viewing the inventors' 2D perception model with the analogy of the Turing machine, what is first identified is that, when the first expressively perceptible dimension is inputted, or when the sound information takes such structure that sounds in audible range continue changing their state and keeps such state for a while, inside of the machine shows that the components inputted themselves act as a message and at the same time transforms the internal conditions of the system. Then, it switches the mode of the gate inserted into the circuit that transmits action of the second imperceptible ultra high frequency from closed mode to open mode. Then when a signal excited by the second dimension of the ultra high-frequency components enters in the open gate, it passes the gate and reaches to the core part of brain containing the reward system to activate the same. This modulates the impression of sounds or the first dimension of perceptible sounds, and outputs the phase of pleasure and beauty in a way that they are emphasized.

The 2D perception model enables comprehensively and without any major contradiction to explain all the facts obtained through the inventors' experiment so far.

6. The diagram of the 2D perception model (FIG. 51) can be viewed as a design drawing plotted in human genes. When reading the diagram from the viewpoint of <inter-areal functional coupling of brain>, it shows a strong effect to transform some important model forming a skeleton of environmental information as a basis of sound ecology and core models thereof as a whole from a mere hypothesis to a fact. For the inventors who created and nourished these models, it was amazing findings causing emotional movement.

First of all, the activation of a group of domains that reacts audible sounds extracted as the first main components by principal component analysis (right and left auditory cortex) completely corresponds to the first dimension of the 2D perception model <message carrier>, and the activation of a group of domains that reacts inaudible sounds of ultra high-frequency extracted as the second main component (the network of core part of brain) completely correspond to the second dimension <modulator>. The activation of these two groups shows that the internal portion of each of them correlates with each other but as a group, each behaves an independent movement. This also fits with the model very well.

Now, let us examine the functional structure of the 2D domain group or <the core part brain networking> that is excited as the second main component by the ultra high-frequency component, which is a <modulator>. The structure can further be divided into the following three units. The first is the <reward system> comprising of the upper core brain or midbrain, the prefrontal cortex, and the thalami and anterior cingulated gyrus as a part of the limbic cortex. The second unit is a group consisting of the brainstem and the hypothalamic area, a part of which overlaps the first unit. The second unit corresponds to the <biologic control system> that undertakes adjustment of the essential part of vital activity, such as automatic nervous system, endocrine system and immunity system, etc. The third unit is the precuneus of the parietal lobe.

The inventors have found that the third unit shows correlation with the $\beta$ wave of the electroencephalogram under the existence of music. From that viewpoint, the inventors consider it possible to name this unit as a candidate of <gate control system> through which the signal excited by ultra high frequency passes on its way to the reward system. The above categorization supports <the hypersonic effect 2D perception model> because of such functional correlation with the first unit <reward system> and the third unit "gate control system".

Then, how do we understand the interaction of the second unit, or <the biologic control system>? In this case, one can find very importantly implicit there, in that first in the history, it tells empirically that the information imperative for survival of human beings exists as <imperative sounds> as if they were essential nutrient.

Let us enter into the details. The core of the second unit biologic control mechanism lies on the automatic nervous system, the endocrine system and the immunity system that is decisively under control of the hypothalamic area, and takes a <central role of homeostasis> to control the physiological activation of the human body to adjust it against changes of the environment. More precisely, first of all, under the environment that is imprinted in genes, it helps physiological activation inherent to human body optimized to such environment work and maintain in good condition. When the environment deviates from that is imprinted in genes, it becomes a major driving force to activate the function of adjustment to such new environment. In addition, when the degree of the deviation is beyond the ability to adjust the human body to the new environment, it runs a self-dismantling program that reverses the direction of biologic activation vector to an abrupt deregulation, and this can cause lifestyle-related diseases, psychosomatic disorder, disturbance of mental and behavior, and developmental disorder. It is the second unit that forms a controlling center for the original biologic activity, adjustment and self-dismantling mechanism. In terms of the action of sounds, the original biologic activation of <the biologic control system> is established with the existence of inaudible ultra high-frequency components. This could directly connect to the concept of <essential nutrition> to lead the concept of <imperative sounds>.

Figure 52:
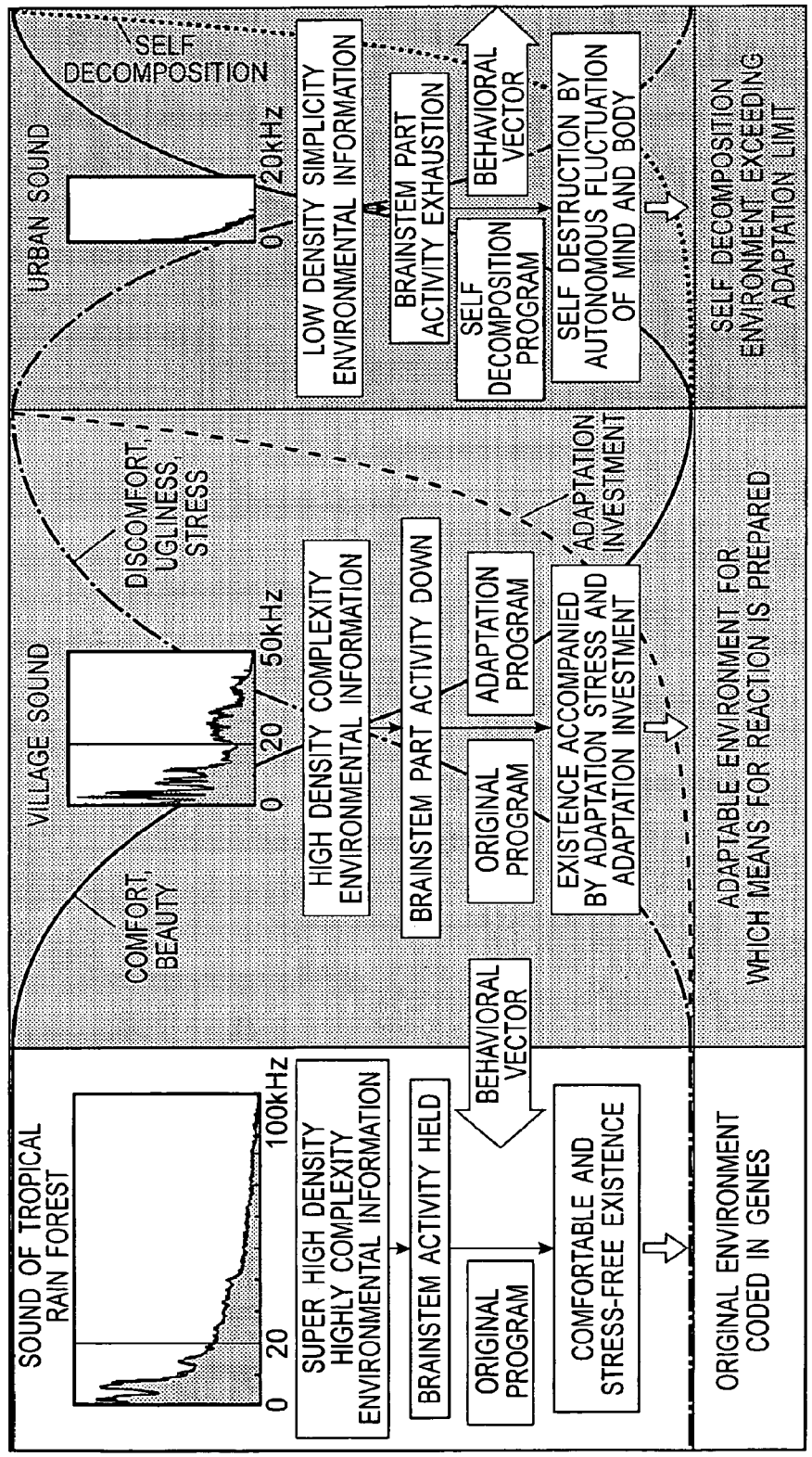
FIG. 52 is a diagram showing that the two-dimensional perception model and the functional relevance between ability regions change the hypothesis into the theory, illustrating that the tropical rain forest inherent model of Homo Sapiens is based on the physiology, psychology and behavior associated control model.

The fact that the second unit and the first unit are connected with each other by the inter-areal functional coupling of brain is, indeed, the evidence that <the physiological, psychological and behavioral control model> exists which integrates the <original-adjustment model>, programmed self-dismantling model and behavioral control model of emotion and sensibility (FIGS. 51 and 52).

The physiological activation vector that correlates the behavioral control and biological control system and leads from original state to adjustment and then to self-dismantling, and the vector that shifts from ultra high-density high complexity to low density simplification, are closely integrated with each other and work in parallel with each other. This needs due attention (FIG. 52), because, our genes and brain are originally in the ultra high-density and highly complex environment, and form a biological activity vector toward the direction of adjustment and self-dismantling to low density and low complexity environment. In other words, it supports that the information environment embedded in our gene and brain is originally set extremely to the side of tropical rainforest type ultra high-density high complexity environment, under the density and complexity spectrum of the global information environment that shifts from tropical rainforest to savanna, meadow, dessert, polar zone or urban area.

Then, the functional correlation between the <hypersonic effect 2D perception model> and the subsystems included in the model is a good element that the <original-adjustment model>, <programmed self-dismantling model>, and <emotion and sensitivity behavioral model> that the inventors have nourished from 1980s, the dawn of environment informatics, to the present, as well as the <original state of tropical rainforest model of the current human being> are, in one set, taken off from mere hypothesis to empirically supported theory. The discovery of the <hypersonic effect> is the first-ever discovery of the "imperative information", or more precisely the discovery of <imperative sound> the fact of which is supported by empirical evidence. The significance of establishment of the 2D perception model and the inter-areal functional coupling of brain supporting the establishment, which led the inventors to enlighten this, is beyond description.

<3-4> Environmental Design Imprinted in Genes

<3-4-1> What Degree Can Music Improve the Acoustic Environment?

1. The history of disharmony among music, humans, and the environment could be traced back to the era when the people in the primitive era abandoned their inherent lifestyle of hunting and gathering in the tropical rainforest and started primary industry, the dawn of civilization. Forest was burned for agriculture, and people wandered around the field for cattle breeding. The abandonment of such life and going into the primary industry is by no means the permanent departure from the forest sound that is imprinted in genes and brain of the contemporary human or modern Homo sapiens. Soon the era of secondary industry came, characterized by a flood of loud destructive noises generated by machines. The era generated the acoustic environment far beyond the tolerability of the inventors. Above all, the booming roar of power machinery that started to exercise an overwhelming influence in Great Britain in the 19th Century and the noises of transportation system scattering around the land, sea and air in the latter half of the 20th Century generated sounds and vibration in the entire environment the degree of which the earth life had never experienced in the history of evolution.

The first countermeasures against the noises of machine appeared in the 19th Century Great Britain in a form that rich people moved their place from the factory area. In the latter half of the 20th Century, sound ecology occupies a larger domain to shield people's life space from various mechanical noises such as traffic noises that disseminated all residential and non-residential area so much that people are not able to escape from them. The sound ecology have always developed and utilized state-of-the-art sound shielding technologies and structures, and techniques to utilize them. In addition to this is the development of broad technical structure from the technology to contain vibration of sound source itself to active servo control (a method to generate signals having completely opposite phase with the noise source by which the noise is cancelled). As the domain has been developed with targeting mostly on restricting the existence of sound, it still is identical with the value structure that the less sounds exists in the environment, the better it is. It does not have any framework of sounds necessary for survival of humans. However, more recently, collaboration with the domain of acoustic environment design is growing with a viewpoint of soundscape.

In the framework of "environmental hygiene", which is one of the new concept of advocating harmonious existence of the environment and humans that appeared in full-scale after the World War II, the acoustic environment is not treated lightly in any manner. Especially, World Health Organization has accumulated examinations for environmental noises from the broad perspective for a long time, and has proactively been proposing recommendations on the invasive action of such noises from the viewpoint of physiology and psychology. Such recommendation will contribute as a guideline for improving laws and regulations on the acoustic environment by each country and local region. At the same time, it has taken an important role by providing target values on research and development of sound ecology. At the end of the 20th Century, the WHO proposed the soundscape as an issue to be addressed in the future.

2. Turning our eyes on the attitude of harmony between human being and the material environment of the modern and current civilization, it shows clearly the necessary amount of nutrition for survival of human being, such as mineral, vitamins, essential amino acid and other numerous ingredients. The background is since the Age of Geographical Discovery, scorbutus threatened sailors during a long period of sailing and can be prevented by taking citrus fruits. In the 19th Century, the concept of <essential nutrition> that was found and established by the process of the modern science and a comprehensive rules to continuously supply such nutrition including unknown ones have been systematically formed in <nutrition science>. In parallel with this is the systemized concept of hazardous and toxic substances probably handed over from the primitive age of hunting and gathering, individual criteria to prevent intake of such substances, for example, maximum allowed intake volume and fatal volume of intake of them (LD50) and the others. On the other hand, as to sounds, at the onset of the 21st Century, while an effort has been taken to exclude inappropriate sounds from the environment, there has not been any scientific recognition that clearly appeals that some type of environmental sounds are necessary and indispensable for survival of contemporary humans.

In other words, while in terms of chemical substances intake, our science and technology provides precise criteria for "those better not to intake" and "those should not intake", in terms of information (or sound in this context), though it tries to exclude "those should not exist" with simple criteria, it does not consider in any manner the "sounds that should exist". This shows a clear contrast.

3. In the civilization of science and technology, environmental sounds have been consistently excluded. However, there are sounds that have been valued and enriched from artistic perspectives. That is "music". Interestingly enough, as time goes by from pre-modern, modern and contemporary era, after going to non-environmentalization under the name of "art", in the latter 20th Century, music flew out and flooded into all environments after integration with electronic media. Above all, such music released into public space passed a strange way to become a subject of regulation after scattering anxiety and abomination around, just the same as other environmental sounds.

In terms of the human history, music has been showing superb effect as an artificial material to supplement sounds in the space and enhance the elements of sensitivity information in the environment. Among them, the effects of music for restraining or healing illness, which have long been focused on since ancient times, have now developed in a form of a <passive musical therapy> and forms a grand system in the modern age. The therapy is in a framework of personal-customized prescription based on preliminary detailed investigation of a patient's uniqueness, and for this reason, it is not feasible to apply such music to a public space of the environment seeking for extremely high level of universality.

On the other hand, there is another genre of background music (BGM) or environmental music that has significantly been developed, aiming at filling gaps of sounds that has been growingly inflating under the high degree of urbanization and industrialization of the 20-th Century and based on the human-historical basis of "music as a supplemental material for the environmental information". As its name literally tells, the BGM originally means making music that is developed at the frontline of perception of human as a background and environmental element. It was probably originated in the 1910s in the U.S.A., when and where the physiological and psychological effects of music for enhancing work efficiency of workers were focused. A <phonograph> invented by Thomas Edison and getting its popularity of people in the times greatly contributed to the development of BGM by providing low cost and easy way of recording and replay music. The initial target of BGM was to enhance work efficiency of workers in factories, from the viewpoint of corporate managers, and to be expected of alleviating a sense of fatigue and stress from the viewpoint of workers. Such efficacy of BGM was greatly accepted and the way for making BGM as a business was widely opened.

Under such a circumstance, in 1934, there appeared on the stage, Muzak, Inc. of a BGM software provider in U.S.A. Muzak, Inc. distributed music using telephone lines, which is an ancestor of the current cable broadcasting service. The business of Muzak, Inc. boomed and various new comers entered in the market. Through many gyrations, BGM have established a large domain in the music distribution market to this date. Muzak, Inc. still occupies an overwhelming and entrenches its position in the domain of BGM, as can be understood from the fact that in the US, BGM or environmental music is called as <Muzak>.

In thinking of BGM, it should be noted how Muzak have uniquely behaved actively in the field of BGM as a pioneer. "Being a specialist of applying music psychologically and physiologically" as its slogan, Muzak, Inc. emphasizes in active marketing and product development applying psychology and physiology since its foundation. Such basic attitude completely negated the characteristics of <autonomous music> in BGM, rather underlined to make it completely a <functional music>. Under such attitude, the framework of "performance and appreciation" was totally discarded, and practical benefit best suited for the objectives of users were thoroughly pursued. Such targets are satisfactorily achieved.

More precisely, "easy listening" is thoroughly pursued not only in programming distribution of music such as selection of music, its output sequence design, and interval setting including long halt time, but also in selection of sound sources (ex. strings are mainly used and woodwind and brass sounds are subordinated to strings by suppressing their sounds as much as possible), simplified arrangement (including simplification of musical instrument formation, harmony development and rhythm structure), compressing dynamic ranges (monotonous performance and greater use of electronic compressors and limiters), and planarization of sound spectrum and monotonization of variations (continuation of narrow frequency range spectrum without any characteristic peak and dip), all of which are carefully arranged. From such efforts, peculiar sounds are effectively created in that the original characteristics of music to stimulate response are strongly suppressed. In fact, the 33 and ⅓-rotation disc system, which had the highest recording efficiency at that time, was invented by Muzak, Inc.

The strategy of Muzak was quite successful. Especially in 1950s and thereafter, the market saw a booming growth of BGM market. During the periods, Muzak expanded its branch network to Europe, the Central and Latin America, Oceania and the Far East. As a result, <Muzak> or Muzak-style BGM flooded in commercial areas such as department stores and retail shops as well as factories and offices, service sectors such as hotels, restaurants, beauty parlors and the like, public spaces including hospitals, railroad stations and government offices, and almost all over the world.

Triggered by this, a quite new musical environment issue emerged that made R. Murray Schafer, Canadian composer, to actively start to pursue the notion of <soundscape>. This was when, as a course of environmentalization of BGM, the listening thereof is forced to unlimited number of people. In the latter 1960s, an international movement of protest was dynamically developed in line with the actualization of such problem. In 1969, the general assembly of the International Music Council under UNESCO held in Paris unanimously adopted the resolution to persecute misuse of BGM as infringement of the right of freedom and of the right of all people to have a calm place, and to request studying this issue from all directions including medicine and jurisprudence.

Schafer was one of the persons who reacted sharply against such a situation, and there is no doubt that it was one of the decisive triggers, which made him propose the idea of <soundscape>. He named such Muzak-style BGM as <moozak or mooze>, and criticized the reckless existence thereof in the public space as "a spill of schizophrenia-like music of all types" and protested by saying "it cheapens the holy art to slaver of sounds. Moozak is the music not to be listened". Followed by this, Muzak changed its target to "audio architecture" by abandoning the name of BGM.

With these as the backgrounds, Schafer proposed the idea of <soundscape> and conceptualized a framework to put it into practice. He himself called it as "acoustic design" named after industrial design originated by Bauhaus in Germany (1919-1933). (Due to the request of the author, "acoustic design" was translated as "soundscape design" the Japanese translation of his book published in 1986. However, in the Destiny Books version published in 1994, the original word of "acoustic design" was used.) In his book, Schafer showed an epoch-making statement that separated his idea from the conventional Western music sound; "This study consists of recording various characteristics of important nature of sounds, with noting down various differences, similarities and tendencies, collecting sounds on the verge of distinction, investigating the impacts of new sounds before they are discharged recklessly in the environment, studying symbolic nature of various sounds for humans and to learn the patterns of people's behaviors triggered by variously different acoustic environment, and aims at use the findings to the future environmental design for human being".

Schafer defines his soundscape study as "to reconfirm music as actions to pursue harmonization of impacts generated by various sounds around us". Soundscape (or acoustic) design can include "forming an environmental model. From this viewpoint, it is connected serially to composing contemporary music". In addition, Keiko Torigoe, one of the missionaries of the thinking of Schafer in Japan says <Soundscape design> never tries to exclude conventional "music", rather, it expands and transforms the framework by placing Western modern music at its center" (translator's comment for "The Tuning of the World"). Such attitude gives soundscape music environmental design (or acoustic design by Schafer) a framework of an artistic action based on the paradigm of Western music. Under this framework, it is in principle difficult to separate the various elements of the governance of Western civilization "genes" of the 19th to 20th Centuries including autonomous, pure, supreme nature that are included in the basic principle of the modern art, expression of ego of composers and the freedom of creation. Schafer himself stresses the supreme inviolability of music by saying "Acoustic design should not be a design that controls in a top-down way".

On the <material civilization stage> that has already been highly matured among the civilization of science and technology, it is already a common idea that "the principle of laisses-faire" advocated by Adam Smith against manufacturing is no more compatible for keeping harmony between humans and the environment, and such principle is being of a past idea under the development of regulations against air, water and wastes. However, comparing to material civilization, on the <information civilization stage> that is still in a significantly primitive phase, the idea of "freedom of creation" for example is still on the throne of inviolability. When this is read using the "equivalence model of material and information" backed by brain science and environment informatics, from the viewpoint of "material" to "information", the unconstrained nature of information manipulation under the name of "creation" based on the supremacy of art cannot be separated with the reckless technological development once observed in the field of "manufacturing".

When this is viewed from the life science, even in the case that the objectives are to preserve and improve "sounds" as <information environment>, the priority must be on assessment and control against manipulation so as to respect the global ecosystem and life on the earth, just the same as the preservation and improvement of "material environment". This requires safety and effectiveness evidenced in a high degree by natural science and the environment manipulated within the extent allowed by such safety and effectiveness but without refusing them. Under such framework, it is difficult to unconditionally give a priority to the supremacy of art.

From such perspective, the aspect of "holy art" that soundscape (or acoustic) design has could plunge its target setting of "expansion of Western music and extension of social functions of artistic music" (Keiko Torigoe, Translator's comment for "The Tuning of the World") into the relationship of trade-off.

Originally speaking, preservation of the environment and unconstrained action of humans could sometimes be a good matching, but basically, these two do not have any system to prevent them from plummeting into the relationship of deadly enemies. It is the Western modern art that the arbitrariness of humans is intellectually rationalized, improved and developed to the maximum with such characteristics as its own identity in the history of human kind. Among such modern art, the philosophy of "absolute music" boomed in the 19th Century by advocating, that "music should not be constrained by anything other than its own rule, and its creative activity should be completely free from any assaults from the society", will be one of the most extreme type of art. In addition, the miserable outcome led by the control of art by <sociological realism> appeared in the former Soviet Union in the 1930s as a reaction against art for art's sake reflects the limitation of modern and contemporary civilization as due results of deregulation of art, which should not be ignored. It is of course not unfeasible for the strategy of soundscape design to try to expand and transform the Western modern music derived from such background so that it can function and contribute to preserve and improve the environment. However, whether or not it should be treated as the best or a highly preferred solution should be determined carefully.

Schafer chooses the following principles as the ones we should learn from, "other than music" that has such significant problems: "1. Respect to your ears and voices: Any environment is harmful if your ears suffer from threshold shift beyond the tolerated level, or when you cannot hear someone's voice, 2. Awareness to the symbolic nature of sounds: They are always beyond the action of functional signals, 3. Knowledge on rhythms and tempo and others of natural soundscape, 4. Understanding of balance mechanism that deviated soundscape returns to the original position by itself. This can be most easily understood by returning back to the philosophy and art in China". Indeed, the guidance possesses a chance of effective development. In fact, the approaches outside of the materials and process of traditional Western art and music seem to produce major fruits of soundscape (acoustic) design, though its history and tradition make no difference, and in spite of the fact that its systemization and verification are still in primitive stage.

As the guidance for soundscape design, Schafer underlines that "which sound we want to protect, help and grow? When we know this, we can see lengthy and monotonous or destructive sounds clearly, and we will be able to know why such sounds should be excluded. Only the comprehensive ability to identify acoustic environment gives us assets to improve soundscape orchestration". In other words, he suggests us to first identify clearly the ideal existence of sounds in the environment, and then establish a norm of "how sounds should be", in order for us to improve the soundscape "orchestration". This statement is to-the-point, because his statement clearly separates itself from the intrinsically groundless numerical criteria for noise regulation in the <environmental hygiene> and the BGM standard that is governed by market economy.

Needless to say, here the decisive meaning lies on the fact that acoustic environment should be selected or set as a <norm>. This is difficult as in the case that the concept of <essential nutrition> was selected, because, listing all and every <essential nutrition> is in principle beyond the ability of analysis and reduction of us both living in current times and in the future. In such case, the inventors believe that setting a concept of "a mass of natural foods that has proven its appropriateness for humans from the viewpoint of evolution" can produce a substantial effect. The statement that can function as the one that indicates a norm should be the one that expresses highly, organically and comprehensively the idea that can include, not exclude "unknown but important structures and elements". For this, one of the effective solutions can be to take a form of "a representational idea indicating the existence of something" that is naturally allowed to latently include not a small number of unknown elements and structures".

However, Schafer does not expressly show the sounds that can be a norm of soundscape design, except for that he perfectly develops his logical structure in terms of his context. In his book, "The Tuning of the World", what is underlined as "the ones expressing eternal perfection" is the "music of the spheres (in the Japanese translation, the name is referred as music of celestial body "which is popular among esoteric people. He sets his idea by tracing back to the idea of Pythagoras as the origin of his idea. (In speaking of the music of spheres, Schafer sometimes picks up the idea of Indian music, "Anahata" to which he says his idea is identical to Anahata.)

The theme of the short "epilogue" of his masterpiece "The Tuning of the World" is the music of spheres. In this epilogue, Schafer states, "it is a music having rational order. The music can be traced back to Greece, especially, Pythagoreans. Pythagoras, who discovered mathematical response in harmonic sound ratio in strings sounds and focused on planets and fixed stars moving in a perfect order, integrated his findings by intuition, and assumes that the movement of these two forms represents the perfect universal rule. Then he correlated mathematics and music". Following to this, Schafer correlated his soundscape design and the sense of Apolon music. As the expression of such sense of music, he picked up "Indian music, Anahata", "thought of Pythagoras", "thinking of thinkers of the medieval age", (probably the idea of "music as a study of moving numbers" derived from ancient Greece) and dodecaphonism by Arnold Schönberg. He states, "the way they are presented is the theory of numbers". There, we can see a thick nuance of hermeticism of thought of Pythagoras.

It is certain that it was Pythagoreans who made the largest trigger that the thought of the Western art music that mainly recognizes "music intrinsically possesses serial and quantitative structure", which was revealed by sound ecology, is recognized mainly as "the discrete and numerical phenomenon". However, in a manner similar to that of the other intellectual assets of Pythagoras, as to where the "music of spheres" came from the inventors have no choice but referring to the records and documents of subsequent times indirectly. Aristotle criticizes and rejects this in his book "De Caleo", by saying as follows. In the reference, "certain people" refers to Pythagoreans.

"Certain people tell like this: On this earth, things that are not as large as this and move not as fast as this emits sounds. Then, when quite a large substance moves, it should inevitably make a sound. There could be no cases that large sounds are not made when the sun, the moon and numerous stars with massive size move in such a high speed. In addition, assuming this fact and that speeds have series of sounds depending upon their movement distance, they assert that the sounds of stars in rotary motion are harmonious. However, it may be unreasonable that we do not actually listen to such sounds together, and they explain the reason as follows: This sound exists when we were born. We cannot distinguish this sound and silence, because a sound and silence can be distinguishable when they are presented together. Just the same thing that a copper blacksmith thinks habitually that both sounds are not distinguishable, similar thing will happen to ordinary people as well".

This context was almost completely succeeded by Schafer, he concludes his masterpiece "The Tuning of the World" by saying "As humans thrives hard for the perfection, all sounds call for silence and eternal life of the <music of spheres>". He at last puts the supreme raison d'etre in silence leaving a certain type of self-contradiction with the philosophy of acoustic environmental design.

The music of spheres can certainly be an expression of "eternal perfection". However, by being silence, this makes it difficult to lead to a concrete <indicator> or <criterion> for creating real environmental sound from the norm. This state hollows out the physical sound structure and signal structure as a target for using the soundscape design system applied to the control of real acoustic environment. It also paralyzes the system to lead it to the course of effectiveness and reliability, or leads it a way to rely on arbitrariness.

The deliverables that have been produced under the soundscape (or acoustic) design continues to provide rich fruits beyond various contradiction and limitations lying deep under its framework, and this trend should be continued in the future. However, this does not support that such contradiction and limitation is ignorable, and cannot connect to an assertion of singleness or high priority of this framework. What is wanted to us as a historical issue is to prepare a new framework that withstands the long-term perspectives without being interrupted by such serious contradictions and limitations.

<3-4-2> Brain-Friendly Acoustic Environmental Design

1. The framework of various approaches that have been established so far will provide us precious assets in starting practical actions for harmonization of sounds and environment. At the same time, it cannot be negated that they are still insufficient to assign the future of the inventors to them. Especially, when coping with the business to ascertain healthy growth of our next generation and conquer social pathology, or the business that consumes public space and funds, it is a pity that we cannot find any existing entities that can perform their due business in a responsible and trustable manner.

Thus, the inventors decided to create a new acoustic environmental design worthy of putting it into practice without any hesitation under our sole principles and responsibility, based on the sound ecology, by reserving to rely linearly on the existing framework of full of limitations but learning from the same. In a word, it is <a sound ecology design friendly to brain that is imprinted into our genes>.

The first step to form this paradigm is to set a comprehensive concept as to what is the ultimate and ideal sound ecology as a <norm> or the target of the work. More precisely, it should be said that the process of thinking itself, which led judgments that a practical norm should be set to acoustic environmental design, forms a part of elements that distinguish this efforts from others.

So far, there have been no norms providing hints and targets to acoustic environmental design that has a role of creating sounds, not excluding sounds, except for the <music of spheres> focused by R. Murray Schafer, or <Anahata> as its equivalent music. Both the music of spheres and Anahata can function as conceptual tools of metaphysics or esotericism, but they cannot show in detail the standard controlling actual sound or the signal and information structure that sounds should possess. If such thing is sought forcibly, the <silence> that contradicts the creation of acoustic ecology will become a norm, and the action of design itself will be hollowed out. The absence of practical reference seen in such a condition is itself the cause why conventional acoustic environmental design has been drifting without any compass.

Indeed, it is not an easy task to set an acoustic ecology reference as a practical scientific concept that can work on the ground of science and technology in which the inventors place themselves. It may have been impossible to do so by using the conventional knowledge level. However, quite recently, the inventors have fortunately seen that various materials are found in the new science and technology. Some of them should be able to act as an element to cause such a situation a historical transformation. By using such materials, the inventors have established, nourished and put into practice consecutively an organic strategy to cause a revival of acoustic environment that is imprinted in human genes into urban space. The followings are the outline of the inventors' efforts.

2. First of all, the inventors focused on <genetic determinism> derived from molecular genetics as one of the valuable intellectual properties that human beings have newly acquired. Based on this, the inventors were able to set a grand prerequisite that "human beings inherently and universally have an ideal acoustic environment imprinted in their genes".

Using the <original-adjustment> model in the environment informatics, the inventors obtained a model that the acoustic structure embedded in human genes is equivalent to that of ecosystem as a cradle of human evolutions and generated such genes through recombination of DNA sequence. In order to explain the environment, an epoch-making recognition was drawn using the knowledge and procedures of the latest evolutionary biology, ecological anthropology and brain science, the <2D perception model of hypersonic effect> that was established by sound ecology using such knowledge and procedures and the discovery of <inter-areal functional coupling of brain>. In summary, it is highly likely that our genes were formed through a repeated recombination of genes centering in tropical rainforest area long before they became human genes. It supports that the original environment imprinted in our genes are the tropical rainforest or that the sounds echoing there is the largest candidate for acoustic environment imprinted in our genes. Based on this idea, the inventors chose the sound space in the tropical rainforest as the largest candidate for the acoustic environmental norm imprinted in genes of the contemporary Homo sapiens, and drew a basic strategy to make the sound signal structure and sound information structure filling there as a reference for environmental sound.

The next step should be to verify the validity of the reference, connect it to actual analysis, design, structuring and assessment of acoustic environment, and set a new framework to make it appropriately function. For this purpose, using <the equivalence model of materials and information for the life on the earth> from the environmental informatics, the inventors drew an idea that there are two categories in sound information accepted by the inventors, that is, <essential information> as sounds that are indispensable for human well-being and <noxious information> as sounds that are injurious to human beings. This is just the same as that materials we may intake have two categories of <essential nutrition> that are indispensable for human well-being" and <toxic substances> that are injurious to human beings. The sound structure, which is essential information here, is the norm of the <brain-friendly acoustic environment>.

Under the recognition of the above, the inventors set a framework to separate sounds existing in the environment into the following three categories:

1. <Essential sounds>, or "the sounds that are indispensable for human well-being".
2. <Functional sounds>, or "the sounds that have a positive effect on human beings".
3. <Noxious sounds>, or "the sounds that are injurious to human beings".

Our civilization, after departure from the stage of material civilization, has a strong recognition of the existence of materials indispensable for human well-being since the dawn thereof, and in the early stage, a concept of <essential nutrition> such as vitamins was established. On the other hand, on the stage of information civilization subsequently appeared, a concept and the existence of <essential information> have still not clearly described and clarified. There are some chances that the <essential sounds> as proposed by the inventors will be a pioneer thereof.

Among the three categories the inventors set, the <essential sounds> and their efficacy should be verified in terms of both sound structure and its functionality. First thing to do is to confirm whether or not artificial spaces, especially the acoustic environment of urban area, that, as the center of the civilization of science and technology has been reached to an intolerable level of mismatch between humans and sound, and the acoustic environment of the tropical rainforest can be clearly distinguished with each other under a certain objective indicator and are relevant as the reference.

For this purpose, the inventors developed a suitable recording and analysis methods to investigate in detail the signal structure of sounds in the tropical rainforest and in urban areas. As a result, the upper limit of the frequency of sounds in the tropical rainforest as a model of original acoustic environment for human beings showed the range of 100 kHz to 130 kHz or above, which are more than 10 times as large as the frequency observed in urban areas i.e. approximately 5 kHz to 15 kHz. The sound structure of the tropical rainforest showed ultra high-density high complexity and is highly changeable, whereas that of urban areas indicated low density, highly simple and is highly monotonous. These results evidenced that there is a possibility that both sounds in the tropical rainforest and urban areas can be highly and precisely comparable in terms of the degree of deviance between the two and the possibility of filling such deviance using such objective indicators of sound signal and information structure, by setting the former sounds as the norm of acoustic environment most fit to human beings and by finding there appropriate indicators to set a reference.

Next, a verification has to be made whether or not the structural characteristics of the tropical rainforest sounds having sounds far beyond the perceptible range of human beings can reflect the functions provided by such sounds to human beings. For this purpose, the results of the rigid model experiments, which the inventors have accumulated for a long time of periods, tell a lot. The inventors first collected and recorded broader types of natural sounds in the tropical rainforest and music having ultra high-density information structure. Then, two forms of specimens were created; one is the original recorded sounds without any processing, and the other is the ones after removing ultra high-frequency inaudible elements to make them closer to urban sounds with low-density. A blind-hold test was conducted to subjects by replaying both specimens with a high fidelity under the conditions that both two specimens were switched over under the same conditions to compare the reaction of the subjects under more than one indicator relating to physiology, psychology and behavior. The experiment revealed with a high statistical significance that when listening to a monotonous urban-type sound with low density, compared to a complex tropical rainforest-type sound with ultra high-density, the activation of core brain part network tend to be lowered, that for all the indicators of physiology, psychology and behavior, the urban-type sound decreases the physical and psychological activity of the subjects or makes human body unfit to such sounds, compared to the tropical rainforest sounds.

Among the core part of brain network which decreased its activity by the urban-type sounds, the brainstem and hypothalamic area, or the element of <biologic body control model> in the inventors' <2D perception model> closely related to gene-related diseases such as lifestyle-related diseases and psychosomatic diseases that have frequently been observed in the urban civilized area. On the other hand, the <behavior control units> such as the midbrain, thalami, cingulated convolution and prefrontal area belong to the <reward system> and decrease in the activity of which may lead to escape behaviors from urban areas due to malaise, mental, behavioral and developmental disorders. Moreover, a perversion of positive and negative behavioral control mode may threaten to cause highly civilization-oriented pathology of eating disorders and "wrist cutting" (self-mutilation).

However, when it is viewed from the opposite direction, this means that establishment of a new acoustic environment based on the norm of <essential sounds> newly developed gave the inventors a chance of releasing human beings from such modern age pathologies.

3. Through the establishment of norms and criteria and verification of their experiments, the inventors have built a new principle for acoustic environmental design. This is the paradigm of <brain-friendly acoustic environmental design>. The essence thereof starts from making the information structure unique to the environmental sounds of tropical rainforest as a reference of <essential sounds>. Next, a comparison is made between the reference and the information structure of sounds in a specific space chosen as a subject to measure the difference closely. Of course, wherever necessary, <functional sounds> are added on this basis to design the targeted sound space, which is within the scope. Then, finally, a comprehensive assessment of effectiveness and safety will be made on them using the brain activity as a core indicator, with other complex sub-indicator system of physiology, psychology and behavior.

The design that establishes a desirable acoustic environment baseline with the highest perfection level means, in principle, to create the tropical rainforest itself. However, this is not feasible in most of the cases in a short- and mid-term perspective. As a next-best measures for such most of the cases, and to supplement the limitation of such scenarios, artificial sounds including electronic media is used for supplementing them. In this respect, the merger of reality and virtual reality or augmented reality or mixed reality should be focused on.

So as to put it into practice, materials, methods and procedures should be there. Particularly, in the case of using electronic media, it is of high priority to develop software to collect, create and edit sound sources having the information structure of tropical rainforest. Needless to say, equally important is development and manufacturing of hardware with a dramatically enhanced performance level compared to conventional one, to record, edit, distribute, replay and present such sounds of ultra high-density and complex nature which are created by such software. In addition, design and construction of a space to develop such a sound source to the real target space, and execution of the design and the construction are required. As to this, the inventors have developed various practical systems that satisfy the high degree of specifications that did not exist so far, with a system developed for research purpose as a prototype.

In this approach, there are an overwhelming number of elements outside of conventional knowledge and technology, such as acoustic environmental design or acoustic design, BGM, soundscape (or acoustic) design, and music therapy. With this in mind, the following clauses will be consumed to explain practical "brain-friendly acoustic design" derived from this approach.

4. First of all, the detailed acoustic structure that the brain-friendly "essential sounds" should possess as an important sound baseline in terms of software is explained. On one hand, <functional sounds> can be found everywhere and is in fact infinite in number, on the other hand, "essential sounds" requires to take the form of a sound and vibration completely the same as the ever-changing and complex environmental sounds of tropical rainforest that have nourished human genes or other sounds of similar structure and quality. The upper limit of the sound frequency extends to approximately 100 kHz far beyond the audible frequency upper level of 20 kHz, or ideally to 130 kHz to 150 kHz. Moreover, such sounds needs to be a tropical rainforest-type <hypersonic sound>, with an ever-changing spectrum form and full of nonconstant fluctuation. At the same time, its sound pressure level has a gap from those in various methods of the conventional acoustic environmental design and the relevant noise control regulations that is in effect today, and required i.e. 50 dBA to 70 dBA, which is well over the value indicated by the various methods and the relevant noise control regulations. The baseline of such sounds is emotionally calm and comfortable, but in terms of information structure, it is full of complexity. The aim is to realize the sound structure of various types based on such essential baseline into the space where people live.

The brain-friendly hypersonic sound criteria as shown here, indeed, includes all and every concepts, design methods and technical specifications that have supported the conventional environmental hygiene, sound ecology, BGM and soundscape, but the specification as a whole requires far beyond such concepts, design methods and technical specifications of conventional type. Due to this reason, conventional methodology, hardware, software and sensitivity cannot be used, as they are, requiring total renewal of almost all of them to make new ones.

More precisely, for both hardware and software, it is essential that they possess superb response and information reproduction level up to the frequency range of more than 100 kHz. As a system satisfying such a high level of demand, the inventors created a hyper-broadband multi-channel, A/D conversion and recording system with a sampling frequency of 5.6448 MHz, 3.072 MHz and 2.8224 MHz based on the high-speed sampling one-bit quantized signal processing system developed by Dr. Yoshio Yamasaki. In addition to this, an optical disc replay system beyond the basic research use, an amplifier system, a presentation speaker system, especially a superb super tweeter system with ultra high-frequency response, which is quite difficult for development, were developed under the upper frequency response level of 130 kHz or above.

As the place of replaying the sounds, 1 channel monaural or 2 channel stereo systems can show a certain degree of effectiveness. However, ideally, speakers should be placed to the right and left and up and down to form an all-directional sound space is formed. As one of the realistic methods to realize such all directional sound space, the inventors developed an effective space allocation system called <Double Helical Matrix System>, and this leads to that the sounds are recorded in 5 channel system consisting of <front left>, <front right>, <rear left>, <rear right> and <center up> speakers with the front and rear speakers moving a double helix course by inversing the direction.

In replaying hypersonic sounds as the essential sounds, as the distance of sounds and the reach of radiation directivity are greatly constrained for ultra high frequency component, the most important element, other than those for audible components, it is essential to conduct a meticulous design by enhancing installation density to limit the distance from the sound sources, making the distance shorter, and elimination of dead angles. The inventors have been engaged in the development of a weatherproof unit that satisfies all of the said conditions, that can be used outdoor, and that can maintain sound quality not affected by such elements.

5. In this case, a new problem should be pointed out, which have probably not been considered so far. That is, the sound space of tropical rainforest as an original sound environmental model for humans does not have any doors or walls to shield the environmental sounds to form it another sound environment. In other words, the entire sound space is a continuous existence and does not have any discontinuous faults. On the current situation in which no grounds for denying the fact can be found and total shielding of sounds may stimulate the alert system in brain, it is at least safe to make the sound space a continuous one. For this purpose, it is necessary to develop structural and electronic media technologies to apply for securing a certain level of sound continuity even if a common environmental sound exists between and penetrate through various walls segmenting finely the urban sound space.

In addition, environmental sounds in tropical rainforest, for an infinite time of period, have not had any <silence> or a blank of sound. In terms of reaction of humans against the sound, the effects of the tropical rainforest type hypersonic sound remains in brain for 130 seconds or so after the sound is disappeared. After that, brain starts to decrease its function. In other words, brain-friendly sounds cannot be retained in brain for a long time, and should be listened to at all times to continue its effects. In addition, forest sounds are not repetitious ones something like a recorded sound. Therefore, it is indeed very effective to record ultra high-density complex contents in a 112 hour-disc and to regenerate them repeatedly to form a sound environment, such sounds cannot guarantee that they are the same in quality as the original natural sounds. It is nevertheless desirable, from the immeasurable sensitivity and retention capacity of our brain against sound environment, that the sound information to be supplied should be at always a fresh one for the receiver just the same as actual forest sounds.

So as to realize this, the following is an example that the inventors developed. First of all, a sound source consisting of a plurality of independent sounds such that any combination of them will not generate destruction of their expressions and functions. Then, the sound source was recorded in a packaged media so that the length of time per package has a prime relationship with each other, for example, in a second, and then, the sound source are repeatedly replayed in a synchronized manner under the accuracy of time lag within $1/10$ seconds or below. Suppose one disc contains 3,181 second-worth of sound information, while the second disc 3,667 seconds, when the two discs are replayed simultaneously, it takes 1,116,4727 seconds or 135 days before the same combination of sounds reappears again. In fact, the inventors extended the length of time that the same combination of sounds reappears to more than 1,000 years using three optical discs using this method.

Figure 58:
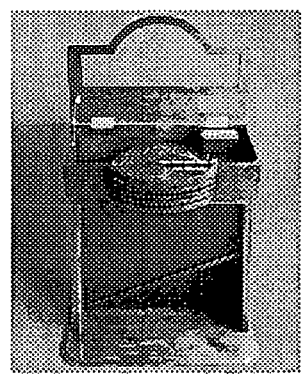
FIG. 58 is a photograph showing an application example of the sound environment design which is suitable or comfortable for a brain, illustrating a hypersonic music box.

Realization of the "brain-friendly sound environment" or the sounds imprinted in our genes in the actual urban artificial environment is nothing less than an unattainable target, thinking of the conventional technological concept. This is because, so as to do so in an ideal and rigid manner, it would be necessary to make electronic medium containing for example ultra high-density multi-dimensional tropical rainforest sound information, which is regenerated permanently so that same combination of sounds will not appear in more than decade years, which is extremely difficult thing. Do we have any solution for this difficult challenge? As one such solution, the inventors have an idea of installing an earth station that distributes electronic environmental information at an appropriate place in the ecosystem having tropical rainforest sounds or its equivalent high quality sounds, which is selected somewhere on the longitude near equator where the time lag between the station and the area to establish the acoustic environment is as small as possible. The data is transmitted permanently through an ultra high-speed communication satellite and large capacity network to develop the "mapping" of the acoustic environment to the target space. In order to overcome time lags, use of an ultra large volume data storage system capable of storing 12-hour equivalent data is within our scope to introduce high quality acoustic information from various places. In addition to this is the utilization of a sound generation system using the movement of water as a source of highly natural hypersonic sounds. The inventors found that water flows and downfalls can generate ultra high frequency of more than 130 kHz with full of fluctuations (FIGS. 23 and 24). These will be used not only as a supplement to the environment, but also takes out the vibration from air or under water in a form of electric signals which will then be supplied as a real time sound or a recorded sound separately or in combination of other sounds. As discussed later, the inventors have developed a musical box that can generate hypersonic sounds at site without using any electronic signal processing (FIGS. 21, 22 and 58).

6. The construction of such acoustic environment using the methods shown above, for the time being, should use a high ratio of artificial sounds including electronic media. When making an access to the tropical rainforest type acoustic environment original for humans using such an environmental construction method, the assessment for the safety and effectiveness should be as rigid as possible because of the high degree of artificial sound usage. The main way of this assessment should necessarily be physiological assessments. However, equally important are sensitivity assessments on the opposite end of physiological assessment which should never be compromised.

For the <physiological assessment>, the point is the non-invasive brain function analysis customized to the objectives. The assessment should desirably be constructed so that multiple methods can be utilized stereoscopically. To this point, the inventors conducted analysis and assessment by organically correlating many indicators including unconstrained electroencephalogram telemetry with FM multiplex data transmission, concentration measurement of neuroactive and immunity substances in bodily fluid, and a large-scale non-invasive brain function analysis, such as PET.

For the "psychological and sensitivity assessment", strictly speaking, it is an assessment of the reaction of sensitivity brain, one domain of physiological reactions. So as to conduct the assessment in a satisfactory manner, it is effective to refer thoroughly the learning and findings of the previously mentioned physiological assessment and establish an experiment plan based on the same. Particularly important is to treat unique time asymmetry of the hypersonic effect. In addition, the <behavioral assessment> having indicators of human behaviors as a total output of physiological and psychological reaction, if the methods and condition setting for their experiments are well designed, will show a tremendous degree of sharpness with highly reproductive results. In addition to them, it gives very valuable findings in that it allows foreseeing the final results in actual fields through an experiment-level pilot test. Of course, in addition to such highly original methodologies, conventional methods such as surveys by observing how people acts and reacts are highly useful in providing precious findings through appropriate condition setting and trials.

The method for supplementing brain-friendly sounds centered on electronic technologies, which is a core part of the urban information environment rehabilitation plan for realizing enhancement of health and amenity of urban areas by providing people a healthy environment and comfort require less burden than land rearrangements and construction of buildings both technologically and economically. Nevertheless, the effects expected by conventional brain function analysis are highly likely to reach to an epoch-making level through preventing the core part of brain from decreasing its activity, because allowing this would induce various problems that are suffering urban people now, such as modern diseases, behavioral and developmental disorders and loss of comfort.

Actual promotion of the <brain-friendly acoustic environmental design> cannot be expressed in word information of "specifications", and finally depends on human factors, such as project controllers who have decision-making authority, for example, total designers, and producers. It requires not only an ability to utilize science and technology, but also a technique of "cooking sounds" or the ability of a sound creator to materialize sounds by integrating detailed sensitivity and emotional elements, such as comfort and beauty. In addition, the larger a project is, the more whether or not the person possesses personality and knowledge to "cook" at his/her disposal, various worldly issues of regime, budget, organization and system, as well as philosophical issues of ecological cosmology, influence the results. This is the issue of selecting human resources, which is extremely crucial to the success or failure of a project. Rather, selection of human resources is the largest challenge. In selecting the right persons, it is dangerous to assess the ability of a person by current standard of "explicit competition". For this, the ability of selecting right person based on the recognition of the new brain functional model, "a part of brain not controlling language and a brain controlling language generated in it", will sure be effective.

7. There are very large, intrinsic and various gaps between the strategies of sound ecology, which aims at harmonizing sounds, humans and environment, and the strategies of other various past approaches. The most fundamental difference between them lies on the relationship of sounds and humans. The sound ecology stands on genetic determinism, while other approaches were all established before such knowledge and thought appeared, and may be positioned at completely different place from them. The genetic determinism tells that the devices for controlling acoustic information processing, or brain and nerve system, are created based on the blueprint of genes, as well as all the other biological activities, and the structure and the function have finite number of innate framework, which is universal to all human being, most part of which cannot be altered or modified. When this idea is used combined by new type of knowledge and information, such as environment informatics, molecular biology, evolution biology, brain science and sensitivity science will generate an effect.

Due to such a background, recognition will be led: the brain should inevitably be controlled by a rigid physiological framework of sensitivity and response against "the sounds as an ultimate messenger from the remote environment". According to such a recognition, it is highly likely that the brain, especially the "behavioral control unit" comprising of core part network determines whether it is an original environment imprinted in genes of human being, or it is an environment where people's life can be sustained with the efforts of adjustment, or it is an environment where adjustment is not feasible and self-dismantling is unavoidable, and transmit the result to mind and body to continue to cause an appropriate reactions against it, through the sounds and vibrations coming from the environment. Sound ecology focuses on this point, and tries to access to the original acoustic environment imprinted in genes led by brain activity, and draw a concept and executed constructing a <brain-friendly acoustic environmental design> that builds the original acoustic environment imprinted in genes while avoiding unqualified sound structures requiring tremendous degree of adjustment efforts especially those significantly unqualified ones that may trigger self-dismantling.

In a practical acoustic environmental design, sound ecology that stands on this strategy have inevitably indicated clear and not a small number of gaps everywhere with the known major approaches that aims at cooperation and harmony between humans and sounds. The sound ecology is unique to the point that it first constructed the <idea of essential information> i.e. the <essential sounds> or <sounds that are indispensable for human well-being> first of its kind in history, decided its norms, and clearly and completely expressed the information structure as criteria of some indicators, and revealed that if the criteria is not fulfilled, some negative impacts will be resulted to human body. It also determines that "silence" is highly abnormal and inappropriate for human genes and the brain, thus, silence is unqualified as a standard or a norm for studying interactions between humans and sounds. This is also a clear distinction with other system and thoughts related to this.

Due to such a large gap, it was a natural consequence that the acoustic space produced by the paradigm of the <brain-friendly acoustic environment> derived from sound ecology showed a major differences of various kinds everywhere against the things that were created by all of the conventional acoustic environmental design methods. First of all, the most noteworthy is the sound pressure level. The baseline of acoustic sounds designed with tropical rainforest as a norm is approximately 50 $dBL_{Aeq}$ at the lowest and more than 70 $dBL_{Aeq}$ at the highest. Most of the case, the sound pressure level should be set to the level that is subject to noise reduction regulations currently in force. Moreover, these sounds appropriately designed are heard calmly and comfortably without feeling them as noise.

Another intrinsic difference with the conventional acoustic environmental design is the existence of <essential sounds> as a baseline, their wide frequency range and high complexity. Conventional way of acoustic design has been done within the range of audible sounds, and not the ones beyond that. Conversely, the <brain-friendly acoustic environmental design> targets the frequency range of 100 kHz as a basis, which is five times as large as the upper limit of the frequency of audible sounds, i.e. 20 kHz, with trying to include 150 kHz as a scope of target wherever possible.

Such an aspect of the <brain-friendly acoustic environmental design>, which is completely different from the conventional ideas, is the essence thereof. The evidence, appropriateness and validity are being examined through a survey of global-scale acoustic environment from a new point of view, various model experiments and assessment using multiple indicators mainly brain function analysis. The improvement of assurance and reliability derived from them shows many distinctions from the conventional methods.

The <brain-friendly acoustic design> has unique characteristics that it allows wider applications. As the first step, basic conditions are organized by constructing a sound baseline satisfying the conditions of the <essential sounds>, then such conditions are kept and maintained to adjust acoustic environment to human's brain. Of course, in many cases, the first step is enough for achieving the final target. When a sound system containing various objet d'art and sequences are introduced as the "functional sounds" on the baseline, the application of the "brain-friendly acoustic environmental sound" will be expanded to variously diversified objectives and brain-friendly structure can likely be established. The <functional sounds> here can contain music. It is quite interesting that this leads to personal preferences of recipients and dependence to receiving conditions can significantly being alleviated, when single music is used as a supplement to the acoustic environment. As a means of introducing appealing "sound objet d'art" while averting negative aspects of emotional sensitivity effects, personal preference and dependence to conditions that music forces to the recipients, use of <functional sounds> applying <dodecaphonism> and <chance-operation> has rationality.

8. In this case, a concrete structure of applying <brain-friendly acoustic environmental design> will be shown (FIG. 59).

Figure 53:
FIG. 53 is a photograph showing an application example of a sound environment design which is suitable or comfortable for a brain, illustrating an accession environment simulator "Studio a".

FIG. 53 is an example of providing short time of deep and comfortable sleep to people working in offices in urban area, called "Good Sleep Studio α". In this case, in a studio, where the interior is designed and arranged by objectives, walls having visual fluctuation of 1/f are installed in a room with an indirect lightening. In the room a video is played. Humidity and temperature are well controlled and the room is filled with aromatic chemical substances. By doing so, the room is closer to the forest environment. Through the high performance replaying system, hypersonic sounds are played as essential sounds and functional sounds to lead the brain stress-free state. While lying down comfortably on a slightly tilted chair of a special design, listeners listen to music and view the video. The system became popular by providing a very comfortable sleeping time to unlimited number of people. The music used here is synchronized to the motion picture. Ultra high frequency of tropical rainforest, Gamelan music of Bali with full of fluctuations, women chorus of Bulgarian folk music and others that are recorded on site by way of high-speed sampling one-bit quantization are edited according to the objectives. The point to lead people to a comfortable sleep is to provide sounds with quite high sound pressure level, from the conventional idea, so that the level comes to 60 dBA to 70 dBA or spontaneously comes to more than 80 dBA at the place of the listener to produce better results. It is interesting enough that here, there is a clear distinction between the conventional idea and the <brain-friendly acoustic environmental design> and shows the effectiveness of the latter. In fact, the acoustic environment imprinted into human gene, or the night in tropical rain forest is a sound palace full of rich resonance, having the baseline of 50 dBA to 60 dBA range, and spontaneously the level can exceed 70 dBA. From this, the fact that the Good Sleep Studio α can provide a short time of nice sleep is not mysterious.

Figure 54:
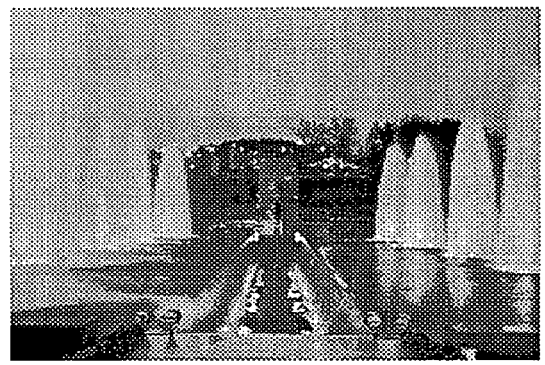
FIG. 54 is a photograph showing an application example of the sound environment design which is suitable or comfortable for a brain, illustrating the International Garden and Greenery Exposition (EXPO '90) Outdoor Pavilion, Water Objet D'art "Aleph".

Another example of applying hypersonic effects to stimulate comfortableness in a large event space is the "Alef" a gigantic water objet d'art. This was exhibited at the outdoor pavilion of the International Garden and Greenery Exposition (EXPO '90). There, in an artificial pond of 40,000 $m^2$, called "the Life of Sea", several tens of fountains with more than one hundred nozzles and one water-separating unit controlled by a computer and a SMPTE time code, and showed a transforming sculpture of water, lightening and music, all of which were synchronized. The water performance unit is highly effective as a generator of ultra high frequency full of fluctuation, which is a necessary element of hypersonic sounds that enhances the activity of the core part of brain. In this venue, the effects were utilized as a combination of essential sounds and functional sounds. Especially, the fountain <Ice Flow> that was originally developed for the exposition abruptly blows up water to form a water pillar of approximately 50 m in height and 5 m in thickness. The large amount of water falling down generates a roaring sound accompanied by large volume of splashes. By placing the pillars closest to the audience and arranging the timing of running, stopping and volume of water, the system is so designed that the audience is surrounded by a robust hypersonic sound shower. The sound pressure, at the position of the audience, can exceed the 70 dBA level. The water-separating unit that generates two walls of waterfall of approximately 40 m in length and 2.3 m in height face to face creates a corridor like "the path of Moses" between the walls. People passing through the corridor (performers, etc.) are completely surrounded and soaked by tremendous hypersonic sounds of waterfall sound (FIG. 54). "Ecophony Gaia" composed originally for the system using environmental sounds of tropical rainforest, folk instrument sounds, such as Gamelan and jegog, electronic instruments and human voices played by 6 channel multi-track sound induces tremendous hypersonic sounds to many audiences. Such a performance strategy was quite effective to attract visitors to the exposition, and the water performance drew attentions of 6.7 million audiences, the largest in all pavilions in the EXPO '90 and the performance was quite successful.

Figure 55:
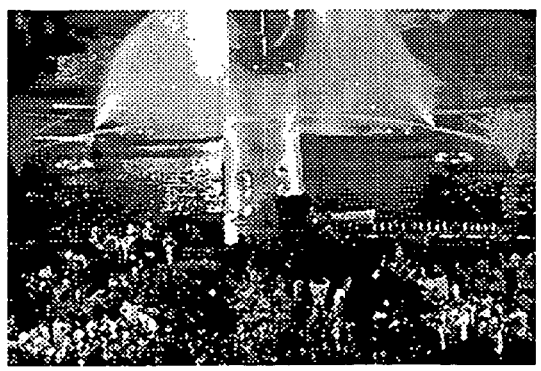
FIG. 55 is a photograph showing an application example of the sound environment design which is suitable or comfortable for a brain, illustrating EXPO '90 National Holiday Large-Scale Outdoor Play, Landscape Opera "Gaia".

Use of water as a sound source is one of the most effective ways of activating the core part of brain by the hypersonic effect. However, a single use of water can just enhance the amenity of the environment. However, when the movement of water and sounds emitted from the movement of water are integrated in a higher level under a special and total arrangement of sensitivity information, such as music and other sound object d'art, light performance, and macroscopic transformation in terms of time, the information environment will make an abrupt change and the sense of celebration or trance of celebration can likely be realized. The hypothesis was evidenced by a great success of "Alef". The landscape opera "Gaia" is a good example of realizing the sensitivity reaction of celebration among infinite number of audiences (FIG. 55). The opera was the largest event for the EXPO '90, and the performance was based on the water sculpture "Alef" and original music "Ecophony Gaia". The music was also used for controlling water. At the center of the exposition site, several hectare of space was reconstructed into the performance space merging the stage and audience space, and the opera was a grand spectrum of approximately 1,500 performers, approximately 50,000 audiences per stage and total performance time of approximately 2 hours. The sound was composed of pre-recorded music, environmental music, live music performance, water sounds full of ultra high frequency and fluctuations generated by the water performance system, and special effects (fireworks and pyrotechnic products). Light and laser beam performances are added to the sounds. The "Gaia" was a proposal of new musical play in a form of a <landscape opera> that the entire landscape performs the mass play consisting of water performance as a main tool of effects and multiple special effects.

As its title shows, the theme of "Gaia" was to depict from the birth of the Earth, conflicts between nature and civilization caused by human being, destruction of the Earth environment, and enlightenment of human being and hymn to the Earth. The sound effects synchronized the visual expressions to show astronomical images including eruption of volcanoes and crustal movements, the primitive tropical rainforest and the life of hunting and gathering, and classical and contemporary wars. The entire performance was highly symbolical, sometimes acoustic sounds with a massive sound pressure was shown in combination with the electronic sounds and a colossal augmented reality space of inseparably combined truth and false was representationally presented. Among them, the acoustic sounds emphasized by impulse waves generated by a ultra high frequency vibration emitted from the water performance system and detonation of pyrotechnic products and the hypersonic sound of merged live and recorded musical performance stimulated strong sensitivity, supporting the performance effect of this opera from non-linguistic and unconscious dimensions, which are the basis of the success in intoxicating both performers and audience.

The next example is "Natural Mandala" exhibited in a major art museum where acoustic sounds of healing and comfort was provided in a space of art exhibition in which visual stimulation plays a main role. In the exhibition space, ultra high-density highly complex environmental art was displayed using full of aromatic natural materials. The baseline was the slightly emphasized environmental sounds of tropical rainforest and water sounds of a broadband recordings as the essential sounds, while as the fundamental sounds, various music and sound object d'art used as the hypersonic sounds were so constructed that these sounds were faintly mixed at a distant landscape. The flow of the sounds was set by the SMPTE time code and led the light performance in a synchronized manner controlled by computer. The light performance was led by such indicators as the space distribution and transformation of illuminance, space shift of the highlighted areas and time course change of color temperature. With the integration of all the above effects, it aimed at realizing healing and comfort to both physiological and sensitive levels. The aim was effectively fulfilled and many visitors to the museum stayed longer time in the exhibition space. The dynamic state measurement data showed that people stayed in the exhibition space longer by 3 hours than in other spaces in the museum.

Figure 56:
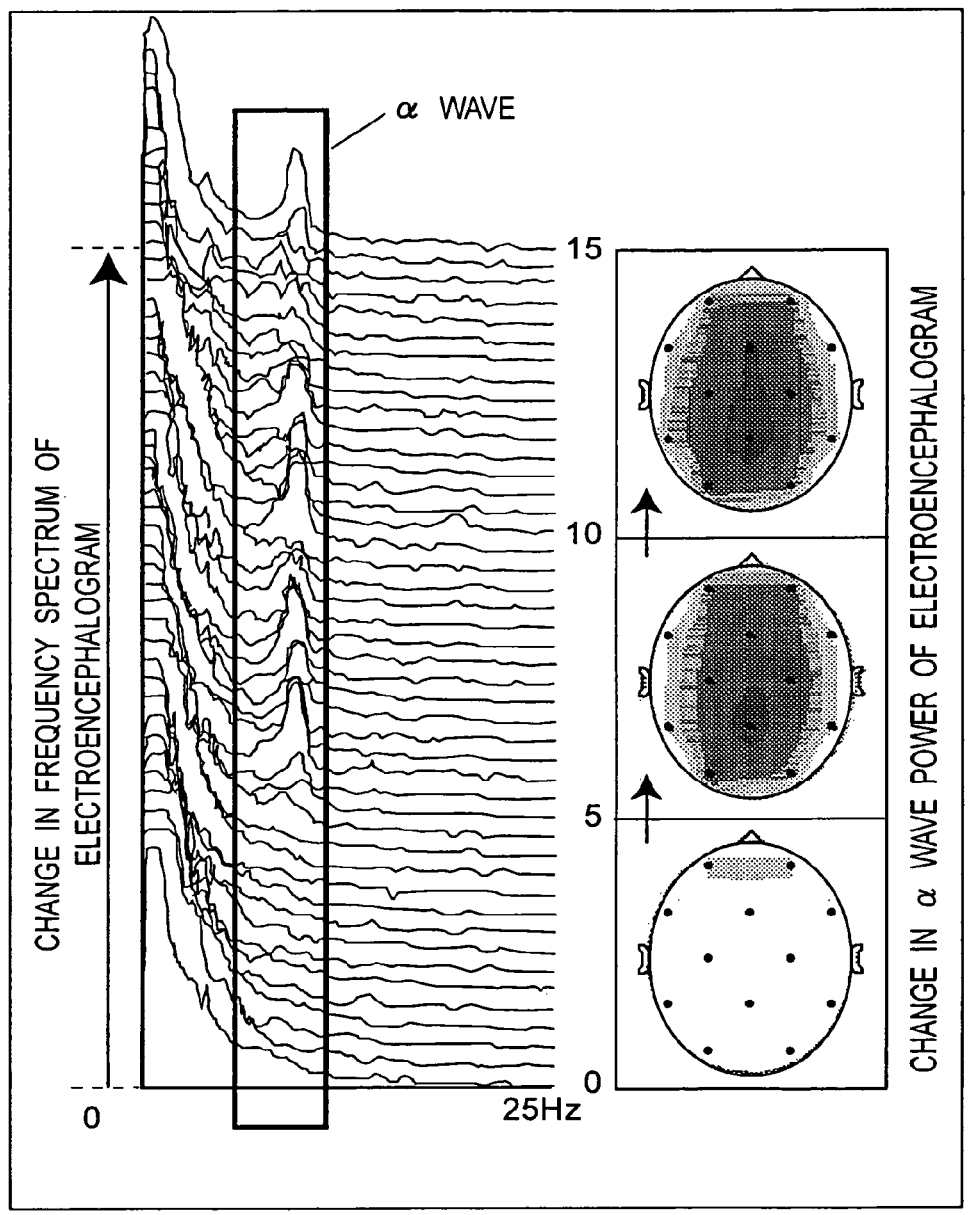
FIG. 56 is a chart showing an application example of the sound environment design which is suitable or comfortable for a brain, illustrating transitions of the electroencephalogram a which reflects an enhancement in the activity of a cerebral stem portion in the media art "Wianter Healing" audio and visual process.

The example of the "Echoscape Wianta Healing", a media art generating healing effects by the concept of "Natural Mandala" transplanted into an ultra high-density audiovisual electronic media. This is a 15-minute work made by editing and arranging the high definition motion picture of arts exhibited at the "Natural Mandala", so that the healing effects can be enhanced to the maximum by synchronizing the picture and the baseline sounds. The baseline for the entire media was set to the music composed as the hypersonic sounds for the "Natural Mandala", which was used as they are as the essential sounds and fundamental sounds. The sounds and motion pictures were presented to viewers comfortably seated. An example of the trend of activation of their core part brain network and the $\alpha$ wave activation of the electroencephalogram as an indicator of the degree of stress-free is shown in FIG. 56. As shown explicitly in the Figure, first of all, they were under a state of strong stress, and thus their $\alpha$ wave was not active. After 5 minutes of listening, the $\alpha$ wave became significantly in a dominating position, and in 10 minutes, the power of the wave reached to the maximum and the state was maintained.

"Sony Mediage Atrium" will be described next. At the center of a commercial building, an acoustic environment of a gigantic atrium was produced. With the area of 700 m$^2$ and 40 m in height, and consisting of 6 layers of gallery, its interior design level is quite high. The space is the center of observation and stay of guests. Therefore, a concept was designed to collect as may guests as possible to this building by providing them a place of comfort and amenity. In doing so, a hypersonic sound space was created where the space design structure is added by artistic flavor to appeal to guests hypersonic effects with symbolic functions consciously and unconsciously. By forming an impression of comfortability and pleasant feelings, it is planned to invite guests to this newly constructed building. The 3D space was constructed by installing a 6-channel system consisting of 3 lines and 2-channel stereo system, by three-dimensionally arranging them at front and rear, right and left and up and down side of the space to form each stereo system as a separated system. The 6-dimensional sound source was created by editing natural environmental sounds by adding the environmental sounds of more than one tropical rainforest, acoustic sounds of central- and east-Europe as essential sounds. A 2-channel stereo recording of ceremonial chorus of Orthodox Churches, and sound effects of electronic sounds analogically treated and synthesized are added to the sound source to make 6-dimension structure. These sounds are replayed by 3 hypersonic SACD players with reinforced ultra high-frequency range characteristics. The output signal is individually controlled by a matrix signal controller and outputted through 4 lines and 146 speaker systems. Each set of the system is driven under unique signal mixing conditions. The whole set of the system is quite effective in enhancing the reality of the sounds by providing all-around stereo images at the corridor, escalators, benches and all the other places.

Figure 57:
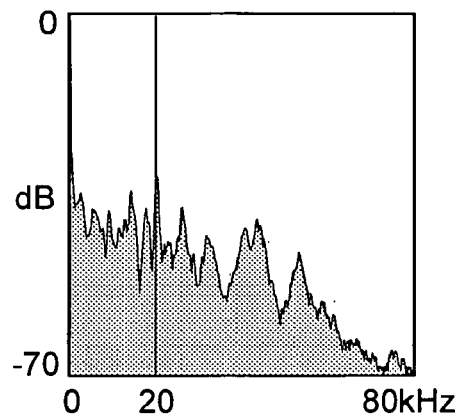
FIG. 57 is a chart showing an application example of the sound environment design which is suitable or comfortable for a brain, illustrating a spectrum indicative of a sound environment of Sony Mediage Atrium.

The system components, such as electronic circuits, speakers as well as cables and other materials, are finely selected so that ultra high-density highly complex and highly transformable nature of the software are converted into actual air vibration to a higher degree (FIG. 57). This is why the acoustic space provides not a small number of people with a beautiful and comfortable reality that they have never experienced. The commercial building enjoyed 10 million visitors in the first year, well above the target of 6 million visitors. One of its great contributors may be the structure of the acoustic space.

"Hypersonic Music Box" will be described next. This was developed as a generator of direct sounds not by way of electronic system. Focusing on the metal sound generating system of a disc type music box, and with a cooperation of Sankyo Seiki Manufacturing Co., Ltd., a music box manufacturer which has a unparalleled technology in the world, a vibration generation mechanism and an acoustic processor that is not found in a classical system were developed to produce a workable sound source as actual music box. The system generates hypersonic sounds of a quite appealing nature containing ultra high frequency component of 120 kHz abundantly and produces very complex fluctuations. The visual design is quite sophisticated, and it is highly expected for applying it for various applications, though it has just been marketed (FIGS. 21, 22 and 58).

9. In the previous chapter, some examples of <brain-friendly acoustic environmental design> based on sound ecology were presented, each of the examples has a different tendency from the others. The similarities among them include that all of them use ultra high-density highly complex, highly transformable sound baseline of essential sounds, and that they are all freely developed under a quite flexible framework in terms of both formalities and contents to cause effects. When they are compared to the conventional approaches of connecting humans and sounds, "Good Sleep Studio α", "Echoscape Wianta Healing" and "Hypersonic Music Box" are categorized to passive musical therapy, while "Natural Mandala" belongs to BGM/environmental music category, and "Sony Mediage Atrium" belongs to acoustic (soundscape) design. However, in terms of the contents and effectiveness, there may be a trend of not a small gap among them. In many cases, the results often show a significant difference of effectiveness against the examples done by conventional approaches that are measurable, analyzable and assessable by certain indicator, and that have similar direction of targets.

However, there are important problems to be noted. That the existence of sound baseline of tropical rainforest, or ultra high-density complex and highly transformable <brain-friendly acoustic environmental design> shows such a significant effectiveness may, strictly speaking, not be applicable to the concept of "betterment" or "improvement". In terms of original acoustic environment fit for human genes, it may be the evidence that the "brain-friendly acoustic environmental design" and its outcome made it clear that our living environment places the air vibration that should be the original form of <essential sounds> under destructive conditions. In other words, it should be understood that the effects of hypersonic sounds as the sound baseline just contributes to "retrieve" the original state, or to "cure" modern diseases, rather than bringing "betterment" or "improvement". It should etch the shape of the existence of a pathology of "lack of essential information" that sounds of urban areas have, which are still likely to have unsolved portions of problems even after treatment by the conventional acoustic environmental improvement measures as a negative picture of the effectiveness of the hypersonic effect-applied brain-friendly acoustic environmental design.

<3-4-3> Environmental Grand Design Sought by Genes

1. The <brain-friendly acoustic environmental design> derived from sound ecology showed an epoch-making effects in producing harmony between sounds and humans using a strategy of constructing an acoustic environment with the baseline as <essential sounds> of tropical rainforest-type information structure that nourished human genes. Then, can the acoustic environmental issues make an approach to the ultimate solution by keeping going to such directions? The inventors tried to a series of experiments on this point.

First of all, the α wave of the electroencephalogram of the subjects was measured while they were listening to audible sounds of Gamelan of Bali and viewing slides of still pictures of tropical rainforest of different resolutions. The power of the α wave started to increase as the resolutions of the pictures grew better. Surprisingly enough, the trend continued even when the resolution reached to a level beyond the subjects' eyesight measured by the Landolt Ring test. As the contents of the still picture changed from geological patterns to complex fractal patterns, the power of the α wave grew larger. This means, just in the case of sounds, the more the optical information stimulating the eyes of the subjects makes a shift from a simple urban style information structure with low-density to a complex tropical rainforest type information structure with ultra high-density, the more brain is activated. The inventors named the phenomenon of brain activation by ultra high-density complex information structure beyond the limitation of perceptions, not limited to a sound, as <Hyper Real Effect>.

Figure 60:
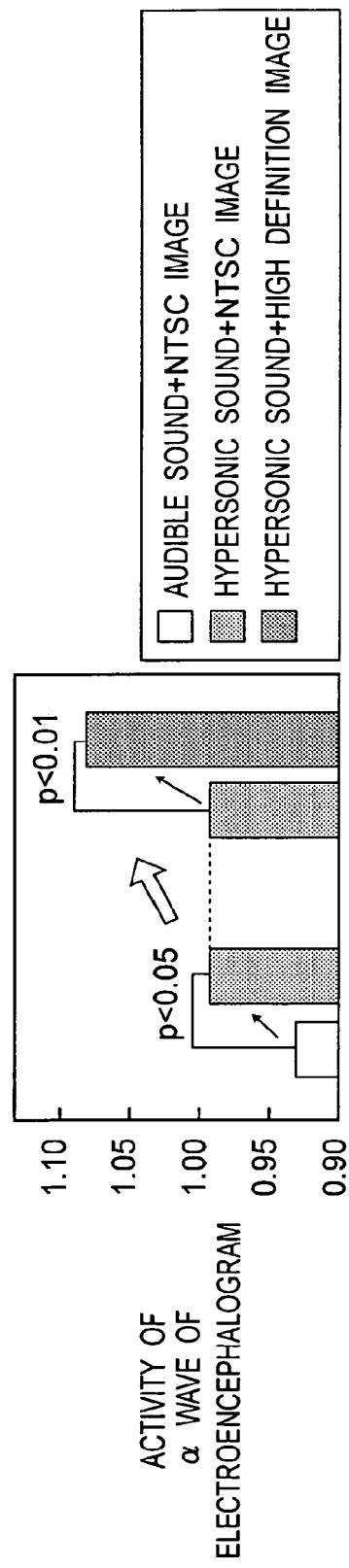
FIG. 60 is a graph showing that a brain activity is enhanced when a density of a sound is increased upon watching a video image, and is further enhanced when an image density is increased more greatly.

Next, the power of the α wave of the electroencephalogram was measured when subjects listened to audible sounds only while viewing a standard NTSC formatted video motion picture followed by the measurement of electroencephalogram while they were viewing the same motion picture while, this time, listening to the same sound under the hypersonic sound state having ultra high frequency. As a result, as expected by the inventors, their α wave power showed stronger when they listened to the hypersonic sounds than when they listened to audible sound only even what they viewed was the same motion picture, indicating that the hypersonic sound works to them as a brain-friendly sound. Then, what will happen when they listened to the sound containing ultra high frequency, while, this time, viewing not a standard NTSC formatted one, but a high-resolution high-definition formatted one? When the resolution density of a picture is raised, the power of the α wave is also amplified. This means, when a sound and light are getting dense approaching to the state of tropical rainforest type, more strong α wave power is exited showing such sound and light are the best match with brain, while in the case of either one of them getting closer to the state, the power of the α wave is less strong (FIG. 60).

As the present experiment suggests, it cannot be negated that the activation of our brain cannot all be controlled by information, such as sound, light, temperature, humidity and smell, when they are given through one single pure individual circuit but that it reacts comprehensively and in an integrated manner against those information inputted through all and every environmental perception circuit at one time. So as to be an "ultimately brain-friendly acoustic environment", all and every environmental information in addition to sound will need to be in a form of tropical rainforest imprinted in the human's brain and genes. In applying <augmented reality> designated currently by sound ecology as effective methods for reconstructing the acoustic environment, it should be desirable that it sets the approach as broader as possible to make a comprehensive design of the information environment in total. Especially, the sound and optical information, two of the messengers from the remote environment, as shown in the previous findings, without any synchronization of both of them, it is difficult to obtain good results.

The total design of <brain-friendly> information environment incorporating the sound, optical and other information as a whole, or the <grand design of brain-friendly environment> means to draw a trigger of dramatic revolution to modern and contemporary environmental design in total just in a similar way as designing the <brain-friendly acoustic environmental design>. There, the possibility that significant part of conventional urban planning and dwelling design that are not effective in making brain function in an appropriate condition are reviewed or discarded as hazardous is not negated. Moreover, it could require drawing and implement a new design principle completely different from any theories and schools of the current urban planning and dwelling design.

In this case, the largest issue is the ultra high-density and complexity unique to the information structure of the tropical rainforest type. In terms of sounds, they are the frequency range wider by several times than audible frequency range and rich fluctuation structure of spectrum. In terms of light, they are the space density far above the human eyesight and diversified fractal structure. From the findings of the inventors' experiments, surprisingly enough, for both sounds and lights, when the information density is decreased to a perceptible level by humans, the receivers" brain activation clearly decreases compared to when it is in the state of ultra high-density beyond the human perceptible level.

These facts tell us that the health of our brain functions cannot be maintained by any information within level recognizable by our consciousness and perceptions, which is surprising enough. In other words, activation of our brain can only be maintained in good health with the existence of an ultra high-density complex and almost completely non-linguistic information world that is extended far beyond the consciousness and perceptions of human being. Under such an information world metabolizing in ultra high speed and in large capacity, at least, there is no room of low speed and low capacity <linguistic brain module> catching up to the same. In other words, the <hyper-real effect> that works strongly to human body and mind beyond the perceptions is controlled by the main body of non-linguistic brain and is placed outside of the Cartesian linguistic brain functions. For a dwelling cultural code of modern and contemporary Western Europe, including urban planning, such recognition means there have appeared a profoundly significant blank area. As the evidence of this, the low-density optical and sound information in the civilized dwelling space, especially in urban areas have already gone to a critical level, according to the findings of the inventors.

The brain reaction against synchronized sounds and lights suggests and requires the design and establishment of the "brain-friendly total information environment" viewed on the "brain-friendly acoustic environment" on the premises that the "brain-friendly acoustic environment" is realized in the maximum level. There, at least, sound and optical information as messengers from the remote environment should be placed under the state of the environment of highly complex information environment having time and space density far beyond the perceptible level, just the same as the tropical rainforest is. In addition, the messengers taking a role of contacting environmental information, such as temperature, humidity, air component containing aromatic chemical substances and ionic structure, should desirably bring messages closer to those brought by the tropical rainforest as much as possible.

The philosophy of designing a dwelling information environment that possesses seeds to respond to such requirements can be found in traditional homestead woodlands, spot gardens and tea ceremony room of Japan. However, it is difficult to find such philosophy in modern and contemporary civilizations or the Western civilization, which gave birth to them. In the following chapter, our discussion will be directed mainly to the remote optical (or visual) information.

2. In <villages> and <rural areas> their natural mode of evolution style, where the ancient human being settled as the simplest mode of living place after discarding their hunting and gathering life and left tropical rainforest, the way they are developed and designed is of highly spontaneous emergence and are easily reflected by the control of genes of original nature, which can be confirmed by our eyes. Under such dwelling environment, a separation from the limit of <brain-friendly original information environment> imprinted in human genes can easily be restrained. In many cases, the characteristics that biological "behavioral control by emotion and sensitivity" that effectively restores autonomously the inclination and fluctuation far away from the original characteristics are maintained. After the civilizations grew and people stepped into a framework of an urban style dwelling, such a control mechanism was significantly lost, and the information environment tended to be left floating while significantly decreasing the centripetal force against the environment imprinted in genes.

As Lewis Munford, who has a keen interest in people's dwelling, called "a city as a vessel of complex civilization", a city is an artificial melting pot as a center of materializing civilization. The progress thereof is, with almost no exception, a great deviation from DNA, a programming system recorded with human's entire biological activation or the original structure and functioning of human's brain, an information central processing unit, and leads humans to disharmony in terms of both material and mind. Backed by such mechanism, the conflicts between urban areas and the original characteristics of humans have shown in the history an attribution as if such conflicts are common throughout all civilizations. In this point, the inventors have opened the way to a new vision by introducing a framework of environmental informatics.

The major background of this issue is related to a bias inherent to urban areas beyond the restoration capacity to the original environment imprinted in human genes. One is a top-down mechanism, which forcibly separates us from the original characteristics through a pressure mechanism of authorities, powers and economic values. Another is a bottom-up mechanism that people inevitably run for survival, which sometimes expresses highly adjustable, or beyond that, self-destructive thoughts and behavioral program. Both compete or cooperate with each other. Sometimes one is superior to another. However, under the full-scale urban style information environment, most of the case, a flow to the original characteristics imprinted in human genes is interrupted, and a pathological vector backing the flow is amplified. In this diagram, the fate of the civilization and a city as its vessel is relieved.

3. When looking back the trend of initiatives in designing urban information environment in the Western civilization, to the ancient times, the medieval era and the early-modern era, mainly the initiatives were taken by the authority of the times in a unitary controlled manner, regardless of the type of such initiatives. More precisely, sensitivity designs were highly valued such functional elements as reigns over dwelling, defense, religious services, trade and entertainment, and such representation of authorities and powers or the indicator of wealth and cultural level of people as dignity, mystery, gorgeousness and flamboyance. Generally, the aspects as norms and symbols relatively tend to be prioritized for functions and applications, and sometimes contribute to degradation of sensitive information environmental quality. Most of them were environmentalized as optical information to appeal visually, and the role of sound information is limited in terms of time and space to <a bell of a church>, or others.

The principle of such an urban information environmental design greatly transformed in the early-modern era characterized by the bourgeois revolution and the Industrial Revolution. It was an outcrop of urban environmental design treating cities as a vessel of ever-developing civilization activities, and accepting priority to the functions and applications of the cities. Under the fresh recognition of "the society composed of a mass of free and equal individuals whose basic human rights are respected", people were allowed to design their own houses and buildings at their disposal as a natural matter of fact in terms of urban design, and this was reflected to the entire city. With the emergence of such conditions, unilateral control by the former absolute authority collapsed, and the priority to sensitive information environmental quality and integrated design were lost. At the same time, the correlations and harmony in design between a part and the whole was threatened.

As a typical case of this, <laissez-faire> commercial and industrial economy that new the industrial bourgeoisies acquired led by Adam Smith generated industrial cities, a new style of environmental design—or rather, de-designed architecture under the state of subordination to applications and functions. The new de-designed architecture filled the environment with smoke and soot and rumbling sounds. The degraded quality of the environmental quality as a result of early-modern economic and industrial activities gave a birth to social movements to retrieve the urban design from the hand of the principle of laissez-faire, triggered by the miserable conditions of the coke-filled cities of Great Britain. This was become a pioneering figure to the modern urban planning.

It is noteworthy that the concept of <urban planning> with a core idea of environmental control was probably an autonomous brake, first of its kind in history, against the principle of the inviolability of personal freedom, unconstrained expression including design or freedom of pursuing profits that the bourgeois revolution acquired. The brake mechanism drew the attention of people to material environmental issues to stop spreading of respiratory disorder and infectious diseases due to the pollution of air and water, the issue of dense population, and improvement of inferior working conditions of factory workers, and triggered an approach to solve them.

After the historical transformation of urban building, or taking-off to urban planning, various proposals were made as to the principles and methods of planning design based on the framework of various thoughts, aesthetics and values—or ideology in broader sense, and a part of them has been put into practice and up to the present date. However, most of the urban planning principles up to now were conceptualized well before the establishment of genetic determinism and the development of brain science, thus, like the existing acoustic environmental design, they do not possess a framework on the rationality of biological science supported by new findings. To this point, it is difficult to rely on it to produce "the grand design of the brain-friendly environment imprinted in genes" as sought by the inventors. Needless to say, they are filled with knowledge, idea and experiences, from which we should learn.

In the urban planning of modern Western Europe, the priority was put on solving individual emergent problems of material level relating to the health and survival of people, such as an efforts to separate noises of power equipment, smoke and soot that were filled in the cities of Great Britain from living space and a project in Paris to removing human excrement from people's living space. As those efforts and projects progressed, a concept of building a modern urban planning that incorporates comprehensive structure of urban areas was emerged. In the framework of the "concept of urban aesthetics" as a part of them, <information environmental design> called by the inventors, came to be included.

The modern and contemporary urban planning sometimes tends to show a certain idea or a series of methods as slogans and provide a kind of Utopia-like proposals based on a unique working hypothesis. Among them, what is classical but is highly appreciated even today includes <Garden City> by Ebenezer Howard and <Cities in Evolution> by Patrick Geddes. The two persons were considered as the fathers of modern urban planning. The model of Howard, especially, considers well the nature of humans as a living creature, and underlines sunshine, fresh air, pure and plenty of water and natural beauty. As to sounds, there are no norms or materials in his model indicating that he might consider them.

Another model that left a great impact on the thought of the world urban planning, except for Howard's Garden City is Le Corbesier who proposed <City Planning by Functionalism>. In contrast to Howard, he stood on the quite affirmative and optimistic attitudes toward the civilization of science and technology, and proposed <purism> demanding an image to machines. His activity tended to be a type of partisanship, ideological and eloquent. He established and led the Congres Internationaux d'Architecture Moderne (CIAM) as his home ground to disseminate his thought. It was one of the epicenters of inorganic design having a simple form expressed functionalism, which was frequently seen in the architecture of the latter half of the 20th Century, and abolished fanciness. There, all the information environmental quality and effects of biological information science were almost out of scope, and they stood thoroughly on design grasped purely from the viewpoint of activation of materialism and applications.

CIAM's "Athens Charter" defines their idea of functions of cities in the four items of dwelling, working, entertainment and transportation, and fulfillment of all of the four items were regarded as the objectives of urban planning. The framework lists the sun, air and greenery as the conditions of a superior dwelling environment, and shows a similarity with Howard's "Garden City" in terms of concepts. However, in terms of practical design, they set a norm of a Greece-conscious geometrical pattern as the shape most appropriate to the machine civilization, and proposed a concept highlighted with lines and right angles. They produced an alignment of numerous monotonous patterns of gray boxes typically characterized by pilotis, rooftop gardens and geometrical patterns. As to sounds, there are no signs that a special interest is paid and guidelines considered to them, just the same as the models of Howard and Geddes . . . .

The setting of simple and straightforward functions that the City Planning by Functionalism possesses is, as typically shown in Le Corbesier's "A Contemporary City of Three Million", promotes separation of city spaces by function, with each of them having a single function in a historical and international horizon, which reflects uniqueness in the modern and contemporary civilization. The "definition of space territory" led by such mono-functionalization of city functions often reflects bipolarization of environmental information structure. Such trend was first seen before the modern urban planning took place, and above all, it tends to make large-in-size and small number of forest parks scattered. The typical example thereof can be seen in Bois de Boulogne in Paris and the Central Park in New York.

4. The city structure to locate large-in-size and small number of forest parks is in the era of modern and contemporary age, universally seen. However, this trend should be said as having very serious problems, from the viewpoints of the inventors who has a viewpoint of "Hyper Real Effect", because doing so means separation of forests, a place of emitting brain-friendly ultra high-density highly complex information from the people's living place to which they are expected to cause physiological effects, and locating them unevenly and separately around the area. For the "brain-friendly environmental design", this means nullification of high quality information resources, which cannot be ignored.

From the baroque style in the early era of urban planning to the avant-garde design theory of the current times, or even in the plan targeting <forest city> in Tapiola in Finland, it should be noted that there are no expressed norms or scientific criteria on the information exchange between the forest environment information sources like trees and bugs and their recipient, humans, which are de-facto left to the hand of designers. Of course, in the recent times, the installation of a certain size of greenery area per unit area of land has been legally required so as to prevent the <heat island phenomenon>, due to all surfaces in urban areas covered by concrete and asphalt. There are still no viewpoints of biological science of best matching between information environment and human's brain as found.

The fact, indeed, is unavoidable, because the fact exists before the inventors proposed the idea of securing essential ultra high-density highly complex information environment in the living space, which is indispensable for the brain for healthy survival of humans. However, it is difficult to apply our <grand design of brain-friendly environment> functioned in the existing major urban planning as they are, which were developed in the era when such idea did not exist. This is because an idea of stopping separation between the information source and people as dwellers is still missing. Judging from the findings of an ongoing experiment by the inventors, in order for the sound and optical information from remote places to be brain-friendly messages, the density should be larger at least by several times than the upper limit of the perception density of human's auditory and visual organs, and special complex structure should be embedded in them as a requisite. The ideal information source emitting such messages, needless to say, is tropical rainforest. However, any forest not belong to it must be the information source having higher adaptability to human's brain than any other things.

In this case, what has not been consciously dealt with but nevertheless is extremely important is the serious fact that the sound and optical information of ultra high-density highly complex nature as sought by inventors' brain and emitted by ecosystem has only a small range of effective range compared to the size of any city. For example, a complex air vibration of 100 kHz or above as an effective "brain-friendly" sound information, can be easily attenuated as it is transmitted through air, which is a natural law. Due to this, while the vibration goes a distance of several meters, the ultra high frequency components may be attenuated to an ignorable level and decrease its effectiveness.

On the other hand, as to the optical information, plant organic structures composing of a forest consist of cells of the size of several tens of microns, and inside of them are <organelles> of less than 1 micron, which is made up of microscopic organic polymers. Their structure is, de facto, infinitely minute. The degree of attenuation per distance of transmission for optical signals, theoretically, is significantly small, compared to sound. However, for the patterns with significantly higher degree of complexity of its minute structure, a signal should be located at point-blank range of the recipient otherwise its structure stimulating the sensitivity of humans cannot be maintained. As the <air perspective>, an important drawing technique of traditional Japanese and Chinese paints tells, the air layers extended between a recipient and the origin of the signal decreases the degree of high-definition, brightness and saturation of optical information in proportion to its thickness. Thus, a picture of a forest distant away significantly loses its ultra high-density high complex characteristics as optical information, and due to this, it is difficult to expect such forest to enhance brain activity on the same level as the image of plants planted nearby.

In addition, the <high level> of brain activation stimulated by the tropical rainforest type ultra high-density highly complex optical and sound information, cannot maintain its level for a long time after the stimulation of input is lost, from the trend of the α wave power of the electroencephalogram, it is highly likely that it decreases to a <low level> and ultimately disappears in approximately 200 to 300 seconds. Therefore, after activating one's brain by the environmental information of an excellent forest, the activation will have disappeared completely by the time one returns home if the forest is distant away from his/her home.

Due to such mechanism, brain can stay in health and in activated state only when, strictly speaking, one is in the forest at all times and incorporate himself/herself with the ultra high-density highly complex information source. The same effects are not expected in a broad view or a distant sound. In this sense, the conventional urban planning that rely on time and space separation and scattering of urban environment information structure is barely in harmony with the principle of constructing the inventors' "brain-friendly environment". Even forests with high assessment, such as Bois de Boulogne in Paris, Grünerward in Berlin, Wienerwald in Vienna, and the Central Park in New York, all of them are separated from the dwelling space. To this point, the effectiveness of such forests should be said as having a certain great limit.

In the "grand design of brain-friendly environment", requiring ultra high-density environmental information requires, for both optical and sound information, regardless of artificial or natural ones, placement of the source at point-blank range. When introducing such conditions of the information environment, it is well understood that regardless of its entire information source being natural ecology system or the system with significant part supplemented with artificial ones, a significant part of the current urban and dwelling design should completely be redesigned.

One of the solutions to this is to construct an information environment based on the principle of phase space in which the entire structure is embedded into a part thereof. More precisely, all elements of the ultra high-density highly complex information environment including parks in a highly matured and highly ideal city are included in any small domains in the city, and highly distributed. This ultimately means realization of a forest type ultra high-density highly complex information environment in a private room.

5. Now, the summary of the <grand design of brain-friendly environment> is explained hereunder based on the phase space principle, though there are many overlaps with the acoustic environmental design.

First of all, it needs to be as close as possible to the environmental information of tropical rainforest of ever minute, ever complex and ever transformable nature. For this purpose, the most desirable thing is to construct a forest ecosystem of tropical rainforest. It is, however, unrealistic. As a realistic solution, when it is artificially supplemented, though this is tentative criteria, an ultra broad band air vibration with full of fluctuation structure supplied in the current urban environment so that the frequency thereof comes to at least 100 kHz or above at the place of the recipient as a sound source similar to actual tropical rainforest sounds. The frequency is equivalent to more than five times as large as that of the upper limit of audible sounds for humans, i.e. 20 kHz.

As to the optical information, a forest is the infinite minute existence, but in the case of supplementing it artificially by installing an ultra high-density wall with the view angle of 0.002 degree or below which is equivalent to five times as large as the fineness of space density visually distinguishable by human eyes as standard i.e. 0.01 degree applying the case of sound information, the tentative target will be supplying ever changing fractal structure information with the density approximately 10 times as large as the currently available high definition TV standard, subject to continuous examination for improvement.

In this case, there is one thing to note when the optical information is supplied through a video motion pictures. Usually and normally, optical input is made continually into the retina of animal eyes in terms of both time and space. Conversely, a video picture is in a form of discontinuous slide show so constructed that <scanning> is first made to draw a line from the left to the right of the screen and then it proceeds to downward consecutively to form a sheet <frame>. Then, the frame is redrawn approximately every one by thirty seconds. Due to the characteristics of afterimage of the human eyes, one just erroneously perceives them as a continuous input. Therefore, strictly speaking, it is required to develop a technology to record, transmit and replay a continuous picture in terms of space and time without any discontinued pieces of frame.

As discussed previously, the ultra high-density highly complex and transformable information can easily lose its various unique elements while it is transmitted through the air. In order to cope with this situation, it is desirable that an environmentalized space is realized in which, the source of information is located at point-blank range of 10 m from the recipient, if possible, or in real sense, approximately 5 m or below from him/her. So as to clear these problems in real meaning, the development of ultra high-density media technology that supplements the urban information environment by a transducer installed at point-blank range will be effective.

Secondly, it needs to secure the continuity of information in terms of time and space between inside of all-directional tropical rainforest information space and its neighboring space and fit the artificial information space to supplement or replace in to the all-directional tropical rainforest information space. For this purpose, as to the artificial supplement of sound environment having the highest all-directional sensitivity of all the information perceptions, it is desirable to construct a full-surround system by setting speakers right and left, up and down and front and left. The tropical rainforest has a characteristics of forming a continuous information space with no walls and doors that shield environmental sounds and landscape visually and auditory. Considering that blinking causes discontinuation of visual information, the requirements as to the adjustability with brain may not be so high. On the other hand, auditory is always in working conditions to all-directions. Therefore, a construction of a sound space in which sounds are not shielded even through doors, is desired with priority to visual sense. Next important thing is to construct a visual space a part of which is continuous. So as to realize this, it is difficult to cope with this just with the conventional design methods and experience of urban zone separation, building construction, interior structuring and contingent facilities. What is required is to think from a different angle and based on this, to develop a new design technique.

Thirdly, it needs to realize "a flow of environmental information that does not yield to termination or repetition", which is the characteristic of the tropical rainforest. In the environment of the tropical rainforest, no environmental information of the same structure and same time and space patterns will be repeated. The fact that our brain have evolved in such a tropical rainforest means that in the course of the evolution process, it has not experienced a repetition of same pattern accurately within a regular interval. Such an information structure should best be avoided. So as to ensure realizing highly the unrepeated total information environment in the high-density dwelling space in the urban area, the method shown for sound information above should be expanded to transform the actual tropical rainforest environmental information into electrical signals and replay it real time at a place with small time lag. In the case of the area that the time lag is not ignorable, one of the advanced way of solving this problem is to record the data in a data storage temporally to overcome the time lag, and continue distribution into the urban environment. A more simple way that is expected to be effective is to develop a system of more than one data replay system synchronized with each other so that each of their replay time comes to a prime relationship, this leads to that the repetition of environmental information including package media or <non-repetitious media technology> is avoided. This is an application of the technique developed for sound regeneration system stated above.

Fourthly, it needs to develop a method to comprehensively optimize the artificial information environment space in total to which electronic media is used. As to this, based on the principle stated in the third item above, all the environmental information in total including temperature, humidity, wind, air component, ion concentration and other physiochemical events and auditory, vision, olfaction and other sensitivity and emotional information are transformed into electric signal, which is then transmitted through a high-speed communication satellite or large-capacity network system in real time to the urban environment and regenerate them as information environment. This method can realize the objectives at an extremely high standard. Of course, the clearance of time lag by developing high-speed ultra high capacity multi-dimensional data storage will be greatly effective.

Fifthly, it is necessary to take appropriate measures to the reality, there is no guarantee that they are perfectly compatible with the nature of the tropical rainforest, even if an excellent artifact may be created. It should be said that realization of the tropical rainforest environment in the urban environment is quite difficult. Moreover, for the short- to mid-term perspective, the reality is quite low. The realistic solution here may be to realize a brain-friendly environment by using the artificially created supplemental information in combination with an effort to co-exist with nature. In this case, placing natural items having a certain degree of tropical rainforest information in the space may be imperative and at least safe. It is necessary to develop creation of a technology for co-existence of natural and artificial items are indispensable so as to avoid existence of brain-unfriendly artificial items peculiar to the urban environment. This issue is similar to the fact that the more synthetic foods we take, the more we need to intake natural foods.

For this purpose, it will be effective to develop a natural high-density sound source that vibrate real time in the space, and to find a way of editing, distributing, and replaying technology that do not require encoding of electronic environmental information. More precisely, the expected is the use of hypersonic music box that directly emit ultra high frequency and water sounds full of fluctuation, development of "acoustic sound source" that is something similar to organic foods, hyper analog technology that does not require transformation to discrete symbol systems, for example the development of motion picture transmission system free of discontinuation by digitizing and of separation in terms of time and space of field and frame that current electronic motion picture possesses.

In addition to this is the development of a dwelling space in which actual natural creatures (plants and bugs included) are organically incorporated within a close distance which may be an issue of high novelty. As its technical resources, as previously mentioned, what are focused on are traditional homestead woodlands, spot gardens and tea ceremony room of Japan. The target is to develop a method to connect the design principles of them and those of designing cities and streets, buildings, and interiors merged with high performance media information technology, and utilize it to produce fruits.

Under such concepts, the inventors will brush up the "grand design of brain-friendly environment imprinted in human genes" and try to spread sounds as a new environmental design paradigm.

6. Considering the past, the mode of urban dwelling that have been nourished as a vessel of modern and contemporary civilizations are highly matured as "material civilization" whereas it is still in a primitive stage in terms of "information civilization" which reflects strongly that the current civilization of science and technology is in a state of asymmetry requiring further development. This is not completely unrelated to the fact that our world was split in two worlds of material and mental worlds based on the Cartesian dualism. Based on this, hardware, belonging to the material world has secured effectiveness, safety and reliability after repeated refinement, by basically standing on scientific and rational attitudes through science and engineering and industrial technology their products of location, materials and structure. However, in the material world, the recognition in relation to the mental world should be excluded based on the dualism.

On the other hand, in terms of software belonging to the Cartesian mental world, based on the same dualism, the principles of "artistic agency" and "freedom of creation" are applied to the design, landscape, sound environment (excluding noise reduction regulations) and other design works of exterior and interior of cities and streets and buildings. However, it has been in the place where it has not have any relationship with a concept of the compelling requirements of protecting people's lives and of guarantee of security. It is still in the stage of conceptualization in which the "information environment" as a concept of biological science and its assessment has not been recognized yet. Except for dynamic structural and functional requirements, it will never be asked what the effectiveness, safety and reliability in terms of biological information science are, or in other word, what the "friendliness toward genes and the brain" means. There, consciousness and its material, low-density simple linguistic information that can be perceived and recognized are too much valued, whereas it has discarded or forgotten high-density non-linguistic information beyond perception. As long as the thought of the modern and contemporary design is applied to urban planning and construction of buildings, it cannot be expected that an action mechanism prevent the density of the environmental information and the complexity from decreasing to the level that is dangerous to the brain function.

Let us see how the negative assets of Descartes have dissociated modern cities from the "brain-friendly environment imprinted in human genes", from the perspective of low-density optical environmental information. The origin may be traced back to the era when Josef Buxton designed a structure made of iron and glass, <the Crystal Palace> for the Great Exhibition held in London in 1851. From an ideological view, a geometrical abstract design that stresses functionality and materials and discards fanciness, was promoted by Walter Gropius with Staatliches Bauhaus in Weimar in Germany one of the centers of the activities, in the first half of the 20th Century. Their activities were so practical and greatly influential. Ludwig Mies van der Rohe, the last principal of the Bauhaus advocated the famous slogan of "Less is more" to show his clear support to low density optical information environment. The thought of Bauhaus was succeeded by "CIAM" home ground of Le Corbesier in a way that is more radical. After the World War II, monotonous "gray concrete cubes" were forested in the urban space of the Western civilization zone. It cannot be negated that the simple and inorganic having geometrical design and discarding fanciness sought by the functionalism, significantly decreases the density of optical information environment appealing to human eyes, and had an expansion effect of disharmony with human's brain.

The <post-modernism> design appeared as a necessary reaction against the "concrete cube" as a symbol of the functionalism called for departure from such geometrical inorganic design of less information, as shown by the criticism by Robert Benchley, an architect, who said "Less is bore" spoofing the saying of Ludwig Mies van der Rohe, "Less is more". They directed themselves toward a departure from monotonous geometrical form of buildings, cities and streets, and introduction of historical architecture including revival of fanciness. Thanks to the CAD (computer aided design) that was in practical use in the latter half of 1970s as a tool to quite easily design complex structures, the trend showed a diversified and variety of developments. However, they mainly focused on macroscopic shape of exterior and interior of buildings, as shown in the residence of Robert Benchley having a complex shape on its roof (designed by Robert Benchley) and the AT&T building in New York (designed by Philip Johnson) having gables with a flavor of Telesterions in Greece, both of which shows a clear difference with the functionalism design. On the other hand, as to the microscopic domain of space beyond the limitation of perception, the post-modernism just stayed in the limitation of "the loss of urban environment with ultra high-density optical information that enhances brain function" which is peculiar to modern and contemporary urban planning and buildings, and stays in a paradigm completely unrelated to an action to retrieve the same.

7. In summary, in modern and contemporary urban planning and environmental measures, establishment of all sound environment (including acoustic design by soundscape) excluding noise pollutions that is under regulation now, and the paradigm of all the optical environmental design including landscape, molding and decoration have never asked of physiological effectiveness and safety as software belonging to other than science. However, from the viewpoint of findings from the new brain science and environmental informatics, for example <an equivalence model of substances and information> and <programmed self-demolishment model>, even software cannot negate any more a chance that it will not cause physical and mental disorders and life-threatening events, if and when it relies totally on the artistic and aesthetic facultativity. Urban software is now in the stage that it is designed and constructed by a scientific and rational procedure on the par with urban hardware to start swiftly to a system that the effectiveness and safety thereof can be scientifically foreseen and assessed.

However, on the other hand, it cannot be negated that this greatly violates the modern and contemporary knowledge structure and social structure reflecting it, which started from the Cartesian dualism, which strongly governs every corner of the modern society. It is now essential to develop the thinking and conceptualization tool that will support such a high hurdle being cleared as swiftly and smoothly as possible. As one of such measures, the paradigm of <grand design of brain-friendly environmental environment imprinted in human genes> is worth being examined with high priority, the inventors believe.

The reason is because the way the brain or material existence of protecting life is put on the center of interest on the stage of <genetic determinism> as a characteristics of this paradigm is especially useful and effective in conquering the Cartesian dualism or making it nullify forcibly. From the psychological world, negating that brain is an organ that practically controls emotion, reason, sensitivity and other movement of mind is empirically and under normal social conventions, impossible. It may be said that to negate this fact has, de facto impossible now for anybody who believes in the though of Edmund Husserl, a phenomenologist who tries to believe <consciousness> only, or who sympathizes John Carew Eccles, a neurophysiologist who abided by mind-body dualism. At the same time, the inventors are in the era when first in history, brain science can be practically utilized. Throughout the 20th Century, an analytical research has been developed through the empirical study using brain damage as a material and electrophysiological methods based on a firm foundation such as detailed study of anatomy. The great advancement of neuromolecular biology and noninvasive brain function analysis opened a way that, brain, formerly in an ultimate black box, can be a subject of scientific approaches. As a result, data and materials to understand the structure and functioning of brain in a rational way have been greatly accumulated. The development of brain science, along with the development of electronic information technology science, is greatly shifting the modern and contemporary civilization of science and technology that have reached its height in a form of the <material civilization> into the side of the <information civilization>. Under such background, it may be time to bring the "grand design of brain-friendly environment imprinted in human genes" on the stage as a new historical issue.

Approaching to the pathology ultimately suffering urban hardware and software as a vessel of the civilization from both theoretical and application point of view and to regenerate or, rather, revive the information environment that is shifting toward urbanization while undergoing destruction means itself to revise the modern and contemporary academic, artistic and technological system and to explore a new way conquering the limit inherent in the same. It will regain the balance between and merge the explicit wisdom of modern and contemporary civilization composed of the wisdom of analysis, the wisdom of logics, the wisdom of communication, and the tacit wisdom of traditions consisting of the wisdom of experience, the wisdom of comprehensiveness, the wisdom of intuition and the wisdom of insight and will be an approach to reconstruct the activity optimized to human genes and the global environment. As a whole, it is exactly to get rid of exclusive adoration to and belief in the linguistic brain function that has governed the modern and contemporary civilization, and to retrieve non-linguistic brain function, or rather the original function of brain to its due original position, by which the activity of brain can be retrieved.

The aspiration of the inventors to retrieve the environment to the original state of the beautiful environment of the good old days will be identical to pioneering a new civilization by conquering the limitation of the modern and contemporary civilization in this way.

Imperial Example 1

A behavioral assessment method for "hypersonic effect" in accordance with the implemental example 1, will be described below.
1. Introduction
Sound which exceeds the audible spectrum for human beings and abundantly contains ultra-high frequency components (HFC) with unsteady fluctuation enforce the $\alpha$-frequency components ($\alpha$-EEG) of the spontaneous electroencephalogram and increase local cerebral blood flow in a deep part of the brain structure to allow sounds to be perceived by the ears more comfortably. The inventors of the present invention call this phenomenon as "hypersonic effect" or "HSE". In order to investigate the phenomenon more easily, the inventors of the present invention has developed a sound source for stably causing HSE and a reproducing system. In order to make the system easily available for those who hope to research HSE and assist further research on the phenomenon by those who are interested in it, the inventors of the present invention have developed their research for 15 or more years. They have often reported details of an experimental method of their own. In this description, an HSE behavioral assessment method using the comfortable listening level (CLL) as a parameter will be reported.

In the research of HSE, it is important to note that many unknown factors such as an HSE appearance mechanism exist and many aspects cannot be grasped by using knowledge and technology on conventional auditory physiology and acoustic psychology. For example, in an experiment using an $\alpha$ wave as a parameter, while sounds were presented, the $\alpha$ wave gradually increased for a few tens of seconds after the presentation of the sounds and after then, remained for about 100 seconds. When this asymmetry in terms of time is disregarded, distinct results cannot be acquired in most experiments. Therefore, in designing an HSE experimental procedure, it is necessary to consider time delay and persistence in this phenomenon.

2. Assessment Method Using Behavioral Reaction as Parameter

There is an only minor sensory difference in sound quality between sounds which exceed 22 kHz and contain unsteady HFC (full range sound: FRS) and the same sounds as FRS except that the above-mentioned HFC are removed (high cut sound: HCS). This difference is subconsciously reflected in the unconscious selection in preference of the listener to the sounds while the listener hears the sounds for a certain time. In some cases, it is effective to apply a method using a non-linguistic behavioral reaction to detect a delicate sound quality difference in a boundary between consciousness and unconsciousness. The inventors of the present invention have applied such method to their researches on HSE.

There are some methods of assessing sensitivity of human beings to sounds by observing active actions of the listener. For example, these methods include (1) acoustic menu, (2) sound source block method and (3) listening level measurement. The former two methods include a procedure in which a subject himself/herself spontaneously switch or finish presentation of sounds at any time. For this reason, an influence of the delay and persistence of HSE cannot be disregarded in experimental results.

On the other hand, since the assessment method using the listening level does not cause the above-mentioned problem, the method is considered to be suitable for the research on HSE. Prior researches by the assessment method using the listening level demonstrate that the listening level is affected by some factors such as reality of input information, physical structure of an acoustic signal and the sense of the listener relating to comfort and discomfort. In addition, the experiment using the listening level as an adjustment means is easier to implement than the experiment using a physiological means. Since the listening level can be assessed under almost the same conditions as those in the prior researches on HSE, the assessment using the listening level can be performed in parallel with physiological assessment and psychological assessment.

In consideration of the above-mentioned matters, the inventors of the present invention have designed an experiment method based on the measurement of the listening level obtained from behavioral response in adjusting the sound volume under conditions of FRS and HCS.

Figure 61:
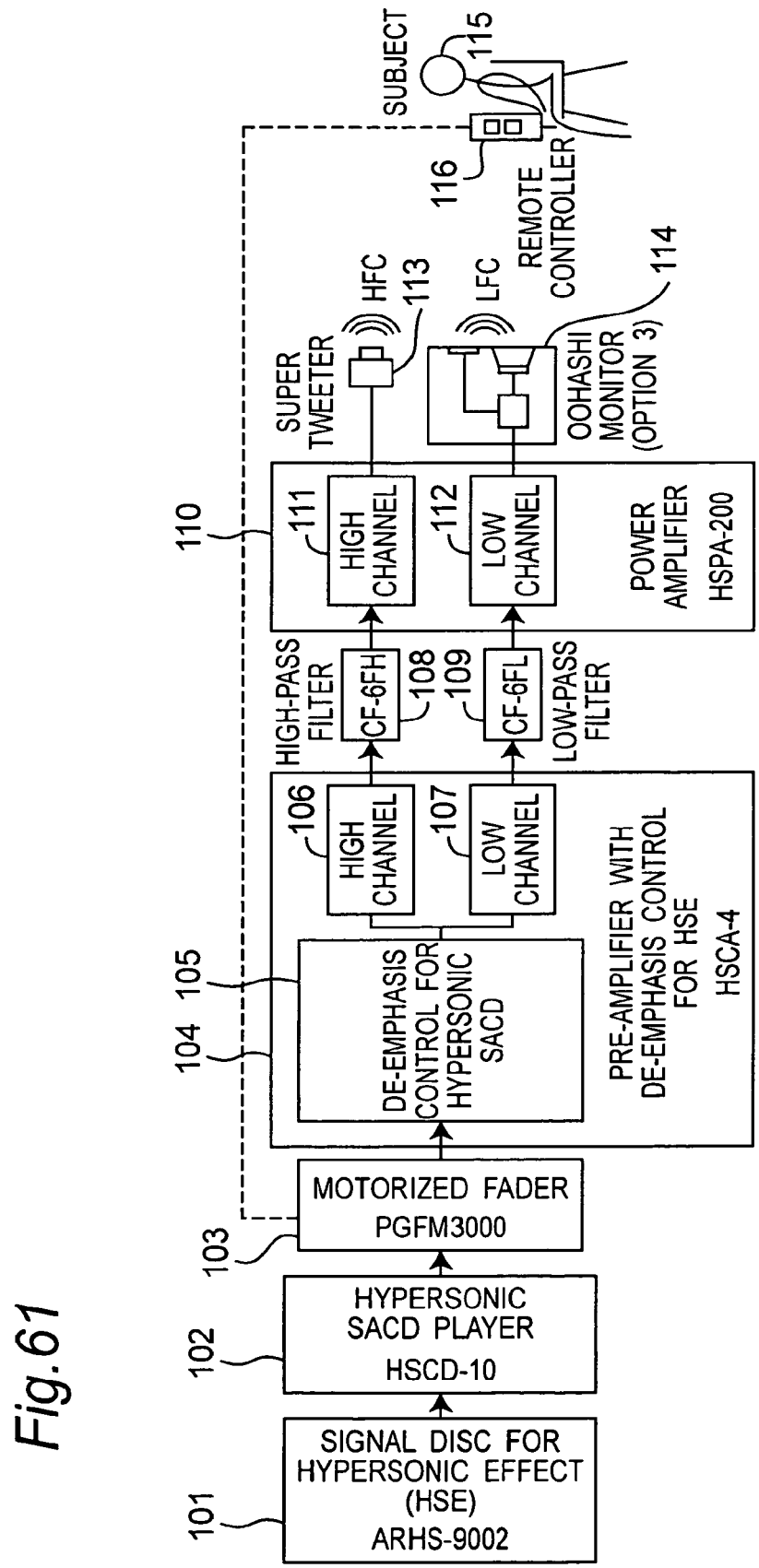
FIG. 61 is a block diagram showing a system for evaluating a behavior using a hypersonic audio system.

3. Behavioral Assessment Method Effective for HSE Detection 3.1 System Structure A sound presentation system used in the HSE research needs to have an excellent frequency characteristic exceeding 100 kHz. For this reason, a sound presentation system based on a high-speed sampling one-bit encoded signal processing method, introduced by Yamazaki, (authentic hypersonic audio system, Action-Research Co., Tokyo Japan) was adopted (FIG. 61). This system is configured as a bi-channel reproducing system capable of avoiding various kinds of confusion when comparing sound quality.

Each subject 115 was asked to adjust sound volume by using a self-made remote controller 116 equipped with an up-down switch. The remote controller 116 controls a motorized fader 103 (PGFM3000, Penny & Giles, Gwent, GB) inserted between a super audio compact disk (SACD) player 102 and a pre-amplifier 104, and this controller was used for a visual or tactile hint to the volume of the amplifier that might not affect the action of adjusting the listening level by the subjects 115.

Using an integral sound-level meter (LA-5111, Ono Sokki Co., Ltd., in Yokohama, Japan), an equivalent continuous A-weighted sound pressure level (equivalent sound level: $L_{Aeq}$) was measured. Since ultra-high frequency components exceeding 20 kHz do not fall within a range of A-weighted measurement values, the presence of the HFC exceeding 22 kHz does not influence the measurement values. In fact, when the same sound volume was set, according to the measurement by the inventors of the present invention, FRS and HCS reproduced by the system caused the almost same measurement value with an error smaller than 0.1 dB ($L_{Aeq}$).

3.2 Sonic Material

Figure 62:
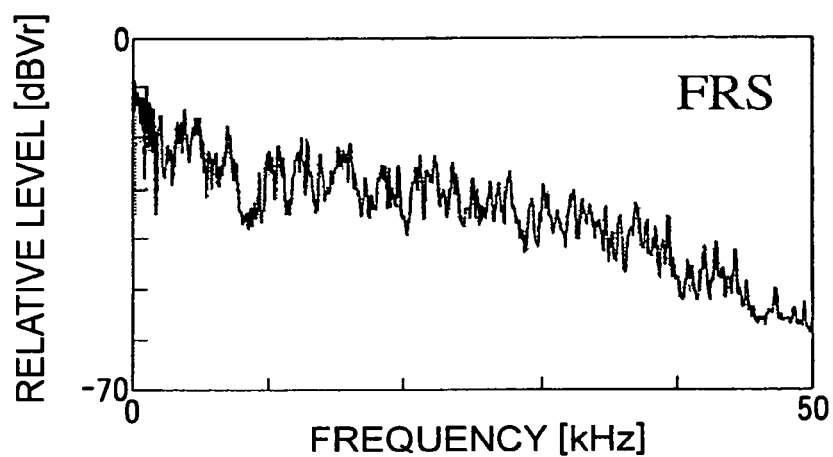
FIG. 62 is a spectral chart showing a power spectrum of a sound material, that is, an FRS (full range sound).
Figure 63:
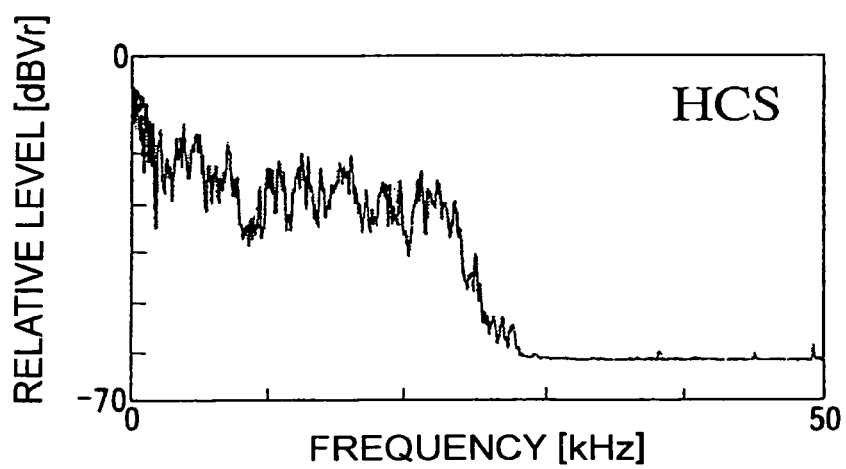
FIG. 63 is a spectral chart showing a power spectrum of the sound material of FIG. 62, that is, an HCS (high cut sound).

As a sonic material (or sound source) for the present experiment, Gamelan music in Bali Island, Indonesia was used. This sound source was recorded in a track 43 of an authentic signal disk 101 (ARHS-9002, Action Research Co., Ltd.) developed with the hypersonic sound system. Using a high pass filter 108 and a low pass filter 109 (CF-6FL/CF-6FH, NF Corporation, Tokyo Japan), which have the cutoff frequency of 22 kHz and the cutoff attenuation (attenuation slope) of 80 dB/octave, the sound source was divided into HFC higher than 22 kHz and low-frequency (audible band) components (LFC) lower than 22 kHz. In the present experiment, two kinds of sounds of FRS and HCS are presented. FRS consists of HFC and LFC presented at the same time, whereas HCS consists of only LFC. The last 60 seconds of the track 43 were repeated six times consecutively. FIG. 62 and FIG. 63 show an average power spectrum for 60 seconds of the two kinds of sounds.

3.3 Subjects

Eight non-handicapped subjects attended the present experiment. For ensuring a satisfactory awakening level to measure subtle biological reaction of the subjects' behavior with high accuracy, the subjects were asked to sleep at least seven hours the day prior to the experiment and wake up at least two hours before the start of the experiment.

3.4 Procedures

Figure 64:
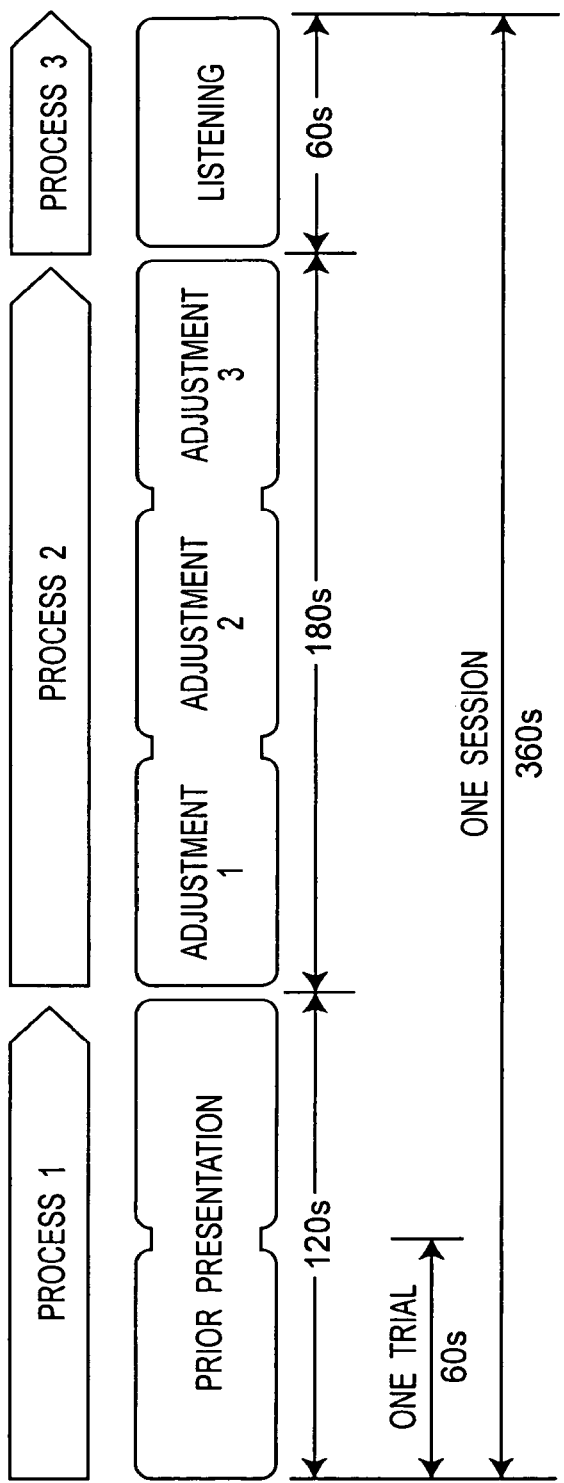
FIG. 64 is a timing chart showing procedures for an experiment according to an implemental example 1.

During the experiment, the subjects were comfortably seated on chairs. The distance between a front face of loudspeakers and ears of the subjects was about two meters. In consideration of time asymmetry occurred in appearance and disappearance of HSE [1], the presentation time was determined as follows (FIG. 64).

One presentation of sonic stimulus for 60 seconds was called as one trial. One session consisted of six trials (360 seconds) and these trials were divided into three processes (processes 1, 2 and 3). Only the same type of sonic stimulus (that is, FRS or HCS) was presented in one session and the subjects were asked to adjust the listening level. The sessions for FRS and HCS each are repeated three times and to offset an influence of order, the presentation sequence was randomized for each subject. The experiment was carried out with the subjects being blindfolded and the object of the experiment was not informed to the subjects.

Process 1 (prior presentation): For the first 120 seconds, the subjects listened to the sonic material with the sound volume adjusted to and fixed at 78.0 dB ($L_{Aeq}$) at a listening position.

Process 2 (adjustment): For the subsequent 180 seconds, the subjects adjusted the sound volume felt to be comfortable by using the remote controller 116.

Process 3 (listening): For the last subsequent 60 seconds, the subjects listened to the sound with the sound volume selected at the last stage of the process 2.

The listening level in the process 3 (listening trial) was regarded as the CLL (Comfortable Listening Level) and an average value for each of FRS and HCS was calculated.

Practice for one session was done prior to the experiment so that the subjects might get accustomed to the experimental procedures and obtain a feeling on the CLL.

Temperature, furniture and, in particular, visual environment were set so as to stabilize the reaction of the subjects and keep comfortability for the subjects. In order to confirm that the experiment was properly carried out, the subjects were requested to answer simple questions for analysis.

4. Results

Figure 65:
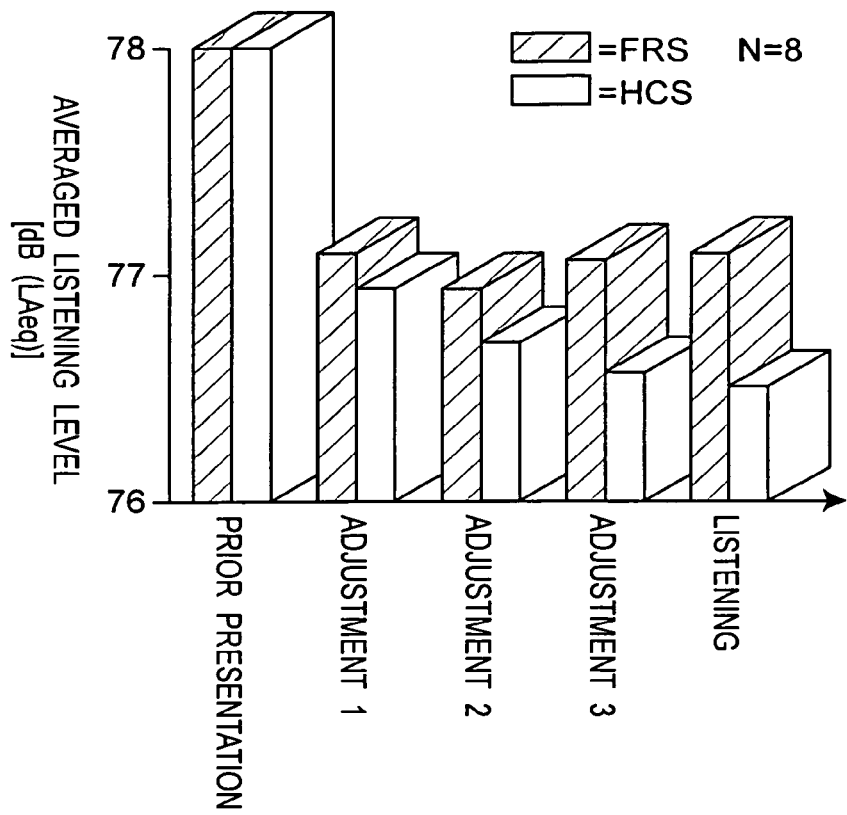
FIG. 65 is a graph showing results of the experiment according to the implemental example 1, illustrating an averaged listening level in FRS and HCS.
Figure 66:
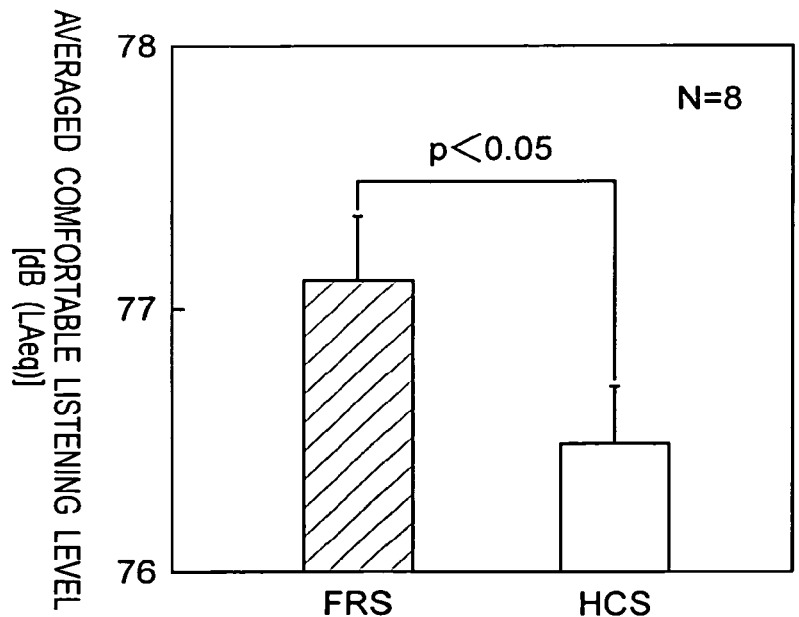
FIG. 66 is a graph showing results of an experiment according to an implemental example 2, illustrating an averaged listening level in FRS and HCS in a process 3.

FIG. 65 shows change in the average values of the listening level of FRS and HCS during the experiment. With the progress of the experiment, the reaction indicating that FRS was accepted with a higher level than HCS became obvious. This result corresponds to the other facts reported by the inventors of the present invention. FIG. 66 shows average values of the CLL for FRS and HCS in the process 3 (listening trial). In the process 3, the subjects listened to the music with the sound volume finally selected by them. The CLL for FRS was 77.1 dB ($L_{aeq}$) and the CLL for HCS was 76.5 dB ($L_{aeq}$). The former is higher than the latter by 0.6 dB ($L_{aeq}$) in average and this difference was statistically significant ($p<0.05$).

5. Conclusion

By measuring the CLL, the inventors of the present invention examined the influence of imperceptible HFC on human beings. The average CLL of the sounds containing HFC exceeding 22 kHz was significantly higher than that of the sounds from which components exceeding 22 kHz were removed. This result implies that the behavioral experiment is effective for the detection and measurement of HSE used with the CLL as a parameter. In comparison with the physiological and psychological studies, which have been for 20 years or more, the behavioral research of HSE using the CLL is still in a germinal stage and requires further data accumulation and sophistication of the experimental procedures. However, in the behavioral research of HSE, comparing with the physiological approach, the loads exerted on the subjects are smaller and the experiment apparatus is simpler. Thus, the behavioral research is suitable for an exploratory approach.

Implemental Example 2

"Research according to composite assessment indexes on influence of a signal structure of ultra-high frequency components exceeding the audible band on reception reaction to the sound" in accordance with the implemental example 2 will be described.

1. Background and Object 1.1 Background

When considering suitability of electronic VR audiovisual information to human beings, the inventors of the present invention note that the signal structure of audiovisual information supplied from the current electronic media tends to be different from the structure essentially existing in the natural world. The space density of visual information via electronic image media depends on the resolution of the media and is definitely lower than the space density of visual information in the natural world, which is actually close to the infinite. Acoustic information via the most widespread digital audio media (sampling frequency of 44.1 kHz, quantization bit count of 16 bits, frequency characteristic DC 5 Hz to 22 kHz) has the structure that frequency components exceeding 20 kHz as an upper limit in the audible band of human beings disappear at a stroke. On the other hand, the frequency of acoustic information in the natural world is often distributed beyond the upper limit in the audible band. For example, investigating frequency characteristics of natural environmental sounds in tropical rain forests regarded as an environment where human genes have been evolutionarily formed according to molecular genetics and the sounds of traditional ethnic musical instruments in matured culture areas having a history of a few hundreds to over one thousand years, the upper limits range from 50 kHz to 100 kHz. In comparison with this, it cannot be denied that the structure of the acoustic information supplied from the current digital audio media has a specific structure in terms of frequency characteristics.

Paying attention to these matters, the inventors of the present invention have found and reported such advantageous effects that audiovisual information having remarkable high-density, complexity and transformability, which exceed a sensory limit and is hard to be explicitly grasped, activates the operation of the brain, that is, "hyper-real effect". As examples, the inventors of the present invention have found such advantageous effects that the sounds (hypersonic sounds=HSS) abundantly containing unsteady ultra-high frequency components exceeding the limit of the audible band enhances the function of the brain (hypersonic effect=HSE) and the phenomenon that super high definition visual information with fractal structure which exceeds visual limit exhibits higher suitability to the brain. The inventors of the present invention have also reported the phenomenon that such high-density audiovisual information dramatically transforms mental activities of human in traditional ceremonies having a historically acknowledged psychophysical conditioning effect.

Based on this backdrop, in this research, focusing on HSE, we made a basic research for effectively realizing creation of a VR sound environment having high suitability to mind and body of human by using superdense electronic acoustic media.

1.2 Related Researches

HSE is a generic term for multi-lateral effects, which increases blood flow in a deep portion of the brain, enhances α wave of electroencephalograms and improves reality and comfort of sounds, and this leads to listening with greater sound volume. Using ultra wideband record of natural sound source abundantly containing ultra-high frequency components (HFC) with unsteady fluctuation which exceeds the upper limit in the audible band as a sonic material, the inventors of the present invention firstly examined human's reactions when sounds obtained by removing the ultra-high frequency components equal to or larger than 22 kHz (high cut sound=HCS) and sounds including the ultra-high frequency components equal to or larger than 22 kHz (full range sound=FRS) are presented. As a result, it was statistically and significantly demonstrated that, as compared with HCS, the fidelity of which is lowered by removing HFC, FRS as sounds reproducing actual natural sounds more faithfully increased blood flow in the brain deep portion including brainstem and thalamus and enhanced the α wave of the electroencephalograms as an indicator of stress-flee in a physiological aspect. At the same time, it was significantly found that FRS forced the listener to feel factors deeply related to the creation of reality and presence, such as "reality", "naturalness" and "depth", more strongly in a psychological aspect and to listen to the sounds with greater sound volume in a behavioral aspect. At this time, it was observed that appearance and disappearance of a biological reaction caused when HSS was presented resulted in a delay from a few seconds to ten-odd seconds and persistence of about 60 to 100 seconds, and obviously, HSE involved inherent time asymmetry. It is noted that the brain deep portion such as the brainstem and thalamus activated at this time is deeply related to diseases including lifestyle-related diseases, psychosomatic disorder and mental and physical disorders, and HSE is considered as the phenomenon which has an important bearing on the creation of reality of the sounds and exerts an unignorable influence on the health of the inventors of the present invention.

Concerning an upper limit of the frequency which may have an influence on the sensitivity of human beings, around 1980, a plurality of researches was made to determine a standard for digital audio media. All of these researches were based on an acoustic psychological assessment method using realizable decision with respect to the presentation of short-time stimulus as an indicator and could not detect the influence of HFC on human beings. On the other hand, by the use of a physiological assessment method using noninvasive brain function measurement and a psychological assessment method using paired comparison, etc. reconstructed based on the physiological opinion thus obtained, it was possible to detect the reaction which involves inherent time asymmetry and covers an unconscious region, which was overlooked according to the conventional experiment methods. Since 1990, opinions supporting the presence of the advantageous effect of ultra-high frequency components have been presented in succession by a plurality of institutions, and this leads to promotion of an increase in density of recent audio media, such as SACD and DVD audio.

Nevertheless, a full-scale research on the advantageous effect of HFC on human beings remains in a germinal stage. For this reason, in parallel with the construction of more accurate experiment environment and fundamental research themes such as clarification of mechanism, applied research has been demanded. For example, when HSE is applied to the creation of VR sound environment, the improvement in reality of sounds, the reduction in stresses due to artificial information stimulus and the realization of the VR sound environment with higher suitability to human's mind and body are expected. In this case, the problems such as which HFC state is suitable and effective, whether or not it is more desirable as the HFC power increases and whether or not an optimum value exists are essential important problems to be examined. However, since the examination has been conventionally made only by a method for comparing the case where HFC exists as the original sound with the case where HFC is completely removed, most of these problems are still unsolved.

1.3. Object

From these viewpoints, this research aimed to obtain a multi-lateral opinion on an optimum HFC state for human beings with a view to apply HSE to VR. For this purpose, an influence on reception reaction to HSS in the case where sounds were presented with the intensity of HFC being varied was examined using three indicators of behavior, psychology and physiology in a correlated manner.

When measurement indicators used in the experiment were set, the "most comfortable listening volume" is selected as an indicator to examine the behavioral reaction. This indicator implies the reaction varies, reflecting acoustic physical structure and the listener's sensitivity reaction of comfort or discomfort. For the psychological reaction, a paired comparison method of Scheffe capable of detecting a subtle difference in sound quality by subjective impression decision (category decision) was adopted and the electroencephalogram (EEG) was selected as a convenient indicator with excellent time resolution to measure the physiological reaction. Then, the behavioral assessment experiment having the greatest restriction in the experimental procedures was firstly carried out and had the subjects adjust the reproduced sound volume in each presentation condition to the level felt to be most comfortable to the subjects. Next, the psychological assessment experiment and the physiological assessment experiment were carried out. The listening volume in these experiments was set to be the reproduction level selected by the subjects in the behavioral assessment experiment.

2. Presentation Apparatus

Figure 67:
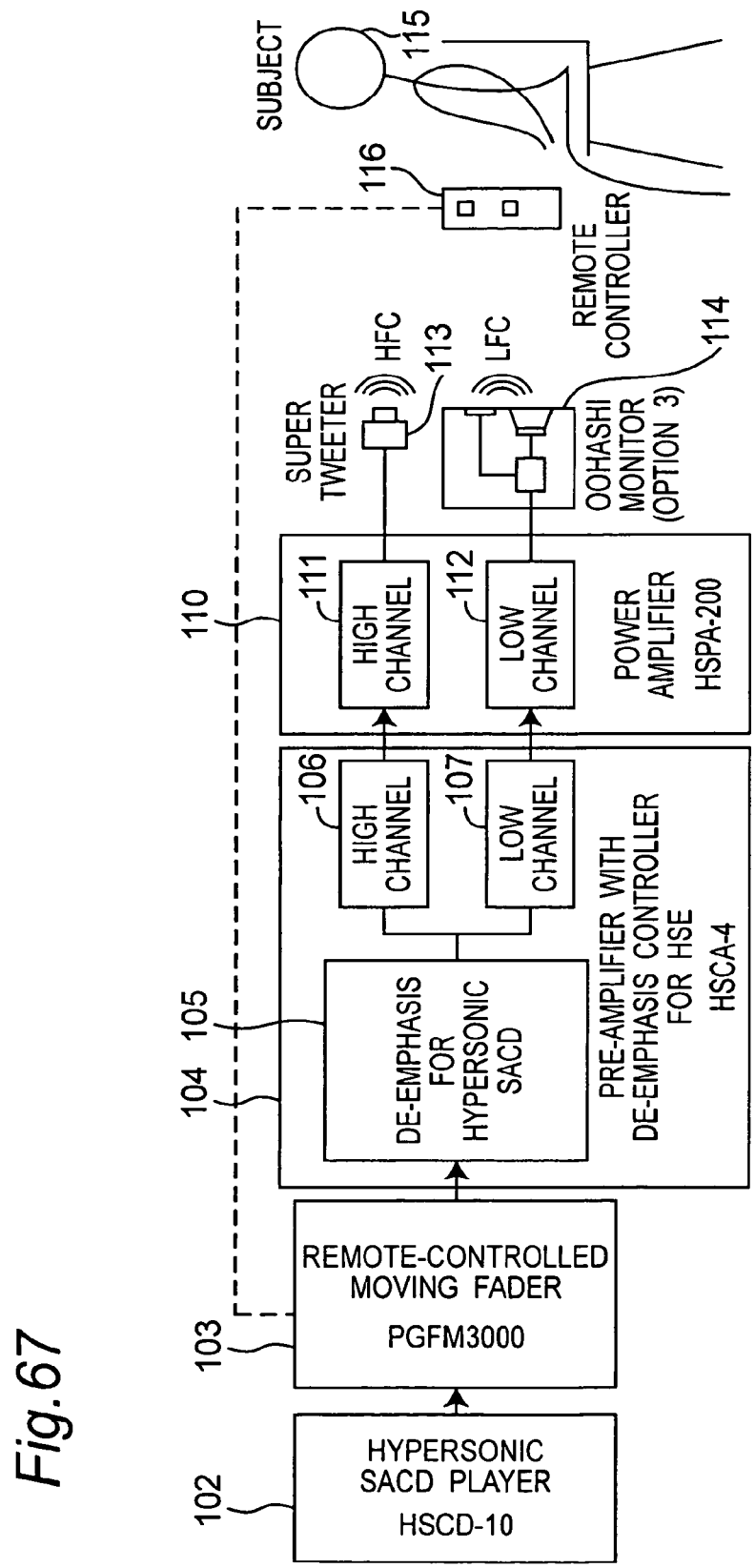
FIG. 67 is a block diagram showing a sound presenting system according to the implemental example 2.

As a sound presentation apparatus, in order to ensure excellent reproduction frequency characteristic up to 100 kHz necessary for this research, a dedicated reproducing system (Authentic Hypersonic Audio System manufactured by Action-Research Co.) independently developed by the inventors of the present invention, in which the effectiveness of HSE was verified using a plurality of indicators, was used (FIG. 67).

As a recording medium, a high-density disk DVD as a nonvolatile solid memory was used and recording in an SACD format was adopted. In signal processing, a high-speed sampling one-bit quantization method of Yamazaki producing actual results in prior researches was used. A signal of 2.8224 MHz and 1 bit was A/D converted by a DSD format-enabled Yamazaki's A/D converter. In order to suppress contamination of a reproduction signal by one-bit noise, which was accompanied by A/D conversion, pre-emphasis was applied to the signal in the process of disk production.

When a disk was reproduced, the hypersonic SACD player 102 (HSCD-10 manufactured by Action-Research Co.) having a response of −6 dB at 100 kHz, in which super high range characteristic was greatly improved by introducing an independently-designed D/A conversion circuit was used. A signal thus reproduced was restored via a predetermined de-emphasis circuit 105 (HDEC-1 manufactured by Action-Research Co.) to be an experiment analog signal.

Figure 68:
FIG. 68 is a photograph showing a remote operation for a volume according to the implemental example 2.

This electric signal was input to the pre-amplifier 104 (HSCA-4 manufactured by Action-Research Co.) having a flat characteristic up to 200 kHz. This pre-amplifier 104 was designed so as to store the de-emphasis circuit 105 therein and reproduce audible band components (low frequency components=LFC) and HFC separately for the purpose of this research. A high quality moving fader 103 (PGFM3000 manufactured by Penny & Gilles) was inserted between the SACD player 102 and the pre-amplifier 104 in the state where remote control was possible. The remote controller 116 was disposed on the subject 115's hand so that the subject 115 could remotely operate the sound volume without any visual and tactile hint to a tab or the like (FIG. 68).

A power amplification stage had a four-channel configuration of two channels for LFC and two channels for HFC and a power amplifier 110 (HSPA-200 manufactured by Action-Research Co.) having an excellent response characteristic up to at least 150 kHz was used. This realized a "bi-channel reproducing system" in which LFC and HFC each were reproduced in separate circuits and thus, a strict experiment capable of avoiding various problems in the presentation system, such as non-flatness in the filter audible band, group delay frequency characteristic due to difference in the circuits and a difference in inter-modulation distortion became possible. Note that monophonic sounds were presented in this research to eliminate complexity of factors and realize an experiment that is more precise.

Figure 69:
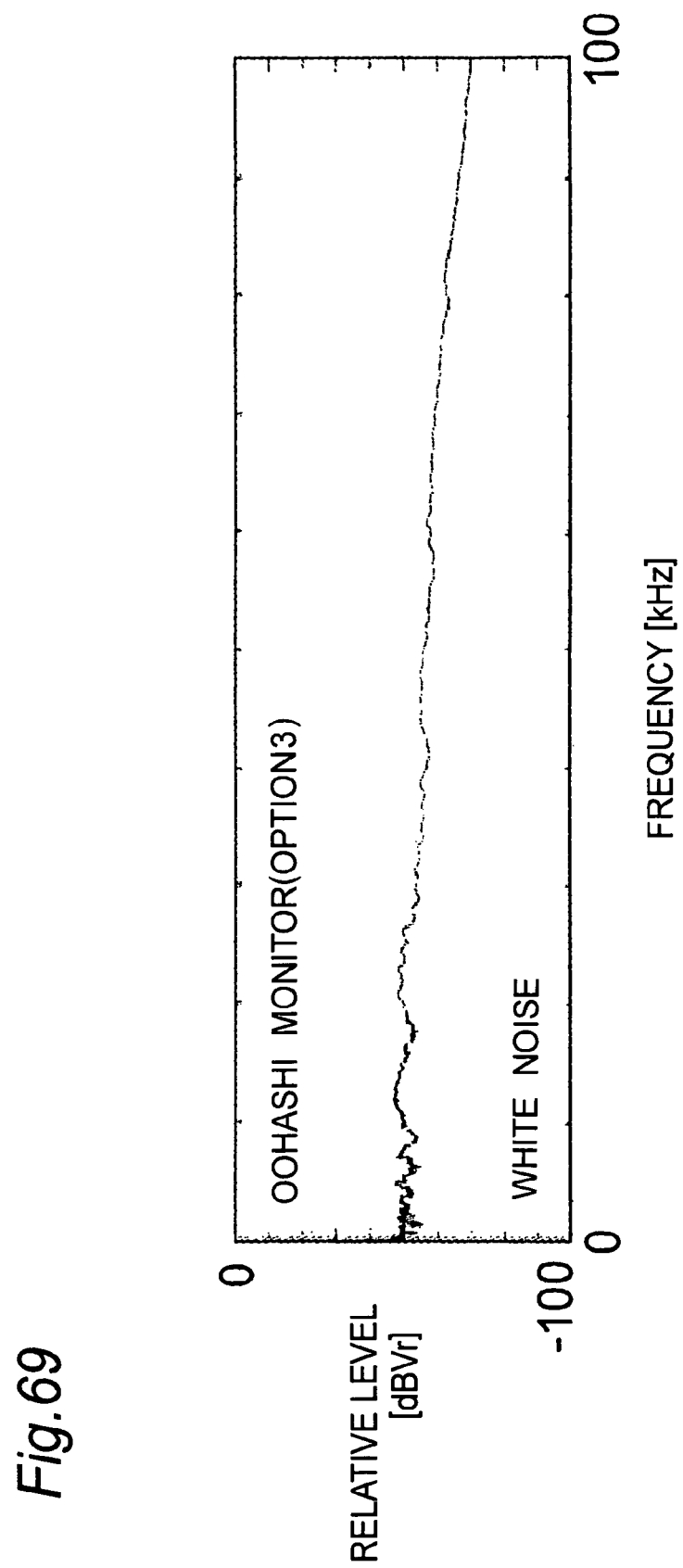
FIG. 69 is a graph showing reproducing frequency characteristics of a loudspeaker system according to the implemental example 2.

As a loudspeaker system, in order to have an excellent response up to about 40 kHz for LFC, an Oohashi monitor (op. 3) 114 (manufactured by Action-Research Co.) configured to have a bending wave-type full range unit in combination with a cone-shaped woofer was used. By adding a super audible band super tweeter 113 (PT-R9 manufactured by Pioneer Corp.) to this, a presentation system capable of reproducing HSS exceeding 100 kHz was realized (FIG. 69).

For the measurement of power spectrum of the presented sounds, a free field capacitor microphone (frequency characteristic of 4 Hz to 100 kHz±2 dB, 4135 type manufactured by Bruel & Kjaer) was disposed at the position of the subjects and its output was analyzed by fast Fourier transform using an automatic FFT analyzer (CF-5220 manufactured by Ono Sokki Co., Ltd.).

3. Presentation Sample

Figure 70:
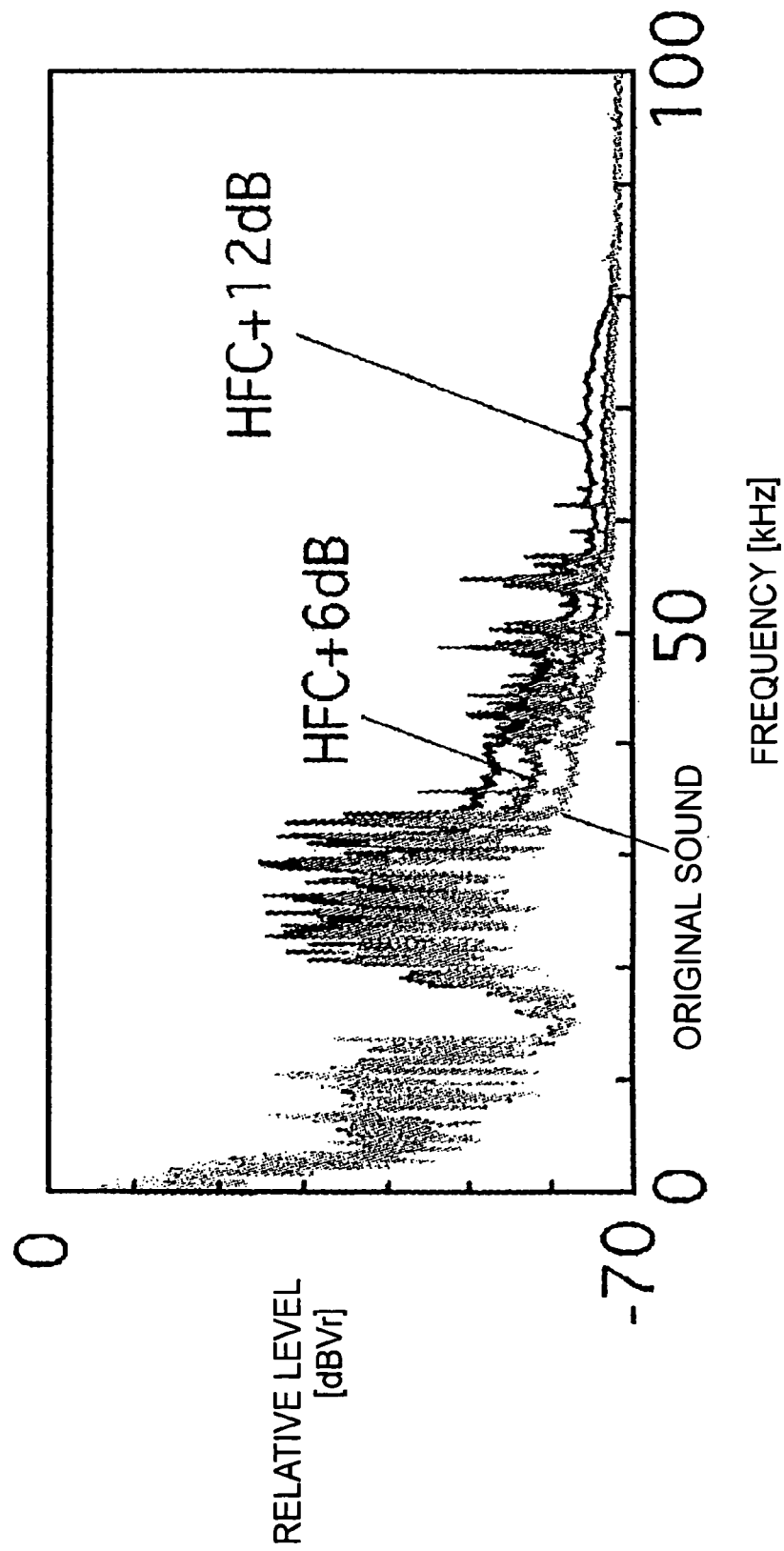
FIG. 70 is a graph showing frequency characteristics of a presenting specimen which are measured in the position of an examinee according to the implemental example 2.

Among the sound source tracks for the experiment in a signal disk (ARHS9002 manufactured by Action-Research Co.) developed along with the dedicated reproducing system, a composition in a musical box disk (track 46) specially developed for this research, which abundantly contains ultra-high frequency components ranging from 70 kHz to 80 kHz momentarily and above 50 kHz on an average of the whole was selected, and the same portion for 60 seconds in the whole 90 seconds were repeatedly reproduced. Based on the sound source, the sound sample presentation conditions in which LFC was made constant and only HFC was electronically intensified in two stages of +6 dB and +12 dB were set and they were referred to as [ultra-high frequency components 6 dB intensified sound] (HFC+6 dB) and [ultra-high frequency components 12 dB intensified sound] (HFC+12 dB), respectively. On the other hand, a sound sample presented at the original level when HFC was not electronically intensified, was referred to as [original sound] (FIG. 70).

It was confirmed in advance by time waveform and frequency spectrum that all of presented condition sounds generated no distortion even when the subjects 115 listened to the sounds at the maximum level. In addition, it was confirmed that equivalent sound level for 60 seconds of each of the [original sound], [HFC+6 dB], and [HFC+12 dB] was measured in the state where the volume of LFC channel in the pre-amplifier 104, was made constant, and that the intensified HFC had no influence on measurement values of the sound-level meter. Furthermore, in order to confirm that the ultra-high frequency components were output at the proper level during the experiment, a measurement microphone was disposed in the vicinity of the subjects 115 and the output signal was monitored in real-time by the FFT analyzer.

Figure 71:
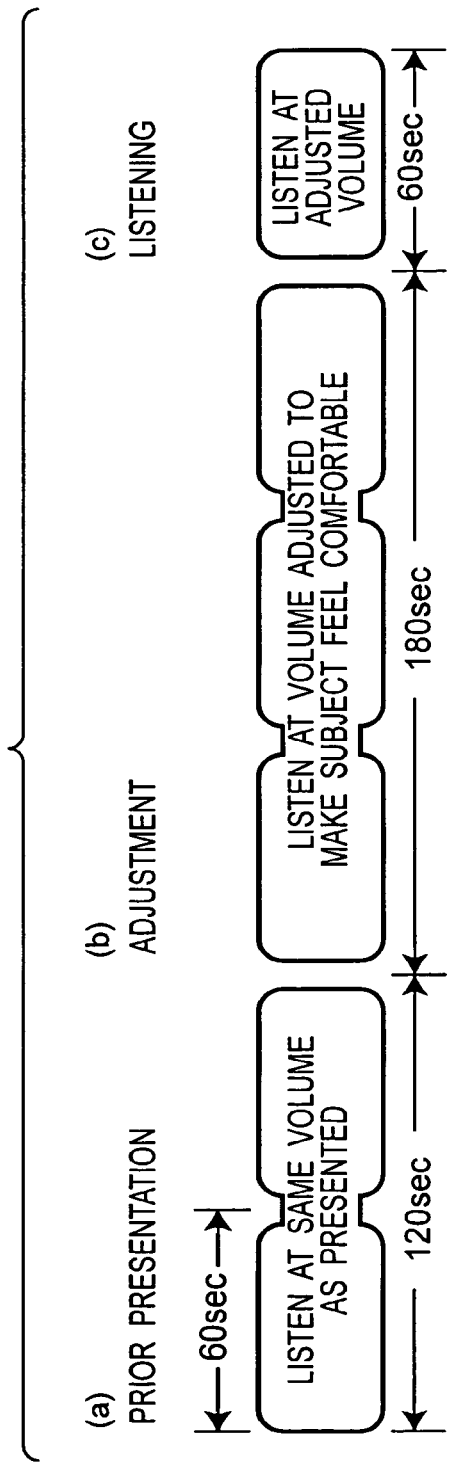
FIG. 71 is a timing chart showing procedures for a behavioral evaluation experiment according to the implemental example 2.

4. Experimental procedures 4.1. Behavioral Assessment Experiment Using the Listening Volume as Indicator Using the presentation apparatus and the samples described in 2 and 3, an experiment was carried out based on the behavioral assessment method, which has been examined and upgraded by the inventors of the present invention (FIG. 71). The following experimental procedures were designed in consideration of the time asymmetry inherent in HSE (a delay from a few seconds to ten-odd seconds and persistence of about 60 to 100 seconds in appearance and disappearance of the biological reaction using the electroencephalogram as an indicator), which was described in 1.2, so that the delay and persistence of the biological reaction might not cause confusion in experimental results.

One presentation of the composition for 60 seconds in the music box disk described in 3. was defined as [one trial], and six trials through below-mentioned steps (1) to (3) constituted one session.

(1) <Prior presentation>: For first 120 seconds (presentation of the 60 second composition at two times=two trials), the subjects 115 listened to the sound with presented sound volume (82.0 dB ($L_{Aeq}$)).

(2) <Adjustment>: For subsequent 180 seconds (presentation of the composition at three times=three trials), the listening volume was adjusted. At this time, the subjects 115 adjusted the sound volume to the volume felt to be pleasant and most comfortable as an overall impression.

(3) <Listening>: For last 60 seconds (presentation of the composition once=one trial), the subjects 115 listened to the sound with the self-adjusted sound volume.

The sessions configured above were performed three times under each of the three conditions [original sound], [HFC+6 dB] and [HFC+12 dB]. All sessions were carried out with the subjects blindfolded and the order of the presentation conditions was randomized between the subjects 115.

The sound volume received by the subjects 115 was measured in real-time as the equivalent sound level for each trial by using an integral wideband precision sound meter (LA-5111 manufactured by Ono Sokki Co., Ltd.). The sound volume, which was adjusted by the subjects 115 and reached finally in the <listening> trial, was regarded as the most comfortable listening volume in each condition and the average value was calculated.

During the experiment, the subjects 115 sat in comfort at the position where the distance between the front face of the loudspeakers and ears was 2 m and adjusted the sound volume by using an up-down switch of the remote controller 116 on hands (FIG. 68). At this time, since the volume controller operated by the subjects 115 controlled the whole output signal from the SACD player, LFC and HFC adjusted in conjunction with each other. The temperature in a laboratory was adjusted to about 25 centigrade and the humidity was adjusted to 40 to 50%. In addition, consideration was given to the indoor furniture so as to improve comfort for the subjects 115 as much as possible. The subjects 115 were 12 non-handicapped adults (5 males, 8 females: average age is 39.6).

Figure 72:
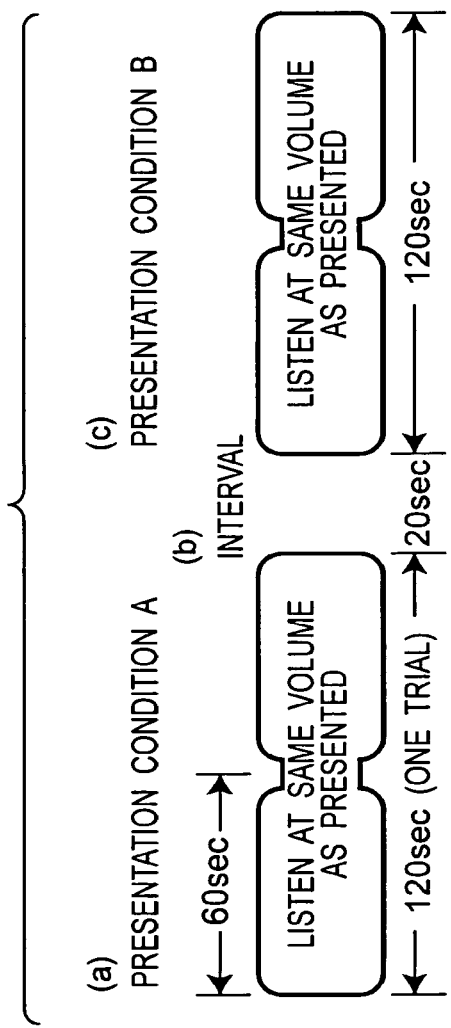
FIG. 72 is a timing chart showing procedures for a psychological evaluation experiment according to the implemental example 2.

4.2. Psychological Assessment Experiment Using Subjective Impression as Indicator Using the presentation apparatus and the samples described in 2 and 3, an experiment was carried out based on the psychological assessment method, which has been established by the inventors of the present invention (FIG. 72).

That is, based on the paired comparison method of Scheffe, that the sound for 60 seconds under one of the three conditions [original sound], [HFC+6 dB] and [HFC+12 dB] was continuously presented twice was defined as one trial and the sounds under two different conditions were presented in pairs for one trial.

According to Ura's modified method, the subjects determined the impression of each sound of all six pairs with five stage assessment axis by using 20 sound quality assessment scales. The sound volume under each condition was presented with the listening volume set by each subject in the behavioral assessment experiment. The obtained scores were inspected by a yardstick and the significance of the difference in sound quality between the three conditions was examined for each assessment scale. As in the behavioral assessment experiment, all experiment steps were carried out with the subjects being blindfolded and the order of the presentation conditions were randomized between the subjects. Like the attendants in the behavioral assessment experiment, the subjects were 12 non-handicapped adults (4 males, 8 females: average age is 39.6).

4.3. Physiological Assessment Experiment Using the Electroencephalogram as Indicator In a manner similar to above, using the presentation apparatus and the samples described in 2 and 3, an experiment was carried out based on the experiment method, which has been upgraded and established by the inventors of the present invention.

In order to reduce the restraint feeling of the subjects as much as possible, the electroencephalogram was measured by a measurement system using a telemetry system (WEE-6112 manufactured by Nihon Kohden Corporation) (FIG. 73) and derivation points were 11 points (Fp1, F7, Fz, F8, C3, C4, T5, Pz, T6, O1, O2) on the scalp based on the International 10-20 method.

Figure 73:
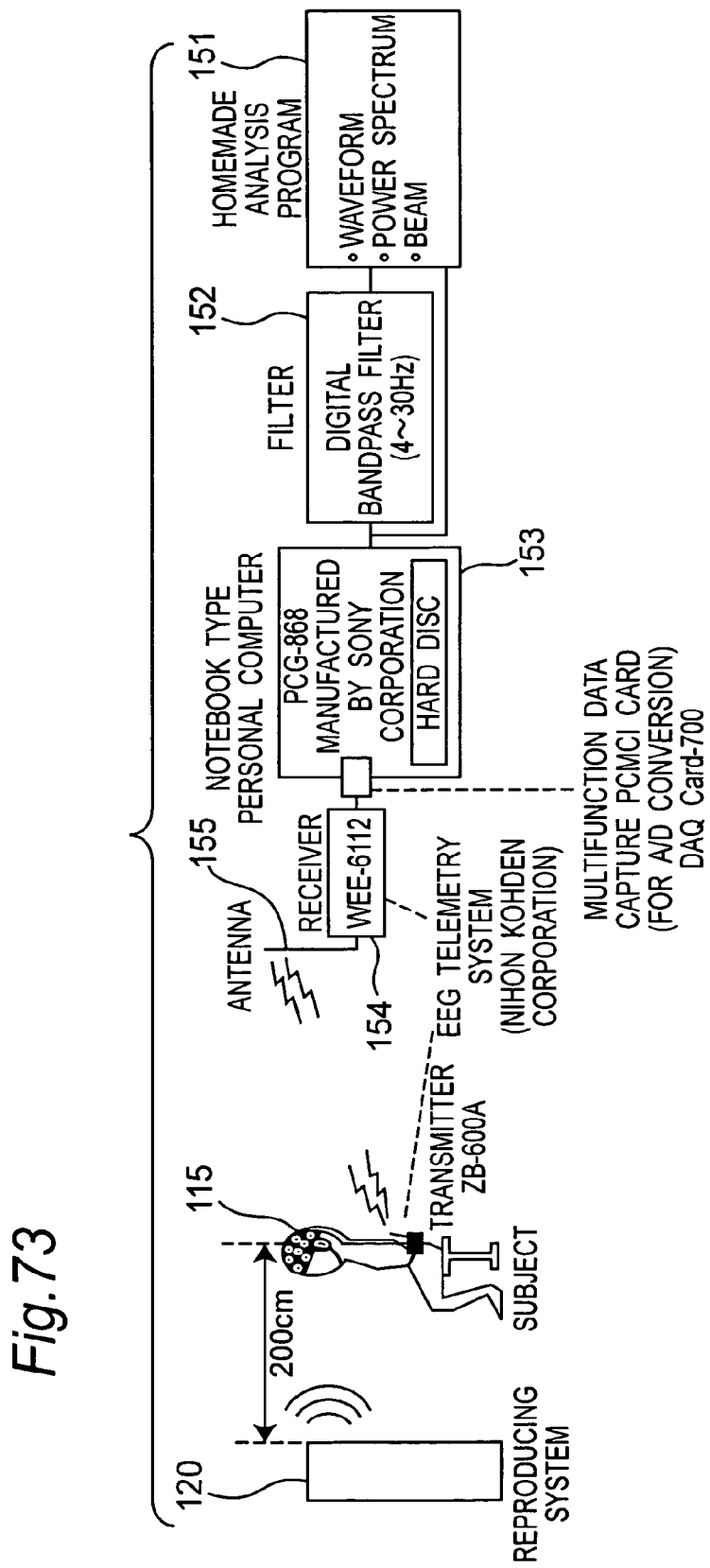
FIG. 73 is a block diagram showing an electroencephalogram measuring system according to the implemental example 2.

Referring to FIG. 73, the reference numeral 120 denotes a reproducing system of sounds having ultra-high frequency components, 151 an analysis program, 152 a digital band pass filter, 153 a personal computer, 154 a receiver and 155 an antenna.

Figure 74:
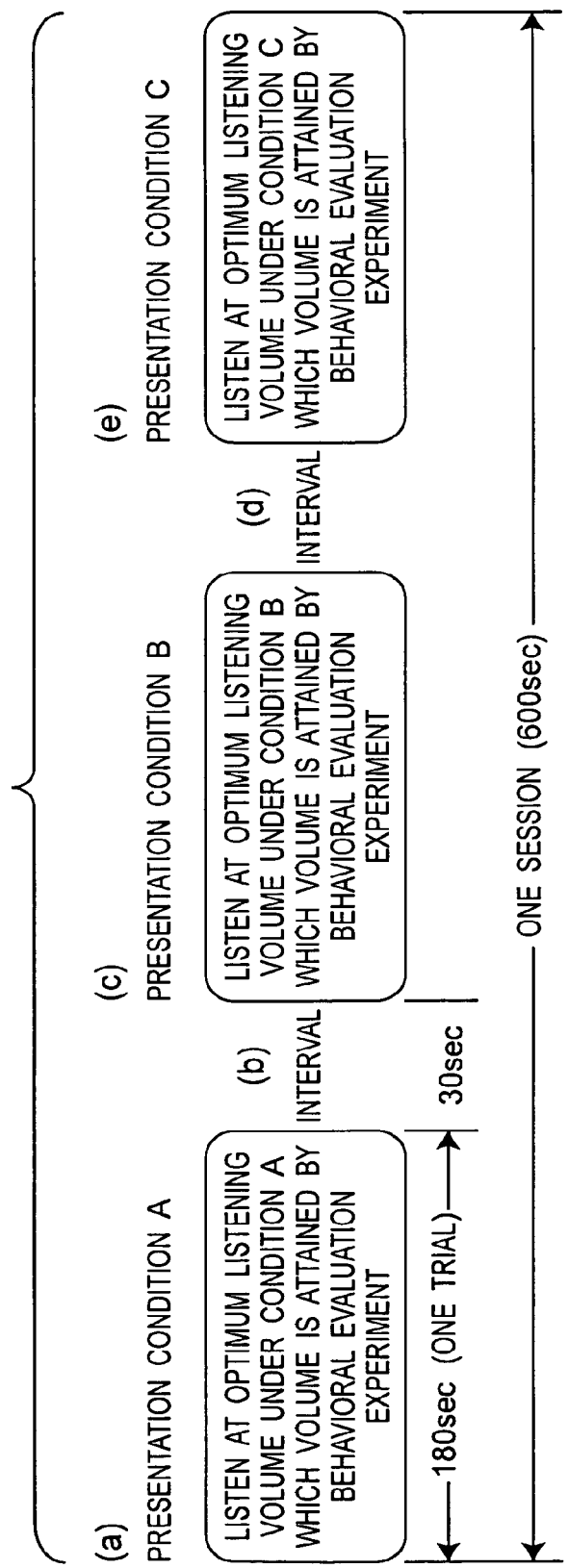
FIG. 74 is a timing chart showing procedures for a physiological evaluation experiment according to the implemental example 2.

The sound under each presentation condition was presented with the listening volume set by each subject in the behavioral assessment experiment. That the sound under one of the three conditions [original sound], [HFC+6 dB] and [HFC+12 dB] was continuously presented for 180 seconds was defined as one trial and that the sounds under the conditions were presented once at intervals of 30 seconds was defined as one session. The experiment consisted of two sessions and after a break following the first session, the second session in which the presentation order was reversed was carried out (FIG. 74).

The electroencephalograms of the subjects under the presentation of the sounds under each condition were measured and potential values in an α wave band of 8 to 13 Hz were calculated for each presentation condition. At this time, in consideration of time asymmetry of HSE, statistic processing for the values after 90 to 180 seconds from the start of sound presentation was performed so that delay and persistence of biological reaction might not cause any confusion. Furthermore, in order to avoid any influence of eye movement, five electrodes in the occipital region were analyzed. The experiment was carried out with the subjects being blindfolded and the order of the presentation conditions was randomized between the subjects. The subjects were 10 non-handicapped adults (4 males, 6 females, average age is 39.0) of the attendants in the behavioral assessment experiment.

5. Conclusion

Figure 75:
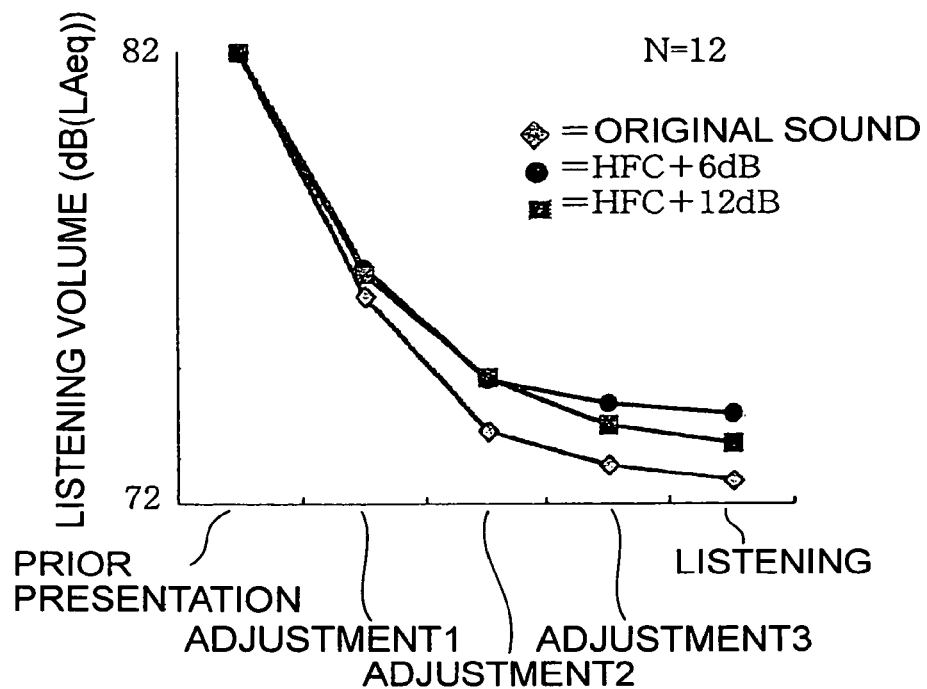
FIG. 75 is a graph showing results of the behavioral evaluation experiment according to the implemental example 2, namely, showing temporal transitions of a listening volume every presented condition.

5.1. Behavioral Assessment Experiment Using the Listening Volume as Indicator FIG. 75 shows temporal transitions of average values for all subjects of the listening volume in each trial of <prior presentation> prior to volume adjustment, three times <adjustment> and the last <listening>. Under all presentation conditions, there is a one-directional change tendency that the listening volume gradually becomes smaller during three <adjustment> trials. This corresponds to the tendency found in the behavioral assessment experiment, which has been conducted by the inventors of the present invention, for assessing an influence of the presence of HFC on the listening volume.

However, in the HFC-intensified [HFC+6 dB] and [HFC+12 dB], in comparison with [original sound], there is a tendency that the listening volume of the subjects became larger. Especially in the sound volume finally adjusted by the subjects in the <listening> trial, the difference was remarkable and [HFC+6 dB] and [HFC+12 dB] were listened with clearly larger volume than [original sound].

Figure 76:
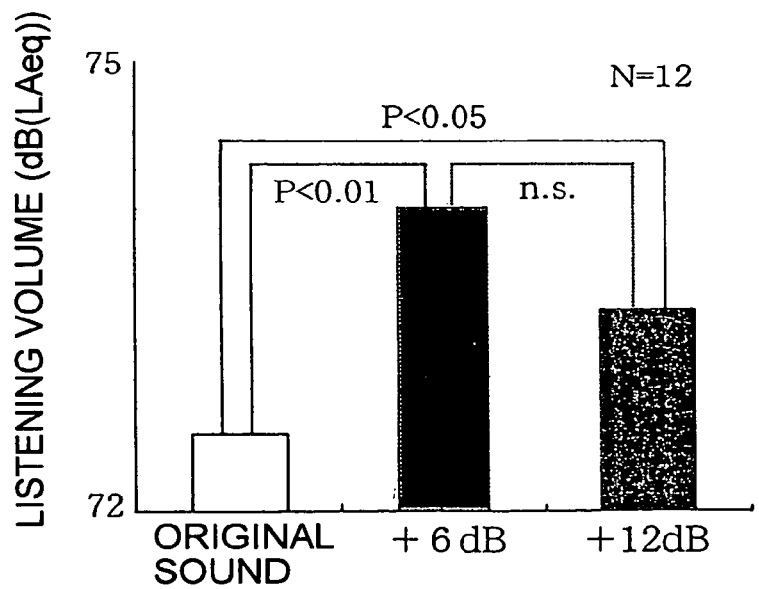
FIG. 76 is a graph showing results of the behavioral evaluation experiment according to the implemental example 2, that is, an averaged value for each presented condition of a listening volume set in a listening trial.

FIG. 76 shows results obtained by averaging the sound volume finally adjusted by the subjects in the <listening> trial by presentation condition. It shows that the listening volume of [original sound] is smallest, whereas the listening volume of [HFC+6 dB] and [HFC+12 dB] is larger. The listening volume of [HFC+6 dB] is slightly larger than that of [HFC+12 dB].

In order to statistically examine an influence of such difference in the intensity of HFC on the listening volume, analysis of variance with repeated measures is carried out. As a result, a main essential effect of the presentation condition is significantly recognized ($F (2, 22)=8.133$, $p<0.01$). This statistically supported that the difference in the potential of HFC has the advantageous effect of varying the listening volume as a whole.

Next, in order to examine whether or not there was a significant difference in the listening volume between the presentation conditions, a t-test of the correlated data is carried out.

As a result, the listening volume of [HFC+6 dB] and [HFC+12 dB] is significantly increased in comparison with [original sound] ([HFC+6 dB]: $p<0.01$, [HFC+12 dB]: $p<0.05$). On the other hand, the difference in the listening volume between of [HFC+6 dB] and [HFC+12 dB] does not reach a statistic significant level. However, there is a tendency that the listening volume of [HFC+6 dB] is slightly larger.

5.2. Psychological Assessment Experiment Using Subjective Impression as Indicator FIG. 77 shows an "average favorable level" indicating the level of average favorability under each condition by all sound quality scales.

It reveals that the HFC-intensified sound is assessed as generally giving a more favorable impression the original sound. Since the tendency is generally most remarkable in +6 dB and the average favorable level of +12 dB is located between that of +6 dB and original sound, this result corresponds to the result in the behavioral assessment experiment in which the sound of +6 dB is adjusted to have the largest listening volume.

FIG. 78 shows results of a statistical test by variance analysis using 20 sound assessment scales in the experiment. It shows the significance of differences in sound quality between [HFC+6 dB] and [original sound], [HFC+12 dB] and [original sound], and [HFC+6 dB] and [HFC+12 dB] from left to right. It reveals that the statistical significant sound quality difference has been detected between [HFC+6 dB] and [original sound] by 9 assessment scales and [HFC+12 dB] and [original sound] by 8 assessment scales.

It is found that the HFC-intensified sound is perceived as a sound having the following features: "realistic", "plenty of information", "natural", "like", "fine", "hydrated", "soft", "rich atmosphere", "not tiring", "ear-pleasing" and "lingering tone" in comparison with the original sound. Since the higher significance between [HFC +6 dB] and [original sound] than that between [HFC+12 dB] and [original sound] was recognized, the result does not conflict with the result in the behavioral assessment experiment.

Figure 79:
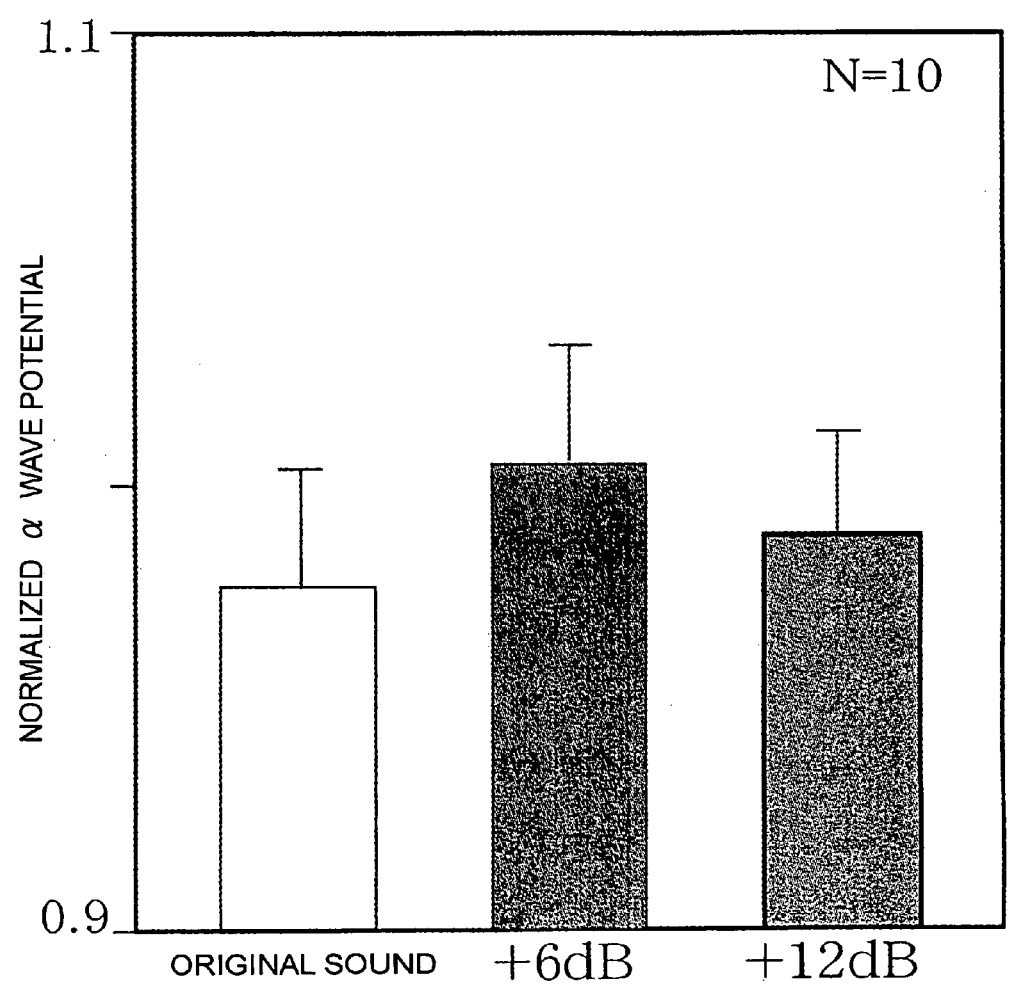
FIG. 79 is a graph showing results of the physiological experiment according to the implemental example 2, that is, an averaged value for each presented condition of a wave potential of electroencephalogram.

5.3. Physiological Assessment Experiment Using the Electroencephalogram as Indicator FIG. 79 shows results obtained by calculating average values of $\alpha$ wave potential for 90 seconds in the latter half of sound presentation under each of the conditions [original sound], [HFC+6 dB] and [HFC+12 dB] and normalizing the average values. The tendency that the $\alpha$ wave power of the electroencephalogram is slightly increased under presentation of [HFC+6 dB] and [HFC+12 dB] in comparison with [original sound], which does not conflict with the result in the behavioral and psychological assessment experiments, was observed.

In order to statistically examine an influence of the difference in the power of ultra-high frequency components on the $\alpha$ wave potential values of electroencephalogram, the analysis of variance was carried out. As a result, no statistical significance between main effects and presentation conditions was found.

6. Examination

The inventors of the present invention have already found statistically-significantly the advantageous effect of causing an action that the sound containing ultra-high frequency components (HFC) exceeding the audible band are listened with a larger sound volume than the sound from which the ultra-high frequency components are removed (stimulus reception action promoting effect).

From this behavioral assessment experiment, it is newly, statistically, and significantly found that the HFC-intensified sound increases the listening volume of the listeners and promotes the stimulus reception action. At the same time, from the psychological assessment experiment, it is statistically-significantly found that the HFC-intensified sound is perceived as more realistic, rich in information, and natural sound, and has the advantageous effect of enhancing favorability and comfort of the sound. Since these advantageous effects due to the intensification of ultra-high frequency components corresponded to HSE's properties found so far, it is considered that there is a high possibility that the intensification of ultra-high frequency components enhances the overall advantageous effects of HSS and improves affinity of human beings to sound.

On the other hand, the results of the physiological assessment experiment using the electroencephalogram as an indicator showed a tendency corresponding to the behavioral and psychological assessment. However, the assessment values in the statistical test do not reach the preset significant level. This may be due to the number of the subjects being too small for the adopted method in the present experiment. Alternatively, it can be interpreted that the behavioral and psychological assessment methods catch the reaction, which is difficult to be extracted according to the physiological assessment method, more sharply.

It is observed from a plurality of indicators that the HFC's advantageous effect as recognized in the present experiment does not increase in proportion to the intensification of the power, and the largest advantageous effect is obtained by +6 dB and reached at the maximum or slightly lowered by +12 dB. It is considered that this result implies a possibility that the HFC's advantageous effect (that is, HSE) has a nonlinear effect structure or optimum point, not flat and linear structure. Furthermore, it is deemed that the reason why the largest advantageous effect is obtained by +6 dB needs to be further examined and considered in detail with a view to the relationship between it and an HSE appearance mechanism.

7. Conclusion

The influence of the difference in the signal intensity of the ultra-high frequency components (HFC) exceeding the audible band on the sound reception reaction is assessed according to the plurality of indicators. As a result, under the experiment conditions set for this research, the advantageous effect due to the intensification of HFC is significantly recognized in the behavioral and psychological assessment experiments. On the other hand, in the physiological assessment experiment, the advantageous effect due to the HFC intensification is not significantly recognized. The tendency that the HFC intensifying the advantageous effect is maximized by HFC+6 dB and reached at the maximum or lowered by HFC+12 dB is observed. This fact demonstrates that the HFC's advantageous effect does not have a linear structure in which the advantageous effect increases in proportion to the intensity.

8. Closing

The above-mentioned research results suggest the effectiveness of the consideration of HFC intensification to create or produce reality in the artificial VR sound space and improve comfort.

In addition, the relationship between the HFC intensification level and the appearance of its effect demonstrates that there is a high possibility that the HFC's advantageous effect has some nonlinear structure or optimum point. This is noteworthy as a finding related to the clarification of the HFC effect mechanism.

In future, the inventors of the present invention hope to make a more detailed examination on the HFC intensification level and the appearance state of its effect and to obtain finding contributing to the creation of a VR sound environment having high affinity and suitability to human beings through the accumulation of these experimental results.

Implemental Example 3

"An influence of presentation conditions of hypersonic sounds on the sound reception reaction—research on hyper-real effect (I)" in accordance with the implemental example 3, will be described below.

1. Introduction

The inventors of the present invention have found the phenomenon that the sounds (hypersonic sounds=HSS) abundantly containing unsteady ultra-high frequency components exceeding the limit of the audible band enhance the function of the brain (hypersonic effect=HSE) and the phenomenon that super high definition visual information with fractal structure which exceeds visual limit exhibits higher suitability to the brain. The inventors of the present invention have also found the phenomenon that such high-density audiovisual information dramatically transforms human mental activities in traditional ceremonies having a historically acknowledged psychophysical conditioning effect. The advantageous effects that the audiovisual information having remarkable high-density, complexity and transformability, which exceeds sensory limits and is hard to be explicitly grasped, activate the operation of the brain, are referred to as "hyper-real effect (HRE)".

In this case, paying attention to HSS, the results as obtained by examining an influence of a change in presentation conditions of the ultra-high frequency components on the reception reaction to HSS in correlation with psychological and physiological influences will be reported.

2. Background and Object of This Research

HSE is a generic term for HSS effects, which increase blood flow in a deep portion of the brain including brainstem and thalamus, enhance $\alpha$ wave of electroencephalograms and makes perceive sounds more comfortably, and this leads to listening with greater sound volume. It is noted that the brain deep portion such as brainstem and thalamus activated at this time is deeply related to diseases including lifestyle-related diseases, psychosomatic disorder and mental and physical disorders, and HSE is considered as the phenomenon which exerts an unignorable influence on the health of human's mind and body.

In this research, as an important examination subject in the case of applying HSE, a change in behavioral reaction at the time when the power of ultra-high frequency components exceeding the upper limit of the audible band was varied was examined and the accompanied psychological and physiological reactions were investigated. Based on the experiment methods upgraded and established by the inventors of the present invention, a behavioral experiment using the stimulus reception action as an indicator was performed mainly as well as a psychological experiment using subjective impression as an indicator and a physiological experiment using the electroencephalogram as an indicator were carried out.

Figure 80:
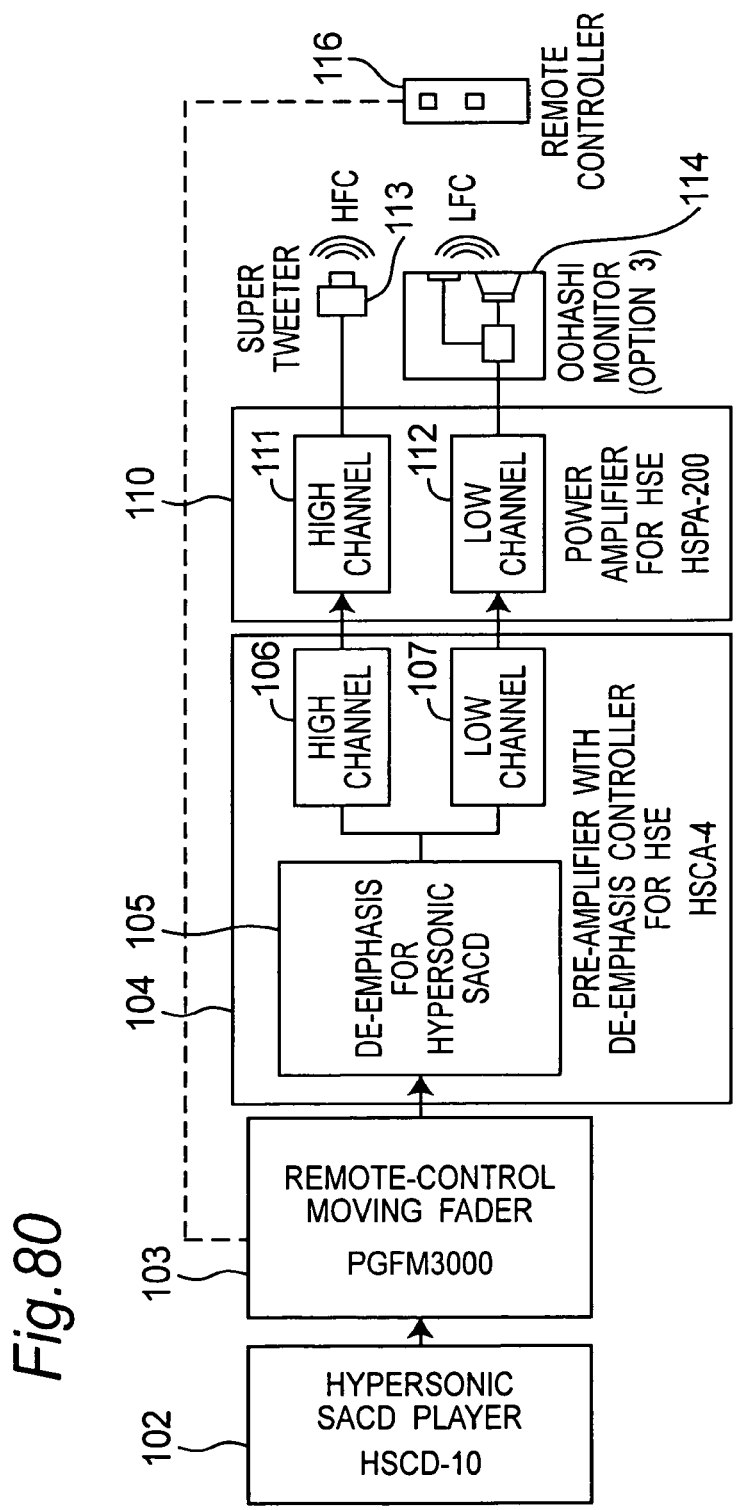
FIG. 80 is a block diagram showing an experimental system according to an implemental example 3.

3. Method 3-1. Apparatus:

As a sound presentation apparatus, in order to realize HSE research with high reproducibility, a dedicated reproducing system (Authentic Hypersonic Audio System manufactured by Action-Research Co.) independently developed by the inventors of the present invention, effectiveness of which was verified, was used (FIG. 80). Monophonic sounds were presented in this research to eliminate complexity of factors and realize experiment that is more precise.

3-2. Presentation Sample

From a sound source for experiment (track 44) in a signal disk (reliable signal disk, ARH9002 manufactured by Action-Research Co.) developed along with the dedicated reproducing system, the same portion for 60 seconds in Gamelan music abundantly containing ultra-high frequency components exceeding 100 kHz momentarily and above 50 kHz continuously were repeatedly reproduced. The sounds under presentation conditions in which low frequency components (LFC) of 22 kHz or less were made constant, and ultra-high frequency components (HFC) exceeding 22 kHz were intensified in two stages of 6 dB and 12 dB by the pre-amplifier 104 and reproduced were set and they were referred to as [+6 dB] and [+12 dB]. On the other hand, the sound under a condition in which HFC was not intensified and the sound was presented at the original level, was referred to as [original sound] (FIG. 81).

It was confirmed in advance by time waveform and frequency spectrum that the sounds presented under all of the presentation conditions generated no distortion even when the subjects 115 listened to the sounds at the maximum level. In addition, it was confirmed that equivalent sound level for 60 seconds of each of the original sound, +6 dB and HFC +12 dB was measured in the state where the output of LFC was made constant and the intensified HFC had no influence on measurement values of the sound-level meter.

Figure 81:
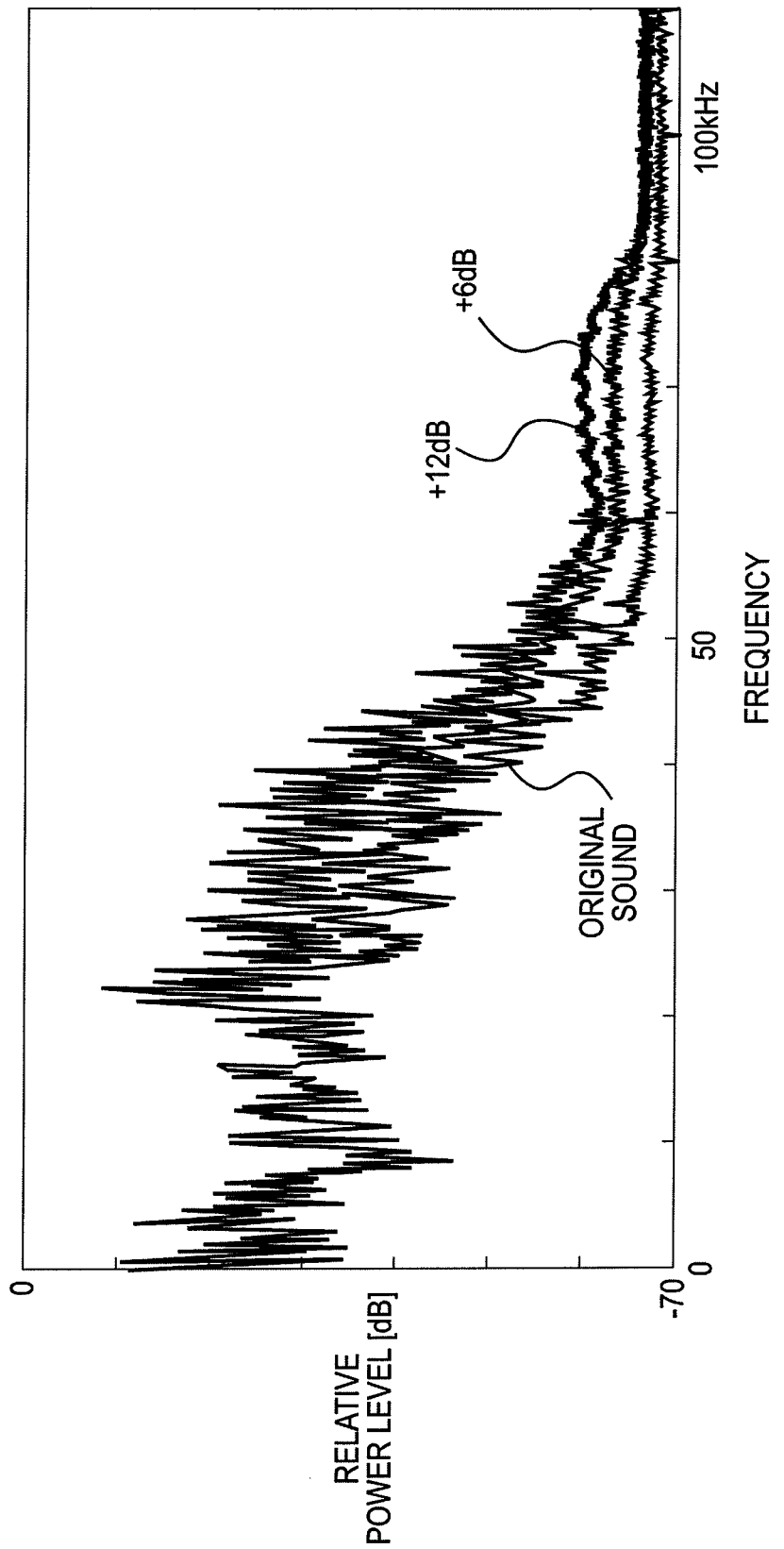
FIG. 81 is a chart showing results of the experiment according to the implemental example 3, that is, a power spectrum of a presented specimen.
Figure 82:
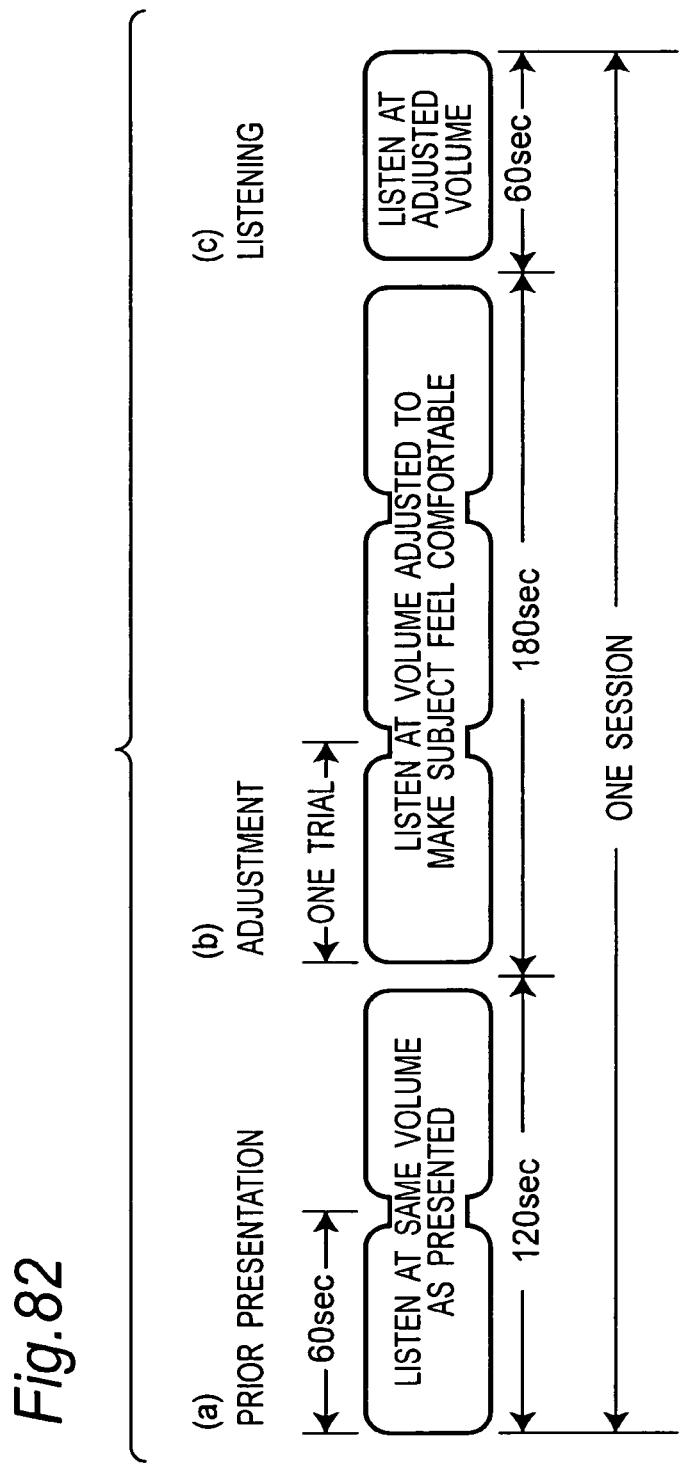
FIG. 82 is a timing chart showing procedures for the experiment according to the implemental example 3.

3-3. Procedures 3-3-1. Behavioral Experiment:

Based on the experiment method upgraded so far, the listening volume under each of the presentation conditions of the original sound, +6 dB and +12 dB was measured (FIGS. 81 and 82). One presentation for 60 seconds of the presentation sample was defined as [one trial] and six trials according to three steps of [prior presentation], [adjustment] and [listening] constituted one session. The presented volume in the prior presentation was 75 dB ($L_{Aeq}$) at the position of the subject (2 m from the front face of the loudspeakers). The session was performed three times under each of the three presentation conditions, that is, nine times in total. The sound volume received by the subjects was measured as the equivalent sound level for each trial by using the integral sound-level meter, values in the [listening] trial were regarded as "optimum listening volume" under the presentation conditions and an average value of them was calculated. The subjects were 15 non-handicapped adults.

3-3-2. Psychological and Physiological Experiments:

Based on the experiment methods established by the inventors of the present invention, the experiments were slightly modified so as to meet the purpose this time and performed. The sound under each presentation condition was reproduced with the optimum listening volume selected by each subject in the behavioral assessment experiment. The subjects were non-handicapped adults who were the attendants of the behavioral experiment as a population (12 persons in the psychological experiment and 10 persons in the physiological experiment).

Figure 83:
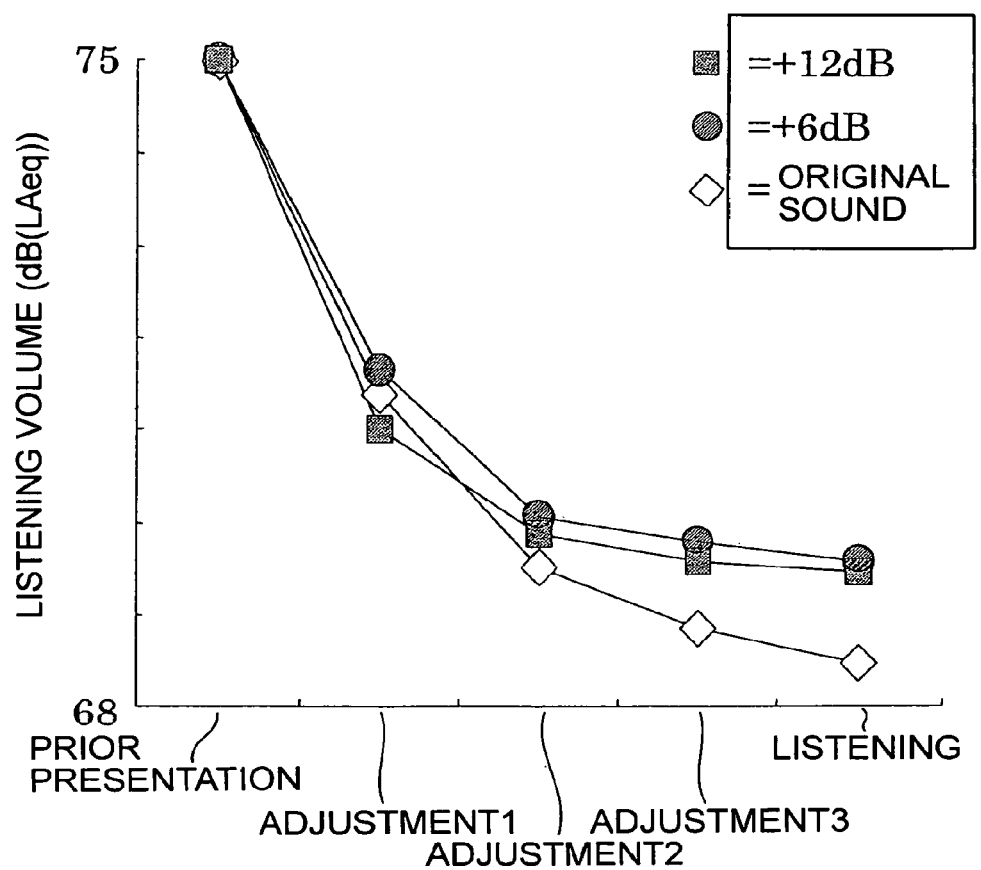
FIG. 83 is a graph showing a result 1 of a behavioral experiment according to the implemental example 3, that is, a temporary transition of an averaged value for each presented condition of a listening volume.

4. Results 4-1. Behavioral Experiment:

FIG. 83 shows temporal transitions of the average value of the listening volume adjusted by the subjects. There is a tendency that the adjusted volume is increased under the HFC-intensified condition greater than under the original sound condition and the difference is remarkable in the listening trial. As a result of variance analysis, the main advantageous effect of the presentation condition is significantly recognized, and it was statistically supported that the difference in the intensity of HFC has the advantageous effect of varying the listening volume.

Figure 84:
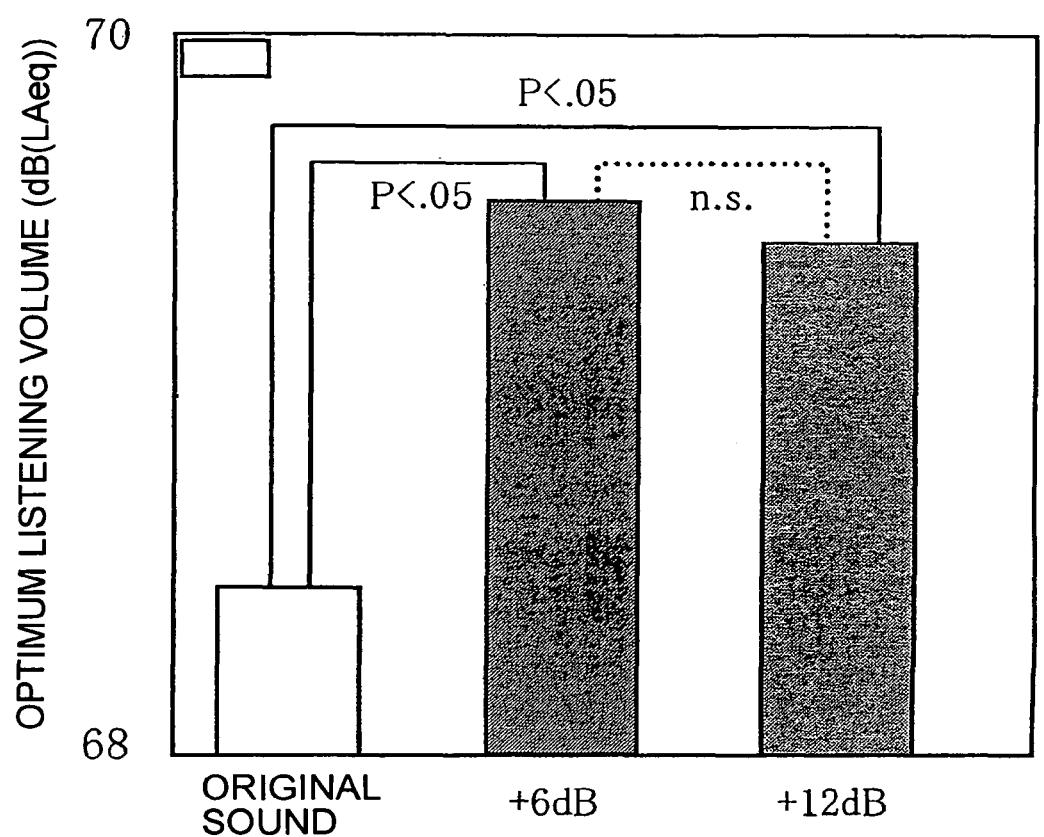
FIG. 84 is a graph showing a result 2 of the behavioral experiment according to the implemental example 3, that is, an averaged value for each presented condition of an optimum listening volume adjusted finally.

FIG. 84 shows results of average values of the optimum listening volume reached in the listening trial by presentation condition. In comparison with the original sound, the listening volume of +6 dB and +12 dB was significantly increased. Furthermore, although the listening volume of +6 dB did not reach the significant level, there was a tendency that the listening volume of +6 dB was slightly increased than that of +12 dB.

Figure 85:
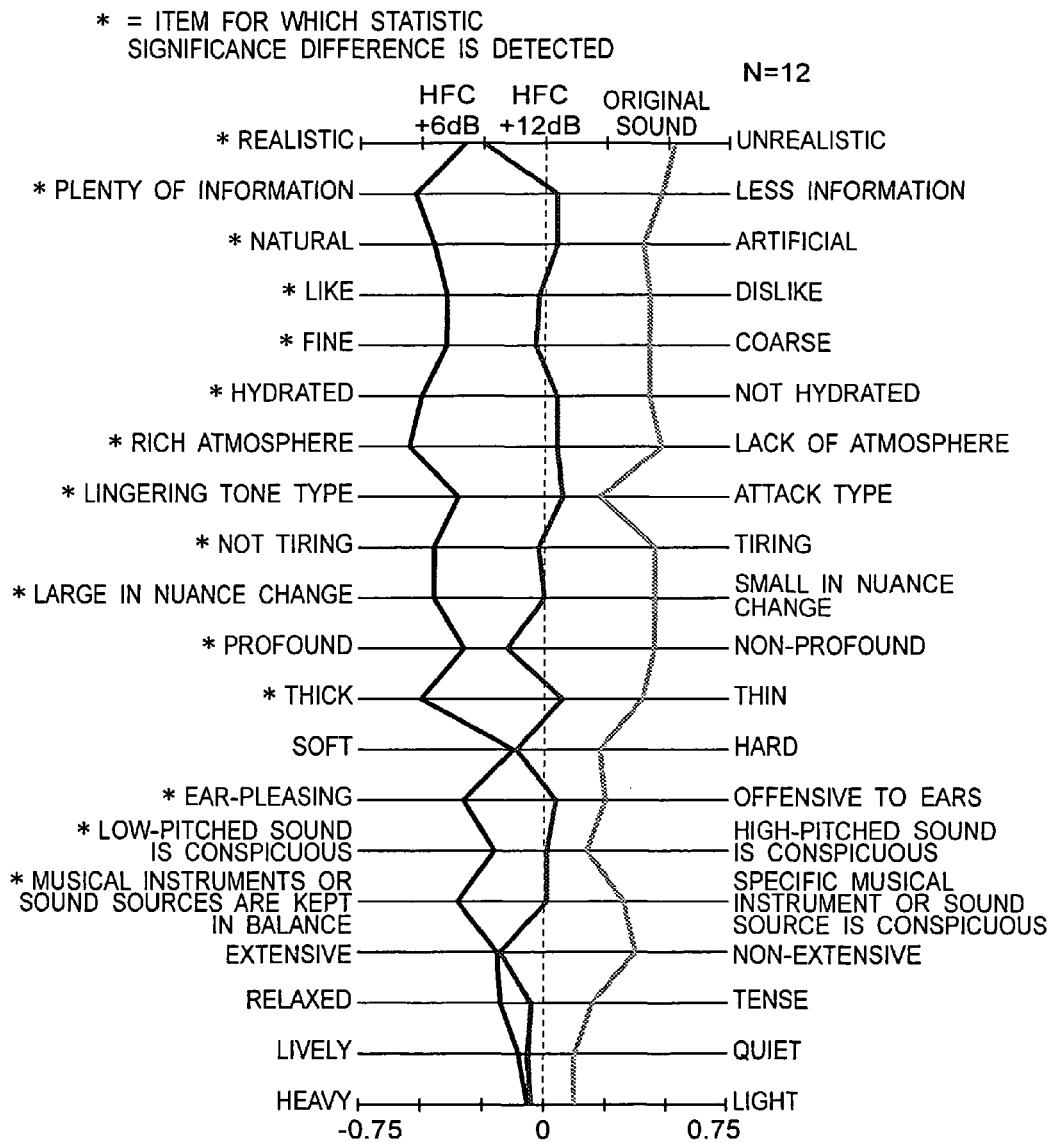
FIG. 85 is a chart showing results of a psychological experiment according to the implemental example 3, that is, a mean degree of taste for each presented condition.
Figure 86:
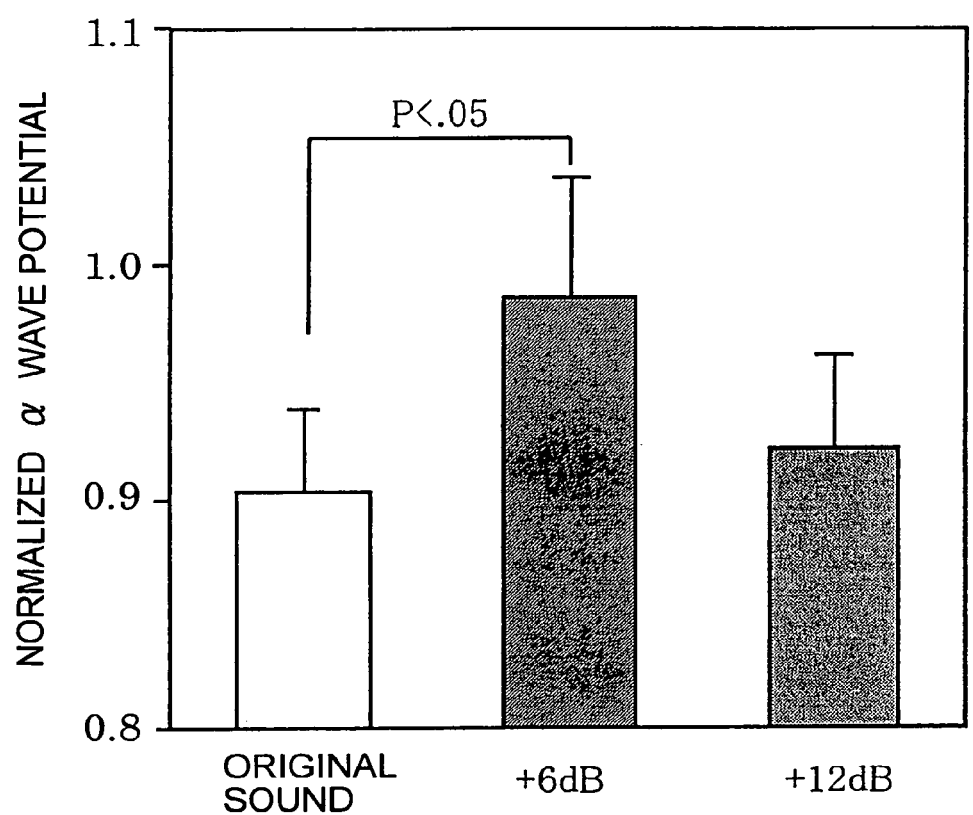
FIG. 86 is a graph showing results of a physiological experiment according to the example 3, that is, an averaged value for each presented condition of the a wave potential of the electroencephalogram for 90 seconds in a second half of a sound presentation.

4-2. Psychological and Physiological Experiments: FIG. 86 shows results of the psychological experiment. It is statistically significantly indicated by 14 assessment scales (item *) that, as subjective impression, the HFC-intensified sound is perceived as more natural, generally favorable and comfortable sound than the original sound. For the assessment scales by which no significant difference in the detection of sound quality difference was found, +6 dB is determined as the most positive sound and +12 dB is located between +6 dB and the original sound, and therefore, the result corresponds to the results of the behavioral experiment (FIG. 85).

Next, as a result of variance analysis of the data obtained in the physiological experiment, the main advantageous effect of the presentation condition is significantly recognized and it was statistically supported that the difference in the intensity of HFC had the advantageous effect of varying the power of the α wave of electroencephalogram (FIG. 86: Results of the physiological experiment: an average value of α wave potential of electroencephalogram for 90 seconds in the latter half of sound presentation by presentation condition). It was observed that the α wave power was enhanced under the HFC-intensified condition in comparison with the original sound, and the difference between +6 dB and the original sound is the significant level of 5%, which was statistically significant. The result does not conflict with the results of the behavioral and psychological experiments in that the α power is slightly enhanced under the presentation of +6 dB than under the presentation of +12 dB.

5. Examination

From the examination described above, it was statistically-significantly proved that the sound in which unsteady ultra-high frequency components are intensified had the advantageous effect of increasing the optimum listening volume in comparison with the original sound and promoting the stimulus reception action. Moreover, from the measurement of the psychological and physiological responses with the behavioral response, it was statistically-significantly proved that the HFC-intensified sound is more natural, realistic, favorable and comfortable than the original sound and enhanced the power of the α wave of electroencephalogram as a stress-free indicator.

Since such phenomenon corresponds to properties of HSE, it is considered that there is a high possibility that the intensification of HFC reinforces the overall advantageous effects of HSS and improves affinity of the sound to the listener.

However, these advantageous effects do not enhance in one direction with the intensification of HFC power, and the tendency that the largest advantageous effect was obtained by +6 dB and the advantageous effect reaches to the maximum or becomes slightly smaller by +12 dB than by +6 dB was observed in the behavioral, psychological and physiological experiments. This result is noteworthy as finding suggesting the possibility that the HFC's advantageous effect (that is, HSE) has a nonlinear effect structure or optimum point, not a flat and linear structure.

Implemental Example 4

"Examination on indoor sound environment improvement effect using hypersonic effect—Research on hyper-real effect (II)" in accordance with the implemental example 4, will be described below.

1. Object

Hyper-real effect (HRE) has advantageous effects of improving comfort in environment, increasing activity of the deep portion in the brain including the brainstem and thalamus, which trigger modern-day illnesses and enhances the power of the α wave of electroencephalogram as a stress-free indicator. By utilizing the series of effects, an improvement in information environment in cities is expected.

Thus, this research is intended to confirm that hypersonic effect (HSE) which has been sufficiently certified in detail under strict experiment environment in laboratories occurs also in the actual world outside of the laboratories using persons living therein as subjects to make a step forward of its application. Concretely speaking, environmental sounds abundantly containing ultra-high frequency components were used as BGM in a library in a high school and using students as subjects in the library, the advantageous effects were detected according to a questionnaire survey method. Its results will be reported.

2. Experiment Method

2-1. Experiment Apparatus

A "hypersonic audio system" developed by the inventors of the present invention, HSE generating advantageous effect of which has been certified by a plurality of indicators, was used. Loudspeakers and a super tweeter were placed on a book stack in the library and the other equipment was placed in a librarian room adjacent to the library.

2-2. Presentation Sample

It is necessary that an experimental presentation sample abundantly contain ultra-high frequency components, which exceed an upper limit of the audible band and include unsteady fluctuation, and reach a level as sensitivity information so as not to conflict with quiet ambience and cause boredom due to long-time repeated presentation. Furthermore, in order to stably realize long-time repeated reproduction in the library, it is desirable that a sound source is recorded in an optical disk, which has an excellent operability and can reproduce sounds stably. As a sound source meeting these requirements, the inventors of the present invention selected natural environmental sound in a tropical rain forest in Java Island among a group of sound sources stored according to the high-speed sampling one-bit quantization method. The sound was edited as a sample for about 53 minutes by an ultra wideband sound editing system and the edited sound was recorded in a SACD using an original AD converter to be a presentation sound source. At the same time, the same sound source was recorded in a CD to prepare a sample containing no components equal to or larger than 22 kHz.

2-3. Experimental procedures

The prepared environmental sound was repeatedly presented under the following three conditions for consecutive eight hours from 9 am to 5 pm a day for two days. [Condition 1] environmental sound abundantly containing ultra-high frequency components (Full Range Sound: FRS environmental sound), [Condition 2] environmental sound containing no components equal to or greater than 22 kHz (High Cut Sound: HCS environmental sound) and [Condition 3] environmental sound is not presented (no presented sound). Under the conditions 1 and 2, the volume in the audible band of the presented sound was adjusted to be about 47 $L_{Aeq}$ at the position of 2 m from the loudspeakers.

2-4. Design of Questionnaire

In contrast to the experiment carried out for subjects in the laboratory, this research used students frequently visiting the library as subjects, and this leads to causing great difficulties in the control of the subjects. In particular, it could not be expected that the subjects experienced the three experiment conditions in the same state and there are some experiences who could be compared with each other. In order to overcome the difficult problem, the inventors of the present invention exercised ingenuity in designing the questionnaire. That is, question items were divided into two blocks and in the first block, according to a normal question setting method, the subjects were asked to answer impression of library environment at the entering in eight assessment items. In the second block, a special question format of asking each subject to compare the inner state before entering the library and after staying in the library, and assess four assessment items. For the assessment items, considering that physiological properties of HSE leads the activation of a basic region in the brain, the question items were devised so as to grasp responses of systems other than the auditory system as well. The questionnaire was written immediately before leaving the library and all of the assessment items were assessed in five stages.

2-5. Subjects

Students visiting the library on each experiment date were requested to answer the questionnaire. Answering to the questionnaire was made voluntary. A total person of 103 answered under the [Condition 1], a total person of 100 under the [Condition 2] and a total person of 144 under the [Condition 3].

2-6. Analysis Method

In order to investigate in which direction and how much the impression of the library under each sound condition diverged from the neutral impression, scores were given by assessment item according to a [t-test of one condition]. Furthermore, in order to investigate how the impression of the library varies depending on the difference in sound condition, scores were given by assessment item according to a [t-test of uncorrelated two conditions].

3. Experimental results

Figure 87:
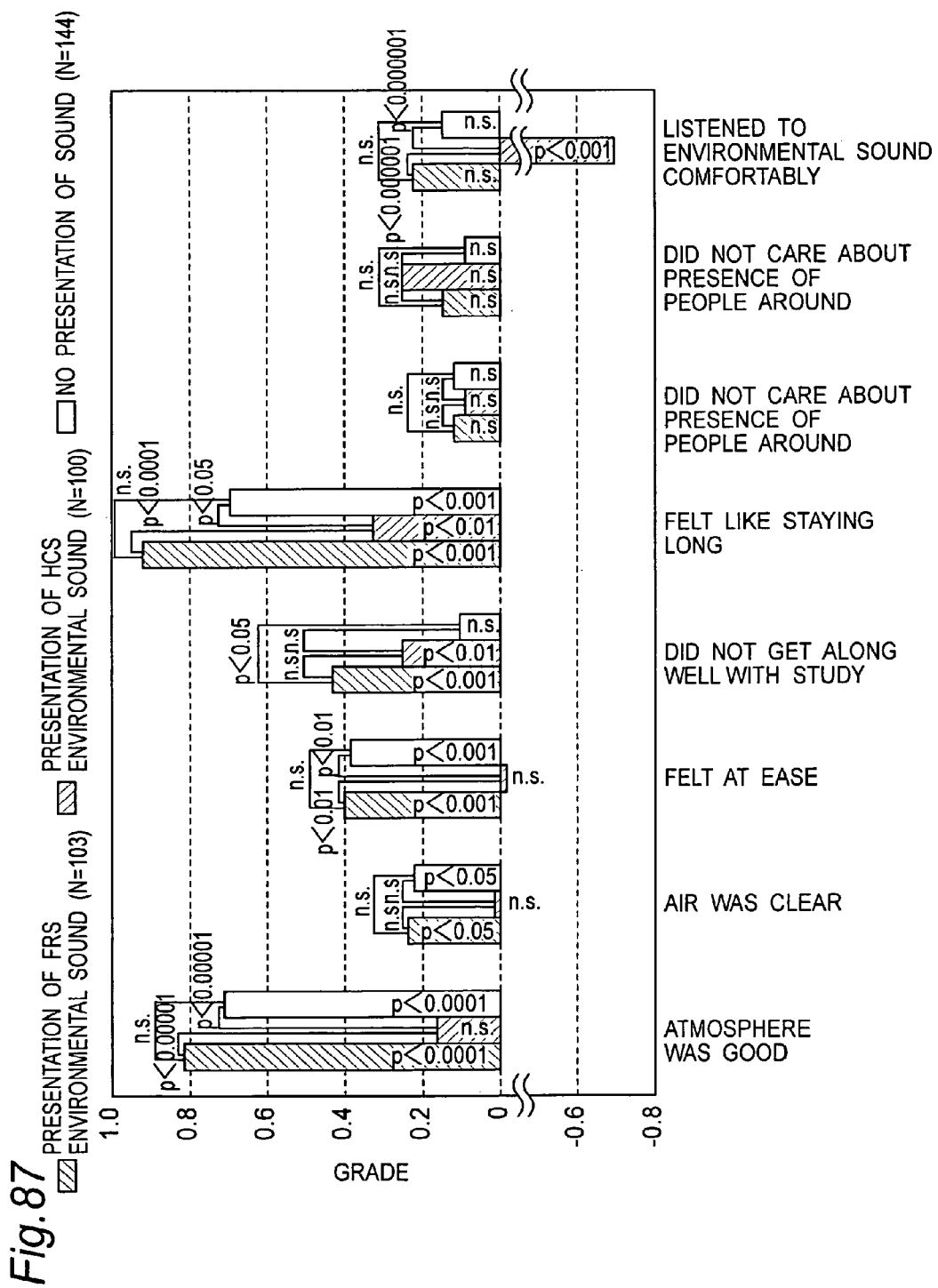
FIG. 87 is a graph showing results of an evaluation in a first block according to an implemental example 4.
Figure 88:
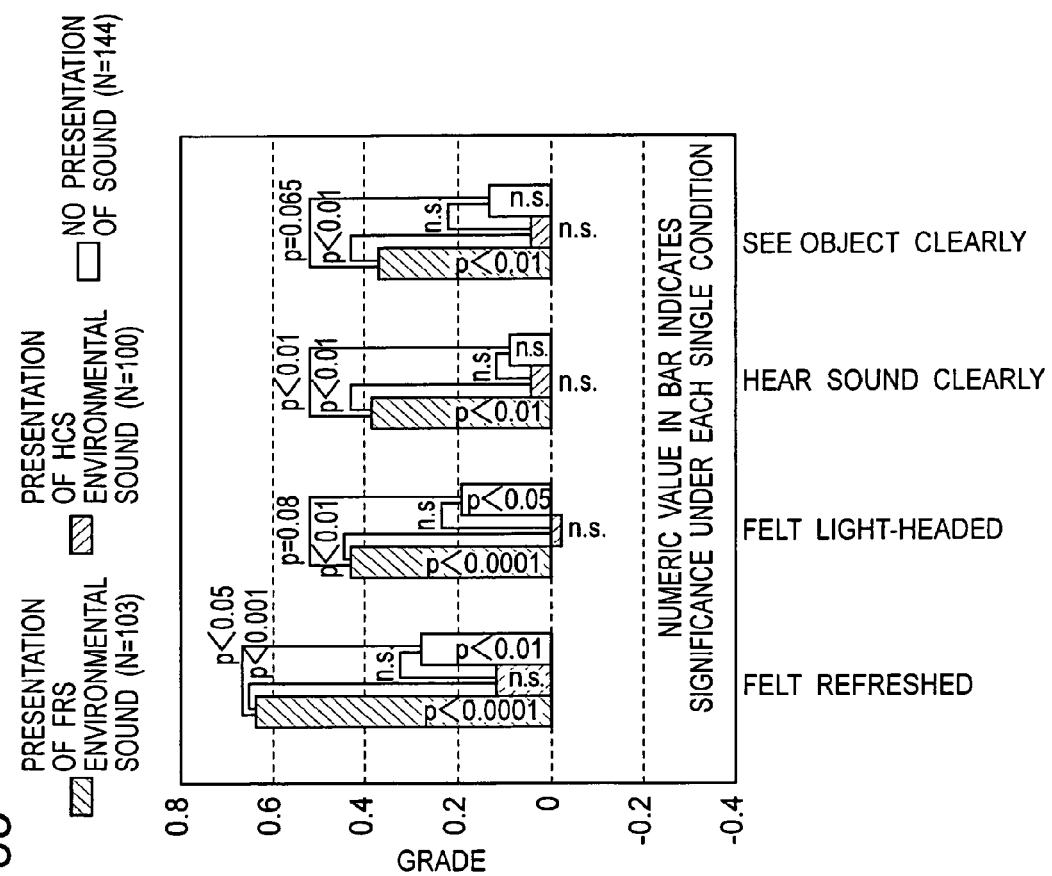
FIG. 88 is a graph showing results of an evaluation in a second block according to the implemental example 4.
Figure 91:
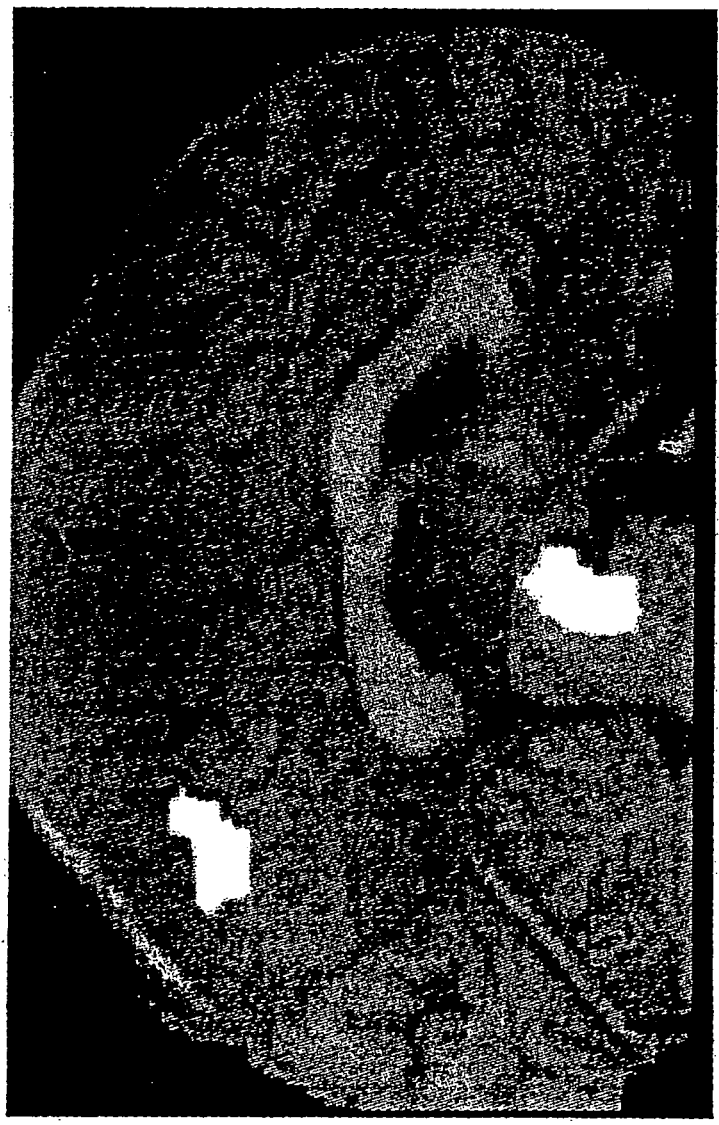
FIG. 91 is a photograph showing a portion indicative of a blood flow phenomenon as compared with a dark sound condition in a single presentation of an audible range component according to the implemental example 6.

FIG. 87 and FIG. 88 show results thereof. Bar charts of the figures showed the score under each condition and the test result was described in each bar. The significance of the difference between the conditions was described by connecting between the bars by lines.

In the question items in the first block, positive assessment having statistical significance was found in the items, "atmosphere was good", "air was clear", "felt at ease" and "felt like staying long" by the FRS environmental sound in the library (FIG. 87). On the other hand, such advantageous effects by the HFC environmental sound were not found. Even in the absence of the presentation of sound, assessment results at the same level as in the FRS environmental sound ware obtained. In the assessment item of "got along well with study", the condition of no presentation of sound was given a highest score, followed by the HCS environmental sound and the FRS environmental sound in this order.

Next, in the question items in the second block, obviously, the FRS environmental sound generally obtained clearly positive assessment. That is, it was found that by experiencing the FRS environmental sound in the library for a certain amount of time, "felt refreshed", "felt light-headed", "hear sound clearly" and "see object clearly" after entering the library were statistically-significantly recognized (FIG. 88). Such advantageous effects were not found by the HCS environmental sound and obtained lower scores than the baseline condition of non-presentation of sound. When no sound was presented, the significant difference appeared in the assessment items, "felt refreshed" and "felt light-headed", whereas the advantageous effects "hear sound clearly" and "see object clearly" were not recognized.

4. Examination

Especially in the question items in the second block, the result found in this research provides a high consistency with the obtained physiological and psychological assessment results relating to HSE. Furthermore, it can be said that the effectiveness of ingenuity newly introduced in the question items in the second block of the questionnaire designed for the present experiment could be confirmed. Moreover, interestingly, that the result suggesting that the activity of the visual information processing system in the brain is improved by experiencing the FRS environmental sound corresponds to the result shown by the analysis in a positron emission tomography method that cerebrocortex visual association area is cooled down by FRS, and implies the possibility that HSE has the advantageous effect of activating the basic area not limited to the classical auditory system in the brain function.

One of reasons why such a result was obtained is because, due to functions inherent in the library, HSE was sufficiently generated and the subjects stayed during the period long enough to change the inner state of the brain. A leading motive for the visiting of the library of the subjects in the present experiment was "relaxation" (38%), which suggests that the students expected a kind of refreshing function from the library. Therefore, it is considered that improving brain functions by upgrading information environment in the library in school as a base is an effective strategy.

Furthermore, the advantageous effect of improving the sound environment in the library was obtained by the FRS environmental sound, whereas such advantageous effect was not obtained by the HCS environmental sound. Thus, it must be noted that BGM using a CD as the most common sound source can have a negative effect.

The present experiment as a whole suggests the possibility that information environment will be dramatically improved by the super high-density acoustic technology. In the future, we hope to advance detailed analysis of data and examine a practical applied strategy of HRE.

Implemental Example 5

"Examination on hypersonic effect using physiologically active substances as indicators—research of hyper-real effect (III)—", in accordance with the implemental example 5, will be described below.

1. Object

Since the deep portion in the brain, as a control center of all physiological functions, in which physiological responses due to the hyper-real effect (the advantageous effect that audiovisual information having remarkable high-density, complexity and transformability activates the working of the brain=HRE) appear closely cooperates with tissues and organs throughout the body via the nervous system, the endocrine system and the immune system, these physiological functions could influence the responses. In order to examine the possibility, paying attention to the hypersonic effect (HSE) which is a type of HRE, the blood was taken from the subjects who was presented to the sound containing unsteady ultra-high frequency components exceeding the upper limit of the audible band (hypersonic sound=HSS) and the sound containing no ultra-high frequency components, and physiologically active substances as indicators contained in the blood were analyzed.

2. Method

Subjects: 16 non-handicapped persons (7 males, 9 females, 22 to 40 years old)

Sound Source: A composition of traditional Gamelan music in Bali Island, which abundantly contains unsteady ultra-high frequency components exceeding the upper limit of the audible band, was digitally recorded by the high-speed sampling one-bit quantization method. The recorded composition was edited to prepare a tape for 40 minutes and the tape was used as a sound sample.

Environment: A properly comfortable listening seat was installed in an enough large listening room. Furniture, furniture, drawings, plantings and the like were appropriately arranged in the periphery of the seat and lighting and air-conditioning were adjusted to improve overall comfort.

Presenting System: A bi-channel system having an almost flat reproduction characteristic up to 100 kHz was configured. It became possible to selectively reproduce [sound containing ultra-high frequency components]/[sound containing no ultra-high frequency components] while theoretically ensuring identification of components in the audible band by turning on or off a switch provided in an ultrahigh frequency range reproduction circuit.

Presentation Conditions: The audible band components (LFC) and the ultra-high frequency components (HFC) exceeding the audible band of the sound sample were combined to set two conditions of FRS (Full Range Sound=LFC+ HFC) and HFC (High Cut Sound)=only LFC). The sound for 40 minutes was presented to all subjects once under each condition, that is, twice in total, and the order of presentation was randomized between the subjects with the subjects being blindfolded. A break for five minutes was provided between two presentations.

Blood Sampling: In order to prevent the provision of stress accompanying blood sampling to the subjects as far as possible, an indwelling needle was previously introduced into a vein of an arm of each subject before the start of the experiment, and a tube was connected thereto as a blood sampling line and kept as it was during the experiment. Every time under each presentation condition, blood was collected from the blood sampling line after a lapse of 35 minutes from the start of presentation. The blood sampling line was made invisible to the subjects and the blood sampling operation was performed without the subjects' visual field so as not to apply stress as much as possible.

Blood Analysis Items: it is to be noted that cellular immunity acting on health maintenance and biological defense throughout the body and endocrine substances relating to mind-body correlation on both of positive and negative aspects, the following items were selected.

Four Cellular Immunity Indicator Items: CD4-positive cell ratio, CD8-positive cell ratio, CD4-positive cell/CD8-positive cell ratio, NK cell activity Six Endocrine Indicator Items: cortisol, adrenaline, noradrenaline, dopamine, beta-endorphin, prolactin Statistic Analysis: Since measurement values varied widely between the subjects in all items, the value obtained by normalizing the measurement values of the subjects in each item (dividing the measurement value under each condition by an average value of values under two conditions), using the average value between the subjects, the significant difference between the conditions was certified by the correlated t-test.

3. Results

FIG. 89 shows average value under each condition in each measurement item and significant difference between the conditions (p-value) in a table (average values (normalized values between the subjects) physiological activity indicator measurement values in blood). Apparent from FIG. 89, the NK cell activity was significantly increased in the presentation of FRS than in the presentation of HCS.

4. Examination

The NK cells destroy and remove cancer cells and virus-infected cells in the immune system and serve to prevent illnesses and maintain health. That the NK cell activity is significantly increased in the presentation of FRS than in the presentation of HCS suggests that HSS has an influence on the action of the immune system, and can be said to lead to health enhancement.

It has been known that the immune system interacts with the brain and full-body nervous system through the transfer of cytokine as one of in vivo information transmitters. There is a possibility that a change in the activity of the nervous system, which is led to the brain deep portion, may cause the response of the immune system through such an interaction.

In addition, physical and psychological stresses caused by disharmony in the experimental procedures contribute to the prevention of HSE occurrence and the confusion of results. In this connection, in the experiment method for collecting blood, the operation including a pain of "needle insertion" and easily causing discomfort and fear, is an essential and unavoidable process. The method for ensuring the blood sampling line adopted this time is also unusual to the non-handicapped subjects, and it is hard to suppress an uncomfortable feeling and scary feeling. Thus, the method has many disadvantages. Therefore, it is too early to affirm that the items other than the NK cell activity for which definite results cannot be obtained are not related to HSE by appearances. The future challenge is to upgrade the method toward suppressing and eliminating factors with negative effects in the occurrence of HSE. There is a high possibility, we think, that with the realization and establishment of the method, any new physiological response to HSE will be found based on the information obtained from blood.

5. Conclusion

In order to examine the possibility of a pervasive influence of hyper-real effect on the physiological functions throughout the body, the response to the sound abundantly containing unsteady ultra-high frequency components exceeding the upper limit of the audible band was investigated by analyzing the physiological activity substances indicator in blood. As a result, in comparison with the case where the sound containing no ultra-high frequency components was presented, a significant increase in the NK cell activity was recognized. This may be possibly a part of the pervasive physiological response in the effects (HSE) that the unsteady sound abundantly containing ultra-high frequency components exceeding the audible band brings about to physiology, psychology and behavior of human beings.

Implemental Example 6

"Neurophysiological examination on hypersonic effect by a positron emission tomography—research on hyper-real effect (IV)" in accordance with the implemental example 6, will be described below.

1. Object

In order to clarify an intracerebral nervous system relating to the appearance of hyper-real effect (the advantageous effect that information having remarkable high-density, complexity and transformability activates the operation of the brain), an influence of the sound abundantly containing ultra-high frequency components exceeding the upper limit of the human's audible band on the brain nervous system was examined using the Positron Emission Tomography (PET).

When the activity of cerebral nerves is increased, an increase in energy metabolism of the relevant brain portion causes an increase in regional cerebral blood flow. So as to grasp the state, it is possible to obtain a tomographic image of the whole brain with high spatial resolution by giving water labeled by oxygen radioactive isotope (15O) to a living body and measuring the intracerebral distribution by PET. By comparing cerebral blood flow distribution at the certain reception of a sensory stimulus or the execution of a motion cognitive task with that under test conditions and finding the area where the regional cerebral blood flow changes, cerebral nerve activity relating to the stimulus reception and task execution can be identified.

2. Method 2-1. PET Measurement

The subjects were 12 non-handicapped adults (8 males, 4 females; 19 to 34 years old). A composition of traditional Gamelan music in Bali Island "Gambung Kuta" (200 seconds) abundantly containing ultra-high frequency components equal to or larger than 20 kHz was used as a sound source. A bi-channel sound reproducing system was placed in a PET measurement room to present the sound sample. Loudspeakers were disposed as opposed to the subject's body with a distance of 1.5 m from the subject's ears and sound pressure was adjusted so as to be sufficiently audible and cause no discomfort. Temperature and humidity in the PET measurement room were adjusted and paying attention to visual information environment, a cable of a sound reproducer and medical equipment necessary for PET measurement were removed from the subject's viewing field by using ambient drawing, planting and furniture to improve comfort for the subjects.

The audible band components (LFC) of the sound sample and the ultra-high frequency components (HFC) exceeding the audible band, were combined to prepare the following four presentation conditions:

(1) FRS (Full Range Sound)=LFC+HFC;
(2) HCS (High Cut Sound)=only LFC;
(3) LCS (Low Cut Sound)=only HFC; and
(4) Baseline=only background noise.

(1), (2) and (4) were presented to six subjects twice and (1), (3) and (4) are presented to the remaining six subjects twice in the randomized order, and regional cerebral blood flow under each condition was measured.

2-2. Data Analysis

The cerebral blood flow image obtained from each subject was analyzed using SPM (Statistical Parametric Mapping) software. After a distortion in the head position during imaging was corrected and the brain of each subject was shaped according to a Talairach standard brain, statistical test was carried out using a general linear model. First of all, by comparing the cerebral blood flow under the experiment conditions with each other, the area where the cerebral blood flow was increased or decreased was identified. After correcting for multiple comparisons by the statistical tests of many pixels, the blood flow changed area was identified with a significant level of $p<0.05$. Furthermore, in order to identify a change tendency, tests without correcting for multiple comparisons were carried out at the same time. Subsequently, by extracting a space-time pattern changing in correlation with each other from data variance and covariance structure with the principle component analysis, extraction of a nerve function network was tried.

3. Results 3-1. Comparison Between Conditions (1) Effect of the Audible Band Components In the presentation of the audible band components, in comparison with the target background noise condition, a significant increase in blood flow in the primary auditory cortex and a decrease in blood flow in the visual association area were recognized (FIG. 90: FRS+HCS vs. Baseline).

(2) Effect of the Ultra-High Frequency Components Alone

In the presentation of the ultra-high frequency components alone, in comparison with the background noise condition, there was no region where blood flow obviously increased or decreased (FIG. 90: LCS vs. Baseline).

(3) Effect of the Ultra-High Frequency Components on the Audible Band Components Reception In the simultaneous presentation of the ultra-high frequency components and the audible band components, in comparison with the background noise condition, a significant increase in blood flow in the primary auditory cortex, an increase in blood flow in the thalamus and upper brainstem and a decrease in blood flow in the visual association area were recognized (FIG. 90: FRS vs. Baseline).

On the other hand, in the presentation of the audible band components alone without containing the ultra-high frequency components, a significant increase in blood flow in the primary auditory cortex was recognized, whereas an increase in blood flow in the thalamus and upper brainstem was not recognized. On the other hand, a decrease in blood flow in the upper brainstem and the precuneus was not recognized (FIG. 90: HCS vs. Baseline).

Comparing the simultaneous presentation of the ultra-high frequency components and the audible band components with the presentation of the audible band components alone, a significant increase in blood flow in the thalamus and upper brainstem was recognized (FIG. 90: FRS vs. HCS).

3-2. Examination on the Nerve Function Network by Principal Component Analysis

Figure 92:
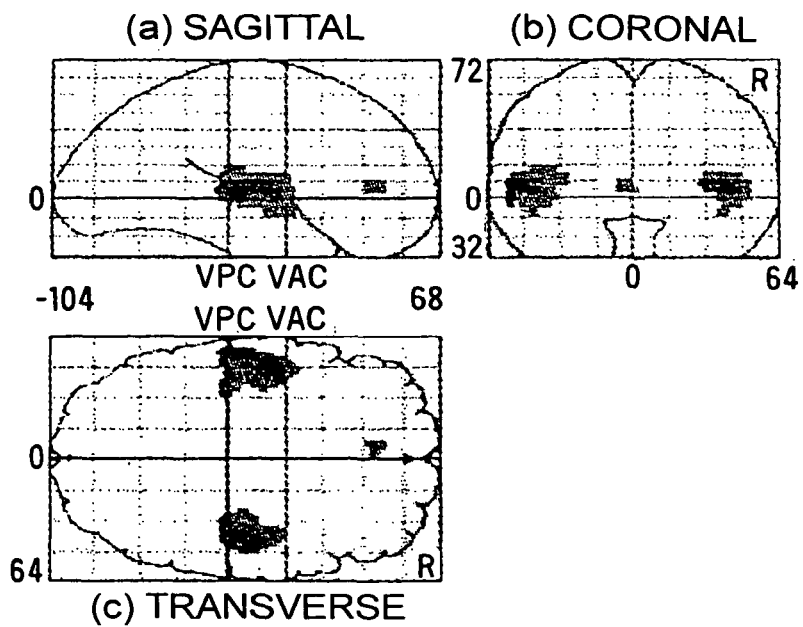
FIG. 92($a$) is a sectional photograph showing a neural function network represented by a main component analysis according to the implemental example 6, illustrating a sagittal plane in a first main component, FIG. 92($b$) is a sectional photograph showing a coronal plane in the first main component of FIG. 92($a$), and FIG. 92($c$) is a sectional photograph showing a transverse plane in the first main component of FIG. 92($a$).

As a first component of the principal component analysis, that is, a largest variation component contained in data, a region including the primary auditory cortex on both sides was visualized (FIG. 92). This component is considered to be a functional network of the auditory nervous system as it took a low value under the baseline condition and a high value under the FRS and HCS conditions.

Figure 93:
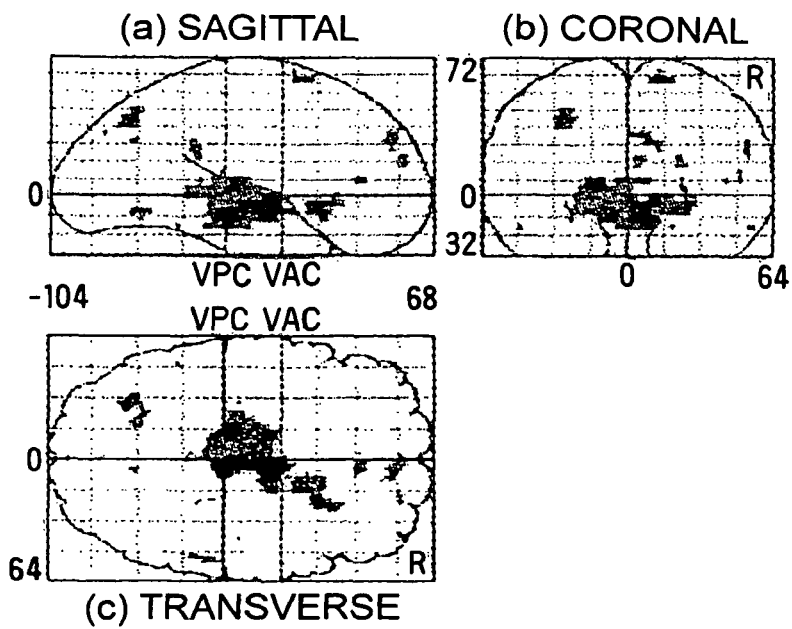
FIG. 93($a$) is a sectional photograph showing a neural function network represented by the main component analysis according to the implemental example 6, illustrating a sagittal plane in a second main component, FIG. 93($b$) is a sectional photograph showing a coronal plane in the second main component of FIG. 93($a$), and FIG. 93($c$) is a sectional photograph showing a transverse plane in the second main component of FIG. 93($a$).

As a second component of the principal component analysis, that is, a largest variation component contained in the data after the variation of the first component is removed, a brain deep portion region including the thalamus and the upper brainstem was visualized (FIG. 93). This is considered to be a functional network leading mutual influence by the ultra-high frequency components as it took a value which becomes higher in the order of FRS>Baseline>HCS.

4. Examination

The two nerve function networks relating to the reception of the sound containing ultra-high frequency components became apparent by the examination according to the positron emission tomography. The first network is a network of the auditory nervous system including the primary auditory cortex on both sides, which is a classical auditory system activated by the audible band components whether or not the presented sound contains ultra-high frequency components. The second network is a network of the brain deep portion including the thalamus and the upper brainstem. This activity is activated by the coexistence of the ultra-high frequency components and the audible band components. However, there is no change when only the ultra-high frequency components are presented, and the activity is suppressed when only the audible band components are presented. Since the brain deep portion is a base of opioid system and monoamine system neural circuits, which are important for the control of the emotional system, the second network is considered to be an emotional system network functioning as a modulator at the reception of sound.

Imperial Example 7

"Physiology of hypersonic effect" in accordance with the implemental example 7 will be described below.

1. Identification of a Nerve Mechanism Related to the Appearance of Hypersonic Effect The inventors of the present invention have found that the sound abundantly containing unsteady components exceeding the upper limit of the human's audible band has the advantageous effect of improving comfort and promoting the stimulus reception action and have reported the advantageous effect as hypersonic effect. A variation in the neural activity guided into the brain by the sound abundantly containing ultra-high frequency components is used as a base for various biological responses including psychological and behavioral reactions of the listener. In this case, in order to clarify the overall picture of the intracerebral neural mechanism related to the appearance of hypersonic effect, the influence of the sound abundantly containing ultra-high frequency components exceeding the upper limit of human's audible band on the cerebral nervous system was examined by the positron emission tomography (PET).

When the activity of cerebral nerves is increased, an increase in the energy metabolism of the relevant brain portion causes an increase in the regional cerebral blood flow. So as to grasp the state, it is possible to obtain a tomographic image of the whole brain with high spatial resolution by giving water labeled by oxygen radioactive isotope ($^{15}O$) to a living body and measuring the intracerebral distribution by PET. By comparing cerebral blood flow distribution at the reception of the certain sensory stimulus or the execution of a motion cognitive task with that under test conditions and finding the area where the regional cerebral blood flow changes, cerebral nerve activity relating to the stimulus reception and task execution can be identified.

1-1. PET Measurement

The subjects were 12 non-handicapped adults. A composition of traditional Gamelan music in Bali Island "Gambung Kuta" (200 seconds) abundantly containing ultra-high frequency components equal to or larger than 20 kHz was used as a sound source. A bi-channel sound reproducing system was placed in a PET measurement room to present the sound sample. Loudspeakers were disposed as opposed to the subject's body with a distance of 1.5 m from the subject's ears and sound pressure was adjusted so as to be sufficiently audible and cause no discomfort. The temperature and humidity in the PET measurement room were adjusted and paying attention to visual information environment, a cable of a sound reproducer and medical equipment necessary for PET measurement were removed from the subject's viewing field by using ambient drawing, planting and furniture to improve comfort for the subjects.

The audible band components (LFC) of the sound sample and the ultra-high frequency components (HFC) exceeding the audible band, were combined to prepare the following four presentation conditions:

(1) FRS (Full Range Sound)=LFC+HFC;
(2) HCS (High Cut Sound)=only LFC;
(3) LCS (Low Cut Sound)=only HFC; and
(4) Baseline=only background noise.

(1), (2) and (4) were presented to six subjects twice and (1), (3) and (4) are presented to the remaining six subjects twice in the randomized order, and regional cerebral blood flow under each condition was measured.

The cerebral blood flow image obtained from each subject was analyzed using SPM (Statistical Parametric Mapping) software. After a distortion in the head position during imaging was corrected and the brain of each subject was shaped according to a Talairach standard brain, statistical test was carried out using a general linear model. First of all, by comparing the cerebral blood flow under the experiment conditions with each other, the area where the cerebral blood flow was increased or decreased was identified. After correcting for multiple comparisons by the statistical tests of many pixels, the blood flow changed area was identified with a significant level of $p<0.05$. Furthermore, in order to identify a change tendency, tests without correcting for multiple comparisons was carried out at the same time. Subsequently, by extracting a space-time pattern changing in correlation with each other from data variance and covariance structure with the principle component analysis, extraction of a nerve function network was tried.

1-2. Results (1) Effect of the Audible Band Components

In the presentation of the audible band components, in comparison with the background noise condition, a significant increase in blood flow in the primary auditory cortex and a decrease in blood flow in the visual association area were recognized (FIG. 94: FRS+HCS vs. Baseline).

(2) Effect of the Ultra-High Frequency Components Alone

In the presentation of the ultra-high frequency components alone, in comparison with the background noise condition, there was no region where blood flow obviously increased or decreased (FIG. 94: LCS vs. Baseline).

(3) Effect of the Ultra-High Frequency Components on the Audible Band Components Reception In the simultaneous presentation of the ultra-high frequency components and the audible band components, in comparison with the background noise condition, a significant increase in blood flow in the primary auditory cortex, an increase in blood flow in the thalamus and upper brainstem and a decrease in blood flow in the visual association area were recognized (FIG. 94: FRS vs. Baseline). On the other hand, in the presentation of the audible band components alone without the ultra-high frequency components, a significant increase in blood flow in the primary auditory cortex was recognized, whereas an increase in blood flow in the thalamus and upper brainstem was not recognized. On the other hand, in addition to the visual association area, a decrease in blood flow in the upper brainstem and the precuneus was not recognized (FIG. 94: HCS vs. Baseline). Comparing the simultaneous presentation of the ultra-high frequency components and the audible band components with the presentation of the audible band components alone directly, a significant increase in blood flow in the upper brainstem and the thalamus was recognized (FIG. 94: FRS vs. HCS).

(4) Overall Picture of the Nerve Network by Principal Component Analysis

As a first component of the principal component analysis, that is, a largest variation component contained in data, a region including the primary auditory cortex on both sides was visualized. This component is considered to be an auditory system network as it took a low value under the baseline condition and a high value under the FRS and HCS conditions.

Figure 95:
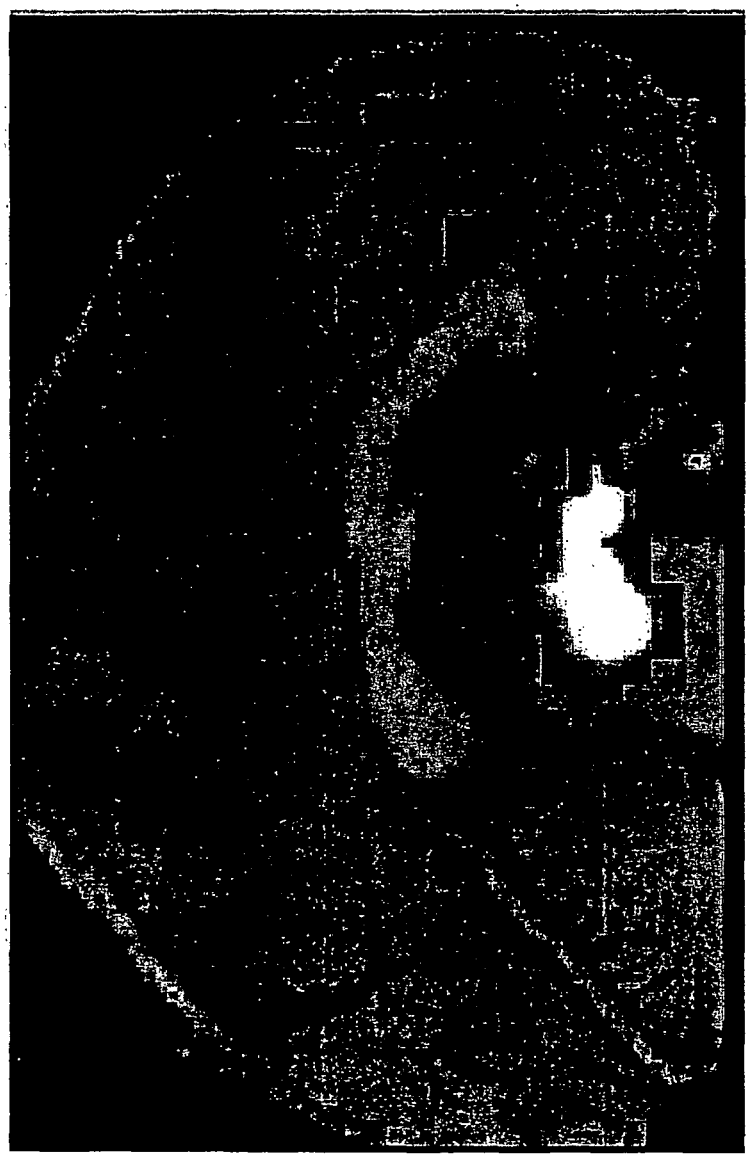
FIG. 95 is a sectional photograph showing a neural network for promoting the generation of a hypersonic effect according to the implemental example 7.

As a second component of the principal component analysis, that is, a largest variation component contained in the data after the variation of the first component is removed, a network extending from the frontal orbital portion to the prefrontal cortex and the cingulated gyrus anterior part was visualized using the brain deep portion including the upper brainstem (mid brain), the hypothalamus and the thalamus as a center was visualized (FIG. 95). This component is considered to be an emotional system and sensory system network leading mutual influence to the reception of the audible band components by the ultra-high frequency components as it took a value which becomes higher in the order of FRS>Baseline>HCS.

2. Examination on the General Biological Reaction Led by Hypersonic Effect

The nerve network supporting the appearance of hypersonic effect clarified by PET is distributed centering on nerve tissues in the upper brainstem, the hypothalamus and the thalamus, which perform brain's basic functions. The brain main parts control the nervous function of the whole brain, and collectively control tissues and organs throughout the body via the automatic nervous system, the endocrine system and the immune system. Therefore, the possibility that a change in the activities of the nerve network including these brain main parts may cause the reaction of the generalized physiological function as well as only the nervous system can be denied. Thus, blood was collected from the subjects listening to the sound abundantly containing ultra-high frequency components and the sound containing no ultra-high frequency components and blood physiological active substance indicators were analyzed.

2-1. Method

The subjects were 16 non-handicapped adults. The sound source used in the experiment by PET was edited to be a sound sample for 40 minutes. A comfortable listening seat was installed in an enough large listening room. Furniture, drawing, planting, and the like, were appropriately arranged in the periphery of the seat and lighting and air-conditioning were adjusted to improve overall comfort. Using a bi-channel system, two conditions of FRS (Full Range Sound=LFC+HFC) and HFC (High Cut Sound=only LFC) were set and the sound for 40 minutes was presented to all subjects once under each condition, that is, twice in total. A break for five minutes was provided between two presentations. The order of presentation was randomized between the subjects and the experiment was carried out with the subjects being blindfolded.

In order to prevent the provision of stress accompanying blood sampling to the subjects as far as possible, an indwelling needle was previously introduced into a vein of an arm of each subject before the start of the experiment, and a tube was connected thereto as a blood sampling line and kept as it was during the experiment. Every time under each presentation condition, blood was collected from the blood sampling line after a lapse of 35 minutes from the start of presentation. The blood sampling line was made invisible to the subjects and the blood sampling operation was performed without the subjects' visual field so as not to apply stress as much as possible.

It is to be noted that cellular immunity acting on health maintenance and biological defense throughout the body and endocrine substances relating to mind-body correlation on both of positive and negative aspects, four cellular immunity indicator items (CD4-positive cell ratio, CD8-positive cell ratio, CD4-positive cell/CD8-positive cell ratio, NK cell activity) and six endocrine indicator items (cortisol, adrenaline, noradrenaline, dopamine, beta-endorphin, prolactin) were measured. Since measurement values varied widely between the subjects in all items, the value obtained by normalizing the measurement values of the subjects in each item (dividing the measurement value under each condition by an average value of values under two conditions), the significant difference between the conditions was certified by the correlated t-test about the average value between the subjects.

2-2. Results

FIG. 96 shows measurement results of each indicator under each condition. It is shown that, in comparison with the presentation of HCS, the NK cell activity is statistically-significantly increased in the presentation of FRS.

3. Examination

The two nerve function networks relating to the reception of the sound containing ultra-high frequency components became apparent by the examination according to PET. The first network is a network of the auditory nervous system including the primary auditory cortex on both sides, which is a classical auditory system activated by the audible band components whether or not the presented sound contains ultra-high frequency components. The second network is a network centering on the brain main parts including the thalamus, the hypothalamus and the upper brainstem. This activity is activated by the coexistence of the ultra-high frequency components and the audible band components. However, there is no change when only the ultra-high frequency components alone are presented, and the activity is suppressed when only the audible band components are presented. Since opioid system and monoamine system neural circuits concentrate in the upper brainstem as a center of the network, it is considered to be an emotional or sensory network which functions as a modulator at the reception of sound.

Furthermore, the brain main parts serve to control the general body function via the endocrine system and the immune system. In this examination, the NK cells, which exhibit a statistically significant difference between FRS and HCS, play the principal role of cellular immunity that destroys and removes cancer cells and virus-infected cells and serves to prevent illnesses and maintain health. At the same time, the NK cell activity also reflects the strong resistance to the stress of the living body. That the NK cell activity is significantly increased in the presentation of FRS than in the presentation of HCS is considered to suggest that the activation of the emotional or sensory nerve network by the sound abundantly containing ultra-high frequency components exceeding the upper limit of the audible band increases the general immune activity through the transfer of cytokine as one of in vivo information transmitters and leads to health enhancement. So far, the inventors of the present invention have reported that unsteady ultra-high frequency components exceeding the upper limit of the audible band are abundantly contained in the natural environmental sound in tropical rain forests with which human beings have become familiar in the course of evolution, while they are hardly contained in the environmental sound in cities. Considering these findings all together, an influence of the unsteady ultra-high frequency components can affect the sound reception reaction as well as health problems inherent in inhabitants in cities.

On the other hand, in this examination, no statistically significant result could be found in the endocrine indicator. As one cause, it is necessary to consider the possibility that the biological reaction caused by discomfort and fear of "needle insertion" for collecting blood disturbs the data. In this examination, although the method for ensuring the blood sampling line to minimize pain by blood sampling is adopted, nevertheless, the possibility an uncomfortable feeling and scary feeling given to the non-handicapped subjects was unignorable cannot be denied. In the future, it is necessary to establish a measurement method having less physical and mental burden to the subjects and make a further examination using the method.

4. Conclusion

An influence of the sound abundantly containing ultra-high frequency components exceeding the upper limit of the audible band on the brain function and the general physiological function is examined. As a result, the activation of the emotional or sensory nerve network centering on the brain main parts is recognized in the brain and an increase of the cell immune activity is detected throughout the body. These results suggest the possibility that the presence or absence of the unsteady ultra-high frequency components may influence the health condition of the listener.

Implemental Example 8

Figure 99:
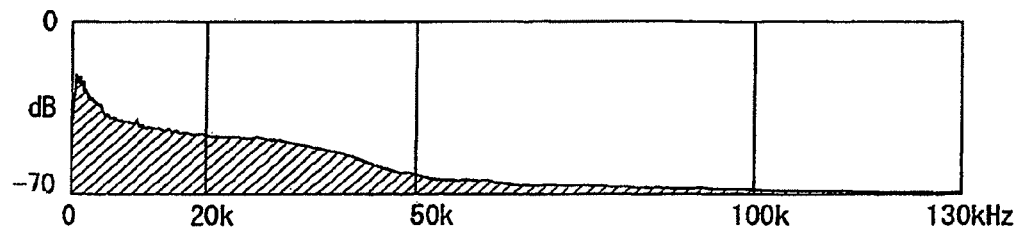
FIG. 99 is a chart showing an FFT spectrum of an environmental sound of a song of a babbling brook in the Mongol plain which is measured by the inventors according to the implemental example 8.
Figure 100:
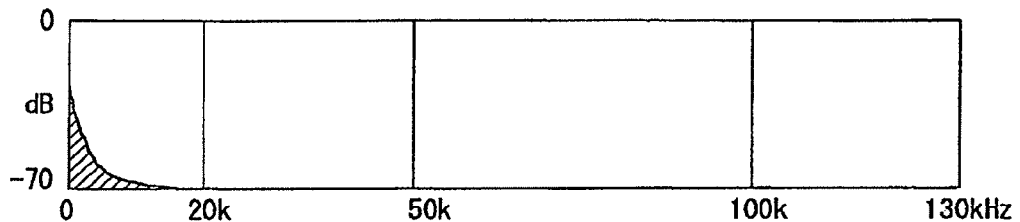
FIG. 100 is a chart showing an FFT spectrum of an environmental sound in a town area of Nakano-ku, in Tokyo, Japan which is measured by the inventors according to the implemental example 8.

In the implemental example 8, comparison between spectrums of tropical rein forest type environmental information and urban space type environmental information and their densities are considered. As an example of the tropical rain forest type environmental information, FIG. 97 shows an FFT spectrum of environmental sound recorded in Borneo Island in Malaysia, FIG. 98 shows an FFT spectrum of environmental sound recorded in Java Island in Republic of Indonesia and FIG. 99 shows an FFT spectrum of environmental sound of babbling of a brook recorded in Mongolic Grassland. In comparison with them, as an example of the urban space type environmental information, FIG. 100 shows an FFT spectrum of environmental sound recorded in an urban area in Nakano-ku, Tokyo. Referring to FIG. 97 to FIG. 100, a horizontal axis of the FFT spectrum indicates the number of air vibrations per second, that is, frequency. A vertical axis indicates in dB power for each frequency, which is estimated by a fast Fourier transform method.

Human's perceptive limit of auditory information is set so that the air vibrations per second may not exceed 20 times (frequency of 20 Hz) and 20,000 times (frequency of 20 kHz). In all of the three examples of tropical rain forest information, auditory information having the density in the pervasive scope of the frequency of 20 Hz to 20 kHz and auditory information having the density in the super-pervasive scope exceeding 20 kHz up to 13 kHz (the number of air vibrations per second is 130,000) coexist. On the other hand, in the example of the urban space type environmental information, the auditory information having the density in the perceptible scope of the frequency of 20 Hz to 20 kHz occupies an overwhelming proportion and the auditory information having the density in the super-perceptible scope hardly exists.

Figure 101:
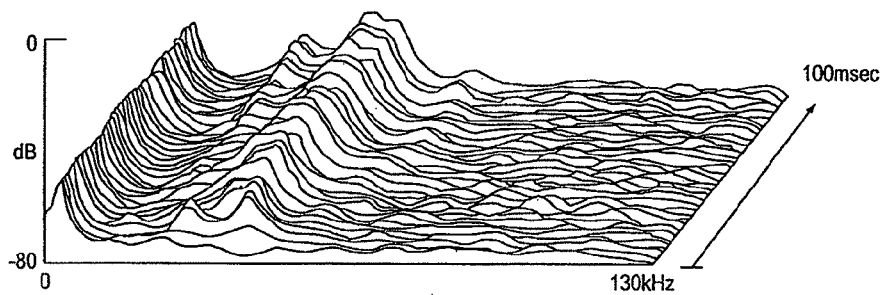
FIG. 101 is a chart showing an ME spectral array of a tropical rain forest environmental sound in Borneo island, the Republic of Malaysia which is measured by the inventors according to the implemental example 8.
Figure 102:
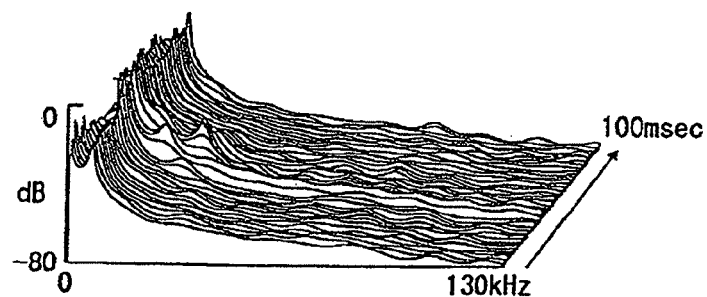
FIG. 102 is a chart showing an ME spectral array of a tropical rain forest environmental sound in Java island, the Republic of Indonesia which is measured by the inventors according to the implemental example 8.
Figure 103:
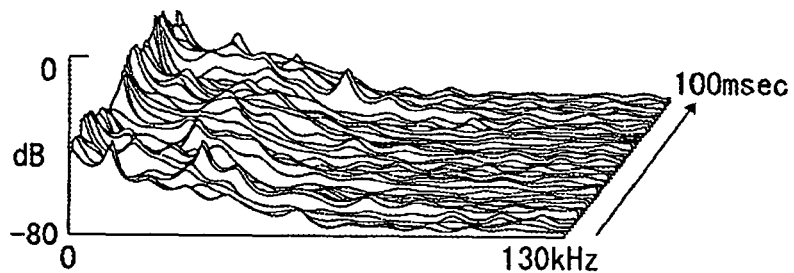
FIG. 103 is a chart showing an ME spectral array of an environmental sound of a song of a babbling brook in the Mongol plain which is measured by the inventors according to the implemental example 8.
Figure 104:
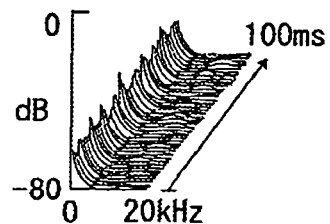
FIG. 104 is a chart showing an ME spectral array of a silent indoor sound in the town area of Nakano-ku, in Tokyo, Japan which is measured by the inventors according to the implemental example 8.
Figure 105:
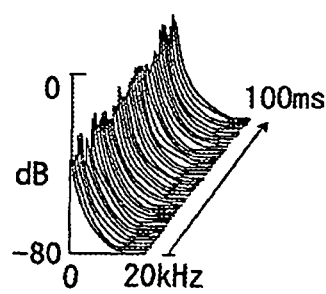
FIG. 105 is a chart showing an ME spectral array of an outdoor noise in the town area of Nakano-ku, in Tokyo, Japan which is measured by the inventors according to the implemental example 8.

Next, ME spectrum arrays will compare each other in complexity. As examples of the tropical rain forest type environmental information, FIG. 101 shows an ME spectrum array of the environmental sound recorded in Borneo Island in Malaysia, FIG. 102 shows an ME spectrum array of the environmental sound recorded in Java Island in Republic of Indonesia and FIG. 103 shows an ME spectrum array of the environmental sound of babbling of a brook recorded in Mongolic Grassland. In comparison with them, as an example of the urban space type environmental information, FIG. 104 and FIG. 105 show ME spectrum arrays of the environmental sound recorded in an urban area in Nakano-ku, Tokyo. In this case, FIG. 104 shows an ME spectrum array of quiet indoor sound and FIG. 105 shows an ME spectrum array of outdoor noise. In FIG. 101 to FIG. 105, a horizontal axis of the ME spectrum indicates the number of air vibrations per second, that is, frequency. A vertical axis indicates power expressed in dB for each frequency, which is estimated by the maximum entropy method. An axis, which extends from the near side of the array toward the backside, indicates progress of time.

As apparent from FIG. 101 to FIG. 103, in the three examples of tropical rain forest type environmental information, in either or both of the audible band or super-audible band exceeding 20 kHz, peak amplitude, frequency or spectrum shape greatly changes at intervals shorter than 10 milliseconds. On the other hand, as apparent from FIGS. 104 and 105, in the example of the urban space type environmental information, the spectrum shape is steady and hardly varies.

FIG. 106 is a table, which summarizes the above-mentioned examinations and shows differences between super perceptual information and perceptual specific information according to the present invention. As shown in FIG. 106, the perceptual specific information is sensory information consisting of only information within perceptual limits. On the other hand, the super perceptual information is sensory information consisting of perceptible information and information exceeding the perceptual limit (preferably exceeding the limit significantly).

Concerning the hearing density of the perceptual specific information, the auditory information density (the number of air vibrations per second) includes only the perceptible band equal to or higher than 20 Hz and equal to 20 kHz or lower than 20 kHz, and concerning the complexity, in the auditory information having the above-mentioned density, the shape of spectrum showing the density and power structure of the auditory information is steady in a time region shorter than 100 milliseconds. On the other hand, concerning the hearing density of the super perceptual information, the auditory information density (the number of air vibrations per second) includes both the perceptible band equal to or higher than 20 Hz and equal to or lower than 20 kHz and the super perceptual band exceeding 20 kHz (at least 100 kHz) and preferably reaching 200 kHz coexist. Concerning the complexity of the super perceptual information, in the auditory information having the above-mentioned density, the shape of spectrum showing the density and power structure of the auditory information is transfigured in a time region equal to or longer than the maximum time of 100 milliseconds and equal to or shorter than the minimum time of 0.5 milliseconds.

Concerning the visual density of the perceptual specific information, the visual stimulus density (the number of pixels/angle of visibility (min)) does not exceed the minimum difference threshold vision. Concerning the complexity, in the visual stimulus having the above-mentioned density or the visual stimulus having a density exceeding this density, fractal dimension (capacity dimension) of the visual information is substantially equal to or larger than 2.0 and less than 2.2. On the other hand, concerning the visual density of the super perceptual information, the visual stimulus density (the number of pixels/angle of visibility (min)) exceeds the minimum difference threshold vision and is preferably ten times as high as the minimum difference threshold, and concerning the complexity, in the visual stimulus having the above-mentioned density, capacity dimension of the visual information is substantially equal to or larger than 2.2 and less than about 3.0.

Furthermore, the information structure of the perceptual specific information includes low-density monotony, steadiness and geometric regularity and has the tendency to deactivate a "sensible brain" (reward nervous system) consisting of the brain deep portion, related monoaminergic projection system and the like. On the other hand, the information structure of the super perceptual information includes super high-density high complexity, unsteadiness and transformability and has the tendency to activate the "sensible brain" (reward nervous system) consisting of the brain deep portion, related monoaminergic projection system and the like.

As has been described, the tropical rain forest type environmental information defined by the inventors of the present invention is super perceptual information as sensory information consisting of perceptible information and information exceeding the perceptible limit (preferably remarkably) and the super perceptual information is generated and realized by the apparatus or system described in the specification and figures of the present application and can be set in a predetermined space including at least one of urban space, housing space and living space. The space generating the tropical rain forest type environmental information may be any predetermined space including indoor space, such as housing space (rooms, etc.), vehicles such as trains, airplanes, boats and ships, and outdoor space such as gardens, parks and forests.

Implemental Example 9

Figure 108:
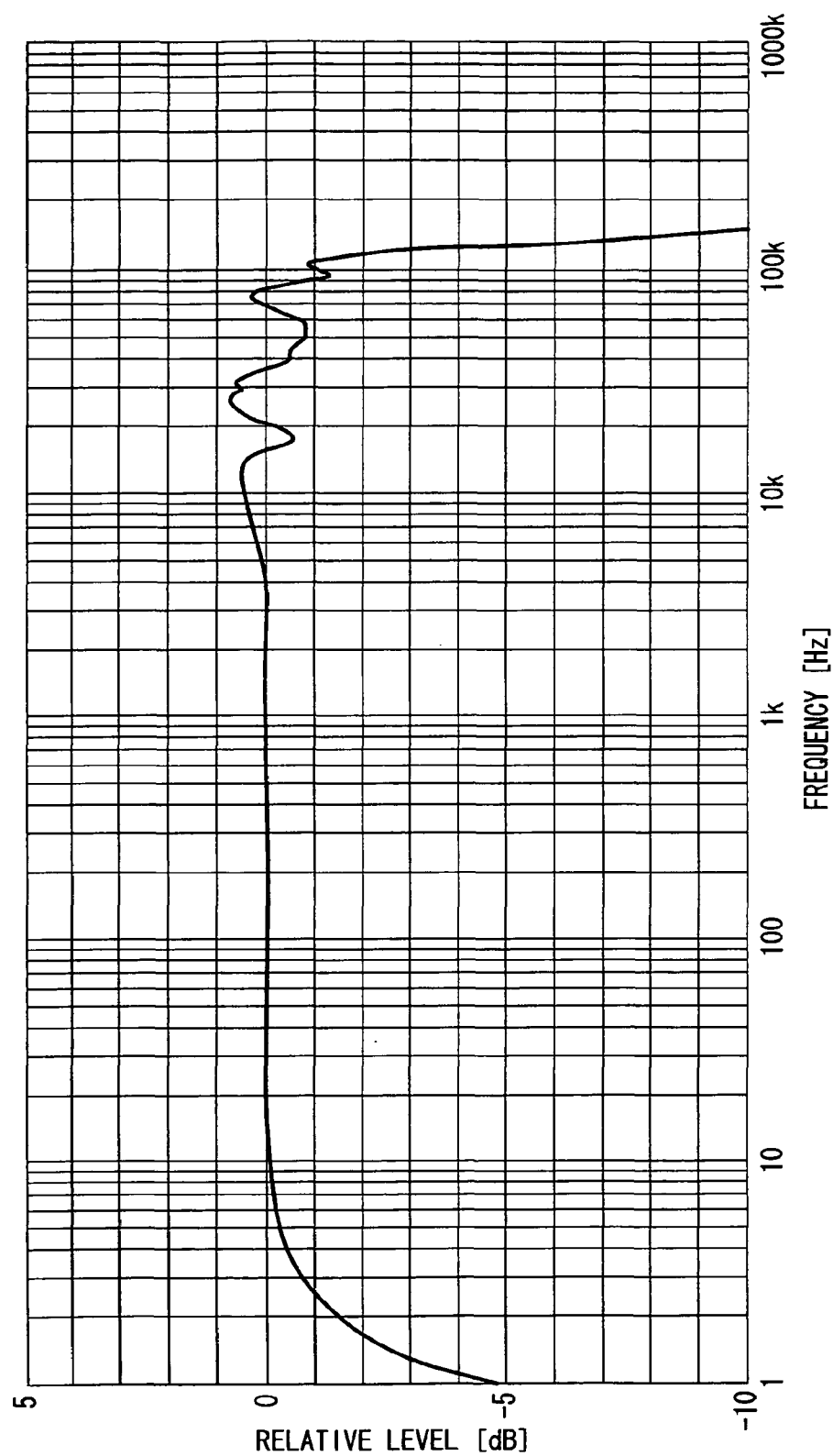
FIG. 108 is a graph showing frequency characteristics of a microphone 201 used in the system of FIG. 107.
Figure 109:
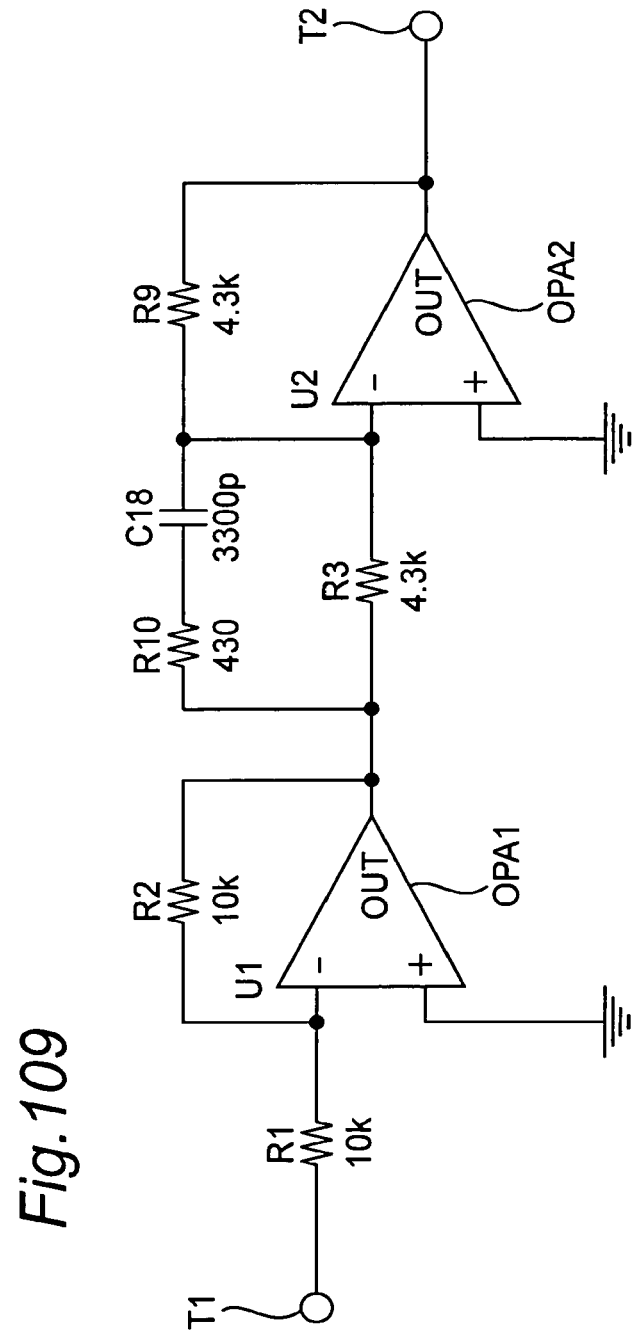
FIG. 109 is a circuit diagram showing a structure of a pre-emphasis circuit 203 used in the system of FIG. 107.

FIG. 107 is a block diagram showing an example of a system of recording super perceptual auditory information in accordance with the implemental example 9. FIG. 108 is a graph showing a frequency characteristic of a microphone 201 used in the system of FIG. 107. FIG. 109 is a circuit diagram showing a configuration of a pre-emphasis circuit 203 used in the system of FIG. 107, FIG. 110 is a graph showing a frequency characteristic of the pre-emphasis circuit 203 of FIGS. 109 and 111 is a graph showing a phase characteristic of the pre-emphasis circuit 203 of FIG. 109.

Referring to FIG. 107, an air vibration holding the super perceptual auditory information is input by the microphone 201 and the air vibration is converted into an electric signal. The microphone 201 has the flat frequency characteristic up to 100 kHz as shown in FIG. 108, preferably reaching the frequency characteristic of 200 kHz. The electric signal obtained by the microphone 201 is amplified by a high-performance microphone amplifier 202 to relatively reduce an influence of the inclusion of noise on the signal. Subsequently, prior to analog/digital conversion, in order to improve the S/N ratio of the super high-density band, which is easy to be subjected to the influence of one-bit noise by the quantization inherent in high-speed one-bit analog/digital conversion, a higher band is amplified by the pre-emphasis circuit 203 having the circuit as shown in FIG. 109 and the frequency characteristic as shown in FIG. 110. As shown in FIG. 109, the pre-emphasis circuit 203 is configured to have two operational amplifiers OPA1 and OPA2, and an input resistance, an input capacitance and a return resistance that are connected to the operational amplifiers, between an input terminal T1 and an output terminal T2. The high-speed one-bit analog/digital conversion has a fundamental disadvantage of adding quantized noise to the super high-density band. In order to prevent this disadvantage, the noise is pushed up to a higher band side. In addition, the higher band may be amplified by the pre-emphasis circuit 203 so that the influence of noise becomes relatively unignorable and then is analog/digital converted, or conversely, the higher band may be reduced after digital/analog conversion and then reproduced into a sound.

Figure 110:
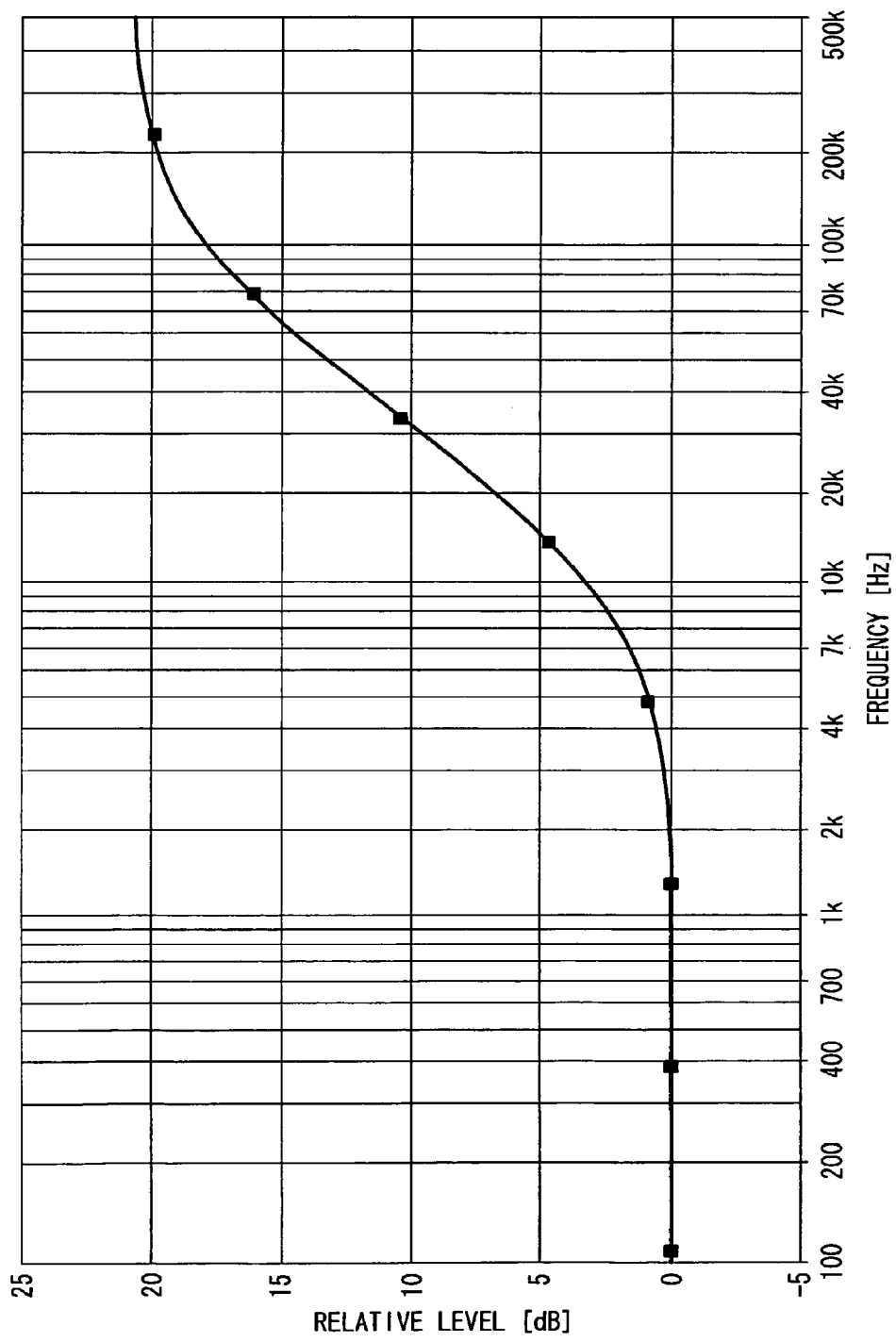
FIG. 110 is a graph showing frequency characteristics of the pre-emphasis circuit 203 of FIG. 109.
Figure 111:
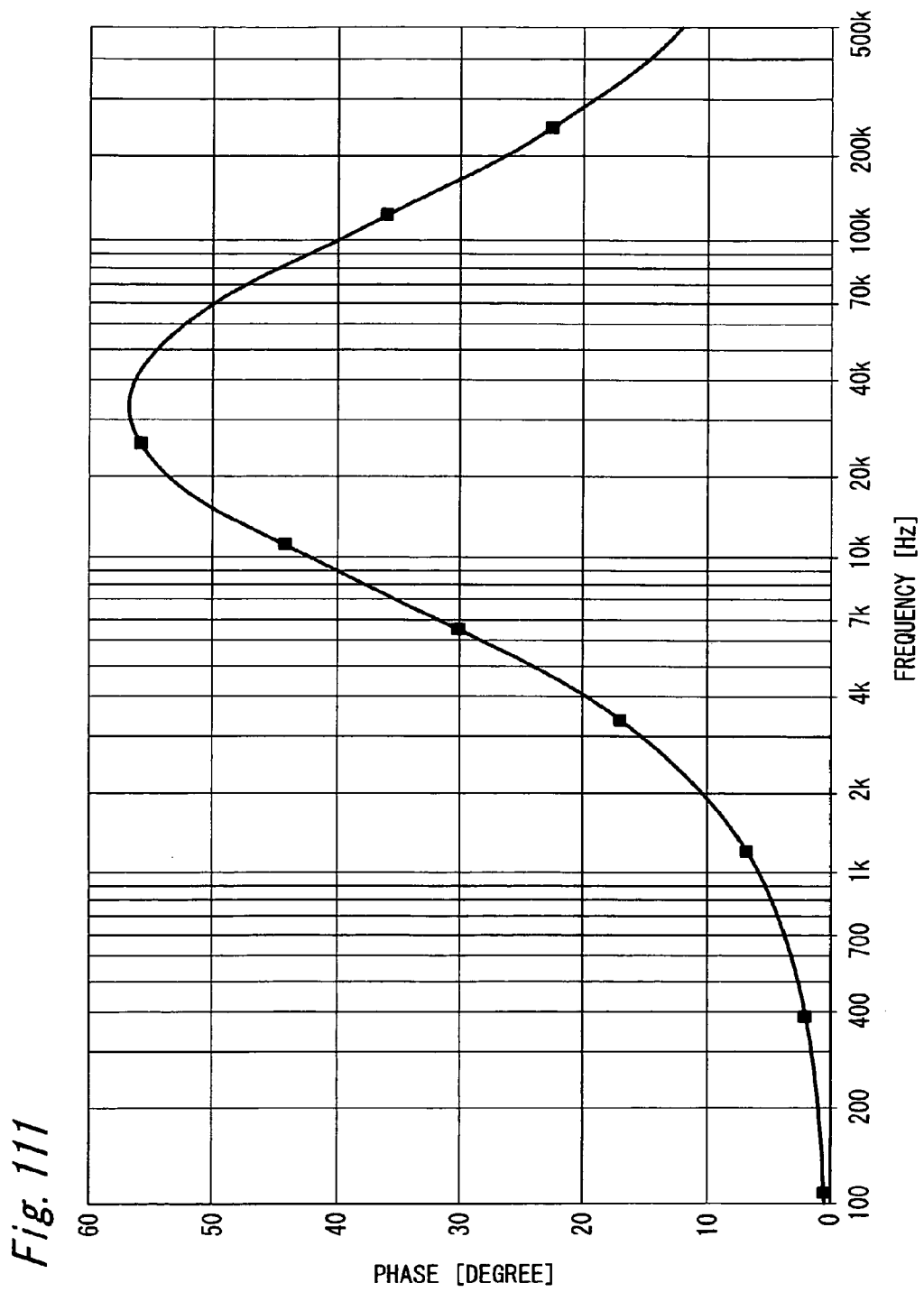
FIG. 111 is a graph showing phase characteristics of the pre-emphasis circuit 203 of FIG. 109.

In the present implemental example, as shown in FIG. 110, the emphasis circuit 203 to which a new idea is incorporated and a de-emphasis circuit 213 are used. This is as follows:

(1) By the frequency characteristic of +20 dB at 200 kHz, for example, it is possible to address the conventionally adopted high-speed one-bit analog/digital conversion with a relatively low density as well as a conversion method having noise in a higher band, which will be developed in future.

(2) Since a simple shelving filter is used, an inverse circuit can be easily built and the frequency characteristic and the phase characteristic of the emphasis circuit 203 and the de-emphasis circuit 213 becomes flat.

(3) The circuit has a simple configuration due to a primary filter. This leads the above-mentioned effect (2).

(4) Due to the phase characteristic, which has a smooth curve without any specific inflexion point, a circuit with less negative effect on the sound quality can be obtained.

The electric signal having passed through the above-mentioned pre-emphasis circuit 203 is digitalized by a high-speed one-bit A/D converter 104. By setting a sampling frequency as, for example, 2.8224 MHz or 5.6448 MHz, an acoustic signal of a higher density than conventional can be recorded. For example, the frequency of −10 dB or −5 dB at 100 kHz is desirable. By recording the electric signal digitalized through the above-mentioned processing in a recording medium, such as a magnetic tape or an optical disk like DVD-RAM, super perceptual auditory information can be recorded. In analog/digital conversion, a method such as PCM conversion having the equivalent quality may be employed.

Although only one channel is described in the above-mentioned implemental example of FIG. 107 for simplification, multi-channelizing is an important requirement for the recording of environmental information.

Implemental Example 10

Figure 112:
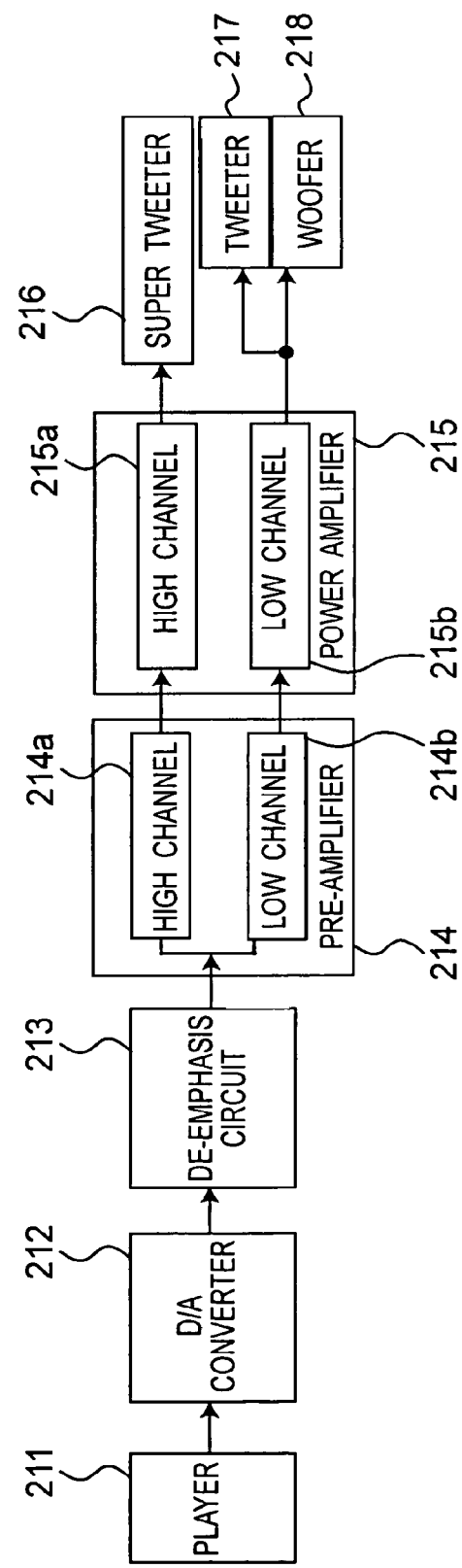
FIG. 112 is a block diagram showing an example of a system for reproducing the super perceptual auditory information according to an implemental example 10.
Figure 113:
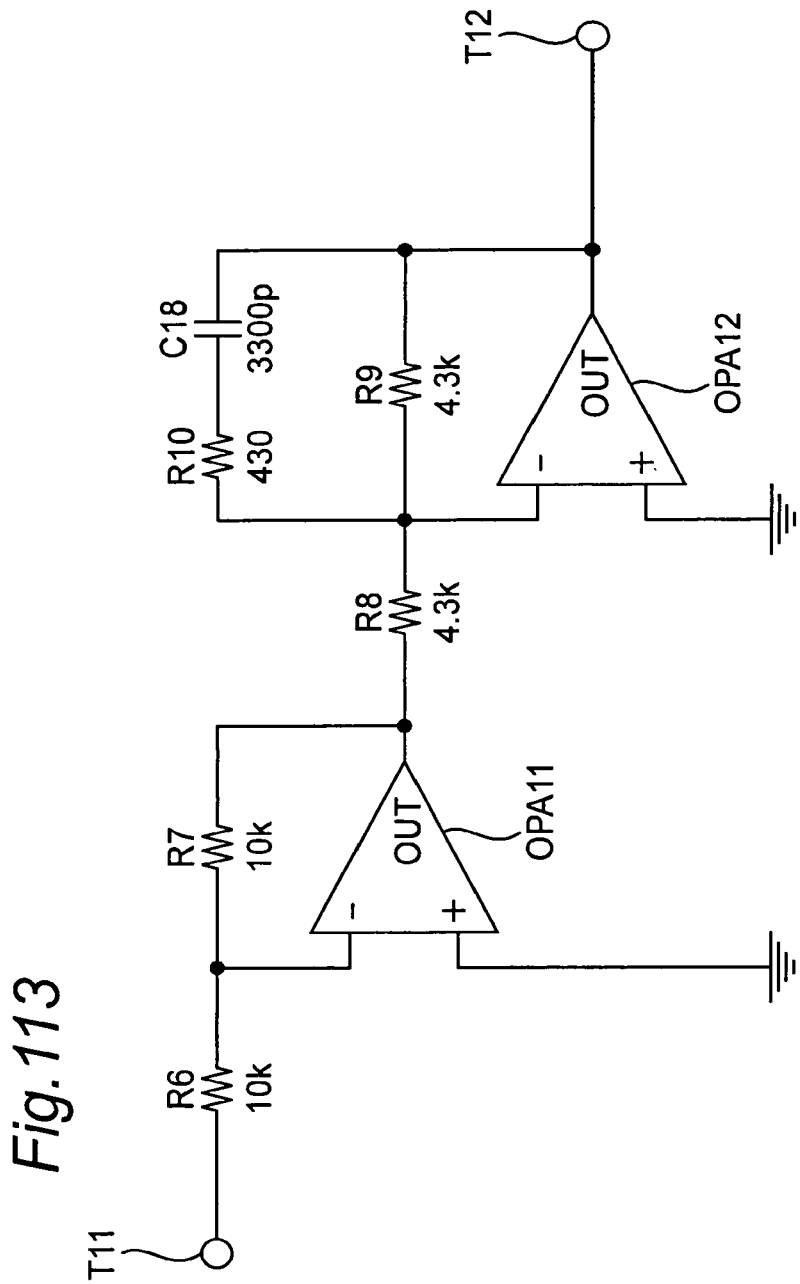
FIG. 113 is a circuit diagram showing a structure of a de-emphasis circuit 213 used in the system of FIG. 112.
Figure 114:
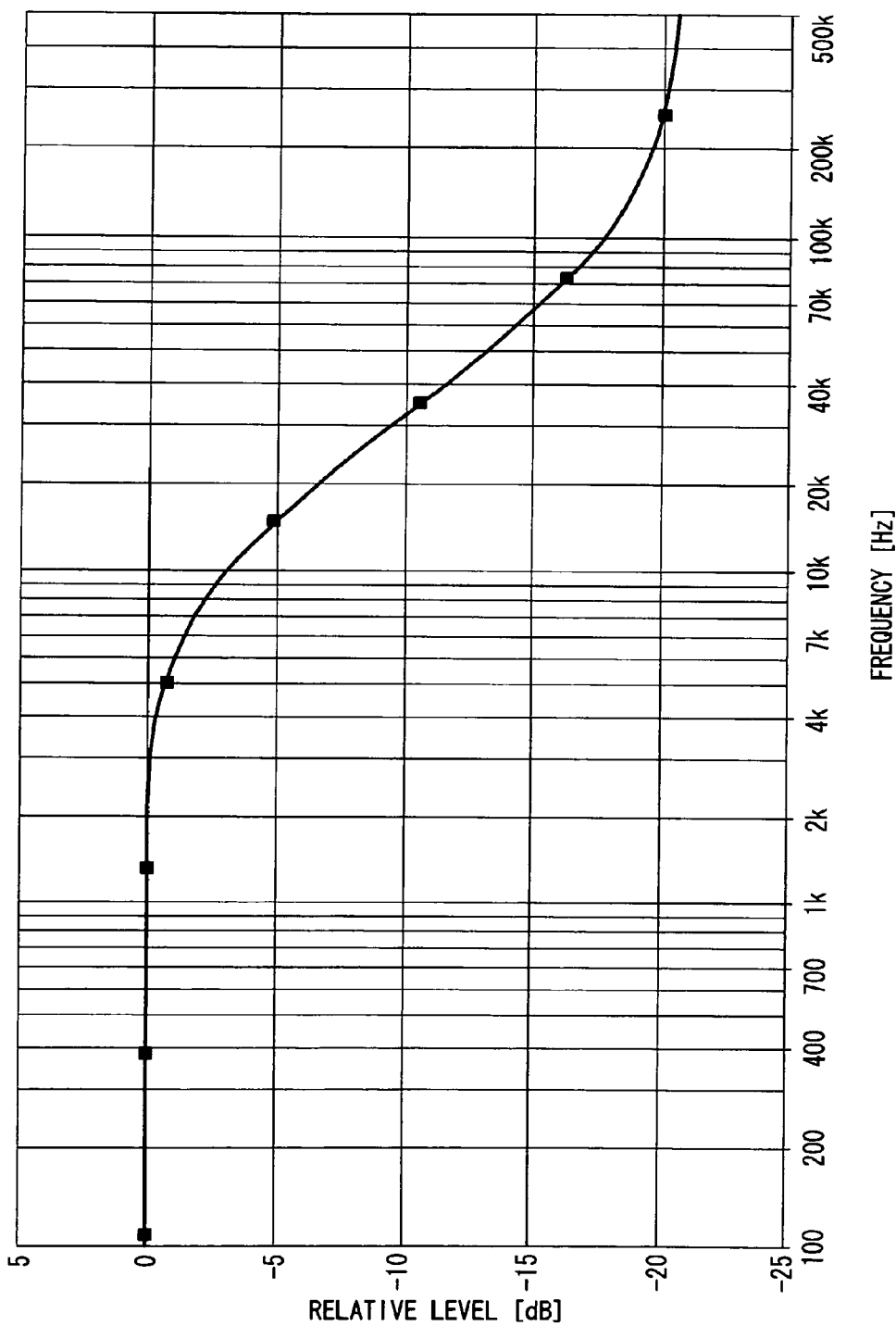
FIG. 114 is a graph showing frequency characteristics of the de-emphasis circuit 213 of FIG. 113.
Figure 115:
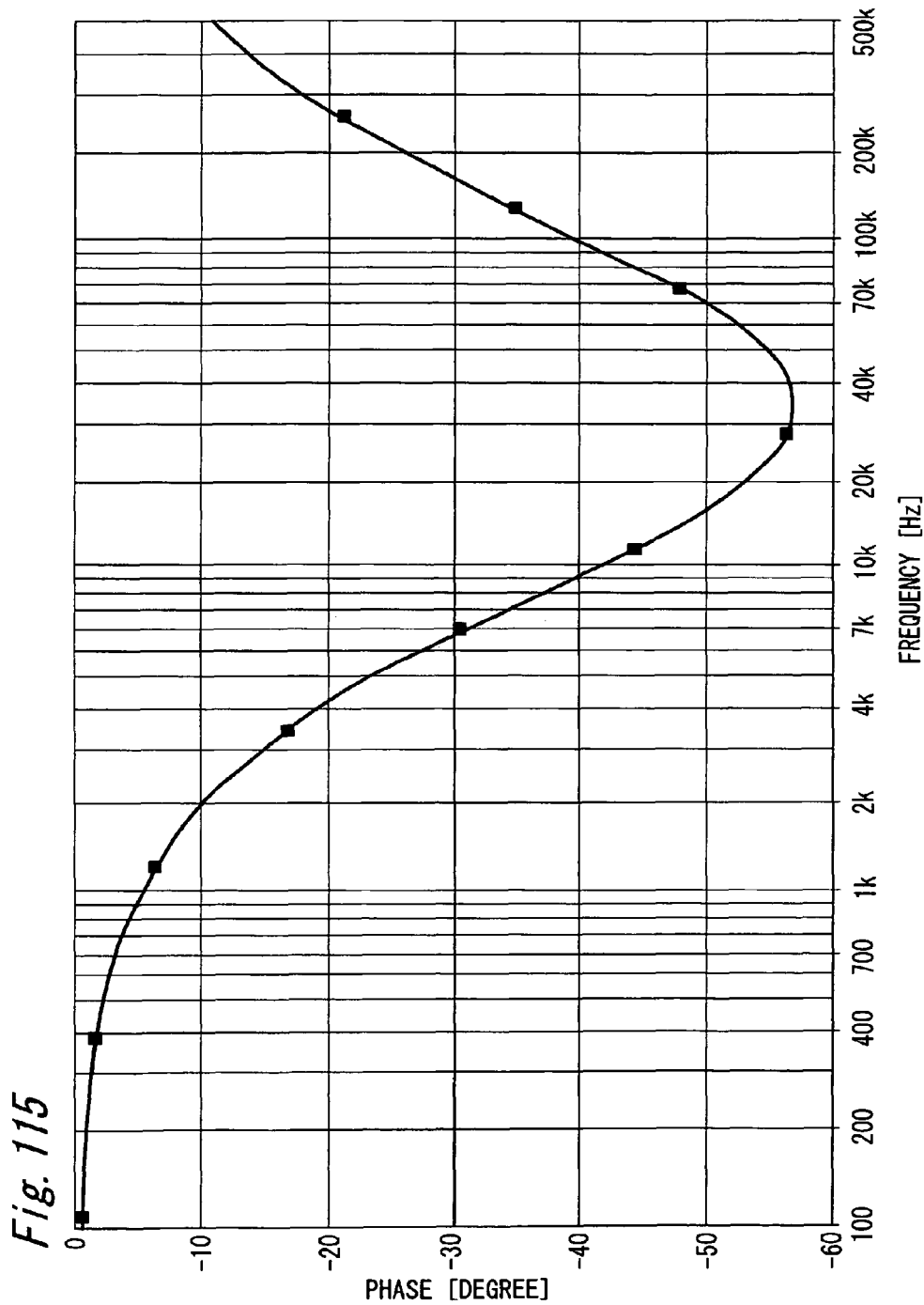
FIG. 115 is a graph showing phase characteristics of the de-emphasis circuit 213 of FIG. 113.

FIG. 112 is a block diagram showing an example of a system of reproducing super perceptual auditory information in accordance with the implemental example 10, and FIG. 113 is a circuit diagram showing a configuration of a de-emphasis circuit 213 used in the system of FIG. 112. FIG. 114 is a graph showing a frequency characteristic of the de-emphasis circuit 213 of FIG. 113 and FIG. 115 is a graph showing a phase characteristic of the de-emphasis circuit 213 of FIG. 113.

Referring to FIG. 112, first of all, a player 211 reads a digital data signal from a recording medium as a super perceptual medium. For example, digital information in a super audio CD widespread as a super perceptual package medium is read by the super audio CD player. Subsequently, the read digital data signal is converted into an analog signal by a D/A converter 212. For example, the super audio CD can theoretically reproduce super high-density band by using high-speed one-bit analog/digital conversion and a direct stream digital (DSD) recording method. However, in order to eliminate the peak of the one-bit noise appearing in the super high-density band, a digital/analog converter built in the conventional super audio CD player has a function of rolling off the super high-density band equal to or larger than 50 kHz to reduce the super perceptual auditory information exceeding 50 kHz. In order to prevent the reduction, by changing a digital/analog conversion circuit so as not to have the peak of one-bit noise in the super high-density band, a function of reproducing an analog signal without reducing information in the super high-density is realized. For example, the frequency of −10 dB or −5 dB at 100 kHz is desirable. In analog/digital conversion, means such as PCM conversion having the equivalent quality may be employed.

Furthermore, in the case of the signal analog/digital converted by the pre-emphasis circuit 203, following digital/analog conversion, de-emphasis processing is performed by the de-emphasis circuit 213 having a frequency characteristic corresponding to the pre-emphasis circuit 203. The de-emphasis circuit 213, as shown in FIG. 113, is configured to have two operational amplifiers OPA1 and OPA2, and an input resistance, an input capacitance and a return resistance, which are connected to the operational amplifiers, between an input terminal T11 and the output terminal T12.

In the present implemental example, as shown in FIG. 113, the de-emphasis circuit 213 to which a new idea is incorporated is used. This is as follows:

(1) By the frequency characteristic of −20 dB at 200 kHz, for example, it is possible to address the conventionally adopted high-speed one-bit analog/digital conversion with a relatively low density as well as a conversion method having a noise floor peak in a higher band, which will be developed in future.

(2) Since a simple shelving filter is used, an inverse circuit of the pre-emphasis circuit 203 shown in FIG. 203 can be easily built and the frequency characteristic and the phase characteristic of pre-emphasis circuit and de-emphasis circuit become flat.

(3) By using a primary filter, the circuit has a simple configuration, and this leads to bringing about the above-mentioned effect (2).

(4) Due to the phase characteristic, which has a smooth curve without any specific inflexion point, a circuit with less negative effect on the sound quality can be obtained.

Next, the electric signal is amplified by a pre-amplifier 214. It is desirable to have the frequency characteristic of −3 dB at 200 kHz, for example, using a high-quality resistance switching attenuator. Then, the electric signal is amplified by a power amplifier 215. In the power amplifier 215, it is desirable to use a power amplifier unit which ensures the frequency response characteristic and transient response characteristic which can address the signal in the super high-density band, have the frequency characteristic of −3 dB at 200 kHz and control a distortion rate to be 0.01%. Finally, the electric signal is converted into sound and the sound is reproduced by three kinds of loudspeaker system 216, 217 and 218. The signal in the super high-density band is reproduced using a super tweeter 216. The signal in the audible band is reproduced by a two-way loudspeaker system consisting of a tweeter 217 and a woofer 218, for example. It is desirable that the loudspeaker system, as a whole, has a flat frequency characteristic from 20 Hz to 100 kHz and covers up to 200 kHz.

Preferably, amplification and reproduction are performed according to a known bi-channel method. That is, one input signal is diverged into signals for super high band and for an audible band as two lines of completely separated output signals. Then, this leads to that acoustic physiological and cognitive psychological experiments for examining effects of the super high-density auditory information can be precisely carried out without coming under the influence of group delay frequency characteristics and cross modulation distortion. Alternatively, a method other than the bi-channel method, in which the super high-density band and the audible band are amplified and reproduced in the same circuit, may be adopted. Although only one channel is described herein for simplification, multi-channelizing is an important requirement for the reproducing of environmental information.

Implemental Example 11

In the implemental example 11, a double helical matrix coordinate method used for a system in which a plurality of loudspeakers is disposed will be described below. In the implemental example 11, the case where double helical matrix is constructed by five-channel surround loudspeakers is illustrated. In the following figures, the following five loudspeakers are used.

(1) Front left loudspeaker FL;
(2) Front right loudspeaker FR;
(3) Rear left loudspeaker RL;
(4) Rear right loudspeaker RR; and
(5) Upper center loudspeaker UC.

Figure 116:
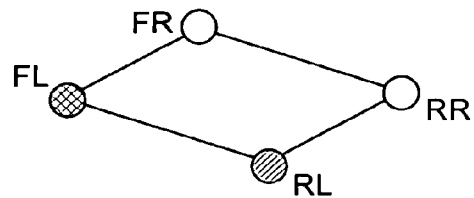
FIG. 116 is a perspective view showing an arrangement of a 4-channel surround sound loudspeaker according to the prior art.
Figure 117:
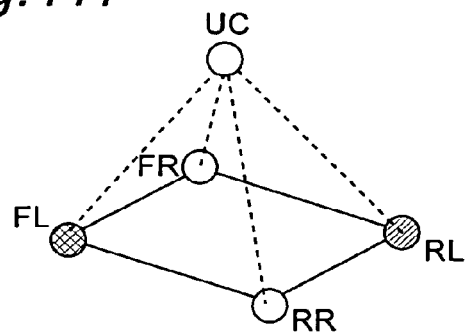
FIG. 117 is a perspective view showing an arrangement of a loudspeaker in a double helical matrix disposed by using the double helical matrix coordination method according to an implemental example 11.

FIG. 116 shows a normal four-channel surround loudspeaker arrangement according to the prior art. In the loudspeaker arrangement, the front left loudspeaker FL and the rear left loudspeaker RL lie on the same left side. Then, the double helical matrix arrangement is such as shown in FIG. 117. Referring to FIG. 117, the front left loudspeaker FL lies on the left side, while the rear left loudspeaker RL is disposed on the right side. Thus, the person within the space faces left sound and right sound even when he/she looks toward any of four sides. The person also listens to all sounds for the five channels. One feature of the double helical matrix is that stereoscopic vision and continuity are realized by adding the upper center loudspeaker UC.

Figure 118:
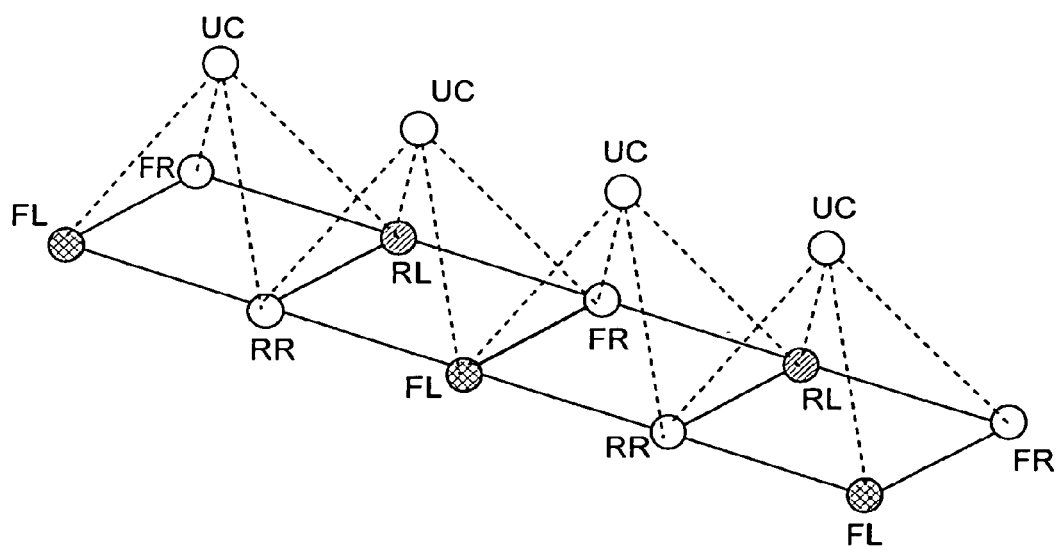
FIG. 118 is a perspective view showing an arrangement of a loudspeaker in which the double helical matrix is disposed continuously and repetitively in one direction by using the double helical matrix coordination method according to the implemental example 11.
Figure 119:
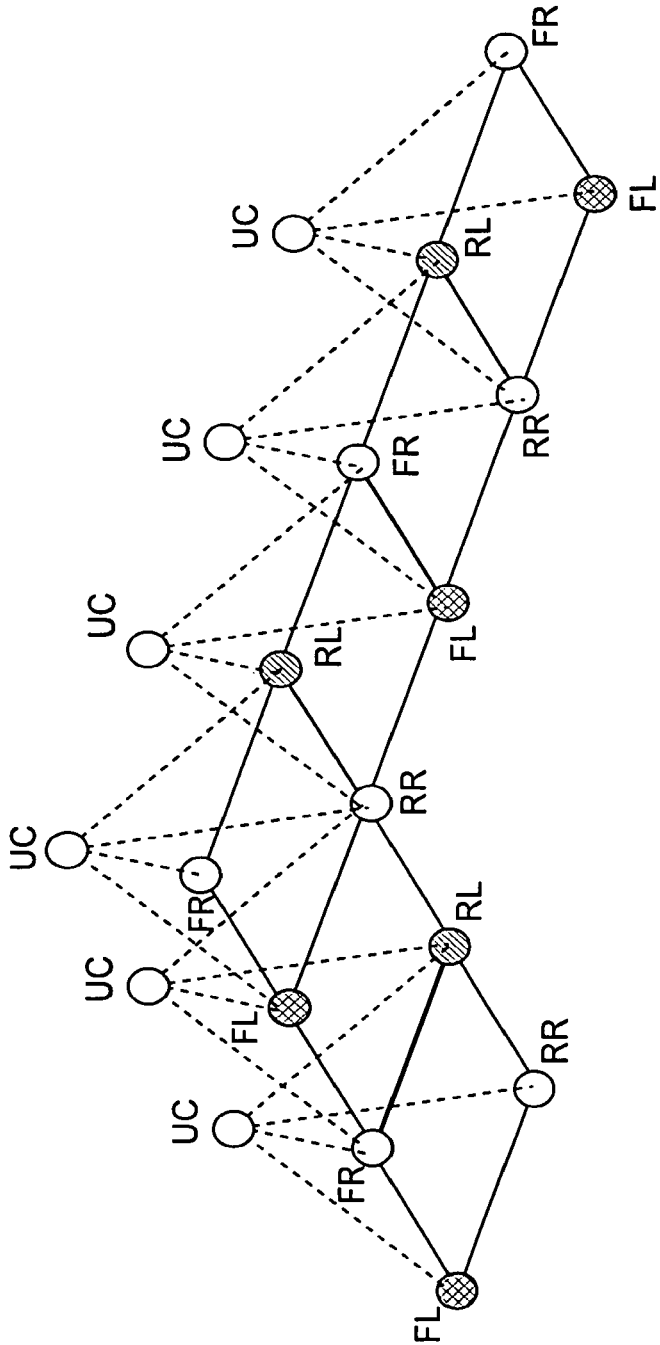
FIG. 119 is a perspective view showing an arrangement of a loudspeaker in which the double helical matrix is disposed continuously and repetitively in two directions by using the double helical matrix coordination method according to the implemental example 11.
Figure 120:
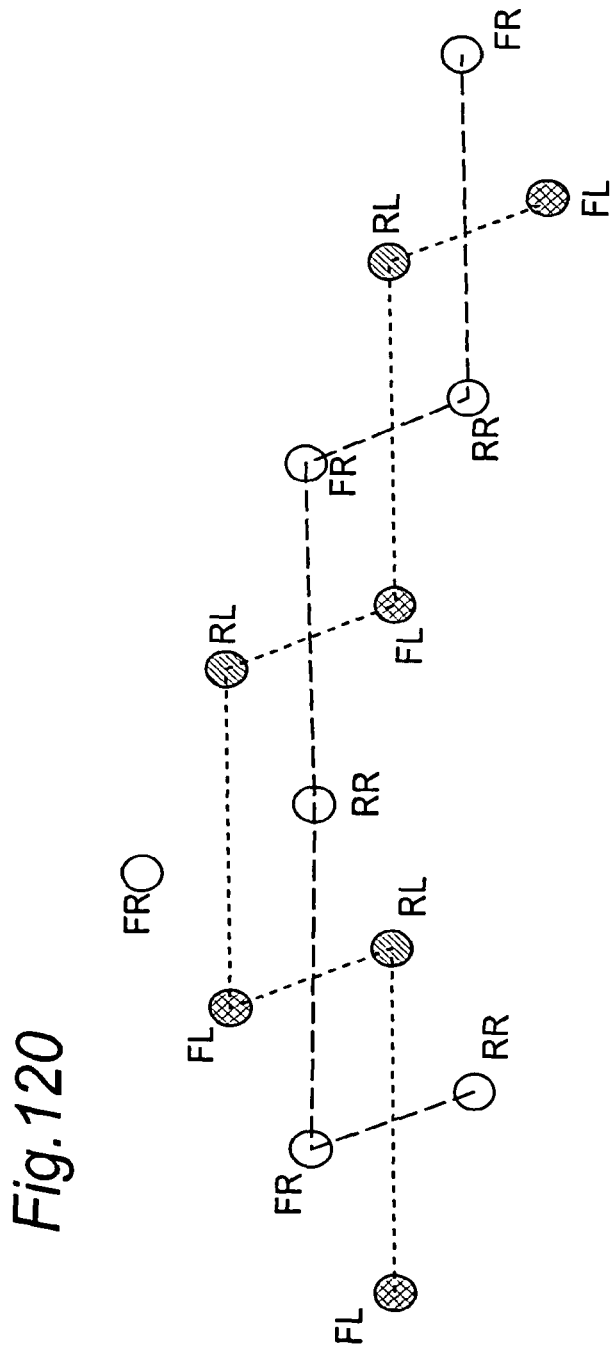

FIG. 118 shows the case where the double helical matrix is continuously arranged in one direction in repeating fashion. In the loudspeaker arrangement of FIG. 118, the person within this space faces left sound and right sound at all times and listens to all sounds for the five channels. FIG. 119 shows the case where the double helical matrix is continuously arranged in two directions in repeating fashion. In the loudspeaker arrangement of FIG. 119, the person within this space faces left sound and right sound at all times and listens to all sounds for the five channels. Furthermore, FIG. 120 is drawn upon paying attention to the sequence of left sound and the sequence of right sound. In FIG. 120, the left sound and the right sound are intertwined with each other, and the left loudspeaker and the right loudspeaker each are aligned in the helical shape by repeating front-rear-front-rear- . . . .

Figure 121:
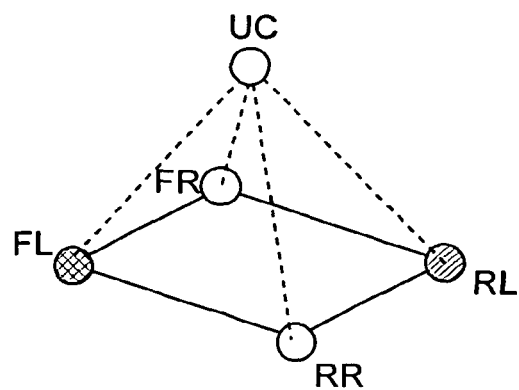
Figure 122:
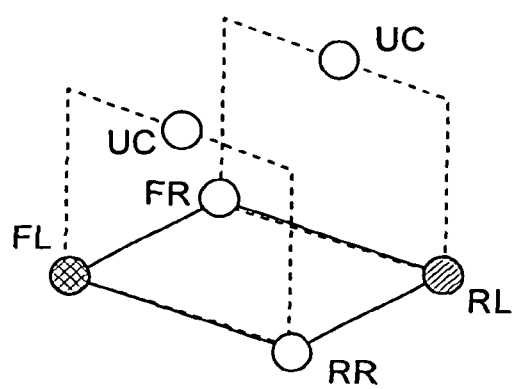

Furthermore, when the double helical matrix is configured by five-channel surround loudspeakers, if it is difficult to provide the upper center loudspeaker UC in the upper center part of the matrix as shown in FIG. 121, by arranging two upper center loudspeakers UC above an intermediate point between the front left loudspeaker FL and the rear right loudspeaker RR and above an intermediate point between the front right loudspeaker FR and the rear left loudspeaker RL, respectively, as shown in FIG. 122, and playing sounds with the same volume, the same effect as in the case where the upper center loudspeaker UC is arranged in the upper center can be obtained.

Figure 123:
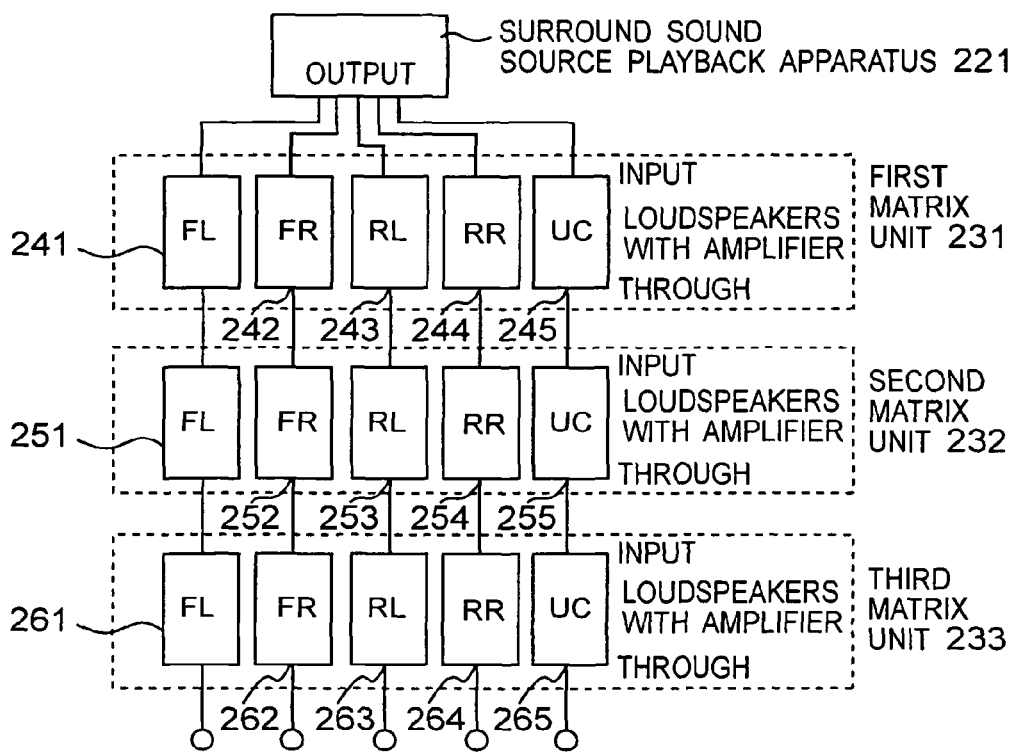
Figure 124:
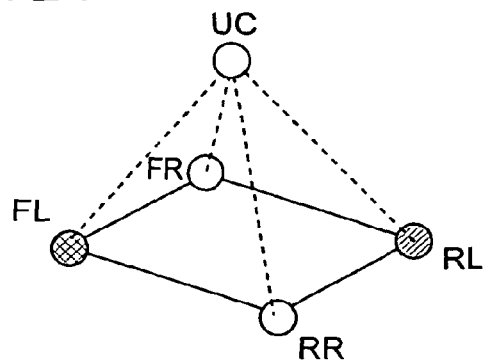
Figure 125:
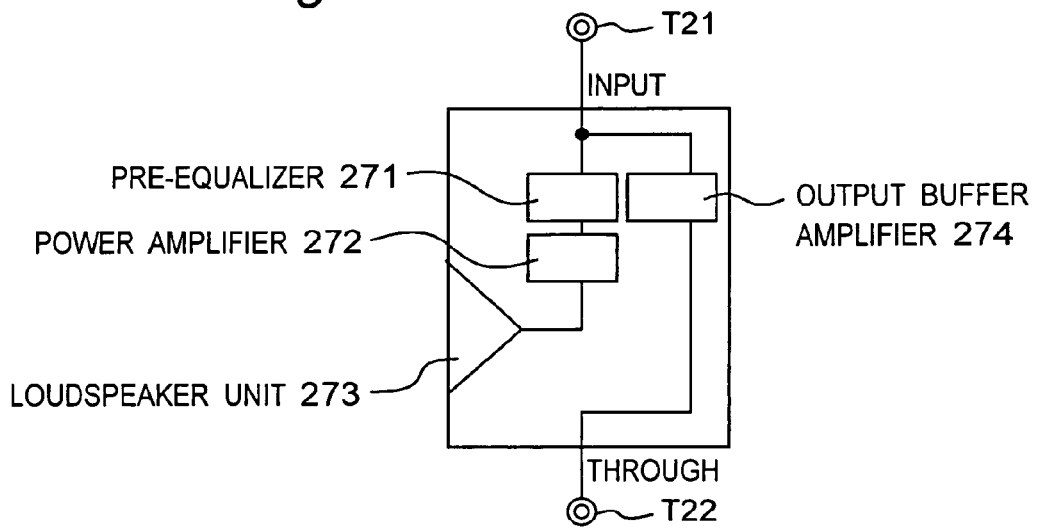

Next, a hardware system for realizing the double helical matrix will be described below with reference to FIG. 123 to FIG. 125. Referring to FIG. 123, a signal from a surround sound source playback apparatus 221 is input to each of input terminals T21 of loudspeakers with amplifier 241 to 245 of a first matrix unit 231 and a through signal output from each of through terminals T22 is input to each of input terminals T21 of loudspeakers with amplifier 251 to 255 of a second matrix unit 232. Then, the through signal output from each of the through terminals T22 of the loudspeakers with amplifier 251 to 255 of a second matrix unit 232 is input to each of input terminals T21 of loudspeakers with amplifier 261 to 265 of a third matrix unit 233 and output from each of through terminals T22 of the loudspeakers with amplifier 261 to 265 of the third matrix unit 233.

In this case, the matrix units 231, 232 and 233 each includes five loudspeakers with amplifier 241 to 265 of the matrix unit and the loudspeakers with amplifier 241 to 265, each has the input terminal T21 and the through terminal T22. A series of the loudspeakers having the same role (for example, the front left loudspeakers FL) reproduce the same sound signal by connecting the through terminals T22 to input terminals T21. The loudspeakers with amplifier 241 to 265 are configured as shown in FIG. 125. That is, the signal input via the input terminal T21 is diverged into two signals, one signal is output to the through terminal T22 via an output buffer amplifier 274 and the other signal is output to a loudspeaker unit 273 via a pre-equalizer 271 and a power amplifier 272 and reproduced. In this case, since the input signal is buffered and amplified by the output buffer amplifier 274, the signal is not attenuated even when a plurality of loudspeakers is connected to each other.

Although the above implemental example of FIG. 123 describes the case where one surround sound source playback apparatus 221 is used, the present invention is not limited to this and two or more surround sound source playback apparatuses 221 may be used.

Figure 126:
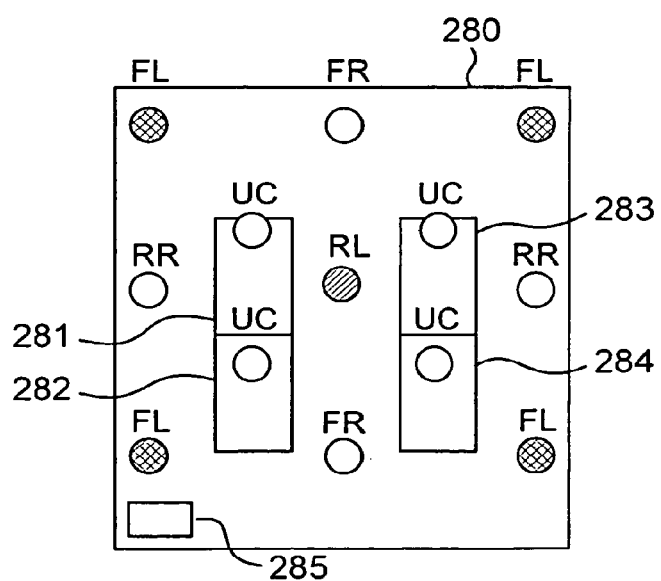

FIG. 126 is a plan view showing an arrangement of the loudspeakers arranged in an office space 280 as a first application example using the double helical matrix coordinate method in accordance with the implemental example 11. Referring to FIG. 126, tables 281 to 285 are arranged in the office space 280 and a 2-column×2-row (4 units) matrix in two dimensions is arranged so as to overlap on sides with each other by the above-mentioned helical matrix coordinate method. In this case, for example, the front left loudspeaker FL, the front right loudspeaker FR, the rear left loudspeaker RL and the rear right loudspeaker RR are placed at the height of 1 to 2 m from the floor face and the upper center speaker UC is placed at the height of 3 to 4 m from the floor face.

Figure 127:
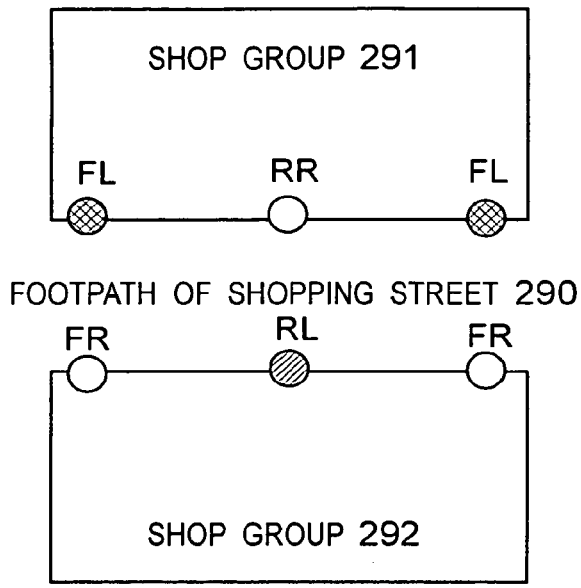

FIG. 127 is a plan view showing an arrangement of the loudspeakers arranged in a shopping street as a second application example using the double helical matrix coordinate method in accordance with the implemental example 11. Referring to FIG. 127, a straight footpath 290 of the shopping street lies between two shop groups 291 and 292. The front left loudspeaker FL, the rear right loudspeaker RR, the front left loudspeaker FL are arranged in this order along the footpath 290 on the side of the shop group 291 and the front right loudspeaker FR, the rear left loudspeaker RL and the front right loudspeaker FR are arranged in this order along the footpath 290 on the side of the shop group 292. That is, a 1-column×2-row (2 units) matrix in one dimension is arranged so as to overlap on sides with each other by the above-mentioned helical matrix coordinate method. In this case, for example, the front left loudspeaker FL, the front right loudspeaker FR, the rear left loudspeaker RL and the rear right loudspeaker RR are placed at the height of 1 to 2 m from the floor face and the upper center speaker UC is placed at the height of 3 to 4 m from the floor face.

Implemental Example 12

In the implemental example 12, a method for generating and displaying still and moving pictures of a fractal pattern will be described below. The fractal pattern can be synthesized according to a method as disclosed in the Japanese Patent Laid-Open Publication No. 9-114992 and the Japanese Patent Laid-Open Publication No. 11-265435. Using the fractal structure existing mainly in the nature recorded in a still or moving picture, the configuration can be set up. However, in the fractal structure, it is necessary that a fractal dimension, for example, capacity dimension described later (f-dimension) is substantially equal to or larger than 2.2 and less than 3.0 and the size extends to the super perceptual region having a fineness exceeding a differential threshold acuity (v-acuity) described later.

Figure 128:
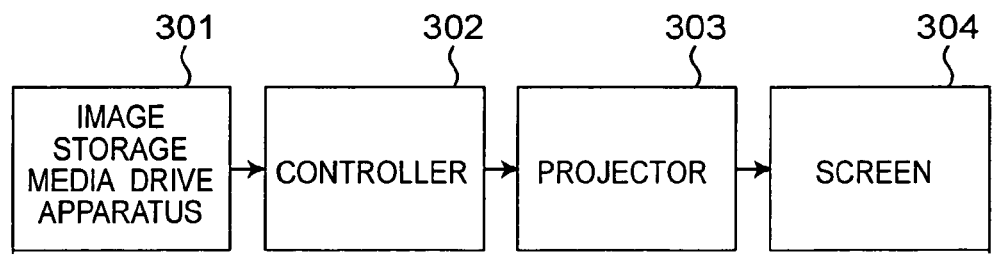

FIG. 128 is a block diagram showing a configuration of a system of presenting a high-density fractal stimulus exceeding to the super perceptual region in accordance with the implemental example 12. A presentation apparatus shown in FIG. 128 is placed in an experiment room, which can shield sound and light from the outside. A controller 302 reads high-density fractal image data having a capacity dimension equal to or larger than 2.2, which is previously stored in an image storage medium (for example, an optical disk), from an image storage media drive apparatus 301 and displays the data on a mat screen 304 provided in front of the viewer by using a high-definition projector 303. At this time, when the viewer looks at, for example, a high-density fractal image of 2048 pixels presented on a screen having the width of 160 cm from a distance of 310 cm, the visual stimulus fineness degree is calculated as 1.19 and it becomes possible to present the high-density fractal visual stimulus extending to the super perceptual region, which exceeds the general acuity of 1.0. A visual angle which the visual stimulus presented at this time occupies in the visual field is 29 degrees, meaning that a wide visual field including peripheral vision is subject to the visual stimulus. The electroencephalogram measurement experiment carried out by the inventors using this system demonstrates that configuration setup by the high-density fractal visual stimulus extending to the super perceptual region statistically-significantly increases the $\alpha$ wave of electroencephalogram.

Furthermore, the definition of the differential acuity (v-acuity) and the capacity dimension (f-dimension) will be described below.

Figure 129:
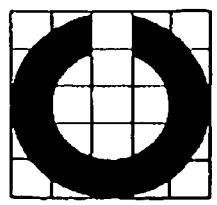

First of all, the differential threshold acuity is correctly called as "minimum readable threshold" and defined as follows. The minimum readable threshold means the minimum size of characters or figures, which can be read or discriminated. A visual target currently widespread to measure the minimum readable threshold is a Landolt ring or Landolt C prescribed in the international ophthalmology congress in 1909. The Landolt ring is, as shown in FIG. 129, drawn in black on a white background and the thickness of the line is defined one fifth of the outer diameter. The task for the viewer is to indicate the direction of a break and a reciprocal of visual angle dimension (unit: arc-minute) of the width in the break which the viewer manage to indicate is used as the visual target of acuity. For example, when the width of the break is 1 arc-minute in visual angle, acuity is 1.0 and when the width of the break is 10 arc-minutes in visual angle, acuity is 0.1.

A standard eyesight test method using the Landolt ring is as follows. Generally, acuity is measured one at time at a distance of 5 m. As to lighting of a standard eyesight test apparatus, in the case of interior lighting, the luminous emittance is set to be 500 rlx±150 rlx and in the case of lighting from the front, the visual surface illuminance is set to be 400 lx to 800 lx as substandard. The viewer is asked to read the visual target from 0.1 in decreasing order of size and the readable minimum target is regarded as the acuity. According to the criteria, when four or five equivalent targets in the same raw are certainly presented and the viewer can have a correct answer to more than half of the presented targets, acuity is determined.

The capacity dimension (f-dimension) is used as a variable representing the capacity dimension among the fractal dimension. The fractal dimension is one of scales representing fractal structure properties and the capacity dimension (f-dimension) is defined as a value obtained according to the following calculation procedures.

First of all, the brightness of each pixel which belongs to a screen constituting the visual stimulus is calculated and the low and the high in brightness is regarded as the level of low and high in the vertical direction relative to the screen to assume a three-dimensional structure. When the three-dimensional structure is expressed by stacking an integral number of unit cubes having a certain dimension, the number of unit cubes constituting the surface part of the three-dimensional structure (a boundary between the three-dimensional structure and the surrounding space) varies depending in the dimension of the unit (fineness in measure). The exponent part of the numerical value of the level that the number of the unit cubes varies expressed by a power of the rate of change in the measure becomes the capacity dimension (fractal dimension).

Implemental Example 13

In the implemental example 13, in a laboratory, the inventors of the present invention carried out an experiment in which the case where only urban environmental sound is presented to subjects was compared with the case where the urban environmental sound to which tropical forest environmental sound was added was presented. Sound recorded in an urban area in Nakano-ku, Tokyo was used as the urban environmental sound and sound recorded in Borneo Island in Malaysia was used as the tropical forest sound. The presentation time was 40 minutes. Physiological assessment by an analysis of blood physiological activity substances (FIG. 130), physiological assessment by electroencephalogram measurement (FIG. 131) and psychological assessment using questionnaire (FIG. 132) were used as assessment items.

Figure 130:
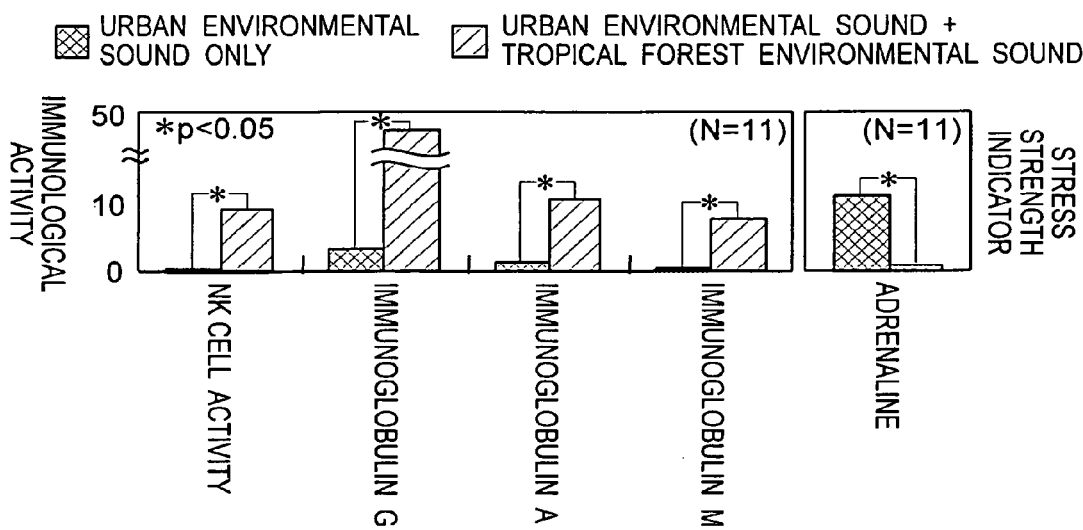

FIG. 130 shows results as obtained by collecting blood from the subjects immediately after the presentation of the sound and analyzing blood physiological substances indicator. As apparent from FIG. 130, it is confirmed that all of NK cell activity, immunoglobulin G, immunoglobulin A and immunoglobulin M, which have advantageous effects of suppressing cancer and preventing virus infection, increase more in the case of only the urban environmental sound than in the case where the tropical forest environmental sound is added and thus, the addition of the tropical forest environmental sound contributes to an increase in immune activity. Furthermore, adrenaline is deemed as an indicator of stress, and it is confirmed that the perceived stress strength is lower in the case of only the urban environmental sound than in the case where the tropical forest environmental sound is added and thus, the addition of the tropical forest environmental sound contributes to a reduction in stress. In this case, a minor stress among stresses is not harmful and often acts on the human's body effectively. However, an excessive stress exceeding the limit results in a breakdown of the function if maintaining constancy of mind and body (homeostasis) causes discomfort and impairs health. According to the present invention, it is possible to set up the environment suitable or comfortable for the brain, that is, the environment without any excessive stress, which is comfortable for human beings.

Figure 131:
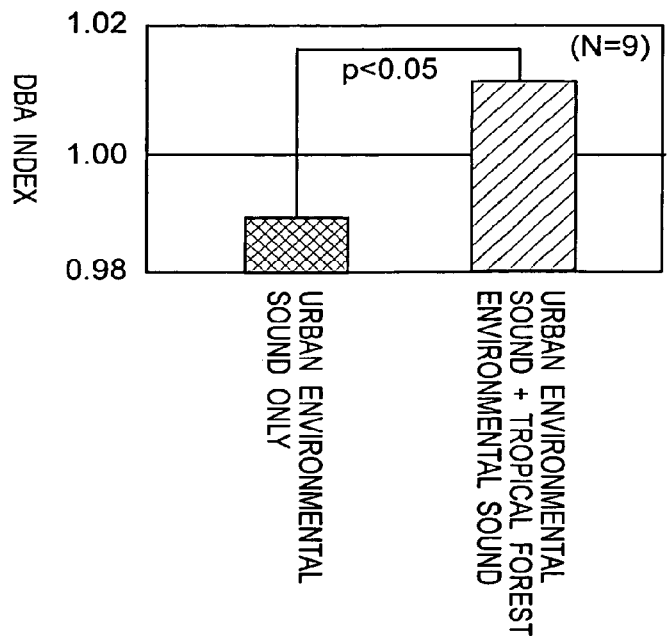

FIG. 131 shows results as obtained by measuring the electroencephalogram for 40 minutes in the presentation of the sound and analyzing the electroencephalogram. An average potential of α two bands (10 Hz to 13 Hz) at seven electrodes on the parietal and occipital regions is obtained and a normalized value for each subject is used for analysis. It is found that this indicator is highly correlated with the activity of the brain deep portion and called as a deep brain activity index (DBA index). It can be statistically-significantly proved that the deep brain activity index is increased more in the case where the tropical forest environmental sound is added than in the case of only the urban environmental sound.

FIG. 132 shows psychological assessment results by the questionnaire method. A horizontal axis represents assessment items and a vertical axis represents average values of scores. It can be statistically-significantly detected that the addition of the tropical forest environmental sound to the urban environmental sound generally improves the comfort of environment and brings about the advantageous effects of improving the brain function and inducing people to the urban environment.

Implemental Example 14

In the implemental example 14, an arrangement of loudspeakers by using a six-dimensional continuous matrix coordinate method will be described below.

FIG. 133 is a perspective view showing an arrangement of four-channel surround loudspeakers in accordance with the prior art. The four-channel surround loudspeakers of FIG. 133 are raised to a predetermined height. Then, channels of sound located between the front and the rear are added and the loudspeakers are referred to as a center left loudspeaker CL and a center right loudspeaker CR. These center left loudspeaker CL and center right loudspeaker CR are disposed at the position slightly above the ground. The loudspeaker arrangement of FIG. 134 is referred to as a matrix in the present implemental example.

Continuous arrangement of the matrix of FIG. 134 in one direction in a repeated fashion results in an arrangement shown in FIG. 135. Referring to FIG. 135, since the left sound comes from the left side and the right sound comes from the right side in any matrix, a sound field is normally formed. In addition, the front sound and the rear sound appears alternately. Furthermore, since there is the sound from the center loudspeakers connecting the front sound to the rear sound, continuous space can be felt.

Furthermore, continuous arrangement of the matrix of FIG. 134 in two directions in a repeated fashion results in an arrangement shown in FIG. 136. Referring to FIG. 136, since there is the left sound line and the right sound line in any matrix, a sound field is normally formed. In addition, the front sound and the rear sound appears alternately. Furthermore, since there is the center sound connecting the front sound to the rear sound, continuous space can be felt.

Next, channels of sound located between the front and the rear are added to the arrangement of four-channel surround loudspeakers of FIG. 133 and the loudspeakers are referred to as a center left loudspeaker CL and a center right loudspeaker CR. In this case, these two loudspeakers CL and CR are disposed upwards. The loudspeaker arrangement of FIG. 137 is referred to as a matrix in accordance with a modification of the implemental example 14.

Continuous arrangement of the matrix of FIG. 137 in one direction in a repeated fashion results in an arrangement shown in FIG. 138. Referring to FIG. 138, since the left sound comes from the left side and the right sound comes from the right side in any matrix, a sound field is normally formed. In addition, the front sound and the rear sound appears alternately. Furthermore, since there is the center sound connecting the front sound to the rear sound, continuous space can be felt.

Furthermore, continuous arrangement of the matrix of FIG. 137 in two directions in a repeated fashion results in an arrangement shown in FIG. 139. Referring to FIG. 139, since there is the left sound line and the right sound line in any matrix, a sound field is formed such that the sound field can be felt normally. In addition, the front sound and the rear sound appears alternately. Furthermore, since there is the center sound connecting the front sound to the rear sound, continuous space can be felt.

In this case, the double helical matrix coordinate method in accordance with the implemental example 11 and the six-dimensional continuous matrix coordinate method in accordance with the implemental example 14 will be summarized as follows.

Summarizing these two matrix coordinate methods in a super ordinate concept, the "loudspeaker matrix coordinate method" can be defined as a loudspeaker coordinate method for constituting a surround sound field, in which a sound source of two or more channels is used and a group of loudspeakers is continuously arranged on a grid or on parallel lines according a certain rule to extend to a space having an arbitrary dimension so that adjacent loudspeakers presenting the sound may present the sound of different channels.

Furthermore, the "loudspeaker double helical matrix coordinate method" can be defined as a loudspeaker matrix coordinate method in which a sound source of five channels (front left, front right, rear left, rear right, upper or lower) or six channels (front left, front right, rear left, rear right, upper or lower left, upper or lower right) is used and a group of loudspeakers presenting the sound are continuously arranged so that the left and right channels are alternated in the shape of a DNA double helix.

Furthermore, the "loudspeaker six-dimensional continuous matrix coordinate method" can be defined as a loudspeaker matrix coordinate method in which a sound source of six channels (front left, front right, rear left, rear right, upper or lower left, upper or lower right) is used, a group of loudspeakers presenting the sound is continuously arranged in the left channel line and the right channel line alternately, and in each line, the front channel and the rear channel are continuously and alternately arranged with the upper (or lower) channel being sandwiched therebetween.

Implemental Example 15

FIG. 140 is a block diagram showing a configuration of a system of reproducing an acoustic signal containing the super perceptual auditory information in accordance with the implemental example 15. A sound environment that includes the super perceptual auditory information can be also set up by installing the system of FIG. 140.

In order to reproduce super high-density air vibration information exceeding the audible band, the following apparatuses are used. That is, a sound signal (for example, a signal written in an optical disk 211A) having a high brain main parts activating effect, in which one or more super high-density components exceeding the upper limit of the audible band are mixed, contained the super perceptual sound source recorded in an electronic medium, such as tropical rain forest environmental sound, Gamelan sound, hypersonic music box sound and electronic sound is read by a player 211 shown in FIG. 112. Subsequently, the read sound signal is reproduced using a D/A converter 212, a pre-amplifier 214A with only high channel, a power amplifier 215A with only high channel and a super tweeter 216 of FIG. 112.

In order to reproduce auditory information of the audible band, a signal of the audible band is read from the sound source which the sound in the audible frequency band, which is not necessarily generated from the same origin as the above-mentioned super high-density components, for example, an arbitrary CD (compact disk) 211B (having a music CD format, for example) by a CD player 211$a$ and the read signal is analog converted by a D/A converter 212$a$. Subsequently, the electric signal is amplified by a headphone power amplifier 215B. Finally, the electric signal is converted into the sound of audible band and reproduced by a headphone 215C. As a reproduction apparatus, the power amplifier and loudspeakers may be used in place of the headphone 215C. Alternatively, a plurality of sets of systems of reproducing auditory information in the audible band may be prepared and a plurality of persons, each may listen to different sounds.

As described above, it becomes possible to set up the environment having the feature of the present invention by reproducing the super high-density air vibration information exceeding the audible band and at the same time, reproducing music or the like recorded in the conventionally used medium to the limited person or space by the headphone 215C or the loudspeakers in the audible band. At this time, the feature of the present invention is that each person can independently reproduce arbitrary auditory information such as his/her favorite specific music and experience the brain main part activation effect by hypersonic effect while enjoying the auditory information.

For the clarification of description, although one super tweeter 216 is described in the present implemental example, a plurality of super tweeters may be adopted.

In the above-described embodiments and implemental examples, according to the method and apparatus for environmental setting and the information for environmental setting, they include a step of arranging means for setting a tropical rain forest type environment based on characteristics of activating human being's essential brain region in response to tropical rain forest type environment information, in a predetermined space including at least one of urban space, housing space and living space, in order to set the space substantially in the tropical rain forest type environment. This leads to activation of the human being's essential brain region to realize an environment suitable for the human being's brain. In this case, the tropical rain forest type environmental information has higher density and higher complexity than those of urban space type environmental information. In this case, the tropical rain forest type environment information includes at least one of auditory information, visual information and super perceptual information of aerial vibration. In addition, the tropical rain forest type environmental information is super perceptual information which is sensory information consisting of perceptible information and information exceeding a perceptual limit. In this case, the means for setting plays back the tropical rain forest type environmental information using at least one of a plurality of loudspeakers arranged by a matrix configuration method, and an apparatus for representing visual information. In addition, the environment suitable for the human being's brain is an environment, which is comfortable for human beings, and which has no excessive stress. Further, the tropical rain forest type environmental information is environmental information for effectively functioning on prevention and treatment of diseases due to stress by realizing the environment suitable for the human being's brain. Accordingly, in comparison with the prior art, the space including the urban space, the housing space and the living space can be made more comfortable environment for human beings. This leads to that it is possible to greatly reduce the stress exerted on human beings in the space, improve mental comfort and maintain good physical health. Moreover, by realizing the environment comfortable for the human's brain, the above-mentioned tropical rain forest type environmental information is environmental information so as to effect the prevention and treatment of illnesses such as modern-day diseases due to stress and can prevent and treat illnesses such as the modern-day diseases.

As described above, a human ancestor branched from the orangutan thirteen million years ago and evolved in a tropical rain forest environment in Africa. This tropical rain forest environment has a higher density and complexity, and is more variable in the above-mentioned acoustic and optical information than the urban environment, and the environment intrinsic in a human gene is deemed to be the tropical rain forest environment. Recent cities have caused a low density and a monotonous environment in contrast to the environment intrinsic in human beings. Many modern-day diseases such as lifestyle-related diseases are considered to arise from a substantial gap between the environment intrinsic in human beings and the urban environment. In order to solve these problems, prevent and treat modern-day diseases, the present invention provides a method for converting the predetermined space including at least one of urban space, housing space and living space into the topical rain forest type environment substantially equivalent to the tropical rain forest environment.

What is claimed is:

1. A signal generator apparatus for generating an environmental setting, the signal generator apparatus comprising:

a signal generator for generating a signal representing a tropical rain forest environment, the tropical rain forest environment signal being a super perceptual signal including a perceptible first sensory signal that is lower than a perceptual upper limit of what a human being can perceive, and an imperceptible second sensory signal that is higher than the perceptual upper limit of what the human being can perceive, the super perceptual signal including:

an auditory signal having a density thereof having both a predetermined perceptible frequency band and an imperceptible frequency band which is higher than an auditory perceptual upper limit, the auditory signal having such a complexity that a shape of a spectrum of the auditory signal has the density and power thereof changing in a non-stationary manner in a time region at least ranging from 100 milliseconds to 0.5 milliseconds as compared with an auditory signal of the perceptible first sensory signal being stationary in a predetermined temporal length; and an image signal having a spatial density of a shape thereof such that a visual stimulus spatial density of the shape of the image signal is higher than a predetermined spatial visual resolution threshold of what the human being can view, the image signal having such a complexity that a spatial fractal dimension of the shape of the image signal is greater than a spatial fractal dimension of a shape of an image signal of the perceptible first sensory signal; and an applying device for applying the signal generated by the signal generator to the human being to activate a reward system of a brain of the human being, the reward system comprising a deep portion of the brain including a brain stem, and a monoaminergic system related to the deep portion of the brain, and for collectively activating the reward system and a biologic control system that undertakes adjustment of an essential part of vital activity including an autonomic nervous system, an endocrine system and an immunity system, the biologic control system including a hypothalamic area and the brain stem to set the human being substantially in the tropical rain forest environment, thereby realizing an environment suitable for the human being's brain.

2. The apparatus as claimed in claim 1, wherein the imperceptible frequency band includes frequencies up to at least 100 kHz.

3. The apparatus as claimed in claim 1, wherein the applying device includes at least one of a display unit for displaying the image signal and a plurality of loudspeakers arranged in a matrix configuration.

* * * * *